US012649003B2

(12) United States Patent
Jaffe et al.

(10) Patent No.: US 12,649,003 B2
(45) Date of Patent: ***Jun. 9, 2026

(54) COMPOSITIONS AND METHODS FOR EPIGENETIC REGULATION OF HBV GENE EXPRESSION

(71) Applicant: nChroma Bio, Inc., Boston, MA (US)

(72) Inventors: Aron Brandon Jaffe, Brookline, MA (US); Noorussahar Abubucker, Watertown, MA (US); Yesseinia Anglero-Rodriguez, Everett, MA (US); Vic Myer, Arlington, MA (US); Angelo Leone Lombardo, Rome (IT); Martino Alfredo Cappelluti, Milan (IT)

(73) Assignee: nChroma Bio, Inc., Boston, MA (US)

( * ) Notice: Subject to any disclaimer, the term of this patent is extended or adjusted under 35 U.S.C. 154(b) by 0 days.

This patent is subject to a terminal disclaimer.

(21) Appl. No.: 19/224,549

(22) Filed: May 30, 2025

(65) Prior Publication Data

US 2025/0288691 A1 Sep. 18, 2025

Related U.S. Application Data

(63) Continuation of application No. 18/762,259, filed on Jul. 2, 2024, now Pat. No. 12,390,538, which is a continuation of application No. PCT/US2024/029529, filed on May 15, 2024.

(60) Provisional application No. 63/581,236, filed on Sep. 7, 2023, provisional application No. 63/516,096, filed on Jul. 27, 2023, provisional application No. 63/502,325, filed on May 15, 2023.

(51) Int. Cl.
| | |
|---|---|
| *C12N 9/22* | (2006.01) |
| *A61K 48/00* | (2006.01) |
| *A61P 31/20* | (2006.01) |
| *C12N 9/10* | (2006.01) |
| *C12N 15/11* | (2006.01) |

(52) U.S. Cl.
CPC ............ *A61K 48/005* (2013.01); *A61P 31/20* (2018.01); *C12N 9/1007* (2013.01); *C12N 9/22* (2013.01); *C12N 15/11* (2013.01); *C12Y 201/01037* (2013.01); *C07K 2319/00* (2013.01); *C07K 2319/80* (2013.01); *C12N 2310/20* (2017.05)

(58) Field of Classification Search
CPC .. C07K 2319/00; C07K 2319/80; C12N 9/22; C12N 15/11; C12N 15/1131; C12N 2320/11; C12Y 201/01037
USPC ......................................................... 435/69.7
See application file for complete search history.

(56) References Cited

PUBLICATIONS

Kwiatkowski et al., Biochemistry 38:11643-11650, 1999.*
Kisselev L., Structure, 2002, vol. 10: 8-9/.*
Wristlock et al., Quarterly Reviews of Biophysics 2003, vol. 36 (3): 307-340.*
Davos et al., Proteins: Structure, Function and Genetics, 2000, vol. 41: 98-107.*
U.S. Appl. No. 18/762,301, filed Jul. 2, 2024, 2024-0382622, Nov. 21, 2024.
U.S. Appl. No. 19/060,404, filed Feb. 21, 2025, 2025-0236847, Jul. 24, 2025.
Brakenhoff et al., "Hepatitis B virus RNA decline without concomitant viral antigen decrease is associated with a low probability of sustained response and hepatitis B surface antigen loss" Aliment Pharmacol Ther. Jan. 2021;53(2):314-320.
Lamontagne et al., "Hepatitis B Virus Molecular Biology and Pathogenesis" Hepatoma Res. 2016;2:163-186 (2016).
Mohebbi et al., "An Overview of Hepatitis B Virus Surface Antigen Secretion Inhibitors" Front Microbiol. Apr. 5, 2018;9:662.

* cited by examiner

*Primary Examiner* — Tekchand Saidha
*Assistant Examiner* — Mohammad Y Meah
(74) *Attorney, Agent, or Firm* — Goodwin Procter LLP

(57) ABSTRACT

This invention relates to compositions, methods, strategies, and treatment modalities related to the epigenetic modification of hepatitis B virus (HBV) genes.

19 Claims, 57 Drawing Sheets

Specification includes a Sequence Listing.

| Group | Treatment | Format | N=6 AAV-HBV | N=6 HBV-Tg |
|---|---|---|---|---|
| 1 | Vehicle | - | 6 | 6 |
| 2 | gRNA011 | WT-Cas9 | 6 | 6 |
| 3 | gRNA011 | CRISPR-Off | 6 | 6 |
| 4 | gRNA003 | CRISPR-Off | 6 | 6 |
| 5 | gRNA016 | CRISPR-Off | 6 | 6 |
| 6 | gRNA016 | 3x-ETR | 6 | 6 |

*gRNAs selected from HepG2-NTCP hits, with 100% match in both A and D genotypes*

Ⓐ HBV Genotype D

AAV-HBV

Ⓑ HBV Genotype A

Tg-HBV

Optimized CRISPR-Off

DNMT 3A 3L

KRAB

+

LNP

Single administration

3 mg/kg

Plasma:
- HBsAg
- HBeAg
- HBV DNA

Liver: Collected for further analysis

FIGURE 15

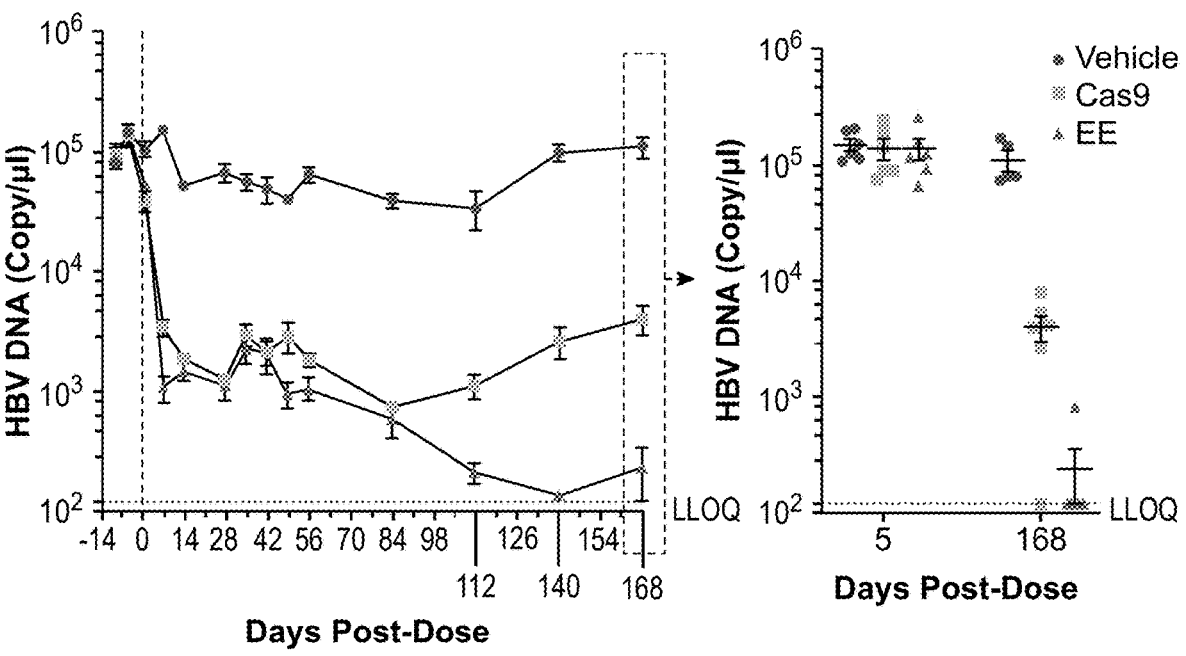
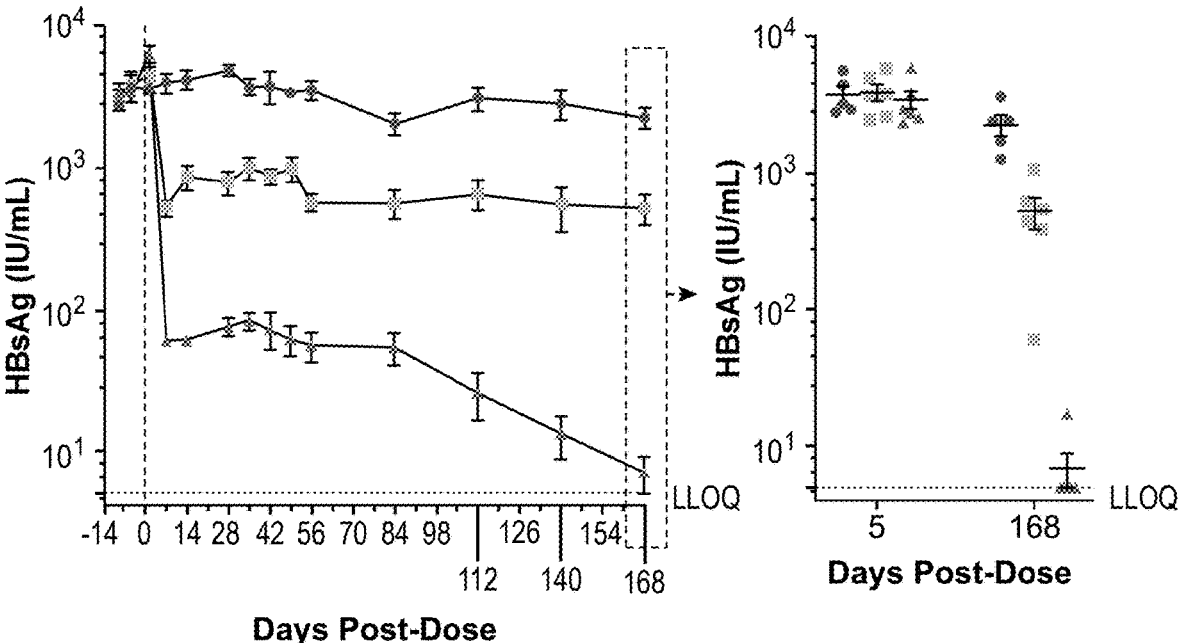
FIGURE 18B

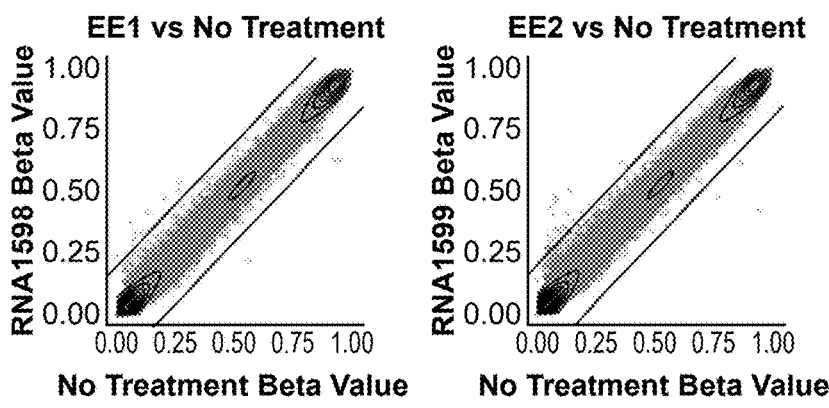
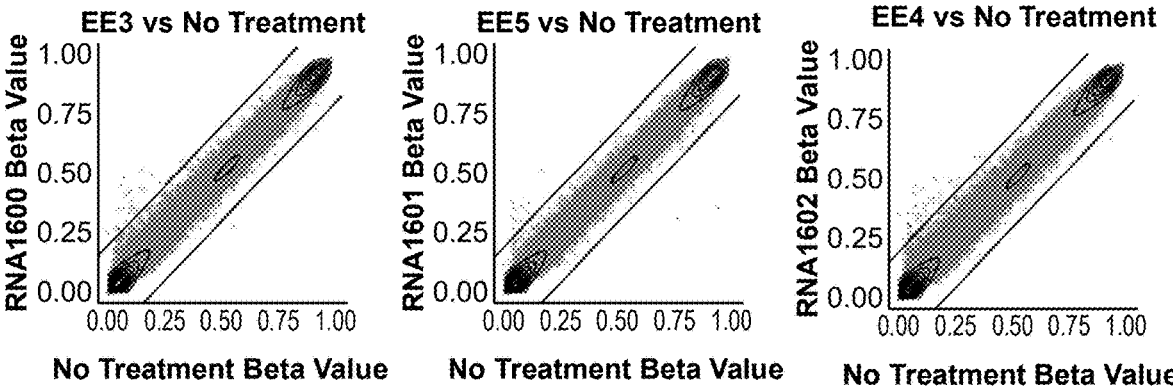
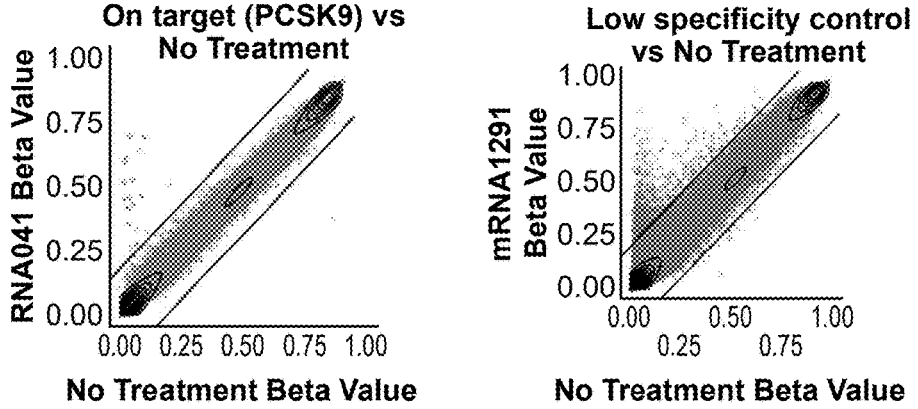
FIGURE 25D

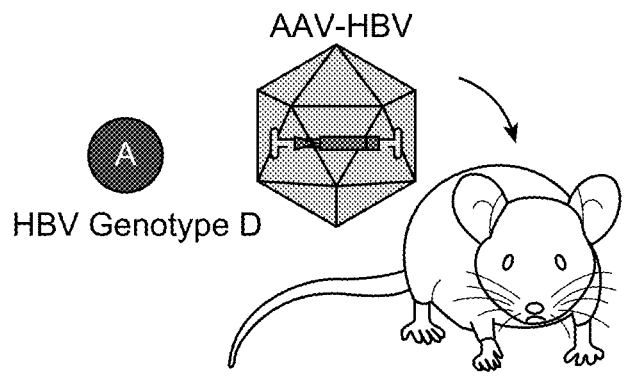
HBV Genotype D    AAV-HBV
Optimized ZF-Off
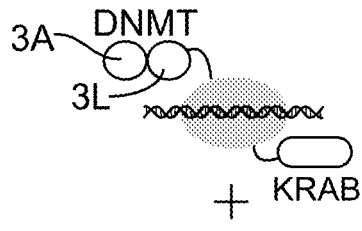
LNP
Single administration
1 mg/kg
FIGURE 26

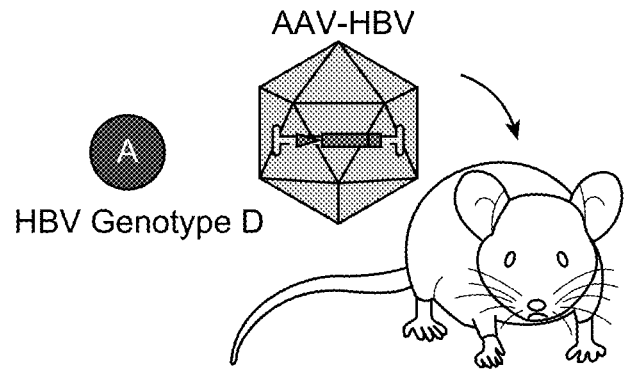
AAV-HBV
HBV Genotype D
ZF-Off
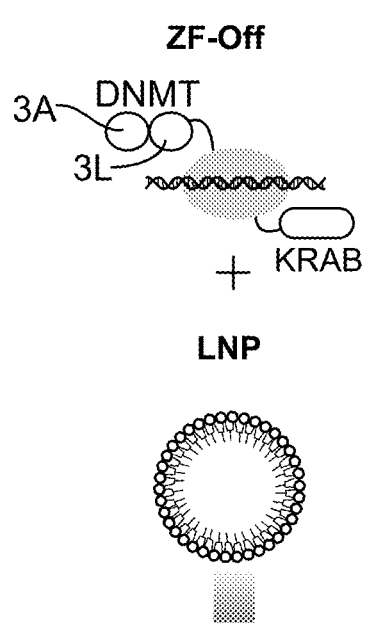
3A DNMT
3L
+ KRAB
LNP
Single administration
0.5 mg/kg
FIGURE 28

COMPOSITIONS AND METHODS FOR EPIGENETIC REGULATION OF HBV GENE EXPRESSION

CROSS-REFERENCE

This application is a continuation of U.S. application Ser. No. 18/762,259, filed on Jul. 2, 2024, U.S. Pat. No. 12,390, 538, which is a continuation of International Application No. PCT/US2024/029529, filed on May 15, 2024, which claims the benefit of U.S. Provisional Application No. 63/502,325, filed May 15, 2023, U.S. Provisional Application No. 63/516,096, filed Jul. 27, 2023, and U.S. Provisional Application No. 63/581,236, filed Sep. 7, 2023, each of which is incorporated herein by reference in its entirety.

SEQUENCE LISTING

The instant application contains a Sequence Listing which has been submitted electronically in XML file format and is hereby incorporated by reference in its entirety. Said XML copy, created on May 30, 2025, is named CMD-002USC3_SL.xml and is 1,448,821 bytes in size.

BACKGROUND OF THE INVENTION

Despite available treatments, chronic hepatitis B (CHB) remains a high unmet medical need, with more than 250 million carriers of hepatitis B virus (HBV) worldwide and approximately 800,000 annual deaths due to HBV-related liver disease. Current approved CHB therapies elicit a functional cure rate (defined as durable HBsAg loss and undetectable serum HBV after completing a course of treatment) of less than 20%. Accordingly, there is a need for improved clinical modalities targeting HBV.

SUMMARY OF THE INVENTION

Some aspects of the present disclosure provide systems, compositions, strategies, and methods for the epigenetic modification of HBV, including HBV in host cells and organisms.

Some aspects of this disclosure provide methods of modifying an epigenetic state of a hepatitis B virus (HBV) gene or genome, comprising contacting the HBV gene or genome with an epigenetic editing system, wherein the epigenetic editing system comprises a first DNA binding domain, a first DNMT domain, and a transcriptional repressor domain or one or more nucleic acid molecules encoding thereof, optionally, wherein the first DNA binding domain binds a first target region of the HBV gene or genome, and wherein the contacting results in a reduction of: number of HBV viral episomes, replication of the HBV gene or genome, and/or expression of a protein product encoded by the HBV gene or genome, wherein said reduction is at least about 20% compared to contacting the HBV gene or genome with a suitable control or without contacting the HBV gene or genome with the epigenetic editing system, and/or wherein said reduction of the number of HBV viral episomes, of replication of the HBV gene or genome, or of expression of a protein product encoded by the HBV gene or genome is at least 20%, at least 60%, at least 70%, at least 80%, at least 90% (i.e., at least a 1-log reduction), at least 95%, at least 99% (i.e., at least a 2-log reduction), or at least 99.9% (i.e., at least a 3-log reduction), compared to the number, replication, and/or expression in the subject before the contacting.

Some aspects of this disclosure provide methods of treating an HBV infection in a subject comprising administering an epigenetic editing system to the subject, wherein the epigenetic editing system comprises a first DNA binding domain, a first DNMT domain, and a transcriptional repressor domain or one or more nucleic acid molecules encoding thereof, optionally, wherein the first DNA binding domain binds a first target region of a HBV gene or genome, and wherein the administering results in a reduction of: number of HBV viral episomes, replication of the HBV gene or genome, and/or expression of a protein product encoded by the HBV gene or genome, wherein said reduction is at least about 20% compared to administering a suitable control or without administering the epigenetic editing system, and/or wherein said reduction of the number of HBV viral episomes, of replication of the HBV gene or genome, or of expression of a protein product encoded by the HBV gene or genome is at least 20%, at least 60%, at least 70%, at least 80%, at least 90%, at least 95%, at least 99%, or at least 99.9%, compared to the number, replication, and/or expression in the subject before administering.

Some aspects of this disclosure provide methods of modulating expression of an HBV gene or genome comprising contacting the HBV gene or genome with an epigenetic editing system, wherein the epigenetic editing system comprises a first DNA binding domain, a first DNMT domain, and a transcriptional repressor domain or one or more nucleic acid molecules encoding thereof, wherein the first DNA binding domain binds a first target region of the HBV gene or genome, and wherein the contacting results in a reduction of expression of a gene product encoded by the HBV gene or genome, optionally, wherein the gene product is a nucleic acid or a protein, wherein said reduction is at least about 20% compared to contacting the HBV genome with a suitable control or without contacting the HBV gene or genome with the epigenetic editing system, and/or wherein said reduction of the number of HBV viral episomes, of replication of the HBV gene or genome, or of expression of a protein product encoded by the HBV gene or genome is at least 20%, at least 60%, at least 70%, at least 80%, at least 90%, at least 95%, at least 99%, or at least 99.9%, compared to the number, replication, and/or expression in the subject before the contacting.

Some aspects of this disclosure provide methods of inhibiting viral replication in a cell infected with an HBV comprising contacting the cell with an epigenetic editing system, wherein the epigenetic editing system comprises a first DNA binding domain, a first DNMT domain, and a transcriptional repressor domain or one or more nucleic acid molecules encoding thereof, optionally, wherein the first DNA binding domain binds a first target region of a HBV gene or genome, and wherein the epigenetic editing system targets a target region of the HBV gene or genome, and wherein the contacting results in a reduction of number of HBV viral episomes or replication of the HBV gene or genome, wherein said reduction is at least about 20% compared to administering a suitable control or without contacting the HBV gene or genome with the epigenetic editing system, and/or wherein said reduction of the number of HBV viral episomes, of replication of the HBV gene or genome, or of expression of a protein product encoded by the HBV gene or genome is at least 20%, at least 60%, at least 70%, at least 80%, at least 90%, at least 95%, at least 99%, or at least 99.9%, compared to the number, replication, and/or expression in the subject before the contacting.

Some aspects of this disclosure provide methods comprising administering an epigenetic editing system to a subject in need thereof, wherein the epigenetic editing system comprises a first DNA binding domain, a first DNMT domain, and a transcriptional repressor domain or one or more nucleic acid molecules encoding thereof, wherein the first DNA binding domain binds a first target region of a HBV gene or genome, and wherein the contacting results in a reduction of: number of HBV viral episomes, replication of the HBV gene or genome, or expression of a protein product encoded by the HBV gene or genome, wherein said reduction is at least about 20% compared to administering a suitable control, and/or wherein said reduction of the number of HBV viral episomes, of replication of the HBV gene or genome, or of expression of a protein product encoded by the HBV gene or genome is at least about 20% compared to the number, replication, and/or expression in the subject before administering.

Some aspects of this disclosure provide methods of inhibiting viral replication in a subject infected with an HBV comprising administering an epigenetic editing system to the subject, wherein the epigenetic editing system comprises a first DNA binding domain, a first DNMT domain, and a transcriptional repressor domain or one or more nucleic acid molecules encoding thereof, wherein the epigenetic editing system targets a target region of the HBV gene or genome, and wherein the administering results in a reduction of number of HBV viral episomes, replication of the HBV gene or genome, or expression of a protein product encoded by an HBV gene or genome, wherein the reduction is at least about 20% compared to administering a suitable control or without administering the epigenetic editing system. In some embodiments, the reduction is at least 20%, at least 30%, at least 40%, at least 50%, at least 60%, at least 70%, at least 80%, at least 90%, at least 95%, at least 99%, or at least 99.9% compared to administering a suitable control or compared to the respective number or level in the subject before the administering. In some embodiments, the reduction is maintained for at least 6 days, for at least 19 days, for at least 27 days, for at least 42 days, or for at least 168 days.

In some embodiments, the contacting further results in a reduction of a protein product. In some embodiments, the protein product comprises an HBV antigen, for example an HBe antigen (HBeAg). In some embodiments, the protein product comprises an HBs antigen (HBsAg).

In some embodiments, the HBV genome is a covalently closed circular DNA (cccDNA) or an HBV integrated DNA. In some embodiments, the HBV genome comprises HBV genotype A, HBV genotype B, HBV genotype C, HBV genotype D, HBV genotype E, HBV genotype F, HBV genotype G or HBV genotype H. In some embodiments, the HBV genome comprises a sequence with at least 80% identity to an HBV genome sequence provided herein. In some embodiments, the first target region is located in a region of the HBV genome within nucleotide 0-303, 1000-2448 or 2802-3182 of an HBV genome provided herein In some embodiments, the first target region of the HBV genome is located in a CpG island. In some embodiments, the first target region of the HBV genome is located in a promotor. In some embodiments, the first target region of the HBV genome is located in a section of the HBV genome that encodes a transcript selected from the group consisting of a pgRNA, a preCore mRNA, a preS mRNA, a S mRNA, and a X mRNA. In some embodiments, the first DNA binding domain comprises a CRISPR-Cas protein. In some embodiments, the epigenetic editing system further comprises a first guide RNA (gRNA) that comprises a region complementary to a strand of the first target region. In some embodiments, the gRNA comprises a sequence selected from a gRNA provided herein, e.g., in Table 12 or 13. In some embodiments, the first DNA binding domain comprises a zinc-finger protein. In some embodiments, the zinc-finger protein comprises a zinc-finger motif with a sequence selected from any zinc finger or zinc finger motif provided herein, e.g., in Table 1. In some embodiments, the zinc-finger protein comprises a sequence of any of the zinc finger epigenetic repressors provided herein. In some embodiments, the transcriptional repressor domain comprises ZIM3 In some embodiments, the first DNMT domain is a DNMT3A domain or a DNMT3L domain. In some embodiments, the first DNMT domain comprises a sequence of a DNMT domain provided herein. In some embodiments, the epigenetic editing system further comprises a second DNMT domain or a nucleic acid encoding thereof. In some embodiments, the second DNMT domain is a DNMT3A domain or a DNMT3L domain. In some embodiments, the second DNMT domain comprises a sequence of a DNMT domain provided herein. In some embodiments, the epigenetic editing system comprises a fusion protein or a nucleic acid encoding thereof, and wherein the fusion protein comprises the first DNA binding domain, the first DNMT domain, the repressor domain and the second DNMT domain. In some embodiments, the fusion protein further comprises a nuclear localization sequence (NLS). In some embodiments, the fusion protein comprises a sequence of a fusion protein provided herein. In some embodiments, the epigenetic editing system further comprises a second DNA binding domain or a nucleic acid encoding thereof, wherein the second DNA binding domain binds a second target region of the HBV genome. In some embodiments, the second target region is located in a region of the HBV genome within nucleotide 0-303, 1000-2448 or 2802-3182. In some embodiments, the second target region of the HBV genome is located in a CpG island. In some embodiments, the second target region of the HBV genome is located in a promotor. In some embodiments, the second target region of the HBV genome is located in a section of the HBV genome that encodes a transcript selected from the group consisting of a pgRNA, a preCore mRNA, a preS mRNA, a S mRNA, and a X mRNA. In some embodiments, the second DNA binding domain comprises a CRISPR-Cas protein. In some embodiments, the epigenetic editing system further comprises a second gRNA that comprises a region complementary to a strand of the second target region. In some embodiments, the gRNA comprises a sequence selected from a gRNA sequence provided herein, e.g., a sequence provided in Table 12 or 13. In some embodiments, the second DNA binding domain comprises a zinc-finger protein. In some embodiments, the zinc-finger protein comprises a zinc-finger motif with a sequence selected from a zinc finger motif sequence provided herein, e.g., a zinc finger motif provided in Table 1. In some embodiments, the zinc-finger protein comprises a sequence of a zinc finger motif provided in Table 1. In some embodiments, the epigenetic editing system comprises a first fusion protein or a first nucleic acid encoding thereof and a second fusion protein or a second nucleic acid encoding thereof, wherein the first fusion protein comprises the first DNA binding domain and the first DNMT domain, and wherein the second fusion protein comprises the second DNA binding domain and the transcriptional repressor domain. In some embodiments, the first fusion protein comprises a sequence of a fusion protein provided herein. In some embodiments, the second fusion protein comprises a sequence of a fusion protein provided herein. In some embodiments, the epigenetic editing system further comprises a third DNA binding domain or a nucleic acid encoding thereof, wherein the third DNA binding domain binds to a third target region of the HBV genome. In some embodiments, the third target region is located in a region of the HBV genome within nucleotide 0-303, 1000-2448 or 2802-3182. In some embodiments, the third target region of the HBV genome is located in a CpG island. In some embodiments, the third target region of the HBV genome is located in a promotor. In some embodiments, the third target region of the HBV genome is located in a section of the HBV genome that encodes a transcript selected from the group consisting of a pgRNA, a preCore mRNA, a preS mRNA, a S mRNA, and a X mRNA. In some embodiments, the third DNA binding domain comprises a CRISPR-Cas protein. In some embodiments, the epigenetic editing system further comprises a third gRNA that comprises a region complementary to a strand of the third target region. In some embodiments, the third gRNA comprises a sequence selected from a gRNA sequence provided herein, e.g., of a gRNA sequence provided in Table 12 or 13. In some embodiments, the third DNA binding domain comprises a zinc-finger protein. In some embodiments, the zinc-finger protein comprises a zinc-finger motif with a sequence selected from a zinc finger motif provided herein. In some embodiments, the zinc-finger protein comprises a sequence of a zinc finger motif provided in Table 1. In some embodiments, the epigenetic editing system further comprises a second DNMT domain or a nucleic acid encoding thereof. In some embodiments, the second DNMT domain is a DNMT3A domain or a DNMT3L domain. In some embodiments, the epigenetic editing system comprises a third fusion protein or a nucleic acid encoding thereof, wherein the third fusion protein comprises the third DNA binding domain and the second DNMT domain. In some embodiments, the third fusion protein comprises a sequence of a fusion protein provided herein. In some embodiments, the epigenetic editing system comprises a nucleic acid sequence provided in Table 18. In some embodiments, the reduction of the number of HBV viral episomes, of replication of the HBV gene or genome, or of expression of a protein product encoded by the HBV gene or genome is at least about 20% compared to the number of HBV viral episomes, of replication of the HBV gene or genome, or of expression of a protein product encoded by the HBV gene or genome measured or observed before contacting the HBV genome with the epigenetic editing system, or before administering the epigenetic editing system to the subject. In some embodiments, the reduction of the number of HBV viral episomes, of replication of the HBV gene or genome, or of expression of a protein product encoded by the HBV gene or genome is at least about 25%, at least about 50%, at least about 75%, at least about 80%, at least about 90%, at least about 95%, at least about 99%, at least about 99.5%, at least about 99.8%, at least about 99.9%, at least about 99.95%, at least about 99.99%, or more than 99.99%, compared to the number of HBV viral episomes, of replication of the HBV gene or genome, or of expression of a protein product encoded by the HBV gene or genome measured or observed before contacting the HBV genome with the epigenetic editing system, or before administering the epigenetic editing system to the subject.

Some aspects of this disclosure provide epigenetic editing systems comprising: a fusion protein or a nucleic acid encoding the fusion protein, wherein the fusion protein comprises: (a) a DNA-binding domain that binds a target region of a HBV gene or genome, (b) a first DNA methyltransferase (DNMT) domain, and (c) a transcriptional repressor domain. In some embodiments, the epigenetic editing system is capable of reducing a number of the HBV viral episome, replication of the HBV, or expression of a gene product encoded by the HBV gene or genome, wherein said reduction is at least about 20% compared to contacting the HBV gene or genome with a suitable control. In some embodiments, the HBV genome is a covalently closed circular DNA (cccDNA) or an HBV integrated DNA. In some embodiments, the HBV genome comprises HBV genotype A, HBV genotype B, HBV genotype C, HBV genotype D, HBV genotype E, HBV genotype F, HBV genotype G or HBV genotype H. In some embodiments, the HBV genome comprises a sequence with at least 80% identity to an HBV genome sequence provided herein. In some embodiments, the target region is located in a region of the HBV genome within nucleotide 0-303, 1000-2448 or 2802-3182 of an HBV genome sequence provided herein. In some embodiments, the target region of the HBV genome is located in a CpG island. In some embodiments, the target region of the HBV genome is located in a promotor. In some embodiments, the target region of the HBV genome is located in a section of the HBV genome that encodes a transcript selected from the group consisting of a pgRNA, a preCore mRNA, a preS mRNA, a S mRNA, and a X mRNA. In some embodiments, the DNA binding domain comprises a CRISPR-Cas protein. In some embodiments, the epigenetic editing system further comprises a gRNA that comprises a region complementary to a strand of the target region. In some embodiments, the gRNA comprises a sequence selected from a gRNA sequence provided herein, e.g., in Table 12 or 13. In some embodiments, the DNA binding domain comprises a zinc-finger protein In some embodiments, the zinc-finger protein comprises a zinc-finger motif with a sequence selected from a zinc finger motif provided herein. In some embodiments, the zinc-finger protein comprises a sequence of a zinc finger motif provided in Table 1. In some embodiments, the transcriptional repressor domain comprises a sequence of a transcriptional repressor provided herein. In some embodiments, the first DNMT domain is a DNMT3A domain or a DNMT3L domain. In some embodiments, the DNMT domain comprises a sequence of a DNMT domain provided herein. In some embodiments, the fusion protein further comprises a second DNMT domain. In some embodiments, the second DNMT domain is a DNMT3A domain or a DNMT3L domain. In some embodiments, the fusion protein further comprises a nuclear localization sequence (NLS). In some embodiments, the fusion protein comprises a sequence of a fusion protein provided herein.

Some aspects of the present disclosure provide epigenetic editing systems comprising: a first fusion protein or a nucleic acid encoding the first fusion protein, wherein the first fusion protein comprises a first DNA binding domain and a first DNMT domain, wherein the first DNA binding domain binds a first target region of a HBV genome, and a second fusion protein or a nucleic acid encoding the second fusion protein, wherein the second fusion protein comprises a second DNA binding domain and a transcriptional repressor domain, wherein the second DNA binding domain binds a second target region of the HBV genome. In some embodiments, the epigenetic editing system is capable of reducing a number of the HBV viral episome, replication of the HBV, or expression of a gene product encoded by the HBV genome, wherein said reduction is at least about 20% compared to contacting the HBV genome with a suitable control. In some embodiments, the HBV genome is a covalently closed circular DNA (cccDNA) or an HBV integrated DNA. In some embodiments, the HBV genome comprises HBV genotype A, HBV genotype B, HBV genotype C, HBV genotype D, HBV genotype E, HBV genotype F, HBV genotype G or HBV genotype H In some embodiments, the HBV genome comprises a sequence with at least 80% identity to an HBV genome provided herein. In some embodiments, the epigenetic editing system further comprises a third fusion protein or a nucleic acid encoding the third fusion protein, wherein the third fusion protein comprises a third DNA binding domain and a second DNMT domain, wherein the third DNA binding domain binds a third target region of the HBV genome. In some embodiments, the first target region, the second target region or the third target region is located in a region of the HBV genome within nucleotide 0-303, 1000-2448 or 2802-3182 of an HBV genome provided herein In some embodiments, the first target region, the second target region or the third target region of the HBV genome is located in a CpG island In some embodiments, the first target region, the second target region or the third target region of the HBV genome is located in a promotor In some embodiments, the first target region, the second target region or the third target region of the HBV genome is located in a section of the HBV genome that encodes a transcript selected from the group consisting of a pgRNA, a preCore mRNA, a preS mRNA, a S mRNA, and a X mRNA In some embodiments, the first DNA binding domain, the second DNA binding domain or the third DNA binding domain comprises a CRISPR-Cas protein. In some embodiments, the epigenetic editing system further comprises a first gRNA that comprises a region complementary to a strand of the first target region, a second gRNA that comprises a region complementary to a strand of the second target region or a third RNA that comprises a region complementary to a strand of the third target region. In some embodiments, the first gRNA comprises a sequence selected from a gRNA sequence provided herein, e.g., provided in Table 12 or 13, the second gRNA comprises a sequence selected from a gRNA sequence provided herein, e.g., provided in Table 12 or 13, and/or the third gRNA comprises a sequence selected from a gRNA sequence provided herein, e.g., provided in Table 12 or 13. In some embodiments, the first DNA binding domain, the second DNA binding domain or the third DNA binding domain comprises a zinc-finger protein In some embodiments, the zinc-finger protein comprises a zinc-finger motif with a sequence selected from a zinc finger motif provided herein In some embodiments, the zinc-finger protein comprises a sequence of a zinc finger motif provided in Table 1. In some embodiments, the transcriptional repressor domain comprises ZIM3. In some embodiments, the first DNMT domain is a DNMT3A domain or a DNMT3L domain. In some embodiments, the first DNMT domain comprises a sequence of a DNMT provided herein. In some embodiments, the second DNMT domain is a DNMT3A domain or a DNMT3L domain. In some embodiments, the second DNMT domain comprises a sequence of a DNMT domain provided herein. In some embodiments, the first fusion protein comprises a sequence of a fusion protein provided herein. In some embodiments, the second fusion protein comprises a sequence of a fusion protein provided herein. In some embodiments, the third fusion protein comprises a sequence of a fusion protein provided herein. In some embodiments, the epigenetic editing system comprises a nucleic acid sequence provided in Table 18. In some embodiments, the reduction of the number of HBV viral episomes, of replication of the HBV gene or genome, or of expression of a protein product encoded by the HBV gene or genome is at least about 20% compared to the number of HBV viral episomes, of replication of the HBV gene or genome, or of expression of a protein product encoded by the HBV gene or genome measured or observed before contacting the HBV genome with the epigenetic editing system, or before administering the epigenetic editing system to the subject. In some embodiments, the reduction of the number of HBV viral episomes, of replication of the HBV gene or genome, or of expression of a protein product encoded by the HBV gene or genome is at least about 25%, at least about 50%, at least about 75%, at least about 80%, at least about 90%, at least about 95%, at least about 99%, at least about 99.5%, at least about 99.8%, at least about 99.9%, at least about 99.95%, at least about 99.99%, or more than 99.99%, compared to the number of HBV viral episomes, of replication of the HBV gene or genome, or of expression of a protein product encoded by the HBV gene or genome measured or observed before contacting the HBV genome with the epigenetic editing system, or before administering the epigenetic editing system to the subject.

Some aspects of the present disclosure provide a method of treating an HDV infection in a subject comprising administering an epigenetic editing system to the subject, wherein the epigenetic editing system comprises a first DNA binding domain, a first DNMT domain, and a transcriptional repressor domain or one or more nucleic acid molecules encoding thereof, wherein the first DNA binding domain binds a first target region of a HBV gene or genome, and wherein the contacting results in a reduction of: number of HDV viral episomes, replication of the HDV gene or genome, or expression of a protein product encoded by the HDV gene or genome, wherein said reduction is at least about 20% compared to administering a suitable control. Some aspects of the present disclosure provide a method of inhibiting viral replication in a cell infected with an HDV comprising administering an epigenetic editing system, wherein the epigenetic editing system comprises a first DNA binding domain, a first DNMT domain, and a transcriptional repressor domain or one or more nucleic acid molecules encoding thereof, wherein the first DNA binding domain binds a first target region of a HBV gene or genome, and wherein the epigenetic editing system targets a target region of the HBV gene or genome, and wherein the contacting results in a reduction of number of HDV viral episomes or replication of the HDV gene or genome, wherein said reduction is at least about 20% compared to administering a suitable control. In some embodiments, the first DNA binding domain comprises a CRISPR-Cas protein. In some embodiments, the epigenetic editing system further comprises a first guide RNA (gRNA) that comprises a region complementary to a strand of the first target region. In some embodiments, the gRNA comprises a sequence selected from a gRNA provided herein, e.g., in Table 12 and/or 13. In some embodiments, the first DNA binding domain comprises a zinc-finger protein. In some embodiments, the zinc-finger protein comprises a zinc-finger motif with a sequence selected from any zinc finger or zinc finger motif provided herein, e.g., in Table 1 or Table 18. In some embodiments, the zinc-finger protein comprises a sequence of any of the zinc finger epigenetic repressors provided herein. In some embodiments, the transcriptional repressor domain comprises ZIM3. In some embodiments, the first DNMT domain is a DNMT3A domain or a DNMT3L domain. In some embodiments, the first DNMT domain comprises a sequence of a DNMT domain provided herein. In some embodiments, the epigenetic editing system further comprises a second DNMT domain or a nucleic acid encoding thereof. In some embodiments, the second DNMT domain is a DNMT3A domain or a DNMT3L domain. In some embodiments, the second DNMT domain comprises a sequence of a DNMT domain provided herein. In some embodiments, the epigenetic editing system comprises a fusion protein or a nucleic acid encoding thereof, and wherein the fusion protein comprises the first DNA binding domain, the first DNMT domain, the repressor domain and the second DNMT domain. In some embodiments, the fusion protein further comprises a nuclear localization sequence (NLS). In some embodiments, the fusion protein comprises a sequence of a fusion protein provided herein. In some embodiments, the first DNA binding domain binds a target region of an HBV gene or genome encoding or controlling expression of an S-antigen. In some embodiments, the epigenetic editing system comprises a nucleic acid sequence provided in Table 18. In some embodiments, the reduction of the number of HBV viral episomes, of replication of the HBV gene or genome, or of expression of a protein product encoded by the HBV gene or genome is at least about 20% compared to the number of HBV viral episomes, of replication of the HBV gene or genome, or of expression of a protein product encoded by the HBV gene or genome measured or observed before contacting the HBV genome with the epigenetic editing system, or before administering the epigenetic editing system to the subject. In some embodiments, the reduction of the number of HBV viral episomes, of replication of the HBV gene or genome, or of expression of a protein product encoded by the HBV gene or genome is at least about 25%, at least about 50%, at least about 75%, at least about 80%, at least about 90%, at least about 95%, at least about 99%, at least about 99.5%, at least about 99.8%, at least about 99.9%, at least about 99.95%, at least about 99.99%, or more than 99.99%, compared to the number of HBV viral episomes, of replication of the HBV gene or genome, or of expression of a protein product encoded by the HBV gene or genome measured or observed before contacting the HBV genome with the epigenetic editing system, or before administering the epigenetic editing system to the subject.

Some aspects of this disclosure provide methods comprising administering an epigenetic editing system to a subject characterized by the presence of detectable levels of HBV DNA, HBsAg, and/or HBeAg in the plasma of the subject, for example, a subject having a chronic HBV infection. In some such embodiments, the epigenetic editing system comprises a first DNA binding domain, a first DNMT domain, and a transcriptional repressor domain or one or more nucleic acid molecules encoding the same, wherein the first DNA binding domain binds a first target region of an HBV gene or genome, and the administering results in a reduction of the level of HBV DNA, the level of HBsAg, and/or the level of HBsAg in the plasma of the subject, and the reduction of the level of HBV DNA, of the level of HBsAg, and/or of the level of HBsAg in the plasma of the subject, is at least 90% (a 1-log reduction) compared to the respective level observed or observable in the plasma of the subject prior to the administering, and the 1-log reduction is maintained for at least 14 days after the administering. In some embodiments, the reduction of the level of HBV DNA in the plasma of the subject is at least 90% (a 1-log reduction). In some embodiments, the reduction of the level of HBV DNA in the plasma of the subject is at least 99% (a 2-log reduction). In some embodiments, the reduction of the level of HBsAg in the plasma of the subject is at least 90% (a 1-log reduction). In some embodiments, the reduction of the level of HBsAg in the plasma of the subject is at least 99% (a 2-log reduction). In some embodiments, the reduction of the level of HBeAg in the plasma of the subject is at least 90% (a 1-log reduction). In some embodiments, the reduction of the level of HBeAg in the plasma of the subject is at least 99% (a 2-log reduction). In some embodiments, the reduction is maintained for at least 21 days. In some embodiments, the reduction is maintained for at least 28 days. In some embodiments, the reduction is maintained for at least 35 days. In some embodiments, the reduction is maintained for at least 42 days. In some embodiments, the reduction is maintained for at least 56 days. In some embodiments, the reduction is maintained for at least 70 days. In some embodiments, the reduction is maintained for at least 84 days. In some embodiments, the reduction is maintained for at least 112 days. In some embodiments, the reduction is maintained for at least 140 days. In some embodiments, the reduction is maintained for at least 168 days. In some embodiments, the reduction is maintained for at least 6 months. In some embodiments, the reduction is maintained for at least 9 months. In some embodiments, the reduction is maintained for at least 12 months. In some embodiments, the reduction is maintained for at least 24 months. In some embodiments, the HBV genome comprises HBV genotype A. In some embodiments, the HBV genome comprises HBV genotype B. In some embodiments, the HBV genome comprises HBV genotype C. In some embodiments, the HBV genome comprises, HBV genotype D. In some embodiments, the HBV genome comprises HBV genotype E. In some embodiments, the HBV genome comprises HBV genotype F. In some embodiments, the HBV genome comprises HBV genotype G. In some embodiments, the HBV genome comprises HBV genotype H. In some embodiments, the HBV genome comprises a sequence with at least 80%, at least 90%, at least 95%, at least 99%, or greater than 99% sequence identity to an HBV genome sequence provided herein. In some embodiments, the first target region is located in a region of the HBV genome within nucleotides 0-303 of an HBV genome provided herein. In some embodiments, the first target region is located within nucleotides 0-303 of SEQ ID NO: 1082. In some embodiments, the first target region is located within nucleotides 0-303 of SEQ ID NO: 1083. In some embodiments, the first target region is located in a region of the HBV genome within nucleotides 1000-2448 of an HBV genome provided herein. In some embodiments, the first target region is located within nucleotides 1000-2448 of SEQ ID NO: 1082. In some embodiments, the first target region is located within nucleotides 1000-2448 of SEQ ID NO: 1083. In some embodiments, the first target region is located in a region of the HBV genome within nucleotides 2802-3182 of an HBV genome provided herein. In some embodiments, the first target region is located within nucleotides 2802-3182 of SEQ ID NO: 1082. In some embodiments, the first target region is located within nucleotides 2802-3182 of SEQ ID NO: 1083. In some embodiments, the first target region of the HBV genome is located in an HBV CpG island (CGI). In some embodiments, the CGI is an HBV canonical CGI. In some embodiments, the CGI is canonical CGI-I. In some embodiments, CGI is canonical CGI-I of HBV genotype D. In some embodiments, CGI-I spans nucleotides 186-288 of SEQ ID NO: 1082 In some embodiments, CGI-I spans nucleotides 186-288 of SEQ ID NO: 1083 In some embodiments, the CGI is canonical CGI-II. In some embodiments, the CGI is canonical CGI-II HBV genotype D. In some embodiments, the CGI is CGI II spans nucleotides 1,217-1,670 of SEQ ID NO: 1082. In some embodiments, the CGI is CGI II spans nucleotides 1,217-1,670 of SEQ ID NO: 1083. In some embodiments, the CGI is canonical CGI-III. In some embodiments, the CGI is canonical CGI-III HBV genotype D. In some embodiments, the CGI is CGI-III spans nucleotides 2,282-2,448 of SEQ ID NO: 1082. In some embodiments, the CGI is CGI-III spans nucleotides 2,282-2,448 of SEQ ID NO: 1083. In some embodiments, the first target region of the HBV genome is located in a promotor. In some embodiments, the first target region of the HBV genome is located in the sp1 promoter. In some embodiments, the first target region of the HBV genome is located in sp2 promoter. In some embodiments, the first target region of the HBV genome is located in cp promoter. In some embodiments, the first target region of the HBV genome is located in xp promoter. In some embodiments, the first target region of the HBV genome is located in an enhancer region. In some embodiments, the first target region of the HBV genome is located in Enh I. In some embodiments, the first target region of the HBV genome is located in Enh II. In some embodiments, the first target region of the HBV genome is located in a section of the HBV genome that encodes a transcript. In some embodiments, the first target region of the HBV genome is located in a section of the HBV genome that encodes a pgRNA transcript. In some embodiments, the first target region of the HBV genome is located in a section of the HBV genome that encodes a preCore RNA transcript. In some embodiments, the first target region of the HBV genome is located in a section of the HBV genome that encodes a preS RNA transcript. In some embodiments, the first target region of the HBV genome is located in a section of the HBV genome that encodes an S RNA transcript. In some embodiments, the first target region of the HBV genome is located in a section of the HBV genome that encodes an HBx RNA transcript. In some embodiments, the first target region of the HBV genome is within 1000, 900, 800, 700, 600, 500, 400, 300, 200, or 100 base pairs (bp) of an HBV transcription start site (TSS). In some embodiments, the TSS is a pg RNA TSS. In some embodiments, the first target region is within 600, within 500, within 400, within 300, within 200, or within 100 base pairs of the pg RNA TSS. In some embodiments, the pg RNA TSS is located at nucleotide 1820 of SEQ ID NO: 1082 or at nucleotide 1820 of SEQ ID NO: 1083. In some embodiments, the first target region is within 600 base pairs of nucleotide 1820 in SEQ ID NO: 1082. In some embodiments, the first target region is within 600 base pairs of nucleotide 1820 in SEQ ID NO: 1083. In some embodiments, the first target region is within 500 base pairs of nucleotide 1820 in SEQ ID NO: 1082. In some embodiments, the first target region is within 500 base pairs of nucleotide 1820 in SEQ ID NO: 1083. In some embodiments, the first target region is within 400 base pairs of nucleotide 1820 in SEQ ID NO: 1082. In some embodiments, the first target region is within 400 base pairs of nucleotide 1820 in SEQ ID NO: 1083. In some embodiments, the first target region is within 300 base pairs of nucleotide 1820 in SEQ ID NO: 1082. In some embodiments, the first target region is within 300 base pairs of nucleotide 1820 in SEQ ID NO: 1083. In some embodiments, the first target region is within 200 base pairs of nucleotide 1820 in SEQ ID NO: 1082. In some embodiments, the first target region is within 200 base pairs of nucleotide 1820 in SEQ ID NO: 1083. In some embodiments, the first target region is within 100 base pairs of nucleotide 1820 in SEQ ID NO: 1082. In some embodiments, the first target region is within 100 base pairs of nucleotide 1820 in SEQ ID NO: 1083. In some embodiments, the TSS is a preC RNA TSS. In some embodiments, the first target region is within 600, within 500, within 400, within 300, within 200, or within 100 base pairs of the preC RNA TSS. In some embodiments, the preC RNA TSS is located at nucleotide 1791 of SEQ ID NO: 1082 or at nucleotide 1791 of SEQ ID NO: 1083. In some embodiments, the first target region is within 600 base pairs of nucleotide 1791 in SEQ ID NO: 1082. In some embodiments, the first target region is within 600 base pairs of nucleotide 1791 in SEQ ID NO: 1083. In some embodiments, the first target region is within 500 base pairs of nucleotide 1791 in SEQ ID NO: 1082. In some embodiments, the first target region is within 500 base pairs of nucleotide 1791 in SEQ ID NO: 1083. In some embodiments, the first target region is within 400 base pairs of nucleotide 1791 in SEQ ID NO: 1082. In some embodiments, the first target region is within 400 base pairs of nucleotide 1791 in SEQ ID NO: 1083. In some embodiments, the first target region is within 300 base pairs of nucleotide 1791 in SEQ ID NO: 1082. In some embodiments, the first target region is within 300 base pairs of nucleotide 1791 in SEQ ID NO: 1083. In some embodiments, the first target region is within 200 base pairs of nucleotide 1791 in SEQ ID NO: 1082. In some embodiments, the first target region is within 200 base pairs of nucleotide 1791 in SEQ ID NO: 1083. In some embodiments, the first target region is within 100 base pairs of nucleotide 1791 in SEQ ID NO: 1082. In some embodiments, the first target region is within 100 base pairs of nucleotide 1791 in SEQ ID NO: 1083. In some embodiments, the TSS is a preS2 RNA TSS. In some embodiments, the first target region is within 600, within 500, within 400, within 300, within 200, or within 100 base pairs of the preS2 RNA TSS. In some embodiments, the preS2 RNA TSS is located at nucleotide 3159 of SEQ ID NO: 1082 or at nucleotide 3159 of SEQ ID NO: 1083. In some embodiments, the first target region is within 600 base pairs of nucleotide 3159 in SEQ ID NO: 1082. In some embodiments, the first target region is within 600 base pairs of nucleotide 3159 in SEQ ID NO: 1083. In some embodiments, the first target region is within 500 base pairs of nucleotide 3159 in SEQ ID NO: 1082. In some embodiments, the first target region is within 500 base pairs of nucleotide 3159 in SEQ ID NO: 1083. In some embodiments, the first target region is within 400 base pairs of nucleotide 3159 in SEQ ID NO: 1082. In some embodiments, the first target region is within 400 base pairs of nucleotide 3159 in SEQ ID NO: 1083. In some embodiments, the first target region is within 300 base pairs of nucleotide 3159 in SEQ ID NO: 1082. In some embodiments, the first target region is within 300 base pairs of nucleotide 3159 in SEQ ID NO: 1083. In some embodiments, the first target region is within 200 base pairs of nucleotide 3159 in SEQ ID NO: 1082. In some embodiments, the first target region is within 200 base pairs of nucleotide 3159 in SEQ ID NO: 1083. In some embodiments, the first target region is within 100 base pairs of nucleotide 3159 in SEQ ID NO: 1082. In some embodiments, the first target region is within 100 base pairs of nucleotide 3159 in SEQ ID NO: 1083. In some embodiments, the TSS is an HBx RNA TSSs. In some embodiments, the first target region is within 600, within 500, within 400, within 300, within 200, or within 100 base pairs of the HBx RNA TSS. In some embodiments, the HBx RNA TSS is located at a nucleotide within the sequence of nucleotides 1243-1338 of SEQ ID NO: 1082 or nucleotides 1243-1338 of SEQ ID NO: 1083. In some embodiments, the first target region is within 600 base pairs of nucleotide 1243 in SEQ ID NO: 1082. In some embodiments, the first target region is within 600 base pairs of nucleotide 1243 in SEQ ID NO: 1083. In some embodiments, the first target region is within 500 base pairs of nucleotide 1243 in SEQ ID NO: 1082. In some embodiments, the first target region is within 500 base pairs of nucleotide 1243 in SEQ ID NO: 1083. In some embodiments, the first target region is within 400 base pairs of nucleotide 1243 in SEQ ID NO: 1082. In some embodiments, the first target region is within 400 base pairs of nucleotide 1243 in SEQ ID NO: 1083. In some embodiments, the first target region is within 300 base pairs of nucleotide 1243 in SEQ ID NO: 1082. In some embodiments, the first target region is within 300 base pairs of nucleotide 1243 in SEQ ID NO: 1083. In some embodiments, the first target region is within 200 base pairs of nucleotide 1243 in SEQ ID NO: 1082. In some embodiments, the first target region is within 200 base pairs of nucleotide 1243 in SEQ ID NO: 1083. In some embodiments, the first target region is within 100 base pairs of nucleotide 1243 in SEQ ID NO: 1082. In some embodiments, the first target region is within 100 base pairs of nucleotide 1243 in SEQ ID NO: 1083. In some embodiments, the first target region is within 600 base pairs of nucleotide 1338 in SEQ ID NO: 1083. In some embodiments, the first target region is within 500 base pairs of nucleotide 1338 in SEQ ID NO: 1082. In some embodiments, the first target region is within 500 base pairs of nucleotide 1338 in SEQ ID NO: 1083. In some embodiments, first target region is within 400 base pairs of nucleotide 1338 in SEQ ID NO: 1082. In some embodiments, the first target region is within 400 base pairs of nucleotide 1338 in SEQ ID NO: 1083. In some embodiments, the first target region is within 300 base pairs of nucleotide 1338 in SEQ ID NO: 1082. In some embodiments, the first target region is within 300 base pairs of nucleotide 1338 in SEQ ID NO: 1083. In some embodiments, the first target region is within 200 base pairs of nucleotide 1338 in SEQ ID NO: 1082. In some embodiments, the first target region is within 200 base pairs of nucleotide 1338 in SEQ ID NO: 1083. In some embodiments, the first target region is within 100 base pairs of nucleotide 1338 in SEQ ID NO: 1082. In some embodiments, the first target region is within 100 base pairs of nucleotide 1338 in SEQ ID NO: 1083. In some embodiments, the reduction is a reduction in the number of HBV viral episomes. In some embodiments, the reduction is a reduction in the number of cccDNA genomes. In some embodiments, the reduction is a reduction in total HBV DNA. In some embodiments, the reduction is a reduction in the replication of the HBV genome. In some embodiments, the reduction is a reduction in a level of expression of a protein product encoded by the HBV genome. In some embodiments, the reduction is a reduction in a level of HBsAg. In some embodiments, the reduction is a reduction in a level of HBeAg. In some embodiments, the reduction is a reduction of total HBV DNA of at least 70%, at least 80%, at least 90%, at least 95%, at least 99%, or at least 99.9%, and the reduction is maintained for at least 14 days after the contacting or the administering. In some embodiments, the reduction is a reduction of HBeAg of at least 70%, at least 80%, at least 90%, at least 95%, at least 99%, or at least 99.9%, and the reduction is maintained for at least 14 days after the contacting or the administering. In some embodiments, the reduction is a reduction of HBsAg of at least 70%, at least 80%, at least 90%, at least 95%, at least 99%, or at least 99.9%, and the reduction is maintained at or below that level for at least 14 days after the contacting or the administering. In some embodiments, the reduction is a reduction of at least 90%. In some embodiments, the reduction is a reduction of at least 95%. In some embodiments, the reduction is a reduction of at least 99%. In some embodiments, the reduction is a reduction of at least 99.9%. In some embodiments, the reduction is maintained for at least 14 days after the contacting or the administering. In some embodiments, the reduction is maintained for at least 21 days. In some embodiments, the reduction is maintained for at least 28 days. In some embodiments, the reduction is maintained for at least 35 days. In some embodiments, the reduction is maintained for at least 42 days. In some embodiments, the reduction is maintained for at least 56 days. In some embodiments, the reduction is maintained for at least 70 days. In some embodiments, the reduction is maintained for at least 84 days. In some embodiments, the reduction is maintained for at least 112 days. In some embodiments, the reduction is maintained for at least 140 days. In some embodiments, the reduction is maintained for at least 168 days. In some embodiments, the reduction is maintained for at least 6 months. In some embodiments, the reduction is maintained for at least 7 months. In some embodiments, the reduction is maintained for at least 8 months. In some embodiments, the reduction is maintained for at least 9 months. In some embodiments, the reduction is maintained for at least 12 months. In some embodiments, the reduction is maintained for at least 18 months. In some embodiments, the reduction is maintained for at least 24 months. In some embodiments, the epigenetic editing system is administered as a monotherapy. Accordingly, in some embodiments, the method does not comprise administering a nucleoside or nucleotide analog (NUC) to the subject. In some embodiments, the method further comprises administering a NUC to the subject. In some embodiments, the first DNA binding domain comprises a CRISPR-Cas protein. In some embodiments, the epigenetic editing system further comprises a first guide RNA (gRNA) that comprises a region complementary to a strand of the first target region. In some embodiments, the gRNA comprises a sequence selected from a gRNA provided herein, and preferably the gRNA comprises a sequence provided in Table 12 or 13. In some embodiments, the first DNA binding domain comprises a zinc-finger protein. In some embodiments, the zinc-finger protein comprises a zinc-finger motif with a sequence selected from any zinc finger or zinc finger motif provided herein, e.g., in Table 1 or Table 18. In some embodiments, the zinc-finger protein comprises a sequence of any of the zinc finger epigenetic repressors provided herein. In some embodiments, the transcriptional repressor domain comprises ZIM3. In some embodiments, the first DNMT domain is a DNMT3A domain or a DNMT3L domain. In some embodiments, the first DNMT domain comprises a sequence of a DNMT domain provided herein. In some embodiments, the epigenetic editing system comprises the fusion protein provided in SEQ ID NO: 1248 or the fusion protein provided in SEQ ID NO: 1252 and at least one guide RNA provided as gRNA #003, gRNA #007, gRNA #008, gRNA #009, gRNA #011, or gRNA #015 herein. Some aspects of this disclosure provide epigenetic editing systems for use in the methods described herein. In some embodiments, the epigenetic editing system comprises a fusion protein or a nucleic acid encoding the fusion protein, and the fusion protein comprises: (a) a DNA-binding domain that binds a target region of a HBV gene or genome, (b) a first DNA methyltransferase (DNMT) domain, and (c) a transcriptional repressor domain. In some embodiments, the fusion protein comprises a sequence of a fusion protein provided herein. In some embodiments, the DNA-binding domain is a CRISPR-Cas DNA binding domain, and the epigenetic editing system comprises at least gRNA provided herein. In some embodiments, the epigenetic editing system comprises the fusion protein provided in SEQ ID NO: 1248 or the fusion protein provided in SEQ ID NO: 1252 and at least one guide RNA provided as gRNA #003, gRNA #007, gRNA #008, gRNA #009, gRNA #011, or gRNA #015 herein.

Other features, objectives, and advantages of the invention are apparent in the detailed description that follows. It should be understood, however, that the detailed description, while indicating embodiments and embodiments of the invention, is given by way of illustration only, not limitation. Various changes and modifications within the scope of the invention will become apparent to those skilled in the art from the detailed description.

BRIEF DESCRIPTION OF THE DRAWINGS

FIG. 15 is a diagram describing the design for in vivo experiments testing CRISPR-off single construct epigenetic editor in combination with individual exemplary gRNAs in AAV-HBV mouse HBV genotype D persistent infection model, and transgenic HBV genotype A mouse persistent infection model, respectively.

FIG. 18B shows results for the single-administration (no redosing) groups and controls to 168 days duration for HBV DNA and HBsAg. The lefthand panels shows the group data at each timepoint, whereas the right-hand panels show the readouts for individual animals at two timepoints. EE=epigenetic editor (CRISPR-off with gRNA #011).

in FIG. 23C, N=3, EE1=PLA002 and gRNA #007, EE2=PLA002 and gRNA #008, EE3=PLA002 and gRNA #009, EE4=PLA002 and gRNA #015, and EE5=PLA002 and gRNA #011).

EE1=PLA002 and gRNA #007, EE2=PLA002 and gRNA #008, EE3=PLA002 and gRNA #009, EE4=PLA002 and gRNA #015, and EE5=PLA002 and gRNA #011. Also shown are results for low specificity and host target gene controls. FIGS. 25C-25D are scatter plots showing methylation levels between treatment (y-axis) and control (x-axis) for 935,000 CpG sites in the human genome. Lines represent thresholds for changes in methylation considered significant (absolute [methylation difference]>=0.2). DMRs are noted on each figure. Results for a host target (PCSK9, next-to-final panel) as well as a low specificity control (final panel) are also shown. FIG. 25C shows the results versus effector only; FIG. 25D shows the results versus no treatment. EE1=PLA002 and gRNA #007, EE2=PLA002 and gRNA #008, EE3=PLA002 and gRNA #009, EE4=PLA002 and gRNA #015, EE5=PLA002 and gRNA #011, EE6=PLA002 and gRNA #003, and EE7=PLA002 and gRNA #016.

FIG. 26 is a schematic of an in vivo experiment testing ZF-off constructs.

FIG. 28 is an experimental schematic for an in vivo study of multiplexing ZF fusion protein effectors.

DETAILED DESCRIPTION OF THE INVENTION

Figure 1:
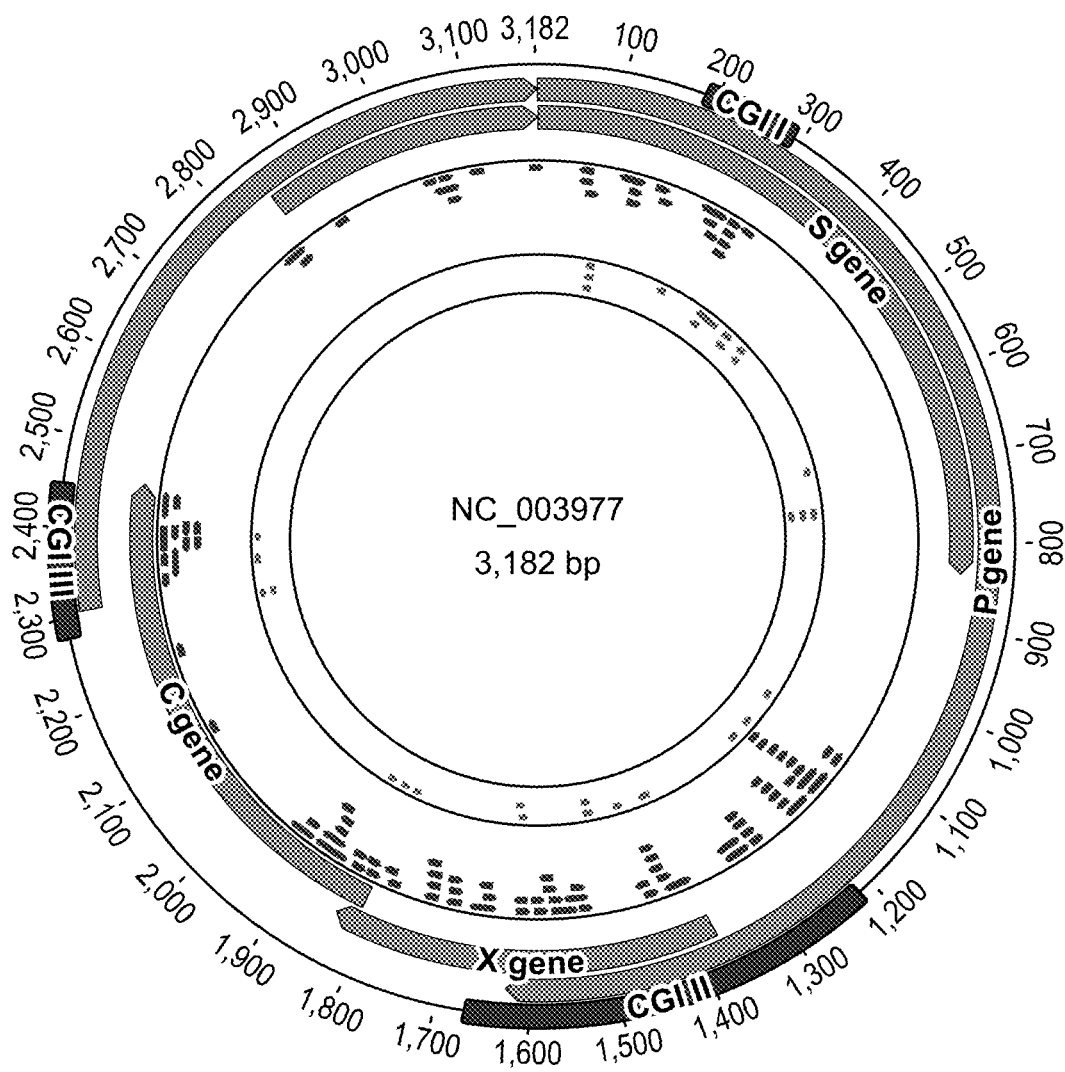
FIG. 1 is a diagram illustrating an exemplary structure of a circular HBV genome. HBV genes and CpG islands are indicated. Exemplary target sites for CRISPR-based epigenetic repressors (red arrows) as well as for zinc-finger-based epigenetic repressors (green arrows) are identified.

The present disclosure provides epigenetic editors, and strategies and methods of using such epigenetic editors, for regulating expression of HBV. By altering expression of HBV, and in particular, by repressing expression of HBV, e.g., of a gene comprised in the HBV genome or a gene product encoded by the HBV genome, the compositions and methods described herein are useful to suppress viral function in infected cells, e.g., in the context of treating an HBV infection in a human subject, or in the context of treating CHB.

The structure and biology of HBV as well as HBV-associated diseases have been reported (see, for example, Yuen, M F., Chen, D S., Dusheiko, G. et al. Hepatitis B virus infection. Nat Rev Dis Primers 4, 18035 (2018), incorporated herein by reference in its entirety).

Exemplary HBV sequences can be found at various NCBI database entries, e.g., representative sequences can be found under accession numbers NC_00397 and U95551, which are incorporated herein by reference in their entirety, and the sequences of which are provided elsewhere herein.

A number of treatment options for HBV has been reported, but there remains a need for effective treatment of HBV infections. Genetic editing approaches targeting HBV genomes for cutting of genomic DNA are associated with a risk of off-target cutting and genomic translocations. The present epigenetic editors and related methods of use have several advantages compared to other genome engineering methods, including increased efficiency, decreased risk of translocation, and durable silencing of HBV.

The present disclosure also provides methods for treating Hepatitis D virus (HDV). HDV is the smallest pathogen known to infect humans. HDV infection is only found in patients infected with HBV, as HDV relies on HBV functions for most of its functions, including viral packaging, infectivity, transmission, and inhibition of host immunity. About 5% of patients with HBV infection also have an HDV infection. HDV uses HBV S-antigen (HBsAg) as a capsid protein, and HDV infection is therefore dependent on HBV S-antigen production. Decreasing HBV S-antigen expression also reduces HDV infectivity. The structure and biology of HDV has been reported (see, for example, Asselah and Rizzetto, Hepatitis D Virus Infection, The New England Journal of Medicine (389; 1; Jul. 6, 2023), incorporated herein by reference in its entirety). In some embodiments of the present disclosure, HDV infection is addressed through methods targeting an HBV gene or genome that reduce the level of HBsAg.

In some embodiments, an epigenetic editor as described herein may comprise one or more fusion proteins, wherein each fusion protein comprises a DNA-binding domain linked to one or more effector domains for epigenetic modification. In certain embodiments, where the DNA-binding domain is a polynucleotide guided DNA-binding domain, the epigenetic editor may further comprise one or more guide polynucleotides. DNA-binding domains, effector domains, and guide polynucleotides of an epigenetic editor as described herein may be selected, e.g., from those described below, in any functional combination.

The epigenetic editors described herein may be expressed in a host cell transiently, or may be integrated in a genome of the host cell; such cells and their progeny are also contemplated by the present disclosure. Both transiently expressed and integrated epigenetic editors or components thereof can effect stable epigenetic modifications. For example, after introducing to a host cell an epigenetic editor described herein, the target gene in the host cell may be stably or permanently repressed or silenced. For example, in some embodiments provided herein, a transiently expressed epigenetic editor comprising a DNMT3A domain, a DNMT3L domain, and a KRAB domain effects stable epigenetic modifications. For example, in some embodiments provided herein, a constitutively expressed epigenetic editor comprising DNMT3A and a DNMT3L domain effects stable epigenetic modifications. In some embodiments, expression of the target gene is reduced or silenced for at least 1 week, at least 2 weeks, at least 3 weeks, at least 4 weeks, at least 5 weeks, at least 6 weeks, at least 7 weeks, at least 2 months, at least 3 months, at least 4 months, at least 5 months, at least 6 months, at least 1 year, at least 2 years, or for the entire lifetime of the cell or the subject carrying the cell, as compared to the level of expression in the absence of the epigenetic editor. The epigenetic modification may be inherited by the progeny of the host cells into which the epigenetic editor was introduced. In some embodiments, the host cell is a liver cell characterized by the presence of an HBV genome in the cell.

The present epigenetic editors may be introduced to a patient in need thereof (e.g., a human patient), e.g., into the patient's hepatocytes, biliary epithelial cells (cholangiocytes), stellate cells, Kupffer cells, and liver sinusoidal endothelial cells.

I. DNA-Binding Domains

An epigenetic editor described herein may comprise one or more DNA-binding domains that direct the effector domain(s) of the epigenetic editor to target sequences within an HBV genome. A DNA-binding domain as described herein may be, e.g., a polynucleotide guided DNA-binding domain, a zinc finger protein (ZFP) domain, a transcription activator like effector (TALE) domain, a meganuclease DNA-binding domain, and the like. Examples of DNA-binding domains can be found in U.S. Pat. No. 11,162,114, which is incorporated by refence herein in its entirety.

In some embodiments, a DNA-binding domain described herein is encoded by its native coding sequence. In other embodiments, the DNA-binding domain is encoded by a nucleotide sequence that has been codon-optimized for optimal expression in human cells.

A. Polynucleotide Guided DNA-Binding Domains

In some embodiments, a DNA-binding domain herein may be a protein domain directed by a guide nucleic acid sequence (e.g., a guide RNA sequence) to a target site in an HBV genome. In certain embodiments, the protein domain may be derived from a CRISPR-associated nuclease, such as a Class I or II CRISPR-associated nuclease. In some embodiments, the protein domain may be derived from a Cas nuclease such as a Type II, Type IIA, Type IIB, Type IIC, Type V, or Type VI Cas nuclease. In certain embodiments, the protein domain may be derived from a Class II Cas nuclease selected from Cas1, Cas1B, Cas2, Cas3, Cas4, Cas5, Cas6, Cas7, Cas8, Cas9, Cas10, Cas14a, Cas14b, Cas14c, CasX, CasY, CasPhi, C2c4, C2c8, C2c9, C2c10, Csy1, Csy2, Csy3, Csel, Csc2, Csc1, Csc2, Csa5, Csn2, Csm2, Csm3, Csm4, Csm5, Csm6, Cmr1, Cmr3, Cmr4, Cmr5, Cmr6, Csb1, Csb2, Csb3, Csx17, Csx14, Csx10, Csx16, CsaX, Csx3, Csx1, Csx1S, Csf1, Csf2, CsO, Csf4, and homologues and modified versions thereof. "Derived from" is used to mean that the protein domain comprises the full polypeptide sequence of the parent protein, or comprises a variant thereof (e.g., with amino acid residue deletions, insertions, and/or substitutions). The variant retains the desired function of the parent protein (e.g., the ability to form a complex with the guide nucleic acid sequence and the target DNA).

In some embodiments, the CRISPR-associated protein domain may be a Cas9 domain described herein. Cas9 may, for example, refer to a polypeptide with at least about 85%, 90%, 91%, 92%, 93%, 94%, 95%, 96%, 97%, 98%, 99%, or 100% sequence identity and/or sequence similarity to a wildtype Cas9 polypeptide described herein. In some embodiments, said wildtype polypeptide is Cas9 from *Streptococcus pyogenes* (NCBI Ref. No. NC_002737.2 (SEQ ID NO: 1)) and/or UniProt Ref. No. Q99ZW2 (SEQ ID NO: 2)). In some embodiments, said wildtype polypeptide is Cas9 from *Staphylococcus aureus* (SEQ ID NO: 3). In some embodiments, the CRISPR-associated protein domain is a Cpf1 domain or protein, or a polypeptide with at least about 85%, 90%, 91%, 92%, 93%, 94%, 95%, 96%, 97%, 98%, 99%, or 100% sequence identity and/or sequence similarity to a wildtype Cpf1 polypeptide described herein (e.g., Cpf1 from *Francisella novicida* (UniProt Ref. No. U2UMQ6 or SEQ ID NO: 4). In certain embodiments, the CRISPR-associated protein domain may be a modified form of the wildtype protein comprising one or more amino acid residue changes such as a deletion, an insertion, or a substitution; a fusion or chimera; or any combination thereof.

Cas9 sequences and structures of variant Cas9 orthologs have been described for various organisms. Exemplary organisms from which a Cas9 domain herein can be derived include, but are not limited to, *Streptococcus pyogenes, Streptococcus thermophilus, Streptococcus sp., Staphylococcus aureus, Listeria innocua, Lactobacillus gasseri, Francisella novicida, Wolinella succinogenes, Sutterella wadsworthensis, Gamma proteobacterium, Neisseria meningitidis, Campylobacter jejuni, Pasteurella multocida, Fibrobacter succinogene, Rhodospirillum rubrum, Nocardiopsis dassonvillei, Streptomyces pristinaespiralis, Streptomyces viridochromogenes, Streptomyces viridochromogenes, Streptosporangium roseum, Alicyclobacillus acidocaldarius, Bacillus pseudomycoides, Bacillus selenitireducens, Exiguobacterium sibiricum, Lactobacillus delbrueckii, Lactobacillus salivarius, Lactobacillus buchneri, Treponema denticola, Microscilla marina, Burkholderiales bacterium, Polaromonas naphthalenivorans, Polaromonas sp., Crocosphaera watsonii, Cyanothece sp., Micro-* *cystis aeruginosa, Synechococcus sp., Acetohalobium arabaticum, Ammonifex degensii, Caldicelulosiruptor becscii, Candidatus Desulforudis, Clostridium botulinum, Clostridium difficile, Finegoldia magna, Natranaerobius thermophilus, Pelotomaculum thermopropionium, Acidithiobacillus caldus, Acidithiobacillus ferrooxidans, Allochromatium vinosum, Marinobacter sp., Nitrosococcus halophilus, Nitrosococcus watsoni, Pseudoalteromonas haloplanktis, Ktedonobacter racemifer, Methanohalobium evestigatum, Anabaena variabilis, Nodularia spumigena, Nostoc sp., Arthrospira maxima, Arthrospira platensis, Arthrospira sp., Lyngbya sp., Microcoleus chthonoplastes, Oscillator ia sp., Petrotoga mobilis, Thermosipho africanus, Streptococcus pasteurianus, Neisseria cinerea, Campylobacter lari, Parvibaculum lavamentivorans, Corynebacterium diphtheria,* and *Acaryochloris marina.* Cas9 sequences also include those from the organisms and loci disclosed in Chylinski et al., *RNA Biol.* (2013) 10 (5): 726-37.

In some embodiments, the Cas9 domain is from *Streptococcus pyogenes.* In some embodiments, the Cas9 domain is from *Staphylococcus aureus.*

Other Cas domains are also contemplated for use in the epigenetic editors herein. These include, for example, those from CasX (Cas12E) (e.g., SEQ ID NO: 5), CasY (Cas12d) (e.g., SEQ ID NO: 6), Casφ (CasPhi) (e.g., SEQ ID NO: 7), Cas12f1 (Cas14a) (e.g., SEQ ID NO: 8), Cas12f2 (Cas14b) (e.g., SEQ ID NO: 9), Cas12f3 (Cas14c) (e.g., SEQ ID NO: 10), and C2c8 (e.g., SEQ ID NO: 11).

For epigenetic editing, the nuclease-derived protein domain (e.g., a Cas9 or Cpf1 domain) may have reduced or no nuclease activity through mutations such that the protein domain does not cleave DNA or has reduced DNA-cleaving activity while retaining the ability to complex with the guide nucleic acid sequence (e.g., guide RNA) and the target DNA. For example, the nuclease activity may be reduced by at least 30%, 35%, 40%, 45%, 50%, 55%, 60%, 65%, 70%, 75%, 80%, 85%, 90%, 95%, or 99% compared to the wildtype domain. In some embodiments, a CRISPR-associated protein domain described herein is catalytically inactive ("dead"). Examples of such domains include, for example, dCas9 ("dead" Cas9), dCpf1, ddCpf1, dCasPhi, ddCas12a, dLbCpf1, and dFnCpf1. A dCas9 protein domain, for example, may comprise one, two, or more mutations as compared to wildtype Cas9 that abrogate its nuclease activity. The DNA cleavage domain of Cas9 is known to include two subdomains: the HNH nuclease subdomain and the RuvC1 subdomain. The HNH subdomain cleaves the strand complementary to the gRNA, whereas the RuvC1 subdomain cleaves the non-complementary strand. Mutations within these subdomains can silence the nuclease activity of Cas9. For example, the mutations D10A (in RuvC1) and H840A (in HNH) completely inactivate the nuclease activity of SpCas9. SaCas9, similarly, may be inactivated by the mutations D10A and N580A. In some embodiments, the dCas9 comprises at least one mutation in the HNH subdomain and/or the RuvC1 subdomain that reduces or abrogates nuclease activity. In some embodiments, the dCas9 only comprises a RuvC1 subdomain, or only comprises an HNH subdomain. It is to be understood that any mutation that inactivates the RuvC1 and/or the HNH domain may be included in a dCas9 herein, e.g., insertion, deletion, or single or multiple amino acid substitution in the RuvC1 domain and/or the HNH domain.

In some embodiments, a dCas9 protein herein comprises a mutation at position(s) corresponding to position D10 (e.g., D10A), H840 (e.g., H840A), or both, of a wildtype SpCas9 sequence as numbered in the sequence provided at UniProt Accession No. Q99ZW2 (SEQ ID NO: 2). In particular embodiments, the dCas9 comprises the amino acid sequence of dSpCas9 (D10A and H840A) (SEQ ID NO: 12).

In some embodiments, a dCas9 protein as described herein comprises a mutation at position(s) corresponding to position D10 (e.g., D10A), N580 (e.g., N580A), or both, of a wildtype SaCas9 sequence (e.g., SEQ ID NO: 9). In particular embodiments, the dCas9 comprises the amino acid sequence of dSaCas9 (D10A and N580A) (SEQ ID NO: 13).

Additional suitable mutations that inactivate Cas9 will be apparent to those of skill in the art based on this disclosure and knowledge in the field and are within the scope of this disclosure. Such mutations may include, but are not limited to, D839A, N863A, and/or K603R in SpCas9. The present disclosure contemplates any mutations that reduce or abrogate the nuclease activity of any Cas9 described herein (e.g., mutations corresponding to any of the Cas9 mutations described herein).

A dCpf1 protein domain may comprise one, two, or more mutations as compared to wildtype Cpf1 that reduce or abrogate its nuclease activity. The Cpf1 protein has a RuvC-like endonuclease domain that is similar to the RuvC domain of Cas9, but does not have an HNH endonuclease domain, and the N-terminal of Cpf1 does not have the alpha-helical recognition lobe of Cas9. In some embodiments, the dCpf1 comprises one or more mutations corresponding to position D917A, E1006A, or D1255A as numbered in the sequence of the *Francisella novicida* Cpf1 protein (FnCpf1; SEQ ID NO: 4). In certain embodiments, the dCpf1 protein comprises mutations corresponding to D917A, E1006A, D1255A, D917A/E1006A, D917A/D1255A, E1006A/D1255A, or D917A/E1006A/D1255A, or corresponding mutation(s) in any of the Cpf1 amino acid sequences described herein. In some embodiments, the dCpf1 comprises a D917A mutation. In particular embodiments, the dCpf1 comprises the amino acid sequence of dFnCpf1 (SEQ ID NO: 14).

Further nuclease inactive CRISPR-associated protein domains contemplated herein include those from, for example, dNmeCas9 (e.g., SEQ ID NO: 15), dCjCas9 (e.g., SEQ ID NO: 16), dSt1Cas9 (e.g., SEQ ID NO: 17), dSt3Cas9 (e.g., SEQ ID NO: 18), dLbCpf1 (e.g., SEQ ID NO: 19), dAsCpf1 (e.g., SEQ ID NO: 20), denAsCpf1 (e.g., SEQ ID NO: 21), dHFAsCpf1 (e.g., SEQ ID NO: 22), dRVRAsCpf1 (e.g., SEQ ID NO: 23), dRRAsCpf1 (e.g., SEQ ID NO: 24), dCasX (e.g., SEQ ID NO: 25), and dCasPhi (e.g., SEQ ID NO: 26).

In some embodiments, a Cas9 domain described herein may be a high fidelity Cas9 domain, e.g., comprising one or more mutations that decrease electrostatic interactions between the Cas9 domain and the sugar-phosphate backbone of DNA to confer increased target binding specificity. In certain embodiments, the high fidelity Cas9 domain may be nuclease inactive as described herein.

A CRISPR-associated protein domain described herein may recognize a protospacer adjacent motif (PAM) sequence in a target gene. A "PAM" sequence is typically a 2 to 6 bp DNA sequence immediately following the sequence targeted by the CRISPR-associated protein domain. The PAM sequence is required for CRISPR protein binding and cleavage but is not part of the target sequence. The CRISPR-associated protein domain may either recognize a naturally occurring or canonical PAM sequence or may have altered PAM specificity. CRISPR-associated protein domains that bind to non-canonical PAM sequences have been described in the art. For example, Cas9 domains that bind non-canonical PAM sequences have been described in Kleinstiver et al., *Nature* (2015) 523 (7561): 481-5 and Kleinstiver et al., *Nat Biotechnol.* (2015) 33:1293-8. Such Cas9 domains may include, for example, those from "VRER (SEQ ID NO: 1261)" SpCas9, "EQR" SpCas9, "VQR" SpCas9, "SpG Cas9," "SpRYCas9," and "KKH" SaCas9. Nuclease inactive versions of these Cas9 domains are also contemplated, such as nuclease inactive VRER (SEQ ID NO: 1261) SpCas9 (e.g., SEQ ID NO: 27), nuclease inactive EQR SpCas9 (e.g., SEQ ID NO: 28), nuclease inactive VQR SpCas9 (e.g., SEQ ID NO: 29), nuclease inactive SpG Cas9 (e.g., SEQ ID NO: 30), nuclease inactive SpRY Cas9 (e.g., SEQ ID NO: 31), and nuclease inactive KKH SaCas9 (e.g., SEQ ID NO: 32). Another example is the Cas9 of *Francisella novicida* engineered to recognize 5'-YG-3' (where "Y" is a pyrimidine).

Additional suitable CRISPR-associated proteins, orthologs, and variants, including nuclease inactive variants and sequences, will be apparent to those of skill in the art based on this disclosure.

Guide RNAs that can be used in conjunction with the CRISPR-associated protein domains herein are further described in Section II below.

B. Zinc Finger Protein Domains

In some embodiments, the DNA-binding domain of an epigenetic editor described herein comprises a zinc finger protein (ZFP) domain (or "ZF domain" as used herein). ZFPs are proteins having at least one zinc finger, and bind to DNA in a sequence-specific manner. A "zinc finger" (ZF) or "zinc finger motif" (ZF motif) refers to a polypeptide domain comprising a beta-beta-alpha ($\beta\beta\alpha$)-protein fold stabilized by a zinc ion. A ZF binds from two to four base pairs of nucleotides, typically three or four base pairs (contiguous or noncontiguous). Each ZF typically comprises approximately 30 amino acids. ZFP domains may contain multiple ZFs that make tandem contacts with their target nucleic acid sequence. A tandem array of ZFs may be engineered to generate artificial ZFPs that bind desired nucleic acid targets. ZFPs may be rationally designed by using databases comprising triplet (or quadruplet) nucleotide sequences and individual ZF amino acid sequences, in which each triplet or quadruplet nucleotide sequence is associated with one or more amino acid sequences of ZFs that bind the particular triplet or quadruplet sequence. See, e.g., U.S. Pat. Nos. 6,453,242, 6,534,261, and 8,772,453.

ZFPs are widespread in eukaryotic cells, and may belong to, e.g., C2H2 class, CCHC class, PHD class, or RING class. An exemplary motif characterizing one class of these proteins (C2H2 class) is -Cys-$(X)_{2-4}$-Cys-$(X)_{12}$-His-$(X)_{3-5}$-His- (SEQ ID NO:1091), where X is any independently chosen amino acid. In some embodiments, a ZFP domain herein may comprise a ZF array comprising sequential C2H2-ZFs each contacting three or more sequential nucleotides. Additional architectures, e.g. as described in Paschon et al., *Nat. Commun.* 10, 1133 (2019), are also possible.

A ZFP domain of an epigenetic editor described herein may include 2, 3, 4, 5, 6, 7, 8, 9, 10, 11, 12, or more ZFs. The ZFP domain may include an array of two-finger or three-finger units, e.g., 3, 4, 5, 6, 7, 8, 9 or 10 or more units, wherein each unit binds a subsite in the target sequence. In some embodiments, a ZFP domain comprising at least three ZFs recognizes a target DNA sequence of 9 or 10 nucleotides. In some embodiments, a ZFP domain comprising at least four ZFs recognizes a target DNA sequence of 12 to 14 nucleotides. In some embodiments, a ZFP domain comprising at least six ZFs recognizes a target DNA sequence of 18 to 21 nucleotides.

In some embodiments, ZFs in a ZFP domain described herein are connected via peptide linkers. The peptide linkers may be, e.g., 2, 3, 4, 5, 6, 7, 8, 9, 10, 11, 12, 13, 14, 15, 16, 17, 18, 19, 20, or more amino acids in length. In some embodiments, a linker comprises 5 or more amino acids. In some embodiments, a linker comprises 7-17 amino acids. The linker may be flexible or rigid.

In some embodiments a zinc finger array may have the sequence:

```
SRPGERPFQCRICMRNFSXXXXXXXXHXXTHTGEKPFQCRICMRNF

SXXXXXXXXHXXTH[linker]FQCRICMRNFSXXXXXXXXHXXTHT

GEKPFQCRICMRNFSXXXXXXXXHXXTH[linker]PFQCRICMRN

FSXXXXXXXXHXXTHTGEKPFQCRICMRNFSXXXXXXXXHXXTHLRG

S (SEQ ID NOs: 1084 and 1258-1259, respectively,
in order of appearance),
``` or a sequence at least 70%, 75%, 80%, 85%, 90%, 95%, 96%, 97%, 98%, or 99% identical thereto, where "XXXXXXX" represents the amino acids of the ZF recognition helix, which confers DNA-binding specificity upon the zinc finger; each X may be independently chosen. In the above sequence, "XX" in italics may be TR, LR or LK, and "[linker]" represents a linker sequence. In some embodiments, the linker sequence is TGSQKP (SEQ ID NO: 1085); this linker may be used when sub-sites targeted by the ZFs are adjacent. In some embodiments, the linker sequence is TGGGGSQKP (SEQ ID NO: 1086); this linker may be used when there is a base between the sub-sites targeted by the zinc fingers. The two indicated linkers may be the same or different.

ZFP domains herein may contain arrays of two or more adjacent ZFs that are directly adjacent to one another (e.g., separated by a short (canonical) linker sequence), or are separated by longer, flexible or structured polypeptide sequences. In some embodiments, directly adjacent fingers bind to contiguous nucleic acid sequences, i.e., to adjacent trinucleotides/triplets. In some embodiments, adjacent fingers cross-bind between each other's respective target triplets, which may help to strengthen or enhance the recognition of the target sequence, and leads to the binding of overlapping sequences. In some embodiments, distant ZFs within the ZFP domain may recognize (or bind to) non-contiguous nucleotide sequences.

The amino acid sequences of the ZF DNA-recognition helices of exemplary ZFP domains herein, and their HBV target sequences, are shown below in Table 1.

TABLE 1

Zinc finger transcriptional repressors for silencing HBV. ZF sequences of exemplary ZFP domains are presented. SEQ ID Nos for target sequences and ZF can be found in Table 18 sequence listing.

| ZFP | SEQ ID | Target Sequence | Start | End | Strd | F1 | F2 | F3 | F4 | F5 | F6 |
|---|---|---|---|---|---|---|---|---|---|---|---|
| ZFP894 | 33 | GATGAGGCAT AGCAGCAG (SEQ ID NO: 102) | 415 | 432 | – | KKEN LLQ (SEQ ID NO: 125) | RQDN LNS (SEQ ID NO: 156) | RSHN LKL (SEQ ID NO: 189) | QSTT LKR (SEQ ID NO: 222) | RNTN LTR (SEQ ID NO: 257) | IKHN LAR (SEQ ID NO: 297) |
| ZFP895 | 34 | GATGAGGCAT AGCAGCAG (SEQ ID NO: 102) | 415 | 432 | – | KKEN LLQ (SEQ ID NO: 125) | RKDY LIS (SEQ ID NO: 157) | RSHN LKL (SEQ ID NO: 189) | QSTT LKR (SEQ ID NO: 222) | RQDN LGR (SEQ ID NO: 258) | VVNN LNR (SEQ ID NO: 298) |
| ZFP896 | 35 | GATGAGGCAT AGCAGCAG (SEQ ID NO: 102) | 415 | 432 | – | KKEN LLQ (SEQ ID NO: 125) | RKDY LIS (SEQ ID NO: 157) | RSHN LRL (SEQ ID NO: 190) | QSTT LKR (SEQ ID NO: 222) | RQDN LGR (SEQ ID NO: 258) | VVNN LNR (SEQ ID NO: 298) |
| ZFP899 | 36 | GATGATTAGG CAGAGGTG (SEQ ID NO: 103) | 1828 | 1845 | – | RRHI LDR (SEQ ID NO: 126) | RQDN LGR (SEQ ID NO: 158) | QSTT LKR (SEQ ID NO: 191) | RRDG LAG (SEQ ID NO: 223) | VHHN LVR (SEQ ID NO: 259) | ISHN LAR (SEQ ID NO: 299) |
| ZFP900 | 37 | GATGATTAGG CAGAGGTG (SEQ ID NO: 103) | 1828 | 1845 | – | RREV LEN (SEQ ID NO: 127) | RRDN LNR (SEQ ID NO: 159) | QSTT LKR (SEQ ID NO: 191) | RRDG LAG (SEQ ID NO: 223) | VHHN LVR (SEQ ID NO: 259) | ISHN LAR (SEQ ID NO: 299) |

TABLE 1-continued

Zinc finger transcriptional repressors for silencing HBV. ZF sequences of
exemplary ZFP domains are presented. SEQ ID Nos for target sequences and
ZF can be found in Table 18 sequence listing.

| ZFP | SEQ ID | Target Sequence | Start | End | Strd | F1 | F2 | F3 | F4 | F5 | F6 |
|---|---|---|---|---|---|---|---|---|---|---|---|
| ZFP901 | 38 | GATGATTAGG CAGAGGTG (SEQ ID NO: 103) | 1828 | 1845 | – | RRAV LDR (SEQ ID NO: 128) | RQDN LGR (SEQ ID NO: 158) | QSTT LKR (SEQ ID NO: 191) | RRDG LAG (SEQ ID NO: 223) | VHHN LVR (SEQ ID NO: 259) | ISHN LAR (SEQ ID NO: 299) |
| ZFP902 | 39 | GGATTCAGCG CCGACGGG (SEQ ID NO: 104) | 1433 | 1450 | – | RQEH LVR (SEQ ID NO: 129) | EGGN LMR (SEQ ID NO: 160) | SDRR DLD (SEQ ID NO: 192) | SFQS YLE (SEQ ID NO: 224) | RPNH LAI (SEQ ID NO: 260) | QS PH LKR (SEQ ID NO: 300) |
| ZFP903 | 40 | GGATTCAGCG CCGACGGG (SEQ ID NO: 104) | 1433 | 1450 | – | RREH LVR (SEQ ID NO: 130) | DPSN LQR (SEQ ID NO: 161) | SDRR DLD (SEQ ID NO: 192) | SFQS YLE (SEQ ID NO: 224) | RPNH LAI (SEQ ID NO: 260) | QS PH LKR (SEQ ID NO: 300) |
| ZFP904 | 41 | GGATTCAGCG CCGACGGG (SEQ ID NO: 104) | 1433 | 1450 | – | RREH LVR (SEQ ID NO: 130) | DMGN LGR (SEQ ID NO: 162) | SDRR DLD (SEQ ID NO: 192) | SFQS YLE (SEQ ID NO: 224) | RPNH LAI (SEQ ID NO: 260) | QS PH LKR (SEQ ID NO: 300) |
| ZFP907 | 42 | GGCAGTAGTC GGAACAGGG (SEQ ID NO: 105) | 90 | 108 | – | KKDH LHR (SEQ ID NO: 131) | QKEI LTR (SEQ ID NO: 163) | QSAH LKR (SEQ ID NO: 193) | ETGS LRR (SEQ ID NO: 225) | QSHS LKS (SEQ ID NO: 261) | ESGH LKR ( SEQ ID NO: 301) |
| ZFP908 | 43 | GGCAGTAGTC GGAACAGGG (SEQ ID NO: 105) | 90 | 108 | – | KKDH LHR (SEQ ID NO: 131) | QKEI LTR (SEQ ID NO: 163) | QSAH LKR (SEQ ID NO: 193) | DRTP LNR (SEQ ID NO: 226) | QSHS LKS (SEQ ID NO: 261) | ESGH LKR (SEQ ID NO: 301) |
| ZFP909 | 44 | GGCAGTAGTC GGAACAGGG (SEQ ID NO: 105) | 90 | 108 | – | KTDH LAR (SEQ ID 132) (SEQ ID NO: 132) | QKEI LTR (SEQ ID NO: 163) | QSAH LKR (SEQ ID NO: 193) | ETGS LRR (SEQ ID 225) (SEQ ID NO: 225) | QKHH LVT (SEQ ID NO: 262) | ENSK LRR (SEQ ID NO: 302) |
| ZFP912 | 45 | GTAAACTGAG CCAGGAGAA (SEQ ID NO: 106) | 664 | 682 | – | QAGN LVR (SEQ ID NO: 133) | QNSH LRR SEQ ID NO: 164) | DLST LRR (SEQ ID NO: 194) | QNEH LKV (SEQ ID NO: 227) | GGTA LRM (SEQ ID NO: 263) | QRSS LVR (SEQ ID NO: 303) |
| ZFP913 | 46 | GTAAACTGAG CCAGGAGAA (SEQ ID NO: 106) | 664 | 682 | – | QRGN LQR (SEQ ID NO: 134) | QTTH LSR (SEQ ID NO: 165) | DGST LRR (SEQ ID NO: 195) | QKTH LAV (SEQ ID NO: 228) | GGTA LRM (SEQ ID NO: 263) | QRSS LVR (SEQ ID NO: 303) |
| ZFP914 | 47 | GTAAACTGAG CCAGGAGAA (SEQ ID NO: 106) | 664 | 682 | – | QRGN LQR (SEQ ID NO: 134) | QTTH LSR (SEQ ID NO: 165) | DLST LRR (SEQ ID NO: 194) | QNEH LKV (SEQ ID NO: 227) | GGSA LSM (SEQ ID NO: 264) | QRSS LVR (SEQ ID NO: 303) |

TABLE 1-continued

Zinc finger transcriptional repressors for silencing HBV. ZF sequences of
exemplary ZFP domains are presented. SEQ ID Nos for target sequences and
ZF can be found in Table 18 sequence listing.

| ZFP | SEQ ID | Target Sequence | Start | End | Strd | F1 | F2 | F3 | F4 | F5 | F6 |
|---|---|---|---|---|---|---|---|---|---|---|---|
| ZFP930 | 48 | ACGGTGGTCT CCATGCGAC (SEQ ID NO: 107) | 1605 | 1623 | − | DRGN LTR (SEQ ID NO: 135) | QARS LRA (SEQ ID NO: 166) | EKAS LIK (SEQ ID NO: 196) | DHSS LKR (SEQ ID NO: 229) | RRFI LSR (SEQ ID NO: 265) | RNDS LKC (SEQ ID NO: 304) |
| ZFP931 | 49 | ACGGTGGTCT CCATGCGAC (SEQ ID NO: 107) | 1605 | 1623 | − | DRGN LTR (SEQ ID NO: 135) | QARS LRA (SEQ ID NO: 166) | DKSS LRK (SEQ ID NO: 197) | DHSS LKR (SEQ ID NO: 229) | RNFI LQR (SEQ ID NO: 266) | RNDT LII (SEQ ID NO: 305) |
| ZFP932 | 50 | ACGGTGGTCT CCATGCGAC (SEQ ID NO: 107) | 1605 | 1623 | − | DRGN LTR (SEQ ID NO: 135) | QARS LRA (SEQ ID NO: 166) | CNGS LKK (SEQ ID NO: 198) | DHSS LKR (SEQ ID NO: 229) | RNFI LQR (SEQ ID NO: 266) | RNDT LII (SEQ ID NO: 305) |
| ZFP933 | 51 | GCTGGATGTG TCTGCGGCG (SEQ ID NO: 108) | 372 | 393 | + | RTDT LAR (SEQ ID NO: 136) | RTDS LPR (SEQ ID NO: 167) | DHSS LKR (SEQ ID NO: 199) | QPHG LAH (SEQ ID NO: 230) | QSAH LKR (SEQ ID NO: 267) | VGNS LSR (SEQ ID NO: 306) |
| ZFP934 | 52 | GCTGGATGTG TCTGCGGCG (SEQ ID NO: 108) | 372 | 393 | + | RTDT LAR (SEQ ID NO: 136) | RTDS LPR (SEQ ID NO: 167) | DHSS LKR (SEQ ID NO: 199) | QPHG LRH (SEQ ID NO: 231) | QSAH LKR (SEQ ID NO: 267) | VGNS LSR (SEQ ID NO: 306) |
| ZFP935 | 53 | GCTGGATGTG TCTGCGGCG (SEQ ID NO: 108) | 372 | 393 | + | RTDT LAR (SEQ ID NO: 136) | RLDM LAR (SEQ ID NO: 168) | DHSS LKR (SEQ ID NO: 199) | QPHG LST (SEQ ID NO: 232) | QQAH LVR (SEQ ID NO: 268) | VHES LKR (SEQ ID NO: 307) |
| ZFP938 | 54 | GTCTGCGAGG CGAGGGAG (SEQ ID NO: 109) | 2381 | 2398 | − | RADN LGR (SEQ ID NO: 137) | RNTH LSY (SEQ ID NO: 169) | RGDG LRR (SEQ ID NO: 200) | RRDN LNR (SEQ ID NO: 233) | RARN LTL (SEQ ID NO: 269) | DPSS LKR (SEQ ID NO: 308) |
| ZFP939 | 55 | GTCTGCGAGG CGAGGGAG (SEQ ID NO: 109) | 2381 | 2398 | − | RADN LGR (SEQ ID NO: 137) | RNTH LSY (SEQ ID NO: 169) | RKLG LLR (SEQ ID NO: 201) | RQDN LGR (SEQ ID NO: 234) | RARN LTL (SEQ ID NO: 269) | DPSS LKR (SEQ ID NO: 308) |
| ZFP940 | 56 | GTCTGCGAGG CGAGGGAG (SEQ ID NO: 109) | 2381 | 2398 | − | RADN LGR (SEQ ID NO: 137) | RNTH LSY (SEQ ID NO: 169) | RKLG LLR (SEQ ID NO: 201) | RQDN LGR (SEQ ID NO: 234) | RRRN LQL (SEQ ID NO: 270) | DHSS LKR (SEQ ID NO: 309) |
| ZFP943 | 57 | GTTGCCGGGC AACGGGGTA (SEQ ID NO: 110) | 1146 | 1164 | − | QQSS LLR (SEQ ID NO: 138) | RREH LVR (SEQ ID NO: 170) | GLTA LRT (SEQ ID NO: 202) | ERAK LIR (SEQ ID NO: 235) | AKRD LDR (SEQ ID NO: 271) | VNSS LTR (SEQ ID NO: 310) |

TABLE 1-continued

Zinc finger transcriptional repressors for silencing HBV. ZF sequences of
exemplary ZFP domains are presented. SEQ ID Nos for target sequences and
ZF can be found in Table 18 sequence listing.

| ZFP | SEQ ID | Target Sequence | Start | End | Strd | F1 | F2 | F3 | F4 | F5 | F6 |
|---|---|---|---|---|---|---|---|---|---|---|---|
| ZFP944 | 58 | GTTGCCGGGC AACGGGGTA (SEQ ID NO: 110) | 1146 | 1164 | – | QQSS LLR (SEQ ID NO: 138) | RREH LVR (SEQ ID NO: 170) | GLTA LRT (SEQ ID NO: 202) | ERAK LIR (SEQ ID NO: 235) | LRKD LVR (SEQ ID NO: 272) | VRHS LTR (SEQ ID NO: 311) |
| ZFP945 | 59 | GTTGCCGGGC AACGGGGTA (SEQ ID NO: 110) | 1146 | 1164 | – | QASA LSR (SEQ ID NO: 139) | RREH LVR (SEQ ID NO: 170) | GLTA LRT (SEQ ID NO: 202) | ERAK LIR (SEQ ID NO: 235) | AKRD LDR (SEQ ID NO: 271) | VNSS LTR (SEQ ID NO: 310) |
| ZFP951 | 60 | CGAGAAAGTG AAAGCCTGC (SEQ ID NO: 111) | 1085 | 1103 | – | RGRN LEM (SEQ ID NO: 140) | DSSV LRR (SEQ ID NO: 171) | QNAN LKR (SEQ ID NO: 203) | QKHH LAV (SEQ ID NO: 236) | QRSN LAR (SEQ ID NO: 273) | QKVH LEA (SEQ ID NO: 312) |
| ZFP952 | 61 | CGAGAAAGTG AAAGCCTGC (SEQ ID NO: 111) | 1085 | 1103 | – | RRRN LDV (SEQ ID NO: 141) | DSSV LRR (SEQ ID NO: 171) | QNAN LKR (SEQ ID NO: 203) | QKHH LAV (SEQ ID NO: 236) | QRSN LAR (SEQ ID NO: 273) | QKVH LEA (SEQ ID NO: 312) |
| ZFP953 | 62 | CGAGAAAGTG AAAGCCTGC (SEQ ID NO: 111) | 1085 | 1103 | – | RGRN LAI (SEQ ID NO: 142) | DSSV LRR (SEQ ID NO: 171) | LKSN LHR (SEQ ID NO: 204) | LKQH LVV (SEQ ID NO: 237) | LKTN LAR (SEQ ID NO: 274) | QKCH LKA SEQ ID NO: 313) |
| ZFP956 | 63 | GAGGCTTGAA CAGTAGGAC (SEQ ID NO: 112) | 1856 | 1874 | – | DGSN LRR (SEQ ID NO: 143) | RIDN LDG (SEQ ID NO: 172) | QRRY LVE (SEQ ID NO: 205) | QQTN LAR (SEQ ID NO: 238) | QRSD LTR (SEQ ID NO: 275) | RGDN LNR (SEQ ID NO: 314) |
| ZFP957 | 64 | GAGGCTTGAA CAGTAGGAC (SEQ ID NO: 112) | 1856 | 1874 | – | DPSN LQR (SEQ ID NO: 144) | RRDN LPK (SEQ ID NO: 173) | TTFN LRV (SEQ ID NO: 206) | QTQN LTR (SEQ ID NO: 239) | HKET LNR (SEQ ID NO: 276) | REDN LGR (SEQ ID NO: 315) |
| ZFP958 | 65 | GAGGCTTGAA CAGTAGGAC (SEQ ID NO: 112) | 1856 | 1874 | – | DPSN LQR (SEQ ID NO: 144) | RRDN LPK (SEQ ID NO: 173) | QRRY LVE (SEQ ID NO: 205) | QQTN LAR (SEQ ID NO: 238) | QRSD LTR (SEQ ID NO: 275) | RGDN LNR (SEQ ID NO: 314) |
| ZFP961 | 66 | GAGGTTGGGG ACTGCGAA (SEQ ID NO: 113) | 312 | 329 | – | QQTN LTR (SEQ ID NO: 145) | ANRT LVH (SEQ ID NO: 174) | EEAN LRR (SEQ ID NO: 207) | RGEH LTR (SEQ ID NO: 240) | TNSS LTR (SEQ ID NO: 277) | RIDN LIR (SEQ ID NO: 316) |
| ZFP962 | 67 | GAGGTTGGGG ACTGCGAA (SEQ ID NO: 113) | 312 | 329 | – | QQTN LTR (SEQ ID NO: 145) | ANRT LVH (SEQ ID NO: 174) | EEAN LRR (SEQ ID NO: 207) | RREH LVR (SEQ ID NO: 241) | MTSS LRR (SEQ ID NO: 278) | RQDN LGR (SEQ ID NO: 317) |
| ZFP963 | 68 | GAGGTTGGGG ACTGCGAA (SEQ ID | 312 | 329 | – | QQTN LTR (SEQ | ANRT LVH (SEQ | EEAN LRR (SEQ | RGEH LTR (SEQ | MTSS LRR (SEQ | RQDN LGR (SEQ |

TABLE 1-continued

Zinc finger transcriptional repressors for silencing HBV. ZF sequences of
exemplary ZFP domains are presented. SEQ ID Nos for target sequences and
ZF can be found in Table 18 sequence listing.

| ZFP | SEQ ID | Target Sequence | Start | End | Strd | F1 | F2 | F3 | F4 | F5 | F6 |
|---|---|---|---|---|---|---|---|---|---|---|---|
| | | NO: 113) | | | | ID NO: 145) | ID NO: 174) | ID NO: 207) | ID NO: 240) | ID NO: 278) | ID NO: 317) |
| ZFP964 | 69 | GATGATGTGG TATTGGGG (SEQ ID NO: 114) | 742 | 762 | + | RATH LTR (SEQ ID NO: 146) | RADV LKG (SEQ ID NO: 175) | QRSS LVR (SEQ ID NO: 208) | RKDA LHV (SEQ ID NO: 242) | VHHN LVR (SEQ ID NO: 259) | ISHN LAR (SEQ ID NO: 299) |
| ZFP965 | 70 | GATGATGTGG TATTGGGG (SEQ ID NO: 114) | 742 | 762 | + | RATH LTR (SEQ ID NO: 146) | RADV LKG (SEQ ID NO: 175) | QSSS LVR (SEQ ID NO: 209) | RKER LAT (SEQ ID NO: 243) | VRHN LTR (SEQ ID NO: 279) | ISHN LAR (SEQ ID NO: 299) |
| ZFP966 | 71 | GATGATGTGG TATTGGGG (SEQ ID NO: 114) | 742 | 762 | + | KKDH LHR (SEQ ID NO: 131) | RKES LTV (SEQ ID NO: 176) | QSSS LVR (SEQ ID NO: 209) | RKER LAT (SEQ ID NO: 243) | VHHN LVR (SEQ ID NO: 259) | ISHN LAR (SEQ ID NO: 299) |
| ZFP969 | 72 | GATGATGTGG TATTGGGGG (SEQ ID NO: 115) | 742 | 763 | + | RVDH LHR (SEQ ID NO: 147) | RREH LSG (SEQ ID NO: 177) | QSSS LVR (SEQ ID NO: 209) | RKER LAT (SEQ ID NO: 243) | VAHN LTR (SEQ ID NO: 280) | ISHN LAR (SEQ ID NO: 299) |
| ZFP970 | 73 | GATGATGTGG TATTGGGGG (SEQ ID NO: 115) | 742 | 763 | + | RKHH LGR (SEQ ID NO: 148) | RREH LTI (SEQ ID NO: 178) | QSSS LVR (SEQ ID NO: 209) | RKER LAT (SEQ ID NO: 243) | VAHN LTR (SEQ ID NO: 280) | ISHN LAR (SEQ ID NO: 299) |
| ZFP971 | 74 | GATGATGTGG TATTGGGGG (SEQ ID NO: 115) | 742 | 763 | + | RVDH LHR (SEQ ID NO: 147) | RS DH LSL (SEQ ID NO: 179) | QSSS LVR (SEQ ID NO: 209) | RKER LAT (SEQ ID NO: 243) | VAHN LTR (SEQ ID NO: 280) | ISHN LAR (SEQ ID NO: 299) |
| ZFP984 | 75 | GCAGTAGTCG GAACAGGG (SEQ ID NO: 116) | 90 | 107 | − | KTDH LAR (SEQ ID NO: 132) | QKEI LTR (SEQ ID NO: 163) | QSAH LKR (SEQ ID NO: 193) | ETGS LRR (SEQ ID NO: 225) | QSSS LVR (SEQ ID NO: 281) | QTNT LGR (SEç ID NO: 318) |
| ZFP985 | 76 | GCAGTAGTCG GAACAGGG (SEQ ID NO: 116) | 90 | 107 | − | KKDH LHR (SEQ ID NO: 131) | QKEI LTR (SEQ ID NO: 163) | QSAH LKR (SEQ ID NO: 193) | ETGS LRR (SEQ ID NO: 225) | QSSS LVR (SEQ ID NO: 281) | QGGT LRR (SEQ ID NO: 319) |
| ZFP986 | 77 | GCAGTAGTCG GAACAGGG (SEQ ID NO: 116) | 90 | 107 | − | KKDH LHR (SEQ ID NO: 131) NO: 131) | QKEI LTR (SEQ ID 163) NO: 163) | QSAH LKR (SEQ ID 193) NO: 193) | DPTS LNR (SEQ ID 244) NO: 244) | QSSS LVR (SEQ ID 281) NO: 281) | QTNT LGR (SEQ ID 318) NO: 318) |

TABLE 1-continued

Zinc finger transcriptional repressors for silencing HBV. ZF sequences of
exemplary ZFP domains are presented. SEQ ID Nos for target sequences and
ZF can be found in Table 18 sequence listing.

| ZFP | SEQ ID | Target Sequence | Start | End | Strd | F1 | F2 | F3 | F4 | F5 | F6 |
|---|---|---|---|---|---|---|---|---|---|---|---|
| ZFP989 | 78 | GCATAGCAGC AGGATGAA (SEQ ID NO: 117) | 409 | 426 | − | QQTN LTR (SEQ ID NO: 145) | VGGN LAR (SEQ ID NO: 180) | KRYN LYQ (SEQ ID NO: 210) | RQDN LNT (SEQ ID NO: 245) | RSHN LKL (SEQ ID NO: 283) | QSTT LKR (SEQ ID NO: 320) |
| ZFP990 | 79 | GCATAGCAGC AGGATGAA (SEQ ID NO: 117) | 409 | 426 | − | QQTN LTR (SEQ ID NO: 145) | VGGN LSR (SEQ ID NO: 181) | KRYN LYQ (SEQ ID NO: 210) | RQDN LNT (SEQ ID NO: 245) | RSHN LRL (SEQ ID NO: 283) | QSTT LKR (SEQ ID NO: 320) |
| ZFP991 | 80 | GCATAGCAGC AGGATGAA (SEQ ID NO: 117) | 409 | 426 | − | QQTN LTR (SEQ ID NO: 145) | VGGN LSR (SEQ ID NO: 181) | KKEN LLQ (SEQ ID NO: 211) | RRDN LKS (SEQ ID NO: 246) | RSHN LKL (SEQ ID NO: 282) | QSTT LKR (SEQ ID NO: 320) |
| ZFP994 | 81 | GGCGTTCACG GTGGTCTCC (SEQ ID NO: 118) | 1612 | 1630 | − | DKSS LRK (SEQ ID NO: 149) | DHSS LKR (SEQ ID NO: 182) | RNFI LQR (SEQ ID NO: 212) | RNDT LII (SEQ ID NO: 247) | TSTL LKR (SEQ ID NO: 284) | LKEH LTR (SEQ ID NO: 321) |
| ZFP995 | 82 | GGCGTTCACG GTGGTCTCC (SEQ ID NO: 118) | 1612 | 1630 | − | CNGS LKK (SEQ ID NO: 150) | DHSS LKR (SEQ ID NO: 182) | RNFI LAR (SEQ ID NO: 213) | RQDI LVV (SEQ ID NO: 248) | HKSS LTR (SEQ ID NO: 285) | ESGH LKR (SEQ ID NO: 301) |
| ZFP996 | 83 | GGCGTTCACG GTGGTCTCC (SEQ ID NO: 118) | 1612 | 1630 | − | CNGS LKK (SEQ ID NO: 150) | DHSS LKR (SEQ ID NO: 182) | RNFI LAR (SEQ ID NO: 213) | RQDI LVV (SEQ ID NO: 248) | TSTL LKR (SEQ ID NO: 284) | LKEH LTR (SEQ ID NO: 321) |
| ZFP999 | 84 | GTTGGTGAGT GATTGGAG (SEQ ID NO: 119) | 327 | 344 | − | TNNN LAR (SEQ ID NO: 151) | RTDS LTL (SEQ ID NO: 183) | QREH LTT (SEQ ID NO: 214) | RRDN LNR (SEQ ID NO: 233) | RRQK LTI (SEQ ID NO: 286) | HKSS LTR (SEQ ID NO: 322) |
| ZFP1000 | 85 | GTTGGTGAGT GATTGGAG (SEQ ID NO: 119) | 327 | 344 | − | TNNN LAR (SEQ ID NO: 151) | RTDS LTL (SEQ ID NO: 183) | QREH LTT (SEQ ID NO: 214) | RGDN LKR (SEQ ID NO: 249) | RRQK LTI (SEQ ID NO: 286) | HKSS LTR (SEQ ID NO: 322) |
| ZFP1001 | 86 | GTTGGTGAGT GATTGGAG (SEQ ID NO: 119) | 327 | 344 | − | TNNN LAR (SEQ ID NO: 151) | RTDS LTL (SEQ ID NO: 183) | QREH LNG (SEQ ID NO: 215) | RGDN LAR (SEQ ID NO: 250) | RRQK LTI (SEQ ID NO: 286) | HKSS LTR (SEQ ID NO: 322) |
| ZFP1005 | 87 | GGAGGTTGGG GACTGCGAA (SEQ ID NO: 120) | 312 | 330 | − | QQTN LTR (SEQ ID NO: 145) | ANRT LVH (SEQ ID NO: 174) | DPAN LRR (SEQ ID NO: 216) | RQEH LVR (SEQ ID NO: 251) | MKHH LGR (SEQ ID NO: 287) | QNSH LRR SEQ ID NO: 323) |
| ZFP1006 | 88 | GGAGGTTGGG GACTGCGAA (SEQ ID | 312 | 330 | − | QQTN LTR (SEQ | ANRT LVH (SEQ | EEAN LRR (SEQ | RREH LVR (SEQ | MKHH LGR (SEQ | QNSH LRR (SEQ |

TABLE 1-continued

Zinc finger transcriptional repressors for silencing HBV. ZF sequences of
exemplary ZFP domains are presented. SEQ ID Nos for target sequences and
ZF can be found in Table 18 sequence listing.

| ZFP | SEQ ID | Target Sequence | Start | End | Strd | F1 | F2 | F3 | F4 | F5 | F6 |
|-----|--------|-----------------|-------|-----|------|----|----|----|----|----|----|
| | | NO: 120) | | | | ID NO: 145) | ID NO: 174) | ID NO: 207) | ID NO: 241) | ID NO: 287) | ID NO: 323) |
| ZFP1007 | 89 | GGAGGTTGGG GACTGCGAA (SEQ ID NO: 120) | 312 | 330 | – | QQTN LTR (SEQ ID NO: 145) | ANRT LVH (SEQ ID NO: 174) | DPAN LRR (SEQ ID NO: 216) | RQEH LVR (SEQ ID NO: 251) | LKQH LVR (SEQ ID NO: 288) | QGGH LAR (SEQ ID NO: 324) |
| ZFP1008 | 90 | GGATGATGTG GTATTGGGG (SEQ ID NO: 121) | 741 | 762 | + | RNTH LAR (SEQ ID NO: 152) | RADV LKG (SEQ ID NO: 175) | QRSS LVR (SEQ ID NO: 208) | RKDA LHV (SEQ ID NO: 242) | QNEH LKV (SEQ ID NO: 289) | QNSH LRR (SEQ ID NO: 323) |
| ZFP1009 | 91 | GGATGATGTG GTATTGGGG (SEQ ID NO: 121) | 741 | 762 | + | RNTH LAR (SEQ ID NO: 152) | RADV LKG (SEQ ID NO: 175) | QSSS LVR (SEQ ID NO: 209) | RKER LAT (SEQ ID NO: 243) | QKTH LAV (SEQ ID NO: 290) | QGGH LKR (SEQ ID NO: 325) |
| ZFP1010 | 92 | GGATGATGTG GTATTGGGG (SEQ ID NO: 121) | 741 | 762 | + | RNTH LAR (SEQ ID NO: 152) | RADV LKG (SEQ ID NO: 175) | QSSS LVR (SEQ ID NO: 209) | RKER LAT (SEQ ID NO: 243) | QKTH LAV (SEQ ID NO: 290) | QNSH LRR (SEQ ID NO: 323) |
| ZFP1013 | 93 | GGATGTGTCT GCGGCGTT (SEQ ID NO: 122) | 375 | 395 | + | HKSS LTR (SEQ ID NO: 153) | ESGH LKR (SEQ ID NO: 184) | RRRN LTL (SEQ ID NO: 217) | DRSS LKR (SEQ ID NO: 252) | QPHS LAV (SEQ ID NO: 291) | QKPH LSR (SEQ ID NO: 326) |
| ZFP1014 | 94 | GGATGTGTCT GCGGCGTT (SEQ ID NO: 122) | 375 | 395 | + | HKSS LTR (SEQ ID NO: 153) | EGGH LKR (SEQ ID NO: 185) | RRRN LQL (SEQ ID NO: 218) | DHSS LKR (SEQ ID NO: 229) | RRQH LQY (SEQ ID NO: 292) | QSAH LKR (SEQ ID NO: 327) |
| ZFP1015 | 95 | GGATGTGTCT GCGGCGTT (SEQ ID NO: 122) | 375 | 395 | + | HKSS LTR (SEQ ID NO: 153) | EGGH LKR (SEQ ID NO: 185) | RRRN LTL (SEQ ID NO: 217) | DRSS LKR (SEQ ID NO: 252) | RRQH LQY (SEQ ID NO: 292) | QSAH LKR (SEQ ID NO: 327) |
| ZFP1018 | 96 | GGGGGTTGCG TCAGCAAAC (SEQ ID NO: 123) | 1184 | 1202 | – | GHTA LRN (SEQ ID NO: 154) | QSGT LHR (SEQ ID NO: 186) | DHSS LKR (SEQ ID NO: 199) | AMRS LMG (SEQ ID NO: 253) | RRSR LVR (SEQ ID NO: 293) | RGEH LTR (SEQ ID NO: 328) |
| ZFP1019 | 97 | GGGGGTTGCG TCAGCAAAC (SEQ ID NO: 123) | 1184 | 1202 | – | GHTA LRN (SEQ ID NO: 154) | QSTT LKR (SEQ ID NO: 187) | DHS S LKR (SEQ ID NO: 199) | QQRS LVG (SEQ ID NO: 254) | EAHH LSR (SEQ ID NO: 294) | RTEH LAR (SEQ ID NO: 329) |
| ZFP1020 | 98 | GGGGGTTGCG TCAGCAAAC (SEQ ID NO: 123) | 1184 | 1202 | – | GHTA LRN (SEQ ID NO: 154) | QSTT LKR (SEQ ID NO: 187) | DHS S LKR (SEQ ID NO: 199) | AMRS LMG (SEQ ID NO: 253) | RQSR LQR (SEQ ID NO: 295) | RREH LVR (SEQ ID NO: 330) |

TABLE 1-continued

Zinc finger transcriptional repressors for silencing HBV. ZF sequences of
exemplary ZFP domains are presented. SEQ ID Nos for target sequences and
ZF can be found in Table 18 sequence listing.

| ZFP | SEQ ID | Target Sequence | Start | End | Strd | F1 | F2 | F3 | F4 | F5 | F6 |
|-----|--------|-----------------|-------|-----|------|----|----|----|----|----|----|
| ZFP1023 | 99 | GTTGTTAGAC GACGAGGCA (SEQ ID NO: 124) | 2342 | 2363 | + | QGET LKR (SEQ ID NO: 155) | RADN LRR (SEQ ID NO: 188) | DKAN LTR (SEQ ID NO: 219) | DQGN LIR (SEQ ID NO: 255) | HRHV LIN (SEQ ID NO: 296) | TNSS LTR (SEQ ID NO: 331) |
| ZFP1024 | 100 | GTTGTTAGAC GACGAGGCA (SEQ ID NO: 124) | 2342 | 2363 | + | QGET LKR (SEQ ID NO: 155) | RADN LRR (SEQ ID NO: 188) | DSSN LRR (SEQ ID NO: 220) | DQGN LIR (SEQ ID NO: 255) | HKSS LTR (SEQ ID NO: 285) | IRTS LKR (SEQ ID NO: 332) |
| ZFP1025 | 101 | GTTGTTAGAC GACGAGGCA (SEQ ID NO: 124) | 2342 | 2363 | + | QGET LKR (SEQ ID NO: 155) | RADN LRR (SEQ ID NO: 188) | EQGN LLR (SEQ ID NO: 221) | DGGN LGR (SEQ ID NO: 256) | HRHV LIN (SEQ ID NO: 296) | TNSS LTR (SEQ ID NO: 331) |

In some embodiments, the ZFP domain of the present epigenetic editor binds to a target sequence provided herein. In further embodiments, the ZFP domain comprises, in order, the F1-F6 amino acid sequences of any one of the zinc finger proteins as shown in Table 1 and Table 18. The F1-F6 amino acid sequences may be placed within the ZF framework sequence of SEQ ID NOs: 1084 and 1258-1259, or within any other ZF framework known in the art.

C. TALEs

In some embodiments, the DNA-binding domain of an epigenetic editor described herein comprises a transcription activator-like effector (TALE) domain. The DNA-binding domain of a TALE comprises a highly conserved sequence of about 33-34 amino acids, with a repeat variable di-residue (RVD) at positions 12 and 13 that is central to the recognition of specific nucleotides. TALEs can be engineered to bind practically any desired DNA sequence. Methods for programming TALEs are known in the art. For example, such methods are described in Carroll et al., *Genet Soc Amer.* (2011) 188 (4): 773-82; Miller et al., *Nat Biotechnol.* (2007) 25 (7): 778-85; Christian et al., *Genetics* (2008) 186 (2): 757-61; Li et al., *Nucl Acids Res.* (2010) 39 (1): 359-72; and Moscou et al., *Science* (2009) 326 (5959): 1501.

D. Other DNA-Binding Domains

Other DNA-binding domains are contemplated for the epigenetic editors described herein. In some embodiments, the DNA-binding domain comprises an argonaute protein domain, e.g., from *Natronobacterium gregoryi* (NgAgo). NgAgo is a ssDNA-guided endonuclease that is guided to its target site by 5′ phosphorylated ssDNA (gDNA), where it produces double-strand breaks. In contrast to Cas9, the NgAgo-gDNA system does not require a protospacer-adjacent motif (PAM). Thus, using a nuclease inactive NgAgo (dNgAgo) can greatly expand the bases that may be targeted. The characterization and use of NgAgo have been described, e.g., in Gao et al., *Nat Biotechnol.* (2016) 34 (7): 768-73; Swarts et al., *Nature* (2014) 507 (7491): 258-61; and Swarts et al., *Nucl Acids Res.* (2015) 43 (10): 5120-9.

In some embodiments, the DNA-binding domain comprises an inactivated nuclease, for example, an inactivated meganuclease. Additional non-limiting examples of DNA-binding domains include tetracycline-controlled repressor (tetR) DNA-binding domains, leucine zippers, helix-loop-helix (HLH) domains, helix-turn-helix domains, β-sheet motifs, steroid receptor motifs, bZIP domains homeodomains, and AT-hooks.

II. Guide Polynucleotides

Epigenetic editors described herein that comprise a polynucleotide guided DNA-binding domain may also include a guide polynucleotide that is capable of forming a complex with the DNA-binding domain. The guide polynucleotide may comprise RNA, DNA, or a mixture of both. For example, where the polynucleotide guided DNA-binding domain is a CRISPR-associated protein domain, the guide polynucleotide may be a guide RNA (gRNA). A "guide RNA" or "gRNA" refers to a nucleic acid that is able to hybridize to a target sequence and direct binding of the CRISPR-Cas complex to the target sequence. Methods of using guide polynucleotide sequences with programmable DNA-binding proteins (e.g., CRISPR-associated protein domains) for site-specific DNA targeting (e.g., to modify a genome) are known in the art.

A guide polynucleotide sequence (e.g., a gRNA sequence) may comprises two parts: 1) a nucleotide sequence comprising a "targeting sequence" that is complementary to a target nucleic acid sequence ("target sequence"), e.g., to a nucleic acid sequence comprised in a genomic target site; and 2) a nucleotide sequence that binds a polynucleotide guided DNA-binding domain (e.g., a CRISPR-Cas protein domain). The nucleotide sequence in 1) may comprise a targeting sequence that is 100% complementary to a genomic nucleic acid sequence, e.g., a nucleic acid sequence comprised in a genomic target site, and thus may hybridize to the target nucleic acid sequence. The nucleotide sequence in 1) may be referred to as, e.g., a crispr RNA, or crRNA. The nucleotide sequence in 2) may be referred to as a scaffold sequence of a guide nucleic acid, e.g., a tracrRNA, or an activating region of a guide nucleic acid, and may comprise a stem-loop structure. Parts 1) and 2) as described above may be fused to form one single guide (e.g., a single guide RNA, or sgRNA), or may be on two separate nucleic acid molecules. In some embodiments, a guide polynucleotide comprises parts 1) and 2) connected by a linker. In some embodiments, a guide polynucleotide comprises parts 1) and 2) connected by a non-nucleic acid linker, for example, a peptide linker or a chemical linker.

Part 2) (the scaffold sequence) of a guide polynucleotide as described herein may be, for example, as described in Jinek et al., *Science* (2012) 337:816-21; U.S. Patent Publication 2016/0208288; or U.S. Patent Publication 2016/0200779. Variants of part 2) are also contemplated by the present disclosure. For example, the tetraloop and stem loop of a gRNA scaffold (tracrRNA) sequence may be modified to include RNA aptamers, which can be bound by specific protein domains. In some embodiments, such modified gRNAs can be used to facilitate the recruitment of repressive or activating domains fused to the protein-interacting RNA aptamers.

see Fu et al., *Nat Biotechnol* (2014) 32 (3): 279-84 and Sternberg et al., *Nature* (2014) 507 (7490): 62-7, each incorporated herein by reference.

In some embodiments, the targeting domain sequence comprises between 17 and 30 nucleotides and corresponds fully to the target sequence (i.e., without any mismatch nucleotides). In some embodiments, however, the targeting domain sequence may comprise one or more, but typically not more than 4, mismatches, e.g., 1, 2, 3, or 4 mismatches. As the targeting domain is part of gRNA, which is an RNA molecule, it will typically comprise ribonucleotides, while the DNA targeting domain will comprise deoxyribonucleotides.

An exemplary illustration of a Cas9 target site, comprising a 22 nucleotide target domain, and an NGG PAM sequence, as well as of a gRNA comprising a targeting domain that fully corresponds to the target sequence (and thus base pairs with full complementarity with the DNA strand complementary to the strand comprising the target sequence and PAM) is provided below:

```
[                    target domain (DNA)           ][ PAM  ]
5'-N-N-N-N-N-N-N-N-N-N-N-N-N-N-N-N-N-N-N-N-N-N-G-G-3' (DNA)
3'-N-N-N-N-N-N-N-N-N-N-N-N-N-N-N-N-N-N-N-N-N-N-C-C-5' (DNA)
   | | | | | | | | | | | | | | | | | | | | | |
5'-N-N-N-N-N-N-N-N-N-N-N-N-N-N-N-N-N-N-N-N-N-N-[ gRNA scaffold]-3' (RNA)
[               targeting domain ( RNA)            ][  binding domain  ]
```

A gRNA as provided herein typically comprises a targeting domain and a binding domain. The targeting domain (also termed "targeting sequence") may comprise a nucleic acid sequence that binds to a target site, e.g., to a genomic nucleic acid molecule within a cell. The target site may be a double-stranded DNA sequence comprising a PAM sequence as well as the target sequence, which is located on An exemplary illustration of a Cas12a target site, comprising a 22 nucleotide target domain, and a TTN PAM sequence, as well as of a gRNA comprising a targeting domain that fully corresponds to the target sequence (and thus base pairs with full complementarity with the DNA strand complementary to the strand comprising the target sequence and PAM) is provided below:

```
[ PAM ][            target domain ( DNA)              ]
5'-T-T-N-N-N-N-N-N-N-N-N-N-N-N-N-N-N-N-N-N-N-N-N-N-3' (DNA)
3'-A-A-N-N-N-N-N-N-N-N-N-N-N-N-N-N-N-N-N-N-N-N-N-N-5' (DNA)
       | | | | | | | | | | | | | | | | | | | | | |
5'-[ gRNA scaffold]-N-N-N-N-N-N-N-N-N-N-N-N-N-N-N-N-N-N-N-N-N-N-3' (RNA)
[ binding domain   ][            targeting domain ( RNA)          ]
``` the same strand as, and directly adjacent to, the PAM sequence. The targeting domain of the gRNA may comprise an RNA sequence that corresponds to the target sequence, i.e., it resembles the sequence of the target domain, sometimes with one or more mismatches, but typically comprising an RNA sequence instead of a DNA sequence. The targeting domain of the gRNA thus may base pair (in full or partial complementarity) with the sequence of the double-stranded target site that is complementary to the target sequence, and thus with the strand complementary to the strand that comprises the PAM sequence. It will be understood that the targeting domain of the gRNA typically does not include a sequence that resembles the PAM sequence. It will further be understood that the location of the PAM may be 5' or 3' of the target sequence, depending on the nuclease employed. For example, the PAM is typically 3' of the target sequence for Cas9 nucleases, and 5' of the target sequence for Cas12a nucleases. For an illustration of the location of the PAM and the mechanism of gRNA binding to a target site, see, e.g., FIG. 1 of Vanegas et al., *Fungal Biol Biotechnol.* (2019) 6:6, which is incorporated by reference herein. For additional illustration and description of the mechanism of gRNA targeting of an RNA-guided nuclease to a target site, While not wishing to be bound by theory, at least in some embodiments, it is believed that the length and complementarity of the targeting domain with the target sequence contributes to specificity of the interaction of the gRNA/Cas9 molecule complex with a target nucleic acid. In some embodiments, the targeting domain of a gRNA provided herein is 5 to 50 nucleotides in length. In some embodiments, the targeting domain is 15 to 25 nucleotides in length. In some embodiments, the targeting domain is 18 to 22 nucleotides in length. In some embodiments, the targeting domain is 19-21 nucleotides in length. In some embodiments, the targeting domain is 15 nucleotides in length. In some embodiments, the targeting domain is 16 nucleotides in length. In some embodiments, the targeting domain is 17 nucleotides in length. In some embodiments, the targeting domain is 18 nucleotides in length. In some embodiments, the targeting domain is 19 nucleotides in length. In some embodiments, the targeting domain is 20 nucleotides in length. In some embodiments, the targeting domain is 21 nucleotides in length. In some embodiments, the targeting domain is 22 nucleotides in length. In some embodiments, the targeting domain is 23 nucleotides in length. In some embodiments, the targeting domain is 24 nucleotides in length. In some embodiments, the targeting domain is 25 nucleotides in length. In certain embodiments, the targeting domain fully corresponds, without mismatch, to a target sequence provided herein, or a part thereof. In some embodiments, the targeting domain of a gRNA provided herein comprises 1 mismatch relative to a target sequence provided herein. In some embodiments, the targeting domain comprises 2 mismatches relative to the target sequence. In some embodiments, the target domain comprises 3 mismatches relative to the target sequence.

Methods for designing, selecting, and validating gRNAs are described herein and known in the art. Software tools can be used to optimize the gRNAs corresponding to a target DNA sequence, e.g., to minimize total off-target activity across the genome. For example, DNA sequence searching algorithms can be used to identify a target sequence in crRNAs of a gRNA for use with Cas9. Exemplary gRNA design tools include the ones described in Bac et al., *Bioinformatics* (2014) 30:1473-5.

Guide polynucleotides (e.g., gRNAs) described herein may be of various lengths. In some embodiments, the length of the spacer or targeting sequence depends on the CRISPR-associated protein component of the epigenetic editor system used. For example, Cas proteins from different bacterial species have varying optimal targeting sequence lengths. Accordingly, the spacer sequence may comprise, e.g., 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, or more than 50 nucleotides in length. In some embodiments, the spacer comprises 10-24, 11-20, 11-16, 18-24, 19-21, or 20 nucleotides in length. In some embodiments, a guide polynucleotide (e.g., gRNA) is from 15-100 (e.g., 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, or 50) nucleotides in length and comprises a spacer sequence of at least 10 (e.g., 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, or 50) contiguous nucleotides complementary to the target sequence. In some embodiments, a guide polynucleotide described herein may be truncated, e.g., by 1, 2, 3, 4, 5, 10, 15, 20, 25, 30, 40, 50 or more nucleotides.

In certain embodiments, 3' end of the HBV target sequence is immediately adjacent to a PAM sequence (e.g., a canonical PAM sequence such as NGG for SpCas9). The degree of complementarity between the targeting sequence of the guide polynucleotide (e.g., the spacer sequence of a gRNA) and the target sequence may be at least 90%, 91%, 92%, 93%, 94%, 95%, 96%, 97%, 98%, 99%, or 100%. In particular embodiments, the targeting and the target sequence may be 100% complementary. In other embodiments, the targeting sequence and the target sequence may contain, e.g., 1, 2, 3, 4, 5, 6, 7, 8, 9, or 10 mismatches.

A guide polynucleotide (e.g., gRNA) may be modified with, for example, chemical alterations and synthetic modifications. A modified gRNA, for instance, can include an alteration or replacement of one or both of the non-linking phosphate oxygens and/or of one or more of the linking phosphate oxygens in the phosphodiester backbone linkage, an alteration of the ribose sugar (e.g., of the 2' hydroxyl on the ribose sugar), an alteration of the phosphate moiety, modification or replacement of a naturally occurring nucleobase, modification or replacement of the ribose-phosphate backbone, modification of 3' end and/or 5' end of the oligonucleotide, replacement of a terminal phosphate group or conjugation of a moiety, cap, or linker, or any combination thereof.

In some embodiments, one or more ribose groups of the gRNA may be modified. Examples of chemical modifications to the ribose group include, but are not limited to, 2'-O-methyl (2'-OMe), 2'-fluoro (2'-F), 2'-deoxy, 2'-O-(2-methoxyethyl) (2'-MOE), 2'-NH2, 2'-O-allyl, 2'-O-ethylamine, 2'-O-cyanoethyl, 2'-O-acetalester, or a bicyclic nucleotide such as locked nucleic acid (LNA), 2'-(5-constrained ethyl (S-cEt)), constrained MOE, or 2'-0,4'-C-aminomethylene bridged nucleic acid (2',4'-BNANC). 2'-O-methyl modification and/or 2'-fluoro modification may increase binding affinity and/or nuclease stability of the gRNA oligonucleotides.

In some embodiments, one or more phosphate groups of the gRNA may be chemically modified. Examples of chemical modifications to a phosphate group include, but are not limited to, a phosphorothioate (PS), phosphonoacetate (PACE), thiophosphonoacetate (thioPACE), amide, triazole, phosphonate, and phosphotriester modification. In some embodiments, a guide polynucleotide described herein may comprise one, two, three, or more PS linkages at or near 5' end and/or 3' end; the PS linkages may be contiguous or noncontiguous.

In some embodiments, the gRNA herein comprises a mixture of ribonucleotides and deoxyribonucleotides and/or one or more PS linkages.

In some embodiments, one or more nucleobases of the gRNA may be chemically modified. Examples of chemically modified nucleobases include, but are not limited to, 2-thiouridine, 4-thiouridine, N6-methyladenosine, pseudouridine, 2,6-diaminopurine, inosine, thymidine, 5-methylcytosine, 5-substituted pyrimidine, isoguanine, isocytosine, and nucleobases with halogenated aromatic groups. Chemical modifications can be made in the spacer region, the tracr RNA region, the stem loop, or any combination thereof.

Table 2 below lists exemplary target sequences for epigenetic modification of HBV, as well as the coordinates of the start and end positions of the targeted site on the HBV genome.

TABLE 2

Targeting Domain Sequences of Exemplary gRNAs Targeting HBV. The following target sites were identified as suitable for targeting with an epigenetic repressor:

| SEQ IDs | Target domain sequence | Start | End | Strand |
|---|---|---|---|---|
| 333 | CCTGCTGGTGGCTCCAGTTC | 57 | 77 | + |
| 334 | CTGAACTGGAGCCACCAGCA | 59 | 79 | - |
| 335 | CCTGAACTGGAGCCACCAGC | 60 | 80 | - |
| 336 | CCTCGAGAAGATTGACGATA | 115 | 135 | - |
| 337 | TCGTCAATCTTCTCGAGGAT | 117 | 137 | + |
| 338 | CGTCAATCTTCTCGAGGATT | 118 | 138 | + |
| 339 | GTCAATCTTCTCGAGGATTG | 119 | 139 | + |
| 340 | AACATGGAGAACATCACATC | 153 | 173 | + |
| 341 | AACATCACATCAGGATTCCT | 162 | 182 | + |
| 342 | CTAGACTCTGCGGTATTGTG | 233 | 253 | - |

TABLE 2-continued

Targeting Domain Sequences of Exemplary gRNAs
Targeting HBV. The following target sites were
identified as suitable for targeting with an
epigenetic repressor:

| SEQ IDs | Target domain sequence | Start | End | Strand |
|---|---|---|---|---|
| 343 | TACCGCAGAGTCTAGACTCG | 238 | 258 | + |
| 344 | CGCAGAGTCTAGACTCGTGG | 241 | 261 | + |
| 345 | CACCACGAGTCTAGACTCTG | 243 | 263 | − |
| 346 | TGGACTTCTCTCAATTTTCT | 261 | 281 | + |
| 347 | GGACTTCTCTCAATTTTCTA | 262 | 282 | + |
| 348 | GACTTCTCTCAATTTTCTAG | 263 | 283 | + |
| 349 | ACTTCTCTCAATTTTCTAGG | 264 | 284 | + |
| 350 | CGAATTTTGGCCAAGACACA | 295 | 315 | − |
| 351 | AGGTTGGGGACTGCGAATTT | 309 | 328 | − |
| 352 | GGCATAGCAGCAGGATGAAG | 408 | 427 | − |
| 353 | AGAAGATGAGGCATAGCAGC | 417 | 436 | − |
| 354 | GCTATGCCTCATCTTCTTGT | 420 | 439 | + |
| 355 | GAAGAACCAACAAGAAGATG | 429 | 448 | − |
| 356 | CATCTTCTTGTTGGTTCTTC | 429 | 448 | + |
| 357 | CCCGTTTGTCCTCTAATTCC | 469 | 488 | + |
| 358 | CCTGGAATTAGAGGACAAAC | 472 | 491 | − |
| 359 | TCCTGGAATTAGAGGACAAA | 473 | 492 | − |
| 360 | TACTAGTGCCATTTGTTCAG | 680 | 699 | + |
| 361 | CCATTTGTTCAGTGGTTCGT | 688 | 707 | + |
| 362 | CATTTGTTCAGTGGTTCGTA | 689 | 708 | + |
| 363 | CCTACGAACCACTGAACAAA | 691 | 710 | − |
| 364 | TTTCAGTTATATGGATGATG | 731 | 750 | + |
| 365 | CAAAAGAAAATTGGTAACAG | 799 | 818 | − |
| 366 | TACCAATTTTCTTTTGTCTT | 803 | 822 | + |
| 367 | ACCAATTTTCTTTTGTCTTT | 804 | 823 | + |
| 368 | ACCCAAAGACAAAAGAAAAT | 808 | 827 | − |
| 369 | TGACATACTTTCCAATCAAT | 975 | 994 | − |
| 370 | CACTTTCTCGCCAACTTACA | 1093 | 1113 | + |
| 371 | CACAGAAAGGCCTTGTAAGT | 1106 | 1126 | − |
| 372 | TGAACCTTTACCCCGTTGCC | 1137 | 1157 | + |
| 373 | GGGCAACGGGGTAAAGGTTC | 1138 | 1158 | − |
| 374 | TTTACCCCGTTGCCCGGCAA | 1143 | 1163 | + |
| 375 | GTTGCCGGGCAACGGGGTAA | 1144 | 1164 | − |
| 376 | CCCGTTGCCCGGCAACGGCC | 1148 | 1168 | + |
| 377 | CTGGCCGTTGCCGGGCAACG | 1150 | 1170 | − |
| 378 | CCTGGCCGTTGCCGGGCAAC | 1151 | 1171 | − |

TABLE 2-continued

Targeting Domain Sequences of Exemplary gRNAs
Targeting HBV. The following target sites were
identified as suitable for targeting with an
epigenetic repressor:

| SEQ IDs | Target domain sequence | Start | End | Strand |
|---|---|---|---|---|
| 379 | ACCTGGCCGTTGCCGGGCAA | 1152 | 1172 | − |
| 380 | GCACAGACCTGGCCGTTGCC | 1158 | 1178 | − |
| 381 | GGCACAGACCTGGCCGTTGC | 1159 | 1179 | − |
| 382 | GCAAACACTTGGCACAGACC | 1169 | 1189 | − |
| 383 | GGGTTGCGTCAGCAAACACT | 1180 | 1200 | − |
| 384 | TTTGCTGACGCAACCCCCAC | 1184 | 1204 | + |
| 385 | CTGACGCAACCCCCACTGGC | 1188 | 1208 | + |
| 386 | TGACGCAACCCCCACTGGCT | 1189 | 1209 | + |
| 387 | GACGCAACCCCCACTGGCTG | 1190 | 1210 | + |
| 388 | AACCCCCACTGGCTGGGGCT | 1195 | 1215 | + |
| 389 | TCCTCTGCCGATCCATACTG | 1255 | 1275 | + |
| 390 | TCCGCAGTATGGATCGGCAG | 1259 | 1279 | − |
| 391 | AGGAGTTCCGCAGTATGGAT | 1265 | 1285 | − |
| 392 | CGGCTAGGAGTTCCGCAGTA | 1270 | 1290 | − |
| 393 | TGCGAGCAAAACAAGCGGCT | 1285 | 1305 | − |
| 394 | CCGCTTGTTTTGCTCGCAGC | 1287 | 1307 | + |
| 395 | CCTGCTGCGAGCAAAACAAG | 1290 | 1310 | − |
| 396 | TGTTTTGCTCGCAGCAGGTC | 1292 | 1312 | + |
| 397 | GCAGCACAGCCTAGCAGCCA | 1376 | 1396 | − |
| 398 | TGCTAGGCTGTGCTGCCAAC | 1380 | 1400 | + |
| 399 | GCTGCCAACTGGATCCTGCG | 1391 | 1411 | + |
| 400 | CTGCCAACTGGATCCTGCGC | 1392 | 1412 | + |
| 401 | CGTCCCGCGCAGGATCCAGT | 1398 | 1418 | − |
| 402 | AAACAAAGGACGTCCCGCGC | 1408 | 1428 | − |
| 403 | GTCCTTTGTTTACGTCCCGT | 1417 | 1437 | + |
| 404 | CGCCGACGGGACGTAAACAA | 1422 | 1442 | − |
| 405 | TGCCGTTCCGACCGACCACG | 1504 | 1523 | + |
| 406 | AGGTGCGCCCCGTGGTCGGT | 1513 | 1533 | − |
| 407 | AGAGAGGTGCGCCCCGTGGT | 1517 | 1537 | − |
| 408 | GTAAAGAGAGGTGCGCCCCG | 1521 | 1541 | − |
| 409 | GGGGCGCACCTCTCTTTACG | 1522 | 1542 | + |
| 410 | CGGGGAGTCCGCGTAAAGAG | 1533 | 1553 | − |
| 411 | CAGATGAGAAGGCACAGACG | 1551 | 1571 | − |
| 412 | GTCTGTGCCTTCTCATCTGC | 1552 | 1572 | + |
| 413 | GGCAGATGAGAAGGCACAGA | 1553 | 1573 | − |
| 414 | GCAGATGAGAAGGCACAGAC | 1553 | 1572 | − |

TABLE 2-continued

Targeting Domain Sequences of Exemplary gRNAs
Targeting HBV. The following target sites were
identified as suitable for targeting with an
epigenetic repressor:

| SEQ IDs | Target domain sequence | Start | End | Strand |
|---|---|---|---|---|
| 415 | ACACGGTCCGGCAGATGAGA | 1562 | 1582 | – |
| 416 | GAAGCGAAGTGCACACGGTC | 1574 | 1594 | – |
| 417 | GAGGTGAAGCGAAGTGCACA | 1579 | 1599 | – |
| 418 | CTTCACCTCTGCACGTCGCA | 1590 | 1610 | + |
| 419 | GGTCTCCATGCGACGTGCAG | 1598 | 1618 | – |
| 420 | TGCCCAAGGTCTTACATAAG | 1640 | 1660 | + |
| 421 | GTCCTCTTATGTAAGACCTT | 1645 | 1665 | – |
| 422 | AGTCCTCTTATGTAAGACCT | 1646 | 1666 | – |
| 423 | GTCTTACATAAGAGGACTCT | 1648 | 1668 | + |
| 424 | AATGTCAACGACCGACCTTG | 1680 | 1700 | + |
| 425 | TTTGAAGTATGCCTCAAGGT | 1694 | 1714 | – |
| 426 | AGTCTTTGAAGTATGCCTCA | 1698 | 1718 | – |
| 427 | AAGACTGTTTGTTTAAAGAC | 1712 | 1732 | + |
| 428 | AGACTGTTTGTTTAAAGACT | 1713 | 1733 | + |
| 429 | CTGTTTGTTTAAAGACTGGG | 1716 | 1736 | + |
| 430 | GTTTAAAGACTGGGAGGAGT | 1722 | 1742 | + |
| 431 | TCTTTGTACTAGGAGGCTGT | 1766 | 1786 | + |
| 432 | AGGAGGCTGTAGGCATAAAT | 1776 | 1796 | + |
| 433 | GTGAAAAAGTTGCATGGTGC | 1810 | 1830 | – |
| 434 | GCAGAGGTGAAAAAGTTGCA | 1816 | 1836 | – |
| 435 | AACAAGAGATGATTAGGCAG | 1832 | 1852 | – |
| 436 | GACATGAACAAGAGATGATT | 1838 | 1858 | – |
| 437 | AGCTTGGAGGCTTGAACAGT | 1860 | 1880 | – |
| 438 | CAAGCCTCCAAGCTGTGCCT | 1866 | 1886 | + |
| 439 | AAGCCTCCAAGCTGTGCCTT | 1867 | 1887 | + |
| 440 | CCTCCAAGCTGTGCCTTGGG | 1871 | 1890 | + |
| 441 | CCACCCAAGGCACAGCTTGG | 1873 | 1893 | – |
| 442 | AGCTGTGCCTTGGGTGGCTT | 1876 | 1896 | + |
| 443 | AAGCCACCCAAGGCACAGCT | 1876 | 1896 | – |
| 444 | GCTGTGCCTTGGGTGGCTTT | 1877 | 1897 | + |
| 445 | CTGTGCCTTGGGTGGCTTTG | 1878 | 1898 | + |
| 446 | TAGCTCCAAATTCTTTATAA | 1916 | 1936 | – |
| 447 | GTAGCTCCAAATTCTTTATA | 1917 | 1937 | – |
| 448 | TAAAGAATTTGGAGCTACTG | 1919 | 1939 | + |
| 449 | ATGACTCTAGCTACCTGGGT | 2097 | 2117 | + |
| 450 | CACATTTCTTGTCTCACTTT | 2211 | 2231 | + |

TABLE 2-continued

Targeting Domain Sequences of Exemplary gRNAs
Targeting HBV. The following target sites were
identified as suitable for targeting with an
epigenetic repressor:

| SEQ IDs | Target domain sequence | Start | End | Strand |
|---|---|---|---|---|
| 451 | TAGTTTCCGGAAGTGTTGAT | 2321 | 2341 | – |
| 452 | CGTCTAACAACAGTAGTTTC | 2334 | 2354 | – |
| 453 | ACTACTGTTGTTAGACGACG | 2337 | 2357 | + |
| 454 | CTGTTGTTAGACGACGAGGC | 2341 | 2361 | + |
| 455 | CGAGGGAGTTCTTCTTCTAG | 2368 | 2388 | – |
| 456 | GCGAGGGAGTTCTTCTTCTA | 2369 | 2389 | – |
| 457 | GGCGAGGGAGTTCTTCTTCT | 2370 | 2390 | – |
| 458 | CTCCCTCGCCTCGCAGACGA | 2380 | 2400 | + |
| 459 | GACCTTCGTCTGCGAGGCGA | 2385 | 2405 | – |
| 460 | AGACCTTCGTCTGCGAGGCG | 2386 | 2406 | – |
| 461 | GATTGAGACCTTCGTCTGCG | 2391 | 2411 | – |
| 462 | GATTGAGATCTTCTGCGACG | 2415 | 2435 | – |
| 463 | GTCGCAGAAGATCTCAATCT | 2416 | 2436 | + |
| 464 | TCGCAGAAGATCTCAATCTC | 2417 | 2437 | + |
| 465 | ATATGGTGACCCACAAAATG | 2807 | 2827 | – |
| 466 | TTTGTGGGTCACCATATTCT | 2810 | 2830 | + |
| 467 | TTGTGGGTCACCATATTCTT | 2811 | 2831 | + |
| 468 | GCTGGATCCAACTGGTGGTC | 2894 | 2914 | – |
| 469 | CACCCCAAAAGGCCTCCGTG | 3026 | 3046 | – |
| 470 | CCTTTTGGGGTGGAGCCCTC | 3034 | 3054 | + |
| 471 | CCTGAGGGCTCCACCCCAAA | 3037 | 3057 | – |
| 472 | GGGGTGGAGCCCTCAGGCTC | 3040 | 3060 | + |
| 473 | GGGTGGAGCCCTCAGGCTCA | 3041 | 3061 | + |
| 474 | CGATTGGTGGAGGCAGGAGG | 3092 | 3112 | – |
| 475 | CTCATCCTCAGGCCATGCAG | 3159 | 3179 | + |
| 102 | GATGAGGCATAGCAGCAG | 415 | 432 | – |
| 103 | GATGATTAGGCAGAGGTG | 1828 | 1845 | – |
| 104 | GGATTCAGCGCCGACGGG | 1433 | 1450 | – |
| 105 | GGCAGTAGTCGGAACAGGG | 90 | 108 | – |
| 106 | GTAAACTGAGCCAGGAGAA | 664 | 682 | – |
| 107 | ACGGTGGTCTCCATGCGAC | 1605 | 1623 | – |
| 108 | GCTGGATGTGTCTGCGGCG | 372 | 393 | + |
| 109 | GTCTGCGAGGCGAGGGAG | 2381 | 2398 | – |
| 110 | GTTGCCGGGCAACGGGGTA | 1146 | 1164 | – |
| 111 | CGAGAAAGTGAAAGCCTGC | 1085 | 1103 | – |
| 112 | GAGGCTTGAACAGTAGGAC | 1856 | 1874 | – |

49

TABLE 2-continued

Targeting Domain Sequences of Exemplary gRNAs
Targeting HBV. The following target sites were
identified as suitable for targeting with an
epigenetic repressor:

| SEQ IDs | Target domain sequence | Start | End | Strand |
|---|---|---|---|---|
| 113 | GAGGTTGGGGACTGCGAA | 312 | 329 | – |
| 114 | GATGATGTGGTATTGGGG | 742 | 762 | + |
| 115 | GATGATGTGGTATTGGGGG | 742 | 763 | + |
| 116 | GCAGTAGTCGGAACAGGG | 90 | 107 | – |
| 117 | GCATAGCAGCAGGATGAA | 409 | 426 | – |
| 118 | GGCGTTCACGGTGGTCTCC | 1612 | 1630 | – |
| 119 | GTTGGTGAGTGATTGGAG | 327 | 344 | – |
| 120 | GGAGGTTGGGGACTGCGAA | 312 | 330 | – |
| 121 | GGATGATGTGGTATTGGGG | 741 | 762 | + |
| 122 | GGATGTGTCTGCGGCGTT | 375 | 395 | + |
| 123 | GGGGGTTGCGTCAGCAAAC | 1184 | 1202 | – |
| 124 | GTTGTTAGACGACGAGGCA | 2342 | 2363 | + |

Target domains identified above that are adjacent to a PAM sequence, e.g., an *S. pyogenes* Cas9 PAM sequence, can be targeted by a CRISPR-based epigenetic repressor, e.g., an epigenetic repressor comprising a dCas9 DNA-binding domain. For example, target sites 1-143 are suitable for dCas9-based epigenetic repressor targeting.

A suitable gRNA for targeting any of the target domain sequences would, in some embodiments, comprise a target domain sequence that is the RNA-equivalent sequence of the provided DNA sequence of the targeting domain sequence (i.e., an RNA nucleotide of that sequence instead of the provided DNA nucleotide, with uracil instead of thymine), and a suitable tracr RNA sequence.

Any tracr sequence known in the art is contemplated for a gRNA described herein. In some embodiments, a gRNA described herein has a tracr sequence shown in Table 3 below, or a tracr sequence at least 70%, 75%, 80%, 85%, 90%, 95%, 96%, 97%, 98%, or 99% identical to the tracr sequence shown below (SEQ: SEQ ID NO).

TABLE 3

Exemplary TRACR Sequences

| SEQ | Sequence (5' to 3') |
|---|---|
| 1087 | GUUUAAGAGCUAUGCUGGAAACAGCAUAGCAAGUUUAAAUA AGGCUAGUCCGUUAUCAACUUGAAAAAGUGGCACCGAGUCG GUGCUUUUUU |
| 1088 | GUUUUAGAGCUAGAAAUAGCAAGUUAAAAUAAGGCUAGUCC GUUAUCAACUUGAAAAAGUGGCACCGAGUCGGUGCUUUU |
| 1089 | GUUUAAGAGCUAAGCUGGAAACAGCAUAGCAAGUUUAAAUA AGGCUAGUCCGUUAUCAACUUGAAAAAGUGGCACCGAGUCG GUGCUUUUUU |
| 1090 | GUUUAAGAGCUAAGCUGGAAACAGCAUAGCAAGUUUAAAUA AGGCUAGUCCGUUAUCAACUUGAAAAAGUGGCACCGAGUCG GUGCUUUUUU |

50

In some embodiments, the gRNA herein is provided to the cell directly (e.g., through an RNP complex together with the CRISPR-associated protein domain). In some embodiments, the gRNA is provided to the cell through an expression vector (e.g., a plasmid vector or a viral vector) introduced into the cell, where the cell then expresses the gRNA from the expression vector. Methods of introducing gRNAs and expression vectors into cells are well known in the art.

III. Effector Domains

Epigenetic editors described herein include one or more effector protein domains (also "epigenetic effector domains," or "effector domains," as used herein) that effect epigenetic modification of a target gene. An epigenetic editor with one or more effector domains may modulate expression of a target gene without altering its nucleobase sequence. In some embodiments, an effector domain described herein may provide repression or silencing of expression of HBV or an HBV gene, e.g., by repressing transcription or by modifying or remodeling HBV chromatin. Such effector domains are also referred to herein as "repression domains," "repressor domains," "epigenetic repressor domains," or "epigenetic repression domains." Non-limiting examples of chemical modifications that may be mediated by effector domains include methylation, demethylation, acetylation, deacetylation, phosphorylation, SUMOylation and/or ubiquitination of DNA or histone residues.

In some embodiments, an effector domain of an epigenetic editor described herein may make histone tail modifications, e.g., by adding or removing active marks on histone tails.

In some embodiments, an effector domain of an epigenetic editor described herein may comprise or recruit a transcription-related protein, e.g., a transcription repressor. The transcription-related protein may be endogenous or exogenous.

In some embodiments, an effector domain of an epigenetic editor described herein may, for example, comprise a protein that directly or indirectly blocks access of a transcription factor to the gene of interest harboring the target sequence.

An effector domain may be a full-length protein or a fragment thereof that retains the epigenetic effector function (a "functional domain"). Functional domains that are capable of modulating (e.g., repressing) gene expression can be derived from a larger protein. For example, functional domains that can reduce target gene expression may be identified based on sequences of repressor proteins. Amino acid sequences of gene expression-modulating proteins may be obtained from available genome browsers, such as the UCSD genome browser or Ensembl genome browser. Protein annotation databases such as UniProt or Pfam can be used to identify functional domains within the full protein sequence. As a starting point, the largest sequence, encompassing all regions identified by different databases, may be tested for gene expression modulation activity. Various truncations then may be tested to identify the minimal functional unit.

Variants of effector domains described herein are also contemplated by the present disclosure. A variant may, for example, refer to a polypeptide with at least about 85%, 90%, 91%, 92%, 93%, 94%, 95%, 96%, 97%, 98%, 99%, or 100% sequence identity and/or sequence similarity to a wildtype effector domain described herein. In particular embodiments, the variant retains at least about 85%, 90%, 91%, 92%, 93%, 94%, 95%, 96%, 97%, 98%, 99%, or 100% of the epigenetic effector function of the wildtype effector domain.

In some embodiments, an epigenetic editor described herein may comprise 1 effector domain, 2 effector domains, 3 effector domains, 4 effector domains, 5 effector domains, 6 effector domains, 7 effector domains, 8 effector domains, 9 effector domains, 10 effector domains, or more. In certain embodiments, the epigenetic editor comprises one or more fusion proteins (e.g., one, two, or three fusion proteins), each with one or more effector domains (e.g., one, two, or three effector domains) linked to a DNA-binding domain. In some embodiments, the effector domains may induce a combination of epigenetic modifications, e.g., transcription repression and DNA methylation, DNA methylation and histone deacetylation, DNA methylation and histone demethylation, DNA methylation and histone methylation, DNA methylation and histone phosphorylation, DNA methylation and histone ubiquitylation, DNA methylation, and histone SUMOylation.

In certain embodiments, an effector domain described herein (e.g., DNMT3A and/or DNMT3L) is encoded by a nucleotide sequence as found in the native genome (e.g., human or murine) for that effector domain. In other embodiments, an effector domain described herein is encoded by a nucleotide sequence that has been codon-optimized for optimal expression in human cells.

Effector domains described herein may include, for example, transcriptional repressors, DNA methyltransferases, and/or histone modifiers, as further detailed below.

A. Transcriptional Repressors

In some embodiments, an epigenetic effector domain described herein mediates repression of a target gene's expression (e.g., transcription). The effector domain may comprise, e.g., a Krüppel-associated box (KRAB) repression domain, a Repressor Element Silencing Transcription Factor (REST) repression domain, a KRAB-associated protein 1 (KAP1) domain, a MAD domain, a FKHR (forkhead in rhabdosarcoma gene) repressor domain, an EGR-1 (early growth response gene product-1) repressor domain, an ets2 repressor factor repressor domain (ERD), a MAD smSIN3 interaction domain (SID), a WRPW motif (SEQ ID NO: 1257) of the hairy-related basic helix-loop-helix (bHLH) repressor proteins, an HP1 alpha chromo-shadow repression domain, an HP1 beta repression domain, or any combination thereof. The effector domain may recruit one or more protein domains that repress expression of the target gene, e.g., through a scaffold protein. In some embodiments, the effector domain may recruit or interact with a scaffold protein domain that recruits a PRMT protein, a HDAC protein, a SETDB1 protein, or a NuRD protein domain.

In some embodiments, the effector domain comprises a functional domain derived from a zinc finger repressor protein, such as a KRAB domain. KRAB domains are found in approximately 400 human ZFP-based transcription factors. Descriptions of KRAB domains may be found, for example, in Ecco et al., *Development* (2017) 144 (15): 2719-29 and Lambert et al., *Cell* (2018) 172:650-65.

In certain embodiments, the effector domain comprises a repression domain (e.g., KRAB) derived from KOX1/ ZNF10, KOX8/ZNF708, ZNF43, ZNF184, ZNF91, HPF4, HTF10, or HTF34. In some embodiments, the effector domain comprises a repression domain (e.g., KRAB) derived from ZIM3, ZNF436, ZNF257, ZNF675, ZNF490, ZNF320, ZNF331, ZNF816, ZNF680, ZNF41, ZNF189, ZNF528, ZNF543, ZNF554, ZNF140, ZNF610, ZNF264, ZNF350, ZNF8, ZNF582, ZNF30, ZNF324, ZNF98, ZNF669, ZNF677, ZNF596, ZNF214, ZNF37, ZNF34, ZNF250, ZNF547, ZNF273, ZNF354, ZFP82, ZNF224, ZNF33, ZNF45, ZNF175, ZNF595, ZNF184, ZNF419, ZFP28-1, ZFP28-2, ZNF18, ZNF213, ZNF394, ZFP1, ZFP14, ZNF416, ZNF557, ZNF566, ZNF729, ZIM2, ZNF254, ZNF764, ZNF785, or any combination thereof. For example, the repression domain may be a KRAB domain derived from KOX1, ZIM3, ZFP28, or ZN627. In particular embodiments, the repression domain is a ZIM3 KRAB domain. In further embodiments, the effector domain is derived from a human protein, e.g., a human ZIM3, a human KOX1, a human ZFP28, or a human ZN627.

Exemplary effector domains that may reduce or silence target gene expression are provided in Table 4 below (SEQ: SEQ ID NO, see Table 18 for sequences of exemplary effector domains). Further examples of repressors and transcriptional repressor domains can be found, e.g., in PCT Patent Publication WO 2021/226077 and Tycko et al., *Cell* (2020) 183 (7): 2020-35, each of which is incorporated herein by reference in its entirety.

TABLE 4

| Exemplary Effector Domains Suitable for Silencing Gene Expression | |
|---|---|
| Protein | SEQ |
| ZIM3 | 495 |
| ZNF436 | 496 |
| ZNF257 | 497 |
| ZNF675 | 498 |
| ZNF490 | 499 |
| ZNF320 | 500 |
| ZNF331 | 501 |
| ZNF816 | 502 |
| ZNF680 | 503 |
| ZNF41 | 504 |
| ZNF189 | 505 |
| ZNF528 | 506 |
| ZNF543 | 507 |
| ZNF554 | 508 |
| ZNF140 | 509 |
| ZNF610 | 510 |
| ZNF264 | 511 |
| ZNF350 | 512 |
| ZNF8 | 513 |
| ZNF582 | 514 |
| ZNF30 | 515 |
| ZNF324 | 516 |
| ZNF98 | 517 |
| ZNF669 | 518 |
| ZNF677 | 519 |
| ZNF596 | 520 |
| ZNF214 | 521 |
| ZNF37A | 522 |
| ZNF34 | 523 |
| ZNF250 | 524 |
| ZNF547 | 525 |
| ZNF273 | 526 |
| ZNF354A | 527 |
| ZFP82 | 528 |
| ZNF224 | 529 |
| ZNF33A | 530 |
| ZNF45 | 531 |
| ZNF175 | 532 |
| ZNF595 | 533 |
| ZNF184 | 534 |
| ZNF419 | 535 |
| ZFP28-1 | 536 |
| ZFP28-2 | 537 |
| ZNF18 | 538 |
| ZNF213 | 539 |
| ZNF394 | 540 |
| ZFP1 | 541 |
| ZFP14 | 542 |

TABLE 4-continued

Exemplary Effector
Domains Suitable for
Silencing Gene Expression

| Protein | SEQ |
|---|---|
| ZNF416 | 543 |
| ZNF557 | 544 |
| ZNF566 | 545 |
| ZNF729 | 546 |
| ZIM2 | 547 |
| ZNF254 | 548 |
| ZNF764 | 549 |
| ZNF785 | 550 |
| ZNF10 (KOX1) | 551 |
| CBX5 (chromoshadow domain) | 552 |
| RYBP (YAF2_RYBP component of PRC1) | 553 |
| YAF2 (YAF2_RYBP component of PRC1) | 554 |
| MGA (component of PRC1.6) | 555 |
| CBX1 (chromoshadow) | 556 |
| SCMH1 (SAM_1/SPM) | 557 |
| MPP8 (Chromodomain) | 558 |
| SUMO3 (Rad60-SLD) | 559 |
| HERC2 (Cyt-b5) | 560 |
| BIN1 (SH3_9) | 561 |
| PCGF2 (RING finger protein domain) | 562 |
| TOX (HMG box) | 563 |
| FOXA1 (HNF3A C-terminal domain) | 564 |
| FOXA2 (HNF3B C-terminal domain) | 565 |
| IRF2BP1 (IRF-2BP1_2 N-terminal domain) | 566 |
| IRF2BP2 (IRF-2BP1_2 N-terminal domain) | 567 |
| IRF2BPL IRF-2BP1_2 N-terminal domain | 568 |
| HOXA13 (homeodomain) | 569 |
| HOXB13 (homeodomain) | 570 |
| HOXC13 (homeodomain) | 571 |
| HOXA11 (homeodomain) | 572 |
| HOXC11 (homeodomain) | 573 |
| HOXC10 (homeodomain) | 574 |
| HOXA10 (homeodomain) | 575 |
| HOXB9 (homeodomain) | 576 |
| HOXA9 (homeodomain) | 577 |
| ZFP28_HUMAN | 578 |
| ZN334_HUMAN | 579 |
| ZN568_HUMAN | 580 |
| ZN37A_HUMAN | 581 |
| ZN181_HUMAN | 582 |
| ZN510_HUMAN | 583 |
| ZN862_HUMAN | 584 |
| ZN140_HUMAN | 585 |
| ZN208_HUMAN | 586 |
| ZN248_HUMAN | 587 |
| ZN571_HUMAN | 588 |
| ZN699_HUMAN | 589 |
| ZN726_HUMAN | 590 |
| ZIK1_HUMAN | 591 |
| ZNF2_HUMAN | 592 |
| Z705F_HUMAN | 593 |
| ZNF14_HUMAN | 594 |
| ZN471_HUMAN | 595 |
| ZN624_HUMAN | 596 |
| ZNF84_HUMAN | 597 |
| ZNF7_HUMAN | 598 |
| ZN891_HUMAN | 599 |
| ZN337_HUMAN | 600 |
| Z705G_HUMAN | 601 |
| ZN529_HUMAN | 602 |
| ZN729_HUMAN | 603 |
| ZN419_HUMAN | 604 |
| Z705A_HUMAN | 605 |
| ZNF45_HUMAN | 606 |
| ZN302_HUMAN | 607 |
| ZN486_HUMAN | 608 |

TABLE 4-continued

Exemplary Effector
Domains Suitable for
Silencing Gene Expression

| Protein | SEQ |
|---|---|
| ZN621_HUMAN | 609 |
| ZN688_HUMAN | 610 |
| ZN33A_HUMAN | 611 |
| ZN554_HUMAN | 612 |
| ZN878_HUMAN | 613 |
| ZN772_HUMAN | 614 |
| ZN224_HUMAN | 615 |
| ZN184_HUMAN | 616 |
| ZN544_HUMAN | 617 |
| ZNF57_HUMAN | 618 |
| ZN283_HUMAN | 619 |
| ZN549_HUMAN | 620 |
| ZN211_HUMAN | 621 |
| ZN615_HUMAN | 622 |
| ZN253_HUMAN | 623 |
| ZN226_HUMAN | 624 |
| ZN730_HUMAN | 625 |
| Z585A_HUMAN | 626 |
| ZN732_HUMAN | 627 |
| ZN681_HUMAN | 628 |
| ZN667_HUMAN | 629 |
| ZN649_HUMAN | 630 |
| ZN470_HUMAN | 631 |
| ZN484_HUMAN | 632 |
| ZN431_HUMAN | 633 |
| ZN382_HUMAN | 634 |
| ZN254_HUMAN | 635 |
| ZN124_HUMAN | 636 |
| ZN607_HUMAN | 637 |
| ZN317_HUMAN | 638 |
| ZN620_HUMAN | 639 |
| ZN141_HUMAN | 640 |
| ZN584_HUMAN | 641 |
| ZN540_HUMAN | 642 |
| ZN75D_HUMAN | 643 |
| ZN555_HUMAN | 644 |
| ZN658_HUMAN | 645 |
| ZN684_HUMAN | 646 |
| RBAK_HUMAN | 647 |
| ZN829_HUMAN | 648 |
| ZN582_HUMAN | 649 |
| ZN112_HUMAN | 650 |
| ZN716_HUMAN | 651 |
| HKR1_HUMAN | 652 |
| ZN350_HUMAN | 653 |
| ZN480_HUMAN | 654 |
| ZN416_HUMAN | 655 |
| ZNF92_HUMAN | 656 |
| ZN100_HUMAN | 657 |
| ZN736_HUMAN | 658 |
| ZNF74_HUMAN | 659 |
| CBX1_HUMAN | 660 |
| ZN443_HUMAN | 661 |
| ZN195_HUMAN | 662 |
| ZN530_HUMAN | 663 |
| ZN782_HUMAN | 664 |
| ZN791_HUMAN | 665 |
| ZN331_HUMAN | 666 |
| Z354C_HUMAN | 667 |
| ZN157_HUMAN | 668 |
| ZN727_HUMAN | 669 |
| ZN550_HUMAN | 670 |
| ZN793_HUMAN | 671 |
| ZN235_HUMAN | 672 |
| ZNF8_HUMAN | 673 |
| ZN724_HUMAN | 674 |
| ZN573_HUMAN | 675 |
| ZN577_HUMAN | 676 |
| ZN789_HUMAN | 677 |
| ZN718_HUMAN | 678 |
| ZN300_HUMAN | 679 |
| ZN383_HUMAN | 680 |
| ZN429_HUMAN | 681 |
| ZN677_HUMAN | 682 |

TABLE 4-continued

TABLE 4-continued

| Exemplary Effector Domains Suitable for Silencing Gene Expression | |
| --- | --- |
| Protein | SEQ |
| ZN850_HUMAN | 683 |
| ZN454_HUMAN | 684 |
| ZN257_HUMAN | 685 |
| ZN264_HUMAN | 686 |
| ZFP82_HUMAN | 687 |
| ZFP14_HUMAN | 688 |
| ZN485_HUMAN | 689 |
| ZN737_HUMAN | 690 |
| ZNF44_HUMAN | 691 |
| ZN596_HUMAN | 692 |
| ZN565_HUMAN | 693 |
| ZN543_HUMAN | 694 |
| ZFP69_HUMAN | 695 |
| SUMO1_HUMAN | 696 |
| ZNF12_HUMAN | 697 |
| ZN169_HUMAN | 698 |
| ZN433_HUMAN | 699 |
| SUMO3_HUMAN | 700 |
| ZNF98_HUMAN | 701 |
| ZN175_HUMAN | 702 |
| ZN347_HUMAN | 703 |
| ZNF25_HUMAN | 704 |
| ZN519_HUMAN | 705 |
| Z585B_HUMAN | 706 |
| ZIM3_HUMAN | 707 |
| ZN517_HUMAN | 708 |
| ZN846_HUMAN | 709 |
| ZN230_HUMAN | 710 |
| ZNF66_HUMAN | 711 |
| ZFP1_HUMAN | 712 |
| ZN713_HUMAN | 713 |
| ZN816_HUMAN | 714 |
| ZN426_HUMAN | 715 |
| ZN674_HUMAN | 716 |
| ZN627_HUMAN | 717 |
| ZNF20_HUMAN | 718 |
| Z587B_HUMAN | 719 |
| ZN316_HUMAN | 720 |
| ZN233_HUMAN | 721 |
| ZN611_HUMAN | 722 |
| ZN556_HUMAN | 723 |
| ZN234_HUMAN | 724 |
| ZN560_HUMAN | 725 |
| ZNF77_HUMAN | 726 |
| ZN682_HUMAN | 727 |
| ZN614_HUMAN | 728 |
| ZN785_HUMAN | 729 |
| ZN445_HUMAN | 730 |
| ZFP30_HUMAN | 731 |
| ZN225_HUMAN | 732 |
| ZN551_HUMAN | 733 |
| ZN610_HUMAN | 734 |
| ZN528_HUMAN | 735 |
| ZN284_HUMAN | 736 |
| ZN418_HUMAN | 737 |
| MPP8_HUMAN | 738 |
| ZN490_HUMAN | 739 |
| ZN805_HUMAN | 740 |
| Z780B_HUMAN | 741 |
| ZN763_HUMAN | 742 |
| ZN285_HUMAN | 743 |
| ZNF85_HUMAN | 744 |
| ZN223_HUMAN | 745 |
| ZNF90_HUMAN | 746 |
| ZN557_HUMAN | 747 |
| ZN425_HUMAN | 748 |
| ZN229_HUMAN | 749 |
| ZN606_HUMAN | 750 |
| ZN155_HUMAN | 751 |
| ZN222_HUMAN | 752 |
| ZN442_HUMAN | 753 |
| ZNF91_HUMAN | 754 |
| ZN135_HUMAN | 755 |
| ZN778_HUMAN | 756 |

| Exemplary Effector Domains Suitable for Silencing Gene Expression | |
| --- | --- |
| Protein | SEQ |
| RYBP_HUMAN | 757 |
| ZN534_HUMAN | 758 |
| ZN586_HUMAN | 759 |
| ZN567_HUMAN | 760 |
| ZN440_HUMAN | 761 |
| ZN583_HUMAN | 762 |
| ZN441_HUMAN | 763 |
| ZNF43_HUMAN | 764 |
| CBX5_HUMAN | 765 |
| ZN589_HUMAN | 766 |
| ZNF10_HUMAN | 767 |
| ZN563_HUMAN | 768 |
| ZN561_HUMAN | 769 |
| ZN136_HUMAN | 770 |
| ZN630_HUMAN | 771 |
| ZN527_HUMAN | 772 |
| ZN333_HUMAN | 773 |
| Z324B_HUMAN | 774 |
| ZN786_HUMAN | 775 |
| ZN709_HUMAN | 776 |
| ZN792_HUMAN | 777 |
| ZN599_HUMAN | 778 |
| ZN613_HUMAN | 779 |
| ZF69B_HUMAN | 780 |
| ZN799_HUMAN | 781 |
| ZN569_HUMAN | 782 |
| ZN564_HUMAN | 783 |
| ZN546_HUMAN | 784 |
| ZFP92_HUMAN | 785 |
| YAF2_HUMAN | 786 |
| ZN723_HUMAN | 787 |
| ZNF34_HUMAN | 788 |
| ZN439_HUMAN | 789 |
| ZFP57_HUMAN | 790 |
| ZNF19_HUMAN | 791 |
| ZN404_HUMAN | 792 |
| ZN274_HUMAN | 793 |
| CBX3_HUMAN | 794 |
| ZNF30_HUMAN | 795 |
| ZN250_HUMAN | 796 |
| ZN570_HUMAN | 797 |
| ZN675_HUMAN | 798 |
| ZN695_HUMAN | 799 |
| ZN548_HUMAN | 800 |
| ZN132_HUMAN | 801 |
| ZN738_HUMAN | 802 |
| ZN420_HUMAN | 803 |
| ZN626_HUMAN | 804 |
| ZN559_HUMAN | 805 |
| ZN460_HUMAN | 806 |
| ZN268_HUMAN | 807 |
| ZN304_HUMAN | 808 |
| ZIM2_HUMAN | 809 |
| ZN605_HUMAN | 810 |
| ZN844_HUMAN | 811 |
| SUMO5_HUMAN | 812 |
| ZN101_HUMAN | 813 |
| ZN783_HUMAN | 814 |
| ZN417_HUMAN | 815 |
| ZN182_HUMAN | 816 |
| ZN823_HUMAN | 817 |
| ZN177_HUMAN | 818 |
| ZN197_HUMAN | 819 |
| ZN717_HUMAN | 820 |
| ZN669_HUMAN | 821 |
| ZN256_HUMAN | 822 |
| ZN251_HUMAN | 823 |
| CBX4_HUMAN | 824 |
| PCGF2_HUMAN | 825 |
| CDY2_HUMAN | 826 |
| CDYL2_HUMAN | 827 |
| HERC2_HUMAN | 828 |
| ZN562_HUMAN | 829 |
| ZN461_HUMAN | 830 |

TABLE 4-continued

Exemplary Effector
Domains Suitable for
Silencing Gene Expression

| Protein | SEQ |
| --- | --- |
| Z324A_HUMAN | 831 |
| ZN766_HUMAN | 832 |
| ID2_HUMAN | 833 |
| TOX_HUMAN | 834 |
| ZN274_HUMAN | 835 |
| SCMH1_HUMAN | 836 |
| ZN214_HUMAN | 837 |
| CBX7_HUMAN | 838 |
| ID1_HUMAN | 839 |
| CREM_HUMAN | 840 |
| SCX_HUMAN | 841 |
| ASCL1_HUMAN | 842 |
| ZN764_HUMAN | 843 |
| SCML2_HUMAN | 844 |
| TWST1_HUMAN | 845 |
| CREB1_HUMAN | 846 |
| TERF1_HUMAN | 847 |
| ID3_HUMAN | 848 |
| CBX8_HUMAN | 849 |
| CBX4_HUMAN | 850 |
| GSX1_HUMAN | 851 |
| NKX22_HUMAN | 852 |
| ATF1_HUMAN | 853 |
| TWST2_HUMAN | 854 |
| ZNF17_HUMAN | 855 |
| TOX3_HUMAN | 856 |
| TOX4_HUMAN | 857 |
| ZMYM3_HUMAN | 858 |
| I2BP1_HUMAN | 859 |
| RHXF1_HUMAN | 860 |
| SSX2_HUMAN | 861 |
| I2BPL_HUMAN | 862 |
| ZN680_HUMAN | 863 |
| CBX1_HUMAN | 864 |
| TRI68_HUMAN | 865 |
| HXA13_HUMAN | 866 |
| PHC3_HUMAN | 867 |
| TCF24_HUMAN | 868 |
| CBX3_HUMAN | 869 |
| HXB13_HUMAN | 870 |
| HEY1_HUMAN | 871 |
| PHC2_HUMAN | 872 |
| ZNF81_HUMAN | 873 |
| FIGLA_HUMAN | 874 |
| SAM11_HUMAN | 875 |
| KMT2B_HUMAN | 876 |
| HEY2_HUMAN | 877 |
| JDP2_HUMAN | 878 |
| HXC13_HUMAN | 879 |
| ASCL4_HUMAN | 880 |
| HHEX_HUMAN | 881 |
| HERC2_HUMAN | 882 |
| GSX2_HUMAN | 883 |
| BIN1_HUMAN | 884 |
| ETV7_HUMAN | 885 |
| ASCL3_HUMAN | 886 |
| PHC1_HUMAN | 887 |
| OTP_HUMAN | 888 |
| I2BP2_HUMAN | 889 |
| VGLL2_HUMAN | 890 |
| HXA11_HUMAN | 891 |
| PDLI4_HUMAN | 892 |
| ASCL2_HUMAN | 893 |
| CDX4_HUMAN | 894 |
| ZN860_HUMAN | 895 |
| LMBL4_HUMAN | 896 |
| PDIP3_HUMAN | 897 |
| NKX25_HUMAN | 898 |
| CEBPB_HUMAN | 899 |
| ISL1_HUMAN | 900 |
| CDX2_HUMAN | 901 |
| PROP1_HUMAN | 902 |
| SIN3B_HUMAN | 903 |
| SMBT1_HUMAN | 904 |

TABLE 4-continued

Exemplary Effector
Domains Suitable for
Silencing Gene Expression

| Protein | SEQ |
| --- | --- |
| HXC11_HUMAN | 905 |
| HXC10_HUMAN | 906 |
| PRS6A_HUMAN | 907 |
| VSX1_HUMAN | 908 |
| NKX23_HUMAN | 909 |
| MTG16_HUMAN | 910 |
| HMX3_HUMAN | 911 |
| HMX1_HUMAN | 912 |
| KIF22_HUMAN | 913 |
| CSTF2_HUMAN | 914 |
| CEBPE_HUMAN | 915 |
| DLX2_HUMAN | 916 |
| ZMYM3_HUMAN | 917 |
| PPARG_HUMAN | 918 |
| PRIC1_HUMAN | 919 |
| UNC4_HUMAN | 920 |
| BARX2_HUMAN | 921 |
| ALX3_HUMAN | 922 |
| TCF15_HUMAN | 923 |
| TERA_HUMAN | 924 |
| VSX2_HUMAN | 925 |
| HXD12_HUMAN | 926 |
| CDX1_HUMAN | 927 |
| TCF23_HUMAN | 928 |
| ALX1_HUMAN | 929 |
| HXA10_HUMAN | 930 |
| RX_HUMAN | 931 |
| CXXC5_HUMAN | 932 |
| SCML1_HUMAN | 933 |
| NFIL3_HUMAN | 934 |
| DLX6_HUMAN | 935 |
| MTG8_HUMAN | 936 |
| CBX8_HUMAN | 937 |
| CEBPD_HUMAN | 938 |
| SEC13_HUMAN | 939 |
| FIP1_HUMAN | 940 |
| ALX4_HUMAN | 941 |
| LHX3_HUMAN | 942 |
| PRIC2_HUMAN | 943 |
| MAGI3_HUMAN | 944 |
| NELL1_HUMAN | 945 |
| PRRX1_HUMAN | 946 |
| MTG8R_HUMAN | 947 |
| RAX2_HUMAN | 948 |
| DLX3_HUMAN | 949 |
| DLX1_HUMAN | 950 |
| NKX26_HUMAN | 951 |
| NAB1_HUMAN | 952 |
| SAMD7_HUMAN | 953 |
| PITX3_HUMAN | 954 |
| WDR5_HUMAN | 955 |
| MEOX2_HUMAN | 956 |
| NAB2_HUMAN | 957 |
| DHX8_HUMAN | 958 |
| FOXA2_HUMAN | 959 |
| CBX6_HUMAN | 960 |
| EMX2_HUMAN | 961 |
| CPSF6_HUMAN | 962 |
| HXC12_HUMAN | 963 |
| KDM4B_HUMAN | 964 |
| LMBL3_HUMAN | 965 |
| PHX2A_HUMAN | 966 |
| EMX1_HUMAN | 967 |
| NC2B_HUMAN | 968 |
| DLX4_HUMAN | 969 |
| SRY_HUMAN | 970 |
| ZN777_HUMAN | 971 |
| NELL1_HUMAN | 972 |
| ZN398_HUMAN | 973 |
| GATA3_HUMAN | 974 |
| BSH_HUMAN | 975 |
| SF3B4_HUMAN | 976 |
| TEAD1_HUMAN | 977 |
| TEAD3_HUMAN | 978 |

TABLE 4-continued

Exemplary Effector
Domains Suitable for
Silencing Gene Expression

| Protein | SEQ |
|---|---|
| RGAP1_HUMAN | 979 |
| PHF1_HUMAN | 980 |
| FOXA1_HUMAN | 981 |
| GATA2_HUMAN | 982 |
| FOXO3_HUMAN | 983 |
| ZN212_HUMAN | 984 |
| IRX4_HUMAN | 985 |
| ZBED6_HUMAN | 986 |
| LHX4_HUMAN | 987 |
| SIN3A_HUMAN | 988 |
| RBBP7_HUMAN | 989 |
| NKX61_HUMAN | 990 |
| TRI68_HUMAN | 991 |
| R51A1_HUMAN | 992 |
| MB3L1_HUMAN | 993 |
| DLX5_HUMAN | 994 |
| NOTC1_HUMAN | 995 |
| TERF2_HUMAN | 996 |
| ZN282_HUMAN | 997 |
| RGS12_HUMAN | 998 |
| ZN840_HUMAN | 999 |
| SPI2B_HUMAN | 1000 |
| PAX7_HUMAN | 1001 |
| NKX62_HUMAN | 1002 |
| ASXL2_HUMAN | 1003 |
| FOXO1_HUMAN | 1004 |
| GATA3_HUMAN | 1005 |
| GATA1_HUMAN | 1006 |
| ZMYM5_HUMAN | 1007 |
| ZN783_HUMAN | 1008 |
| SPI2B_HUMAN | 1009 |
| LRP1_HUMAN | 1010 |
| MIXL1_HUMAN | 1011 |
| SGT1_HUMAN | 1012 |
| LMCD1_HUMAN | 1013 |
| CEBPA_HUMAN | 1014 |
| GATA2_HUMAN | 1015 |
| SOX14_HUMAN | 1016 |
| WTIP_HUMAN | 1017 |
| PRP19_HUMAN | 1018 |
| CBX6_HUMAN | 1019 |
| NKX11_HUMAN | 1020 |
| RBBP4_HUMAN | 1021 |
| DMRT2_HUMAN | 1022 |
| SMCA2_HUMAN | 1023 |
| ZNF10_HUMAN | 1024 |
| EED_HUMAN | 1025 |
| RCOR1_HUMAN | 1026 |

A functional analog of any one of the above-listed proteins, i.e., a molecule having the same or substantially the same biological function (e.g., retaining 70% or more, 80% or more, 90% or more, 95% or more, or 98% or more) of the protein's transcription factor function) is encompassed by the present disclosure. For example, the functional analog may be an isoform or a variant of the above-listed protein, e.g., containing a portion of the above protein with or without additional amino acid residues and/or containing mutations relative to the above protein. In some embodiments, the functional analog has a sequence identity that is at least 75, 80, 85, 90, 95, 98, or 99% to one of the sequences listed in Table 4. Homologs, orthologs, and mutants of the above-listed proteins are also contemplated.

In certain embodiments, an epigenetic editor described herein comprises a KRAB domain derived from KOX1, ZIM3, ZFP28, or ZN627, and/or an effector domain derived from KAP1, MECP2, HPla, HP1b, CBX8, CDYL2, TOX, TOX3, TOX4, EED, EZH2, RBBP4, RCOR1, or SCML2, optionally wherein the parental protein is a human protein.

In particular embodiments, an epigenetic editor described herein comprises a domain derived from KOX1, ZIM3, ZFP28, and/or ZN627, optionally wherein the parental protein is a human protein. In certain embodiments, the epigenetic editor may comprise a KRAB domain derived from KOX1 (ZNF10), e.g., a human KOX1. In certain embodiments, the epigenetic editor may comprise a KRAB domain derived from ZIM3 (ZNF657 or ZNF264), e.g., a human ZIM3. In certain embodiments, the epigenetic editor may comprise a KRAB domain derived from ZFP28, e.g., a human ZFP28. In certain embodiments, the epigenetic editor may comprise a KRAB domain derived from ZN627, e.g., a human ZN627. In certain embodiments, an epigenetic editor described herein may comprise a CDYL2, e.g., a human CDYL2, and/or a TOX domain (e.g., a human TOX domain) in combination with a KOX1 KRAB domain (e.g., a human KOX1 KRAB domain).

In certain embodiments, an epigenetic effector described herein comprises a repression domain derived from ZNF10 (SEQ ID NO: 1024). For example, the repression domain may comprise the sequence of SEQ ID NO: 1024, or a sequence at least 75%, 80%, 85%, 90%, 91%, 92%, 93%, 94%, 95%, 96%, 97%, 98%, or 99% identical to SEQ ID NO: 1024.

B. DNA Methyltransferases

In some embodiments, an effector domain of an epigenetic editor described herein alters target gene expression through DNA modification, such as methylation. Highly methylated areas of DNA tend to be less transcriptionally active than less methylated areas. DNA methylation occurs primarily at CpG sites (shorthand for "C-phosphate-G-" or "cytosine-phosphate-guanine" sites). Many mammalian genes have promoter regions near or including CpG islands (nucleic acid regions with a high frequency of CpG dinucleotides).

An effector domain described herein may be, e.g., a DNA methyltransferase (DNMT) or a catalytic domain thereof, or may be capable of recruiting a DNA methyltransferase. DNMTs encompass enzymes that catalyze the transfer of a methyl group to a DNA nucleotide, such as canonical cytosine-5 DNMTs that catalyze the addition of methyl groups to genomic DNA (e.g., DNMT1, DNMT3A, DNMT3B, and DNMT3C). This term also encompasses non-canonical family members that do not catalyze methylation themselves but that recruit (including activate) catalytically active DNMTs; a non-limiting example of such a DNMT is DNMT3L. See, e.g., Lyko, Nat Review (2018) 19:81-92. Unless otherwise indicated, a DNMT domain may refer to a polypeptide domain derived from a catalytically active DNMT (e.g., DNMT1, DNMT3A, and DNMT3B) or from a catalytically inactive DNMT (e.g., DNMT3L). A DNMT may repress expression of the target gene through the recruitment of repressive regulatory proteins. In some embodiments, the methylation is at a CG (or CpG) dinucleotide sequence. In some embodiments, the methylation is at a CHG or CHH sequence, where H is any one of A, T, or C. In some embodiments, DNMTs in the epigenetic editors may include, e.g., DNMT1, DNMT3A, DNMT3B, and/or DNMT3C. In some embodiments, the DNMT is a mammalian (e.g., human or murine) DNMT. In particular embodiments, the DNMT is DNMT3A (e.g., human DNMT3A). In certain embodiments, an epigenetic editor described herein comprises a DNMT3A domain comprising SEQ ID NO: 1028, or a sequence at least 75%, 80%, 85%, 90%, 91%, 92%, 93%, 94%, 95%, 96%, 97%, 98%, or 99% identical to SEQ ID NO: 1028. In certain embodiments, an epigenetic editor described herein comprises a DNMT3A domain comprising SEQ ID NO: 1029, or a sequence at least 75%, 80%, 85%, 90%, 91%, 92%, 93%, 94%, 95%, 96%, 97%, 98%, or 99% identical to SEQ ID NO: 1029. In some embodiments, the DNMT3A domain may have, e.g., a mutation at position H739 (such as H739A or H739E), R771 (such as R771L) and/or R836 (such as R836A or R836Q), or any combination thereof (numbering according to SEQ ID NO: 1028).

In some embodiments, an effector domain described herein may be a DNMT-like domain. As used herein a "DNMT-like domain" is a regulatory factor of DNA methyltransferase that may activate or recruit other DNMT domains, but does not itself possess methylation activity. In some embodiments, the DNMT-like domain is a mammalian (e.g., human or mouse) DNMT-like domain. In certain embodiments, the DNMT-like domain is DNMT3L, which may be, for example, human DNMT3L or mouse DNMT3L. In certain embodiments, an epigenetic editor described herein comprises a DNMT3L domain comprising SEQ ID NO: 1032, or a sequence at least 75%, 80%, 85%, 90%, 91%, 92%, 93%, 94%, 95%, 96%, 97%, 98%, or 99% identical to SEQ ID NO: 1032. In certain embodiments, an epigenetic editor herein comprises a DNMT3L domain comprising SEQ ID NO: 1033, or a sequence at least 75%, 80%, 85%, 90%, 91%, 92%, 93%, 94%, 95%, 96%, 97%, 98%, or 99% identical to SEQ ID NO: 1033. In certain embodiments, an epigenetic editor described herein comprises a DNMT3L domain comprising SEQ ID NO: 1034, or a sequence at least 75%, 80%, 85%, 90%, 91%, 92%, 93%, 94%, 95%, 96%, 97%, 98%, or 99% identical to SEQ ID NO: 1034. In certain embodiments, an epigenetic editor described herein comprises a DNMT3L domain comprising SEQ ID NO: 1035, or a sequence at least 75%, 80%, 85%, 90%, 91%, 92%, 93%, 94%, 95%, 96%, 97%, 98%, or 99% identical to SEQ ID NO: 1035. In some embodiments, the DNMT3L domain may have, e.g., a mutation corresponding to that at position D226 (such as D226V), Q268 (such as Q268K), or both (numbering according to SEQ ID NO: 1032).

In certain embodiments, an epigenetic editor herein may comprise comprising both DNMT and DNMT-like effector domains. For example, the epigenetic editor may comprise a DNMT3A-3L domain, wherein DNMT3A and DNMT3L may be covalently linked. In other embodiments, an epigenetic editor described herein may comprise an effector domain that comprises only a DNMT3A domain (e.g., human DNMT3A), or only a DNMT-like domain (e.g., DNMT3L, which may be human or mouse DNMT3L).

Table 5 below provides exemplary methyltransferases from which an effector domain of an epigenetic editor described herein may be derived. See Table 18 for sequences of these exemplary methyltransferases.

TABLE 5

| Exemplary DNA Methyltransferase Sequences | | | |
|---|---|---|---|
| Protein Name | Species | Target | Protein Sequence |
| DNMT1 | Human | 5mC | SEQ ID NO: 1027 |
| DNMT3A | Human | 5mC | SEQ ID NO: 1028 |
| DNMT3A (catalytic domain) | Human | 5mC | SEQ ID NO: 1029 |
| DNMT3B | Human | 5mC | SEQ ID NO: 1030 |
| DNMT3C | Mouse | 5mC | SEQ ID NO: 1031 |
| DNMT3L | Human | 5mC | SEQ ID NO: 1032 |
| DNMT3L (catalytic domain) | Human | 5mC | SEQ ID NO: 1033 |
| DNMT3L | Mouse | 5mC | SEQ ID NO: 1034 |
| DNMT3L (catalytic domain) | Mouse | 5mC | SEQ ID NO: 1035 |
| TRDMT1 (DNMT2) | Human | tRNA 5mC | SEQ ID NO: 1036 |
| M.MpeI | Mycoplasma penetrans | 5mC | SEQ ID NO: 1037 |
| M.SssI | Spiroplasma monobiae | 5mC | SEQ ID NO: 1038 |
| M.HpaII | Haemophilus parainfluenzae | 5mC (CCGG) | SEQ ID NO: 1039 |
| M.AluI | Arthrobacter luteus | 5mC (AGCT) | SEQ ID NO: 1040 |
| M.HaeIII | Haemophilus aegyptius | 5mC (GGCC) | SEQ ID NO: 1041 |
| M.HhaI | Haemophilus haemolyticus | 5mC (GCGC) | SEQ ID NO: 1042 |
| M.MspI | Moraxella | 5mC (CCGG) | SEQ ID NO: 1043 |
| Masc1 | Ascobolus | 5mC | SEQ ID NO: 1044 |
| MET1 | Arabidopsis | 5mC | SEQ ID NO: 1045 |
| Masc2 | Ascobolus | 5mC | SEQ ID NO: 1046 |
| Dim-2 | Neurospora | 5mC | SEQ ID NO: 1047 |
| dDnmt2 | Drosophila | 5mC | SEQ ID NO: 1048 |
| Pmt1 | S. pombe | 5mC | SEQ ID NO: 1049 |
| DRM1 | Arabidopsis | 5mC | SEQ ID NO: 1050 |
| DRM2 | Arabidopsis | 5mC | SEQ ID NO: 1051 |
| CMT1 | Arabidopsis | 5mC | SEQ ID NO: 1052 |
| CMT2 | Arabidopsis | 5mC | SEQ ID NO: 1053 |
| CMT3 | Arabidopsis | 5mC | SEQ ID NO: 1054 |
| Rid | Neurospora | 5mC | SEQ ID NO: 1055 |
| hsdM gene | bacteria (E. coli, strain 12) | m6A | SEQ ID NO: 1056 |
| hsdS gene | bacteria (E. coli, strain 12) | m6A | SEQ ID NO: 1057 |
| M.TaqI | Bacteria (Thermus aquaticus) | m6A | SEQ ID NO: 1058 |
| M.EcoDam | E. coli | m6A | SEQ ID NO: 1059 |
| M.CcrMI | Caulobacter crescentus | m6A | SEQ ID NO: 1060 |
| CamA | Clostridioides difficile | m6A | SEQ ID NO: 1061 |

A functional analog of any one of the above-listed proteins, i.e., a molecule having the same or substantially the same biological function (e.g., retaining 70% or more, 80% or more, 90% or more, 95% or more, or 98% or more) of the protein's DNA methylation function or recruiting function) is encompassed by the present disclosure. For example, the functional analog may be an isoform or a variant of the above-listed protein, e.g., containing a portion of the above protein with or without additional amino acid residues and/or containing mutations relative to the above protein. In some embodiments, the functional analog has a sequence identity that is at least 75, 80, 85, 90, 95, 98, or 99% to one of the sequences listed in Table 5. In some embodiments, the effector domain herein comprises only the functional domain (or functional analog thereof), e.g., the catalytical domain or recruiting domain, of the above-listed proteins.

As used herein, a DNMT domain (e.g., a DNMT3A domain or a DNMT3L domain) refers to a protein domain that is identical to the parental protein (e.g., a human or murine DNMT3A or DNMT3L) or a functional analog thereof (e.g., having a functional fragment, such as a catalytic fragment or recruiting fragment, of the parental protein; and/or having mutations that improve the activity of the DNMT protein).

An epigenetic editor herein may effect methylation at, e.g., 1, 2, 3, 4, 5, 6, 7, 8, 9, 10, 11, 12, 13, 14, 15, 16, 17, 18, 19, 20, 30, 40, 50, 60, 70, 80, 90, 100, 200, 300, 400, 500, 600, 700, 800, 900, or 1000 or more CpG dinucleotide sequences in the target gene or chromosome. The CpG dinucleotide sequences may be located within or near the target gene in CpG islands, or may be located in a region that is not a CpG island. A CpG island generally refers to a nucleic acid sequence or chromosome region that comprises a high frequency of CpG dinucleotides. For example, a CpG island may comprise at least 50% GC content. The CpG island may have a high observed-to-expected CpG ratio, for example, an observed-to-expected CpG ratio of at least 60%. As used herein, an observed-to-expected CpG ratio is determined by Number of CpG*(sequence length)/(Number of C*Number of G). In some embodiments, the CpG island has an observed-to-expected CpG ratio of at least 60%, 70%, 80%, 90% or more. A CpG island may be a sequence or region of, e.g., at least 200, 250, 300, 350, 400, 450, 500, 550, 600, 650, 700, 750, or 800 nucleotides. In some embodiments, only 1, or less than 2, 3, 4, 5, 6, 7, 8, 9, 10, 11, 12, 13, 14, 15, 16, 17, 18, 19, 20, 30, 40, or 50 CpG dinucleotides are methylated by the epigenetic editor.

In some embodiments, an epigenetic editor herein effects methylation at a hypomethylated nucleic acid sequence, i.e., a sequence that may lack methyl groups on the 5-methyl cytosine nucleotides (e.g., in CpG) as compared to a standard control. Hypomethylation may occur, for example, in aging cells or in cancer (e.g., early stages of neoplasia) relative to a younger cell or non-cancer cell, respectively.

In some embodiments, an epigenetic editor described herein induces methylation at a hypermethylated nucleic acid sequence.

In some embodiments, methylation may be introduced by the epigenetic editor at a site other than a CpG dinucleotide. For example, the target gene sequence may be methylated at the C nucleotide of CpA, CpT, or CpC sequences. In some embodiments, an epigenetic editor comprises a DNMT3A domain and effects methylation at CpG, CpA, CpT, CpC sequences, or any combination thereof. In some embodiments, an epigenetic editor comprises a DNMT3A domain that lacks a regulatory subdomain and only maintains a catalytic domain. In some embodiments, the epigenetic editor comprising a DNMT3A catalytic domain effects methylation exclusively at CpG sequences. In some embodiments, an epigenetic editor comprising a DNMT3A domain that comprises a mutation, e.g. a R836A or R836Q mutation (numbering according to SEQ ID NO: 1028), has higher methylation activity at CpA, CpC, and/or CpT sequences as compared to an epigenetic editor comprising a wildtype DNMT3A domain.

C. Histone Modifiers

In some embodiments, an effector domain of an epigenetic editor herein mediates histone modification. Histone modifications play a structural and biochemical role in gene transcription, such as by formation or disruption of the nucleosome structure that binds to the histone and prevents gene transcription. Histone modifications may include, for example, acetylation, deacetylation, methylation, phosphorylation, ubiquitination, SUMOylation and the like, e.g., at their N-terminal ends ("histone tails"). These modifications maintain or specifically convert chromatin structure, thereby controlling responses such as gene expression, DNA replication, DNA repair, and the like, which occur on chromosomal DNA. Post-translational modification of histones is an epigenetic regulatory mechanism and is considered essential for the genetic regulation of eukaryotic cells. Recent studies have revealed that chromatin remodeling factors such as SWI/SNF, RSC, NURF, NRD, and the like, which facilitate transcription factor access to DNA by modifying the nucleosome structure; histone acetyltransferases (HATs) that regulate the acetylation state of histones; and histone deacetylases (HDACs), act as important regulators.

In particular, the unstructured N-termini of histones may be modified by acetylation, deacetylation, methylation, ubiquitylation, phosphorylation, SUMOylation, ribosylation, citrullination O-GlcNAcylation, crotonylation, or any combination thereof. For example, histone acetyltransferases (HATs) utilize acetyl-CoA as a cofactor and catalyze the transfer of an acetyl group to the epsilon amino group of the lysine side chains. This neutralizes the lysine's positive charge and weakens the interactions between histones and DNA, thus opening the chromosomes for transcription factors to bind and initiate transcription. Acetylation of K14 and K9 lysines of histone H3 by histone acetyltransferase enzymes may be linked to transcriptional competence in humans. Lysine acetylation may directly or indirectly create binding sites for chromatin-modifying enzymes that regulate transcriptional activation. On the other hand, histone methylation of lysine 9 of histone H3 may be associated with heterochromatin, or transcriptionally silent chromatin.

In certain embodiments, an effector domain of an epigenetic editor described herein comprises a histone methyltransferase domain. The effector domain may comprise, for example, a DOT1L domain, a SET domain, a SUV39H1 domain, a G9a/EHMT2 protein domain, an EZH1 domain, an EZH2 domain, a SETDB1 domain, or any combination thereof. In particular embodiments, the effector domain comprises a histone-lysine-N-methyltransferase SETDB1 domain.

In some embodiments, the effector domain comprises a histone deacetylase protein domain. In certain embodiments, the effector domain comprises a HDAC family protein domain, for example, a HDAC1, HDAC3, HDAC5, HDAC7, or HDAC9 protein domain. In particular embodiments, the effector domain comprises a nucleosome remodeling and deacetylase complex (NURD), which removes acetyl groups from histones.

D. Other Effector Domains

In some embodiments, the effector domain comprises a tripartite motif containing protein (TRIM28, TIF1-beta, or KAP1). In certain embodiments, the effector domain comprises one or more KAP1 proteins. A KAP1 protein in an epigenetic editor herein may form a complex with one or more other effector domains of the epigenetic editor or one or more proteins involved in modulation of gene expression in a cellular environment. For example, KAP1 may be recruited by a KRAB domain of a transcriptional repressor. A KAP1 protein domain may interact with or recruit one or more protein complexes that reduces or silences gene expression. In some embodiments, KAP1 interacts with or recruits a histone deacetylase protein, a histone-lysine methyltransferase protein, a chromatin remodeling protein, and/ or a heterochromatin protein. For example, a KAP1 protein domain may interact with or recruit a heterochromatin protein 1 (HP1) protein, a SETDB1 protein, an HDAC protein, and/or a NuRD protein complex component. In some embodiments, a KAP1 protein domain interacts with or recruits a ZFP90 protein (e.g., isoform 2 of ZFP90), and/or a FOXP3 protein. An exemplary KAP1 amino acid sequence is shown in SEQ ID NO: 1062.

In some embodiments, the effector domain comprises a protein domain that interacts with or is recruited by one or more DNA epigenetic marks. For example, the effector domain may comprise a methyl CpG binding protein 2 (MECP2) protein that interacts with methylated DNA nucleotides in the target gene (which may or may not be at a CpG island of the target gene). An MECP2 protein domain in an epigenetic editor described herein may induce condensed chromatin structure, thereby reducing or silencing expression of the target gene. In some embodiments, an MECP2 protein domain in an epigenetic editor described herein may interact with a histone deacetylase (e.g. HDAC), thereby repressing or silencing expression of the target gene. In some embodiments, an MECP2 protein domain in an epigenetic editor described herein may block access of a transcription factor or transcriptional activator to the target sequence, thereby repressing or silencing expression of the target gene. An exemplary MECP2 amino acid sequence is shown in SEQ ID NO: 1063.

Also contemplated as effector domains for the epigenetic editors described herein are, e.g., a chromoshadow domain, a ubiquitin-2 like Rad60 SUMO-like (Rad60-SLD/SUMO) domain, a chromatin organization modifier domain (Chromo) domain, a Yaf2/RYBP C-terminal binding motif domain (YAF2_RYBP), a CBX family C-terminal motif domain (CBX7_C), a zinc finger C3HC4 type (RING finger) domain (ZF-C3HC4_2), a cytochrome b5 domain (Cyt-b5), a helix-loop-helix domain (HLH), a helix-hairpin-helix motif domain (e.g., HHH_3), a high mobility group box domain (HMG-box), a basic leucine zipper domain (e.g., bZIP_1 or bZIP_2), a Myb_DNA-binding domain, a homeodomain, a MYM-type Zinc finger with FCS sequence domain (ZF-FCS), an interferon regulatory factor 2-binding protein zinc finger domain (IRF-2BP1_2), an SSX repression domain (SSXRD), a B-box-type zinc finger domain (ZF-B_box), a CXXC zinc finger domain (ZF-CXXC), a regulator of chromosome condensation 1 domain (RCC1), an SRC homology 3 domain (SH3_9), a sterile alpha motif domain (SAM_1), a sterile alpha motif domain (SAM_2), a sterile alpha motif/Pointed domain (SAM_PNT), a Vestigial/Tondu family domain (Vg_Tdu), a LIM domain, an RNA recognition motif domain (RRM_1), a paired amphipathic helix domain (PAH), a proteasomal ATPase OB C-terminal domain (Prot_ATP_ID_OB), a nervy homology 2 domain (NHR2), a hinge domain of cleavage stimulation factor subunit 2 (CSTF2_hinge), a PPAR gamma N-terminal region domain (PPARgamma_N), a CDC48 N-terminal domain (CDC48_2), a WD40 repeat domain (WD40), a Fip1 motif domain (Fip1), a PDZ domain (PDZ_6), a Von Willebrand factor type C domain (VWC), a NAB conserved region 1 domain (NCD1), an S1 RNA-binding domain (S1), an HNF3 C-terminal domain (HNF_C), a Tudor domain (Tudor_2), a histone-like transcription factor (CBF/NF-Y) and archacal histone domain (CBFD_NFYB_HMF), a zinc finger protein domain (DUF3669), an EGF-like domain (cEGF), a GATA zinc finger domain (GATA), a TEA/ATTS domain (TEA), a phorbol esters/diacylglycerol binding domain (C1-1), polycomb-like MTF2 factor 2 domain (Mtf2_C), a transactivation domain of FOXO protein family (FOXO-TAD), a homeobox KN domain (Homeobox_KN), a BED zinc finger domain (ZF-BED), a zinc finger of C3HC4-type RING domain (ZF-C3HC4_4), a RAD51 interacting motif domain (RAD51_interact), a p55-binding region of a methyl-CpG-binding domain protein MBD (MBDa), a Notch domain, a Raf-like Ras-binding domain (RBD), a Spin/Ssty family domain (Spin-Ssty), a PHD finger domain (PHD_3), a Low-density lipoprotein receptor domain class A (Ldl_recept_a), a CS domain, a DM DNA-binding domain, and a QLQ domain.

In some embodiments, the effector domain is a protein domain comprising a YAF2_RYBP domain or homeodomain or any combination thereof. In certain embodiments, the homeodomain of the YAF2_RYBP domain is a PRD domain, an NKL domain, a HOXL domain, or a LIM domain. In particular embodiments, the YAF2_RYBP domain may comprise a 32 amino acid Yaf2/RYBP C-terminal binding motif domain (32 aa RYBP).

In some embodiments, the effector domain comprises a protein domain selected from a group consisting of SUMO3 domain, Chromo domain from M phase phosphoprotein 8 (MPP8), chromoshadow domain from Chromobox 1 (CBX1), and SAM_1/SPM domain from Scm Polycomb Group Protein Homolog 1 (SCMH1).

In some embodiments, the effector domain comprises an HNF3 C-terminal domain (HNF_C). The HNF_C domain may be from FOXA1 or FOXA2. In certain embodiments, the HNF_C domain comprises an EH1 (engrailed homology 1) motif.

In some embodiments, the effector domain may comprise an interferon regulatory factor 2-binding protein zinc finger domain (IRF-2BP1_2), a Cyt-b5 domain from DNA repair factor HERC2 E3 ligase, a variant SH3 domain (SH3_9) from Bridging Integrator 1 (BIN1), an HMG-box domain from transcription factor TOX or ZF-C3HC4-2 RING finger domain from the polycomb component PCGF2, a Chromodomain-helicase-DNA binding protein 3 (CHD3) domain, or a ZNF783 domain.

IV. Epigenetic Editors

Provided herein are epigenetic editors, also referred to herein as epigenetic editing systems, that direct epigenetic modification(s) to a target sequence in a gene of interest, e.g., using one or more DNA-binding domains as described herein and one or more effector domains (e.g., epigenetic repression domains) as described herein, in any combination. The DNA-binding domain (in concert with a guide polynucleotide such as one described herein, where the DNA-binding domain is a polynucleotide guided DNA-binding domain) directs the effector domain to epigenetically modify the target sequence, resulting in gene repression or silencing that may be durable and inheritable across cell generations. In some aspects, the epigenetic editors described herein can repress or silence genes reversibly or irreversibly in cells.

In particular embodiments, an epigenetic editor described herein comprises one or more fusion proteins, each comprising (1) DNA-binding domain(s) and (2) effector domain (s). The effector domains may be on one or more fusion proteins comprised by the epigenetic editor. For example, a single fusion protein may comprise all of the effector domains with a DNA-binding domain. Alternatively, the effector domains or subsets thereof may be on separate fusion proteins, each with a DNA-binding domain (which may be the same or different). A fusion protein described herein may further comprise one or more linkers (e.g., peptide linkers), detectable tags, nuclear localization signals (NLSs), or any combination thereof. As used herein, a "fusion protein" refers to a chimeric protein in which two or more coding sequences (e.g., for DNA-binding domain(s) and/or effector domain(s)) are covalently or non-covalently joined, directly or indirectly.

In some embodiments, an epigenetic editor described herein comprises 2, 3, 4, 5, 6, 7, 8, 9, 10, or more effector (e.g., repression) domains, which may be identical or different. In certain embodiments, two or more of said effector domains function synergistically. Combinations of effector domains may comprise DNA methylation domains, histone deacetylation domains, histone methylation domains, and/or scaffold domains that recruit any of the above. For example, an epigenetic editor described herein may comprise one or more transcriptional repressor domains (e.g., a KRAB domain such as KOX1, ZIM3, ZFP28, or ZN627 KRAB) in combination with one or more DNA methylation domains (e.g., a DNMT domain) and/or recruiter domain (e.g., a DNMT3L domain). Such an epigenetic editor may comprise, for instance, a KRAB domain, a DNMT3A domain, and a DNMT3L domain. An epigenetic editor can comprise a DNMT3A domain and a DNMT3L domain and preferably further comprise a KRAB domain. In some embodiments, the epigenetic editor further comprises an additional effector domain (e.g., a KAP1, MECP2, HP1b, CBX8, CDYL2, TOX, TOX3, TOX4, EED, RBBP4, RCOR1, or SCML2 domain). In some embodiments, the additional effector domain is a CDYL2, TOX, TOX3, TOX4, or HPla domain. For example, an epigenetic editor described herein may comprise a CDYL2 and/or a TOX domain in combination with a KRAB domain (e.g., a KOX1 KRAB domain).

A. Linkers

A fusion protein as described herein may comprise one or more linkers that connect components of the epigenetic editor. A linker may be a peptide or non-peptide linker.

In some embodiments, one or more linkers utilized in an epigenetic editor provided herein is a peptide linker, i.e., a linker comprising a peptide moiety. A peptide linker can be any length applicable to the epigenetic editor fusion proteins described herein. In some embodiments, the linker can comprise a peptide between 1 and 200 (e.g., between 1 and 80) amino acids. In some embodiments, the linker comprises from 1 to 5, 1 to 10, 1 to 20, 1 to 30, 1 to 40, 1 to 50, 1 to 60, 1 to 80, 1 to 100, 1 to 150, 1 to 200, 5 to 10, 5 to 20, 5 to 30, 5 to 40, 5 to 60, 5 to 80, 5 to 100, 5 to 150, 5 to 200, 10 to 20, 10 to 30, 10 to 40, 10 to 50, 10 to 60, 10 to 80, 10 to 100, 10 to 150, 10 to 200, 20 to 30, 20 to 40, 20 to 50, 20 to 60, 20 to 80, 20 to 100, 20 to 150, 20 to 30, 30 to 40, 30 to 50, 30 to 60, 30 to 80, 30 to 100, 30 to 150, 30 to 200, 40 to 50, 40 to 60, 40 to 80, 40 to 100, 40 to 150, 40 to 200, 50 to 60 50 to 80, 50 to 100, 50 to 150, 50 to 200, 60 to 80, 60 to 100, 60 to 150, 60 to 200, 80 to 100, 80 to 150, 80 to 200, 100 to 150, 100 to 200, or 150 to 200 amino acids in length. Longer or shorter linkers are also contemplated. In some embodiments, the peptide linker is 3, 4, 5, 6, 7, 8, 9, 10, 11, 12, 13, 14, 15, 16, 17, 18, 19, 20, 25, 30, 25, 40, 45, 50, 55, 60, 65, 70, 75, 80, 85, 90, 95, or 100 amino acids in length. For example, the peptide linker may be 4, 5, 16, 20, 24, 27, 32, 40, 64, 92, or 104 amino acids in length. The peptide linker may be a flexible or rigid linker. In particular embodiments, the peptide linker comprises the amino acid sequence of any one of SEQ ID NOs: 1064-1068 or a sequence at least 75%, 80%, 85%, 90%, 91%, 92%, 93%, 94%, 95%, 96%, 97%, 98%, or 99% identical thereto.

In certain embodiments, the peptide linker is an XTEN linker. Such a linker may comprise part of the XTEN sequence (Schellenberger et al., *Nat Biotechnol* (2009) 27 (1): 1186-90), an unstructured hydrophilic polypeptide consisting only of residues G, S, P, T, E, and A. The term "XTEN" as used herein refers to a recombinant peptide or polypeptide lacking hydrophobic amino acid residues. XTEN linkers typically are unstructured and comprise a limited set of natural amino acids. Fusion of XTEN to proteins alters its hydrodynamic properties and reduces the rate of clearance and degradation of the fusion protein. These XTEN fusion proteins are produced using recombinant technology, without the need for chemical modifications, and degraded by natural pathways. The XTEN linker may be, for example, 5, 10, 16, 20, 26, or 80 amino acids in length. In some embodiments, the XTEN linker is 16 amino acids in length. In some embodiments, the XTEN linker is 80 amino acids in length. In certain embodiments, the XTEN linker may be XTEN10, XTEN16, XTEN20, or XTEN80. In certain embodiments, the XTEN linker may comprise the amino acid sequence of any one of SEQ ID NOs: 1069-1073 and 1092 or a sequence at least 75%, 80%, 85%, 90%, 91%, 92%, 93%, 94%, 95%, 96%, 97%, 98%, or 99% identical thereto. In some embodiments, the XTEN linker may be XTEN10, XTEN16, XTEN20, or XTEN80.

In some embodiments, one or more linkers utilized in an epigenetic editor provided herein is a non-peptide linker. For example, the linker may be a carbon bond, a disulfide bond, or carbon-heteroatom bond. In certain embodiments, the linker is a carbon-nitrogen bond of an amide linkage. In certain embodiments, the linker is a cyclic or acyclic, substituted or unsubstituted, or branched or unbranched aliphatic or heteroaliphatic linker.

In some embodiments, one or more linkers utilized in an epigenetic editor provided herein is polymeric (e.g., polyethylene, polyethylene glycol, polyamide, polyester, etc.). The linker may comprise, for example, a monomer, dimer, or polymer of aminoalkanoic acid; an aminoalkanoic acid (e.g., glycine, ethanoic acid, alanine, beta-alanine, 3-aminopropanoic acid, 4-aminobutanoic acid, 5-pentanoic acid, etc.); a monomer, dimer, or polymer of aminohexanoic acid (Ahx); or a polyethylene glycol moiety (PEG); or an aryl or heteroaryl moiety. In certain embodiments, the linker may be based on a carbocyclic moiety (e.g., cyclopentane or cyclohexane) or a phenyl ring. The linker may include functionalized moieties to facilitate attachment of a nucleophile (e.g., thiol, amino) from the peptide to the linker. Any electrophile may be used as part of the linker. Exemplary electrophiles include, but are not limited to, activated esters, activated amides, alkyl halides, aryl halides, acyl halides, and isothiocyanates.

Various linker lengths and flexibilities can be employed between any two components of an epigenetic editor (e.g., between an effector domain (e.g., a repressor domain) and a DNA-binding domain (e.g., a Cas9 domain), between a first effector domain and a second effector domain, etc.). The linkers may range from very flexible linkers, such as glycine/serine-rich linkers, to more rigid linkers, in order to achieve the optimal length for effector domain activity for the specific application. In some embodiments, the more flexible linkers are glycine/serine-rich linkers (GS-rich linkers), where more than 45% (e.g., more than 48, 50, 55, 60, 70, 80, or 90%) of the residues are glycine or serine residues. Non-limiting examples of the GS-rich linkers are (GGGGS)n (SEQ ID NO: 485), (G)n (SEQ ID NO: 1260), and W linker. In some embodiments, the more rigid linkers are in the form of the form (EAAAK)n (SEQ ID NO: 487), (SGGS)n (SEQ ID NO: 488), and (XP)n (SEQ ID NO: 489). In the aforementioned formulae of flexible and rigid linkers, n may be any integer between 1 and 30. In some embodiments, n is 1, 2, 3, 4, 5, 6, 7, 8, 9, 10, 11, 12, 13, 14, or 15. In some embodiments, the linker comprises a (GGS) n motif, wherein n is 1, 3, or 7 (SEQ ID NO: 490). In some embodiments, the linker comprises a (GGGGS) n motif, wherein n is 4 (SEQ ID NO: 491).

In some embodiments, a linker in an epigenetic editor described herein comprises a nuclear localization signal, for example, with the amino acid sequence of any one of SEQ ID NOs: 1074-1079. In some embodiments, a linker in an epigenetic editor described herein comprises an expression tag, e.g., a detectable tag such as a green fluorescence protein.

B. Nuclear Localization Signals

A fusion protein described herein may comprise one or more nuclear localization signals, and in certain embodiments, may comprise two or more nuclear localization signals. For example, the fusion protein may comprise 1, 2, 3, 4, or 5 nuclear localization signals. As used herein, a "nuclear localization signal" (NLS) is an amino acid sequence that directs proteins to the nucleus. In certain embodiments, the NLS may be an SV40 NLS. The fusion protein may comprise an NLS at its N-terminus, C-terminus, or both, and/or an NLS may be embedded in the middle of the fusion protein (e.g., at the N- or C-terminus of a DNA-binding domain or an effector domain). In certain embodiments, an NLS comprises the amino acid sequence of any one of SEQ ID NOs: 1074-1079, or a sequence at least 75%, 80%, 85%, 90%, 91%, 92%, 93%, 94%, 95%, 96%, 97%, 98%, or 99% identical to the selected sequence. Additional NLSs are known in the art.

C. Tags

Epigenetic editors provided herein may comprise one or more additional sequences ("tags") for tracking, detection, and localization of the editors. In some embodiments, the epigenetic editor comprises 1, 2, 3, 4, 5, 6, 7, 8, 9, 10 or more detectable tags. Each of the detectable tags may be the same or different.

For example, an epigenetic editor fusion protein may comprise cytoplasmic localization sequences, export sequences, such as nuclear export sequences, or other localization sequences, as well as sequence tags that are useful for solubilization, purification, or detection of the fusion proteins. Suitable protein tags provided herein include, but are not limited to, biotin carboxylase carrier protein (BCCP) tags, myc-tags, calmodulin-tags, FLAG-tags, hemagglutinin (HA)-tags, poly-histidine tags (also referred to as histidine tags or His-tags), maltose binding protein (MBP)-tags, nus-tags, glutathione-S-transferase (GST)-tags, green fluorescent protein (GFP)-tags, thioredoxin-tags, S-tags, Softags (e.g., Softag 1 or Softag 3), strep-tags, biotin ligase tags, FlAsH tags, V5 tags, and SBP-tags. Additional suitable sequences will be apparent to those of skill in the art. Sequences disclosed herein that are presented with tag sequences included are also contemplated without the presented tag sequences; similarly, sequences disclosed herein without tag sequences are also contemplated to include the addition of suitable tag sequences apparent to those of skill in the art.

D. Fusion Protein Configurations

A fusion protein of an epigenetic editor described herein may have its components structured in different configurations. For example, the DNA-binding domain may be at the C-terminus, the N-terminus, or in between two or more epigenetic effector domains or additional domains. In some embodiments, the DNA-binding domain is at the C-terminus of the epigenetic editor. In some embodiments, the DNA-binding domain is at the N-terminus of the epigenetic editor. In some embodiments, the DNA-binding domain is linked to one or more nuclear localization signals. In some embodiments, the DNA-binding domain is flanked by an epigenetic effector domain and/or an additional domain on both sides. In some embodiments, where "DBD" indicates DNA-binding domain and "ED" indicates effector domain, the epigenetic editor comprises the configuration of:

N']-[ED1]-[DBD]-[ED2]-[C'
N']-[ED1]-[DBD]-[ED2]-[ED3]-[C'
N']-[ED1]-[ED2]-[DBD]-[ED3]-[C'
or
N']-[ED1]-[ED2]-DBD]-[ED3]-[ED4]-[C'.

In some embodiments, an epigenetic editor comprises a DNA-binding domain (DBD), a DNA methyltransferase (DNMT) domain, and a transcriptional repressor ("repressor") domain that represses or silences expression of a target gene. The DBD, DNMT, and transcriptional repressor domains may be any as described herein, in any combination. For example, an epigenetic editor can comprise a DBD, a DNMT3A domain, and a DNMT3L domain. An epigenetic editor can comprise a DBD, a DNMT3A domain, a DNMT3L domain, and preferably further comprise a KRAB domain. In some embodiments, the epigenetic editor comprises a fusion protein with the configuration of:

N']-[DNA methyltransferase domain]-[DBD]-[repressor domain]-[C'
N']-[repressor domain]-[DBD]-[DNA methyltransferase domain]-[C'
N']-[DNA methyltransferase domain]-[repressor domain]-[DBD]-[C'
or
N']-[repressor domain]-[DNA methyltransferase domain]-[DBD]-[C'.

In some embodiments, a connecting structure "]-[" in any one of the epigenetic editor structures is a linker, e.g., a peptide linker; a detectable tag; a peptide bond; a nuclear localization signal; and/or a promoter or regulatory sequence. In an epigenetic editor structure, the multiple connecting structures "]-[" may be the same or may each be a different linker, tag, NLS, or peptide bond. In particular embodiments, the DNA methyltransferase domain comprises DNMT3A, DNMT3L, or both. In particular embodiments, the DBD is a catalytically inactive polynucleotide guided DNA-binding domain (e.g., a dCas9) or a ZFP domain. In particular embodiments, the repressor domain is a KRAB domain.

In some embodiments, the epigenetic editor comprises a configuration selected from N']-[DNMT3A-DNMT3L]-[DBD]-[KRAB]-[C'
N']-[KRAB]-[DBD]-[DNMT3A-DNMT3L]-[C'
N']-[KRAB]-[DBD]-[DNMT3A]-[C'

N']-[DNMT3A]-[DBD]-[KRAB]-[C'
N']-[KRAB]-[DBD]-[DNMT3A]-[DNMT3L]-[C'
N']-[DNMT3A]-[DNMT3L]-[DBD]-[KRAB]-[C'
N']-[DNMT3A]-[DBD]-[C'
N']-[DBD]-[DNMT3A]-[C'
N']-[DNMT3L]-[DBD]-[C'
N']-[DBD]-[DNMT3L]-[C' wherein [DNMT3A-DNMT3L] indicates that the DNMT3A and DNMT3L domains are directly fused via a peptide bond, and wherein the connecting structure]-[is any one of the linkers as described herein, a detectable tag, an affinity domain, a peptide bond, a nuclear localization signal, a promoter, and/or a regulatory sequence. The DBD, KRAB, DNMT3A, and DNMT3L domains may be any as described herein, in any combination. In particular embodiments, the DBD is a CRISPR-associated protein domain (e.g., dCas9) or a ZFP domain; the KRAB domain is derived from KOX1, ZIM3, ZFP28, or ZN627; the DNMT3A domain is a human DNMT3A domain; and the DNMT3L domain is a human or mouse DNMT3L domain; any combination of these components is also contemplated by the present disclosure.

In some embodiments, the epigenetic editor comprises a configuration selected from N']-[DNMT3A]-[DBD]-[SETDB1]-[C'
N']-[DNMT3A]-[DNMT3L]-[DBD]-[SETDB1]-[C'
N']-[DNMT3A-DNMT3L]-[DBD]-[SETDB1]-[C'
N']-[SETDB1]-[DBD]-[DNMT3A]-[DNMT3L]-[C'
N']-[SETDB1]-[DBD]-[DNMT3A]-[C' wherein [DNMT3A-DNMT3L] indicates that the DNMT3A and DNMT3L domains are directly fused via a peptide bond, and wherein the connecting structure]-[ is any one of the linkers as described herein, a detectable tag, an affinity domain, a peptide bond, a nuclear localization signal, a promoter, and/or a regulatory sequence. The DBD, SETDB1, DNMT3A, and DNMT3L domains may be any as described herein, in any combination. In particular embodiments, the DBD is a CRISPR-associated protein domain (e.g., dCas9) or a ZFP domain; the SETDB1 domain is derived from human SETDB1, ZIM3, ZFP28, or ZN627; the DNMT3A domain is a human DNMT3A domain; and the DNMT3L domain is a human or mouse DNMT3L domain; any combination of these components is also contemplated by the present disclosure.

Particular constructs contemplated herein include:

DNMT3A-DNMT3L-XTEN80-NLS-dCas9-NLS-XTEN16-KOX1 KRAB (Configuration 1), and
DNMT3A-DNMT3L-XTEN80-NLS-ZFP domain-NLS-XTEN16-KOX1 KRAB (Configuration 2).

In particular embodiments, the DNMT3L and DNMT3A are both derived from human parental proteins. In particular embodiments, the DNMT3L and DNMT3A are derived from human and mouse parental proteins, respectively. In particular embodiments, the DNMT3L and DNMT3A are derived from mouse and human parental proteins, respectively. In particular embodiments, the DNMT3L and DNMT3A are both derived from mouse parental proteins. In some embodiments, the dCas9 is dSpCas9. In some embodiments, the KOX1 is human KOX1.

In particular embodiments, a fusion construct described herein may have Configuration 1 and comprise SEQ ID NO: 1080, or a sequence at least 75%, 80%, 85%, 90%, 91%, 92%, 93%, 94%, 95%, 96%, 97%, 98%, or 99% identical thereto. In SEQ ID NO: 1080 below, the XTEN linkers are underlined, the NLS sequences are bolded, the DNMT3A sequence is italicized, the DNMT3L sequence is underlined and italicized, the dCas9 domain is bolded and italicized, and the KOX1 KRAB domain is underlined and bolded:

(SEQ ID NO: 1080)

MNHDQEFDPPKVYPPVPAEKRKPIRVLSLFDGIATGLLVLKDLGIQVDRYIASEVCEDSI

TVGMVRHQGKIMYVGDVRSVTQKHIQEWGPFDLVIGGSPCNDLSIVNPARKGLYEGTGRL

FFEFYRLLHDARPKEGDDRPFFWLFENVVAMGVSDKRDISRFLESNPVMIDAKEVSAAHR

ARYFWGNLPGMNRPLASTVNDKLELQECLEHGRIAKFSKVRTITTRSNSIKQGKDQHFPV

FMNEKEDILWCTEMERVFGFPVHYTDVSNMSRLARQRLLGRSWSVPVIRHLFAPLKEYFA

CVSSGNSNANSRGPSFSSGLVPLSLRGSHMGPMEIYKTVSAWKRQPVRVLSLFRNIDKVL

KSLGFLESGSGSGGGTLKYVEDVTNVVRRDVEKWGPFDLVYGSTQPLGSSCDRCPGWYMF

QFHRILQYALPRQESQRPFFWIFMDNLLLTEDDQETTTRFLQTEAVTLQDVRGRDYQNAM

RVWSNIPGLKSKHAPLTPKEEEYLQAQVRSRSKLDAPKVDLLVKNCLLPLREYFKYFSQN

SLPLGGPSSGAPPPSGGSPAGSPTSTEEGTSESATPESGPGTSTEPSEGSAPGSPAGSPT

STEEGTSTEPSEGSAPGTSTEPSEPKKKRKVYMDKKYSIGLAIGTNSVGWAVITDEYKVP

SKKFKVLGNTDRHSIKKNLIGALLFDSGETAEATRLKRTARRRYTRRKNRICYLQEIFSN

EMAKVDDSFFHRLEESFLVEEDKKHERHPIFGNIVDEVAYHEKYPTIYHLRKKLVDSTDK

ADLRLIYLALAHMIKFRGHFLIEGDLNPDNSDVDKLFIQLVQTYNQLFEENPINASGVDA

KAILSARLSKSRRLENLIAQLPGEKKNGLFGNLIALSLGLTPNFKSNFDLAEDAKLQLSK

DTYDDDLDNLLAQIGDQYADLFLAAKNLSDAILLSDILRVNTEITKAPLSASMIKRYDEH

HQDLTLLKALVRQQLPEKYKEIFFDQSKNGYAGYIDGGASQEEFYKFIKPILEKMDGTEE

LLVKLNREDLLRKQRTFDNGSIPHQIHLGELHAILRRQEDFYPFLKDNREKIEKILTFRI

PYYVGPLARGNSRFAWMTRKSEETITPWNFEEVVDKGASAQSFIERMTNFDKNLPNEKVL

-continued

PKHSLLYEYFTVYNELTKVKYVTEGMRKPAFLSGEQKKAIVDLLFKTNRKVTVKQLKEDY

FKKIECFDSVEISGVEDRFNASLGTYHDLLKIIKDKDFLDNEENEDILEDIVLTLTLFED

REMIEERLKTYAHLFDDKVMKQLKRRRYTGWGRLSRKLINGIRDKQSGKTILDFLKSDGF

ANRNFMQLIHDDSLTFKEDIQKAQVSGQGDSLHEHIANLAGSPAIKKGILQTVKVVDELV

KVMGRHKPENIVIEMARENQTTQKGQKNSRERMKRIEEGIKELGSQILKEHPVENTQLQN

EKLYLYYLQNGRDMYVDQELDINRLSDYDVDAIVPQSFLKDDSIDNKVLTRSDKNRGKSD

NVPSEEVVKKMKNYWRQLLNAKLITQRKFDNLTKAERGGLSELDKAGFIKRQLVETRQIT

KHVAQILDSRMNTKYDENDKLIREVKVITLKSKLVSDFRKDFQFYKVREINNYHHAHDAY

LNAVVGTALIKKYPKLESEFVYGDYKVYDVRKMIAKSEQEIGKATAKYFFYSNIMNFFKT

EITLANGEIRKRPLIETNGETGEIVWDKGRDFATVRKVLSMPQVNIVKKTEVQTGGFSKE

SILPKRNSDKLIARKKDWDPKKYGGFDSPTVAYSVLVVAKVEKGKSKKLKSVKELLGITI

MERSSFEKNPIDFLEAKGYKEVKKDLIIKLPKYSLFELENGRKRMLASAGELQKGNELAL

PSKYVNFLYLASHYEKLKGSPEDNEQKQLFVEQHKHYLDEIIEQISEFSKRVILADANLD

KVLSAYNKHRDKPIREQAENIIHLFTLTNLGAPAAFKYFDTTIDRKRYTSTKEVLDATLI

HQSITGLYETRIDLSQLGGDPKKKRKVSGSETPGTSESATPESTGRTLVTFKDVFVDFTR

EEWKLLDTAQQIVYRNVMLENYKNLVSLGYQLTKPDVILRLEKGEEP

In particular embodiments, a fusion construct described herein may have Configuration 2 and comprise SEQ ID NO: 1081, or a sequence at least 75%, 80%, 85%, 90%, 91%, 92%, 93%, 94%, 95%, 96%, 97%, 98%, or 99% identical thereto. In SEQ ID NO: 1081 below, the XTEN linkers are underlined, the NLS sequences are bolded and underlined, the DNMT3A sequence is italicized, the DNMT3L sequence is underlined and italicized, the ZFP domain is bolded, and the KOX1 KRAB domain is underlined and bolded. Variable amino acids represented by Xs are the amino acids of the DNA-recognition helix of the zinc finger and XX in italics may be either TR, LR or LK.

MNHDQEFDPPKVYPPVPAEKRKPIRVLSLFDGIATGLLVLKDLGIQVDRYIASEVCEDSI

TVGMVRHQGKIMYVGDVRSVTQKHIQEWGPFDLVIGGSPCNDLSIVNPARKGLYEGTGRL

FFEFYRLLHDARPKEGDDRPFFWLFENVVAMGVSDKRDISRFLESNPVMIDAKEVSAAHR

ARYFWGNLPGMNRPLASTVNDKLELQECLEHGRIAKFSKVRTITTRSNSIKQGKDQHFPV

FMNEKEDILWCTEMERVFGFPVHYTDVSNMSRLARQRLLGRSWSVPVIRHLFAPLKEYFA

CVSSGNSNANSRGPSFSSGLVPLSLRGSHMGPMEIYKTVSAWKRQPVRVLSLFRNIDKVL

KSLGFLESGSGSGGGTLKYVEDVTNVVRRDVEKWGPFDLVYGSTQPLGSSCDRCPGWYMF

QFHRILQYALPRQESQRPFFWIFMDNLLLTEDDQETTTRFLQTEAVTLQDVRGRDYQNAM

RVWSNIPGLKSKHAPLTPKEEEYLQAQVRSRSKLDAPKVDLLVKNCLLPLREYFKYFSQN

SLPLGGPSSGAPPPSGGSPAGSPTSTEEGTSESATPESGPGTSTEPSEGSAPGSPAGSPT

STEEGTSTEPSEGSAPGTSTEPSEPKKKRKVYSRPGERPFQCRICMRNFSXXXXXXXHXX

THTGEKPFQCRICMRNFSXXXXXXXHXXTH[linker]PFQCRICMRNFSXXXXXXXHXX

THTGEKPFQCRICMRNFSXXXXXXXHXXTH[linker]PFQCRICMRNFSXXXXXXXHXX

THTGEKPFQCRICMRNFSXXXXXXXHXXTHLRGSPKKKRKVSGSETPGTSESATPESTGR

TLVTFKDVFVDFTREEWKLLDTAQQIVYRNVMLENYKNLVSLGYQLTKPDVILRLEKGEE

P (SEQ ID NOs: 1081, 1262 and 1263, respectively, in order of appearance)

In certain embodiments, the six "XXXXXXX" regions in SEQ ID NO: 1081, 1262 or 1263 comprise, in order, the F1-F6 amino acid sequences shown in Table 1. [linker] represents a linker sequence. In some embodiments, one or both linker sequences may be TGSQKP (SEQ ID NO: 1085). In some embodiments, one or both linker sequences may be TGGGGSQKP (SEQ ID NO: 1086). In some embodiments, one linker sequence may have the amino acid sequence of SEQ ID NO: 1085 and the other linker sequence may have the amino acid sequence of SEQ ID NO: 1086.

Multiple epigenetic editors may be used to effect activation or repression of a target gene or multiple target genes. For example, an epigenetic editor fusion protein comprising a DNA-binding domain (e.g., a dCas9 domain) and an effector domain may be co-delivered with two or more guide polynucleotides (e.g., gRNAs), each targeting a different target DNA sequence. The target sites for two of the DNA-binding domains may be the same or in the vicinity of each other, or separated by, for example, about 100 base pairs, about 200 base pairs, about 300 base pairs, about 400 base pairs, about 500 base pairs, or about 600 or more base pairs. In addition, when targeting double-strand DNA, such as an endogenous gene locus, the guide polynucleotides may target the same or different strands (one or more to the positive strand and/or one or more to the negative strand).

V. Target Sequences

An epigenetic editor herein may be directed to an HBV target sequence to effect epigenetic modification of HBV or an HBV gene. As used herein, a "target sequence," a "target site," or a "target region" is a nucleic acid sequence present in a genome or gene of interest, e.g., in an HBV genome or an HBV gene; in some instances, the target sequence may be outside but in the vicinity of the gene of interest wherein methylation or binding by a repressor of the target sequence represses expression of the gene. In some embodiments, the target sequence may be a hypomethylated or hypermethylated nucleic acid sequence.

The structure and biology of HBV as well as HBV-associated diseases have been reported (see, for example, Yuen, M F., Chen, D S., Dusheiko, G. et al. Hepatitis B virus infection. Nat Rev Dis Primers 4, 18035 (2018); R. Koshy and W. H. Caselman (Eds.), Hepatitis B Virus: Molecular Mechanism in Disease and Novel Strategies for Antiviral Therapy, Imperial College Press, London (1998), ISBN 1783262737; the entire contents of each of which are incorporated herein by reference). HBV genotypes and sub-types, as well as their genomic, transcript, and protein sequences have been described and are known to the skilled artisan. Some exemplary HBV sequences, e.g., those under accession numbers NC_00397 and U95551 are provided elsewhere herein, and the entire content of each such database entry is incorporated herein by reference.

Without wishing to be bound by any particular theory, it has been reported that HBV persists as a covalently closed circular DNA (cccDNA) of approximately 3.2 kb, as well as in an integrated form. The HBV genome has been extensively characterized. The HBV genome has been shown to comprise four genes (the S gene, the P gene, the C gene, and the X gene), regulated by four promoter elements (sp1, sp2, cp and xp) and two enhancer elements (Enh I and Enh II) that control the expression of four defined (and overlapping) protein-encoding open reading frames (S, C, X, and P). See FIG. 1. The HBV genome has been described to express six major viral RNA transcripts encoding the viral proteins: (1) the preCore (preC) RNA, which encodes the C protein (also referred to as Core protein, HBe Antigen, or HBeAg); (2), the pre-genomic (pg) RNA, which encodes the two viral proteins C (core) and P (polymerase), and also serves as the template for the synthesis of viral DNA, which is mediated by the reverse transcriptase activity of the viral P protein once pg RNA and the P protein are encapsidated into the nucleocapsids formed by the C protein; (3) the large surface protein (preS1) RNA, which encodes the Large S Antigen (also referred to as L-HBsAg); (4) the middle surface protein (preS2) RNA, which encodes the Middle S Antigen (also referred to as M-HBsAg); (5) the small surface protein(S) RNA, which encodes the Small S Antigen (also referred to as S-HBsAg); and (6) the X protein (HBx) RNA, which encodes the X protein. Transcription start sites (TSSs) as well as the termination site of the HBV transcripts have been mapped in various HBV genotypes and sub-types. Notably, HBV transcripts have been described to terminate at a single termination/polyadenylation signal located downstream of the Hbx CDS and comprising a canonical ATAAA motif. It has further been reported that HBV DNA may be methylated by infected cells and such methylation has been postulated to correlate with inhibition of viral gene expression. However, naturally occurring cell-mediated methylation of viral DNA is typically insufficient to silence viral expression to a level that would result in control of HBV infection. DNA methylation typically occurs at CpG dinucleotides. Several CpG-rich genomic regions, also referred to as CpG islands or CGIs, have been identified in the HBV genome. CGIs are typically identified in HBV genomic sequences as sequences of a specific minimal length (e.g., at least 100 bp) that comprise a minimum percentage of G and C nucleotides (e.g., at least 50% or at least 60% GC content) and a ratio of observed vs. expected CpG dinucleotides of at least 0.6. CGIs satisfying these criteria have been identified in all HBV genotypes, and it has been demonstrated that HBV genomes typically contain three CpG islands (CGI-I, CHI-II, and CGI-III, respectively), which are also sometimes referred to as 'conventional' HBV CpG islands. Some HBV genotypes or sub-types have been reported to comprise additional, 'non-conventional' CGIs. FIG. 1 is a diagram illustrating an exemplary structure of a circular HBV genome (the underlying sequence of which is provided herein as SEQ ID NO: 1082), identifying the coding regions of HBV genes and CpG islands CGI-I-III. See, for example, M. J. Kosovsky, et al., The regulation of hepatitis B virus gene expression: an overview of the cis- and trans-acting components in R. Koshy and W. H. Caselman (Eds.), Hepatitis B Virus: Molecular Mechanism in Disease and Novel Strategies for Antiviral Therapy, Imperial College Press, London (1998), ISBN 1783262737; Miller et al Compact organization of the hepatitis B virus genome. Hepatology. 1989 February; 9 (2): 322-7; Stadelmayer et al., Full-length 5'RACE identifies all major HBV transcripts in HBV-infected hepatocytes and patient serum. J Hepatol. 2020 July; 73 (1): 40-51; Meier-Stephenson et al., Comprehensive Analysis of Hepatitis B Virus Promoter Region Mutations. Viruses. 2018 Nov. 1; 10 (11): 603; Vivekanandan et al., Hepatitis B viral DNA is methylated in liver tissues. J Viral Hepat. 2008, 15 (2): 103-7; Chen et al., Detection of hepatitis B virus DNA in hepatocellular carcinoma: methylation of integrated viral DNA. J Virol Methods. 1988, 19 (3-4): 257-63; Zhang et al., Comparative Analysis of CpG Islands among HBV Genotypes. PLOS ONE 2013, 8 (2): e56711; Jain et al., Comprehensive DNA methylation analysis of hepatitis B virus genome in infected liver tissues. Sci Rep 5, 10478 (2015); Low et al., Hepatitis B virus DNA methylation and its potential role in chronic hepatitis B. Expert Reviews in Molecular Medicine. 2023; 25: e11; Hou et al., CpG islands of hepatitis B virus genome isolated from Chinese patients. Gene (2015) 561:261-267; Mouzannar et al., The Post-Transcriptional Regulatory Element of Hepatitis B Virus: From Discovery to Therapy. Viruses. 2024 Mar. 29; 16 (4): 528; Peng et al., Nonproductive Hepatitis B Virus Covalently Closed Circular DNA Generates HBx-Related Transcripts from the HBx/Enhancer I Region and Acquires Reactivation by Superinfection in Single Cells. J Virol. 2023 Jan. 31; 97 (1): c0171722; Altinel et al., Single-Nucleotide Resolution Mapping of Hepatitis B Virus Promoters in Infected Human Livers and Hepatocellular Carcinoma. J Virol. 2016 Nov. 14; 90 (23): 10811-10822; the entire contents of each of which, and, where applicable, including any supplemental information, are incorporated herein by reference.

The target sequence (also referred to herein as target site or target region) of an epigenetic editor provided herein may be any suitable HBV sequence.

The target sequence may be in any part of a target gene. In some embodiments, the target sequence is part of or near a noncoding sequence of the gene. In some embodiments, the target sequence is part of an exon of the gene. In some embodiments, the target sequence is part of or near a transcriptional regulatory sequence of the gene, such as a promoter or an enhancer. In some embodiments, the target sequence is adjacent to, overlaps with, or encompasses a CpG island, e.g., a CpG island identified within the HBV genome. In some embodiments, the target sequence is outside of a CpG island. In certain embodiments, the target sequence is within about 3000, 2900, 2800, 2700, 2600, 2500, 2400, 2300, 2200, 2100, 2000, 1900, 1800, 1700, 1600, 1500, 1400, 1300, 1200, 1100, 1000, 900, 800, 700, 600, 500, 400, 300, 200, or 100 base pairs (bp) flanking an HBV TSS. In certain embodiments, the target sequence is within 500 bp flanking the HBV TSS. In certain embodiments, the target sequence is within 1000 bp flanking the HBV TSS.

Some exemplary embodiments in which the target sequence is part of a target gene are provided herein and additional embodiments will be apparent to the skilled artisan based on the present disclosure and the knowledge of the genomic structure of HBV in the art. For example, in some embodiments, the target sequence is part of the HBV S gene, the HBV P gene, the HBV C gene, or the HBV X gene. In some embodiments, the target sequence is part of the HBV S gene. In some embodiments, the target sequence is part of the HBV P gene. In some embodiments, the target sequence is part of the HBV C gene. In some embodiments, the target sequence is part of the HBV X gene. Some exemplary embodiments in which the target sequence is part of a noncoding sequence of a target gene are provided herein and additional embodiments will be apparent to the skilled artisan based on the present disclosure and the knowledge of the genomic structure of HBV in the art. For example, in some embodiments the target sequence is part of a noncoding sequence of the HBV S gene, of the HBV P gene, of the HBV C gene, or of the HBV X gene. For example, in some embodiments, the target sequence is part of a noncoding sequence of the HBV S gene. In some embodiments, the target sequence is part of a noncoding sequence of the HBV P gene. In some embodiments, the target sequence is part of a noncoding sequence of the HBV C gene. In some embodiments, the target sequence is part of a noncoding sequence of the HBV X gene. Noncoding sequences of the various HBV genes are known in the art and include, for example, the promoter and enhancer sequences of the HBV genome.

Accordingly, in some embodiments, the target sequence is part of an HBV promoter sequence (e.g., of a promoter sequence within the HBV genome driving the transcription of one of the HBV transcripts described elsewhere herein, including, for example, of a sequence of the sp1, the sp2, the cp, and the xp promoter elements). In some embodiments, the target sequences is part of an HBV enhancer sequence (e.g., of the Enh I or of the Enh II sequence).

Some exemplary embodiments, in which the target sequence is adjacent to, overlaps with, or encompasses a CpG island, e.g., a CpG island identified within the HBV genome include embodiments in which the target sequence is adjacent to, overlaps with, or encompasses a conventional CGI of HBV, e.g., CGI I, CGI II, or CGI III. CGIs of HBV have been identified and described in numerous publications and are thus known to the skilled artisan. Bioinformatics tools for the identification of CGIs in any specific HBV sequence, e.g., in a sequence of a specific HBV genotype or sub-type, or in an HBV sequence isolated from a patient, are known in the art, including, for example, EMBOSS CpG plot (EMBL-EBI) and Methprimer (Li L C and Dahiya R. MethPrimer: designing primers for methylation PCRs. Bioinformatics. 2002 November; 18 (11): 1427-31). Conventional CGIs of HBV include CGI I, which overlaps the S and the P gene ORFs; CGI-II, which overlaps the P gene and X gene ORFs; and CGI III, which overlaps the C gene and P gene ORFs (see FIG. 1). In some embodiments, an HBV CGI is identified as a sequence within the HBV genome that is (1) at least 100 nucleotides long; (2) is characterized by a GC content of at least 50%; and (3) is characterized by an observed-to-expected CpG dinucleotide ratio of at least 0.6. According to these criteria, in the exemplary HBV genome referenced in FIG. 1, i.e., NC_003977 (provided herein as SEQ ID NO: 1082), CGI I spans nucleotides 186-288, CGI II spans nucleotides 1,217-1,670, and CGI III spans nucleotides 2,282-2,448 (see FIG. 1). CGIs of HBV fulfilling these criteria, including conventional HBV CGIs I-III, of other HBV sequences, including other genotypes, sub-types, or specific HBV sequences, will be apparent to the skilled artisan. In some embodiments, the target sequence overlaps with HBV CGI I. In some embodiments, the target sequence overlaps with HBV CGI II. In some embodiments, the target sequence overlaps with CGI III.

Exemplary embodiments in which the target sequence is within about 3000, 2900, 2800, 2700, 2600, 2500, 2400, 2300, 2200, 2100, 2000, 1900, 1800, 1700, 1600, 1500, 1400, 1300, 1200, 1100, 1000, 900, 800, 700, 600, 500, 400, 300, 200, or 100 base pairs (bp) flanking an HBV TSS (transcription start site) include embodiments, in which the target sequence is within the respective number of base pairs of the TSS of any of the six major viral RNA transcripts, i.e., the TSS of the preCore (pre-C) RNA, the TSS of the pre-genomic (pg)RNA, the TSS of the large surface protein (preS1) RNA, the TSS of the middle surface protein (preS2) RNA, the TSS of the small surface protein(S) RNA, and the TSS of the X protein (HBx) RNA. The positions of the transcription start sites of the various HBV transcripts have been identified in various HBV genotypes and sub-types and are thus known to the skilled artisan. For example, for HBV of genotype D, as exemplified by NCBI database entries NC_003977 and U95551.1 (provided as SEQ ID NOs 1082 and 1083 herein), the TSS of the pg RNA transcript has been identified as nucleotide 1820, the TSS of the pre-C RNA as nucleotide 1791, and the TSS of the pre-S2 RNA as nucleotide 3159. The initiation of HBx RNA transcripts encoded by HBV genomes has been reported to not be limited to a single nucleotide, but to be spread over a short sequence. For example, TSSs for canonical HBx transcripts have been reported to initiate closely upstream of the first ATG in the sequence encoding the X protein, with HBx transcript TSS positions having been mapped to nucleotides 1243-1338 of HBV of genotype D, as exemplified by NCBI database entries NC_003977 and U95551.1 (provided as SEQ ID NOS 1082 and 1083 herein). TSSs for additional transcripts have also been identified and TSSs have been mapped to various HBV genotypes and sub-types.

In some embodiments in which the target sequence is within about 3000, 2900, 2800, 2700, 2600, 2500, 2400, 2300, 2200, 2100, 2000, 1900, 1800, 1700, 1600, 1500, 1400, 1300, 1200, 1100, 1000, 900, 800, 700, 600, 500, 400, 300, 200, or 100 base pairs (bp) flanking an HBV TSS, the HBV TSS is an HBV pg RNA TSS. For example, in some embodiments provided herein, the target sequence of an epigenetic editor is within 100 bp flanking an HBV pg RNA TSS, e.g., within 100 bp of nucleotide 1820 of SEQ ID NO: 1082 or 1083. In some embodiments provided herein, the target sequence of an epigenetic editor is within 200 bp flanking an HBV pg RNA TSS, e.g., within 200 bp of nucleotide 1820 of SEQ ID NO: 1082 or 1083. In some embodiments provided herein, the target sequence of an epigenetic editor is within 300 bp flanking an HBV pg RNA TSS, e.g., within 300 bp of nucleotide 1820 of SEQ ID NO: 1082 or 1083. In some embodiments provided herein, the target sequence of an epigenetic editor is within 400 bp flanking an HBV pg RNA TSS, e.g., within 400 bp of nucleotide 1820 of SEQ ID NO: 1082 or 1083. In some embodiments provided herein, the target sequence of an epigenetic editor is within 500 bp flanking an HBV pg RNA TSS, e.g., within 500 bp of nucleotide 1820 of SEQ ID NO: 1082 or 1083. In some embodiments provided herein, the target sequence of an epigenetic editor is within 600 bp flanking an HBV pg RNA TSS, e.g., within 600 bp of nucleotide 1820 of SEQ ID NO: 1082 or 1083.

In some embodiments in which the target sequence is within about 3000, 2900, 2800, 2700, 2600, 2500, 2400, 2300, 2200, 2100, 2000, 1900, 1800, 1700, 1600, 1500, 1400, 1300, 1200, 1100, 1000, 900, 800, 700, 600, 500, 400, 300, 200, or 100 base pairs (bp) flanking an HBV TSS, the HBV TSS is an HBV preCore (preC) RNA TSS. For example, in some embodiments provided herein, the target sequence of an epigenetic editor is within 100 bp flanking an HBV preC RNA TSS, e.g., within 100 bp of nucleotide 1791 of SEQ ID NO: 1082 or 1083. In some embodiments provided herein, the target sequence of an epigenetic editor is within 200 bp flanking an HBV preC RNA TSS, e.g., within 200 bp of nucleotide 1791 of SEQ ID NO: 1082 or 1083. In some embodiments provided herein, the target sequence of an epigenetic editor is within 300 bp flanking an HBV preC RNA TSS, e.g., within 300 bp of nucleotide 1791 of SEQ ID NO: 1082 or 1083. In some embodiments provided herein, the target sequence of an epigenetic editor is within 400 bp flanking an HBV preC RNA TSS, e.g., within 400 bp of nucleotide 1791 of SEQ ID NO: 1082 or 1083. In some embodiments provided herein, the target sequence of an epigenetic editor is within 500 bp flanking an HBV preC RNA TSS, e.g., within 500 bp of nucleotide 1791 of SEQ ID NO: 1082 or 1083.

In some embodiments in which the target sequence is within about 3000, 2900, 2800, 2700, 2600, 2500, 2400, 2300, 2200, 2100, 2000, 1900, 1800, 1700, 1600, 1500, 1400, 1300, 1200, 1100, 1000, 900, 800, 700, 600, 500, 400, 300, 200, or 100 base pairs (bp) flanking an HBV TSS, the HBV TSS is an HBV preS2 RNA TSS. For example, in some embodiments provided herein, the target sequence of an epigenetic editor is within 100 bp flanking an HBV preS2 RNA TSS, e.g., within 100 bp of nucleotide 3159 of SEQ ID NO: 1082 or 1083. In some embodiments provided herein, the target sequence of an epigenetic editor is within 200 bp flanking an HBV preS2 RNA TSS, e.g., within 200 bp of nucleotide 3159 of SEQ ID NO: 1082 or 1083. In some embodiments provided herein, the target sequence of an epigenetic editor is within 300 bp flanking an HBV preS2 RNA TSS, e.g., within 300 bp of nucleotide 3159 of SEQ ID NO: 1082 or 1083. In some embodiments provided herein, the target sequence of an epigenetic editor is within 400 bp flanking an HBV preS2 RNA TSS, e.g., within 400 bp of nucleotide 3159 of SEQ ID NO: 1082 or 1083. In some embodiments provided herein, the target sequence of an epigenetic editor is within 500 bp flanking an HBV preS2 RNA TSS, e.g., within 500 bp of nucleotide 3159 of SEQ ID NO: 1082 or 1083.

In some embodiments in which the target sequence is within about 3000, 2900, 2800, 2700, 2600, 2500, 2400, 2300, 2200, 2100, 2000, 1900, 1800, 1700, 1600, 1500, 1400, 1300, 1200, 1100, 1000, 900, 800, 700, 600, 500, 400, 300, 200, or 100 base pairs (bp) flanking an HBV TSS, the HBV TSS is an HBV HBx RNA TSS. For example, in some embodiments provided herein, the target sequence of an epigenetic editor is within 100 bp flanking an HBV HBx RNA TSS, e.g., within 100 bp of nucleotide 1243 of SEQ ID NO: 1082 or 1083. In some embodiments provided herein, the target sequence of an epigenetic editor is within 200 bp flanking an HBV HBx RNA TSS, e.g., within 200 bp of nucleotide 1243 of SEQ ID NO: 1082 or 1083. In some embodiments provided herein, the target sequence of an epigenetic editor is within 300 bp flanking an HBV HBx RNA TSS, e.g., within 300 bp of nucleotide 1243 of SEQ ID NO: 1082 or 1083. In some embodiments provided herein, the target sequence of an epigenetic editor is within 400 bp flanking an HBV HBx RNA TSS, e.g., within 400 bp of nucleotide 1243 of SEQ ID NO: 1082 or 1083. In some embodiments provided herein, the target sequence of an epigenetic editor is within 500 bp flanking an HBV HBx RNA TSS, e.g., within 500 bp of nucleotide 1243 of SEQ ID NO: 1082 or 1083. In some embodiments provided herein, the target sequence of an epigenetic editor is within 600 bp flanking an HBV HBx RNA TSS, e.g., within 600 bp of nucleotide 1243 of SEQ ID NO: 1082 or 1083.

In some embodiments in which the target sequence is within about 3000, 2900, 2800, 2700, 2600, 2500, 2400, 2300, 2200, 2100, 2000, 1900, 1800, 1700, 1600, 1500, 1400, 1300, 1200, 1100, 1000, 900, 800, 700, 600, 500, 400, 300, 200, or 100 base pairs (bp) flanking an HBV TSS, the HBV TSS is an HBV HBx RNA TSS. For example, in some embodiments provided herein, the target sequence of an epigenetic editor is within 100 bp flanking an HBV HBx RNA TSS, e.g., within 100 bp of nucleotide 1338 of SEQ ID NO: 1082 or 1083. In some embodiments provided herein, the target sequence of an epigenetic editor is within 200 bp flanking an HBV HBx RNA TSS, e.g., within 200 bp of nucleotide 1338 of SEQ ID NO: 1082 or 1083. In some embodiments provided herein, the target sequence of an epigenetic editor is within 300 bp flanking an HBV HBx RNA TSS, e.g., within 300 bp of nucleotide 1338 of SEQ ID NO: 1082 or 1083. In some embodiments provided herein, the target sequence of an epigenetic editor is within 400 bp flanking an HBV HBx RNA TSS, e.g., within 400 bp of nucleotide 1338 of SEQ ID NO: 1082 or 1083. In some embodiments provided herein, the target sequence of an epigenetic editor is within 500 bp flanking an HBV HBx RNA TSS, e.g., within 500 bp of nucleotide 1338 of SEQ ID NO: 1082 or 1083. In some embodiments provided herein, the target sequence of an epigenetic editor is within 600 bp flanking an HBV HBx RNA TSS, e.g., within 600 bp of nucleotide 1338 of SEQ ID NO: 1082 or 1083.

In some embodiments in which the target sequence is within about 3000, 2900, 2800, 2700, 2600, 2500, 2400, 2300, 2200, 2100, 2000, 1900, 1800, 1700, 1600, 1500, 1400, 1300, 1200, 1100, 1000, 900, 800, 700, 600, 500, 400, 300, 200, or 100 base pairs (bp) flanking an HBV TSS, the HBV TSS is an HBV HBx RNA TSS. For example, in some embodiments provided herein, the target sequence of an epigenetic editor is within 100 bp flanking an HBV HBx RNA TSS, e.g., within 100 bp of nucleotide 1243 and within 100 bp of nucleotide 1338 of SEQ ID NO: 1082 or 1083. In some embodiments provided herein, the target sequence of an epigenetic editor is within 200 bp flanking an HBV HBx RNA TSS, e.g., within 200 bp of nucleotide 1243 and within 200 bp of nucleotide 1338 of SEQ ID NO: 1082 or 1083. In some embodiments provided herein, the target sequence of an epigenetic editor is within 300 bp flanking an HBV HBx RNA TSS, e.g., within 300 bp of nucleotide 1243 and within 300 bp of nucleotide 1338 of SEQ ID NO: 1082 or 1083. In some embodiments provided herein, the target sequence of an epigenetic editor is within 400 bp flanking an HBV HBx RNA TSS, e.g., within 400 bp of nucleotide 1243 and within 400 bp of nucleotide 1338 of SEQ ID NO: 1082 or 1083. In some embodiments provided herein, the target sequence of an epigenetic editor is within 500 bp flanking an HBV HBx RNA TSS, e.g., within 500 bp of nucleotide 1243 and within 500 bp of nucleotide 1338 of SEQ ID NO: 1082 or 1083. In some embodiments provided herein, the target sequence of an epigenetic editor is within 600 bp flanking an HBV HBx RNA TSS, e.g., within 600 bp of nucleotide 1243 and within 600 bp of nucleotide 1338 of SEQ ID NO: 1082 or 1083.

In some embodiments, the target sequence may hybridize to a guide polynucleotide sequence (e.g., gRNA) complexed with a fusion protein comprising a polynucleotide guided DNA-binding domain (e.g., a CRISPR protein such as dCas9) and effector domain(s). The guide polynucleotide sequence may be designed to have complementarity to the target sequence, or identity to the opposing strand of the target sequence. In some embodiments, the guide polynucleotide comprises a spacer sequence that is about 80%, 85%, 90%, 91%, 92%, 93%, 94%, 95%, 96%, 97%, 98% or 99% identical to a protospacer sequence in the target sequence. In particular embodiments, the guide polynucleotide comprises a spacer sequence that is 100% identical to a protospacer sequence in the target sequence.

In some embodiments, where the DNA-binding domain of an epigenetic editor described herein is a zinc finger array, the target sequence may be recognized by said zinc finger array.

In some embodiments, where the DNA-binding domain of an epigenetic editor described herein is a TALE, the target sequence may be recognized by said TALE.

A target sequence described herein may be specific to one genotype of HBV, to one copy of am HBV target gene, or may be specific to one allele of an HBV target gene. In some embodiments, however, the target sequence may be conserved across two or more HBV genotypes, across two or more copies of an HBV gene, and across alleles of an HBV gene. Accordingly, the epigenetic modification and modulation of expression thereof may be specific to one copy or one allele of the target gene, or, in other embodiments, may be universal to different HBV genotypes, or HBV gene copies or alleles.

In some embodiments, the target sequence is comprised in the following sequence:

```
>NC_003977.2 Hepatitis B virus (strain ayw) genome
                                    (SEQ ID No. 1082)
AATTCCACAACCTTCCACCAAACTCTGCAAGATCCCAGAGTGAGAGGCCT

GTATTTCCCTGCTGGTGGCTCCAGTTCAGGAACAGTAAACCCTGTTCTGA

CTACTGCCTCTCCCTTATCGTCAATCTTCTCGAGGATTGGGGACCCTGCG

CTGAACATGGAGAACATCACATCAGGATTCCTAGGACCCCTTCTCGTGTT

ACAGGCGGGGTTTTCTTGTTGACAAGAATCCTCACAATACCGCAGAGTC

TAGACTCGTGGTGGACTTCTCTCAATTTTCTAGGGGGAACTACCGTGTGT

CTTGGCCAAAATTCGCAGTCCCCAACCTCCAATCACTCACCAACCTCTTG

TCCTCCAACTTGTCCTGGTTATCGCTGGATGTGTCTGCGGCGTTTTATCA

TCTTCCTCTTCATCCTGCTGCTATGCCTCATCTTCTTGTTGGTTCTTCTG

GACTATCAAGGTATGTTGCCCGTTTGTCCTCTAATTCCAGGATCCTCAAC

AACCAGCACGGGACCATGCCGGACCTGCATGACTACTGCTCAAGGAACCT

CTATGTATCCCTCCTGTTGCTGTACCAAACCTTCGGACGGAAATTGCACC

TGTATTCCCATCCCATCATCCTGGGCTTTCGGAAAATTCCTATGGGAGTG

GGCCTCAGCCCGTTTCTCCTGGCTCAGTTTACTAGTGCCATTTGTTCAGT

GGTTCGTAGGGCTTTCCCCCACTGTTTGGCTTTCAGTTATATGGATGATG

TGGTATTGGGGGCCAAGTCTGTACAGCATCTTGAGTCCCTTTTTACCGCT

GTTACCAATTTTCTTTTGTCTTTGGGTATACATTTAAACCCTAACAAAAC

AAAGAGATGGGGTTACTCTCTAAATTTTATGGGTTATGTCATTGGATGTT

ATGGGTCCTTGCCACAAGAACACATCATACAAAAAATCAAAGAATGTTTT

AGAAAACTTCCTATTAACAGGCCTATTGATTGGAAAGTATGTCAACGAAT

TGTGGGTCTTTTGGGTTTTGCTGCCCCTTTTACACAATGTGGTTATCCTG

CGTTGATGCCTTTGTATGCATGTATTCAATCTAAGCAGGCTTTCACTTTC

TCGCCAACTTACAAGGCCTTTCTGTGTAAACAATACCTGAACCTTTACCC

CGTTGCCCGGCAACGGCCAGGTCTGTGCCAAGTGTTTGCTGACGCAACCC

CCACTGGCTGGGGCTTGGTCATGGGCCATCAGCGCATGCGTGGAACCTTT

TCGGCTCCTCTGCCGATCCATACTGCGGAACTCCTAGCCGCTTGTTTTGC

TCGCAGCAGGTCTGGAGCAAACATTATCGGGACTGATAACTCTGTTGTCC

TATCCCGCAAATATACATCGTTTCCATGGCTGCTAGGCTGTGCTGCCAAC

TGGATCCTGCGCGGGACGTCCTTTGTTTACGTCCCGTCGGCGCTGAATCC

TGCGGACGACCCTTCTCGGGGTCGCTTGGGACTCTCTCGTCCCCTTCTCC

GTCTGCCGTTCCGACCGACCACGGGGCGCACCTCTCTTTACGCGGACTCC

CCGTCTGTGCCTTCTCATCTGCCGGACCGTGTGCACTTCGCTTCACCTCT

GCACGTCGCATGGAGACCACCGTGAACGCCCACCAAATATTGCCCAAGGT

CTTACATAAGAGGACTCTTGGACTCTCAGCAATGTCAACGACCGACCTTG

AGGCATACTTCAAAGACTGTTTGTTTAAAGACTGGGAGGAGTTGGGGGAG

GAGATTAGGTTAAAGGTCTTTGTACTAGGAGGCTGTAGGCATAAATTGGT

CTGCGCACCAGCACCATGCAACTTTTTCACCTCTGCCTAATCATCTCTTG

TTCATGTCCTACTGTTCAAGCCTCCAAGCTGTGCCTTGGGTGGCTTTGGG
```

US 12,649,003 B2

83
-continued

GCATGGACATCGACCCTTATAAAGAATTTGGAGCTACTGTGGAGTTACTC

TCGTTTTTGCCTTCTGACTTCTTTCCTTCAGTACGAGATCTTCTAGATAC

CGCCTCAGCTCTGTATCGGGAAGCCTTAGAGTCTCCTGAGCATTGTTCAC

CTCACCATACTGCACTCAGGCAAGCAATTCTTTGCTGGGGGGAACTAATG

ACTCTAGCTACCTGGGTGGGTGTTAATTTGGAAGATCCAGCGTCTAGAGA

CCTAGTAGTCAGTTATGTCAACACTAATATGGGCCTAAAGTTCAGGCAAC

TCTTGTGGTTTCACATTTCTTGTCTCACTTTTGGAAGAGAAACAGTTATA

GAGTATTTGGTGTCTTTCGGAGTGTGGATTCGCACTCCTCCAGCTTATAG

ACCACCAAATGCCCCTATCCTATCAACACTTCCGGAGACTACTGTTGTTA

GACGACGAGGCAGGTCCCCTAGAAGAAGAACTCCCTCGCCTCGCAGACGA

AGGTCTCAATCGCCGCGTCGCAGAAGATCTCAATCTCGGGAATCTCAATG

TTAGTATTCCTTGGACTCATAAGGTGGGGAACTTTACTGGGCTTTATTCT

TCTACTGTACCTGTCTTTAATCCTCATTGGAAAACACCATCTTTTCCTAA

TATACATTTACACCAAGACATTATCAAAAAATGTGAACAGTTTGTAGGCC

CACTCACAGTTAATGAGAAAAGAAGATTGCAATTGATTATGCCTGCCAGG

TTTTATCCAAAGGTTACCAAATATTTACCATTGGATAAGGGTATTAAACC

TTATTATCCAGAACATCTAGTTAATCATTACTTCCAAACTAGACACTATT

TACACACTCTATGGAAGGCGGGTATATTATATAAGAGAGAAACAACACAT

AGCGCCTCATTTTGTGGGTCACCATATTCTTGGGAACAAGATCTACAGCA

TGGGGCAGAATCTTTCCACCAGCAATCCTCTGGGATTCTTTCCCGACCAC

CAGTTGGATCCAGCCTTCAGAGCAAACACCGCAAATCCAGATTGGGACTT

CAATCCCAACAAGGACACCTGGCCAGACGCCAACAAGGTAGGAGCTGGAG

CATTCGGGCTGGGTTTCACCCCACCGCACGGAGGCCTTTTGGGGTGGAGC

CCTCAGGCTCAGGGCATACTACAAACTTTGCCAGCAAATCCGCCTCCTGC

CTCCACCAATCGCCAGTCAGGAAGGCAGCCTACCCCGCTGTCTCCACCTT

TGAGAAACACTCATCCTCAGGCCATGCAGTGG

FIG. 1 provides a diagram illustrating the structure of a circular HBV genome comprising SEQ ID NO: 1082. The coding regions of the HBV genes and CpG islands CGI-I-III are identified. Nucleotides 2309-1625 of SEQ ID NO: 1082 encode the P protein (NCBI reference number YP_009173866.1). Nucleotides 2850-837 of SEQ ID NO: 1082 encode the long surface protein (L-HBSAG or LHBS; NCBI reference number YP_009173869.1). Nucleotides 3174-837 of SEQ ID NO: 1082 encode the middle surface protein (M-HBsAg or MHBS; NCBI reference number YP_009173870.1). Nucleotides 157-837 of SEQ ID NO: 1082 encode the small surface protein (S-HBsAg or SHBs; NCBI reference number YP_009173871.1). Nucleotides 1816-2454 of SEQ ID NO: 1082 encode the C Protein (core protein, NCBI reference number AAB59971.1). Nucleotides 1376-1840 of SEQ ID NO: 1082 encode the X protein (HBx, NCBI reference number YP_009173867.1). CGI I spans nucleotides 186-288, CGI II spans nucleotides 1,217-1,670, and CGI III spans nucleotides 2,282-2,448. See, NCBI database entry NC_003977.2. TSSs of various transcripts have been mapped: pg RNA TSS: 1820; pre-C RNA TSS: 1791; pre-S2 RNA TSS: 3159; HBx RNA TSSs: 1243-1338. The ATAAA motif of the transcription termination/polyadenylation site is located at nucleotide 1919. See references cited elsewhere herein. See also, e.g., Abraham, T. M. and Loeb, D. D., The topology of hepatitis B virus pregenomic RNA promotes its replication, J. Virol. 81 (21), 11577-11584 (2007); Chen, A., Kao, Y. F. and Brown, C. M., Translation of the first upstream ORF in the hepatitis B virus pregenomic RNA modulates translation at the core and polymerase initiation codons, Nucleic Acids Res. 33 (4), 1169-1181 (2005); Borisova, G. P., Pumpen, P. P., Bychko, V. V., Pushko, P. M., Kalis, Y. V., Dishler, A. V., Gren, E. Y., Tsibinogin, V. V. and Kukain, R. A., Structure and expression of the gene of the core antigen of human hepatitis B virus (HBV) in Escherichia coli cells, Dokl. Biochem. 279, 386-390 (1985); Galibert, F., Mandart, E., Fitoussi, F., Tiollais, P. and Charnay, P., Nucleotide sequence of the hepatitis B virus genome (subtype ayw) cloned in E. coli, Nature 281 (5733), 646-650 (1979), the entire contents of each of which are incorporated herein by reference.

In some embodiments, the target sequence is comprised in the following sequence:

>U95551.1 Hepatitis B virus subtype ayw, complete genome
(SEQ ID No. 1083)
AATTCCACAACCTTTCACCAAACTCTGCAAGATCCCAGAGTGAGAGGCCT

GTATTTCCCTGCTGGTGGCTCCAGTTCAGGAGCAGTAAACCCTGTTCCGA

CTACTGCCTCTCCCTTATCGTCAATCTTCTCGAGGATTGGGGACCCTGCG

CTGAACATGGAGAACATCACATCAGGATTCCTAGGACCCCTTCTCGTGTT

ACAGGCGGGGTTTTTCTTGTTGACAAGAATCCTCACAATACCGCAGAGTC

TAGACTCGTGGTGGACTTCTCTCAATTTTCTAGGGGGAACTACCGTGTGT

CTTGGCCAAAATTCGCAGTCCCCAACCTCCAATCACTCACCAACCTCCTG

TCCTCCAACTTGTCCTGGTTATCGCTGGATGTGTCTGCGGCGTTTTATCA

TCTTCCTCTTCATCCTGCTGCTATGCCTCATCTTCTTGTTGGTTCTTCTG

GACTATCAAGGTATGTTGCCCGTTTGTCCTCTAATTCCAGGATCCTCAAC

CACCAGCACGGGACCATGCCGAACCTGCATGACTACTGCTCAAGGAACCT

CTATGTATCCCTCCTGTTGCTGTACCAAACCTTCGGACGGAAATTGCACC

TGTATTCCCATCCCATCATCCTGGGCTTTCGGAAAATTCCTATGGGAGTG

GGCCTCAGCCCGTTTCTCCTGGCTCAGTTTACTAGTGCCATTTGTTCAGT

GGTTCGTAGGGCTTTCCCCCACTGTTTGGCTTTCAGTTATATGGATGATG

TGGTATTGGGGGCCAAGTCTGTACAGCATCTTGAGTCCCTTTTTACCGCT

GTTACCAATTTTCTTTTGTCTTTGGGTATACATTTAAACCCTAACAAAAC

AAAGAGATGGGGTTACTCTCTGAATTTTATGGGTTATGTCATTGGAAGTT

ATGGGTCCTTGCCACAAGAACACATCATACAAAAAATCAAAGAATGTTTT

AGAAAACTTCCTATTAACAGGCCTATTGATTGGAAAGTATGTCAACGAAT

TGTGGGTCTTTTGGGTTTTGCTGCCCCATTTACACAATGTGGTTATCCTG

CGTTAATGCCCTTGTATGCATGTATTCAATCTAAGCAGGCTTTCACTTTC

TCGCCAACTTACAAGGCCTTTCTGTGTAAACAATACCTGAACCTTTACCC

CGTTGCCCGGCAACGGCCAGGTCTGTGCCAAGTGTTTGCTGACGCAACCC

CCACTGGCTGGGGCTTGGTCATGGGCCATCAGCGCGTGCGTGGAACCTTT

TCGGCTCCTCTGCCGATCCATACTGCGGAACTCCTAGCCGCTTGTTTTGC

-continued

```
TCGCAGCAGGTCTGGAGCAAACATTATCGGGACTGATAACTCTGTTGTCC

TCTCCCGCAAATATACATCGTATCCATGGCTGCTAGGCTGTGCTGCCAAC

TGGATCCTGCGCGGGACGTCCTTTGTTTACGTCCCGTCGGCGCTGAATCC

TGCGGACGACCCTTCTCGGGGTCGCTTGGGACTCTCTCGTCCCCTTCTCC

GTCTGCCGTTCCGACCGACCACGGGGCGCACCTCTCTTTACGCGGACTCC

CCGTCTGTGCCTTCTCATCTGCCGGACCGTGTGCACTTCGCTTCACCTCT

GCACGTCGCATGGAGACCACCGTGAACGCCCACCGAATGTTGCCCAAGGT

CTTACATAAGAGGACTCTTGGACTCTCTGCAATGTCAACGACCGACCTTG

AGGCATACTTCAAAGACTGTTTGTTTAAAGACTGGGAGGAGTTGGGGGAG

GAGATTAGATTAAAGGTCTTTGTACTAGGAGGCTGTAGGCATAAATTGGT

CTGCGCACCAGCACCATGCAACTTTTTCACCTCTGCCTAATCATCTCTTG

TTCATGTCCTACTGTTCAAGCCTCCAAGCTGTGCCTTGGGTGGCTTTGGG

GCATGGACATCGACCCTTATAAAGAATTTGGAGCTACTGTGGAGTTACTC

TCGTTTTTGCCTTCTGACTTCTTTCCTTCAGTACGAGATCTTCTAGATAC

CGCCTCAGCTCTGTATCGGGAAGCCTTAGAGTCTCCTGAGCATTGTTCAC

CTCACCATACTGCACTCAGGCAAGCAATTCTTTGCTGGGGGGAACTAATG

ACTCTAGCTACCTGGGTGGGTGTTAATTTGGAAGATCCAGCATCTAGAGA

CCTAGTAGTCAGTTATGTCAACACTAATATGGGCCTAAAGTTCAGGCAAC

TCTTGTGGTTTCACATTTCTTGTCTCACTTTTGGAAGAGAAACCGTTATA

GAGTATTTGGTGTCTTTCGGAGTGTGGATTCGCACTCCTCCAGCTTATAG

ACCACCAAATGCCCCTATCCTATCAACACTTCCGGAAACTACTGTTGTTA

GACGACGAGGCAGGTCCCCTAGAAGAAGAACTCCCTCGCCTCGCAGACGA

AGGTCTCAATCGCCGCGTCGCAGAAGATCTCAATCTCGGGAACCTCAATG

TTAGTATTCCTTGGACTCATAAGGTGGGGAACTTTACTGGTCTTTATTCT

TCTACTGTACCTGTCTTTAATCCTCATTGGAAAACACCATCTTTTCCTAA

TATACATTTACACCAAGACATTATCAAAAAATGTGAACAGTTTGTAGGCC

CACTTACAGTTAATGAGAAAAGAAGATTGCAATTGATTATGCCTGCTAGG

TTTTATCCAAAGGTTACCAAATATTTACCATTGGATAAGGGTATTAAACC

TTATTATCCAGAACATCTAGTTAATCATTACTTCCAAACTAGACACTATT

TACACACTCTATGGAAGGCGGGTATATTATATAAGAGAGAAACAACACAT

AGCGCCTCATTTTGTGGGTCACCATATTCTTGGGAACAAGATCTACAGCA

TGGGGCAGAATCTTTCCACCAGCAATCCTCTGGGATTCTTTCCCGACCAC

CAGTTGGATCCAGCCTTCAGAGCAAACACAGCAAATCCAGATTGGGACTT

CAATCCCAACAAGGACACCTGGCCAGACGCCAACAAGGTAGGAGCTGGAG

CATTCGGGCTGGGTTTCACCCCACCGCACGGAGGCCTTTTGGGGTGGAGC

CCTCAGGCTCAGGGCATACTACAAACTTTGCCAGCAAATCCGCCTCCTGC

CTCCACCAATCGCCAGACAGGAAGGCAGCCTACCCCGCTGTCTCCACCTT

TGAGAAACACTCATCCTCAGGCCATGCAGTGG.
```

Annotation of SEQ ID NO: 1083: P protein CDS: 2309-1625; L-HBSAG CDS: 2850-837; M-HBsAg CDS: 3174-837; S-HBsAg CDS: 157-837; C Protein CDS: 1816-2454; X protein CDS: 1376-1840; CGI I: 186-288; CGI II: 1,217-1,670; CGI III: 2,282-2,448; pg RNA TSS: 1820; pre-C RNA TSS: 1791; pre-S2 RNA TSS: 3159; HBx RNA TSSs: 1243-1338; termination/polyA site: 1919. See references cited elsewhere herein.

VI. Epigenetic Modifications

An epigenetic editor described herein may perform sequence-specific epigenetic modification(s) (e.g., alteration of chemical modification(s)) of a target gene that harbors the target sequence. Such epigenetic modulation may be safer and more easily reversible than modulation due to gene editing, e.g., with generation of DNA double-strand breaks. In some embodiments, the epigenetic modulation may reduce or silence the target gene. In some embodiments, the modification is at a specific site of the target sequence. In some embodiments, the modification is at a specific allele of the target gene. Accordingly, the epigenetic modification may result in modulated (e.g., reduced) expression of one copy of a target gene harboring a specific allele, and not the other copy of the target gene. In some embodiments, the specific allele is associated with a disease, condition, or disorder.

In some embodiments, the epigenetic modification reduces or abolishes transcription of the target gene harboring the target sequence. In some embodiments, the epigenetic modification reduces or abolishes transcription of a copy of the target gene harboring a specific allele recognized by the epigenetic editor. In some embodiments, the epigenetic editor reduces the level of or eliminates expression of a protein encoded by the target gene. In some embodiments, the epigenetic editor reduces the level of or eliminates expression of a protein encoded by a copy of the target gene harboring a specific allele recognized by the epigenetic editor. The target HBV gene may be epigenetically modified in vitro, ex vivo, or in vivo.

The effector domain of an epigenetic editor described herein may alter (e.g., deposit or remove) a chemical modification at a nucleotide of the target gene or at a histone associated with the target gene. The chemical modification may be altered at a single nucleotide or a single histone, or may be altered at 2, 3, 4, 5, 6, 7, 8, 9, 10, 11, 12, 13, 14, 15, 16, 17, 18, 19, 20, 30, 40, 50, 60, 70, 80, 90, 100, 200, 300, 400, 500, 600, 700, 800, 900, 1000, 1500, 2000, 2500, 3000 or more nucleotides.

In some embodiments, an effector domain of an epigenetic editor described herein may alter a CpG dinucleotide within the target gene. In some embodiments, all CpG dinucleotides within 2000, 1500, 1000, 500, or 200 bps flanking a target sequence (e.g., in an alteration site as described herein) are altered according to a modification type described herein, as compared to the original state of the gene or the gene in a comparable cell not contacted with the epigenetic editor. In some embodiments, at least 1, 2, 3, 4, 5, 6, 7, 8, 9, 10, 11, 12, 13, 14, 15, 16, 17, 18, 19, 20, 25, 30, 35, 40, 45, 50, 60, 70, 80, 90, 100, 150, 200, 250, 300, 350, 400, 450, 500, 550, 600, 650, 700 or more of the CpG dinucleotides are altered as compared to the original state of the gene or the gene in a comparable cell not contacted with the epigenetic editor. In some embodiments, at least 5%, 6%, 7%, 8%, 9%, 10%, 15%, 20%, 25%, 30%, 35%, 40%, 45%, 50%, 55%, 60%, 65%, 70%, 75%, 80%, 85%, 90%, 95%, 96%, 97%, 98%, or 99% of the CpG dinucleotides are altered as compared to the original state of the gene or the gene in a comparable cell not contacted with the epigenetic editor. In some embodiments, one single CpG dinucleotide is altered, as compared to the original state of the gene or the gene in a comparable cell not contacted with the epigenetic editor.

An effector domain of an epigenetic editor described herein may alter a histone modification state of a histone associated with or bound to the target gene. For example, an effector domain may deposit a modification on one or more lysine residues of histone tails of histones associated with the target gene. In some embodiments, the effector domain may result in deacetylation of one or more histone tails of histones associated with the target gene, thereby reducing or silencing expression of the target gene. In some embodiments, the histone modification state is a methylation state. For example, the effector domain may result in a H3K9, H3K27 or H4K20 methylation (e.g. one or more of a H3K9me2, H3K9me3, H3K27me2, H3K27me3, and H4K20me3 methylation) at one or more histone tails associated with the target gene, thereby reducing or silencing expression of the target gene.

In some embodiments, all histone tails of histones bound to DNA nucleotides within 2000, 1500, 1000, 500, or 200 bps flanking the target sequence are altered according to a modification type as described herein, as compared to the original state of the chromosome or the chromosome in a comparable cell not contacted with the epigenetic editor. In some embodiments, at least 1, 2, 3, 4, 5, 6, 7, 8, 9, 10, 11, 12, 13, 14, 15, 16, 17, 18, 19, 20, 25, 30, 35, 40, 45, 50, 55, 60, 65, 70, 75, 80, 85, 90, 95, 100, 105, 110, 115, 120 or more histone tails of the bound histones are altered as compared to the original state of the chromosome or the chromosome in a comparable cell not contacted with the epigenetic editor. In some embodiments, at least 5%, 6%, 7%, 8%, 9%, 10%, 15%, 20%, 25%, 30%, 35%, 40%, 45%, 50%, 55%, 60%, 65%, 70%, 75%, 80%, 85%, 90%, 95%, 96%, 97%, 98%, or 99% of histone tails of the bound histones are altered as compared to the original state of the chromosome or the chromosome in a comparable cell not contacted with the epigenetic editor. For example, one single histone tail of the bound histones may be altered as compared to the original state of the chromosome or the chromosome in a comparable cell not contacted with the epigenetic editor. As another example, one single bound histone octamer may be altered as compared to the original state of the chromosome or the chromosome in a comparable cell not contacted with the epigenetic editor.

The chemical modification deposited at target gene DNA nucleotides or histone residues may be at or in close proximity to a target sequence in the target gene. In some embodiments, an effector domain of an epigenetic editor described herein alters a chemical modification state of a nucleotide or histone tail bound to a nucleotide 100-200, 200-300, 300-400, 400-55, 500-600, 600-700, or 700-800 nucleotides 5' or 3' to the target sequence in the target gene. In some embodiments, an effector domain alters a chemical modification state of a nucleotide or histone tail bound to a nucleotide within 10, 20, 30, 40, 50, 60, 70, 80, 90, 100, 200, 300, 400, 500, 600, 700, 800, 900, 1000, 1100, 1200, 1300, 1400, 1500, 1600, 1700, 1800, 1900, or 2000 nucleotides flanking the target sequence. As used herein, "flanking" refers to nucleotide positions 5' to 5' end of and 3' to the 3' end of a particular sequence, e.g. a target sequence.

In some embodiments, an effector domain mediates or induces a chemical modification change of a nucleotide or a histone tail bound to a nucleotide distant from a target sequence. Such modification may be initiated near the target sequence, and may subsequently spread to one or more nucleotides in the target gene distant from the target sequence. For example, an effector domain may initiate alteration of a chemical modification state of one or more nucleotides or one or more histone residues bound to one or more nucleotides within 10, 20, 30, 40, 50, 60, 70, 80, 90, 100, 200, 300, 400, 500 nucleotides flanking the target sequence, and the chemical modification state alteration may spread to one or more nucleotides at least 100, 200, 300, 400, 500, 600, 700, 800, 900, 1000, 1100, 1200, 1300, 1400, 1500, 1600, 1700, 1800, 1900, 2000, 2500, 3000, or more nucleotides from the target sequence in the target gene, either upstream or downstream of the target sequence. In certain embodiments, the chemical modification may be initiated at less than 2, 3, 5, 10, 20, 30, 40, 50, or 100 nucleotides in the target gene and spread to at least 100, 200, 300, 400, 500, 600, 700, 800, 900, 1000, 2000, or more nucleotides in the target gene. In some embodiments, the chemical modification spreads to nucleotides in the entire target gene. Additional proteins or transcription factors, for example, transcription repressors, methyltransferases, or transcription regulation scaffold proteins, may be involved in the spreading of the chemical modification. Alternatively, the epigenetic editor alone may be involved.

In some embodiments, an epigenetic editor described herein reduces expression of a target gene by at least about 20%, at least about 30%, at least about 40%, at least about 50%, at least about 60%, at least about 70%, at least about 80%, at least about 90%, at least about 95%, at least about 99%, or more, as measured by transcription of the target gene in a cell, a tissue, or a subject as compared to a control cell, control tissue, or a control subject (e.g., in the absence of the epigenetic editor). In some embodiments, the epigenetic editors described herein reduces expression of a copy of target gene by at least about 20%, at least about 30%, at least about 40%, at least about 50%, at least about 60%, at least about 70%, at least about 80%, at least about 90%, at least about 95%, at least about 99%, at least about 99.9%, or more, as measured by transcription of the copy of the target gene in a cell, a tissue, or a subject as compared to a control cell, control tissue, or a control subject. For example, in some embodiments, an epigenetic editor described herein reduces expression of an HBV target gene in vitro or in vivo (e.g., as measured as the level of an HBV biomarker in a subject), by at least 20%, at least 30%, at least 40%, at least 50%, at least 60%, at least 70%, at least 80%, at least 90%, at least 95%, at least 99%, at least 99.9%, or more, as measured for example, by transcription of the target gene, or by assessing an HBV biomarker (e.g., plasma HBV DNA, plasma HBVsAg, or plasma HBVeAg) in a cell, a tissue, or a subject contacted or administered with the epigenetic editor as compared to a control cell, control tissue, or a control subject (e.g., in the absence of the epigenetic editor). In certain embodiments, the copy of the target gene harbors a specific sequence or allele recognized by the epigenetic editor. In particular embodiments, the epigenetically modified copy encodes a functional protein, and accordingly an epigenetic editor disclosed herein may reduce or abolish expression and/or function of the protein. For example, an epigenetic editor described herein may reduce expression and/or function of a protein encoded by the target gene by at least 3-fold, at least 4-fold, at least 5-fold, at least 6-fold, at least 7-fold, at least 8-fold, at least 9-fold, at least 10-fold, at least 11-fold, at least 12-fold, at least 13-fold, at least 14-fold, at least 15-fold, at least 20-fold, at least 25-fold, at least 30-fold, at least 35-fold, at least 40-fold, at least 45-fold, at least 50-fold, at least 60-fold, at least 70-fold, at least 80-fold, at least 90-fold, or at least 100 fold in a cell, a tissue, or a subject as compared to a control cell, control tissue, or a control subject.

Modulation of target gene expression can be assayed by determining any parameter that is indirectly or directly affected by the expression of the target gene. Such parameters include, e.g., changes in RNA or protein levels; changes in protein activity; changes in product levels; changes in downstream gene expression; changes in transcription or activity of reporter genes such as, for example, luciferase, CAT, beta-galactosidase, or GFP; changes in signal transduction; changes in phosphorylation and dephosphorylation; changes in receptor-ligand interactions; changes in concentrations of second messengers such as, for example, cGMP, CAMP, IP3, and $Ca^{2+}$; changes in cell growth; changes in neovascularization; and/or changes in any functional effect of gene expression. Measurements can be made in vitro, in vivo, and/or ex vivo, and can be made by conventional methods, e.g., measurement of RNA or protein levels, measurement of RNA stability, and/or identification of downstream or reporter gene expression. Readout can be by way of, for example, chemiluminescence, fluorescence, colorimetric reactions, antibody binding, inducible markers, ligand binding assays, changes in intracellular second messengers such as cGMP and inositol triphosphate (IP3), changes in intracellular calcium levels; cytokine release, and the like.

Methods for determining the expression level of a gene, for example the target of an epigenetic editor, may include, e.g., determining the transcript level of a gene by reverse transcription PCR, quantitative RT-PCR, droplet digital PCR (ddPCR), Northern blot, RNA sequencing, DNA sequencing (e.g., sequencing of complementary deoxyribonucleic acid (cDNA) obtained from RNA); next generation (Next-Gen) sequencing, nanopore sequencing, pyrosequencing, or Nanostring sequencing. Levels of protein expressed from a gene may be determined, e.g., by Western blotting, enzyme linked immuno-absorbance assays, mass-spectrometry, immunohistochemistry, or flow cytometry analysis. Gene expression product levels may be normalized to an internal standard such as total messenger ribonucleic acid (mRNA) or the expression level of a particular gene, e.g., a housekeeping gene.

In some embodiments, the effect of an epigenetic editor in modulating target gene expression may be examined using a reporter system. For example, an epigenetic editor may be designed to target a reporter gene encoding a reporter protein, such as a fluorescent protein. Expression of the reporter gene in such a model system may be monitored by, e.g., flow cytometry, fluorescence-activated cell sorting (FACS), or fluorescence microscopy. In some embodiments, a population of cells may be transfected with a vector that harbors a reporter gene. The vector may be constructed such that the reporter gene is expressed when the vector transfects a cell. Suitable reporter genes include genes encoding fluorescent proteins, for example green, yellow, cherry, cyan or orange fluorescent proteins. The population of cells carrying the reporter system may be transfected with DNA, mRNA, or vectors encoding the epigenetic editor targeting the reporter gene.

VII. Pharmaceutical Compositions

Another aspect of the present disclosure is a pharmaceutical composition comprising as an active ingredient (or as the sole active ingredient) one or more epigenetic editors described herein or component(s) (e.g., fusion proteins and/or guide polynucleotides) thereof, or nucleic acid molecule(s) encoding said epigenetic editors or component(s) thereof. For example, a pharmaceutical composition may comprise nucleic acid molecule(s) encoding the fusion protein(s) (and guide polynucleotides, where applicable) of an epigenetic editor described herein. In some embodiments, separate pharmaceutical compositions comprise the fusion protein(s) and the guide polynucleotide(s). In some embodiments, multiple pharmaceutical compositions, each comprising one epigenetic editor, are administered simultaneously. A pharmaceutical composition may also comprise cells that have undergone epigenetic modification(s) mediated or induced by an epigenetic editor provided herein.

Generally, the epigenetic editors described herein or component(s) thereof, or nucleic acid molecule(s) encoding said epigenetic editors or component(s) thereof, of the present disclosure are suitable to be administered as a formulation in association with one or more pharmaceutically acceptable excipient(s), e.g., as described below.

The term "excipient" is used herein to describe any ingredient other than the compound(s) of the present disclosure. The choice of excipient(s) will to a large extent depend on factors such as the particular mode of administration, the effect of the excipient on solubility and stability, and the nature of the dosage form. As used herein, "pharmaceutically acceptable excipient" includes any and all solvents, dispersion media, coatings, antibacterial and antifungal agents, isotonic and absorption delaying agents, and the like that are physiologically compatible. Some examples of pharmaceutically acceptable excipients are water, saline, phosphate buffered saline, dextrose, glycerol, ethanol and the like, as well as combinations thereof. In many cases, it will be preferable to include isotonic agents, for example, sugars, polyalcohols such as mannitol, sorbitol, or sodium chloride in the composition. Additional examples of pharmaceutically acceptable substances are wetting agents or minor amounts of auxiliary substances such as wetting or emulsifying agents, preservatives, or buffers, which enhance the shelf life or effectiveness of the antibody.

Formulations of a pharmaceutical composition suitable for parenteral administration typically comprise the active ingredient combined with a pharmaceutically acceptable carrier, such as sterile water or sterile isotonic saline. Such formulations may be prepared, packaged, or sold in a form suitable for bolus administration or for continuous administration. In some embodiments, the epigenetic editor or its component(s) are introduced to target cells in the form of nucleic acid molecule(s) encoding the epigenetic editor or its component(s); accordingly, the pharmaceutical compositions herein comprise the nucleic acid molecule(s). Such nucleic acid molecule(s) may be, for example, DNA, RNA or mRNA, and/or modified nucleic acid sequence(s) (e.g., with chemical modifications, a 5' cap, or one or more 3' modifications). In some embodiments, the nucleic acid molecule(s) may be delivered as naked DNA or RNA, for instance by means of transfection or electroporation, or can be conjugated to molecules (e.g., N-acetylgalactosamine) promoting uptake by target cells. In some embodiments, the nucleic acid molecule(s) may be in nucleic acid expression vector(s), which may include expression control sequences such as promoters, enhancers, transcription signal sequences, transcription termination sequences, introns, polyadenylation signals, Kozak consensus sequences, internal ribosome entry sites (IRES), etc. Such expression control sequences are well known in the art. A vector may also comprise a sequence encoding a signal peptide (e.g., for nuclear localization, nucleolar localization, or mitochondrial localization), associated with (e.g., inserted into or fused to) a sequence coding for a protein.

Examples of vectors include, but are not limited to, plasmid vectors; viral vectors based on vaccinia virus, poliovirus, adenovirus, adeno-associated virus, SV40, herpes simplex virus, human immunodeficiency virus, retrovirus (e.g., Murine Leukemia Virus, or spleen necrosis virus, vectors derived from retroviruses such as Rous Sarcoma Virus, Harvey Sarcoma Virus, avian leukosis virus, a lentivirus, human immunodeficiency virus, myeloproliferative sarcoma virus, and mammary tumor virus); and other recombinant vectors. In certain embodiments, the vector is a plasmid or a viral vector. Viral particles may also be used to deliver nucleic acid molecule(s) encoding epigenetic editors or component(s) thereof as described herein. For example, "empty" viral particles can be assembled to contain any suitable cargo. Viral vectors and viral particles may also be engineered to incorporate targeting ligands to alter target tissue specificity.

In certain embodiments, an epigenetic editor as described herein or component(s) thereof are encoded by nucleic acid sequence(s) present in one or more viral vectors, or a suitable capsid protein of any viral vector. Examples of viral vectors include adeno-associated viral vectors (e.g., derived from AAV3, AAV3b, AAV4, AAV5, AAV6, AAV7, AAV8, AAV9, AAVrh8, AAV10, and/or variants thereof); retroviral vectors (e.g., Maloney murine leukemia virus, MML-V), adenoviral vectors (e.g., AD100), lentiviral vectors (e.g., HIV and FIV-based vectors), and herpesvirus vectors (e.g., HSV-2).

In some embodiments, delivery involves an adeno-associated virus (AAV) vector. AAV vector delivery may be particularly useful where the DNA-binding domain of an epigenetic editor fusion protein is a zinc finger array. Without wishing to be bound by any theory, the smaller size of zinc finger arrays compared to larger DNA-binding domains such as Cas protein domains may allow such a fusion protein to be conveniently packed in viral vectors such as an AAV vector.

Any AAV serotype, e.g., human AAV serotype, can be used for an AAV vector as described herein, including, but not limited to, AAV serotype 1 (AAV1), AAV serotype 2 (AAV2), AAV serotype 3 (AAV3), AAV serotype 4 (AAV4), AAV serotype 5 (AAV5), AAV serotype 6 (AAV6), AAV serotype 7 (AAV7), AAV serotype 8 (AAV8), AAV serotype 9 (AAV9), AAV serotype 10 (AAV10), and AAV serotype 11 (AAV11), as well as variants thereof. In some embodiments, an AAV variant has at least 90%, 91%, 92%, 93%, 94%, 95%, 96%, 97%, 98%, or 99% amino acid sequence identity to a wildtype AAV. In certain embodiments, the AAV variant may be engineered such that its capsid proteins have reduced immunogenicity or enhanced transduction ability in humans. In some instances, one or more regions of at least two different AAV serotype viruses are shuffled and reassembled to generate a chimeric variant. For example, a chimeric AAV may comprise inverted terminal repeats (ITRs) that are of a heterologous serotype compared to the serotype of the capsid. The resulting chimeric AAV can have a different antigenic reactivity or recognition compared to its parental serotypes. In some embodiments, a chimeric variant of an AAV includes amino acid sequences from 2, 3, 4, 5, or more different AAV serotypes.

Non-viral systems are also contemplated for delivery as described herein. Non-viral systems include, but are not limited to, nucleic acid transfection methods including electroporation, sonoporation, calcium phosphate transfection, microinjection, DNA biolistics, lipid-mediated transfection, transfection through heat shock, compacted DNA-mediated transfection, lipofection, cationic agent-mediated transfection, and transfection with liposomes, immunoliposomes, or cationic facial amphiphiles (CFAs). In certain embodiments, one or more mRNAs encoding epigenetic editor fusion proteins as described herein may be co-electroporated with one or more guide polynucleotides (e.g., gRNAs) as described herein. One important category of non-viral nucleic acid vectors is nanoparticles, which can be organic (e.g., lipid) or inorganic (e.g., gold). For instance, organic (e.g. lipid and/or polymer) nanoparticles can be suitable for use as delivery vehicles in certain embodiments of this disclosure.

In some embodiments, delivery is accomplished using a lipid nanoparticle (LNP). LNP compositions are typically sized on the order of micrometers or smaller and may include a lipid bilayer. In some embodiments, a LNP refers to any particle that has a diameter of less than 1000 nm, 500 nm, 250 nm, 200 nm, 150 nm, 100 nm, 75 nm, 50 nm, or 25 nm. Nanoparticle compositions encompass lipid nanoparticles (LNPs), liposomes (e.g., lipid vesicles), and lipoplexes.

An LNP as described herein may be made from cationic, anionic, or neutral lipids. In some embodiments, an LNP may comprise neutral lipids, such as the fusogenic phospholipid 1,2-Dioleoyl-sn-glycero-3-phosphoethanolamine (DOPE) or the membrane component cholesterol, as helper lipids to enhance transfection activity and nanoparticle stability. In some embodiments, an LNP may comprise hydrophobic lipids, hydrophilic lipids, or both hydrophobic and hydrophilic lipids. Any lipid or combination of lipids that are known in the art can be used to produce an LNP. The lipids may be combined in any molar ratios to produce the LNP. In some embodiments, the LNP is a liver-targeting (e.g., preferentially or specifically targeting the liver) LNP.

LNP formulations and methods of LNP delivery that can be used will be apparent to those skilled in the art based on the present disclosure and the state of the art. Non-limiting exemplary compositions and methods can be found in Shah, R., Eldridge, D., Palombo, E., and Harding, I., Lipid Nanoparticles: Production, Characterization and Stability, Springer, 2015, ISBN-13 978-3319107103; Ziegler, S., Lipid Nanoparticles: Advances in Research and Applications, Nova Science Pub., Inc, ISBN-13 978-1536186536; Mitchell, M. J., Billingsley, M. M., Haley, R. M. et al. *Engineering precision nanoparticles for drug delivery*, Nat Rev Drug Discov 20, 101-124 (2021); Hou, X., Zaks, T., Langer, R. et al. *Lipid nanoparticles for mRNA delivery*. Nat Rev Mater 6, 1078-1094 (2021); *Lipid-Nanoparticle-Based Delivery of CRISPR/Cas9 Genome-Editing Components*, Pardis Kazemian, Si-Yue Yu, Sarah B. Thomson, Alexandra Birkenshaw, Blair R. Leavitt, and Colin J. D. Ross. Molecular Pharmaceutics 2022 19 (6), 1669-1686; Cullis P R, Hope M J. *Lipid Nanoparticle Systems for Enabling Gene Therapies*, Mol Ther. 2017 Jul. 5; 25 (7): 1467-1475; Hatit, M. Z. C., Lokugamage, M. P., Dobrowolski, C. N. et al. *Species-dependent in vivo mRNA delivery and cellular responses to nanoparticles*, Nat. Nanotechnol. 17, 310-318 (2022); Lam, K., Schreiner, P., Leung, A., Stainton, P., Reid, S., Yaworski, E., Lutwyche, P. and Heyes, J. (2023), *Optimizing Lipid Nanoparticles for Delivery in Primates*, Adv. Mater; Dilliard, S. A., Siegwart, D. J. *Passive, active and endogenous organ-targeted lipid and polymer nanoparticles for delivery of genetic drugs*, Nat Rev Mater (2023); Kasiewicz, L. N., et. al., *Lipid nanoparticles incorporating a GalNAc ligand enable in vivo liver ANGPTL3 editing in wild-type and somatic LDLR knockout non-human primates*, bioRxiv 2021.11.08.467731, doi: https://doi.org/10.1101/2021.11.08.467731; Tombácz, I., et. al., *Highly efficient CD4+ T cell targeting and genetic recombination using engineered CD4+ cell-homing mRNA-LNPs*, Molecular Therapy, Volume 29, Issue 11, 2021, 3293-3304; Cheng, Q., Wei, T., Farbiak, L. et al. *Selective organ targeting (SORT) nanoparticles for tissue-specific mRNA delivery and CRISPR Cas gene editing*, Nat. Nanotechnol. 15, 313-320 (2020); Zhang, Y., et. al., *Lipids and Lipid Derivatives for RNA Delivery*, Chemical Reviews 2021 121 (20); Lam, K., et. al, Unsaturated, *Trialkyl Ionizable Lipids are Versatile Lipid-Nanoparticle Components for Therapeutic and Vaccine Applications*, Adv. Mater. 2023, 35; Han, X., Zhang, H., Butowska, K. et al. *An ionizable lipid toolbox for RNA delivery*, Nat Commun 12, 7233 (2021); U.S. Pat. Nos. 9,364,435; 8,058,069; 8,822,668; 8,492,359; 11,141,378; 9,518,272; 9,404,127; 9,006,417; 7,901,708; 9,005,654; 9,878,042; 9,682,139; 8,642,076; 9,593,077; 9,415,109; 9,701,623; 10,369,226; 9,999,673; 9,301,923; 10,342,761; 10,137,201; International Patent Application PCT/US2014/070882; International Publication No. WO2015199952A1; International Publication No. WO2017075531A1; International Publication No. WO2018081480A1; International Publication No. WO2016081029A1; European Application No. EP3852911A2; each of which are incorporated herein by reference in their entirety. The ordinarily skilled artisan will be able to identify an appropriate LNP and method of delivery based on the present disclosure and the state of the art. The present disclosure is not limited in this respect.

Other methods of delivery to target cells will be known to those skilled in the art and can be used with the compositions of the present disclosure.

Any type of cell may be targeted for delivery of an epigenetic editor or component(s) thereof as described herein. For example, the cells may be eukaryotic or prokaryotic. In some embodiments, the cells are mammalian (e.g., human) cells. Human cells may include, for example, hepatocytes, biliary epithelial cells (cholangiocytes), stellate cells, Kupffer cells, and liver sinusoidal endothelial cells.

In some embodiments, an epigenetic editor described herein, or component(s) thereof, are delivered to a host cell for transient expression, e.g., via a transient expression vector. Transient expression of the epigenetic editor or its component(s) may result in prolonged or permanent epigenetic modification of the target gene. For example, the epigenetic modification may be stable for at least 1, 2, 3, 4, 5, 6, 7, 8, 9, 10. 11, or 12 weeks or more; or 3, 4, 5, 6, 7, 8, 9, 10, 11, or 12 months or more, after introduction of the epigenetic editor into the host cell. The epigenetic modification may be maintained after one or more mitotic and/or meiotic events of the host cell. In particular embodiments, the epigenetic modification is maintained across generations in offspring generated or derived from the host cell.

VIII. Therapeutic Uses of Epigenetic Editors

The present disclosure also provides methods for treating or preventing a condition in a subject, comprising administering to the subject an epigenetic editor or pharmaceutical composition as described herein. The epigenetic editor may effectuate an epigenetic modification of a target polynucleotide sequence in a target gene associated with a disease, condition, or disorder in the subject, thereby modulating expression of the target gene to treat or prevent the disease, condition, or disorder. In some embodiments, the epigenetic editor reduces the expression of the target gene to an extent sufficient to achieve a desired effect, e.g., a therapeutically relevant effect such as the prevention or treatment of the disease, condition, or disorder.

In some embodiments, a subject is administered a system for modulating (e.g., repressing) expression of HBV or of an HBV gene, wherein the system comprises (1) the fusion protein(s) and, where relevant, guide polynucleotide(s) of an epigenetic editor as described herein, or (2) nucleic acid molecules encoding said fusion protein(s) and, where relevant, guide polynucleotide(s).

"Treat," "treating" and "treatment" refer to a method of alleviating or abrogating a biological disorder and/or at least one of its attendant symptoms. As used herein, to "alleviate" a disease, disorder or condition means reducing the severity and/or occurrence frequency of the symptoms of the disease, disorder, or condition. Further, references herein to "treatment" include references to curative, palliative and prophylactic treatment. In some embodiments, as compared with an equivalent untreated control, alleviating a symptom may involve reduction of the symptom by at least 3%, 5%, 10%, 20%, 40%, 50%, 60%, 80%, 90%, 95%, 98%, 99%, 99.5%, 99.9%, or 100% as measured by any standard technique.

In some embodiments, the subject may be a mammal, e.g., a human. In some embodiments, the subject is selected from a non-human primate such as chimpanzee, cynomolgus monkey, or macaque, and other apes and monkey species.

Some aspects of this disclosure provide methods comprising administering an epigenetic editing system to a subject characterized by the presence of detectable levels of HBV DNA, HBsAg, and/or HBeAg in the plasma of the subject, for example, a subject having a chronic HBV infection. In some such embodiments, the epigenetic editing system comprises a first DNA binding domain, a first DNMT domain, and a transcriptional repressor domain or one or more nucleic acid molecules encoding the same, wherein the first DNA binding domain binds a first target region of an HBV gene or genome, and the administering results in a reduction of the level of HBV DNA, the level of HBsAg, and/or the level of HBsAg in the plasma of the subject, and the reduction of the level of HBV DNA, of the level of HBsAg, and/or of the level of HBsAg in the plasma of the subject, is at least 90% (a 1-log reduction) compared to the respective level observed or observable in the plasma of the subject prior to the administering, and the 1-log reduction is maintained for at least 14 days after the administering. In some embodiments, the reduction of the level of HBV DNA in the plasma of the subject is at least 90% (a 1-log reduction). In some embodiments, the reduction of the level of HBV DNA in the plasma of the subject is at least 99% (a 2-log reduction). In some embodiments, the reduction of the level of HBsAg in the plasma of the subject is at least 90% (a 1-log reduction). In some embodiments, the reduction of the level of HBsAg in the plasma of the subject is at least 99% (a 2-log reduction). In some embodiments, the reduction of the level of HBeAg in the plasma of the subject is at least 90% (a 1-log reduction). In some embodiments, the reduction of the level of HBeAg in the plasma of the subject is at least 99% (a 2-log reduction). In some embodiments, the reduction is maintained for at least 21 days. In some embodiments, the reduction is maintained for at least 28 days. In some embodiments, the reduction is maintained for at least 35 days. In some embodiments, the reduction is maintained for at least 42 days. In some embodiments, the reduction is maintained for at least 56 days. In some embodiments, the reduction is maintained for at least 70 days. In some embodiments, the reduction is maintained for at least 84 days. In some embodiments, the reduction is maintained for at least 112 days. In some embodiments, the reduction is maintained for at least 140 days. In some embodiments, the reduction is maintained for at least 168 days. In some embodiments, the reduction is maintained for at least 6 months. In some embodiments, the reduction is maintained for at least 9 months. In some embodiments, the reduction is maintained for at least 12 months. In some embodiments, the reduction is maintained for at least 24 months. In some embodiments, the HBV genome comprises HBV genotype A. In some embodiments, the HBV genome comprises HBV genotype B. In some embodiments, the HBV genome comprises HBV genotype C. In some embodiments, the HBV genome comprises, HBV genotype D. In some embodiments, the HBV genome comprises HBV genotype E. In some embodiments, the HBV genome comprises HBV genotype F. In some embodiments, the HBV genome comprises HBV genotype G. In some embodiments, the HBV genome comprises HBV genotype H. In some embodiments, the HBV genome comprises a sequence with at least 80%, at least 90%, at least 95%, at least 99%, or greater than 99% sequence identity to an HBV genome sequence provided herein. In some embodiments, the first target region is located in a region of the HBV genome within nucleotides 0-303 of an HBV genome provided herein. In some embodiments, the first target region is located within nucleotides 0-303 of SEQ ID NO: 1082. In some embodiments, the first target region is located within nucleotides 0-303 of SEQ ID NO: 1083. In some embodiments, the first target region is located in a region of the HBV genome within nucleotides 1000-2448 of an HBV genome provided herein. In some embodiments, the first target region is located within nucleotides 1000-2448 of SEQ ID NO: 1082. In some embodiments, the first target region is located within nucleotides 1000-2448 of SEQ ID NO: 1083. In some embodiments, the first target region is located in a region of the HBV genome within nucleotides 2802-3182 of an HBV genome provided herein. In some embodiments, the first target region is located within nucleotides 2802-3182 of SEQ ID NO: 1082. In some embodiments, the first target region is located within nucleotides 2802-3182 of SEQ ID NO: 1083. In some embodiments, the first target region of the HBV genome is located in an HBV CpG island (CGI). In some embodiments, the CGI is an HBV canonical CGI. In some embodiments, the CGI is canonical CGI-I. In some embodiments, CGI is canonical CGI-I of HBV genotype D. In some embodiments, CGI-I spans nucleotides 186-288 of SEQ ID NO: 1082 In some embodiments, CGI-I spans nucleotides 186-288 of SEQ ID NO: 1083 In some embodiments, the CGI is canonical CGI-II. In some embodiments, the CGI is canonical CGI-II HBV genotype D. In some embodiments, the CGI is CGI II spans nucleotides 1,217-1,670 of SEQ ID NO: 1082. In some embodiments, the CGI is CGI II spans nucleotides 1,217-1,670 of SEQ ID NO: 1083. In some embodiments, the CGI is canonical CGI-III. In some embodiments, the CGI is canonical CGI-III HBV genotype D. In some embodiments, the CGI is CGI-III spans nucleotides 2,282-2,448 of SEQ ID NO: 1082. In some embodiments, the CGI is CGI-III spans nucleotides 2,282-2,448 of SEQ ID NO: 1083. In some embodiments, the first target region of the HBV genome is located in a promotor. In some embodiments, the first target region of the HBV genome is located in the sp1 promoter. In some embodiments, the first target region of the HBV genome is located in sp2 promoter. In some embodiments, the first target region of the HBV genome is located in cp promoter. In some embodiments, the first target region of the HBV genome is located in xp promoter. In some embodiments, the first target region of the HBV genome is located in an enhancer region. In some embodiments, the first target region of the HBV genome is located in Enh I. In some embodiments, the first target region of the HBV genome is located in Enh II. In some embodiments, the first target region of the HBV genome is located in a section of the HBV genome that encodes a transcript. In some embodiments, the first target region of the HBV genome is located in a section of the HBV genome that encodes a pgRNA transcript. In some embodiments, the first target region of the HBV genome is located in a section of the HBV genome that encodes a preCore RNA transcript. In some embodiments, the first target region of the HBV genome is located in a section of the HBV genome that encodes a preS RNA transcript. In some embodiments, the first target region of the HBV genome is located in a section of the HBV genome that encodes an S RNA transcript. In some embodiments, the first target region of the HBV genome is located in a section of the HBV genome that encodes an HBx RNA transcript. In some embodiments, the first target region of the HBV genome is within 1000, 900, 800, 700, 600, 500, 400, 300, 200, or 100 base pairs (bp) of an HBV transcription start site (TSS). In some embodiments, the TSS is a pg RNA TSS. In some embodiments, the first target region is within 600, within 500, within 400, within 300, within 200, or within 100 base pairs of the pg RNA TSS. In some embodiments, the pg RNA TSS is located at nucleotide 1820 of SEQ ID NO: 1082 or at nucleotide 1820 of SEQ ID NO: 1083. In some embodiments, the first target region is within 600 base pairs of nucleotide 1820 in SEQ ID NO: 1082. In some embodiments, the first target region is within 600 base pairs of nucleotide 1820 in SEQ ID NO: 1083. In some embodiments, the first target region is within 500 base pairs of nucleotide 1820 in SEQ ID NO: 1082. In some embodiments, the first target region is within 500 base pairs of nucleotide 1820 in SEQ ID NO: 1083. In some embodiments, the first target region is within 400 base pairs of nucleotide 1820 in SEQ ID NO: 1082. In some embodiments, the first target region is within 400 base pairs of nucleotide 1820 in SEQ ID NO: 1083. In some embodiments, the first target region is within 300 base pairs of nucleotide 1820 in SEQ ID NO: 1082. In some embodiments, the first target region is within 300 base pairs of nucleotide 1820 in SEQ ID NO: 1083. In some embodiments, the first target region is within 200 base pairs of nucleotide 1820 in SEQ ID NO: 1082. In some embodiments, the first target region is within 200 base pairs of nucleotide 1820 in SEQ ID NO: 1083. In some embodiments, the first target region is within 100 base pairs of nucleotide 1820 in SEQ ID NO: 1082. In some embodiments, the first target region is within 100 base pairs of nucleotide 1820 in SEQ ID NO: 1083. In some embodiments, the TSS is a preC RNA TSS. In some embodiments, the first target region is within 600, within 500, within 400, within 300, within 200, or within 100 base pairs of the preC RNA TSS. In some embodiments, the preC RNA TSS is located at nucleotide 1791 of SEQ ID NO: 1082 or at nucleotide 1791 of SEQ ID NO: 1083. In some embodiments, the first target region is within 600 base pairs of nucleotide 1791 in SEQ ID NO: 1082. In some embodiments, the first target region is within 600 base pairs of nucleotide 1791 in SEQ ID NO: 1083. In some embodiments, the first target region is within 500 base pairs of nucleotide 1791 in SEQ ID NO: 1082. In some embodiments, the first target region is within 500 base pairs of nucleotide 1791 in SEQ ID NO: 1083. In some embodiments, the first target region is within 400 base pairs of nucleotide 1791 in SEQ ID NO: 1082. In some embodiments, the first target region is within 400 base pairs of nucleotide 1791 in SEQ ID NO: 1083. In some embodiments, the first target region is within 300 base pairs of nucleotide 1791 in SEQ ID NO: 1082. In some embodiments, the first target region is within 300 base pairs of nucleotide 1791 in SEQ ID NO: 1083. In some embodiments, the first target region is within 200 base pairs of nucleotide 1791 in SEQ ID NO: 1082. In some embodiments, the first target region is within 200 base pairs of nucleotide 1791 in SEQ ID NO: 1083. In some embodiments, the first target region is within 100 base pairs of nucleotide 1791 in SEQ ID NO: 1082. In some embodiments, the first target region is within 100 base pairs of nucleotide 1791 in SEQ ID NO: 1083. In some embodiments, the TSS is a preS2 RNA TSS. In some embodiments, the first target region is within 600, within 500, within 400, within 300, within 200, or within 100 base pairs of the preS2 RNA TSS. In some embodiments, the preS2 RNA TSS is located at nucleotide 3159 of SEQ ID NO: 1082 or at nucleotide 3159 of SEQ ID NO: 1083. In some embodiments, the first target region is within 600 base pairs of nucleotide 3159 in SEQ ID NO: 1082. In some embodiments, the first target region is within 600 base pairs of nucleotide 3159 in SEQ ID NO: 1083. In some embodiments, the first target region is within 500 base pairs of nucleotide 3159 in SEQ ID NO: 1082. In some embodiments, the first target region is within 500 base pairs of nucleotide 3159 in SEQ ID NO: 1083. In some embodiments, the first target region is within 400 base pairs of nucleotide 3159 in SEQ ID NO: 1082. In some embodiments, the first target region is within 400 base pairs of nucleotide 3159 in SEQ ID NO: 1083. In some embodiments, the first target region is within 300 base pairs of nucleotide 3159 in SEQ ID NO: 1082. In some embodiments, the first target region is within 300 base pairs of nucleotide 3159 in SEQ ID NO: 1083. In some embodiments, the first target region is within 200 base pairs of nucleotide 3159 in SEQ ID NO: 1082. In some embodiments, the first target region is within 200 base pairs of nucleotide 3159 in SEQ ID NO: 1083. In some embodiments, the first target region is within 100 base pairs of nucleotide 3159 in SEQ ID NO: 1082. In some embodiments, the first target region is within 100 base pairs of nucleotide 3159 in SEQ ID NO: 1083. In some embodiments, the TSS is an HBx RNA TSSs. In some embodiments, the first target region is within 600, within 500, within 400, within 300, within 200, or within 100 base pairs of the HBx RNA TSS. In some embodiments, the HBx RNA TSS is located at a nucleotide within the sequence of nucleotides 1243-1338 of SEQ ID NO: 1082 or nucleotides 1243-1338 of SEQ ID NO: 1083. In some embodiments, the first target region is within 600 base pairs of nucleotide 1243 in SEQ ID NO: 1082. In some embodiments, the first target region is within 600 base pairs of nucleotide 1243 in SEQ ID NO: 1083. In some embodiments, the first target region is within 500 base pairs of nucleotide 1243 in SEQ ID NO: 1082. In some embodiments, the first target region is within 500 base pairs of nucleotide 1243 in SEQ ID NO: 1083. In some embodiments, the first target region is within 400 base pairs of nucleotide 1243 in SEQ ID NO: 1082. In some embodiments, the first target region is within 400 base pairs of nucleotide 1243 in SEQ ID NO: 1083. In some embodiments, the first target region is within 300 base pairs of nucleotide 1243 in SEQ ID NO: 1082. In some embodiments, the first target region is within 300 base pairs of nucleotide 1243 in SEQ ID NO: 1083. In some embodiments, the first target region is within 200 base pairs of nucleotide 1243 in SEQ ID NO: 1082. In some embodiments, the first target region is within 200 base pairs of nucleotide 1243 in SEQ ID NO: 1083. In some embodiments, the first target region is within 100 base pairs of nucleotide 1243 in SEQ ID NO: 1082. In some embodiments, the first target region is within 100 base pairs of nucleotide 1243 in SEQ ID NO: 1083. In some embodiments, the first target region is within 600 base pairs of nucleotide 1338 in SEQ ID NO: 1083. In some embodiments, the first target region is within 500 base pairs of nucleotide 1338 in SEQ ID NO: 1082. In some embodiments, the first target region is within 500 base pairs of nucleotide 1338 in SEQ ID NO: 1083. In some embodiments, first target region is within 400 base pairs of nucleotide 1338 in SEQ ID NO: 1082. In some embodiments, the first target region is within 400 base pairs of nucleotide 1338 in SEQ ID NO: 1083. In some embodiments, the first target region is within 300 base pairs of nucleotide 1338 in SEQ ID NO: 1082. In some embodiments, the first target region is within 300 base pairs of nucleotide 1338 in SEQ ID NO: 1083. In some embodiments, the first target region is within 200 base pairs of nucleotide 1338 in SEQ ID NO: 1082. In some embodiments, the first target region is within 200 base pairs of nucleotide 1338 in SEQ ID NO: 1083. In some embodiments, the first target region is within 100 base pairs of nucleotide 1338 in SEQ ID NO: 1082. In some embodiments, the first target region is within 100 base pairs of nucleotide 1338 in SEQ ID NO: 1083. In some embodiments, the reduction is a reduction in the number of HBV viral episomes. In some embodiments, the reduction is a reduction in the number of cccDNA genomes. In some embodiments, the reduction is a reduction in total HBV DNA. In some embodiments, the reduction is a reduction in the replication of the HBV genome. In some embodiments, the reduction is a reduction in a level of expression of a protein product encoded by the HBV genome. In some embodiments, the reduction is a reduction in a level of HBsAg. In some embodiments, the reduction is a reduction in a level of HBeAg. In some embodiments, the reduction is a reduction of total HBV DNA of at least 70%, at least 80%, at least 90%, at least 95%, at least 99%, or at least 99.9%, and the reduction is maintained for at least 14 days after the contacting or the administering. In some embodiments, the reduction is a reduction of HBeAg of at least 70%, at least 80%, at least 90%, at least 95%, at least 99%, or at least 99.9%, and the reduction is maintained for at least 14 days after the contacting or the administering. In some embodiments, the reduction is a reduction of HBsAg of at least 70%, at least 80%, at least 90%, at least 95%, at least 99%, or at least 99.9%, and the reduction is maintained at or below that level for at least 14 days after the contacting or the administering. In some embodiments, the reduction is a reduction of at least 90%. In some embodiments, the reduction is a reduction of at least 95%. In some embodiments, the reduction is a reduction of at least 99%. In some embodiments, the reduction is a reduction of at least 99.9%. In some embodiments, the reduction is maintained for at least 14 days after the contacting or the administering. In some embodiments, the reduction is maintained for at least 21 days. In some embodiments, the reduction is maintained for at least 28 days. In some embodiments, the reduction is maintained for at least 35 days. In some embodiments, the reduction is maintained for at least 42 days. In some embodiments, the reduction is maintained for at least 56 days. In some embodiments, the reduction is maintained for at least 70 days. In some embodiments, the reduction is maintained for at least 84 days. In some embodiments, the reduction is maintained for at least 112 days. In some embodiments, the reduction is maintained for at least 140 days. In some embodiments, the reduction is maintained for at least 168 days. In some embodiments, the reduction is maintained for at least 6 months. In some embodiments, the reduction is maintained for at least 7 months. In some embodiments, the reduction is maintained for at least 8 months. In some embodiments, the reduction is maintained for at least 9 months. In some embodiments, the reduction is maintained for at least 12 months. In some embodiments, the reduction is maintained for at least 18 months. In some embodiments, the reduction is maintained for at least 24 months. In some embodiments, the epigenetic editing system is administered as a monotherapy. Accordingly, in some embodiments, the method does not comprise administering a nucleoside or nucleotide analog (NUC) to the subject. In some embodiments, the method further comprises administering a NUC to the subject. In some embodiments, the first DNA binding domain comprises a CRISPR-Cas protein. In some embodiments, the epigenetic editing system further comprises a first guide RNA (gRNA) that comprises a region complementary to a strand of the first target region. In some embodiments, the gRNA comprises a sequence selected from a gRNA provided herein, and preferably the gRNA comprises a sequence provided in Table 12 or 13. In some embodiments, the first DNA binding domain comprises a zinc-finger protein. In some embodiments, the zinc-finger protein comprises a zinc-finger motif with a sequence selected from any zinc finger or zinc finger motif provided herein, e.g., in Table 1 or Table 18. In some embodiments, the zinc-finger protein comprises a sequence of any of the zinc finger epigenetic repressors provided herein. In some embodiments, the transcriptional repressor domain comprises ZIM3. In some embodiments, the first DNMT domain is a DNMT3A domain or a DNMT3L domain. In some embodiments, the first DNMT domain comprises a sequence of a DNMT domain provided herein. In some embodiments, the epigenetic editing system comprises the fusion protein provided in SEQ ID NO: 1248 or the fusion protein provided in SEQ ID NO: 1252 and at least one guide RNA provided as gRNA #003, gRNA #007, gRNA #008, gRNA #009, gRNA #011, or gRNA #015 herein. Some aspects of this disclosure provide epigenetic editing systems for use in the methods described herein. In some embodiments, the epigenetic editing system comprises a fusion protein or a nucleic acid encoding the fusion protein, and the fusion protein comprises: (a) a DNA-binding domain that binds a target region of a HBV gene or genome, (b) a first DNA methyltransferase (DNMT) domain, and (c) a transcriptional repressor domain. In some embodiments, the fusion protein comprises a sequence of a fusion protein provided herein. In some embodiments, the DNA-binding domain is a CRISPR-Cas DNA binding domain, and the epigenetic editing system comprises at least gRNA provided herein. In some embodiments, the epigenetic editing system comprises the fusion protein provided in SEQ ID NO: 1248 or the fusion protein provided in SEQ ID NO: 1252 and at least one guide RNA provided as gRNA #003, gRNA #007, gRNA #008, gRNA #009, gRNA #011, or gRNA #015 herein.

In some embodiments, the subject is a mammalian subject having, or having been diagnosed with, a Hepatitis B virus (HBV) infection. In some embodiments, the subject is a mammalian subject having, or having been diagnosed with, a Hepatitis D virus infection.

In some embodiments, the subject is a mammalian subject, for example, a human subject, having, or having been diagnosed with, a Hepatitis B virus (HBV) infection. In some embodiments, the subject is a mammalian subject, for example, a human subject, having, or having been diagnosed with Hepatitis B In some embodiments, the subject is a mammalian subject, for example, a human subject, having, or having been diagnosed with, a Hepatitis D virus infection. In some embodiments, a patient to be treated with an epigenetic editor of the present disclosure has received prior treatment for the condition to be treated (e.g., an HBV and/or HDV infection, or Hepatitis B). In other embodiments, the patient has not received such prior treatment. In some embodiments, the patient has failed on (or is refractory to) a prior treatment for the condition (e.g., a prior HBV treatment).

In some embodiments, contacting the HBV gene or genome or a cell with an epigenetic editor as described herein results in a reduction of: number of HBV viral episomes, replication of the HBV gene or genome, or expression of a protein product encoded by the HBV gene or genome. In some embodiments, the reduction is at least about 20%, at least about 30%, at least about 40%, at least about 50%, at least about 60%, at least about 70%, at least about 80%, or at least about 90% compared to contacting the HBV gene or genome or the cell with a suitable control or without contacting the HBV gene or genome or the cell with the epigenetic editor described herein. In some embodiments, the reduction is maintained for at least 6 days, 19 days, 27 days, 42 days, or 168 days. In some embodiments, the protein product comprises a HBe antigen or a HBs antigen.

In some embodiments, administering to the subject an epigenetic editor or pharmaceutical composition as described herein results in a reduction of: number of HBV viral episomes, replication of the HBV gene or genome, or expression of a protein product encoded by the HBV gene or genome. In some embodiments, the reduction is at least about 20%, at least about 30%, at least about 40%, at least about 50%, at least about 60%, at least about 70%, at least about 80%, or at least about 90% compared to administering a suitable control or without administering the epigenetic editor or pharmaceutical composition described herein. In some embodiments, the reduction is maintained for at least 6 days, 19 days, 27 days, 42 days, or 168 days. In some embodiments, the protein product comprises a HBe antigen or a HBs antigen.

An epigenetic editor of the present disclosure may be administered in a therapeutically effective amount to a patient with a condition described herein. "Therapeutically effective amount," as used herein, refers to an amount of the therapeutic agent being administered that will relieve to some extent one or more of the symptoms of the disorder being treated, and/or result in clinical endpoint(s) desired by healthcare professionals. An effective amount for therapy may be measured by its ability to stabilize disease progression and/or ameliorate symptoms in a patient, and preferably to reverse disease progression. The ability of an epigenetic editor of the present disclosure to reduce or silence HBV expression may be evaluated by in vitro assays, e.g., as described herein, as well as in suitable animal models that are predictive of the efficacy in humans. Suitable dosage regimens will be selected in order to provide an optimum therapeutic response in each particular situation, for example, administered as a single bolus or as a continuous infusion, and with possible adjustment of the dosage as indicated by the exigencies of each case.

An epigenetic editor of the present disclosure may be administered without additional therapeutic treatments, i.e., as a stand-alone therapy (monotherapy). Alternatively, treatment with an epigenetic editor of the present disclosure may include at least one additional therapeutic treatment (combination therapy). In some embodiments, the additional therapeutic agent is any known in the art to treat an HBV infection. The current standard therapy for HBV employs nucleoside/nucleotide analogs (NUCs) and interferon (IFN). NUCs are viral polymerase and reverse transcriptase inhibitors that can efficiently suppress HBV viral replication, resulting in rapid HBV DNA reduction. NUCs do not directly target HBV cccDNA transcription, but NUC treatment of human HBV patients has been reported to reduce plasma HBV biomarkers such as HBeAg and HBsAg tp some extent. Prolonged therapy with NUCs is frequently associated with the pathogen developing a resistance to the treatment, but some NUCs have been reported to be able to achieve long-term viral suppression and halt disease progression. IFN-based therapy has both direct antiviral and immunomodulatory effects, and has been reported to prevent the formation of replication-competent pregenomic RNA-containing HBV capsids, or otherwise accelerates their degradation, thereby inhibiting HBV replication. See, e.g., Su et al., Improving clinical outcomes of chronic hepatitis B virus infection. Expert Rev Gastroenterol Hepatol. 2015; 9:141-154; European Association for the Study of the Liver. EASL clinical practice guidelines: management of chronic hepatitis B virus infection. J Hepatol. 2012; 57:167-185; Wieland et al., Intrahepatic induction of alpha/beta interferon eliminates viral RNA-containing capsids in hepatitis B virus transgenic mice. J Virol. 2000; and Wieland et al., Interferon prevents formation of replication-competent hepatitis B virus RNA-containing nucleocapsids. Proc Natl Acad Sci USA. 2005; 102:9913-9917, the entire contents of each of which are incorporated herein by reference.

In some embodiments, an epigenetic editor of the present disclosure is administered to a subject in need thereof, e.g., a subject having an HBV infection, without additional therapeutic treatment, e.g., without the co-administration of NUCs or IFN, or any other therapeutic treatment aimed at HBV, i.e., as a stand-alone therapy (monotherapy). In some such embodiments, a durable reduction of an HBV biomarker (e.g., as measured as the plasma level of HBV DNA, HBsAg, or HBeAG) by at least 20%, at least 30%, at least 40%, at least 50%, at least 60%, at least 70%, at least 80%, at least 90%, at least 95%, at least 99%, at least 99.9%, or more, is achieved over a time period of at least 14 days, at least 21 days, at least 28 days, at least 35 days, at least 42 days, at least 56 days, at least 70 days, at least 84 days, at least 112 days, at least 140 days, at least 168 days, at least 6 months, at least 7 months, at least 8 months, at least 9 months, at least 10 months, at least 11 months, at least 12 months, at least 18 months, at least 24 months, or longer, after a single-dose administration of the epigenetic editor to the subject.

In some embodiments, an epigenetic editor of the present disclosure is administered to a subject in need thereof, e.g., a subject having an HBV infection, in combination with (i.e., in temporal proximity) at least one additional HBV therapeutics, e.g., with NUCs and/or IFN therapeutics, or with any other therapeutic treatment aimed at HBV, i.e., as a combination therapy (monotherapy). In some such embodiments, a durable reduction of an HBV biomarker (e.g., as measured as the plasma level of HBV DNA, HBsAg, or HBeAG) by at least 20%, at least 30%, at least 40%, at least 50%, at least 60%, at least 70%, at least 80%, at least 90%, at least 95%, at least 99%, at least 99.9%, or more, is achieved over a time period of at least 14 days, at least 21 days, at least 28 days, at least 35 days, at least 42 days, at least 56 days, at least 70 days, at least 84 days, at least 112 days, at least 140 days, at least 168 days, at least 6 months, at least 7 months, at least 8 months, at least 9 months, at least 10 months, at least 11 months, at least 12 months, at least 18 months, at least 24 months, or longer.

An epigenetic editor of the present disclosure may be administered without additional therapeutic treatments, i.e., as a stand-alone therapy (monotherapy). Alternatively, treatment with an epigenetic editor of the present disclosure may include at least one additional therapeutic treatment (combination therapy). In some embodiments, the additional therapeutic agent is any known in the art to HBV and/or HDV. In some embodiments, therapeutic agents include, but are not limited to, antivirals, such as entecavir, tenofovir, lamivudine, telvivudine, bictegravir, emtricitabine, or defovir, as well as immune modulators, such as pegylated interferon and interferon alpha.

The epigenetic editors or components thereof (or nucleic acid molecules encoding the epigenetic editors or components thereof) of the present disclosure may be administered by any method accepted in the art (e.g., parenterally, intravenously, intradermally, or intramuscularly).

The epigenetic editors or components thereof (or nucleic acid molecules encoding the epigenetic editors or components thereof) of the present disclosure may be administered to a subject once, twice, three times, or 4, 5, 6, 7, 8, 9, 10, or more times. In some embodiments, the one, two, three, or 4, 5, 6, 7, 8, 9, 10, or more administrations of epigenetic editors or components thereof (or nucleic acid molecules encoding the epigenetic editors or components thereof) are in temporal proximity, e.g., within 1 day, 2 days, 3 days, 4 days, 5 days, 6 days, 1 week, 2 weeks, 4 weeks, 1 month or two months of each other. In some embodiments, a subject is re-dosed with the epigenetic editors or components thereof (or nucleic acid molecules encoding the epigenetic editors or components thereof) of the present disclosure for at least one more time after an initial dose. In some cases, a subject is administered with a subsequent dose of the epigenetic editors or components thereof (or nucleic acid molecules encoding the epigenetic editors or components thereof) of the present disclosure, which target a different DNA region of the HBV genome than the DNA region of the HBV genome that is targeted by the epigenetic editors or components thereof that the subject receives at the initial dose. In some cases, a subject is administered with multiple doses (e.g., 2, 3, 4, 5, 6, 7, 8, 9, 10, or more) of the same epigenetic editors or components thereof (or nucleic acid molecules encoding the epigenetic editors or components thereof) of the present disclosure. In some cases, a subject is administered with a single dose of different epigenetic editors or components thereof (or nucleic acid molecules encoding the epigenetic editors or components thereof) of the present disclosure, at least two of which target different DNA regions of the HBV genome. In some cases, a subject is administered with multiple doses (e.g., 2, 3, 4, 5, 6, 7, 8, 9, 10, or more) of different epigenetic editors or components thereof (or nucleic acid molecules encoding the epigenetic editors or components thereof) of the present disclosure, at least two of which target different DNA regions of the HBV genome. In some embodiments, redosing of the epigenetic editors or components thereof (or nucleic acid molecules encoding the epigenetic editors or components thereof) of the present disclosure has a better therapeutic efficacy than a single dose of the same, e.g., more potent suppression of HBV replication, or more profound reduction in HBV DNA and/or HBV antigens (e.g., HBsAg, HBeAg, and/or HBV core antigen (HBeAg)) present in the subject, e.g., in the circulation system and/or liver of the subject.

XII. Definitions

The term "nucleic acid" as used herein refers to any oligonucleotide or polynucleotide containing nucleotides (e.g., deoxyribonucleotides or ribonucleotides) in either single- or double-strand form, and includes DNA and RNA. "Nucleotides" contain a sugar deoxyribose (DNA) or ribose (RNA), a base, and a phosphate group, and are linked together through the phosphate groups. "Bases" include purines and pyrimidines, which include natural compounds such as adenine, thymine, guanine, cytosine, uracil, inosine, and natural analogs; as well as synthetic derivatives of purines and pyrimidines, which include, but are not limited to, modified versions which place new reactive groups such as amines, alcohols, thiols, carboxylates, alkylhalides, etc. Nucleic acids may contain known nucleotide analogs and/or modified backbone residues or linkages, which may be synthetic, naturally occurring, and non-naturally occurring. Such nucleotide analogs, modified residues, and modified linkages are well known in the art, and may provide a nucleic acid molecule with enhanced cellular uptake, reduced immunogenicity, and/or increased stability in the presence of nucleases.

As used herein, an "isolated" or "purified" nucleic acid molecule is a nucleic acid molecule that exists apart from its native environment. For example, an "isolated" or "purified" nucleic acid molecule (1) has been separated away from the nucleic acids of the genomic DNA or cellular RNA of its source of origin; and/or (2) does not occur in nature. In some embodiments, an "isolated" or "purified" nucleic acid molecule is a recombinant nucleic acid molecule.

It will be understood that in addition to the specific proteins and nucleic acid molecules mentioned herein, the present disclosure also contemplates the use of variants, derivatives, homologs, and fragments thereof. A variant of any given sequence may have the specific sequence of residues (whether amino acid or nucleic acid residues) modified in such a manner that the polypeptide or polynucleotide in question substantially retains at least one of its endogenous functions. A variant sequence can be obtained by addition, deletion, substitution, modification, replacement and/or variation of at least one residue present in the naturally-occurring sequence (in some embodiments, no more than 1, 2, 3, 4, 5, 6, 7, 8, 9, 10, 15, or 20 residues). For specific proteins described herein (e.g., KRAB, dCas9, DNMT3A, and DNMT3L proteins described herein), the present disclosure also contemplates any of the protein's naturally occurring forms, or variants or homologs that retain at least one of its endogenous functions (e.g., at least 50%, 60%, 70%, 80%, 90%, 85%, 96%, 97%, 98%, or 99% of its function as compared to the specific protein described).

As used herein, a homologue of any polypeptide or nucleic acid sequence contemplated herein includes sequences having a certain homology with the wildtype amino acid and nucleic sequence. A homologous sequence may include a sequence, e.g. an amino acid sequence which may be at least 50%, 55%, 65%, 75%, 85%, 90%, 91%, 92%<93%, 94%, 95%, 96%, 97%, 98%, or 99% identical to the subject sequence. The term "percent identical" in the context of amino acid or nucleotide sequences refers to the percent of residues in two sequences that are the same when aligned for maximum correspondence. In some embodiments, the length of a reference sequence aligned for comparison purposes is at least 30%, (e.g., at least 40, 50, 60, 70, 80, or 90%, or 100%) of the reference sequence. Sequence identity may be measured using sequence analysis software (for example, Sequence Analysis Software Package of the Genetics Computer Group, University of Wisconsin Biotechnology Center, 1710 University Avenue, Madison, Wis. 53705, BLAST, BESTFIT, GAP, or PILEUP/PRETTYBOX programs). Such software matches identical or similar sequences by assigning degrees of homology to various substitutions, deletions, and/or other modifications. In an exemplary approach to determining the degree of identity, a BLAST program may be used, with a probability score between e-3 and e-100 indicating a closely related sequence.

The percent identity of two nucleotide or polypeptide sequences is determined by, e.g., BLAST® using default parameters (available at the U.S. National Library of Medicine's National Center for Biotechnology Information website). In some embodiments, the length of a reference sequence aligned for comparison purposes is at least 30%, (e.g., at least 40, 50, 60, 70, 80, or 90%) of the reference sequence.

It will be understood that the numbering of the specific positions or residues in polypeptide sequences depends on the particular protein and numbering scheme used. Numbering might be different, e.g., in precursors of a mature protein and the mature protein itself, and differences in sequences from species to species may affect numbering. One of skill in the art will be able to identify the respective residue in any homologous protein and in the respective encoding nucleic acid by methods well known in the art, e.g., by sequence alignment and determination of homologous residues.

The term "modulate" or "alter" refers to a change in the quantity, degree, or extent of a function. For example, an epigenetic editor as described herein may modulate the activity of a promoter sequence by binding to a motif within the promoter, thereby inducing, enhancing, or suppressing transcription of a gene operatively linked to the promoter sequence. As other examples, an epigenetic editor as described herein may block RNA polymerase from transcribing a gene, or may inhibit translation of an mRNA transcript. The terms "inhibit," "repress," "suppress," "silence" and the like, when used in reference to an epigenetic editor or a component thereof as described herein, refers to decreasing or preventing the activity (e.g., transcription) of a nucleic acid sequence (e.g., a target gene) or protein relative to the activity of the nucleic acid sequence or protein in the absence of the epigenetic editor or component thereof. The term may include partially or totally blocking activity, or preventing or delaying activity. The inhibited activity may be, e.g., 10%, 20%, 30%, 40%, 50%, 60%, 70%, 75%, 80%, 85%, 90%, 91%, 92%, 93%, 94%, 95%, 96%, 97%, 98%, 99%, or 99.9% less than that of a control, or may be, e.g., at least 1.5-fold, 2-fold, 3-fold, 4-fold, 5-fold, or 10-fold less than that of a control. For example, in some embodiments, the inhibited activity (e.g., the transcription or expression of an HBV target gene, or the level of an HBV biomarker) may be at least 70% less than that of a control. In some embodiments, the inhibited activity may be at least 80% less than that of a control. In some embodiments, the inhibited activity may be at least 90% less than that of a control (1 log reduction). In some embodiments, the inhibited activity may be at least 91% less than that of a control. In some embodiments, the inhibited activity may be at least 92% less than that of a control. In some embodiments, the inhibited activity may be at least 93% less than that of a control. In some embodiments, the inhibited activity may be at least 94% less than that of a control. In some embodiments, the inhibited activity may be at least 95% less than that of a control. In some embodiments, the inhibited activity may be at least 96% less than that of a control. In some embodiments, the inhibited activity may be at least 97% less than that of a control. In some embodiments, the inhibited activity may be at least 98% less than that of a control. In some embodiments, the inhibited activity may be at least 99% less than that of a control (2 log reduction). In some embodiments, the inhibited activity may be at least 99.9% less than that of a control (3 log reduction).

The term "about" or "approximately" means within an acceptable error range for the particular value as determined by one of ordinary skill in the art, which will depend in part on how the value is measured or determined, e.g., the limitations of the measurement system. For example, "about" can mean within one or more than one standard deviation, per the practice in the given value. Where particular values are described in the application and claims, unless otherwise stated, the term "about" should be assumed to mean an acceptable error range for the particular value.

Ranges provided herein are understood to be shorthand for all of the values within the range. For example, a range of 1 to 50 is understood to include any number, combination of numbers, or sub-range from the group consisting of 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, or 50, as well as all intervening decimal values between the aforementioned integers such as, for example, 1.1, 1.2, 1.3, 1.4, 1.5, 1.6, 1.7, 1.8, and 1.9. With respect to sub-ranges, "nested sub-ranges" that extend from either end point of the range are specifically contemplated. For example, a nested sub-range of an exemplary range of 1 to 50 may comprise 1 to 10, 1 to 20, 1 to 30, and 1 to 40 in one direction, or 50 to 40, 50 to 30, 50 to 20, and 50 to 10 in the other direction.

Unless otherwise defined herein, scientific and technical terms used in connection with the present disclosure shall have the meanings that are commonly understood by those of ordinary skill in the art. Exemplary methods and materials are described below, although methods and materials similar or equivalent to those described herein can also be used in the practice or testing of the present disclosure. In case of conflict, the present specification, including definitions, will control. Further, unless otherwise required by context, singular terms shall include pluralities and plural terms shall include the singular. Throughout this specification and embodiments, the words "have" and "comprise," or variations such as "has," "having," "comprises," or "comprising," will be understood to imply the inclusion of a stated integer or group of integers but not the exclusion of any other integer or group of integers. The recitation of a listing of elements herein includes any of the elements singly or in any combination. The recitation of an embodiment herein includes that embodiment as a single embodiment, or in combination with any other embodiment(s) herein. All publications, patents, patent applications, and other references mentioned herein, including, where applicable, any supplementary information, are incorporated by reference in their entirety. To the extent that references incorporated by reference contradict the disclosure contained in the specification, the specification is intended to supersede and/or take precedence over any such contradictory material. Although a number of documents are cited herein, this citation does not constitute an admission that any of these documents forms part of the common general knowledge in the art.

LISTINGS OF EXEMPLARY EMBODIMENTS

In order that the present disclosure may be better understood, the following listings of exemplary embodiments is provided. This listing is for purposes of illustration of certain embodiments only. Additional embodiments will be apparent to the skilled artisan based on the present disclosure, and the listing below is not to be construed as limiting the scope of the present disclosure.

LISTING #1 of exemplary embodiments:

1. A method of modifying an epigenetic state of a hepatitis B virus (HBV) gene or genome, comprising contacting the HBV gene or genome with an epigenetic editing system, wherein the epigenetic editing system comprises a first DNA binding domain, a first DNMT domain, and a transcriptional repressor domain or one or more nucleic acid molecules encoding the same, wherein the first DNA binding domain binds a first target region of the HBV gene or genome, and wherein the contacting results in a reduction of:

number of HBV viral episomes, replication of the HBV gene or genome, and/or expression of a protein product encoded by the HBV gene or genome, wherein the reduction is at least about 50%, and preferably wherein the reduction is at least 60%, at least 70%, at least 80%, at least 90%, at least 95%, at least 99%, or greater than 99%, compared to contacting the HBV gene or genome with a suitable control.

2. A method of treating an HBV infection in a subject comprising administering an epigenetic editing system to the subject, wherein the epigenetic editing system comprises a first DNA binding domain, a first DNMT domain, and a transcriptional repressor domain or one or more nucleic acid molecules encoding thereof, wherein the first DNA binding domain binds a first target region of a HBV gene or genome, and wherein the administering results in a reduction of:

number of HBV viral episomes, replication of the HBV gene or genome, and/or expression of a protein product encoded by the HBV gene or genome, wherein the reduction is at least 60%, at least 70%, at least 80%, at least 90%, at least 95%, at least 99%, or greater than 99%, compared to administering a suitable control.

3. A method of modulating expression of an HBV gene or genome comprising contacting the HBV gene or genome with an epigenetic editing system, wherein the epigenetic editing system comprises a first DNA binding domain, a first DNMT domain, and a transcriptional repressor domain or one or more nucleic acid molecules encoding thereof, wherein the first DNA binding domain binds a first target region of the HBV gene or genome, and wherein the contacting results in a reduction of expression of a gene product encoded by the HBV gene or genome, optionally, wherein the gene product is a nucleic acid or a protein, wherein the reduction is at least 60%, at least 70%, at least 80%, at least 90%, at least 95%, at least 99%, or greater than 99%, compared to contacting the HBV genome with a suitable control.

4. A method of inhibiting viral replication in a cell infected with an HBV comprising administering an epigenetic editing system, wherein the epigenetic editing system comprises
a first DNA binding domain, a first DNMT domain, and
a transcriptional repressor domain or one or more
nucleic acid molecules encoding thereof,
wherein the first DNA binding domain binds a first target
region of a HBV gene or genome, and wherein the
epigenetic editing system targets a target region of the
HBV gene or genome, and
wherein the administering results in a reduction of num-
ber of HBV viral episomes or replication of the HBV
gene or genome,
wherein the reduction is at least 60%, at least 70%, at least
80%, at least 90%, at least 95%, at least 99%, or greater
than 99%, compared to administering a suitable con-
trol.

5. The method of any one of embodiments 1-4, wherein
the reduction is at least 70%.

6. The method of any one of embodiments 1-4, wherein
the reduction is at least 80%.

7. The method of any one of embodiments 1-4, wherein
the reduction is at least 90%.

8. The method of any one of embodiments 1-4, wherein
the reduction is at least 95%.

9. The method of any one of embodiments 1-4, wherein
the reduction is at least 99%.

10. The method of any one of embodiments 1-4, wherein
the reduction is greater than 99%.

11. The method of any one of embodiments 1-10, wherein
the HBV genome is a covalently closed circular DNA
(cccDNA).

12. The method of any one of embodiments 1-10, wherein
the HBV genome is an HBV integrated DNA.

13. The method of any one of embodiments 1-12, wherein
the HBV genome comprises HBV genotype A.

14. The method of any one of embodiments 1-12, wherein
the HBV genome comprises HBV genotype B.

15. The method of any one of embodiments 1-12, wherein
the HBV genome comprises HBV genotype C.

16. The method of any one of embodiments 1-12, wherein
the HBV genome comprises, HBV genotype D.

17. The method of any one of embodiments 1-12, wherein
the HBV genome comprises HBV genotype E.

18. The method of any one of embodiments 1-12, wherein
the HBV genome comprises HBV genotype F.

19. The method of any one of embodiments 1-12, wherein
the HBV genome comprises HBV genotype G.

20. The method of any one of embodiments 1-12, wherein
the HBV genome comprises HBV genotype H.

21. The method of any one of embodiments 1-12, wherein
the HBV genome comprises a sequence with at least
80%, at least 90%, at least 95%, at least 99%, or greater
than 99% sequence identity to an HBV genome
sequence provided herein.

22. The method of any one of embodiments 1-21, wherein
the first target region is located in a region of the HBV
genome within nucleotides 0-303 of an HBV genome
provided herein.

23. The method of any one of embodiments 1-21, wherein
the first target region is located within nucleotides
0-303 of SEQ ID NO: 1082.

24. The method of any one of embodiments 1-21, wherein
the first target region is located within nucleotides
0-303 of SEQ ID NO: 1083.

25. The method of any one of embodiments 1-21, wherein
the first target region is located in a region of the HBV
genome within nucleotides 1000-2448 of an HBV
genome provided herein.

26. The method of any one of embodiments 1-21, wherein
the first target region is located within nucleotides
1000-2448 of SEQ ID NO: 1082.

27. The method of any one of embodiments 1-21, wherein
the first target region is located within nucleotides
1000-2448 of SEQ ID NO: 1083.

28. The method of any one of embodiments 1-21, wherein
the first target region is located in a region of the HBV
genome within nucleotides 2802-3182 of an HBV
genome provided herein.

29. The method of any one of embodiments 1-21, wherein
the first target region is located within nucleotides
2802-3182 of SEQ ID NO: 1082.

30. The method of any one of embodiments 1-21, wherein
the first target region is located within nucleotides
2802-3182 of SEQ ID NO: 1083.

31. The method of any one of embodiments 1-21, wherein
the first target region of the HBV genome is located in
an HBV CpG island (CGI).

32. The method of embodiment 31, wherein the CGI is an
HBV canonical CGI.

33. The method of embodiment 31, wherein the CGI is
canonical CGI-I.

34. The method of embodiment 31, wherein the CGI is
canonical CGI-I of HBV genotype D.

35. The method of embodiment 33, wherein CGI-I spans
nucleotides 186-288 of SEQ ID NO: 1082.

36. The method of embodiment 33, wherein CGI-I spans
nucleotides 186-288 of SEQ ID NO: 1083.

37. The method of embodiment 31, wherein the CGI is
canonical CGI-II.

38. The method of embodiment 31, wherein the CGI is
canonical CGI-II HBV genotype D.

39. The method of embodiment 38, wherein the CGI is
CGI II spans nucleotides 1,217-1,670 of SEQ ID NO:
1082.

40. The method of embodiment 38, wherein the CGI is
CGI II spans nucleotides 1,217-1,670 of SEQ ID NO:
1083.

41. The method of embodiment 31, wherein the CGI is
canonical CGI-III.

42. The method of embodiment 31, wherein the CGI is
canonical CGI-III HBV genotype D.

43. The method of embodiment 42, wherein the CGI is
CGI-III spans nucleotides 2,282-2,448 of SEQ ID NO:
1082.

44. The method of embodiment 42, wherein the CGI is
CGI-III spans nucleotides 2,282-2,448 of SEQ ID NO:
1083.

45. The method of any one of embodiments 1-21, wherein
the first target region of the HBV genome is located in
a promotor.

46. The method of embodiment 45, wherein the first target
region of the HBV genome is located in the sp1
promoter.

47. The method of embodiment 45, wherein the first target
region of the HBV genome is located in sp2 promoter.

48. The method of embodiment 45, wherein the first target
region of the HBV genome is located in cp promoter.

49. The method of embodiment 45, wherein the first target
region of the HBV genome is located in xp promoter.

50. The method of any one of embodiments 1-21, wherein
the first target region of the HBV genome is located in
an enhancer region.

51. The method of embodiment 50, wherein the first target
region of the HBV genome is located in Enh I.

52. The method of embodiment 50, wherein the first target region of the HBV genome is located in Enh II.

53. The method of any one of embodiments 1-21, wherein the first target region of the HBV genome is located in a section of the HBV genome that encodes a transcript.

54. The method of embodiment 53, wherein the first target region of the HBV genome is located in a section of the HBV genome that encodes a pgRNA transcript.

55. The method of embodiment 53, wherein the first target region of the HBV genome is located in a section of the HBV genome that encodes a preCore RNA transcript.

56. The method of embodiment 53, wherein the first target region of the HBV genome is located in a section of the HBV genome that encodes a preS RNA transcript.

57. The method of embodiment 53, wherein the first target region of the HBV genome is located in a section of the HBV genome that encodes an S RNA transcript.

58. The method of embodiment 53, wherein the first target region of the HBV genome is located in a section of the HBV genome that encodes an HBx RNA transcript.

59. The method of any one of embodiments 1-21, wherein the first target region of the HBV genome is within 1000, 900, 800, 700, 600, 500, 400, 300, 200, or 100 base pairs (bp) of an HBV transcription start site (TSS).

60. The method of embodiment 59, wherein the TSS is a pg RNA TSS.

61. The method of embodiment 60, wherein the first target region is within 600, within 500, within 400, within 300, within 200, or within 100 base pairs of the pg RNA TSS.

62. The method of embodiment 60, wherein the pg RNA TSS is located at nucleotide 1820 of SEQ ID NO: 1082 or at nucleotide 1820 of SEQ ID NO: 1083.

63. The method of embodiment 60, wherein the first target region is within 600 base pairs of nucleotide 1820 in SEQ ID NO: 1082.

64. The method of embodiment 60, wherein the first target region is within 600 base pairs of nucleotide 1820 in SEQ ID NO: 1083.

65. The method of embodiment 60, wherein the first target region is within 500 base pairs of nucleotide 1820 in SEQ ID NO: 1082.

66. The method of embodiment 60, wherein the first target region is within 500 base pairs of nucleotide 1820 in SEQ ID NO: 1083.

67. The method of embodiment 60, wherein the first target region is within 400 base pairs of nucleotide 1820 in SEQ ID NO: 1082.

68. The method of embodiment 60, wherein the first target region is within 400 base pairs of nucleotide 1820 in SEQ ID NO: 1083.

69. The method of embodiment 60, wherein the first target region is within 300 base pairs of nucleotide 1820 in SEQ ID NO: 1082.

70. The method of embodiment 60, wherein the first target region is within 300 base pairs of nucleotide 1820 in SEQ ID NO: 1083.

71. The method of embodiment 60, wherein the first target region is within 200 base pairs of nucleotide 1820 in SEQ ID NO: 1082.

72. The method of embodiment 60, wherein the first target region is within 200 base pairs of nucleotide 1820 in SEQ ID NO: 1083.

73. The method of embodiment 60, wherein the first target region is within 100 base pairs of nucleotide 1820 in SEQ ID NO: 1082 or wherein the first target region is within 100 base pairs of nucleotide 1820 in SEQ ID NO: 1083.

74. The method of embodiment 59, wherein the TSS is a preC RNA TSS.

75. The method of embodiment 74, wherein the first target region is within 600, within 500, within 400, within 300, within 200, or within 100 base pairs of the preC RNA TSS.

76. The method of embodiment 74, wherein the preC RNA TSS is located at nucleotide 1791 of SEQ ID NO: 1082 or at nucleotide 1791 of SEQ ID NO: 1083.

77. The method of embodiment 74, wherein the first target region is within 600 base pairs of nucleotide 1791 in SEQ ID NO: 1082.

78. The method of embodiment 74, wherein the first target region is within 600 base pairs of nucleotide 1791 in SEQ ID NO: 1083.

79. The method of embodiment 74, wherein the first target region is within 500 base pairs of nucleotide 1791 in SEQ ID NO: 1082.

80. The method of embodiment 74, wherein the first target region is within 500 base pairs of nucleotide 1791 in SEQ ID NO: 1083.

81. The method of embodiment 74, wherein the first target region is within 400 base pairs of nucleotide 1791 in SEQ ID NO: 1082.

82. The method of embodiment 74, wherein the first target region is within 400 base pairs of nucleotide 1791 in SEQ ID NO: 1083.

83. The method of embodiment 74, wherein the first target region is within 300 base pairs of nucleotide 1791 in SEQ ID NO: 1082.

84. The method of embodiment 74, wherein the first target region is within 300 base pairs of nucleotide 1791 in SEQ ID NO: 1083.

85. The method of embodiment 74, wherein the first target region is within 200 base pairs of nucleotide 1791 in SEQ ID NO: 1082.

86. The method of embodiment 74, wherein the first target region is within 200 base pairs of nucleotide 1791 in SEQ ID NO: 1083.

87. The method of embodiment 74, wherein the first target region is within 100 base pairs of nucleotide 1791 in SEQ ID NO: 1082.

88. The method of embodiment 74, wherein the first target region is within 100 base pairs of nucleotide 1791 in SEQ ID NO: 1083.

89. The method of embodiment 59, wherein the TSS is a preS2 RNA TSS.

90. The method of embodiment 89, wherein the first target region is within 600, within 500, within 400, within 300, within 200, or within 100 base pairs of the preS2 RNA TSS.

91. The method of embodiment 89, wherein the preS2 RNA TSS is located at nucleotide 3159 of SEQ ID NO: 1082 or at nucleotide 3159 of SEQ ID NO: 1083.

92. The method of embodiment 89, wherein the first target region is within 600 base pairs of nucleotide 3159 in SEQ ID NO: 1082.

93. The method of embodiment 89, wherein the first target region is within 600 base pairs of nucleotide 3159 in SEQ ID NO: 1083.

94. The method of embodiment 89, wherein the first target region is within 500 base pairs of nucleotide 3159 in SEQ ID NO: 1082.

95. The method of embodiment 89, wherein the first target region is within 500 base pairs of nucleotide 3159 in SEQ ID NO: 1083.

96. The method of embodiment 89, wherein the first target region is within 400 base pairs of nucleotide 3159 in SEQ ID NO: 1082.

97. The method of embodiment 89, wherein the first target region is within 400 base pairs of nucleotide 3159 in SEQ ID NO: 1083.

98. The method of embodiment 89, wherein the first target region is within 300 base pairs of nucleotide 3159 in SEQ ID NO: 1082.

99. The method of embodiment 89, wherein the first target region is within 300 base pairs of nucleotide 3159 in SEQ ID NO: 1083.

100. The method of embodiment 89, wherein the first target region is within 200 base pairs of nucleotide 3159 in SEQ ID NO: 1082.

101. The method of embodiment 89, wherein the first target region is within 200 base pairs of nucleotide 3159 in SEQ ID NO: 1083.

102. The method of embodiment 89, wherein the first target region is within 100 base pairs of nucleotide 3159 in SEQ ID NO: 1082.

103. The method of embodiment 89, wherein the first target region is within 100 base pairs of nucleotide 3159 in SEQ ID NO: 1083.

104. The method of embodiment 89, wherein the TSS is an HBx RNA TSSs.

105. The method of embodiment 104, wherein the first target region is within 600, within 500, within 400, within 300, within 200, or within 100 base pairs of the HBx RNA TSS.

106. The method of embodiment 105, wherein the HBx RNA TSS is located at a nucleotide within the sequence of nucleotides 1243-1338 of SEQ ID NO: 1082 or nucleotides 1243-1338 of SEQ ID NO: 1083.

107. The method of embodiment 105, wherein the first target region is within 600 base pairs of nucleotide 1243 in SEQ ID NO: 1082.

108. The method of embodiment 105, wherein the first target region is within 600 base pairs of nucleotide 1243 in SEQ ID NO: 1083.

109. The method of embodiment 105, wherein the first target region is within 500 base pairs of nucleotide 1243 in SEQ ID NO: 1082.

110. The method of embodiment 105, wherein the first target region is within 500 base pairs of nucleotide 1243 in SEQ ID NO: 1083.

111. The method of embodiment 105, wherein the first target region is within 400 base pairs of nucleotide 1243 in SEQ ID NO: 1082.

112. The method of embodiment 105, wherein the first target region is within 400 base pairs of nucleotide 1243 in SEQ ID NO: 1083.

113. The method of embodiment 105, wherein the first target region is within 300 base pairs of nucleotide 1243 in SEQ ID NO: 1082.

114. The method of embodiment 105, wherein the first target region is within 300 base pairs of nucleotide 1243 in SEQ ID NO: 1083.

115. The method of embodiment 105, wherein the first target region is within 200 base pairs of nucleotide 1243 in SEQ ID NO: 1082.

116. The method of embodiment 105, wherein the first target region is within 200 base pairs of nucleotide 1243 in SEQ ID NO: 1083.

117. The method of embodiment 105, wherein the first target region is within 100 base pairs of nucleotide 1243 in SEQ ID NO: 1082.

118. The method of embodiment 105, wherein the first target region is within 100 base pairs of nucleotide 1243 in SEQ ID NO: 1083.

119. The method of embodiment 105, wherein the first target region is within 600 base pairs of nucleotide 1338 in SEQ ID NO: 1083.

120. The method of embodiment 105, wherein the first target region is within 500 base pairs of nucleotide 1338 in SEQ ID NO: 1082.

121. The method of embodiment 105, wherein the first target region is within 500 base pairs of nucleotide 1338 in SEQ ID NO: 1083.

122. The method of embodiment 105, wherein the first target region is within 400 base pairs of nucleotide 1338 in SEQ ID NO: 1082.

123. The method of embodiment 105, wherein the first target region is within 400 base pairs of nucleotide 1338 in SEQ ID NO: 1083.

124. The method of embodiment 105, wherein the first target region is within 300 base pairs of nucleotide 1338 in SEQ ID NO: 1082.

125. The method of embodiment 105, wherein the first target region is within 300 base pairs of nucleotide 1338 in SEQ ID NO: 1083.

126. The method of embodiment 105, wherein the first target region is within 200 base pairs of nucleotide 1338 in SEQ ID NO: 1082.

127. The method of embodiment 105, wherein the first target region is within 200 base pairs of nucleotide 1338 in SEQ ID NO: 1083.

128. The method of embodiment 105, wherein the first target region is within 100 base pairs of nucleotide 1338 in SEQ ID NO: 1082.

129. The method of embodiment 105, wherein the first target region is within 100 base pairs of nucleotide 1338 in SEQ ID NO: 1083.

130. The method of any one of embodiments 1-129, wherein the reduction is a reduction in the number of HBV viral episomes.

131. The method of embodiment 130, wherein the reduction is a reduction in the number of cccDNA genomes.

132. The method of embodiment 130, wherein the reduction is a reduction in total HBV DNA.

133. The method of any one of embodiments 1-129, wherein the reduction is a reduction in the replication of the HBV genome.

134. The method of any one of embodiments 1-129, wherein the reduction is a reduction in a level of expression of a protein product encoded by the HBV genome.

135. The method of embodiment 130, wherein the reduction is a reduction in a level of HBsAg.

136. The method of embodiment 130, wherein the reduction is a reduction in a level of HBeAg.

137. The method of any one of embodiments 1-129, wherein the reduction is a reduction of total HBV DNA of at least 70%, at least 80%, at least 90%, at least 95%, at least 99%, or at least 99.9%, and wherein the reduction is maintained for at least 14 days after the contacting or the administering.

138. The method of any one of embodiments 1-129, wherein the reduction is a reduction of HBeAg of at least 70%, at least 80%, at least 90%, at least 95%, at least 99%, or at least 99.9%, and wherein the reduction is maintained for at least 14 days after the contacting or the administering.

139. The method of any one of embodiments 1-129, wherein the reduction is a reduction of HBsAg of at least 70%, at least 80%, at least 90%, at least 95%, at least 99%, or at least 99.9%, and wherein the reduction is maintained at or below that level for at least 14 days after the contacting or the administering.

140. The method of any one of embodiments 137-139, wherein the reduction is a reduction of at least 90%.

141. The method of any one of embodiments 137-139, wherein the reduction is a reduction of at least 95%.

142. The method of any one of embodiments 137-139, wherein the reduction is a reduction of at least 99%.

143. The method of any one of embodiments 137-139, wherein the reduction is a reduction of at least 99.9%.

144. The method of any one of embodiments 140-143, wherein the reduction is maintained for at least 14 days after the contacting or the administering.

145. The method of embodiment 144, wherein the reduction is maintained for at least 21 days.

146. The method of embodiment 144, wherein the reduction is maintained for at least 28 days.

147. The method of embodiment 144, wherein the reduction is maintained for at least 35 days.

148. The method of embodiment 144, wherein the reduction is maintained for at least 42 days.

149. The method of embodiment 144, wherein the reduction is maintained for at least 56 days.

150. The method of embodiment 144, wherein the reduction is maintained for at least 70 days.

151. The method of embodiment 144, wherein the reduction is maintained for at least 84 days.

152. The method of embodiment 144, wherein the reduction is maintained for at least 112 days.

153. The method of embodiment 144, wherein the reduction is maintained for at least 140 days.

154. The method of embodiment 144, wherein the reduction is maintained for at least 168 days.

155. The method of embodiment 144, wherein the reduction is maintained for at least 6 months.

156. The method of embodiment 144, wherein the reduction is maintained for at least 7 months.

157. The method of embodiment 144, wherein the reduction is maintained for at least 8 months.

158. The method of embodiment 144, wherein the reduction is maintained for at least 9 months.

159. The method of embodiment 144, wherein the reduction is maintained for at least 12 months.

160. The method of embodiment 144, wherein the reduction is maintained for at least 18 months.

161. The method of embodiment 144, wherein the reduction is maintained for at least 24 months.

162. The method of any one of embodiments 1-161, wherein the method does not comprise contacting the HBV gene or genome with a nucleoside or nucleotide analog (NUC) or wherein the method does not comprise administering a NUC to the subject.

163. The method of any one of embodiments 1-162, wherein the method further comprises contacting the HBV gene or genome with a nucleoside or nucleotide analog (NUC) or wherein the method further comprises administering a NUC to the subject.

164. The method of any one of embodiments 1-163, wherein the first DNA binding domain comprises a CRISPR-Cas protein.

165. The method of embodiment 164, wherein the epigenetic editing system further comprises a first guide RNA (gRNA) that comprises a region complementary to a strand of the first target region.

166. The method of embodiment 165, wherein the gRNA comprises a sequence selected from a gRNA provided herein, preferably wherein the gRNA comprises a sequence provided in Table 12 or 13.

167. The method of any one of embodiments 1-164, wherein the first DNA binding domain comprises a zinc-finger protein.

168. The method of embodiment 167, wherein the zinc-finger protein comprises a zinc-finger motif with a sequence selected from any zinc finger or zinc finger motif provided herein, e.g., in Table 1 or Table 18.

169. The method of embodiment 167 or 168, wherein the zinc-finger protein comprises a sequence of any of the zinc finger epigenetic repressors provided herein.

170. The method of any one of embodiments 1-169, wherein the transcriptional repressor domain comprises ZIM3.

171. The method of any one of embodiments 1-170, wherein the first DNMT domain is a DNMT3A domain or a DNMT3L domain.

172. The method of embodiment 171, wherein the first DNMT domain comprises a sequence of a DNMT domain provided herein.

173. The method of any one of embodiments 1-172, wherein the epigenetic editing system further comprises a second DNMT domain or a nucleic acid encoding thereof.

174. The method of embodiment 173, wherein the second DNMT domain is a DNMT3A domain or a DNMT3L domain.

175. The method of embodiment 173 or 174, wherein the second DNMT domain comprises a sequence of a DNMT domain provided herein.

176. The method of any one of embodiments 173-175, wherein the epigenetic editing system comprises a fusion protein or a nucleic acid encoding thereof, and wherein the fusion protein comprises the first DNA binding domain, the first DNMT domain, the repressor domain and the second DNMT domain.

177. The method of embodiment 176, wherein the fusion protein further comprises a nuclear localization sequence (NLS).

178. The method of embodiment 177, wherein the fusion protein comprises a sequence of a fusion protein provided herein.

179. The method of any one of embodiments 1-178, wherein the epigenetic editing system further comprises a second DNA binding domain or a nucleic acid encoding a second DNA binding domain, wherein the second DNA binding domain binds a second target region of the HBV genome.

180. The method of embodiment 179, wherein the second target region is a target region recited in any of embodiments 22-129.

181. The method of embodiment 179 or 180, wherein the second DNA binding domain comprises a CRISPR-Cas protein.

182. The method of any one of embodiments 1-180, wherein the epigenetic editing system comprises at least one CRISPR-Cas DNA binding domain and at least two different gRNAs.

183. The method of embodiment 182, wherein the epigenetic editing system comprises a first gRNA binding the first HBV target region and a second gRNA binding a second HBV target region, wherein the first and second target regions are not identical.

184. The method of embodiment 183, wherein the first gRNA comprises a gRNA sequence provided herein, e.g., a sequence provided in Table 12 or 13, and wherein the second gRNA comprises a different gRNA sequence provided herein, e.g., a sequence provided in Table 12 or 13.

185. The method of embodiment 179, wherein the second DNA binding domain comprises a zinc-finger protein.

186. The method of embodiment 185, wherein the zinc-finger protein of the second DNA binding domain comprises a zinc-finger motif with a sequence selected from a zinc finger motif sequence provided herein, e.g., a zinc finger motif provided in Table 1.

187. The method of embodiment 185 or 186, wherein the zinc-finger protein of the second DNA binding domain comprises a sequence of a zinc finger motif provided in Table 1.

188. The method of any one of embodiments 179-187, wherein the epigenetic editing system comprises a first fusion protein or a first nucleic acid encoding thereof and a second fusion protein or a second nucleic acid encoding thereof, wherein the first fusion protein comprises the first DNA binding domain and the first DNMT domain, and wherein the second fusion protein comprises the second DNA binding domain and the transcriptional repressor domain.

189. The method of embodiment 188, wherein the first fusion protein comprises a sequence of a fusion protein provided herein.

190. The method of embodiment 188 or 189, wherein the second fusion protein comprises a sequence of a fusion protein provided herein.

191. The method of any one of embodiments 179-190, wherein the epigenetic editing system further comprises a third DNA binding domain or a nucleic acid encoding a third DNA binding domain, wherein the third DNA binding domain binds to a third target region of the HBV genome, optionally, wherein the third DNA binding domain comprises a comprises at least one CRISPR-Cas DNA binding domain, optionally wherein the epigenetic editing system comprises a third gRNA comprising a sequence complementary to a strand of a third HBV target region, optionally wherein the third gRNA comprises a gRNA sequence provided herein, optionally, a gRNA sequence provided in Table 12 or 13, optionally, wherein the third DNA binding domain is comprised in a fusion protein comprising a DNMT domain and a transcriptional repressor domain, optionally, wherein the fusion protein is a fusion protein provided herein.

192. A method, comprising administering an epigenetic editing system to a subject, wherein the subject is characterized by the presence of detectable levels of HBV DNA, HBsAg, and/or HBeAg in the plasma of the subject, wherein the epigenetic editing system comprises a first DNA binding domain, a first DNMT domain, and a transcriptional repressor domain or one or more nucleic acid molecules encoding the same, wherein the first DNA binding domain binds a first target region of an HBV gene or genome, wherein the administering results in a reduction of the level of HBV DNA, the level of HBsAg, and/or the level of HBsAg in the plasma of the subject, wherein the reduction of the level of HBV DNA, of the level of HBsAg, and/or of the level of HBsAg in the plasma of the subject, is at least 90% (a 1-log reduction) compared to the respective level observed or observable in the plasma of the subject prior to the administering, and wherein the 1-log reduction is maintained for at least 14 days after the administering.

193. The method of embodiment 192, wherein the reduction of the level of HBV DNA in the plasma of the subject is at least 90% (a 1-log reduction).

194. The method of embodiment 192, wherein the reduction of the level of HBV DNA in the plasma of the subject is at least 99% (a 2-log reduction).

195. The method of embodiment 192, wherein the reduction of the level of HBsAg in the plasma of the subject is at least 90% (a 1-log reduction).

196. The method of embodiment 192, wherein the reduction of the level of HBsAg in the plasma of the subject is at least 99% (a 2-log reduction).

197. The method of embodiment 192, wherein the reduction of the level of HBeAg in the plasma of the subject is at least 90% (a 1-log reduction).

198. The method of embodiment 192, wherein the reduction of the level of HBeAg in the plasma of the subject is at least 99% (a 2-log reduction).

199. The method of any one of embodiments 192-198, wherein the reduction is maintained for at least 21 days.

200. The method of any one of embodiments 192-198, wherein the reduction is maintained for at least 28 days.

201. The method of any one of embodiments 192-198, wherein the reduction is maintained for at least 35 days.

202. The method of any one of embodiments 192-198, wherein the reduction is maintained for at least 42 days.

203. The method of any one of embodiments 192-198, wherein the reduction is maintained for at least 56 days.

204. The method of any one of embodiments 192-198, wherein the reduction is maintained for at least 70 days.

205. The method of any one of embodiments 192-198, wherein the reduction is maintained for at least 84 days.

206. The method of any one of embodiments 192-198, wherein the reduction is maintained for at least 112 days.

207. The method of any one of embodiments 192-198, wherein the reduction is maintained for at least 140 days.

208. The method of any one of embodiments 192-198, wherein the reduction is maintained for at least 168 days.

209. The method of any one of embodiments 192-198, wherein the reduction is maintained for at least 6 months.

210. The method of any one of embodiments 192-198, wherein the reduction is maintained for at least 9 months.

211. The method of any one of embodiments 192-198, wherein the reduction is maintained for at least 12 months.

212. The method of any one of embodiments 192-198, wherein the reduction is maintained for at least 24 months.

213. The method of any one of embodiments 192-212, wherein the HBV genome comprises HBV genotype A.

214. The method of any one of embodiments 192-212, wherein the HBV genome comprises HBV genotype B.

215. The method of any one of embodiments 192-212, wherein the HBV genome comprises HBV genotype C.

216. The method of any one of embodiments 192-212, wherein the HBV genome comprises, HBV genotype D.

217. The method of any one of embodiments 192-212, wherein the HBV genome comprises HBV genotype E.

218. The method of any one of embodiments 192-212, wherein the HBV genome comprises HBV genotype F.

219. The method of any one of embodiments 192-212, wherein the HBV genome comprises HBV genotype G.

220. The method of any one of embodiments 192-212, wherein the HBV genome comprises HBV genotype H.

221. The method of any one of embodiments 192-212, wherein the HBV genome comprises a sequence with at least 80%, at least 90%, at least 95%, at least 99%, or greater than 99% sequence identity to an HBV genome sequence provided herein.

222. The method of any one of embodiments 192-221, wherein the first target region is located in a region of the HBV genome within nucleotides 0-303 of an HBV genome provided herein.

223. The method of any one of embodiments 192-221, wherein the first target region is located within nucleotides 0-303 of SEQ ID NO: 1082.

224. The method of any one of embodiments 192-221, wherein the first target region is located within nucleotides 0-303 of SEQ ID NO: 1083.

225. The method of any one of embodiments 192-221, wherein the first target region is located in a region of the HBV genome within nucleotides 1000-2448 of an HBV genome provided herein.

226. The method of any one of embodiments 192-221, wherein the first target region is located within nucleotides 1000-2448 of SEQ ID NO: 1082.

227. The method of any one of embodiments 192-221, wherein the first target region is located within nucleotides 1000-2448 of SEQ ID NO: 1083.

228. The method of any one of embodiments 192-221, wherein the first target region is located in a region of the HBV genome within nucleotides 2802-3182 of an HBV genome provided herein.

229. The method of any one of embodiments 192-221, wherein the first target region is located within nucleotides 2802-3182 of SEQ ID NO: 1082.

230. The method of any one of embodiments 192-221, wherein the first target region is located within nucleotides 2802-3182 of SEQ ID NO: 1083.

231. The method of any one of embodiments 192-221, wherein the first target region of the HBV genome is located in an HBV CpG island (CGI).

232. The method of embodiment 231, wherein the CGI is an HBV canonical CGI.

233. The method of embodiment 231, wherein the CGI is canonical CGI-I.

234. The method of embodiment 231, wherein the CGI is canonical CGI-I of HBV genotype D.

235. The method of embodiment 233, wherein CGI-I spans nucleotides 186-288 of SEQ ID NO: 1082.

236. The method of embodiment 233, wherein CGI-I spans nucleotides 186-288 of SEQ ID NO: 1083.

237. The method of embodiment 231, wherein the CGI is canonical CGI-II.

238. The method of embodiment 231, wherein the CGI is canonical CGI-II HBV genotype D.

239. The method of embodiment 238, wherein the CGI is CGI II spans nucleotides 1,217-1,670 of SEQ ID NO: 1082.

240. The method of embodiment 238, wherein the CGI is CGI II spans nucleotides 1,217-1,670 of SEQ ID NO: 1083.

241. The method of embodiment 231, wherein the CGI is canonical CGI-III.

242. The method of embodiment 231, wherein the CGI is canonical CGI-III HBV genotype D.

243. The method of embodiment 242, wherein the CGI is CGI-III spans nucleotides 2,282-2,448 of SEQ ID NO: 1082.

244. The method of embodiment 242, wherein the CGI is CGI-III spans nucleotides 2,282-2,448 of SEQ ID NO: 1083.

245. The method of any one of embodiments 192-221, wherein the first target region of the HBV genome is located in a promotor.

246. The method of embodiment 245, wherein the first target region of the HBV genome is located in the sp1 promoter.

247. The method of embodiment 245, wherein the first target region of the HBV genome is located in sp2 promoter.

248. The method of embodiment 245, wherein the first target region of the HBV genome is located in cp promoter.

249. The method of embodiment 245, wherein the first target region of the HBV genome is located in xp promoter.

250. The method of any one of embodiments 192-221, wherein the first target region of the HBV genome is located in an enhancer region.

251. The method of embodiment 250, wherein the first target region of the HBV genome is located in Enh I.

252. The method of embodiment 250, wherein the first target region of the HBV genome is located in Enh II.

253. The method of any one of embodiments 192-221, wherein the first target region of the HBV genome is located in a section of the HBV genome that encodes a transcript.

254. The method of embodiment 253, wherein the first target region of the HBV genome is located in a section of the HBV genome that encodes a pgRNA transcript.

255. The method of embodiment 253, wherein the first target region of the HBV genome is located in a section of the HBV genome that encodes a preCore RNA transcript.

256. The method of embodiment 253, wherein the first target region of the HBV genome is located in a section of the HBV genome that encodes a preS RNA transcript.

257. The method of embodiment 253, wherein the first target region of the HBV genome is located in a section of the HBV genome that encodes an S RNA transcript.

258. The method of embodiment 253, wherein the first target region of the HBV genome is located in a section of the HBV genome that encodes an HBx RNA transcript.

259. The method of any one of embodiments 192-221, wherein the first target region of the HBV genome is within 1000, 900, 800, 700, 600, 500, 400, 300, 200, or 100 base pairs (bp) of an HBV transcription start site (TSS).

260. The method of embodiment 259, wherein the TSS is a pg RNA TSS.

261. The method of embodiment 260, wherein the first target region is within 600, within 500, within 400, within 300, within 200, or within 100 base pairs of the pg RNA TSS.

262. The method of embodiment 260, wherein the pg RNA TSS is located at nucleotide 1820 of SEQ ID NO: 1082 or at nucleotide 1820 of SEQ ID NO: 1083.

263. The method of embodiment 260, wherein the first target region is within 600 base pairs of nucleotide 1820 in SEQ ID NO: 1082.

264. The method of embodiment 260, wherein the first target region is within 600 base pairs of nucleotide 1820 in SEQ ID NO: 1083.

265. The method of embodiment 260, wherein the first target region is within 500 base pairs of nucleotide 1820 in SEQ ID NO: 1082.

266. The method of embodiment 260, wherein the first target region is within 500 base pairs of nucleotide 1820 in SEQ ID NO: 1083.

267. The method of embodiment 260, wherein the first target region is within 400 base pairs of nucleotide 1820 in SEQ ID NO: 1082.

268. The method of embodiment 260, wherein the first target region is within 400 base pairs of nucleotide 1820 in SEQ ID NO: 1083.

269. The method of embodiment 260, wherein the first target region is within 300 base pairs of nucleotide 1820 in SEQ ID NO: 1082.

270. The method of embodiment 260, wherein the first target region is within 300 base pairs of nucleotide 1820 in SEQ ID NO: 1083.

271. The method of embodiment 260, wherein the first target region is within 200 base pairs of nucleotide 1820 in SEQ ID NO: 1082.

272. The method of embodiment 260, wherein the first target region is within 200 base pairs of nucleotide 1820 in SEQ ID NO: 1083.

273. The method of embodiment 260, wherein the first target region is within 100 base pairs of nucleotide 1820 in SEQ ID NO: 1082 or wherein the first target region is within 100 base pairs of nucleotide 1820 in SEQ ID NO: 1083.

274. The method of embodiment 259, wherein the TSS is a preC RNA TSS.

275. The method of embodiment 274, wherein the first target region is within 600, within 500, within 400, within 300, within 200, or within 100 base pairs of the preC RNA TSS.

276. The method of embodiment 274, wherein the preC RNA TSS is located at nucleotide 1791 of SEQ ID NO: 1082 or at nucleotide 1791 of SEQ ID NO: 1083.

277. The method of embodiment 274, wherein the first target region is within 600 base pairs of nucleotide 1791 in SEQ ID NO: 1082.

278. The method of embodiment 274, wherein the first target region is within 600 base pairs of nucleotide 1791 in SEQ ID NO: 1083.

279. The method of embodiment 274, wherein the first target region is within 500 base pairs of nucleotide 1791 in SEQ ID NO: 1082.

280. The method of embodiment 274, wherein the first target region is within 500 base pairs of nucleotide 1791 in SEQ ID NO: 1083.

281. The method of embodiment 274, wherein the first target region is within 400 base pairs of nucleotide 1791 in SEQ ID NO: 1082.

282. The method of embodiment 274, wherein the first target region is within 400 base pairs of nucleotide 1791 in SEQ ID NO: 1083.

283. The method of embodiment 274, wherein the first target region is within 300 base pairs of nucleotide 1791 in SEQ ID NO: 1082.

284. The method of embodiment 274, wherein the first target region is within 300 base pairs of nucleotide 1791 in SEQ ID NO: 1083.

285. The method of embodiment 274, wherein the first target region is within 200 base pairs of nucleotide 1791 in SEQ ID NO: 1082.

286. The method of embodiment 274, wherein the first target region is within 200 base pairs of nucleotide 1791 in SEQ ID NO: 1083.

287. The method of embodiment 274, wherein the first target region is within 100 base pairs of nucleotide 1791 in SEQ ID NO: 1082.

288. The method of embodiment 274, wherein the first target region is within 100 base pairs of nucleotide 1791 in SEQ ID NO: 1083.

289. The method of embodiment 259, wherein the TSS is a preS2 RNA TSS.

290. The method of embodiment 289, wherein the first target region is within 600, within 500, within 400, within 300, within 200, or within 100 base pairs of the preS2 RNA TSS.

291. The method of embodiment 289, wherein the preS2 RNA TSS is located at nucleotide 3159 of SEQ ID NO: 1082 or at nucleotide 3159 of SEQ ID NO: 1083.

292. The method of embodiment 289, wherein the first target region is within 600 base pairs of nucleotide 3159 in SEQ ID NO: 1082.

293. The method of embodiment 289, wherein the first target region is within 600 base pairs of nucleotide 3159 in SEQ ID NO: 1083.

294. The method of embodiment 289, wherein the first target region is within 500 base pairs of nucleotide 3159 in SEQ ID NO: 1082.

295. The method of embodiment 289, wherein the first target region is within 500 base pairs of nucleotide 3159 in SEQ ID NO: 1083.

296. The method of embodiment 289, wherein the first target region is within 400 base pairs of nucleotide 3159 in SEQ ID NO: 1082.

297. The method of embodiment 289, wherein the first target region is within 400 base pairs of nucleotide 3159 in SEQ ID NO: 1083.

298. The method of embodiment 289, wherein the first target region is within 300 base pairs of nucleotide 3159 in SEQ ID NO: 1082.

299. The method of embodiment 289, wherein the first target region is within 300 base pairs of nucleotide 3159 in SEQ ID NO: 1083.

300. The method of embodiment 289, wherein the first target region is within 200 base pairs of nucleotide 3159 in SEQ ID NO: 1082.

301. The method of embodiment 289, wherein the first target region is within 200 base pairs of nucleotide 3159 in SEQ ID NO: 1083.

302. The method of embodiment 289, wherein the first target region is within 100 base pairs of nucleotide 3159 in SEQ ID NO: 1082.

303. The method of embodiment 289, wherein the first target region is within 100 base pairs of nucleotide 3159 in SEQ ID NO: 1083.

304. The method of embodiment 259, wherein the TSS is an HBx RNA TSSs.

305. The method of embodiment 304, wherein the first target region is within 600, within 500, within 400, within 300, within 200, or within 100 base pairs of the HBx RNA TSS.

306. The method of embodiment 304, wherein the HBx RNA TSS is located at a nucleotide within the sequence of nucleotides 1243-1338 of SEQ ID NO: 1082 or nucleotides 1243-1338 of SEQ ID NO: 1083.

307. The method of embodiment 304, wherein the first target region is within 600 base pairs of nucleotide 1243 in SEQ ID NO: 1082.

308. The method of embodiment 304, wherein the first target region is within 600 base pairs of nucleotide 1243 in SEQ ID NO: 1083.

309. The method of embodiment 304, wherein the first target region is within 500 base pairs of nucleotide 1243 in SEQ ID NO: 1082.

310. The method of embodiment 304, wherein the first target region is within 500 base pairs of nucleotide 1243 in SEQ ID NO: 1083.

311. The method of embodiment 304, wherein the first target region is within 400 base pairs of nucleotide 1243 in SEQ ID NO: 1082.

312. The method of embodiment 304, wherein the first target region is within 400 base pairs of nucleotide 1243 in SEQ ID NO: 1083.

313. The method of embodiment 304, wherein the first target region is within 300 base pairs of nucleotide 1243 in SEQ ID NO: 1082.

314. The method of embodiment 304, wherein the first target region is within 300 base pairs of nucleotide 1243 in SEQ ID NO: 1083.

315. The method of embodiment 304, wherein the first target region is within 200 base pairs of nucleotide 1243 in SEQ ID NO: 1082.

316. The method of embodiment 304, wherein the first target region is within 200 base pairs of nucleotide 1243 in SEQ ID NO: 1083.

317. The method of embodiment 304, wherein the first target region is within 100 base pairs of nucleotide 1243 in SEQ ID NO: 1082.

318. The method of embodiment 304, wherein the first target region is within 100 base pairs of nucleotide 1243 in SEQ ID NO: 1083.

319. The method of embodiment 304, wherein the first target region is within 600 base pairs of nucleotide 1338 in SEQ ID NO: 1083.

320. The method of embodiment 304, wherein the first target region is within 500 base pairs of nucleotide 1338 in SEQ ID NO: 1082.

321. The method of embodiment 304, wherein the first target region is within 500 base pairs of nucleotide 1338 in SEQ ID NO: 1083.

322. The method of embodiment 304, wherein the first target region is within 400 base pairs of nucleotide 1338 in SEQ ID NO: 1082.

323. The method of embodiment 304, wherein the first target region is within 400 base pairs of nucleotide 1338 in SEQ ID NO: 1083.

324. The method of embodiment 304, wherein the first target region is within 300 base pairs of nucleotide 1338 in SEQ ID NO: 1082.

325. The method of embodiment 304, wherein the first target region is within 300 base pairs of nucleotide 1338 in SEQ ID NO: 1083.

326. The method of embodiment 304, wherein the first target region is within 200 base pairs of nucleotide 1338 in SEQ ID NO: 1082.

327. The method of embodiment 304, wherein the first target region is within 200 base pairs of nucleotide 1338 in SEQ ID NO: 1083.

328. The method of embodiment 304, wherein the first target region is within 100 base pairs of nucleotide 1338 in SEQ ID NO: 1082.

329. The method of embodiment 304, wherein the first target region is within 100 base pairs of nucleotide 1338 in SEQ ID NO: 1083.

330. The method of any one of embodiments 192-329, wherein the reduction is a reduction in the number of HBV viral episomes.

331. The method of embodiment 330, wherein the reduction is a reduction in the number of cccDNA genomes.

332. The method of embodiment 330, wherein the reduction is a reduction in total HBV DNA.

333. The method of any one of embodiments 192-329, wherein the reduction is a reduction in the replication of the HBV genome.

334. The method of any one of embodiments 192-329, wherein the reduction is a reduction in a level of expression of a protein product encoded by the HBV genome.

335. The method of embodiment 330, wherein the reduction is a reduction in a level of HBsAg.

336. The method of embodiment 330, wherein the reduction is a reduction in a level of HBeAg.

337. The method of any one of embodiments 192-329, wherein the reduction is a reduction of total HBV DNA of at least 70%, at least 80%, at least 90%, at least 95%, at least 99%, or at least 99.9%, and wherein the reduction is maintained for at least 14 days after the contacting or the administering.

338. The method of any one of embodiments 192-329, wherein the reduction is a reduction of HBeAg of at least 70%, at least 80%, at least 90%, at least 95%, at least 99%, or at least 99.9%, and wherein the reduction is maintained for at least 14 days after the contacting or the administering.

339. The method of any one of embodiments 192-329, wherein the reduction is a reduction of HBsAg of at least 70%, at least 80%, at least 90%, at least 95%, at least 99%, or at least 99.9%, and wherein the reduction is maintained at or below that level for at least 14 days after the contacting or the administering.

340. The method of any one of embodiments 337-339, wherein the reduction is a reduction of at least 90%.

341. The method of any one of embodiments 337-339, wherein the reduction is a reduction of at least 95%.

342. The method of any one of embodiments 337-339, wherein the reduction is a reduction of at least 99%.

343. The method of any one of embodiments 337-339, wherein the reduction is a reduction of at least 99.9%.

344. The method of any one of embodiments 340-343, wherein the reduction is maintained for at least 14 days after the contacting or the administering.

345. The method of embodiment 344, wherein the reduction is maintained for at least 21 days.

346. The method of embodiment 344, wherein the reduction is maintained for at least 28 days.

347. The method of embodiment 344, wherein the reduction is maintained for at least 35 days.

348. The method of embodiment 344, wherein the reduction is maintained for at least 42 days.

349. The method of embodiment 344, wherein the reduction is maintained for at least 56 days.

350. The method of embodiment 344, wherein the reduction is maintained for at least 70 days.

351. The method of embodiment 344, wherein the reduction is maintained for at least 84 days.

352. The method of embodiment 344, wherein the reduction is maintained for at least 112 days.

353. The method of embodiment 344, wherein the reduction is maintained for at least 140 days.

354. The method of embodiment 344, wherein the reduction is maintained for at least 168 days.

355. The method of embodiment 344, wherein the reduction is maintained for at least 6 months.

356. The method of embodiment 344, wherein the reduction is maintained for at least 7 months.

357. The method of embodiment 344, wherein the reduction is maintained for at least 8 months.

358. The method of embodiment 344, wherein the reduction is maintained for at least 9 months.

359. The method of embodiment 344, wherein the reduction is maintained for at least 12 months.

360. The method of embodiment 344, wherein the reduction is maintained for at least 18 months.

361. The method of embodiment 344, wherein the reduction is maintained for at least 24 months.

362. The method of any one of embodiments 192-361, wherein the method does not comprise contacting the HBV gene or genome with a nucleoside or nucleotide analog (NUC) or wherein the method does not comprise administering a NUC to the subject.

363. The method of any one of embodiments 192-362, wherein the method further comprises contacting the HBV gene or genome with a nucleoside or nucleotide analog (NUC) or wherein the method further comprises administering a NUC to the subject.

364. The method of any one of embodiments 192-363, wherein the first DNA binding domain comprises a CRISPR-Cas protein.

365. The method of embodiment 364, wherein the epigenetic editing system further comprises a first guide RNA (gRNA) that comprises a region complementary to a strand of the first target region.

366. The method of embodiment 365, wherein the gRNA comprises a sequence selected from a gRNA provided herein, preferably wherein the gRNA comprises a sequence provided in Table 12 or 13.

367. The method of any one of embodiments 192-364, wherein the first DNA binding domain comprises a zinc-finger protein.

368. The method of embodiment 367, wherein the zinc-finger protein comprises a zinc-finger motif with a sequence selected from any zinc finger or zinc finger motif provided herein, e.g., in Table 1 or Table 18.

369. The method of embodiment 367 or 368, wherein the zinc-finger protein comprises a sequence of any of the zinc finger epigenetic repressors provided herein.

370. The method of any one of embodiments 192-369, wherein the transcriptional repressor domain comprises ZIM3.

371. The method of any one of embodiments 192-370, wherein the first DNMT domain is a DNMT3A domain or a DNMT3L domain.

372. The method of embodiment 371, wherein the first DNMT domain comprises a sequence of a DNMT domain provided herein.

373. The method of any one of embodiments 1-372, wherein the epigenetic editing system comprises the fusion protein provided in SEQ ID NO: 1248 or the fusion protein provided in SEQ ID NO: 1252 and at least one guide RNA, wherein the guide RNA is the guide RNA provided as gRNA #003, gRNA #007, gRNA #008, gRNA #009, gRNA #011, or gRNA #015 herein.

374. An epigenetic editing system for use in the method of any one of embodiments 1-373, comprising:

a fusion protein or a nucleic acid encoding the fusion protein, wherein the fusion protein comprises:

(a) a DNA-binding domain that binds a target region of a HBV gene or genome, (b) a first DNA methyltransferase (DNMT) domain, and (c) a transcriptional repressor domain.

375. The epigenetic editing system of embodiment 374, wherein the fusion protein comprises a sequence of a fusion protein provided herein.

376. The epigenetic editing system of embodiment 374 or 375, wherein the DNA-binding domain is a CRISPR-Cas DNA binding domain, and wherein the epigenetic editing system comprises at least gRNA provided herein.

377. The epigenetic editing system of embodiment 374, wherein the epigenetic editing system comprises the fusion protein provided in SEQ ID NO: 1248 or the fusion protein provided in SEQ ID NO: 1252 and at least one guide RNA, wherein the guide RNA is the guide RNA provided as gRNA #003, gRNA #007, gRNA #008, gRNA #009, gRNA #011, or gRNA #015 herein.

378. An epigenetic editing system comprising:

1. a first fusion protein or a nucleic acid encoding the first fusion protein, wherein the first fusion protein comprises a first DNA binding domain and a first DNMT domain, wherein the first DNA binding domain binds a first target region of a HBV genome, and 2. a second fusion protein or a nucleic acid encoding the second fusion protein, wherein the second fusion protein comprises a second DNA binding domain and a transcriptional repressor domain, wherein the second DNA binding domain binds a second target region of the HBV genome.

379. The epigenetic system of embodiment 378, wherein the epigenetic editing system is capable of reducing a number of the HBV viral episome, replication of the HBV, or expression of a gene product encoded by the HBV genome, wherein said reduction is at least about 20% compared to contacting the HBV genome with a suitable control.

380. The epigenetic system of embodiment 378 or 379, wherein the HBV genome is a covalently closed circular DNA (cccDNA) or an HBV integrated DNA.

381. The epigenetic system of embodiments 378-380, wherein the HBV genome comprises HBV genotype A, HBV genotype B, HBV genotype C, HBV genotype D, HBV genotype E, HBV genotype F, HBV genotype G or HBV genotype H.

382. The epigenetic system of embodiments 378-381, wherein the HBV genome comprises a sequence with at least 80% identity to an HBV genome provided herein.

383. The epigenetic system of embodiments 378-381, further comprising a third fusion protein or a nucleic acid encoding the third fusion protein, wherein the third fusion protein comprises a third DNA binding domain and a second DNMT domain, wherein the third DNA binding domain binds a third target region of the HBV genome.

384. The epigenetic system of embodiment 383, wherein the first target region, the second target region or the third target region is located in a region of the HBV genome within nucleotide 0-303, 1000-2448 or 2802-3182 of an HBV genome provided herein.

385. The epigenetic system of embodiment 383, wherein the first target region, the second target region or the third target region of the HBV genome is located in a CpG island.

386. The epigenetic system of embodiment 383, wherein the first target region, the second target region or the third target region of the HBV genome is located in a promotor.

387. The epigenetic system of embodiment 383, wherein the first target region, the second target region or the third target region of the HBV genome is located in a section of the HBV genome that encodes a transcript selected from the group consisting of a pgRNA, a precure mRNA, a preS mRNA, a S mRNA, and a X mRNA.

388. The epigenetic system of embodiment 383, wherein the first DNA binding domain, the second DNA binding domain or the third DNA binding domain comprises a CRISPR-Cas protein.

389. The epigenetic system of embodiment 388, wherein the epigenetic editing system further comprises a first gRNA that comprises a region complementary to a strand of the first target region, a second gRNA that comprises a region complementary to a strand of the second target region or a third RNA that comprises a region complementary to a strand of the third target region.

390. The epigenetic system of embodiment 389, wherein the first gRNA comprises a sequence selected from a gRNA sequence provided herein, e.g., provided in Table 12 or 13, the second gRNA comprises a sequence selected from a gRNA sequence provided herein, e.g., provided in Table 12 or 13, and/or the third gRNA comprises a sequence selected from a gRNA sequence provided herein, e.g., provided in Table 12 or 13.

391. The epigenetic system of embodiment 383, wherein the first DNA binding domain, the second DNA binding domain or the third DNA binding domain comprises a zinc-finger protein.

392. The epigenetic system of embodiment 391, wherein the zinc-finger protein comprises a zinc-finger motif with a sequence selected from a zinc finger motif provided herein.

393. The epigenetic system of embodiment 391 or 392, wherein the zinc-finger protein comprises a sequence of a zinc finger motif provided in Table 1.

394. The epigenetic system of embodiments 378-393, wherein the transcriptional repressor domain comprises ZIM3.

395. The epigenetic system of embodiments 378-394, wherein the first DNMT domain is a DNMT3A domain or a DNMT3L domain.

396. The epigenetic system of embodiment 395, wherein the first DNMT domain comprises a sequence of a DNMT provided herein.

397. The epigenetic system of embodiment 383, wherein the second DNMT domain is a DNMT3A domain or a DNMT3L domain.

398. The epigenetic system of embodiment 397, wherein the second DNMT domain comprises a sequence of a DNMT domain provided herein.

399. The epigenetic system of embodiment 378-398, wherein the first fusion protein comprises a sequence of a fusion protein provided herein.

400. The epigenetic system of embodiments 378-399, wherein the second fusion protein comprises a sequence of a fusion protein provided herein.

401. The epigenetic system of embodiments 383-399, wherein the third fusion protein comprises a sequence of a fusion protein provided herein.

402. The method of any one of embodiments 1-401, wherein the epigenetic editing system comprises a nucleic acid sequence provided in Table 18.

LISTING #2 of exemplary embodiments:

1. A method of modifying an epigenetic state of a hepatitis B virus (HBV) gene or genome, comprising contacting the HBV gene or genome with an epigenetic editing system,
wherein the epigenetic editing system comprises
a first DNA binding domain, a first DNMT domain, and a transcriptional repressor domain or one or more nucleic acid molecules encoding thereof,
and
wherein the contacting results in a reduction of:
number of HBV viral episomes,
replication of the HBV gene or genome, or
expression of a protein product encoded by the HBV gene or genome,
wherein the reduction is at least about 20% compared to contacting the HBV gene or genome with a suitable control or without contacting the HBV gene or genome with the epigenetic editing system.

2. A method of treating an HBV infection in a subject comprising administering an epigenetic editing system to the subject,
wherein the epigenetic editing system comprises
a first DNA binding domain, a first DNMT domain, and a transcriptional repressor domain or one or more nucleic acid molecules encoding thereof,
and
wherein the administering results in a reduction of:
number of HBV viral episomes,
replication of the HBV gene or genome, or
expression of a protein product encoded by an HBV gene or genome,
wherein the reduction is at least about 20% compared to administering a suitable control or without administering the epigenetic editing system.

3. A method of modulating expression of an HBV gene or genome comprising contacting the HBV gene or genome with an epigenetic editing system,
wherein the epigenetic editing system comprises
a first DNA binding domain, a first DNMT domain, and a transcriptional repressor domain or one or more nucleic acid molecules encoding thereof,
and
wherein the contacting results in a reduction of expression of a gene product encoded by the HBV gene or genome, optionally, wherein the gene product is a nucleic acid or a protein,
wherein the reduction is at least about 20% compared to contacting the HBV gene or genome with a suitable control or without contacting the HBV gene or genome with the epigenetic editing system.

4. A method of inhibiting viral replication in a cell infected with an HBV comprising contacting the cell with an epigenetic editing system, wherein the epigenetic editing system comprises a first DNA binding domain, a first DNMT domain, and a transcriptional repressor domain or one or more nucleic acid molecules encoding thereof, wherein the epigenetic editing system targets a target region of an HBV gene or genome, and wherein the contacting results in a reduction of number of HBV viral episomes or replication of the HBV gene or genome, wherein the reduction is at least about 20% compared to contacting the cell with a suitable control or without contacting the cell with the epigenetic editing system.

5. A method of inhibiting viral replication in a subject infected with an HBV comprising administering an epigenetic editing system to the subject, wherein the epigenetic editing system comprises a first DNA binding domain, a first DNMT domain, and a transcriptional repressor domain or one or more nucleic acid molecules encoding thereof, wherein the epigenetic editing system targets a target region of the HBV gene or genome, and wherein the administering results in a reduction of number of HBV viral episomes, replication of the HBV gene or genome, or expression of a protein product encoded by an HBV gene or genome, wherein the reduction is at least about 20% compared to administering a suitable control or without administering the epigenetic editing system.

6. The method of embodiment 2 or 5, wherein the reduction is at least about 30%, about 40%, about 50%, about 60% or about 70% compared to administering the suitable control.

7. The method of any one of embodiments 1, and 3-4, wherein the reduction is at least about 30%, about 40%, about 50%, about 60% or about 70% compared to contacting with the suitable control.

8. The method of any one of embodiments 1-7, wherein the reduction is maintained for at least 6 days, 19 days, 27 days, 42 days, or 168 days.

9. The method of embodiment 4, wherein the contacting further results in a reduction of a protein product.

10. The method of embodiment 5, wherein the administering further results in a reduction of a protein product.

11. The method of any one of embodiments 1-2 and 9-10, wherein the protein product comprises a HBe antigen.

12. The method of any one of embodiments 1-2 and 9-10, wherein the protein produce comprises a HBs antigen.

13. The method of any one of embodiments 1-12, wherein the HBV genome is a covalently closed circular DNA (cccDNA) or an HBV integrated DNA.

14. The method of any one of embodiments 1-13, wherein the HBV genome comprises HBV genotype A, HBV genotype B, HBV genotype C, HBV genotype D, HBV genotype E, HBV genotype F, HBV genotype G or HBV genotype H.

15. The method of any one of embodiments 1-14, wherein the HBV genome comprises a sequence with at least 80% identity to an HBV genome sequence provided herein.

16. The method of embodiment 15, wherein the first target region is located in a region of the HBV genome within nucleotide 0-303, 1000-2448 or 2802-3182 of an HBV genome provided herein.

17. The method of any one of embodiments 1-15, wherein the first target region of the HBV genome is located in a CpG island.

18. The method of any one of embodiments 1-15, wherein the first target region of the HBV genome is located in a promotor.

19. The method of any one of embodiments 1-15, wherein the first target region of the HBV genome is located in a section of the HBV genome that encodes a transcript selected from the group consisting of a pgRNA, a precure mRNA, a preS mRNA, a S mRNA, and a X mRNA.

20. The method of any one of embodiments 1-19, wherein the first DNA binding domain comprises a CRISPR-Cas protein.

21. The method of any one of embodiments 1-20, wherein the epigenetic editing system further comprises a first guide RNA (gRNA) that comprises a region complementary to a strand of the first target region.

22. The method of embodiment 21, wherein the gRNA comprises a sequence selected from a gRNA provided herein, e.g., in Table 12 and/or 13.

23. The method of any one of embodiments 1-19, wherein the first DNA binding domain comprises a zinc-finger protein.

24. The method of embodiment 23, wherein the zinc-finger protein comprises a zinc-finger motif with a sequence selected from any zinc finger or zinc finger motif provided herein, e.g., in Table 1 or Table 18.

25. The method of embodiment 23 or 24, wherein the zinc-finger protein comprises a sequence of any of the zinc finger epigenetic repressors provided herein.

26. The method of any one of embodiments 1-25, wherein the transcriptional repressor domain comprises ZIM3.

27. The method of any one of embodiments 1-26, wherein the first DNMT domain is a DNMT3A domain or a DNMT3L domain.

28. The method of embodiment 27, wherein the first DNMT domain comprises a sequence of a DNMT domain provided herein.

29. The method of any one of embodiments 1-28, wherein the epigenetic editing system further comprises a second DNMT domain or a nucleic acid encoding thereof.

30. The method of embodiments 29, wherein the second DNMT domain is a DNMT3A domain or a DNMT3L domain.

31. The method of embodiment 30, wherein the second DNMT domain comprises a sequence of a DNMT domain provided herein.

32. The method of any one of embodiments 29-31, wherein the epigenetic editing system comprises a fusion protein or a nucleic acid encoding thereof, and wherein the fusion protein comprises the first DNA binding domain, the first DNMT domain, the repressor domain and the second DNMT domain.

33. The method of embodiment 32, wherein the fusion protein further comprises a nuclear localization sequence (NLS).

34. The method of embodiment 33, wherein the fusion protein comprises a sequence of a fusion protein provided herein.

35. The method of any one of embodiments 1-34, wherein the epigenetic editing system further comprises a second DNA binding domain or a nucleic acid encoding thereof, wherein the second DNA binding domain binds a second target region of the HBV genome.

36. The method of embodiment 35, wherein the second target region is located in a region of the HBV genome within nucleotide 0-303, 1000-2448 or 2802-3182.

37. The method of embodiment 35, wherein the second target region of the HBV genome is located in a CpG island.

38. The method of embodiment 35, wherein the second target region of the HBV genome is located in a promotor.

39. The method of embodiment 35, wherein the second target region of the HBV genome is located in a section of the HBV genome that encodes a transcript selected from the group consisting of a pgRNA, a precure mRNA, a preS mRNA, a S mRNA, and a X mRNA.

40. The method of any one of embodiments 35-39, wherein the second DNA binding domain comprises a CRISPR-Cas protein.

41. The method of embodiment 40, wherein the epigenetic editing system further comprises a second gRNA that comprises a region complementary to a strand of the second target region.

42. The method of embodiment 41, wherein the gRNA comprises a sequence selected from a gRNA sequence provided herein, e.g., a sequence provided in Table 12 and/or 13.

43. The method of any one of embodiments 35-39, wherein the second DNA binding domain comprises a zinc-finger protein.

44. The method of embodiment 43, wherein the zinc-finger protein comprises a zinc-finger motif with a sequence selected from a zinc finger motif sequence provided herein, e.g., a zinc finger motif provided in Table 1 and/or 18.

45. The method of embodiment 43 or 44, wherein the zinc-finger protein comprises a sequence of a zinc finger motif provided in Table 1 and/or 18.

46. The method of any one of embodiments 35-45, wherein the epigenetic editing system comprises a first fusion protein or a first nucleic acid encoding thereof and a second fusion protein or a second nucleic acid encoding thereof, wherein the first fusion protein comprises the first DNA binding domain and the first DNMT domain, and wherein the second fusion protein comprises the second DNA binding domain and the transcriptional repressor domain.

47. The method of embodiment 46, wherein the first fusion protein comprises a sequence of a fusion protein provided herein.

48. The method of embodiment 46, wherein the second fusion protein comprises a sequence of a fusion protein provided herein.

49. The method of any one of embodiments 46-48, wherein the epigenetic editing system further comprises a third DNA binding domain or a nucleic acid encoding thereof, wherein the third DNA binding domain binds to a third target region of the HBV genome.

50. The method of embodiment 49, wherein the third target region is located in a region of the HBV genome within nucleotide 0-303, 1000-2448 or 2802-3182.

51. The method of embodiment 49, wherein the third target region of the HBV genome is located in a CpG island.

52. The method of embodiment 49, wherein the third target region of the HBV genome is located in a promotor.

53. The method of embodiment 49, wherein the third target region of the HBV genome is located in a section of the HBV genome that encodes a transcript selected from the group consisting of a pgRNA, a precure mRNA, a preS mRNA, a S mRNA, and a X mRNA.

54. The method of any one of embodiments 49-53, wherein the third DNA binding domain comprises a CRISPR-Cas protein.

55. The method of embodiment 54, wherein the epigenetic editing system further comprises a third gRNA that comprises a region complementary to a strand of the third target region.

56. The method of embodiment 55, wherein the third gRNA comprises a sequence selected from a gRNA sequence provided herein, e.g., of a gRNA sequence provided in Table 12 and/or 13.

57. The method of any one of embodiments 49-53, wherein the third DNA binding domain comprises a zinc-finger protein.

58. The method of embodiment 57, wherein the zinc-finger protein comprises a zinc-finger motif with a sequence selected from a zinc finger motif provided herein.

59. The method of embodiment 57 or 58, wherein the zinc-finger protein comprises a sequence of a zinc finger motif provided in Table 1 and/or 18.

60. The method of any one of embodiments 49-59, wherein the epigenetic editing system further comprises a second DNMT domain or a nucleic acid encoding thereof.

61. The method of embodiment 60, wherein the second DNMT domain is a DNMT3A domain or a DNMT3L domain.

62. The method of embodiment 61, wherein the epigenetic editing system comprises a third fusion protein or a nucleic acid encoding thereof, wherein the third fusion protein comprises the third DNA binding domain and the second DNMT domain.

63. The method of embodiment 62, wherein the third fusion protein comprises a sequence of a fusion protein provided herein.

64. An epigenetic editing system comprising:

a fusion protein or a nucleic acid encoding the fusion protein, wherein the fusion protein comprises:

(a) a DNA-binding domain that binds a target region of a HBV gene or genome, (b) a first DNA methyltransferase (DNMT) domain, and (c) a transcriptional repressor domain.

65. The epigenetic system of embodiment 64, wherein the epigenetic editing system is capable of reducing a number of the HBV viral episome, replication of the HBV, or expression of a gene product encoded by the HBV gene or genome, wherein said reduction is at least about 20% compared to contacting the HBV gene or genome with a suitable control.

66. The epigenetic system of embodiment 64 or 65, wherein the HBV genome is a covalently closed circular DNA (cccDNA) or an HBV integrated DNA.

67. The epigenetic system of any one of embodiments 64-66, wherein the HBV genome comprises HBV genotype A, HBV genotype B, HBV genotype C, HBV genotype D, HBV genotype E, HBV genotype F, HBV genotype G or HBV genotype H.

68. The epigenetic system of any one of embodiments 64-67, wherein the HBV genome comprises a sequence with at least 80% identity to an HBV genome sequence provided herein.

69. The epigenetic system of any one of embodiments 64-68, wherein the target region is located in a region of the HBV genome within nucleotide 0-303, 1000-2448 or 2802-3182 of an HBV genome sequence provided herein.

70. The epigenetic system of any one of embodiments 64-68, wherein the target region of the HBV genome is located in a CpG island.

71. The epigenetic system of any one of embodiments 63-68, wherein the target region of the HBV genome is located in a promotor.

72. The epigenetic system of any one of embodiments 63-68, wherein the target region of the HBV genome is located in a section of the HBV genome that encodes a transcript selected from the group consisting of a pgRNA, a precure mRNA, a preS mRNA, a S mRNA, and a X mRNA.

73. The epigenetic system of embodiments 63-72, wherein the DNA binding domain comprises a CRISPR-Cas protein.

74. The epigenetic system of embodiment 73, wherein the epigenetic editing system further comprises a gRNA that comprises a region complementary to a strand of the target region.

75. The epigenetic system of embodiment 74, wherein the gRNA comprises a sequence selected from a gRNA sequence provided herein, e.g., in Table 12 and/or 13.

76. The epigenetic system of any one of embodiments 63-72, wherein the DNA binding domain comprises a zinc-finger protein.

77. The epigenetic system of embodiment 76, wherein the zinc-finger protein comprises a zinc-finger motif with a sequence selected from a zinc finger motif provided herein.

78. The epigenetic system of embodiment 76 or 77, wherein the zinc-finger protein comprises a sequence of a zinc finger motif provided in Table 1 and/or 18.

79. The epigenetic system of any one of embodiments 63-78, wherein the transcriptional repressor domain comprises a sequence of a transcriptional repressor provided herein.

80. The epigenetic system of any one of embodiments 63-79, wherein the first DNMT domain is a DNMT3A domain or a DNMT3L domain.

81. The epigenetic system of embodiment 80, wherein the DNMT domain comprises a sequence of a DNMT domain provided herein.

82. The epigenetic system of any one of embodiments 63-81, wherein the fusion protein further comprises a second DNMT domain.

83. The epigenetic system of embodiment 82, wherein the second DNMT domain is a DNMT3A domain or a DNMT3L domain.

84. The epigenetic system of any one of embodiments 63-83, wherein the fusion protein further comprises a nuclear localization sequence (NLS).

85. The epigenetic system of embodiment 84, wherein the fusion protein comprises a sequence of a fusion protein provided herein.

86. An epigenetic editing system comprising:

a first fusion protein or a nucleic acid encoding the first fusion protein, wherein the first fusion protein comprises a first DNA binding domain and a first DNMT domain, wherein the first DNA binding domain binds a first target region of a HBV genome, and a second fusion protein or a nucleic acid encoding the second fusion protein, wherein the second fusion protein comprises a second DNA binding domain and a transcriptional repressor domain, wherein the second DNA binding domain binds a second target region of the HBV genome.

87. The epigenetic system of embodiment 86, wherein the epigenetic editing system is capable of reducing a number of the HBV viral episome, replication of the HBV, or expression of a gene product encoded by the HBV genome, wherein said reduction is at least about 20% compared to contacting the HBV genome with a suitable control.

88. The epigenetic system of embodiment 86 or 87, wherein the HBV genome is a covalently closed circular DNA (cccDNA) or an HBV integrated DNA.

89. The epigenetic system of any one of embodiments 86-88, wherein the HBV genome comprises HBV genotype A, HBV genotype B, HBV genotype C, HBV genotype D, HBV genotype E, HBV genotype F, HBV genotype G or HBV genotype H.

90. The epigenetic system of any one of embodiments 86-89, wherein the HBV genome comprises a sequence with at least 80% identity to an HBV genome provided herein.

91. The epigenetic system of any one of embodiments 86-89, further comprising a third fusion protein or a nucleic acid encoding the third fusion protein, wherein the third fusion protein comprises a third DNA binding domain and a second DNMT domain, wherein the third DNA binding domain binds a third target region of the HBV genome.

92. The epigenetic system of embodiment 91, wherein the first target region, the second target region or the third target region is located in a region of the HBV genome within nucleotide 0-303, 1000-2448 or 2802-3182 of an HBV genome provided herein.

93. The epigenetic system of embodiment 91, wherein the first target region, the second target region or the third target region of the HBV genome is located in a CpG island.

94. The epigenetic system of embodiment 91, wherein the first target region, the second target region or the third target region of the HBV genome is located in a promotor.

95. The epigenetic system of embodiment 91, wherein the first target region, the second target region or the third target region of the HBV genome is located in a section of the HBV genome that encodes a transcript selected from the group consisting of a pgRNA, a precure mRNA, a preS mRNA, a S mRNA, and a X mRNA.

96. The epigenetic system of embodiment 91, wherein the first DNA binding domain, the second DNA binding domain or the third DNA binding domain comprises a CRISPR-Cas protein.

97. The epigenetic system of embodiment 96, wherein the epigenetic editing system further comprises a first gRNA that comprises a region complementary to a strand of the first target region, a second gRNA that comprises a region complementary to a strand of the second target region or a third RNA that comprises a region complementary to a strand of the third target region.

98. The epigenetic system of embodiment 97, wherein the first gRNA comprises a sequence selected from a gRNA sequence provided herein, e.g., provided in Table 12 and/or 13, the second gRNA comprises a sequence selected from a gRNA sequence provided herein, e.g., provided in Table 12 and/or 13, and/or the third gRNA comprises a sequence selected from a gRNA sequence provided herein, e.g., provided in Table 12 and/or 13.

99. The epigenetic system of embodiment 91, wherein the first DNA binding domain, the second DNA binding domain or the third DNA binding domain comprises a zinc-finger protein.

100. The epigenetic system of embodiment 99, wherein the zinc-finger protein comprises a zinc-finger motif with a sequence selected from a zinc finger motif provided herein.

101. The epigenetic system of embodiment 99 or 100, wherein the zinc-finger protein comprises a sequence of a zinc finger motif provided in Table 1 and/or 18.

102. The epigenetic system of any one of embodiments 86-101, wherein the transcriptional repressor domain comprises ZIM3.

103. The epigenetic system of any one of embodiments 86-102, wherein the first DNMT domain is a DNMT3A domain or a DNMT3L domain.

104. The epigenetic system of embodiment 103, wherein the first DNMT domain comprises a sequence of a DNMT provided herein.

105. The epigenetic system of embodiment 91, wherein the second DNMT domain is a DNMT3A domain or a DNMT3L domain.

106. The epigenetic system of embodiment 105, wherein the second DNMT domain comprises a sequence of a DNMT domain provided herein.

107. The epigenetic system of any one of embodiment 86-106, wherein the first fusion protein comprises a sequence of a fusion protein provided herein.

108. The epigenetic system of any one of embodiments 86-107, wherein the second fusion protein comprises a sequence of a fusion protein provided herein.

109. The epigenetic system of any one of embodiments 91-107, wherein the third fusion protein comprises a sequence of a fusion protein provided herein.

110. The method of any one of embodiments 1-63, wherein the epigenetic editing system comprises a nucleic acid sequence provided in Table 18.

111. A method of treating an HDV infection in a subject comprising administering an epigenetic editing system to the subject,
wherein the epigenetic editing system comprises
a first DNA binding domain, a first DNMT domain, and a transcriptional repressor domain or one or more nucleic acid molecules encoding thereof,
wherein the first DNA binding domain binds a first target region of a HBV gene or genome, and
wherein the contacting results in a reduction of:
number of HDV viral episomes,
replication of the HDV gene or genome, or
expression of a protein product encoded by the HDV gene or genome,
wherein said reduction is at least about 20% compared to administering a suitable control.

112. A method of inhibiting viral replication in a cell infected with an HDV comprising administering an epigenetic editing system, wherein the epigenetic editing system comprises
a first DNA binding domain, a first DNMT domain, and a transcriptional repressor domain or one or more nucleic acid molecules encoding thereof,
wherein the first DNA binding domain binds a first target region of a HBV gene or genome, and wherein the epigenetic editing system targets a target region of the HBV gene or genome, and
wherein the contacting results in a reduction of number of HDV viral episomes or replication of the HDV gene or genome,
wherein said reduction is at least about 20% compared to administering a suitable control.

113. The method of embodiment 111 or 112, wherein the first DNA binding domain comprises a CRISPR-Cas protein.

114. The method of embodiment 113, wherein the epigenetic editing system further comprises a first guide RNA (gRNA) that comprises a region complementary to a strand of the first target region.

115. The method of embodiment 114, wherein the gRNA comprises a sequence selected from a gRNA provided herein, e.g., in Table 12 and/or 13.

116. The method of embodiment 111 or 112, wherein the first DNA binding domain comprises a zinc-finger protein.

117. The method of embodiment 116, wherein the zinc-finger protein comprises a zinc-finger motif with a sequence selected from any zinc finger or zinc finger motif provided herein, e.g., in Table 1 and/or 18.

118. The method of embodiment 116 or 117, wherein the zinc-finger protein comprises a sequence of any of the zinc finger epigenetic repressors provided herein.

119. The method of any one of embodiments 111-118, wherein the transcriptional repressor domain comprises ZIM3.

120. The method of any one of embodiments 111-119, wherein the first DNMT domain is a DNMT3A domain or a DNMT3L domain.

121. The method of embodiment 120, wherein the first DNMT domain comprises a sequence of a DNMT domain provided herein.

122. The method of any one of embodiments 111-121, wherein the epigenetic editing system further comprises a second DNMT domain or a nucleic acid encoding thereof.

123. The method of embodiment 122, wherein the second DNMT domain is a DNMT3A domain or a DNMT3L domain.

124. The method of embodiment 123, wherein the second DNMT domain comprises a sequence of a DNMT domain provided herein.

125. The method of any one of embodiments 122-123, wherein the epigenetic editing system comprises a fusion protein or a nucleic acid encoding thereof, and wherein the fusion protein comprises the first DNA binding domain, the first DNMT domain, the repressor domain and the second DNMT domain.

126. The method of embodiment 125, wherein the fusion protein further comprises a nuclear localization sequence (NLS).

127. The method of embodiment 126, wherein the fusion protein comprises a sequence of a fusion protein provided herein.

128. The method of any one of embodiments 111-127, wherein the first DNA binding domain binds a target region of an HBV gene or genome encoding or controlling expression of an S-antigen.

In order that the present disclosure may be better understood, the following examples are set forth. These examples are for purposes of illustration only and are not to be construed as limiting the scope of the present disclosure in any manner.

EXAMPLES

Example 1: Selection of Target HBV Sequences for Epigenetic Silencing

Target sequences were manually and computationally designed using the representative HBV genome sequences (SEQ ID Nos. 1082, 1083) as a reference:

While target site design focused on CpG islands identified within the HBV genome, target sites outside of HBV CpG islands were also considered.

Table 2 presents some representative target sites that were identified as suitable for targeting with an epigenetic repressor.

Target domains identified above that are adjacent to a PAM sequence, e.g., an *S. pyogenes* Cas9 PAM sequence, can be targeted by a CRISPR-based epigenetic repressor, e.g., an epigenetic repressor comprising a dCas9 DNA-binding domain. For example, target sites 1-143 are suitable for dCas9-based epigenetic repressor targeting. FIG. 1 provides an overview over the position of the target sites identified in the HBV genome.

Figure 2:
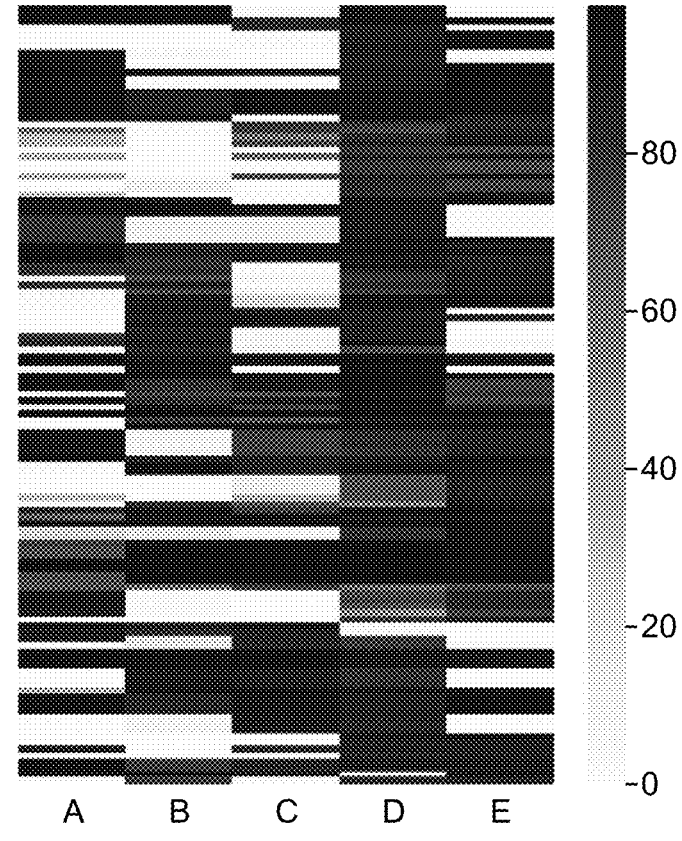
FIG. 2 is a heat map showing conservation of guide RNA target domains across different HBV genotypes.
Figure 3:
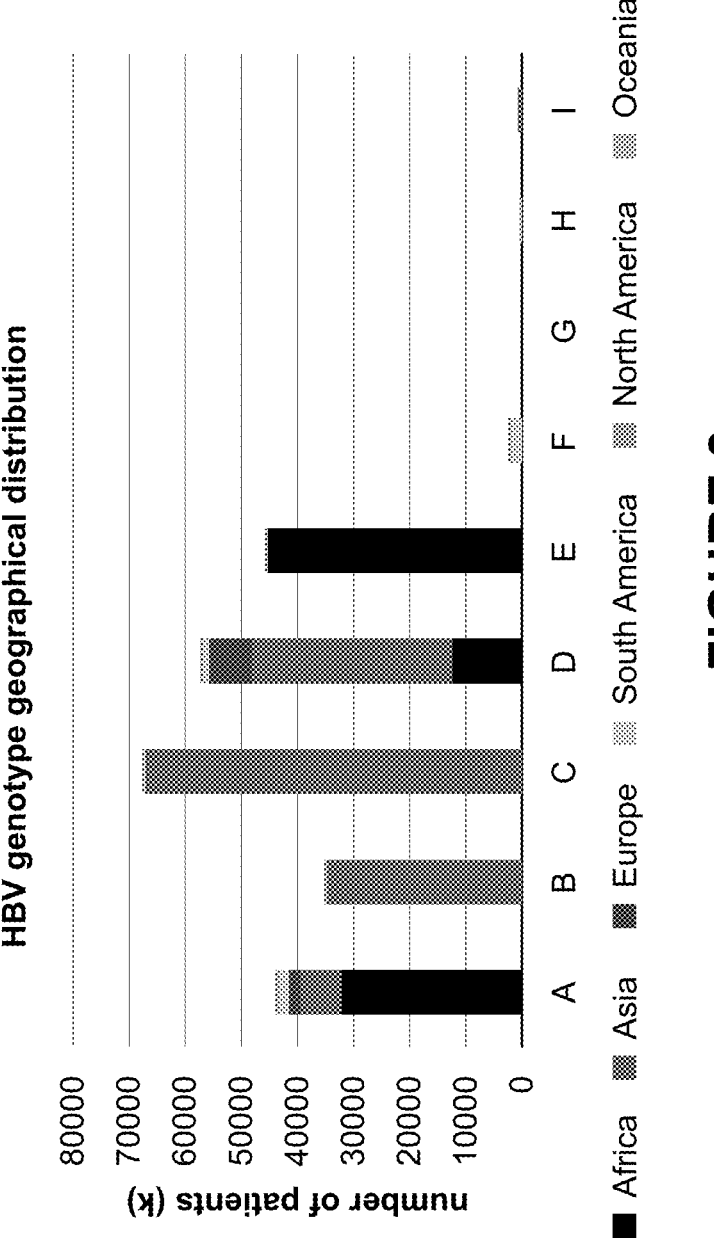
FIG. 3 is a bar graph illustrating the geographical distribution of different HBV genotypes.

Target sites were analyzed for conservation across HBV genotypes A-E (FIGS. 2 and 3). Some target sites were identified that were well conserved across two or more, or in some cases all, HBV genotypes. Targeting such conserved sites allows for silencing different genotypes with the same epigenetic repressor.

Example 2: Guide RNA Assays in HepAD38 HBV Cells

The HepAD38 cell line expresses the HBV genome under a doxycycline-inducible promoter (see, e.g., Ladner et al., Inducible expression of human hepatitis B virus (HBV) in stably transfected hepatoblastoma cells: a novel system for screening potential inhibitors of HBV replication. Antimicrob. Agents Chemother. 41:1715-1720 (1997), incorporated herein by reference).

Figure 4A:
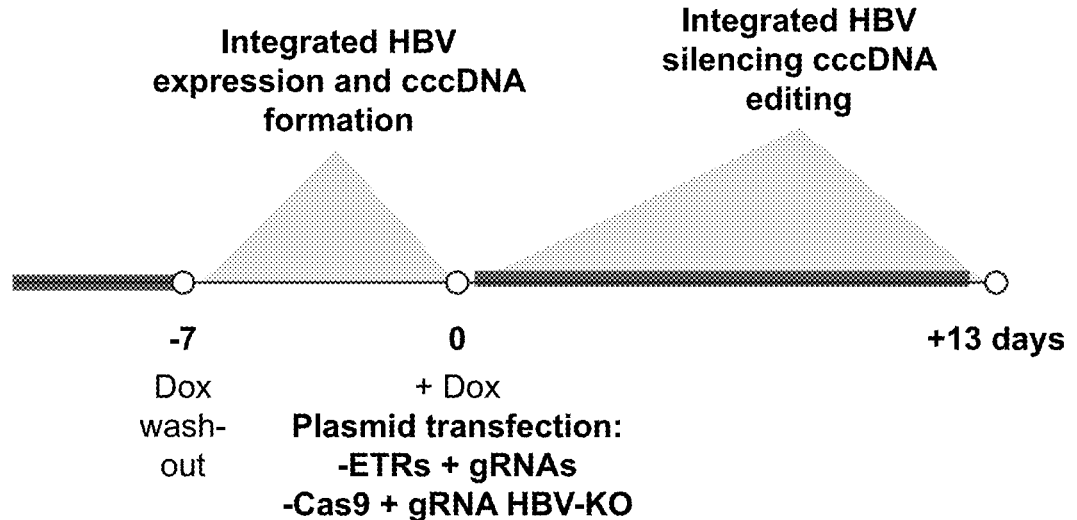
FIG. 4A is a diagram describing the experimental timeline for testing different CRISPR-based epigenetic repressors in HepAD38 cells, which express HPV in a doxycycline-inducible manner.
Figure 4B:
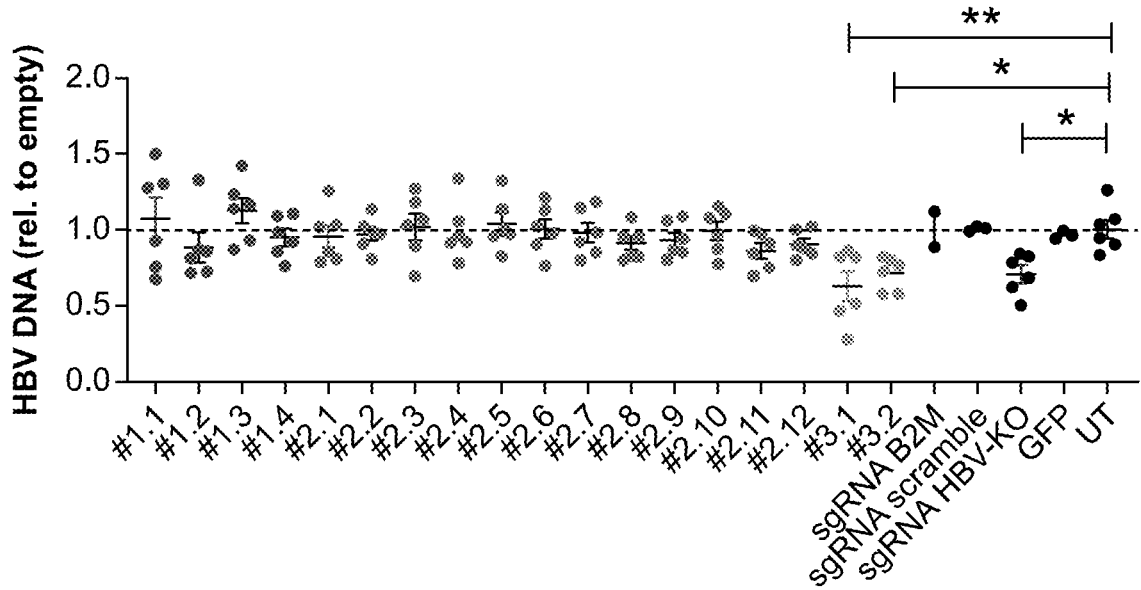
FIG. 4B is a diagram showing the repression of HBV by various CRISPR-based epigenetic repressors (#1.1-3.2). Controls: UT: untransfected control; GFP: transfection control without repressor; HBV-KO: CRISPR nuclease mediated knockout; sgRNA scramble: CRISPR-based repressor with sgRNA not targeting HBV; B2M: CRISPR-based repressor with sgRNA targeting B2M.

Results are shown in FIGS. 4A and B.

Example 3: Guide RNA Assays in HepG2-NTCP Cells

HepG2 cells were engineered by lentiviral transduction to express the human NTCP receptor which is used by hepatitis B virus (HBV) to infect the cells.

HBV viral particles were produced using the HepAD38 cell line. HepAD38 is a subclone, derived from HepG2 cell line, that expresses HBV genome (genotype D subtype ayw) under the transcriptional control of a tetracycline-responsive promoter in a TET-OFF system.

A triple combination of Engineered Transcriptional Repressors (ETRs) consisting of three plasmids expressing dCas9-KRAB, dCas9-DNMT3A and dCas9-DNMT3L was used in combination with one or more of the designed sgRNAs.

LNPs were formulated using GENVOY ILM Lipid Mix (Precision Nanosystem) and the formulator Nanoassemblr Spark (Precision Nanosystem). LNPs were formulated according to the manufacturer's recommendations with Nitrogen:Phosphate (NP) ratio equal to 6 and flow rate ratio (FRR) 2:1. The RNA payload was diluted to a final concentration of 350 ng/uL in the PNI formulation buffer. The ETRs, dCas9-KRAB, dCas9-DNMT3A, dCas9-DNMT3L and each of the 121 sgRNA were mixed at 1:1:1:4 ratio. The RNA mix, the Genvoy lipid mix (25 mM) and PBS were loaded each in the dedicated chambers of the Spark cartridge and formulated. The quality of the formulated LNPs was evaluated quantifying the packaged mRNA using Quant-it™ RiboGreen RNA Assay Kit (Thermo Fisher) and sizing the LNP by Dynamic Light Scattering (Zetasizer, Malvern Panalytic).

HepG2-NTCP cells were plated at 20,000 cells/well in collagen coated 96 well plates. After 24 h cells were infected with HBV at 5,000 multiplicity of genome equivalent (MGE) and 16 h after viral inoculum was removed, cells were washed with PBS, and fresh media was added. Three days post-infection, using LNPs, each sgRNA and the mRNAs encoding each of the components of the triple constructs of ETRs (dCas9-KRAB, dCas9-DNMT3A, dCas9-DNMT3L) were delivered. Three days after, LNP was removed, medium was replaced, and cells were maintained in complete medium for three days.

Viral antigens HBeAg and HBsAg were quantified 6 days after LNP removal using ELISA assays. Data were normalized to a non-targeting guide designed against the mouse PCSK9 and control 3.2 gRNA was used as positive control. Cells viability assay were performed and normalized to non-targeting control.

The Table below provides amino acid sequences of exemplary epigenetic editors used in the gRNA screen (the ETR constructs):

TABLE 6

| amino acid sequences of exemplary epigenetic editors | | |
|---|---|---|
| SEQ ID NO | Description | Amino acid sequence |
| 476 | dCas9:G:KRAB | MYPYDVPDYASPKKKRKVEASDKKYSIGLAIGTNSVGWAVITDEYKVPSKKFK VLGNTDRHSIKKNLIGALLFDSGETAEATRLKRTARRRYTRRKNRICYLQEIF SNEMAKVDDSFFHRLEESFLVEEDKKHERHPIFGNIVDEVAYHEKYPTIYHLR KKLVDSTDKADLRLIYLALAHMIKERGHFLIEGDLNPDNSDVDKLFIQLVQTY NQLFEENPINASGVDAKAILSARLSKSRRLENLIAQLPGEKKNGLFGNLIALS LGLTPNFKSNFDLAEDAKLQLSKDTYDDDLDNLLAQIGDQYADLFLAAKNLSD AILLSDILRVNTEITKAPLSASMIKRYDEHHQDLTLLKALVRQQLPEKYKEIF FDQSKNGYAGYIDGGASQEEFYKFIKPILEKMDGTEELLVKLNREDLLRKQRT FDNGSIPHQIHLGELHAILRRQEDFYPFLKDNREKIEKILTFRIPYYVGPLAR GNSRFAWMTRKSEETITPWNFEEVVDKGASAQSFIERMTNFDKNLPNEKVLPK HSLLYEYFTVYNELTKVKYVTEGMRKPAFLSGEQKKAIVDLLFKTNRKVTVKQ LKEDYFKKIECFDSVEISGVEDRENASLGTYHDLLKIIKDKDFLDNEENEDIL |

TABLE 6-continued

| amino acid sequences of exemplary epigenetic editors |
|---|

| SEQ ID NO | Description | Amino acid sequence |
|---|---|---|
|  |  | EDIVLTLTLFEDREMIEERLKTYAHLEDDKVMKQLKRRRYTGWGRLSRKLING IRDKQSGKTILDFLKSDGFANRNFMQLIHDDSLTFKEDIQKAQVSGQGDSLHE HIANLAGSPAIKKGILQTVKVVDELVKVMGRHKPENIVIEMARENQTTQKGQK NSRERMKRIEEGIKELGSQILKEHPVENTQLQNEKLYLYYLQNGRDMYVDQEL DINRLSDYDVDAIVPQSFLKDDSIDNKVLTRSDKNRGKSDNVPSEEVVKKMKN YWRQLLNAKLITQRKFDNLTKAERGGLSELDKAGFIKRQLVETRQITKHVAQI LDSRMNTKYDENDKLIREVKVITLKSKLVSDFRKDFQFYKVREINNYHHAHDA YLNAVVGTALIKKYPKLESEFVYGDYKVYDVRKMIAKSEQEIGKATAKYFFYS NIMNFFKTEITLANGEIRKRPLIETNGETGEIVWDKGRDFATVRKVLSMPQVN IVKKTEVQTGGFSKESILPKRNSDKLIARKKDWDPKKYGGFDSPTVAYSVLVV AKVEKGKSKKLKSVKELLGITIMERSSFEKNPIDFLEAKGYKEVKKDLIIKLP KYSLFELENGRKRMLASAGELQKGNELALPSKYVNFLYLASHYEKLKGSPEDN EQKQLFVEQHKHYLDEIIEQISEFSKRVILADANLDKVLSAYNKHRDKPIREQ AENIIHLFTLTNLGAPAAFKYFDTTIDRKRYTSTKEVLDATLIHQSITGLYET RIDLSQLGGDSPKKKRKVGVDGSGGGALSPQHSAVTQGSIIKNKEGMDAKSLT AWSRTLVTFKDVFVDFTREEWKLLDTAQQIVYRNVMLENYKNLVSLGYQLTKP DVILRLEKGEEPWLVEREIHQETHPDSETAFEIKSSV* <br> <u>YPYDVPDYA</u> - HA-Tag (SEQ ID NO: 479) <br> GSGGG - Linker (SEQ ID NO: 480) |
| 477 | dCas9:G:DNMT3A | M<u>YPYDVPDYA</u>SPKKKRKVEASDKKYSIGLAIGTNSVGWAVITDEYKVPSKKFK VLGNTDRHS<u>IKKNLIG</u>ALLFDSGETAEATRLKRTARRRYTRRKNRICYLQEIF SNEMAKVDDSFFHRLEESFLVEEDKKHERHPIFGNIVDEVAYHEKYPTIYHLR KKLVDSTDKADLRLIYLALAHMIKFRGHFLIEGDLNPDNSDVDKLFIQLVQTY NQLFEENPINASGVDAKAILSARLSKSRRLENLIAQLPGEKKNGLFGNLIALS LGLTPNFKSNFDLAEDAKLQLSKDTYDDDLDNLLAQIGDQYADLFLAAKNLSD AILLSDILRVNTEITKAPLSASMIKRYDEHHQDLTLLKALVRQQLPEKYKEIF FDQSKNGYAGYIDGGASQEEFYKFIKPILEKMDGTEELLVKLNREDLLRKQRT FDNGSIPHQIHLGELHAILRRQEDFYPFLKDNREKIEKILTFRIPYYVGPLAR GNSRFAWMTRKSEETITPWNFEEVVDKGASAQSFIERMTNFDKNLPNEKVLPK HSLLYEYFTVYNELTKVKYVTEGMRKPAFLSGEQKKAIVDLLFKTNRKVTVKQ LKEDYFKKIECFDSVEISGVEDRFNASLGTYHDLLKIIKDKDELDNEENEDIL EDIVLTLTLFEDREMIEERLKTYAHLFDDKVMKQLKRRRYTGWGRLSRKLING IRDKQSGKTILDFLKSDGFANRNFMQLIHDDSLTFKEDIQKAQVSGQGDSLHE HIANLAGSPAIKKGILQTVKVVDELVKVMGRHKPENIVIEMARENQTTQKGQK NSRERMKRIEEGIKELGSQILKEHPVENTQLQNEKLYLYYLQNGRDMYVDQEL DINRLSDYDVDAIVPQSFLKDDSIDNKVLTRSDKNRGKSDNVPSEEVVKKMKN YWRQLLNAKLITQRKFDNLTKAERGGLSELDKAGFIKRQLVETRQITKHVAQI LDSRMNTKYDENDKLIREVKVITLKSKLVSDFRKDFQFYKVREINNYHHAHDA YLNAVVGTALIKKYPKLESEFVYGDYKVYDVRKMIAKSEQEIGKATAKYFFYS NIMNFFKTEITLANGEIRKRPLIETNGETGEIVWDKGRDFATVRKVLSMPQVN IVKKTEVQTGGFSKESILPKRNSDKLIARKKDWDPKKYGGFDSPTVAYSVLVV AKVEKGKSKKLKSVKELLGITIMERSSFEKNPIDFLEAKGYKEVKKDLIIKLP KYSLFELENGRKRMLASAGELQKGNELALPSKYVNFLYLASHYEKLKGSPEDN EQKQLFVEQHKHYLDEIIEQISEFSKRVILADANLDKVLSAYNKHRDKPIREQ AENIIHLFTLTNLGAPAAFKYFDTTIDRKRYTSTKEVLDATLIHQSITGLYET RIDLSQLGGDSPKKKRKVGVDGSGGGTYGLLRRREDWPSRLQMFANNHDQEF DPPKVYPPVPAEKRKPIRVLS<u>LF</u>DGIATGLLVLKDLGIQVDRYIASEVCEDSI TVGMVRHQGKIMYVGDVRSVTQKHIQEWGPFDLVIGGSPCNDLSIVNPARKGL YEGTGRLFFEYRLLHDARPKEGDDRPFFWLFENVVAMGVSDKRDISRFLESN PVMIDAKEVSAAHRARYFWGNLPGMNRPLASTVNDKLELQECLEHGRIAKFSK VRTITTRSNSIKQGKDQHFPVFMNEKEDILWCTEMERVFGFPVHYTDVSNMSR LARQRLLGRSWSVPVIRHLFAPLKEYFACV* <br> <u>YPYDVPDYA</u> - HA-Tag (SEQ ID NO: 479) <br> GSGGG - Linker (SEQ ID NO: 480) |
| 478 | dCas9:G:hDNMT3L | M<u>YPYDVPDYA</u>SPKKKRKVEASDKKYSIGLAIGTNSVGWAVITDEYKVPSKKEK VLGNTDRHS<u>IKKNLIG</u>ALLFDSGETAEATRLKRTARRRYTRRKNRICYLQEIF SNEMAKVDDSFFHRLEESFLVEEDKKHERHPIFGNIVDEVAYHEKYPTIYHLR KKLVDSTDKADLRLIYLALAHMIKFRGHFLIEGDLNPDNSDVDKLFIQLVQTY NQLFEENPINASGVDAKAILSARLSKSRRLENLIAQLPGEKKNGLFGNLIALS LGLTPNFKSNFDLAEDAKLQLSKDTYDDDLDNLLAQIGDQYADLFLAAKNLSD AILLSDILRVNTEITKAPLSASMIKRYDEHHQDLTLLKALVRQQLPEKYKEIF FDQSKNGYAGYIDGGASQEEFYKFIKPILEKMDGTEELLVKLNREDLLRKQRT FDNGSIPHQIHLGELHAILRRQEDFYPFLKDNREKIEKILTFRIPYYVGPLAR GNSRFAWMTRKSEETITPWNFEEVVDKGASAQSFIERMTNFDKNLPNEKVLPK HSLLYEYFTVYNELTKVKYVTEGMRKPAFLSGEQKKAIVDLLFKTNRKVTVKQ LKEDYFKKIECFDSVEISGVEDRFNASLGTYHDLLKIIKDKDELDNEENEDIL EDIVLTLTLFEDREMIEERLKTYAHLEDDKVMKQLKRRRYTGWGRLSRKLING IRDKQSGKTILDFLKSDGFANRNFMQLIHDDSLTFKEDIQKAQVSGQGDSLHE HIANLAGSPAIKKGILQTVKVVDELVKVMGRHKPENIVIEMARENQTTQKGQK NSRERMKRIEEGIKELGSQILKEHPVENTQLQNEKLYLYYLQNGRDMYVDQEL DINRLSDYDVDAIVPQSFLKDDSIDNKVLTRSDKNRGKSDNVPSEEVVKKMKN YWRQLLNAKLITQRKFDNLTKAERGGLSELDKAGFIKRQLVETRQITKHVAQI LDSRMNTKYDENDKLIREVKVITLKSKLVSDFRKDFQFYKVREINNYHHAHDA |

TABLE 6-continued

| SEQ | | |
|---|---|---|
| ID NO | Description | Amino acid sequence |

|  |  | YLNAVVGTALIKKYPKLESEFVYGDYKVYDVRKMIAKSEQEIGKATAKYFFYS |
|  |  | NIMNFFKTEITLANGEIRKRPLIETNGETGEIVWDKGRDFATVRKVLSMPQVN |
|  |  | IVKKTEVQTGGFSKESILPKRNSDKLIARKKDWDPKKYGGFDSPTVAYSVLVV |
|  |  | AKVEKGKSKKLKSVKELLGITIMERSSFEKNPIDFLEAKGYKEVKKDLIIKLP |
|  |  | KYSLFELENGRKRMLASAGELQKGNELALPSKYVNFLYLASHYEKLKGSPEDN |
|  |  | EQKQLFVEQHKHYLDEIIEQISEFSKRVILADANLDKVLSAYNKHRDKPIREQ |
|  |  | AENIIHLFTLTNLGAPAAFKYFDTTIDRKRYTSTKEVLDATLIHQSITGLYET |
|  |  | RIDLSQLGGDSPKKKRKVGVDGSGGGMAAIPALDPEAEPSMDVILVGSSELSS |
|  |  | SVSPGTGRDLIAYEVKANQRNIEDICICCGSLQVHTQHPLFEGGICAPCKDKF |
|  |  | LDALFLYDDDGYQSYCSICCSGETLLICGNPDCTRCYCFECVDSLVGPGTSGK |
|  |  | VHAMSNWVCYLCLPSSRSGLLQRRRKWRSQLKAFYDRESENPLEMFETVPVWR |
|  |  | RQPVRVLSLFEDIKKELTSLGFLESGSDPGQLKHVVDVTDTVRKDVEEWGPED |
|  |  | LVYGATPPLGHTCDRPPSWYLFQFHRLLQYARPKPGSPRPFFWMFVDNLVLNK |
|  |  | EDLDVASRFLEMEPVTIPDVHGGSLQNAVRVWSNIPAIRSRHWALVSEEELSL |
|  |  | LAQNKQSSKLAAKWPTKLVKNCFLPLREYFKYFSTELTSSL* |
|  |  | <u>YPYDVPDYA</u> - HA-Tag (SEQ ID NO: 479) |
|  |  | GSGGG - Linker (SEQ ID NO: 480) |
| 479 | HA-Tag | YPYDVPDYA |
| 480 | linker | GSGGG |

The Table below provides amino acid sequences and polynucleotide sequences of exemplary epigenetic editors

TABLE 7

| | sequences of exemplary epigenetic editors | |
|---|---|---|

| SEQ | | |
|---|---|---|
| ID NO | Description | Sequence |

| 481 | PLA001 amino acid sequence | MPKKKRKVPKKKRKVYNHDQEFDPPKVYPPVPAEKRKPIRVLSLEDGIATG |
|  |  | LLVLKDLGIQVDRYIASEVCEDSITVGMVRHQGKIMYVGDVRSVTQKHIQE |
|  |  | WGPFDLVIGGSPCNDLSIVNPARKGLYEGTGRLFFEFYRLLHDARPKEGDD |
|  |  | RPFFWLFENVVAMGVSDKRDISRFLESNPVMIDAKEVSAAHRARYFWGNLP |
|  |  | GMNRPLASTVNDKLELQECLEHGRIAKFSKVRTITTRSNSIKQGKDQHFPV |
|  |  | FMNEKEDILWCTEMERVFGFPVHYTDVSNMSRLARQRLLGRSWSVPVIRHL |
|  |  | FAPLKEYFACVSSGNSNANSRGPSFSSGLVPLSLRGSHMAAIPALDPEAEP |
|  |  | SMDVILVGSSELSSSVSPGTGRDLIAYEVKANQRNIEDICICCGSLQVHTQ |
|  |  | HPLFEGGICAPCKDKFLDALFLYDDDGYQSYCSICCSGETLLICGNPDCTR |
|  |  | CYCFECVDSLVGPGTSGKVHAMSNWVCYLCLPSSRSGLLQRRRKWRSQLKA |
|  |  | FYDRESENPLEMFETVPVWRRQPVRVLSLFEDIKKELTSLGFLESGSDPGQ |
|  |  | LKHVVDVTDTVRKDVEEWGPFDLVYGATPPLGHTCDRPPSWYLFQFHRLLQ |
|  |  | YARPKPGSPRPFFWMFVDNLVLNKEDLDVASRFLEMEPVTIPDVHGGSLQN |
|  |  | AVRVWSNIPAIRSRHWALVSEEELSLLAQNKQSSKLAAKWPTKLVKNCFLP |
|  |  | LREYFKYFSTELTSSLGGPSSGAPPPSGGSPAGSPTSTEEGTSESATPESG |
|  |  | PGTSTEPSEGSAPGSPAGSPTSTEEGTSTEPSEGSAPGTSTEPSELEDKKY |
|  |  | SIGLAIGTNSVGWAVITDEYKVPSKKFKVLGNTDRHSIKKNLIGALLFDSG |
|  |  | ETAEATRLKRTARRRYTRRKNRICYLQEIFSNEMAKVDDSFFHRLEESFLV |
|  |  | EEDKKHERHPIFGNIVDEVAYHEKYPTIYHLRKKLVDSTDKADLRLIYLAL |
|  |  | AHMIKFRGHFLIEGDLNPDNSDVDKLFIQLVQTYNQLFEENPINASGVDAK |
|  |  | AILSARLSKSRRLENLIAQLPGEKKNGLFGNLIALSLGLTPNFKSNFDLAE |
|  |  | DAKLQLSKDTYDDDLDNLLAQIGDQYADLFLAAKNLSDAILLSDILRVNTE |
|  |  | ITKAPLSASMIKRYDEHHQDLTLLKALVRQQLPEKYKEIFFDQSKNGYAGY |
|  |  | IDGGASQEEFYKFIKPILEKMDGTEELLVKLNREDLLRKQRTEDNGSIPHQ |
|  |  | IHLGELHAILRRQEDFYPFLKDNREKIEKILTFRIPYYVGPLARGNSRFAW |
|  |  | MTRKSEETITPWNFEEVVDKGASAQSFIERMTNFDKNLPNEKVLPKHSLLY |
|  |  | EYFTVYNELTKVKYVTEGMRKPAFLSGEQKKAIVDLLFKTNRKVTVKQLKE |
|  |  | DYFKKIECFDSVEISGVEDRFNASLGTYHDLLKIIKDKDELDNEENEDILE |
|  |  | DIVLTLTLFEDREMIEERLKTYAHLEDDKVMKQLKRRRYTGWGRLSRKLIN |
|  |  | GIRDKQSGKTILDFLKSDGFANRNFMQLIHDDSLTFKEDIQKAQVSGQGDS |
|  |  | LHEHIANLAGSPAIKKGILQTVKVVDELVKVMGRHKPENIVIEMARENQTT |
|  |  | QKGQKNSRERMKRIEEGIKELGSQILKEHPVENTQLQNEKLYLYYLQNGRD |
|  |  | MYVDQELDINRLSDYDVDAIVPQSFLKDDSIDNKVLTRSDKNRGKSDNVPS |
|  |  | EEVVKKMKNYWRQLLNAKLITQRKFDNLTKAERGGLSELDKAGFIKRQLVE |
|  |  | TRQITKHVAQILDSRMNTKYDENDKLIREVKVITLKSKLVSDFRKDFQFYK |
|  |  | VREINNYHHAHDAYLNAVVGTALIKKYPKLESEFVYGDYKVYDVRKMIAKS |
|  |  | EQEIGKATAKYFFYSNIMNFFKTEITLANGEIRKRPLIETNGETGEIVWDK |
|  |  | GRDFATVRKVLSMPQVNIVKKTEVQTGGFSKESILPKRNSDKLIARKKDWD |
|  |  | PKKYGGFDSPTVAYSVLVVAKVEKGKSKKLKSVKELLGITIMERSSFEKNP |
|  |  | IDFLEAKGYKEVKKDLIIKLPKYSLFELENGRKRMLASAGELQKGNELALP |

TABLE 7-continued sequences of exemplary epigenetic editors

| SEQ ID NO | Description | Sequence |
|---|---|---|
| | | SKYVNFLYLASHYEKLKGSPEDNEQKQLFVEQHKHYLDEIIEQISEFSKRV<br>ILADANLDKVLSAYNKHRDKPIREQAENIIHLFTLTNLGAPAAFKYFDTTI<br>DRKRYTSTKEVLDATLIHQSITGLYETRIDLSQLGGDSPKKKRKVGVDGSS<br>GSETPGTSESATPESTGDSVAFEDVAVNFTLEEWALLDPSQKNLYRDVMRE<br>TFRNLASVGKQWEDQNIEDPFKIPRRNISHIPERLCESKEGGQGEESADYK<br>DDDDKAPKKKRKVPKKKRKV |
| 482 | PLA001<br>polynucleotide<br>sequence | ATGCCAAAAAAGAAGAGAAAGGTACCGAAGAAAAAAAGAAAGGTATACAAT<br>CACGATCAGGAGTTCGACCCCCCTAAGGTGTACCCACCAGTGCCTGCAGAG<br>AAGAGGAAGCCAATCCGGGTGCTGAGCCTGTTTGATGGCATCGCCACCGGC<br>CTGCTGGTGCTGAAGGATCTGGGCATCCAGGTGGACCGGTACATCGCCTCC<br>GAGGTGTGCGAGGATTCTATCACCGTGGGCATGGTGCGCCACCAGGGCAAG<br>ATCATGTATGTGGGCGACGTGCGGTCCGTGACACAGAAGCACATCCAGGAG<br>TGGGGCCCATTCGATCTGGTGATCGGCGGCAGCCCTGTAATGACCTGTCC<br>ATCGTGAACCCTGCAAGGAAGGGACTGTACGAGGGAACCGGCCGGCTGTTC<br>TTTGAGTTTTATAGACTGCTGCACGACGCCAGGCCTAAGGAGGGCGACGAT<br>AGACCATTCTTTTGGCTGTTCGAGAATGTGGTGGCTATGGGCGTGAGCGAT<br>AAGAGGGACATCTCCAGGTTTCTGGAGTCTAACCCCGTGATGATCGATGCA<br>AAGGAGGTGTCCGCCGCACACAGAGCCAGGTATTTCTGGGGCAATCTGCCA<br>GGAATGAACAGGCCACTGGCAAGCACCGTGAATGACAAGCTGGAGCTGCAG<br>GAGTGCCTGGAGCACGGAAGGATCGCCAAGTTTTCCAAGGTGCGCACAATC<br>ACCACACGGAGCAATTCCATCAAGCAGGGCAAGGATCAGCACTTCCCCGTG<br>TTCATGAACGAGAAGGAGGACATCCTGTGGTGTACCGAGATGGAGAGAGTG<br>TTCGGCTTTCCAGTGCACTACACAGACGTGTCTAACATGAGCAGGCTGGCA<br>AGGCAGCGGCTGCTGGGCAGATCTTGGAGCGTGCCCGTGATCAGGCACCTG<br>TTCGCCCCTCTGAAGGAGTATTTTGCCTGCGTGAGCAGCGGCAACTCCAAT<br>GCCAACAGCCGGGGCCCCTCTTTCAGCTCCGGATTGGTGCCTCTGAGCCTG<br>AGGGGCTCCCACATGGCAGCAATCCCCGCCCTGGACCCCGAGGCCGAGCCT<br>AGCATGGACGTGATCCTGGTGGGCTCTAGCGAGCTGTCCTCTAGCGTGTCT<br>CCAGGAACCGGAAGGGATCTGATCGCATACGAGGTGAAGGCCAATCAGCGG<br>AACATCGAGGACATCTGTATCTGCTGTGGCAGCCTGCAGGTGCACACACAG<br>CACCCACTGTTCGAGGGAGGAATCTGCGCACCCTGTAAGGATAAGTTCCTG<br>GACGCCCTGTTTCTGTACGACGATGACGGCTACCAGTCCTATTGCTCTATC<br>TGCTGTTCCGGCGAGACCCTGCTGATCTGCGGCAATCCAGATTGTACAAGG<br>TGCTATTGTTTTGAGTGCGTGGACTCTCTGGTGGGACCAGGCACCAGCGGA<br>AAGGTGCACGCCATGTCCAACTGGGTGTGCTACCTGTGCCTGCCATCCTCT<br>CGCCAGCGGACTGCTGCAGCGGAGAAGGAAGTGGAGATCCCAGCTGAAGGCC<br>TTCTATGATAGGGAGTCTGAGAACCCCCTGGAGATGTTTGAGACCGTGCCA<br>GTGTGGCGCCGGCAGCCCGTGAGGGTGCTGAGCCTGTTCGAGGATATCAAG<br>AAGGAGCTGACATCCCTGGGCTTTCTGGAGTCCGGCTCTGACCCCGGACAG<br>CTGAAGCACGTGGTGGATGTGACCGACACAGTGCCGGAAGGATGTGGAGGAG<br>TGGGGCCCTTTCGACCTGGTGTACGGAGCAACCCCTCCACTGGGACACACA<br>TGCGACAGACCCCCTTCTTGGTACCTGTTCCAGTTTCACCGCCTGCTGCAG<br>TATGCAAGGCCAAAGCCAGGCAGCCCTAGACCATTCTTTTGGATGTTCGTG<br>GATAATCTGGTGCTGAACAAGGAGGATCTGGACGTGGCCAGCAGGTTTCTG<br>GAGATGGAGCCAGTGACCATCCCAGACGTGCACGGCGGCTCCCTGCAGAAT<br>GCCGTGCGCGTGTGGTCTAACATCCCTGCCATCAGAAGCAGGCACTGGGCA<br>CTGGTGAGCGAGGAGGAGCTGTCCCTGCTGGCCCAGAATAAGCAGAGCAGC<br>AAGCTGGCCGCCAAGTGGCCTACAAAGCTGGTGAAGAACTGCTTCCTGCCA<br>CTGCGGGAGTACTTCAAGTATTTTTCCACCGAGCTGACATCTAGCCTGGGA<br>GGACCCTCCTCTGGCGCCCCACCACCTAGCGGCGGCTCCCCTGCCGGCTCT<br>CCAACCAGCACAGAGGAGGGCACCAGCGAGTCCGCCACACCAGAGTCTGGA<br>CCTGGCACCAGCACAGAGCCATCCGAGGGCTCTGCCCCAGGCTCTCCTGCA<br>GGCAGCCCTACCTCCACCGAAGAGGGCACCAGCACAGAGCCTTCTGAGGGC<br>AGCGCCCCAGGCACCTCTACAGAGCCAAGCGAGCTCGAGGACAAGAAGTAC<br>AGCATCGGCCTGGCCATCGGCACCAACTCTGTGGGCTGGGCCGTGATCACC<br>GACGAGTACAAGGTGCCCAGCAAGAAATTCAAGGTGCTGGGCAACACCGAC<br>CGGCACAGCATCAAGAAGAACCTGATCGGAGCCCTGCTGTTCGACAGCGGC<br>GAAACAGCCGAGGCCACCCGGCTGAAGAGAACCGCCAGAAGAAGATACACC<br>AGACGGAAGAACCGGATCTGCTATCTGCAAGAGATCTTCAGCAACGAGATG<br>GCCAAGGTGGACGACAGCTTCTTCCACAGACTGGAAGAGTCCTTCCTGGTG<br>GAAGAGGATAAGAAGCACGAGCGGCACCCCATCTTCGGCAACATCGTGGAC<br>GAGGTGGCCTACCACGAGAAGTACCCCACCATCTACCACCTGAGAAAGAAA<br>CTGGTGGACAGCACCGACAAGGCCGACCTGCGGCTGATCTATCTGGCCCTG<br>GCCCACATGATCAAGTTCCGGGGCCACTTCCTGATCGAGGGCGACCTGAAC<br>CCCGACAACAGCGACGTGGACAAGCTGTTCATCCAGCTGGTGCAGACCTAC<br>AACCAGCTGTTCGAGGAAAACCCCATCAACGCCAGCGGCGTGGACGCCAAG<br>GCCATCCTGTCTGCCAGACTGAGCAAGAGCAGACGGCTGGAAAATCTGATC<br>GCCCAGCTGCCCGGCGAGAAGAAGAATGGCCTGTTCGGCAACCTGATTGCC<br>CTGAGCCTGGGCCTGACCCCCAACTTCAAGAGCAACTTCGACCTGGCCGAG<br>GATGCCAAACTGCAGCTGAGCAAGGACACCTACGACGACGACCTGGACAAC<br>CTGCTGGCCCAGATCGGCGACCAGTACGCCGACCTGTTTCTGGCCGCCAAG<br>AACCTGTCCGACGCCATCCTGCTGAGCGACATCCTGAGAGTGAACACCGAG<br>ATCACCAAGGCCCCCCTGAGCGCCTCTATGATCAAGAGATACGACGAGCAC<br>CACCAGGACCTGACCCTGCTGAAAGCTCTCGTGCGGCAGCAGCTGCCTGAG |

TABLE 7-continued

| sequences of exemplary epigenetic editors | | |
|---|---|---|

| SEQ ID NO | Description | Sequence |
|---|---|---|
| | | AAGTACAAAGAGATTTTCTTCGACCAGAGCAAGAACGGCTACGCCGGCTAC |
| | | ATTGACGGCGGAGCCAGCCAGGAAGAGTTCTACAAGTTCATCAAGCCCATC |
| | | CTGGAAAAGATGGACGGCACCGAGGAACTGCTCGTGAAGCTGAACAGAGAG |
| | | GACCTGCTGCGGAAGCAGCGGACCTTCGACAACGGCAGCATCCCCCACCAG |
| | | ATCCACCTGGGAGAGCTGCACGCCATTCTGCGGCGGCAGGAAGATTTTTAC |
| | | CCATTCCTGAAGGACAACCGGGAAAAGATCGAGAAGATCCTGACCTTCCGC |
| | | ATCCCCTACTACGTGGGCCCTCTGGCCAGGGGAAACAGCAGATTCGCCTGG |
| | | ATGACCAGAAAGAGCGAGGAAACCATCACCCCCTGGAACTTCGAGGAAGTG |
| | | GTGGACAAGGGCGCTTCCGCCCAGAGCTTCATCGAGCGGATGACCAACTTC |
| | | GATAAGAACCTGCCCAACGAGAAGGTGCTGCCCAAGCACAGCCTGCTGTAC |
| | | GAGTACTTCACCGTGTATAACGAGCTGACCAAAGTGAAATACGTGACCGAG |
| | | GGAATGAGAAAGCCCGCCTTCCTGAGCGGCGAGCAGAAAAAGGCCATCGTG |
| | | GACCTGCTGTTCAAGACCAACCGGAAAGTGACCGTGAAGCAGCTGAAAGAG |
| | | GACTACTTCAAGAAAATCGAGTGCTTCGACTCCGTGGAAATCTCCGGCGTG |
| | | GAAGATCGGTTCAACGCCTCCCTGGGCACATACCACGATCTGCTGAAAATT |
| | | ATCAAGGACAAGGACTTCCTGGACAATGAGGAAAACGAGGACATTCTGGAA |
| | | GATATCGTGCTGACCCTGACACTGTTTGAGGACAGAGAGATGATCGAGGAA |
| | | CGGCTGAAAACCTATGCCCACCTGTTCGACGACAAAGTGATGAAGCAGCTG |
| | | AAGCGGCGGAGATACACCGGCTGGGGCAGGCTGAGCCGGAAGCTGATCAAC |
| | | GGCATCCGGGACAAGCAGTCCGGCAAGACAATCCTGGATTTCCTGAAGTCC |
| | | GACGGCTTCGCCAACAGAAACTTCATGCAGCTGATCCACGACGACAGCCTG |
| | | ACCTTTAAAGAGGACATCCAGAAAGCCCAGGTGTCCGGCCAGGGCGATAGC |
| | | CTGCACGAGCACATTGCCAATCTGGCCGGCAGCCCCGCCATTAAGAAGGGC |
| | | ATCCTGCAGACAGTGAAGGTGGTGGACGAGCTCGTGAAAGTGATGGGCCGG |
| | | CACAAGCCCGAGAACATCGTGATCGAAATGGCCAGAGAGAACCAGACCACC |
| | | CAGAAGGGACAGAAGAACAGCCGCGAGAGAATGAAGCGGATCGAAGAGGGC |
| | | ATCAAAGAGCTGGGCAGCCAGATCCTGAAAGAACACCCCGTGGAAAACACC |
| | | CAGCTGCAGAACGAGAAGCTGTACCTGTACTACCTGCAGAATGGGcGGGAT |
| | | ATGTACGTGGACCAGGAACTGGACATCAACCGGCTGTCCGACTACGATGTG |
| | | GACGCCATCGTGCCTCAGAGCTTTCTGAAGGACGACTCCATCGACAACAAG |
| | | GTGCTGACCAGAAGCGACAAGAACCGGGGCAAGAGCGACAACGTGCCCTCC |
| | | GAAGAGGTCGTGAAGAAGATGAAGAACTACTGGCGGCAGCTGCTGAACGCC |
| | | AAGCTGATTACCCAGAGAAAGTTCGACAATCTGACCAAGGCCGAGAGAGGC |
| | | GGCCTGAGCGAACTGGATAAGGCCGGCTTCATCAAGAGACAGCTGGTGGAA |
| | | ACCCGGCAGATCACAAAGCACGTGGCACAGATCCTGGACTCCCGGATGAAC |
| | | ACTAAGTACGACGAGAATGACAAGCTGATCCGGGAAGTGAAAGTGATCACC |
| | | CTGAAGTCCAAGCTGGTGTCCGATTTCCGGAAGGATTTCCAGTTTTACAAA |
| | | GTGCGCGAGATCAACAACTACCACCACGCCCACGACGCCTACCTGAACGCC |
| | | GTCGTGGGAACCGCCCTGATCAAAAAGTACCCTAAGCTGGAAAGCGAGTTC |
| | | GTGTACGGCGACTACAAGGTGTACGACGTGCGGAAGATGATCGCCAAGAGC |
| | | GAGCAGGAAATCGGCAAGGCTACCGCCAAGTACTTCTTCTACAGCAACATC |
| | | ATGAACTTTTTCAAGACCGAGATTACCCTGGCCAACGGCGAGATCCGGAAG |
| | | CGGCCTCTGATCGAGACAAACGGCGAAACCGGGGAGATCGTGTGGGATAAG |
| | | GGCCGGGATTTTGCCACCGTGCGGAAAGTGCTGAGCATGCCCCAAGTGAAT |
| | | ATCGTGAAAAAGACCGAGGTGCAGACAGGCGGCTTCAGCAAAGAGTCTATC |
| | | CTGCCCAAGAGGAACAGCGATAAGCTGATCGCCAGAAAGAAGGACTGGGAC |
| | | CCTAAGAAGTACGGCGGCTTCGACAGCCCCACCGTGGCCTATTCTGTGCTG |
| | | GTGGTGGCCAAAGTGGAAAAGGGCAAGTCCAAGAAACTGAAGAGTGTGAAA |
| | | GAGCTGCTGGGGATCACCATCATGGAAAGAAGCAGCTTCGAGAAGAATCCC |
| | | ATCGACTTTCTGGAAGCCAAGGGCTACAAAGAAGTGAAAAAGGACCTGATC |
| | | ATCAAGCTGCCTAAGTACTCCCTGTTCGAGCTGGAAAACGGCCGGAAGAGA |
| | | ATGCTGGCCTCTGCCGGCGAACTGCAGAAGGGAAACGAACTGGCCCTGCCC |
| | | TCCAAATATGTGAACTTCCTGTACCTGGCCAGCCACTATGAGAAGCTGAAG |
| | | GGCTCCCCCGAGGATAATGAGCAGAAACAGCTGTTTGTGGAACAGCACAAG |
| | | CACTACCTGGACGAGATCATCGAGCAGATCAGCGAGTTCTCCAAGAGAGTG |
| | | ATCCTGGCCGACGCTAATCTGGACAAAGTGCTGTCCGCCTACAACAAGCAC |
| | | CGGGATAAGCCCATCAGAGAGCAGGCCGAGAATATCATCCACCTGTTTACC |
| | | CTGACCAATCTGGGAGCCCCTGCCGCCTTCAAGTACTTTGACACCACCATC |
| | | GACCGGAAGAGGTACACCAGCACCAAAGAGGTGCTGGACGCCACCCTGATC |
| | | CACCAGAGCATCACCGGCCTGTACGAGACACGGATCGACCTGTCTCAGCTG |
| | | GGAGGCGACAGCCCCAAGAAGAAGAGAAAGGTGGGAGTCGACGGATCCAGC |
| | | GGCTCCGAGACCCCAGGCACATCTGAGAGCGCCACCCCTGAGTCCACCGGT |
| | | GACTCCGTTGCTTTCGAGGACGTGGCCGTGAACTTCACACTTGAGGAATGG |
| | | GCCTTGCTCGACCCAAGTCAGAAGAATCTGTACAGAGACGTGATGCGGGAG |
| | | ACATTCAGGAATCTCGCCAGTGTCGGAAAGCAGTGGGAAGACCAGAACATC |
| | | GAAGATCCTTTCAAGATACCACGGCGCAATATCTCCCACATTCCTGAGAGG |
| | | CTGTGTGAATCTAAGGAAGGCGGACAAGGTGAGGAAAGCGCTGATTACAAA |
| | | GATGATGACGATAAAGCCCCCAAGAAGAAAAGGAAGGTCCCAAAGAAAAAA |
| | | AGAAAGGTGTGA |
| 483 | PLA002 Amino acid sequence | MPKKKRKVPKKKRKVYNHDQEFDPPKVYPPVPAEKRKPIRVLSLFDGIATG LLVLKDLGIQVDRYIASEVCEDSITVGMVRHQGKIMYVGDVRSVTQKHIQE WGPFDLVIGGSPCNDLSIVNPARKGLYEGTGRLFFEFYRLLHDARPKEGDD RPFFWLFENVVAMGVSDKRDISRFLESNPVMIDAKEVSAAHRARYFWGNLP GMNRPLASTVNDKLELQECLEHGRIAKFSKVRTITTRSNSIKQGKDQHFPV |

TABLE 7-continued sequences of exemplary epigenetic editors

| SEQ ID NO | Description | Sequence |
|---|---|---|

|  |  | FMNEKEDILWCTEMERVFGFPVHYTDVSNMSRLARQRLLGRSWSVPVIRHL |
|  |  | FAPLKEYFACVSSGNSNANSRGPSFSSGLVPLSLRGSHMAAIPALDPEAEP |
|  |  | SMDVILVGSSELSSSVSPGTGRDLIAYEVKANQRNIEDICICCGSLQVHTQ |
|  |  | HPLFEGGICAPCKDKFLDALFLYDDDGYQSYCSICCSGETLLICGNPDCTR |
|  |  | CYCFECVDSLVGPGTSGKVHAMSNWVCYLCLPSSRSGLLQRRRKWRSQLKA |
|  |  | FYDRESENPLEMFETVPVWRRQPVRVLSLFEDIKKELTSLGFLESGSDPGQ |
|  |  | LKHVVDVTDTVRKDVEEWGPFDLVYGATPPLGHTCDRPPSWYLFQFHRLLQ |
|  |  | YARPKPGSPRPFFWMFVDNLVLNKEDLDVASRFLEMEPVTIPDVHGGSLQN |
|  |  | AVRVWSNIPAIRSRHWALVSEEELSLLAQNKQSSKLAAKWPTKLVKNCFLP |
|  |  | LREYFKYFSTELTSSLGGPSSGAPPPSGGSPAGSPTSTEEGTSESATPESG |
|  |  | PGTSTEPSEGSAPGSPAGSPTSTEEGTSTEPSEGSAPGTSTEPSELEDKKY |
|  |  | SIGLAIGTNSVGWAVITDEYKVPSKKFKVLGNTDRHSIKKNLIGALLEDSG |
|  |  | ETAEATRLKRTARRRYTRRKNRICYLQEIFSNEMAKVDDSFFHRLEESFLV |
|  |  | EEDKKHERHPIFGNIVDEVAYHEKYPTIYHLRKKLVDSTDKADLRLIYLAL |
|  |  | AHMIKFRGHFLIEGDLNPDNSDVDKLFIQLVQTYNQLFEENPINASGVDAK |
|  |  | AILSARLSKSRRLENLIAQLPGEKKNGLFGNLIALSLGLTPNEKSNFDLAE |
|  |  | DAKLQLSKDTYDDDLDNLLAQIGDQYADLFLAAKNLSDAILLSDILRVNTE |
|  |  | ITKAPLSASMIKRYDEHHQDLTLLKALVRQQLPEKYKEIFFDQSKNGYAGY |
|  |  | IDGGASQEEFYKFIKPILEKMDGTEELLVKLNREDLLRKQRTFDNGSIPHQ |
|  |  | IHLGELHAILRRQEDFYPFLKDNREKIEKILTFRIPYYVGPLARGNSRFAW |
|  |  | MTRKSEETITPWNFEEVVDKGASAQSFIERMTNFDKNLPNEKVLPKHSLLY |
|  |  | EYFTVYNELTKVKYVTEGMRKPAFLSGEQKKAIVDLLEKTNRKVTVKQLKE |
|  |  | DYFKKIECFDSVEISGVEDRFNASLGTYHDLLKIIKDKDFLDNEENEDILE |
|  |  | DIVLTLTLFEDREMIEERLKTYAHLFDDKVMKQLKRRRYTGWGRLSRKLIN |
|  |  | GIRDKQSGKTILDFLKSDGFANRNFMQLIHDDSLTFKEDIQKAQVSGQGDS |
|  |  | LHEHIANLAGSPAIKKGILQTVKVVDELVKVMGRHKPENIVIEMARENQTT |
|  |  | QKGQKNSRERMKRIEEGIKELGSQILKEHPVENTQLQNEKLYLYYLQNGRD |
|  |  | MYVDQELDINRLSDYDVDAIVPQSFLKDDSIDNKVLTRSDKNRGKSDNVPS |
|  |  | EEVVKKMKNYWRQLLNAKLITQRKFDNLTKAERGGLSELDKAGFIKRQLVE |
|  |  | TRQITKHVAQILDSRMNTKYDENDKLIREVKVITLKSKLVSDFRKDFQFYK |
|  |  | VREINNYHHAHDAYLNAVVGTALIKKYPKLESEFVYGDYKVYDVRKMIAKS |
|  |  | EQEIGKATAKYFFYSNIMNFFKTEITLANGEIRKRPLIETNGETGEIVWDK |
|  |  | GRDFATVRKVLSMPQVNIVKKTEVQTGGFSKESILPKRNSDKLIARKKDWD |
|  |  | PKKYGGFDSPTVAYSVLVVAKVEKGKSKKLKSVKELLGITIMERSSFEKNP |
|  |  | IDFLEAKGYKEVKKDLIIKLPKYSLFELENGRKRMLASAGELQKGNELALP |
|  |  | SKYVNFLYLASHYEKLKGSPEDNEQKQLFVEQHKHYLDEIIEQISEFSKRV |
|  |  | ILADANLDKVLSAYNKHRDKPIREQAENIIHLFTLTNLGAPAAFKYEDTTI |
|  |  | DRKRYTSTKEVLDATLIHQSITGLYETRIDLSQLGGDSPKKKRKVGVDGSS |
|  |  | GSETPGTSESATPESTGMNNSQGRVTFEDVTVNFTQGEWQRLNPEQRNLYR |
|  |  | DVMLENYSNLVSVGQGETTKPDVILRLEQGKEPWLEEEEVLGSGRAEKNGD |
|  |  | IGGQIWKPKDVKESLSADYKDDDDKAPKKKRKVPKKKRKV |

| 484 | PLA002 polynucleotide sequence | ATGCCAAAAAAGAAGAGAAAGGTACCGAAGAAAAAAAGAAAGGTATACAAT |
|  |  | CACGATCAGGAGTTCGACCCCCCTAAGGTGTACCCACCAGTGCCTGCAGAG |
|  |  | AAGAGGAAGCCAATCCGGGTGCTGAGCCTGTTTGATGGCATCGCCACCGGC |
|  |  | CTGCTGGTGCTGAAGGATCTGGGCATCCAGGTGGACCGGTACATCGCCTCC |
|  |  | GAGGTGTGCGAGGATTCTATCACCGTGGGCATGGTGCGCCACCAGGGCAAG |
|  |  | ATCATGTATGTGGGCGACGTGCGGTCCGTGACACAGAAGCACATCCAGGAG |
|  |  | TGGGGCCCATTCGATCTGGTGATCGGCGGCAGCCCCTGTAATGACCTGTCC |
|  |  | ATCGTGAACCCTGCAAGGAAGGGACTGTACGAGGGAACCGGCCGGCTGTTC |
|  |  | TTTGAGTTTTATAGACTGCTGCACGACGCCAGGCCTAAGGAGGGCGACGAT |
|  |  | AGACCATTCTTTTGGCTGTTCGAGAATGTGGTGGCTATGGGCGTGAGCGAT |
|  |  | AAGAGGGACATCTCCAGGTTTCTGGAGTCTAACCCCGTGATGATCGATGCA |
|  |  | AAGGAGGTGTCCGCCGCACACAGAGCCAGGTATTTCTGGGGCAATCTGCCA |
|  |  | GGAATGAACAGGCCACTGGCAAGCACCGTGAATGACAAGCTGGAGCTGCAG |
|  |  | GAGTGCCTGGAGCACGGAAGGATCGCCAAGTTTTCCAAGGTGCGCACAATC |
|  |  | ACCACACGGAGCAATTCCATCAAGCAGGGCAAGGATCAGCACTTCCCCGTG |
|  |  | TTCATGAACGAGAAGGAGGACATCCTGTGGTGTACCGAGATGGAGAGAGTG |
|  |  | TTCGGCTTTCCAGTGCACTACACAGACGTGTCTAACATGAGCAGGCTGGCA |
|  |  | AGGCAGCGGCTGCTGGGCAGATCTTGGAGCGTGCCCGTGATCAGGCACCTG |
|  |  | TTCGCCCCTCTGAAGGAGTATTTTGCCTGCGTGAGCAGCGGCAACTCCAAT |
|  |  | GCCAACAGCCGGGGCCCCTCTTTCAGCTCCGGATTGGTGCCTCTGAGCCTG |
|  |  | AGGGGCTCCCACATGGCAGCAATCCCCGCCCTGGACCCCGAGGCCGAGCCT |
|  |  | AGCATGGACGTGATCCTGGTGGGCTCTAGCGAGCTGTCCTCTAGCGTGTCT |
|  |  | CCAGGAACCGGAAGGGATCTGATCGCATACGAGGTGAAGGCCAATCAGCGG |
|  |  | AACATCGAGGACATCTGTATCTGCTGTGGCAGCCTGCAGGTGCACACACAG |
|  |  | CACCCACTGTTCGAGGGAGGAATCTGCGCACCCTGTAAGGATAAGTTCCTG |
|  |  | GACGCCCTGTTTCTGTACGACGATGACGGCTACCAGTCCTATTGCTCTATC |
|  |  | TGCTGTTCCGGCGAGACCCTGCTGATCTGCGGCAATCCAGATTGTACAAGG |
|  |  | TGCTATTGTTTTGAGTGCGTGGACTCTCTGGTGGGACCAGGCACCAGCGGA |
|  |  | AAGGTGCACGCCATGTCCAACTGGGTGTGCTACCTGTGCCTGCCATCCTCT |
|  |  | CGCAGCGGACTGCTGCAGCGGAGAAGGAAGTGGAGATCCCAGCTGAAGGCC |
|  |  | TTCTATGATAGGGAGTCTGAGAACCCCCTGGAGATGTTTGAGACCGTGCCA |
|  |  | GTGTGGCGCCGGCAGCCCGTGAGGGTGCTGAGCCTGTTCGAGGATATCAAG |
|  |  | AAGGAGCTGACATCCCTGGGCTTTCTGGAGTCCGGCTCTGACCCCGGACAG |

TABLE 7-continued sequences of exemplary epigenetic editors

| SEQ ID NO | Description | Sequence |
|---|---|---|

CTGAAGCACGTGGTGGATGTGACCGACACAGTGCGGAAGGATGTGGAGGAG
TGGGGCCCTTTCGACCTGGTGTACGGAGCAACCCCTCCACTGGGACACACA
TGCGACAGACCCCCTTCTTGGTACCTGTTCCAGTTTCACCGCCTGCTGCAG
TATGCAAGGCCAAAGCCAGGCAGCCCTAGACCATTCTTTTGGATGTTCGTG
GATAATCTGGTGCTGAACAAGGAGGATCTGGACGTGGCCAGCAGGTTTCTG
GAGATGGAGCCAGTGACCATCCCAGACGTGCACGGCGGCTCCCTGCAGAAT
GCCGTGCGCGTGTGGTCTAACATCCCTGCCATCAGAAGCAGGCACTGGGCA
CTGGTGAGCGAGGAGGAGCTGTCCCTGCTGGCCCAGAATAAGCAGAGCAGC
AAGCTGGCCGCCAAGTGGCCTACAAAGCTGGTGAAGAACTGCTTCCTGCCA
CTGCGGGAGTACTTCAAGTATTTTTCCACCGAGCTGACATCTAGCCTGGGA
GGACCCTCCTCTGGCGCCCCACCACCTAGCGGCGGCTCCCCTGCCGGCTCT
CCAACCAGCACAGAGGAGGGCACCAGCGAGTCCGCCACACCAGAGTCTGGA
CCTGGCACCAGCACAGAGCCATCCGAGGGCTCTGCCCCAGGCTCTCCTGCA
GGCAGCCCTACCTCCACCGAAGAGGGCACCAGCACAGAGCCTTCTGAGGGC
AGCGCCCCAGGCACCTCTACAGAGCCAAGCGAGCTCGAGGACAAGAAGTAC
AGCATCGGCCTGGCCATCGGCACCAACTCTGTGGGCTGGGCCGTGATCACC
GACGAGTACAAGGTGCCCAGCAAGAAATTCAAGGTGCTGGGCAACACCGAC
CGGCACAGCATCAAGAAGAACCTGATCGGAGCCCTGCTGTTCGACAGCGGC
GAAACAGCCGAGGCCACCCGGCTGAAGAGAACCGCCAGAAGAAGATACACC
AGACGGAAGAACCGGATCTGCTATCTGCAAGAGATCTTCAGCAACGAGATG
GCCAAGGTGGACGACAGCTTCTTCCACAGACTGGAAGAGTCCTTCCTGGTG
GAAGAGGATAAGAAGCACGAGCGGCACCCCATCTTCGGCAACATCGTGGAC
GAGGTGGCCTACCACGAGAAGTACCCCACCATCTACCACCTGAGAAAGAAA
CTGGTGGACAGCACCGACAAGGCCGACCTGCGGCTGATCTATCTGGCCCTG
GCCCACATGATCAAGTTCCGGGGCCACTTCCTGATCGAGGGCGACCTGAAC
CCCGACAACAGCGACGTGGACAAGCTGTTCATCCAGCTGGTGCAGACCTAC
AACCAGCTGTTCGAGGAAAACCCCATCAACGCCAGCGGCGTGGACGCCAAG
GCCATCCTGTCTGCCAGACTGAGCAAGAGCAGACGGCTGGAAAATCTGATC
GCCCAGCTGCCCGGCGAGAAGAAGAATGGCCTGTTCGGCAACCTGATTGCC
CTGAGCCTGGGCCTGACCCCCAACTTCAAGAGCAACTTCGACCTGGCCGAG
GATGCCAAACTGCAGCTGAGCAAGGACACCTACGACGACGACCTGGACAAC
CTGCTGGCCCAGATCGGCGACCAGTACGCCGACCTGTTTCTGGCCGCCAAG
AACCTGTCCGACGCCATCCTGCTGAGCGACATCCTGAGAGTGAACACCGAG
ATCACCAAGGCCCCCCTGAGCGCCTCTATGATCAAGAGATACGACGAGCAC
CACCAGGACCTGACCCTGCTGAAAGCTCTCGTGCGGCAGCAGCTGCCTGAG
AAGTACAAAGAGATTTTCTTCGACCAGAGCAAGAACGGCTACGCCGGCTAC
ATTGACGGCGGAGCCAGCCAGGAAGAGTTCTACAAGTTCATCAAGCCCATC
CTGGAAAAGATGGACGGCACCGAGGAACTGCTCGTGAAGCTGAACAGAGAG
GACCTGCTGCGGAAGCAGCGGACCTTCGACAACGGCAGCATCCCCCACCAG
ATCCACCTGGGAGAGCTGCACGCCATTCTGCGCGCGGCAGGAAGATTTTTAC
CCATTCCTGAAGGACAACCGGGAAAAGATCGAGAAGATCCTGACCTTCCGC
ATCCCCTACTACGTGGGCCCTCTGGCCAGGGGAAACAGCAGATTCGCCTGG
ATGACCAGAAAGAGCGAGGAAACCATCACCCCCTGGAACTTCGAGGAAGTG
GTGGACAAGGGCGCTTCCGCCCAGAGCTTCATCGAGCGGATGACCAACTTC
GATAAGAACCTGCCCAACGAGAAGGTGCTGCCCAAGCACAGCCTGCTGTAC
GAGTACTTCACCGTGTATAACGAGCTGACCAAAGTGAAATACGTGACCGAG
GGAATGAGAAAGCCCGCCTTCCTGAGCGGCGAGCAGAAAAAGGCCATCGTG
GACCTGCTGTTCAAGACCAACCGGAAAGTGACCGTGAAGCAGCTGAAAGAG
GACTACTTCAAGAAAATCGAGTGCTTCGACTCCGTGGAAATCTCCGGCGTG
GAAGATCGGTTCAACGCCTCCCTGGGCACATACCACGATCTGCTGAAAATT
ATCAAGGACAAGGACTTCCTGGACAATGAGGAAAACGAGGACATTCTGGAA
GATATCGTGCTGACCCTGACACTGTTTGAGGACAGAGAGATGATCGAGGAA
CGGCTGAAAACCTATGCCCACCTGTTCGACGACAAAGTGATGAAGCAGCTG
AAGCGGCGGAGATACACCGGCTGGGGCAGGCTGAGCCGGAAGCTGATCAAC
GGCATCCGGGACAAGCAGTCCGGCAAGACAATCCTGGATTTCCTGAAGTCC
GACGGCTTCGCCAACAGAAACTTCATGCAGCTGATCCACGACGACAGCCTG
ACCTTTAAAGAGGACATCCAGAAAGCCCAGGTGTCCGGCCAGGGCGATAGC
CTGCACGAGCACATTGCCAATCTGGCCGGCAGCCCCGCCATTAAGAAGGGC
ATCCTGCAGACAGTGAAGGTGGTGGACGAGCTCGTGAAAGTGATGGGCCGG
CACAAGCCCGAGAACATCGTGATCGAAATGGCCAGAGAGAACCAGACCACC
CAGAAGGGACAGAAGAACAGCCGCGAGAGAATGAAGCGGATCGAAGAGGGC
ATCAAAGAGCTGGGCAGCCAGATCCTGAAAGAACACCCCGTGGAAAACACC
CAGCTGCAGAACGAGAAGCTGTACCTGTACTACCTGCAGAATGGGCGGGAT
ATGTACGTGGACCAGGAACTGGACATCAACCGGCTGTCCGACTACGATGTG
GACGCCATCGTGCCTCAGAGCTTTCTGAAGGACGACTCCATCGACAACAAG
GTGCTGACCAGAAGCGACAAGAACCGGGGCAAGAGCGACAACGTGCCCTCC
GAAGAGGTCGTGAAGAAGATGAAGAACTACTGGCGGCAGCTGCTGAACGCC
AAGCTGATTACCCAGAGAAAGTTCGACAATCTGACCAAGGCCGAGAGAGGC
GGCCTGAGCGAACTGGATAAGGCCGGCTTCATCAAGAGACAGCTGGTGGAA
ACCCGGCAGATCACAAAGCACGTGGCACAGATCCTGGACTCCCGGATGAAC
ACTAAGTACGACGAGAATGACAAGCTGATCCGGGAAGTGAAAGTGATCACC
CTGAAGTCCAAGCTGGTGTCCGATTTCCGGAAGGATTTCCAGTTTTACAAA
GTGCGCGAGATCAACAACTACCACCACGCCCACGACGCCTACCTGAACGCC
GTCGTGGGAACCGCCCTGATCAAAAAGTACCCTAAGCTGGAAAGCGAGTTC
GTGTACGGCGACTACAAGGTGTACGACGTGCGGAAGATGATCGCCAAGAGC

TABLE 7-continued sequences of exemplary epigenetic editors

| SEQ ID NO | Description | Sequence |
|---|---|---|
| | | GAGCAGGAAATCGGCAAGGCTACCGCCAAGTACTTCTTCTACAGCAACATC |
| | | ATGAACTTTTTCAAGACCGAGATTACCCTGGCCAACGGCGAGATCCGGAAG |
| | | CGGCCTCTGATCGAGACAAACGGCGAAACCGGGGAGATCGTGTGGGATAAG |
| | | GGCCGGGATTTTGCCACCGTGCGGAAAGTGCTGAGCATGCCCCAAGTGAAT |
| | | ATCGTGAAAAAGACCGAGGTGCAGACAGGCGGCTTCAGCAAAGAGTCTATC |
| | | CTGCCCAAGAGGAACAGCGATAAGCTGATCGCCAGAAAGAAGGACTGGGAC |
| | | CCTAAGAAGTACGGCGGCTTCGACAGCCCCACCGTGGCCTATTCTGTGCTG |
| | | GTGGTGGCCAAAGTGGAAAAGGGCAAGTCCAAGAAACTGAAGAGTGTGAAA |
| | | GAGCTGCTGGGGATCACCATCATGGAAAGAAGCAGCTTCGAGAAGAATCCC |
| | | ATCGACTTTCTGGAAGCCAAGGGCTACAAAGAAGTGAAAAAGGACCTGATC |
| | | ATCAAGCTGCCTAAGTACTCCCTGTTCGAGCTGGAAAACGGCCGGAAGAGA |
| | | ATGCTGGCCTCTGCCGGCGAACTGCAGAAGGGAAACGAACTGGCCCTGCCC |
| | | TCCAAATATGTGAACTTCCTGTACCTGGCCAGCCACTATGAGAAGCTGAAG |
| | | GGCTCCCCCGAGGATAATGAGCAGAAACAGCTGTTTGTGGAACAGCACAAG |
| | | CACTACCTGGACGAGATCATCGAGCAGATCAGCGAGTTCTCCAAGAGAGTG |
| | | ATCCTGGCCGACGCTAATCTGGACAAAGTGCTGTCCGCCTACAACAAGCAC |
| | | CGGGATAAGCCCATCAGAGAGCAGGCCGAGAATATCATCCACCTGTTTACC |
| | | CTGACCAATCTGGGAGCCCCTGCCGCCTTCAAGTACTTTGACACCACCATC |
| | | GACCGGAAGAGGTACACCAGCACCAAAGAGGTGCTGGACGCCACCCTGATC |
| | | CACCAGAGCATCACCGGCCTGTACGAGACACGGATCGACCTGTCTCAGCTG |
| | | GGAGGCGACAGCCCCAAGAAGAAGAGAAAGGTGGGAGTCGACGGATCCAGC |
| | | GGCTCCGAGACCCCAGGCACATCTGAGAGCGCCACCCCTGAGTCCACCGGT |
| | | ATGAACAATTCACAGGGGGAGAGTGACATTCGAAGACGTGACCGTGAACTTC |
| | | ACCCAGGGAGAATGGCAGCGCTTGAACCCAGAACAAAGGAACCTCTATCGG |
| | | GACGTGATGCTGGAAAACTACTCAAATTTGGTGAGCGTTGGGCAGGGTGAG |
| | | ACCACTAAGCCTGACGTGATCCTGAGATTGGAACAGGGCAAGGAGCCTTGG |
| | | CTCGAGGAAGAGGAAGTCCTGGGCTCAGGGAGGGCCGAGAAAAACGGTGAT |
| | | ATAGGAGGCCAGATATGGAAGCCTAAGGACGTCAAGGAGAGCCTGAGCGCT |
| | | GATTACAAAGATGATGACAAGCCCCCAAGAAGAAAAGGAAGGTCCCA |
| | | AAGAAAAAAAGAAAGGTGTGA |
| 492 | PLA003 amino acid sequence | MPKKKRKVPKKKRKVYNHDQEFDPPKVYPPVPAEKRKPIRVLSLEDGIATG |
| | | LLVLKDLGIQVDRYIASEVCEDSITVGMVRHQGKIMYVGDVRSVTQKHIQE |
| | | WGPFDLVIGGSPCNDLSIVNPARKGLYEGTGRLFFEFYRLLHDARPKEGDD |
| | | RPFFWLFENVVAMGVSDKRDISRFLESNPVMIDAKEVSAAHRARYFWGNLP |
| | | GMNRPLASTVNDKLELQECLEHGRIAKFSKVRTITTRSNSIKQGKDQHFPV |
| | | FMNEKEDILWCTEMERVFGFPVHYTDVSNMSRLARQRLLGRSWSVPVIRHL |
| | | FAPLKEYFACVSSGNSNANSRGPSFSSGLVPLSLRGSHMAAIPALDPEAEP |
| | | SMDVILVGSSELSSSVSPGTGRDLIAYEVKANQRNIEDICICCGSLQVHTQ |
| | | HPLFEGGICAPCKDKFLDALFLYDDDGYQSYCSICCSGETLLICGNPDCTR |
| | | CYCFECVDSLVGPGTSGKVHAMSNWVCYLCLPSSRSGLLQRRRKWRSQLKA |
| | | FYDRESENPLEMFETVPVWRRQPVRVLSLFEDIKKELTSLGFLESGSDPGQ |
| | | LKHVVDVTDTVRKDVEEWGPFDLVYGATPPLGHTCDRPPSWYLFQFHRLLQ |
| | | YARPKPGSPRPFFWMFVDNLVLNKEDLDVASRFLEMEPVTIPDVHGGSLQN |
| | | AVRVWSNIPAIRSRHWALVSEEELSLLAQNKQSSKLAAKWPTKLVKNCFLP |
| | | LREYFKYFSTELTSSLGGPSSGAPPPSGGSPAGSPTSTEEGTSESATPESG |
| | | PGTSTEPSEGSAPGSPAGSPTSTEEGTSTEPSEGSAPGTSTEPSELEDKKY |
| | | SIGLAIGTNSVGWAVITDEYKVPSKKFKVLGNTDRHSIKKNLIGALLFDSG |
| | | ETAEATRLKRTARRRYTRRKNRICYLQEIFSNEMAKVDDSFFHRLEESFLV |
| | | EEDKKHERHPIFGNIVDEVAYHEKYPTIYHLRKKLVDSTDKADLRLIYLAL |
| | | AHMIKFRGHFLIEGDLNPDNSDVDKLFIQLVQTYNQLFEENPINASGVDAK |
| | | AILSARLSKSRRLENLIAQLPGEKKNGLFGNLIALSLGLTPNFKSNFDLAE |
| | | DAKLQLSKDTYDDDLDNLLAQIGDQYADLFLAAKNLSDAILLSDILRVNTE |
| | | ITKAPLSASMIKRYDEHHQDLTLLKALVRQQLPEKYKEIFFDQSKNGYAGY |
| | | IDGGASQEEFYKFIKPILEKMDGTEELLVKLNREDLLRKQRTEDNGSIPHQ |
| | | IHLGELHAILRRQEDFYPFLKDNREKIEKILTFRIPYYVGPLARGNSRFAW |
| | | MTRKSEEITPWNFEEVVDKGASAQSFIERMTNFDKNLPNEKVLPKHSLLY |
| | | EYFTVYNELTKVKYVTEGMRKPAFLSGEQKKAIVDLLFKTNRKVTVKQLKE |
| | | DYFKKIECFDSVEISGVEDRFNASLGTYHDLLKIIKDKDELDNEENEDILE |
| | | DIVLTLTLFEDREMIEERLKTYAHLFDDKVMKQLKRRRYTGWGRLSRKLIN |
| | | GIRDKQSGKTILDFLKSDGFANRNFMQLIHDDSLTFKEDIQKAQVSGQGDS |
| | | LHEHIANLAGSPAIKKGILQTVKVVDELVKVMGRHKPENIVIEMARENQTT |
| | | QKGQKNSRERMKRIEEGIKELGSQILKEHPVENTQLQNEKLYLYYLQNGRD |
| | | MYVDQELDINRLSDYDVDAIVPQSFLKDDSIDNKVLTRSDKNRGKSDNVPS |
| | | EEVVKKMKNYWRQLLNAKLITQRKFDNLTKAERGGLSELDKAGFIKRQLVE |
| | | TRQITKHVAQILDSRMNTKYDENDKLIREVKVITLKSKLVSDFRKDFQFYK |
| | | VREINNYHHAHDAYLNAVVGTALIKKYPKLESEFVYGDYKVYDVRKMIAKS |
| | | EQEIGKATAKYFFYSNIMNFFKTEITLANGEIRKRPLIETNGETGEIVWDK |
| | | GRDFATVRKVLSMPQVNIVKKTEVQTGGFSKESILPKRNSDKLIARKKDWD |
| | | PKKYGGFDSPTVAYSVLVVAKVEKGKSKKLKSVKELLGITIMERSSFEKNP |
| | | IDFLEAKGYKEVKKDLIIKLPKYSLFELENGRKRMLASAGELQKGNELALP |
| | | SKYVNFLYLASHYEKLKGSPEDNEQKQLFVEQHKHYLDEIIEQISEFSKRV |
| | | ILADANLDKVLSAYNKHRDKPIREQAENIIHLFTLTNLGAPAAFKYFDTTI |
| | | DRKRYTSTKEVLDATLIHQSITGLYETRIDLSQLGGDSPKKKRKVGVDGSS |
| | | GSETPGTSESATPESTGMNNSQGRVTFEDVTVNFTQGEWQRLNPEQRNLYR |

TABLE 7-continued sequences of exemplary epigenetic editors

| SEQ ID NO | Description | Sequence |
|---|---|---|
| | | DVMLENYSNLVSVGQGETTKPDVILRLEQGKEPWLEEEEVLGSGRAEKNGD IGGQIWKPKDVKESLSAPKKKRKVPKKKRKV |
| 493 | PLA003 full plasmid sequence | GGGCGCTCGAGCAGGTTCAGAAGGAGATCAAAAACCCCCAAGGATCAAACA TGCCAAAAAAGAAGAGAAAGGTACCGAAGAAAAAAAGAAAGGTATACAATC ACGATCAGGAGTTCGACCCCCCTAAGGTGTACCCACCAGTGCCTGCAGAGA AGAGGAAGCCAATCCGGGTGCTGAGCCTGTTTGATGGCATCGCCACCGGCC TGCTGGTGCTGAAGGATCTGGGCATCCAGGTGGACCGGTACATCGCCTCCG AGGTGTGCGAGGATTCTATCACCGTGGGCATGGTGCGCCACCAGGGCAAGA TCATGTATGTGGGCGACGTGCGGTCCGTGACACAGAAGCACATCCAGGAGT GGGGCCCATTCGATCTGGTGATCGGCGGCAGCCCCTGTAATGACCTGTCCA TCGTGAACCCTGCAAGGAAGGGACTGTACGAGGGAACCGGCCGGCTGTTCT TTGAGTTTTATAGACTGCTGCACGACGCCAGGCCTAAGGAGGGCGACGATA GACCATTCTTTTGGCTGTTCGAGAATGTGGTGGCTATGGGCGTGAGCGATA AGAGGGACATCTCCAGGTTTCTGGAGTCTAACCCCGTGATGATCGATGCAA AGGAGGTGTCCGCCGCACACAGAGCCAGGTATTTCTGGGGCAATCTGCCAG GAATGAACAGGCCACTGGCAAGCACCGTGAATGACAAGCTGGAGCTGCAGG AGTGCCTGGAGCACGGAAGGATCGCCAAGTTTTCCAAGGTGCGCACAATCA CCACACGGAGCAATTCCATCAAGCAGGGCAAGGATCAGCACTTCCCCGTGT TCATGAACGAGAAGGAGGACATCCTGTGGTGTACCGAGATGGAGAGAGTGT TCGGCTTTCCAGTGCACTACACAGACGTGTCTAACATGAGCAGGCTGGCAA GGCAGCGGCTGCTGGGCAGATCTTGGAGCGTGCCCGTGATCAGGCACCTGT TCGCCCCTCTGAAGGAGTATTTTGCCTGCGTGAGCAGCGGCAACTCCAATG CCAACAGCCGGGGCCCCTCTTTCAGCTCCGGATTGGTGCCTCTGAGCCTGA GGGGCTCCCACATGGCAGCAATCCCCGCCCTGGACCCCGAGGCCGAGCCTA GCATGGACGTGATCCTGGTGGGCTCTAGCGAGCTGTCCTCTAGCGTGTCTC CAGGAACCGGAAGGGATCTGATCGCATACGAGGTGAAGGCCAATCAGCGGA ACATCGAGGACATCTGTATCTGCTGTGGCAGCCTGCAGGTGCACACACAGC ACCCACTGTTCGAGGGAGGAATCTGCGCACCCTGTAAGGATAAGTTCCTGG ACGCCCTGTTTCTGTACGACGATGACGGCTACCAGTCCTATTGCTCTATCT GCTGTTCCGGCGAGACCCTGCTGATCTGCGGCAATCCAGATTGTACAAGGT GCTATTGTTTTGAGTGCGTGGACTCTCTGGTGGGACCAGGCACCAGCGGAA AGGTGCACGCCATGTCCAACTGGGTGTGCTACCTGTGCCTGCCATCCTCTC GCAGCGGACTGCTGCAGCGGAGAAGGAAGTGGAGATCCCAGCTGAAGGCCT TCTATGATAGGGAGTCTGAGAACCCCCTGGAGATGTTTGAGACCGTGCCAG TGTGGCGCCGGCAGCCCGTGAGGGTGCTGAGCCTGTTCGAGGATATCAAGA AGGAGCTGACATCCCTGGGCTTTCTGGAGTCCGGCTCTGACCCCGGACAGC TGAAGCACGTGGTGGATGTGACCGACACAGTGCGGAAGGATGTGGAGGAGT GGGGCCCTTTCGACCTGGTGTACGGAGCAACCCCTCCACTGGGACACACAT GCGACAGACCCCCTTCTTGGTACCTGTTCCAGTTTCACCGCCTGCTGCAGT ATGCAAGGCCAAAGCCAGGCAGCCCTAGACCATTCTTTTGGATGTTCGTGG ATAATCTGGTGCTGAACAAGGAGGATCTGGACGTGGCCAGCAGGTTTCTGG AGATGGAGCCAGTGACCATCCCAGACGTGCACGGCGGCTCCCTGCAGAATG CCGTGCGCGTGTGGTCTAACATCCCTGCCATCAGAAGCAGGCACTGGGCAC TGGTGAGCGAGGAGGAGCTGTCCCTGCTGGCCCAGAATAAGCAGAGCAGCA AGCTGGCCGCCAAGTGGCCTACAAAGCTGGTGAAGAACTGCTTCCTGCCAC TGCGGGAGTACTTCAAGTATTTTTCCACCGAGCTGACATCTAGCCTGGGAG GACCCTCCTCTGGCGCCCCACCACCTAGCGGCGGCTCCCCTGCCGGCTCTC CAACCAGCACAGAGGAGGGCACCAGCGAGTCCGCCACACCAGAGTCTGGAC CTGGCACCAGCACAGAGCCATCCGAGGGCTCTGCCCCAGGCTCTCCTGCAG GCAGCCCTACCTCCACCGAAGAGGGCACCAGCACAGAGCCTTCTGAGGGCA GCGCCCCAGGCACCTCTACAGAGCCAAGCGAGCTCGAGGACAAGAAGTACA GCATCGGCCTGGCCATCGGCACCAACTCTGTGGGCTGGGCCGTGATCACCG ACGAGTACAAGGTGCCCAGCAAGAAATTCAAGGTGCTGGGCAACACCGACC GGCACAGCATCAAGAAGAACCTGATCGGAGCCCTGCTGTTCGACAGCGGCG AAACAGCCGAGGCCACCCGGCTGAAGAGAACCGCCAGAAGAAGATACACCA GACGGAAGAACCGGATCTGCTATCTGCAAGAGATCTTCAGCAACGAGATGG CCAAGGTGGACGACAGCTTCTTCCACAGACTGGAAGAGTCCTTCCTGGTGG AAGAGGATAAGAAGCACGAGCGGCACCCCATCTTCGGCAACATCGTGGACG AGGTGGCCTACCACGAGAAGTACCCCACCATCTACCACCTGAGAAAGAAAC TGGTGGACAGCACCGACAAGGCCGACCTGCGGCTGATCTATCTGGCCCTGG CCCACATGATCAAGTTCCGGGGCCACTTCCTGATCGAGGGCGACCTGAACC CCGACAACAGCGACGTGGACAAGCTGTTCATCCAGCTGGTGCAGACCTACA ACCAGCTGTTCGAGGAAAACCCCATCAACGCCAGCGGCGTGGACGCCAAGG CCATCCTGTCTGCCAGACTGAGCAAGAGCAGACGGCTGGAAAATCTGATCG CCCAGCTGCCCGGCGAGAAGAAGAATGGCCTGTTCGGCAACCTGATTGCCC TGAGCCTGGGCCTGACCCCCAACTTCAAGAGCAACTTCGACCTGGCCGAGG ATGCCAAACTGCAGCTGAGCAAGGACACCTACGACGACGACCTGGACAACC TGCTGGCCCAGATCGGCGACCAGTACGCCGACCTGTTTCTGGCCGCCAAGA ACCTGTCCGACGCCATCCTGCTGAGCGACATCCTGAGAGTGAACACCGAGA TCACCAAGGCCCCCCTGAGCGCCTCTATGATCAAGAGATACGACGAGCACC ACCAGGACCTGACCCTGCTGAAAGCTCTCGTGCGGCAGCAGCTGCCTGAGA AGTACAAAGAGATTTTCTTCGACCAGAGCAAGAACGGCTACGCCGGCTACA TTGACGGCGGAGCCAGCCAGGAAGAGTTCTACAAGTTCATCAAGCCCATCC TGGAAAAGATGGACGGCACCGAGGAACTGCTCGTGAAGCTGAACAGAGAGG |

TABLE 7-continued sequences of exemplary epigenetic editors

| SEQ ID NO | Description | Sequence |
|-----------|-------------|----------|
| | | ACCTGCTGCGGAAGCAGCGGACCTTCGACAACGGCAGCATCCCCCACCAGA |
| | | TCCACCTGGGAGAGCTGCACGCCATTCTGCGGCGGCAGGAAGATTTTTACC |
| | | CATTCCTGAAGGACAACCGGGAAAAGATCGAGAAGATCCTGACCTTCCGCA |
| | | TCCCCTACTACGTGGGCCCTCTGGCCAGGGGAAACAGCAGATTCGCCTGGA |
| | | TGACCAGAAAGAGCGAGGAAACCATCACCCCCTGGAACTTCGAGGAAGTGG |
| | | TGGACAAGGGCGCTTCCGCCCAGAGCTTCATCGAGCGGATGACCAACTTCG |
| | | ATAAGAACCTGCCCAACGAGAAGGTGCTGCCCAAGCACAGCCTGCTGTACG |
| | | AGTACTTCACCGTGTATAACGAGCTGACCAAAGTGAAATACGTGACCGAGG |
| | | GAATGAGAAAGCCCGCCTTCCTGAGCGGCGAGCAGAAAAAGGCCATCGTGG |
| | | ACCTGCTGTTCAAGACCAACCGGAAAGTGACCGTGAAGCAGCTGAAAGAGG |
| | | ACTACTTCAAGAAAATCGAGTGCTTCGACTCCGTGGAAATCTCCGGCGTGG |
| | | AAGATCGGTTCAACGCCTCCCTGGGCACATACCACGATCTGCTGAAAATTA |
| | | TCAAGGACAAGGACTTCCTGGACAATGAGGAAAACGAGGACATTCTGGAAG |
| | | ATATCGTGCTGACCCTGACACTGTTTGAGGACAGAGAGATGATCGAGGAAC |
| | | GGCTGAAAACCTATGCCCACCTGTTCGACGACAAAGTGATGAAGCAGCTGA |
| | | AGCGGCGGAGATACACCGGCTGGGGCAGGCTGAGCCGGAAGCTGATCAACG |
| | | GCATCCGGGACAAGCAGTCCGGCAAGACAATCCTGGATTTCCTGAAGTCCG |
| | | ACGGCTTCGCCAACAGAAACTTCATGCAGCTGATCCACGACGACAGCCTGA |
| | | CCTTTAAAGAGGACATCCAGAAAGCCCAGGTGTCCGGCCAGGGCGATAGCC |
| | | TGCACGAGCACATTGCCAATCTGGCCGGCAGCCCCGCCATTAAGAAGGGCA |
| | | TCCTGCAGACAGTGAAGGTGGTGGACGAGCTCGTGAAAGTGATGGGCCGGC |
| | | ACAAGCCCGAGAACATCGTGATCGAAATGGCCAGAGAGAACCAGACCACCC |
| | | AGAAGGGACAGAAGAACAGCCGCGAGAGAATGAAGCGGATCGAAGAGGGCA |
| | | TCAAAGAGCTGGGCAGCCAGATCCTGAAAGAACACCCCGTGGAAAACACCC |
| | | AGCTGCAGAACGAGAAGCTGTACCTGTACTACCTGCAGAATGGGCGGGATA |
| | | TGTACGTGGACCAGGAACTGGACATCAACCGGCTGTCCGACTACGATGTGG |
| | | ACGCCATCGTGCCTCAGAGCTTTCTGAAGGACGACTCCATCGACAACAAGG |
| | | TGCTGACCAGAAGCGACAAGAACCGGGGCAAGAGCGACAACGTGCCCTCCG |
| | | AAGAGGTCGTGAAGAAGATGAAGAACTACTGGCGGCAGCTGCTGAACGCCA |
| | | AGCTGATTACCCAGAGAAAGTTCGACAATCTGACCAAGGCCGAGAGAGGCG |
| | | GCCTGAGCGAACTGGATAAGGCCGGCTTCATCAAGAGACAGCTGGTGGAAA |
| | | CCCGGCAGATCACAAAGCACGTGGCACAGATCCTGGACTCCCGGATGAACA |
| | | CTAAGTACGACGAGAATGACAAGCTGATCCGGGAAGTGAAAGTGATCACCC |
| | | TGAAGTCCAAGCTGGTGTCCGATTTCCGGAAGGATTTCCAGTTTTACAAAG |
| | | TGCGCGAGATCAACAACTACCACCACGCCCACGACGCCTACCTGAACGCCG |
| | | TCGTGGGAACCGCCCTGATCAAAAAGTACCCTAAGCTGGAAAGCGAGTTCG |
| | | TGTACGGCGACTACAAGGTGTACGACGTGCGGAAGATGATCGCCAAGAGCG |
| | | AGCAGGAAATCGGCAAGGCTACCGCCAAGTACTTCTTCTACAGCAACATCA |
| | | TGAACTTTTTCAAGACCGAGATTACCCTGGCCAACGGCGAGATCCGGAAGC |
| | | GGCCTCTGATCGAGACAAACGGCGAAACCGGGGAGATCGTGTGGGATAAGG |
| | | GCCGGGATTTTGCCACCGTGCGGAAAGTGCTGAGCATGCCCCAAGTGAATA |
| | | TCGTGAAAAAGACCGAGGTGCAGACAGGCGGCTTCAGCAAAGAGTCTATCC |
| | | TGCCCAAGAGGAACAGCGATAAGCTGATCGCCAGAAAGAAGGACTGGGACC |
| | | CTAAGAAGTACGGCGGCTTCGACAGCCCCACCGTGGCCTATTCTGTGCTGG |
| | | TGGTGGCCAAAGTGGAAAAGGGCAAGTCCAAGAAACTGAAGAGTGTGAAAG |
| | | AGCTGCTGGGGATCACCATCATGGAAAGAAGCAGCTTCGAGAAGAATCCCA |
| | | TCGACTTTCTGGAAGCCAAGGGCTACAAAGAAGTGAAAAAGGACCTGATCA |
| | | TCAAGCTGCCTAAGTACTCCCTGTTCGAGCTGGAAAACGGCCGGAAGAGAA |
| | | TGCTGGCCTCTGCCGGCGAACTGCAGAAGGGAAACGAACTGGCCCTGCCCT |
| | | CCAAATATGTGAACTTCCTGTACCTGGCCAGCCACTATGAGAAGCTGAAGG |
| | | GCTCCCCCGAGGATAATGAGCAGAAACAGCTGTTTGTGGAACAGCACAAGC |
| | | ACTACCTGGACGAGATCATCGAGCAGATCAGCGAGTTCTCCAAGAGAGTGA |
| | | TCCTGGCCGACGCTAATCTGGACAAAGTGCTGTCCGCCTACAACAAGCACC |
| | | GGGATAAGCCCATCAGAGAGCAGGCCGAGAATATCATCCACCTGTTTACCC |
| | | TGACCAATCTGGGAGCCCCTGCCGCCTTCAAGTACTTTGACACCACCATCG |
| | | ACCGGAAGAGGTACACCAGCACCAAAGAGGTGCTGGACGCCACCCTGATCC |
| | | ACCAGAGCATCACCGGCCTGTACGAGACACGGATCGACCTGTCTCAGCTGG |
| | | GAGGCGACAGCCCCAAGAAGAGAGAAAGGTGGGAGTCGACGGATCCAGCG |
| | | GCTCCGAGACCCCAGGCACATCTGAGAGCGCCACCCCTGAGTCCACCGGTA |
| | | TGAACAATTCACAGGGGAGAGTGACATTCGAAGACGTGACCGTGAACTTCA |
| | | CCCAGGGAGAATGGCAGCGCTTGAACCCAGAACAAAGGAACCTCTATCGGG |
| | | ACGTGATGCTGGAAAACTACTCAAATTTGGTGAGCGTTGGGCAGGGTGAGA |
| | | CCACTAAGCCTGACGTGATCCTGAGATTGGAACAGGGCAAGGAGCCTTGGC |
| | | TCGAGGAAGAGGAAGTCCTGGGCTCAGGGAGGGCCGAGAAAAACGGTGATA |
| | | TAGGAGGCCAGATATGGAAGCCTAAGGACGTCAAGGAGAGCCTGAGCGCTC |
| | | CCAAGAAGAAAAGGAAGGTCCCAAAGAAAAAAAGAAAGGTGTGAGGATCCT |
| | | GAGTCTAGAAATCAACCTCTGGATTACAAAATTTGTGAAAGATTGACTGGT |
| | | ATTCTTAACTATGTTGCTCCTTTTACGCTATGTGGATACGCTGCTTTAATG |
| | | CCTTTGTATCATGCTATTGCTTCCCGTATGGCTTTCATTTTCTCCTCCTTG |
| | | TATAAATCCTGGTTGCTGTCTCTTTATGAGGAGTTGTGGCCCGTTGTCAGG |
| | | CAACGTGGCGTGGTGTGCACTGTGTTTGCTGACGCAACCCCCACTGGTTGG |
| | | GGCATTGCCACCACCTGTCAGCTCCTTTCCGGGACTTTCGCTTTCCCCCTC |
| | | CCTATTGCCACGGCGGAACTCATCGCCGCCTGCCTTGCCCGCTGCTGGACA |
| | | GGGGCTCGGCTGTTGGGCACTGACAATTCCGTGGTGTTGTCGGGGAAATCA |
| | | TCGTCCTTTCCTTGGCTGCTCGCCTGTGTTGCCACCTGGATTCTGCGCGGG |

TABLE 7-continued sequences of exemplary epigenetic editors

| SEQ ID NO | Description | Sequence |
|---|---|---|
| | | ACGTCCTTCTGCTACGTCCCTTCGGCCCTCAATCCAGCGGACCTTCCTTCC CGCGGCCTGCTGCCGGCTCTGCGGCCTCTTCCGCGTCTTCGCCTTCGCCCT CAGACGAGTCGGATCTCCCTTTGGGCCGCCTCCCCGCCTGTTAATTAAAAA AAAAAAAAAAAAAAAAAAAAAAAAAAAAAAAAAAAAAAAAAAAAAAAAAAA AAAAAAAAAAAAAAAAAAAAAAAAAAAAAAAAAAAAAAAAAAAAGCTTGA AGAGCCTAGTGGCGCCTGATGCGGTATTTTCTCCTTACGCATCTGTGCGGT ATTTCACACCGCATAATCCAGCACAGTGGCGGCCCGTTTAAACCCGCTGAT CAGCCTCGACTGTGCCTTCTAGTTGCCAGCCATCTGTTGTTTGCCCCTCCC CCGTGCCTTCCTTGACCCTGGAAGGTGCCACTCCCACTGTCCTTTCCTAAT AAAATGAGGAAATTGCATCGCATTGTCTGAGTAGGTGTCATTCTATTCTGG GGGGTGGGGTGGGGCAGGACAGCAAGGGGGAGGATTGGGAAGACAATAGCA GGCATGCTGGGGATGCGGTGGGCTCTATGGCTTCTGAGGCGGAAAGAACCA GCTGCATTAATGAATCGGCCAACGCGCGGGGAGAGGCGGTTTGCGTATTGG GCGCTCTTCCGCTTCCTCGCTCACTGACTCGCTGCGCTCGGTCGTTCGGCT GCGGCGAGCGGTATCAGCTCACTCAAAGGCGGTAATACGGTTATCCACAGA ATCAGGGGATAACGCAGGAAAGAACATGTGAGCAAAAGGCCAGCAAAAGGC CAGGAACCGTAAAAAGGCCGCGTTGCTGGCGTTTTTCCATAGGCTCCGCCC CCCTGACGAGCATCACAAAAATCGACGCTCAAGTCAGAGGTGGCGAAACCC GACAGGACTATAAAGATACCAGGCGTTTCCCCCTGGAAGCTCCCTCGTGCG CTCTCCTGTTCCGACCCTGCCGCTTACCGGATACCTGTCCGCCTTTCTCCC TTCGGGAAGCGTGGCGCTTTCTCATAGCTCACGCTGTAGGTATCTCAGTTC GGTGTAGGTCGTTCGCTCCAAGCTGGGCTGTGTGCACGAACCCCCCGTTCA GCCCGACCGCTGCGCCTTATCCGGTAACTATCGTCTTGAGTCCAACCCGGT AAGACACGACTTATCGCCACTGGCAGCAGCCACTGGTAACAGGATTAGCAG AGCGAGGTATGTAGGCGGTGCTACAGAGTTCTTGAAGTGGTGGCCTAACTA CGGCTACACTAGAAGAACAGTATTTGGTATCTGCGCTCTGCTGAAGCCAGT TACCTTCGGAAAAAGAGTTGGTAGCTCTTGATCCGGCAAACAAACCACCGC TGGTAGCGGTGGTTTTTTTGTTTGCAAGCAGCAGATTACGCGCAGAAAAAA AGGATCTCAAGAAGATCCTTTGATCTTTTCTACGGGGTCTGACGCTCAGTG GAACGAAAACTCACGTTAAGGGATTTTGGTCATGAGATTATCAAAAAGGAT CTTCACCTAGATCCTTTTAAATTAAAAATGAAGTTTTAAATCAATCTAAAG TATATATGAGTAAACTTGGTCTGACAGTTAGAAAAACTCATCGAGCATCAA ATGAAACTGCAATTTATTCATATCAGGATTATCAATACCATATTTTTGAAA AAGCCGTTTCTGTAATGAAGGAGAAAACTCACCGAGGCAGTTCCATAGGAT GGCAAGATCCTGGTATCGGTCTGCGATTCCGACTCGTCCAACATCAATACA ACCTATTAATTTCCCCTCGTCAAAAATAAGGTTATCAAGTGAGAAATCACC ATGAGTGACGACTGAATCCGGTGAGAATGGCAAAAGTTTATGCATTTCTTT CCAGACTTGTTCAACAGGCCAGCCATTACGCTCGTCATCAAAATCACTCGC ATCAACCAAACCGTTATTCATTCGTGATTGCGCCTGAGCGAAACGAAATAC GCGATCGCTGTTAAAAGGACAATTACAAACAGGAATCGAATGCAACCGGCG CAGGAACACTGCCAGCGCATCAACAATATTTTCACCTGAATCAGGATATTC TTCTAATACCTGGAATGCTGTTTTCCCAGGGATCGCAGTGGTGAGTAACCA TGCATCATCAGGAGTACGGATAAAATGCTTGATGGTCGGAAGAGGCATAAA TTCCGTCAGCCAGTTTAGTCTGACCATCTCATCTGTAACATCATTGGCAAC GCTACCTTTGCCATGTTTCAGAAACAACTCTGGCGCATCGGGCTTCCCATA CAATCGATAGATTGTCGCACCTGATTGCCCGACATTATCGCGAGCCCATTT ATACCCATATAAATCAGCATCCATGTTGGAATTTAATCGCGGCCTAGAGCA AGACGTTTCCCGTTGAATATGGCTCATACTCTTCCTTTTTCAATATTATTG AAGCATTTATCAGGGTTATTGTCTCATGAGCGGATACATATTTGAATGTAT TTAGAAAAATAAACAAATAGGGGTTCCGCGCACATTTCCCCGAAAAGTGCC ACCTGACGTCGATCGACGGATCGGGAGATCTCCCGATCCCCTATGGTGCAC TCTCAGTACAATCTGCTCTGATGCCGCATAGTTAAGCCAGTATCTGCTCCC TGCTTGTGTGTTGGAGGTCGCTGAGTAGTGCGCGAGCAAAATTTAAGCTAC AACAAGGCAAGGCTTGACCGACAATTGCATGAAGAATCTGCTTAGGGTTAG GCGTTTTGCGCTGCTTCGCGATGTACGGGCCAGATATACGCGTTGACATTG ATTATTGACTAGTTATTAATAGTAATCAATTACGGGGTCATTAGTTCATAG CCCATATATGGAGTTCCGCGTTACATAACTTACGGTAAATGGCCCGCCTGG CTGACCGCCCAACGACCCCCGCCCATTGACGTCAATAATGACGTATGTTCC CATAGTAACGCCAATAGGGACTTTCCATTGACGTCAATGGGTGGAGTATTT ACGGTAAACTGCCCACTTGGCAGTACATCAAGTGTATCATATGCCAAGTAC GCCCCCTATTGACGTCAATGACGGTAAATGGCCCGCCTGGCATTATGCCCA GTACATGACCTTATGGGACTTTCCTACTTGGCAGTACATCTACGTATTAGT CATCGCTATTACCATGGTGATGCGGTTTTGGCAGTACATCAATGGGCGTGG ATAGCGGTTTGACTCACGGGGATTTCCAAGTCTCCACCCCATTGACGTCAA TGGGAGTTTGTTTTGGCACCAAAATCAACGGGACTTTCCAAAATGTCGTAA CAACTCCGCCCCATTGACGCAAATGGGCGGTAGGCGTGTACGGTGGGAGGT CTATATAAGCAGAGCTCTCTGGCTAACTAGAGAACCCACTGCTTACTGGCT TATCGAAATTAATACGACTCACTATAAG |
| 494 | PLA003 plasmid coding sequence | ATGCCAAAAAGAAGAGAAAGGTACCGAAGAAAAAAGAAAGGTATACAAT CACGATCAGGAGTTCGACCCCCCTAAGGTGTACCCACCAGTGCCTGCAGAG AAGAGGAAGCCAATCCGGGTGCTGAGCCTGTTTGATGGCATCGCCACCGGC CTGCTGGTGCTGAAGGATCTGGGCATCCAGGTGGACCGGTACATCGCCTCC GAGGTGTGCGAGGATTCTATCACCGTGGGCATGGTGCGCCACCAGGGCAAG ATCATGTATGTGGGCGACGTGCGGTCCGTGACACAGAAGCACATCCAGGAG |

TABLE 7-continued sequences of exemplary epigenetic editors

| SEQ ID NO | Description | Sequence |
|---|---|---|
| | | TGGGGCCCATTCGATCTGGTGATCGGCGGCAGCCCCTGTAATGACCTGTCC |
| | | ATCGTGAACCCTGCAAGGAAGGGACTGTACGAGGGAACCGGCCGGCTGTTC |
| | | TTTGAGTTTTATAGACTGCTGCACGACGCCAGGCCTAAGGAGGGCGACGAT |
| | | AGACCATTCTTTTGGCTGTTCGAGAATGTGGTGGCTATGGGCGTGAGCGAT |
| | | AAGAGGGACATCTCCAGGTTTCTGGAGTCTAACCCCGTGATGATCGATGCA |
| | | AAGGAGGTGTCCGCCGCACACAGAGCCAGGTATTTCTGGGGCAATCTGCCA |
| | | GGAATGAACAGGCCACTGGCAAGCACCGTGAATGACAAGCTGGAGCTGCAG |
| | | GAGTGCCTGGAGCACGGAAGGATCGCCAAGTTTTCCAAGGTGCGCACAATC |
| | | ACCACACGGAGCAATTCCATCAAGCAGGGCAAGGATCAGCACTTCCCCGTG |
| | | TTCATGAACGAGAAGGAGGACATCCTGTGGTGTACCGAGATGGAGAGAGTG |
| | | TTCGGCTTTCCAGTGCACTACACAGACGTGTCTAACATGAGCAGGCTGGCA |
| | | AGGCAGCGGCTGCTGGGCAGATCTTGGAGCGTGCCCGTGATCAGGCACCTG |
| | | TTCGCCCCTCTGAAGGAGTATTTTGCCTGCGTGAGCAGCGGCAACTCCAAT |
| | | GCCAACAGCCGGGGCCCCTCTTTCAGCTCCGGATTGGTGCCTCTGAGCCTG |
| | | AGGGGGCTCCCACATGGCAGCAATCCCCGCCCTGGACCCCGAGGCCGAGCCT |
| | | AGCATGGACGTGATCCTGGTGGGCTCTAGCGAGCTGTCCTCTAGCGTGTCT |
| | | CCAGGAACCGGAAGGGATCTGATCGCATACGAGGTGAAGGCCAATCAGCGG |
| | | AACATCGAGGACATCTGTATCTGCTGTGGCAGCCTGCAGGTGCACACACAG |
| | | CACCCACTGTTCGAGGGAGGAATCTGCGCACCCTGTAAGGATAAGTTCCTG |
| | | GACGCCCTGTTTCTGTACGACGATGACGGCTACCAGTCCTATTGCTCTATC |
| | | TGCTGTTCCGGCGAGACCCTGCTGATCTGCGGCAATCCAGATTGTACAAGG |
| | | TGCTATTGTTTTGAGTGCGTGGACTCTCTGGTGGGACCAGGCACCAGCGGA |
| | | AAGGTGCACGCCATGTCCAACTGGGTGTGCTACCTGTGCCTGCCATCCTCT |
| | | CGCAGCGGACTGCTGCAGCGGAGAAGGAAGTGGAGATCCCAGCTGAAGGCC |
| | | TTCTATGATAGGGAGTCTGAGAACCCCCTGGAGATGTTTGAGACCGTGCCA |
| | | GTGTGGCGCCGGCAGCCCGTGAGGGTGCTGAGCCTGTTCGAGGATATCAAG |
| | | AAGGAGCTGACATCCCTGGGCTTTCTGGAGTCCGGCTCTGACCCCGGACAG |
| | | CTGAAGCACGTGGTGGATGTGACCGACACAGTGCGGAAGGATGTGGAGGAG |
| | | TGGGGCCCTTTCGACCTGGTGTACGGAGCAACCCCTCCACTGGGACACACA |
| | | TGCGACGACCCCCTTCTTGGTACCTGTTCCAGTTTCACCGCCTGCTGCAG |
| | | TATGCAAGGCCAAAGCCAGGCAGCCCTAGACCATTCTTTTGGATGTTCGTG |
| | | GATAATCTGGTGCTGAACAAGGAGGATCTGGACGTGGCCAGCAGGTTTCTG |
| | | GAGATGGAGCCAGTGACCATCCCAGACGTGCACGGCGGCTCCCTGCAGAAT |
| | | GCCGTGCGCGTGTGGTCTAACATCCCTGCCATCAGAAGCAGGCACTGGGCA |
| | | CTGGTGAGCGAGGAGGAGCTGTCCCTGCTGGCCCAGAATAAGCAGAGCAGC |
| | | AAGCTGGCCGCCAAGTGGCCTACAAAGCTGGTGAAGAACTGCTTCCTGCCA |
| | | CTGCGGGAGTACTTCAAGTATTTTTCCACCGAGCTGACATCTAGCCTGGGA |
| | | GGACCCTCCTCTGGCGCCCCACCACCTAGCGGCGGCTCCCCTGCCGGCTCT |
| | | CCAACCAGCACAGAGGAGGGCACCAGCGAGTCCGCCACACCAGAGTCTGGA |
| | | CCTGGCACCAGCACAGAGCCATCCGAGGGCTCTGCCCCAGGCTCTCCTGCA |
| | | GGCAGCCCTACCTCCACCGAAGAGGGCACCAGCACAGAGCCTTCTGAGGGC |
| | | AGCGCCCCAGGCACCTCTACAGAGCCAAGCGAGCTCGAGGACAAGAAGTAC |
| | | AGCATCGGCCTGGCCATCGGCACCAACTCTGTGGGCTGGGCCGTGATCACC |
| | | GACGAGTACAAGGTGCCCAGCAAGAAATTCAAGGTGCTGGGCAACACCGAC |
| | | CGGCACAGCATCAAGAAGAACCTGATCGGAGCCCTGCTGTTCGACAGCGGC |
| | | GAAACAGCCGAGGCCACCCGGCTGAAGAGAACCGCCAGAAGAAGATACACC |
| | | AGACGGAAGAACCGGATCTGCTATCTGCAAGAGATCTTCAGCAACGAGATG |
| | | GCCAAGGTGGACGACAGCTTCTTCCACAGACTGGAAGAGTCCTTCCTGGTG |
| | | GAAGAGGATAAGAAGCACGAGCGGCACCCCATCTTCGGCAACATCGTGGAC |
| | | GAGGTGGCCTACCACGAGAAGTACCCCACCATCTACCACCTGAGAAAGAAA |
| | | CTGGTGGACAGCACCGACAAGGCCGACCTGCGGCTGATCTATCTGGCCCTG |
| | | GCCCACATGATCAAGTTCCGGGGCCACTTCCTGATCGAGGGCGACCTGAAC |
| | | CCCGACAACAGCGACGTGGACAAGCTGTTCATCCAGCTGGTGCAGACCTAC |
| | | AACCAGCTGTTCGAGGAAAACCCCATCAACGCCAGCGGCGTGGACGCCAAG |
| | | GCCATCCTGTCTGCCAGACTGAGCAAGAGCAGACGGCTGGAAAATCTGATC |
| | | GCCCAGCTGCCCGGCGAGAAGAAGAATGGCCTGTTCGGCAACCTGATTGCC |
| | | CTGAGCCTGGGCCTGACCCCCAACTTCAAGAGCAACTTCGACCTGGCCGAG |
| | | GATGCCAAACTGCAGCTGAGCAAGGACACCTACGACGACGACCTGGACAAC |
| | | CTGCTGGCCCAGATCGGCGACCAGTACGCCGACCTGTTTCTGGCCGCCAAG |
| | | AACCTGTCCGACGCCATCCTGCTGAGCGACATCCTGAGAGTGAACACCGAG |
| | | ATCACCAAGGCCCCCCTGAGCGCCTCTATGATCAAGAGATACGACGAGCAC |
| | | CACCAGGACCTGACCCTGCTGAAAGCTCTCGTGCGGCAGCAGCTGCCTGAG |
| | | AAGTACAAAGAGATTTTCTTCGACCAGAGCAAGAACGGCTACGCCGGCTAC |
| | | ATTGACGGCGGAGCCAGCCAGGAAGAGTTCTACAAGTTCATCAAGCCCATC |
| | | CTGGAAAAGATGGACGGCACCGAGGAACTGCTCGTGAAGCTGAACAGAGAG |
| | | GACCTGCTGCGGAAGCAGCGGACCTTCGACAACGGCAGCATCCCCCACCAG |
| | | ATCCACCTGGGAGAGCTGCACGCCATTCTGCGGCGGCAGGAAGATTTTTAC |
| | | CCATTCCTGAAGGACAACCGGGAAAAGATCGAGAAGATCCTGACCTTCCGC |
| | | ATCCCCTACTACGTGGGCCCTCTGGCCAGGGGAAACAGCAGATTCGCCTGG |
| | | ATGACCAGAAAGAGCGAGGAAACCATCACCCCCTGGAACTTCGAGGAAGTG |
| | | GTGGACAAGGGCGCTTCCGCCCAGAGCTTCATCGAGCGGATGACCAACTTC |
| | | GATAAGAACCTGCCCAACGAGAAGGTGCTGCCCAAGCACAGCCTGCTGTAC |
| | | GAGTACTTCACCGTGTATAACGAGCTGACCAAAGTGAAATACGTGACCGAG |
| | | GGAATGAGAAAGCCCGCCTTCCTGAGCGGCGAGCAGAAAAAGGCCATCGTG |
| | | GACCTGCTGTTCAAGACCAACCGGAAAGTGACCGTGAAGCAGCTGAAAGAG |

TABLE 7-continued sequences of exemplary epigenetic editors

| SEQ ID NO | Description | Sequence |
|---|---|---|

```
GACTACTTCAAGAAAATCGAGTGCTTCGACTCCGTGGAAATCTCCGGCGTG
GAAGATCGGTTCAACGCCTCCCTGGGCACATACCACGATCTGCTGAAAATT
ATCAAGGACAAGGACTTCCTGGACAATGAGGAAAACGAGGACATTCTGGAA
GATATCGTGCTGACCCTGACACTGTTTGAGGACAGAGAGATGATCGAGGAA
CGGCTGAAAACCTATGCCCACCTGTTCGACGACAAAGTGATGAAGCAGCTG
AAGCGGCGGAGATACACCGGCTGGGGCAGGCTGAGCCGGAAGCTGATCAAC
GGCATCCGGGACAAGCAGTCCGGCAAGACAATCCTGGATTTCCTGAAGTCC
GACGGCTTCGCCAACAGAAACTTCATGCAGCTGATCCACGACGACAGCCTG
ACCTTTAAAGAGGACATCCAGAAAGCCCAGGTGTCCGGCCAGGGCGATAGC
CTGCACGAGCACATTGCCAATCTGGCCGGCAGCCCCGCCATTAAGAAGGGC
ATCCTGCAGACAGTGAAGGTGGTGGACGAGCTCGTGAAAGTGATGGGCCGG
CACAAGCCCGAGAACATCGTGATCGAAATGGCCAGAGAGAACCAGACCACC
CAGAAGGGACAGAAGAACAGCCGCGAGAGAATGAAGCGGATCGAAGAGGGC
ATCAAAGAGCTGGGCAGCCAGATCCTGAAAGAACACCCCGTGGAAAACACC
CAGCTGCAGAACGAGAAGCTGTACCTGTACTACCTGCAGAATGGGCGGGAT
ATGTACGTGGACCAGGAACTGGACATCAACCGGCTGTCCGACTACGATGTG
GACGCCATCGTGCCTCAGAGCTTTCTGAAGGACGACTCCATCGACAACAAG
GTGCTGACCAGAAGCGACAAGAACCGGGGCAAGAGCGACAACGTGCCCTCC
GAAGAGGTCGTGAAGAAGATGAAGAACTACTGGCGGCAGCTGCTGAACGCC
AAGCTGATTACCCAGAGAAAGTTCGACAATCTGACCAAGGCCGAGAGAGGC
GGCCTGAGCGAACTGGATAAGGCCGGCTTCATCAAGAGACAGCTGGTGGAA
ACCCGGCAGATCACAAAGCACGTGGCACAGATCCTGGACTCCCGGATGAAC
ACTAAGTACGACGAGAATGACAAGCTGATCCGGGAAGTGAAAGTGATCACC
CTGAAGTCCAAGCTGGTGTCCGATTTCCGGAAGGATTTCCAGTTTTACAAA
GTGCGCGAGATCAACAACTACCACCACGCCCACGACGCCTACCTGAACGCC
GTCGTGGGAACCGCCCTGATCAAAAAGTACCCTAAGCTGGAAAGCGAGTTC
GTGTACGGCGACTACAAGGTGTACGACGTGCGGAAGATGATCGCCAAGAGC
GAGCAGGAAATCGGCAAGGCTACCGCCAAGTACTTCTTCTACAGCAACATC
ATGAACTTTTTCAAGACCGAGATTACCCTGGCCAACGGCGAGATCCGGAAG
CGGCCTCTGATCGAGACAAACGGCGAAACCGGGGAGATCGTGTGGGATAAG
GGCCGGGATTTTGCCACCGTGCGGAAAGTGCTGAGCATGCCCCAAGTGAAT
ATCGTGAAAAAGACCGAGGTGCAGACAGGCGGCTTCAGCAAAGAGTCTATC
CTGCCCAAGAGGAACAGCGATAAGCTGATCGCCAGAAAGAAGGACTGGGAC
CCTAAGAAGTACGGCGGCTTCGACAGCCCCACCGTGGCCTATTCTGTGCTG
GTGGTGGCCAAAGTGGAAAAGGGCAAGTCCAAGAAACTGAAGAGTGTGAAA
GAGCTGCTGGGGATCACCATCATGGAAAGAAGCAGCTTCGAGAAGAATCCC
ATCGACTTTCTGGAAGCCAAGGGCTACAAAGAAGTGAAAAAGGACCTGACC
ATCAAGCTGCCTAAGTACTCCCTGTTCGAGCTGGAAAACGGCCGGAAGAGA
ATGCTGGCCTCTGCCGGCGAACTGCAGAAGGGAAACGAACTGGCCCTGCCC
TCCAAATATGTGAACTTCCTGTACCTGGCCAGCCACTATGAGAAGCTGAAG
GGCTCCCCCGAGGATAATGAGCAGAAACAGCTGTTTGTGGAACAGCACAAG
CACTACCTGGACGAGATCATCGAGCAGATCAGCGAGTTCTCCAAGAGAGTG
ATCCTGGCCGACGCTAATCTGGACAAAGTGCTGTCCGCCTACAACAAGCAC
CGGGATAAGCCCATCAGAGAGCAGGCCGAGAATATCATCCACCTGTTTACC
CTGACCAATCTGGGAGCCCCTGCCGCCTTCAAGTACTTTGACACCACCATC
GACCGGAAGAGGTACACCAGCACCAAAGAGGTGCTGGACGCCACCCTGATC
CACCAGAGCATCACCGGCCTGTACGAGACACGGATCGACCTGTCTCAGCTG
GGAGGCGACAGCCCCAAGAAGAAGAGAAAGGTGGGAGTCGACGGATCCAGC
GGCTCCGAGACCCCAGGCACATCTGAGAGCGCCACCCCTGAGTCCACCGGT
ATGAACAATTCACAGGGGAGAGTGACATTCGAAGACGTGACCGTGAACTTC
ACCCAGGGAGAATGGCAGCGCTTGAACCCAGAACAAAGGAACCTCTATCGG
GACGTGATGCTGGAAAACTACTCAAATTTGGTGAGCGTTGGGCAGGGTGAG
ACCACTAAGCCTGACGTGATCCTGAGATTGGAACAGGGCAAGGAGCCTTGG
CTCGAGGAAGAGGAAGTCCTGGGCTCAGGGAGGGCCGAGAAAAACGGTGAT
ATAGGAGGCCAGATATGGAAGCCTAAGGACGTCAAGGAGAGCCTGAGCGCT
CCCAAGAAGAAAAGGAAGGTCCCAAAGAAAAAAAGAAAGGTGTGA
```

---

Table 8 below lists components of the fusion polypeptide PLA001 and their corresponding amino acid position in the fusion polypeptide sequence (SEQ ID No. 481) set forth in Table 7.

TABLE 8 annotation of PLA001 amino acid sequence

|  | Type | Start | End | Length |
|---|---|---|---|---|
| SV40 NLS | CDS | 2 | 8 | 7 |
| SV40 NLS | CDS | 9 | 15 | 7 |
| DNMT3A | CDS | 17 | 317 | 301 |

TABLE 8-continued annotation of PLA001 amino acid sequence

|  | Type | Start | End | Length |
|---|---|---|---|---|
| Linker | CDS | 318 | 344 | 27 |
| DNMT3L full-length | CDS | 345 | 730 | 386 |
| XTEN80 | CDS | 731 | 810 | 80 |
| dCas9 | CDS | 811 | 2180 | 1370 |
| NLS | CDS | 2181 | 2187 | 7 |
| XTEN16 | CDS | 2188 | 2208 | 21 |
| ZN627 | CDS | 2211 | 2290 | 80 |
| FLAG | CDS | 2293 | 2300 | 8 |

TABLE 8-continued

| annotation of PLA001 amino acid sequence | | | | |
|---|---|---|---|---|
| | Type | Start | End | Length |
| SV40 NLS | CDS | 2302 | 2308 | 7 |
| SV40 NLS | CDS | 2309 | 2315 | 7 |

Table 9 below lists components of the polynucleotide encoding the fusion polypeptide PLA001 and their corresponding nucleotide position in the polynucleotide sequence (SEQ ID No. 482) set forth in Table 7.

TABLE 9

| annotation of PLA001 polynucleotide sequence | | | | |
|---|---|---|---|---|
| Name | Type | Minimum | Maximum | Length |
| SV40 NLS | CDS | 4 | 24 | 21 |
| SV40 NLS | CDS | 25 | 44 | 20 |
| DNMT3A | CDS | 49 | 951 | 903 |
| Linker | CDS | 952 | 1032 | 81 |
| DNMT3L full-length | CDS | 1033 | 2190 | 1158 |
| XTEN80 | CDS | 2191 | 2430 | 240 |
| dCas9 | CDS | 2431 | 6540 | 4110 |
| NLS | CDS | 6541 | 6561 | 21 |
| XTEN16 | CDS | 6562 | 6624 | 63 |
| ZN627 | CDS | 6631 | 6870 | 240 |
| FLAG | CDS | 6877 | 6900 | 24 |
| SV40 NLS | CDS | 6904 | 6924 | 21 |
| SV40 NLS | CDS | 6925 | 6945 | 21 |

Table 10 below lists components of the fusion polypeptide PLA002 and their corresponding amino acid position in the fusion polypeptide sequence (SEQ ID No. 483) set forth in Table 7.

TABLE 10

| annotation of PLA002 amino acid sequence | | | | |
|---|---|---|---|---|
| Name | Type | Minimum | Maximum | Length |
| SV40 NLS | CDS | 2 | 8 | 7 |
| SV40 NLS | CDS | 9 | 15 | 7 |

TABLE 10-continued

| annotation of PLA002 amino acid sequence | | | | |
|---|---|---|---|---|
| Name | Type | Minimum | Maximum | Length |
| DNMT3A | CDS | 17 | 317 | 301 |
| Linker | CDS | 318 | 344 | 27 |
| DNMT3L full-length | CDS | 345 | 730 | 386 |
| XTEN80 | CDS | 731 | 810 | 80 |
| dCas9 | CDS | 811 | 2180 | 1370 |
| NLS | CDS | 2181 | 2187 | 7 |
| XTEN16 | CDS | 2188 | 2208 | 21 |
| ZIM3 | CDS | 2211 | 2310 | 100 |
| FLAG | CDS | 2313 | 2320 | 8 |
| SV40 NLS | CDS | 2322 | 2328 | 7 |
| SV40 NLS | CDS | 2329 | 2335 | 7 |

Table 11 below lists components of the polynucleotide encoding the fusion polypeptide PLA002 and their corresponding nucleotide position in the polynucleotide sequence (SEQ ID No. 484) set forth in Table 7.

TABLE 11

| annotation of PLA002 polynucleotide sequence | | | | |
|---|---|---|---|---|
| Name | Type | Minimum | Maximum | Length |
| SV40 NLS | CDS | 4 | 24 | 21 |
| SV40 NLS | CDS | 25 | 45 | 21 |
| DNMT3A | CDS | 49 | 951 | 903 |
| Linker | CDS | 952 | 1032 | 81 |
| DNMT3L full-length | CDS | 1033 | 2190 | 1158 |
| XTEN80 | CDS | 2191 | 2430 | 240 |
| dCas9 | CDS | 2431 | 6540 | 4110 |
| NLS | CDS | 6541 | 6561 | 21 |
| XTEN16 | CDS | 6562 | 6624 | 63 |
| ZIM3 | CDS | 6631 | 6930 | 300 |
| FLAG | CDS | 6937 | 6960 | 24 |
| SV40 NLS | CDS | 6964 | 6984 | 21 |
| SV40 NLS | CDS | 6985 | 7005 | 21 |
| stop | terminator | 7006 | 7008 | 3 |

Table 12 below provides gRNA sequence tested.

TABLE 12

| Exemplary gRNA sequences | | | | |
|---|---|---|---|---|
| SEQ IDs | Target domain sequence | SEQ IDs | gRNA sequence | |
| 333 | CCTGCTGGTG GCTCCAGTTC | 10 | CCUGCUGGUGGCUCCAGUUCGUUUAAGAGCUAAGCUGGAAACAGCAUAGCAAGUUUAAAU | |
| | | 93 | AAGGCUAGUCCGUUAUCAACUUGAAAAAGUGGCACCGAGUCGGUGCUUUUUU | |
| 334 | CTGAACTGGA GCCACCAGCA | 10 | CUGAACUGGAGCCACCAGCAGUUUAAGAGCUAAGCUGGAAACAGCAUAGCAAGUUUAAAU | |
| | | 94 | AAGGCUAGUCCGUUAUCAACUUGAAAAAGUGGCACCGAGUCGGUGCUUUUUU | |
| 335 | CCTGAACTGG AGCCACCAGC | 10 | CCUGAACUGGAGCCACCAGCGUUUAAGAGCUAAGCUGGAAACAGCAUAGCAAGUUUAAAU | |
| | | 95 | AAGGCUAGUCCGUUAUCAACUUGAAAAAGUGGCACCGAGUCGGUGCUUUUUU | |
| 336 | CCTCGAGAAG ATTGACGATA | 10 | CCUCGAGAAGAUUGACGAUAGUUUAAGAGCUAAGCUGGAAACAGCAUAGCAAGUUUAAAU | |
| | | 96 | AAGGCUAGUCCGUUAUCAACUUGAAAAAGUGGCACCGAGUCGGUGCUUUUUU | |
| 337 | TCGTCAATCT TCTCGAGGAT | 10 | UCGUCAAUCUUCUCGAGGAUGUUUAAGAGCUAAGCUGGAAACAGCAUAGCAAGUUUAAAU | |
| | | 97 | AAGGCUAGUCCGUUAUCAACUUGAAAAAGUGGCACCGAGUCGGUGCUUUUUU | |
| 338 | CGTCAATCTT CTCGAGGATT | 10 | CGUCAAUCUUCUCGAGGAUUGUUUAAGAGCUAAGCUGGAAACAGCAUAGCAAGUUUAAAU | |
| | | 98 | AAGGCUAGUCCGUUAUCAACUUGAAAAAGUGGCACCGAGUCGGUGCUUUUUU | |

TABLE 12-continued

Exemplary gRNA sequences

| SEQ IDs | Target domain sequence | SEQ IDs | gRNA sequence |
|---|---|---|---|
| 339 | GTCAATCTTC TCGAGGATTG | 10 99 | GUCAAUCUUCUCGAGGAUUGGUUUUAAGAGCUAAGCUGGAAACAGCAUAGCAAGUUUAAAU AAGGCUAGUCCGUUAUCAACUUGAAAAAGUGGCACCGAGUCGGUGCUUUUUU |
| 340 | AACATGGAGA ACATCACATC | 11 00 | AACAUGGAGAACAUCACAUCGUUUUAAGAGCUAAGCUGGAAACAGCAUAGCAAGUUUAAAU AAGGCUAGUCCGUUAUCAACUUGAAAAAGUGGCACCGAGUCGGUGCUUUUUUU |
| 341 | AACATCACAT CAGGATTCCT | 11 01 | AACAUCACAUCAGGAUUCCUGUUUUAAGAGCUAAGCUGGAAACAGCAUAGCAAGUUUAAAU AAGGCUAGUCCGUUAUCAACUUGAAAAAGUGGCACCGAGUCGGUGCUUUUUUU |
| 342 | CTAGACTCTG CGGTATTGTG | 11 02 | CUAGACUCUGCGGUAUUGUGGUUUUAAGAGCUAAGCUGGAAACAGCAUAGCAAGUUUAAAU AAGGCUAGUCCGUUAUCAACUUGAAAAAGUGGCACCGAGUCGGUGCUUUUUUU |
| 343 | TACCGCAGAG TCTAGACTCG | 11 03 | UACCGCAGAGUCUAGACUCGGUUUUAAGAGCUAAGCUGGAAACAGCAUAGCAAGUUUAAAU AAGGCUAGUCCGUUAUCAACUUGAAAAAGUGGCACCGAGUCGGUGCUUUUUUU |
| 344 | CGCAGAGTCT AGACTCGTGG | 11 04 | CGCAGAGUCUAGACUCGUGGGUUUUAAGAGCUAAGCUGGAAACAGCAUAGCAAGUUUAAAU AAGGCUAGUCCGUUAUCAACUUGAAAAAGUGGCACCGAGUCGGUGCUUUUUUU |
| 345 | CACCACGAGT CTAGACTCTG | 11 05 | CACCACGAGUCUAGACUCUGGUUUUAAGAGCUAAGCUGGAAACAGCAUAGCAAGUUUAAAU AAGGCUAGUCCGUUAUCAACUUGAAAAAGUGGCACCGAGUCGGUGCUUUUUUU |
| 346 | TGGACTTCTC TCAATTTTCT | 11 06 | UGGACUUCUCUCAAUUUUCUGUUUUAAGAGCUAAGCUGGAAACAGCAUAGCAAGUUUAAAU AAGGCUAGUCCGUUAUCAACUUGAAAAAGUGGCACCGAGUCGGUGCUUUUUUU |
| 347 | GGACTTCTCT CAATTTTCTA | 11 07 | GGACUUCUCUCAAUUUUCUAGUUUUAAGAGCUAAGCUGGAAACAGCAUAGCAAGUUUAAAU AAGGCUAGUCCGUUAUCAACUUGAAAAAGUGGCACCGAGUCGGUGCUUUUUUU |
| 348 | GACTTCTCTC AATTTTCTAG | 11 08 | GACUUCUCUCAAUUUUCUAGGUUUUAAGAGCUAAGCUGGAAACAGCAUAGCAAGUUUAAAU AAGGCUAGUCCGUUAUCAACUUGAAAAAGUGGCACCGAGUCGGUGCUUUUUUU |
| 349 | ACTTCTCTCA ATTTTCTAGG | 11 09 | ACUUCUCUCAAUUUUCUAGGGUUUUAAGAGCUAAGCUGGAAACAGCAUAGCAAGUUUAAAU AAGGCUAGUCCGUUAUCAACUUGAAAAAGUGGCACCGAGUCGGUGCUUUUUUU |
| 350 | CGAATTTTGG CCAAGACACA | 11 10 | CGAAUUUUGGCCAAGACACAGUUUUAAGAGCUAAGCUGGAAACAGCAUAGCAAGUUUAAAU AAGGCUAGUCCGUUAUCAACUUGAAAAAGUGGCACCGAGUCGGUGCUUUUUUU |
| 351 | AGGTTGGGGA CTGCGAATTT | 11 11 | AGGUUGGGGACUGCGAAUUUGUUUUAAGAGCUAAGCUGGAAACAGCAUAGCAAGUUUAAAU AAGGCUAGUCCGUUAUCAACUUGAAAAAGUGGCACCGAGUCGGUGCUUUUUUU |
| 352 | GGCATAGCAG CAGGATGAAG | 11 12 | GGCAUAGCAGCAGGAUGAAGGUUUUAAGAGCUAAGCUGGAAACAGCAUAGCAAGUUUAAAU AAGGCUAGUCCGUUAUCAACUUGAAAAAGUGGCACCGAGUCGGUGCUUUUUUU |
| 353 | AGAAGATGAG GCATAGCAGC | 11 13 | AGAAGAUGAGGCAUAGCAGCGUUUUAAGAGCUAAGCUGGAAACAGCAUAGCAAGUUUAAAU AAGGCUAGUCCGUUAUCAACUUGAAAAAGUGGCACCGAGUCGGUGCUUUUUUU |
| 354 | GCTATGCCTC ATCTTCTTGT | 11 14 | GCUAUGCCUCAUCUUCUUGUGUUUUAAGAGCUAAGCUGGAAACAGCAUAGCAAGUUUAAAU AAGGCUAGUCCGUUAUCAACUUGAAAAAGUGGCACCGAGUCGGUGCUUUUUUU |
| 355 | GAAGAACCAA CAAGAAGATG | 11 15 | GAAGAACCAACAAGAAGAUGGUUUUAAGAGCUAAGCUGGAAACAGCAUAGCAAGUUUAAAU AAGGCUAGUCCGUUAUCAACUUGAAAAAGUGGCACCGAGUCGGUGCUUUUUUU |
| 356 | CATCTTCTTG TTGGTTCTTC | 11 16 | CAUCUUCUUGUUGGUUCUUCGUUUUAAGAGCUAAGCUGGAAACAGCAUAGCAAGUUUAAAU AAGGCUAGUCCGUUAUCAACUUGAAAAAGUGGCACCGAGUCGGUGCUUUUUUU |
| 357 | CCCGTTTGTC CTCTAATTCC | 11 17 | CCCGUUUGUCCUCUAAUUCCGUUUUAAGAGCUAAGCUGGAAACAGCAUAGCAAGUUUAAAU AAGGCUAGUCCGUUAUCAACUUGAAAAAGUGGCACCGAGUCGGUGCUUUUUUU |
| 358 | CCTGGAATTA GAGGACAAAC | 11 18 | CCUGGAAUUAGAGGACAAACGUUUUAAGAGCUAAGCUGGAAACAGCAUAGCAAGUUUAAAU AAGGCUAGUCCGUUAUCAACUUGAAAAAGUGGCACCGAGUCGGUGCUUUUUUU |
| 359 | TCCTGGAATT AGAGGACAAA | 11 19 | UCCUGGAAUUAGAGGACAAAGUUUUAAGAGCUAAGCUGGAAACAGCAUAGCAAGUUUAAAU AAGGCUAGUCCGUUAUCAACUUGAAAAAGUGGCACCGAGUCGGUGCUUUUUUU |
| 360 | TACTAGTGCC ATTTGTTCAG | 11 20 | UACUAGUGCCAUUUGUUCAGGUUUUAAGAGCUAAGCUGGAAACAGCAUAGCAAGUUUAAAU AAGGCUAGUCCGUUAUCAACUUGAAAAAGUGGCACCGAGUCGGUGCUUUUUUU |
| 361 | CCATTTGTTC AGTGGTTCGT | 11 21 | CCAUUUGUUCAGUGGUUCGUGUUUUAAGAGCUAAGCUGGAAACAGCAUAGCAAGUUUAAAU AAGGCUAGUCCGUUAUCAACUUGAAAAAGUGGCACCGAGUCGGUGCUUUUUUU |
| 362 | CATTTGTTCA GTGGTTCGTA | 11 22 | CAUUUGUUCAGUGGUUCGUAGUUUUAAGAGCUAAGCUGGAAACAGCAUAGCAAGUUUAAAU AAGGCUAGUCCGUUAUCAACUUGAAAAAGUGGCACCGAGUCGGUGCUUUUUUU |
| 363 | CCTACGAACC ACTGAACAAA | 11 23 | CCUACGAACCACUGAACAAAGUUUUAAGAGCUAAGCUGGAAACAGCAUAGCAAGUUUAAAU AAGGCUAGUCCGUUAUCAACUUGAAAAAGUGGCACCGAGUCGGUGCUUUUUUU |

TABLE 12-continued

Exemplary gRNA sequences

| SEQ IDs | Target domain sequence | SEQ IDs | gRNA sequence |
|---------|------------------------|---------|---------------|
| 364 | TTTCAGTTAT ATGGATGATG | 11 24 | UUUCAGUUAUAUGGAUGAUGGUUUAAGAGCUAAGCUGGAAACAGCAUAGCAAGUUUAAAU AAGGCUAGUCCGUUAUCAACUUGAAAAAGUGGCACCGAGUCGGUGCUUUUUU |
| 365 | CAAAAGAAAA TTGGTAACAG | 11 25 | CAAAAGAAAAUUGGUAACAGGUUUAAGAGCUAAGCUGGAAACAGCAUAGCAAGUUUAAAU AAGGCUAGUCCGUUAUCAACUUGAAAAAGUGGCACCGAGUCGGUGCUUUUUU |
| 366 | TACCAATTTT CTTTTGTCTT | 11 26 | UACCAAUUUUCUUUUGUCUUGUUUAAGAGCUAAGCUGGAAACAGCAUAGCAAGUUUAAAU AAGGCUAGUCCGUUAUCAACUUGAAAAAGUGGCACCGAGUCGGUGCUUUUUU |
| 367 | ACCAATTTTC TTTTGTCTTT | 11 27 | ACCAAUUUUCUUUUGUCUUUGUUUAAGAGCUAAGCUGGAAACAGCAUAGCAAGUUUAAAU AAGGCUAGUCCGUUAUCAACUUGAAAAAGUGGCACCGAGUCGGUGCUUUUUU |
| 368 | ACCCAAAGAC AAAAGAAAAT | 11 28 | ACCCAAAGACAAAAGAAAAUGUUUAAGAGCUAAGCUGGAAACAGCAUAGCAAGUUUAAAU AAGGCUAGUCCGUUAUCAACUUGAAAAAGUGGCACCGAGUCGGUGCUUUUUU |
| 369 | TGACATACTT TCCAATCAAT | 11 29 | UGACAUACUUUCCAAUCAAUGUUUAAGAGCUAAGCUGGAAACAGCAUAGCAAGUUUAAAU AAGGCUAGUCCGUUAUCAACUUGAAAAAGUGGCACCGAGUCGGUGCUUUUUU |
| 370 | CACTTTCTCG CCAACTTACA | 11 30 | CACUUUCUCGCCAACUUACAGUUUAAGAGCUAAGCUGGAAACAGCAUAGCAAGUUUAAAU AAGGCUAGUCCGUUAUCAACUUGAAAAAGUGGCACCGAGUCGGUGCUUUUUU |
| 371 | CACAGAAAGG CCTTGTAAGT | 11 31 | CACAGAAAGGCCUUGUAAGUGUUUAAGAGCUAAGCUGGAAACAGCAUAGCAAGUUUAAAU AAGGCUAGUCCGUUAUCAACUUGAAAAAGUGGCACCGAGUCGGUGCUUUUUU |
| 372 | TGAACCTTTA CCCCGTTGCC | 11 32 | UGAACCUUUACCCCGUUGCCGUUUAAGAGCUAAGCUGGAAACAGCAUAGCAAGUUUAAAU AAGGCUAGUCCGUUAUCAACUUGAAAAAGUGGCACCGAGUCGGUGCUUUUUU |
| 373 | GGGCAACGGG GTAAAGGTTC | 11 33 | GGGCAACGGGGUAAAGGUUCGUUUAAGAGCUAAGCUGGAAACAGCAUAGCAAGUUUAAAU AAGGCUAGUCCGUUAUCAACUUGAAAAAGUGGCACCGAGUCGGUGCUUUUUU |
| 374 | TTTACCCCGT TGCCCGGCAA | 11 34 | UUUACCCCGUUGCCCGGCAAGUUUAAGAGCUAAGCUGGAAACAGCAUAGCAAGUUUAAAU AAGGCUAGUCCGUUAUCAACUUGAAAAAGUGGCACCGAGUCGGUGCUUUUUU |
| 375 | GTTGCCGGGC AACGGGGTAA | 11 35 | GUUGCCGGGCAACGGGGUAAGUUUAAGAGCUAAGCUGGAAACAGCAUAGCAAGUUUAAAU AAGGCUAGUCCGUUAUCAACUUGAAAAAGUGGCACCGAGUCGGUGCUUUUUU |
| 376 | CCCGTTGCCC GGCAACGGCC | 11 36 | CCCGUUGCCCGGCAACGGCCGUUUAAGAGCUAAGCUGGAAACAGCAUAGCAAGUUUAAAU AAGGCUAGUCCGUUAUCAACUUGAAAAAGUGGCACCGAGUCGGUGCUUUUUU |
| 377 | CTGGCCGTTG CCGGGCAACG | 11 37 | CUGGCCGUUGCCGGGCAACGGUUUAAGAGCUAAGCUGGAAACAGCAUAGCAAGUUUAAAU AAGGCUAGUCCGUUAUCAACUUGAAAAAGUGGCACCGAGUCGGUGCUUUUUU |
| 378 | CCTGGCCGTT GCCGGGCAAC | 11 38 | CCUGGCCGUUGCCGGGCAACGUUUAAGAGCUAAGCUGGAAACAGCAUAGCAAGUUUAAAU AAGGCUAGUCCGUUAUCAACUUGAAAAAGUGGCACCGAGUCGGUGCUUUUUU |
| 379 | ACCTGGCCGT TGCCGGGCAA | 11 39 | ACCUGGCCGUUGCCGGGCAAGUUUAAGAGCUAAGCUGGAAACAGCAUAGCAAGUUUAAAU AAGGCUAGUCCGUUAUCAACUUGAAAAAGUGGCACCGAGUCGGUGCUUUUUU |
| 380 | GCACAGACCT GGCCGTTGCC | 11 40 | GCACAGACCUGGCCGUUGCCGUUUAAGAGCUAAGCUGGAAACAGCAUAGCAAGUUUAAAU AAGGCUAGUCCGUUAUCAACUUGAAAAAGUGGCACCGAGUCGGUGCUUUUUU |
| 381 | GGCACAGACC TGGCCGTTGC | 11 41 | GGCACAGACCUGGCCGUUGCGUUUAAGAGCUAAGCUGGAAACAGCAUAGCAAGUUUAAAU AAGGCUAGUCCGUUAUCAACUUGAAAAAGUGGCACCGAGUCGGUGCUUUUUU |
| 382 | GCAAACACTT GGCACAGACC | 11 42 | GCAAACACUUGGCACAGACCGUUUAAGAGCUAAGCUGGAAACAGCAUAGCAAGUUUAAAU AAGGCUAGUCCGUUAUCAACUUGAAAAAGUGGCACCGAGUCGGUGCUUUUUU |
| 383 | GGGTTGCGTC AGCAAACACT | 11 43 | GGGUUGCGUCAGCAAACACUGUUUAAGAGCUAAGCUGGAAACAGCAUAGCAAGUUUAAAU AAGGCUAGUCCGUUAUCAACUUGAAAAAGUGGCACCGAGUCGGUGCUUUUUU |
| 384 | TTTGCTGACG CAACCCCCAC | 11 44 | UUUGCUGACGCAACCCCCACGUUUAAGAGCUAAGCUGGAAACAGCAUAGCAAGUUUAAAU AAGGCUAGUCCGUUAUCAACUUGAAAAAGUGGCACCGAGUCGGUGCUUUUUU |
| 385 | CTGACGCAAC CCCCACTGGC | 11 45 | CUGACGCAACCCCCACUGGCGUUUAAGAGCUAAGCUGGAAACAGCAUAGCAAGUUUAAAU AAGGCUAGUCCGUUAUCAACUUGAAAAAGUGGCACCGAGUCGGUGCUUUUUU |
| 386 | TGACGCAACC CCCACTGGCT | 11 46 | UGACGCAACCCCCACUGGCUGUUUAAGAGCUAAGCUGGAAACAGCAUAGCAAGUUUAAAU AAGGCUAGUCCGUUAUCAACUUGAAAAAGUGGCACCGAGUCGGUGCUUUUUU |
| 387 | GACGCAACCC CCACTGGCTG | 11 47 | GACGCAACCCCCACUGGCUGGUUUAAGAGCUAAGCUGGAAACAGCAUAGCAAGUUUAAAU AAGGCUAGUCCGUUAUCAACUUGAAAAAGUGGCACCGAGUCGGUGCUUUUUU |

TABLE 12-continued

Exemplary gRNA sequences

| SEQ IDs | Target domain sequence | SEQ IDs | gRNA sequence |
|---|---|---|---|
| 388 | AACCCCCACT GGCTGGGGCT | 11 48 | AACCCCCACUGGCUGGGGCUGUUUUAAGAGCUAAGCUGGAAACAGCAUAGCAAGUUUAAAU AAGGCUAGUCCGUUAUCAACUUGAAAAAGUGGCACCGAGUCGGUGCUUUUUU |
| 389 | TCCTCTGCCG ATCCATACTG | 11 49 | UCCUCUGCCGAUCCAUACUGGUUUUAAGAGCUAAGCUGGAAACAGCAUAGCAAGUUUAAAU AAGGCUAGUCCGUUAUCAACUUGAAAAAGUGGCACCGAGUCGGUGCUUUUUU |
| 390 | TCCGCAGTAT GGATCGGCAG | 11 50 | UCCGCAGUAUGGAUCGGCAGGUUUUAAGAGCUAAGCUGGAAACAGCAUAGCAAGUUUAAAU AAGGCUAGUCCGUUAUCAACUUGAAAAAGUGGCACCGAGUCGGUGCUUUUUU |
| 391 | AGGAGTTCCG CAGTATGGAT | 11 51 | AGGAGUUCCGCAGUAUGGAUGUUUUAAGAGCUAAGCUGGAAACAGCAUAGCAAGUUUAAAU AAGGCUAGUCCGUUAUCAACUUGAAAAAGUGGCACCGAGUCGGUGCUUUUUU |
| 392 | CGGCTAGGAG TTCCGCAGTA | 11 52 | CGGCUAGGAGUUCCGCAGUAGUUUUAAGAGCUAAGCUGGAAACAGCAUAGCAAGUUUAAAU AAGGCUAGUCCGUUAUCAACUUGAAAAAGUGGCACCGAGUCGGUGCUUUUUU |
| 393 | TGCGAGCAAA ACAAGCGGCT | 11 53 | UGCGAGCAAAACAAGCGGCUGUUUUAAGAGCUAAGCUGGAAACAGCAUAGCAAGUUUAAAU AAGGCUAGUCCGUUAUCAACUUGAAAAAGUGGCACCGAGUCGGUGCUUUUUU |
| 394 | CCGCTTGTTT TGCTCGCAGC | 11 54 | CCGCUUGUUUUGCUCGCAGCGUUUUAAGAGCUAAGCUGGAAACAGCAUAGCAAGUUUAAAU AAGGCUAGUCCGUUAUCAACUUGAAAAAGUGGCACCGAGUCGGUGCUUUUUU |
| 395 | CCTGCTGCGA GCAAAACAAG | 11 55 | CCUGCUGCGAGCAAAACAAGGUUUUAAGAGCUAAGCUGGAAACAGCAUAGCAAGUUUAAAU AAGGCUAGUCCGUUAUCAACUUGAAAAAGUGGCACCGAGUCGGUGCUUUUUU |
| 396 | TGTTTTGCTC GCAGCAGGTC | 11 56 | UGUUUUGCUCGCAGCAGGUCGUUUUAAGAGCUAAGCUGGAAACAGCAUAGCAAGUUUAAAU AAGGCUAGUCCGUUAUCAACUUGAAAAAGUGGCACCGAGUCGGUGCUUUUUU |
| 397 | GCAGCACAGC CTAGCAGCCA | 11 57 | GCAGCACAGCCUAGCAGCCAGUUUUAAGAGCUAAGCUGGAAACAGCAUAGCAAGUUUAAAU AAGGCUAGUCCGUUAUCAACUUGAAAAAGUGGCACCGAGUCGGUGCUUUUUU |
| 398 | TGCTAGGCTG TGCTGCCAAC | 11 58 | UGCUAGGCUGUGCUGCCAACGUUUUAAGAGCUAAGCUGGAAACAGCAUAGCAAGUUUAAAU AAGGCUAGUCCGUUAUCAACUUGAAAAAGUGGCACCGAGUCGGUGCUUUUUU |
| 399 | GCTGCCAACT GGATCCTGCG | 11 59 | GCUGCCAACUGGAUCCUGCGGUUUUAAGAGCUAAGCUGGAAACAGCAUAGCAAGUUUAAAU AAGGCUAGUCCGUUAUCAACUUGAAAAAGUGGCACCGAGUCGGUGCUUUUUU |
| 400 | CTGCCAACTG GATCCTGCGC | 11 60 | CUGCCAACUGGAUCCUGCGCGUUUUAAGAGCUAAGCUGGAAACAGCAUAGCAAGUUUAAAU AAGGCUAGUCCGUUAUCAACUUGAAAAAGUGGCACCGAGUCGGUGCUUUUUU |
| 401 | CGTCCCGCGC AGGATCCAGT | 11 61 | CGUCCCGCGCAGGAUCCAGUGUUUUAAGAGCUAAGCUGGAAACAGCAUAGCAAGUUUAAAU AAGGCUAGUCCGUUAUCAACUUGAAAAAGUGGCACCGAGUCGGUGCUUUUUU |
| 402 | AAACAAAGGA CGTCCCGCGC | 11 62 | AAACAAAGGACGUCCCGCGCGUUUUAAGAGCUAAGCUGGAAACAGCAUAGCAAGUUUAAAU AAGGCUAGUCCGUUAUCAACUUGAAAAAGUGGCACCGAGUCGGUGCUUUUUU |
| 403 | GTCCTTTGTT TACGTCCCGT | 11 63 | GUCCUUUGUUUACGUCCCGUGUUUUAAGAGCUAAGCUGGAAACAGCAUAGCAAGUUUAAAU AAGGCUAGUCCGUUAUCAACUUGAAAAAGUGGCACCGAGUCGGUGCUUUUUU |
| 404 | CGCCGACGGG ACGTAAACAA | 11 64 | CGCCGACGGGACGUAAACAAGUUUUAAGAGCUAAGCUGGAAACAGCAUAGCAAGUUUAAAU AAGGCUAGUCCGUUAUCAACUUGAAAAAGUGGCACCGAGUCGGUGCUUUUUU |
| 405 | TGCCGTTCCG ACCGACCACG | 11 65 | UGCCGUUCCGACCGACCACGGUUUUAAGAGCUAAGCUGGAAACAGCAUAGCAAGUUUAAAU AAGGCUAGUCCGUUAUCAACUUGAAAAAGUGGCACCGAGUCGGUGCUUUUUU |
| 406 | AGGTGCGCCC CGTGGTCGGT | 11 66 | AGGUGCGCCCCGUGGUCGGUGUUUUAAGAGCUAAGCUGGAAACAGCAUAGCAAGUUUAAAU AAGGCUAGUCCGUUAUCAACUUGAAAAAGUGGCACCGAGUCGGUGCUUUUUU |
| 407 | AGAGAGGTGC GCCCCGTGGT | 11 67 | AGAGAGGUGCGCCCCGUGGUGUUUUAAGAGCUAAGCUGGAAACAGCAUAGCAAGUUUAAAU AAGGCUAGUCCGUUAUCAACUUGAAAAAGUGGCACCGAGUCGGUGCUUUUUU |
| 408 | GTAAAGAGAG GTGCGCCCCG | 11 68 | GUAAAGAGAGGUGCGCCCCGGUUUUAAGAGCUAAGCUGGAAACAGCAUAGCAAGUUUAAAU AAGGCUAGUCCGUUAUCAACUUGAAAAAGUGGCACCGAGUCGGUGCUUUUUU |
| 409 | GGGGCGCACC TCTCTTTACG | 11 69 | GGGGCGCACCUCUCUUUACGGUUUUAAGAGCUAAGCUGGAAACAGCAUAGCAAGUUUAAAU AAGGCUAGUCCGUUAUCAACUUGAAAAAGUGGCACCGAGUCGGUGCUUUUUU |
| 410 | CGGGGAGTCC GCGTAAAGAG | 11 70 | CGGGGAGUCCGCGUAAAGAGGUUUUAAGAGCUAAGCUGGAAACAGCAUAGCAAGUUUAAAU AAGGCUAGUCCGUUAUCAACUUGAAAAAGUGGCACCGAGUCGGUGCUUUUUU |
| 411 | CAGATGAGAA GGCACAGACG | 11 71 | CAGAUGAGAAGGCACAGACGGUUUUAAGAGCUAAGCUGGAAACAGCAUAGCAAGUUUAAAU AAGGCUAGUCCGUUAUCAACUUGAAAAAGUGGCACCGAGUCGGUGCUUUUUU |
| 412 | GTCTGTGCCT TCTCATCTGC | 11 72 | GUCUGUGCCUUCUCAUCUGCGUUUUAAGAGCUAAGCUGGAAACAGCAUAGCAAGUUUAAAU AAGGCUAGUCCGUUAUCAACUUGAAAAAGUGGCACCGAGUCGGUGCUUUUUU |

TABLE 12-continued

Exemplary gRNA sequences

| SEQ IDs | Target domain sequence | SEQ IDs | gRNA sequence |
|---|---|---|---|
| 413 | GGCAGATGAG AAGGCACAGA | 11 73 | GGCAGAUGAGAAGGCACAGAGUUUAAGAGCUAAGCUGGAAACAGCAUAGCAAGUUUAAAU AAGGCUAGUCCGUUAUCAACUUGAAAAAGUGGCACCGAGUCGGUGCUUUUUU |
| 414 | GCAGATGAGA AGGCACAGAC | 11 74 | GCAGAUGAGAAGGCACAGACGUUUAAGAGCUAAGCUGGAAACAGCAUAGCAAGUUUAAAU AAGGCUAGUCCGUUAUCAACUUGAAAAAGUGGCACCGAGUCGGUGCUUUUUU |
| 415 | ACACGGTCCG GCAGATGAGA | 11 75 | ACACGGUCCGGCAGAUGAGAGUUUAAGAGCUAAGCUGGAAACAGCAUAGCAAGUUUAAAU AAGGCUAGUCCGUUAUCAACUUGAAAAAGUGGCACCGAGUCGGUGCUUUUUU |
| 416 | GAAGCGAAGT GCACACGGTC | 11 76 | GAAGCGAAGUGCACACGGUCGUUUAAGAGCUAAGCUGGAAACAGCAUAGCAAGUUUAAAU AAGGCUAGUCCGUUAUCAACUUGAAAAAGUGGCACCGAGUCGGUGCUUUUUU |
| 417 | GAGGTGAAGC GAAGTGCACA | 11 77 | GAGGUGAAGCGAAGUGCACAGUUUAAGAGCUAAGCUGGAAACAGCAUAGCAAGUUUAAAU AAGGCUAGUCCGUUAUCAACUUGAAAAAGUGGCACCGAGUCGGUGCUUUUUU |
| 418 | CTTCACCTCT GCACGTCGCA | 11 78 | CUUCACCUCUGCACGUCGCAGUUUAAGAGCUAAGCUGGAAACAGCAUAGCAAGUUUAAAU AAGGCUAGUCCGUUAUCAACUUGAAAAAGUGGCACCGAGUCGGUGCUUUUUU |
| 419 | GGTCTCCATG CGACGTGCAG | 11 79 | GGUCUCCAUGCGACGUGCAGGUUUAAGAGCUAAGCUGGAAACAGCAUAGCAAGUUUAAAU AAGGCUAGUCCGUUAUCAACUUGAAAAAGUGGCACCGAGUCGGUGCUUUUUU |
| 420 | TGCCCAAGGT CTTACATAAG | 11 80 | UGCCCAAGGUCUUACAUAAGGUUUAAGAGCUAAGCUGGAAACAGCAUAGCAAGUUUAAAU AAGGCUAGUCCGUUAUCAACUUGAAAAAGUGGCACCGAGUCGGUGCUUUUUU |
| 421 | GTCCTCTTAT GTAAGACCTT | 11 81 | GUCCUCUUAUGUAAGACCUUGUUUAAGAGCUAAGCUGGAAACAGCAUAGCAAGUUUAAAU AAGGCUAGUCCGUUAUCAACUUGAAAAAGUGGCACCGAGUCGGUGCUUUUUU |
| 422 | AGTCCTCTTA TGTAAGACCT | 11 82 | AGUCCUCUUAUGUAAGACCUGUUUAAGAGCUAAGCUGGAAACAGCAUAGCAAGUUUAAAU AAGGCUAGUCCGUUAUCAACUUGAAAAAGUGGCACCGAGUCGGUGCUUUUUU |
| 423 | GTCTTACATA AGAGGACTCT | 11 83 | GUCUUACAUAAGAGGACUCUGUUUAAGAGCUAAGCUGGAAACAGCAUAGCAAGUUUAAAU AAGGCUAGUCCGUUAUCAACUUGAAAAAGUGGCACCGAGUCGGUGCUUUUUU |
| 424 | AATGTCAACG ACCGACCTTG | 11 84 | AAUGUCAACGACCGACCUUGGUUUAAGAGCUAAGCUGGAAACAGCAUAGCAAGUUUAAAU AAGGCUAGUCCGUUAUCAACUUGAAAAAGUGGCACCGAGUCGGUGCUUUUUU |
| 425 | TTTGAAGTAT GCCTCAAGGT | 11 85 | UUUGAAGUAUGCCUCAAGGUGUUUAAGAGCUAAGCUGGAAACAGCAUAGCAAGUUUAAAU AAGGCUAGUCCGUUAUCAACUUGAAAAAGUGGCACCGAGUCGGUGCUUUUUU |
| 426 | AGTCTTTGAA GTATGCCTCA | 11 86 | AGUCUUUGAAGUAUGCCUCAGUUUAAGAGCUAAGCUGGAAACAGCAUAGCAAGUUUAAAU AAGGCUAGUCCGUUAUCAACUUGAAAAAGUGGCACCGAGUCGGUGCUUUUUU |
| 427 | AAGACTGTTT GTTTAAAGAC | 11 87 | AAGACUGUUUGUUUAAAGACGUUUAAGAGCUAAGCUGGAAACAGCAUAGCAAGUUUAAAU AAGGCUAGUCCGUUAUCAACUUGAAAAAGUGGCACCGAGUCGGUGCUUUUUU |
| 428 | AGACTGTTTG TTTAAAGACT | 11 88 | AGACUGUUUGUUUAAAGACUGUUUAAGAGCUAAGCUGGAAACAGCAUAGCAAGUUUAAAU AAGGCUAGUCCGUUAUCAACUUGAAAAAGUGGCACCGAGUCGGUGCUUUUUU |
| 429 | CTGTTTGTTT AAAGACTGGG | 11 89 | CUGUUUGUUUAAAGACUGGGGUUUAAGAGCUAAGCUGGAAACAGCAUAGCAAGUUUAAAU AAGGCUAGUCCGUUAUCAACUUGAAAAAGUGGCACCGAGUCGGUGCUUUUUU |
| 430 | GTTTAAAGAC TGGGAGGAGT | 11 90 | GUUUAAAGACUGGGAGGAGUGUUUAAGAGCUAAGCUGGAAACAGCAUAGCAAGUUUAAAU AAGGCUAGUCCGUUAUCAACUUGAAAAAGUGGCACCGAGUCGGUGCUUUUUU |
| 431 | TCTTTGTACT AGGAGGCTGT | 11 91 | UCUUUGUACUAGGAGGCUGUGUUUAAGAGCUAAGCUGGAAACAGCAUAGCAAGUUUAAAU AAGGCUAGUCCGUUAUCAACUUGAAAAAGUGGCACCGAGUCGGUGCUUUUUU |
| 432 | AGGAGGCTGT AGGCATAAAT | 11 92 | AGGAGGCUGUAGGCAUAAAUGUUUAAGAGCUAAGCUGGAAACAGCAUAGCAAGUUUAAAU AAGGCUAGUCCGUUAUCAACUUGAAAAAGUGGCACCGAGUCGGUGCUUUUUU |
| 433 | GTGAAAAAGT TGCATGGTGC | 11 93 | GUGAAAAAGUUGCAUGGUGCGUUUAAGAGCUAAGCUGGAAACAGCAUAGCAAGUUUAAAU AAGGCUAGUCCGUUAUCAACUUGAAAAAGUGGCACCGAGUCGGUGCUUUUUU |
| 434 | GCAGAGGTGA AAAAGTTGCA | 11 94 | GCAGAGGUGAAAAAGUUGCAGUUUAAGAGCUAAGCUGGAAACAGCAUAGCAAGUUUAAAU AAGGCUAGUCCGUUAUCAACUUGAAAAAGUGGCACCGAGUCGGUGCUUUUUU |
| 435 | AACAAGAGAT GATTAGGCAG | 11 95 | AACAAGAGAUGAUUAGGCAGGUUUAAGAGCUAAGCUGGAAACAGCAUAGCAAGUUUAAAU AAGGCUAGUCCGUUAUCAACUUGAAAAAGUGGCACCGAGUCGGUGCUUUUUU |
| 436 | GACATGAACA AGAGATGATT | 11 96 | GACAUGAACAAGAGAUGAUUGUUUAAGAGCUAAGCUGGAAACAGCAUAGCAAGUUUAAAU AAGGCUAGUCCGUUAUCAACUUGAAAAAGUGGCACCGAGUCGGUGCUUUUUU |

TABLE 12-continued

Exemplary gRNA sequences

| SEQ IDs | Target domain sequence | SEQ IDs | gRNA sequence |
|---|---|---|---|
| 437 | AGCTTGGAGG CTTGAACAGT | 11 97 | AGCUUGGAGGCUUGAACAGUGUUUUAAGAGCUAAGCUGGAAACAGCAUAGCAAGUUUAAAU AAGGCUAGUCCGUUAUCAACUUGAAAAAGUGGCACCGAGUCGGUGCUUUUUU |
| 438 | CAAGCCTCCA AGCTGTGCCT | 11 98 | CAAGCCUCCAAGCUGUGCCUGUUUUAAGAGCUAAGCUGGAAACAGCAUAGCAAGUUUAAAU AAGGCUAGUCCGUUAUCAACUUGAAAAAGUGGCACCGAGUCGGUGCUUUUUUU |
| 439 | AAGCCTCCAA GCTGTGCCTT | 11 99 | AAGCCUCCAAGCUGUGCCUUGUUUUAAGAGCUAAGCUGGAAACAGCAUAGCAAGUUUAAAU AAGGCUAGUCCGUUAUCAACUUGAAAAAGUGGCACCGAGUCGGUGCUUUUUUU |
| 440 | CCTCCAAGCT GTGCCTTGGG | 12 00 | CCUCCAAGCUGUGCCUUGGGGUUUUAAGAGCUAAGCUGGAAACAGCAUAGCAAGUUUAAAU AAGGCUAGUCCGUUAUCAACUUGAAAAAGUGGCACCGAGUCGGUGCUUUUUUU |
| 441 | CCACCCAAGG CACAGCTTGG | 12 01 | CCACCCAAGGCACAGCUUGGGUUUUAAGAGCUAAGCUGGAAACAGCAUAGCAAGUUUAAAU AAGGCUAGUCCGUUAUCAACUUGAAAAAGUGGCACCGAGUCGGUGCUUUUUUU |
| 442 | AGCTGTGCCT TGGGTGGCTT | 12 02 | AGCUGUGCCUUGGGUGGCUUGUUUUAAGAGCUAAGCUGGAAACAGCAUAGCAAGUUUAAAU AAGGCUAGUCCGUUAUCAACUUGAAAAAGUGGCACCGAGUCGGUGCUUUUUUU |
| 443 | AAGCCACCCA AGGCACAGCT | 12 03 | AAGCCACCCAAGGCACAGCUGUUUUAAGAGCUAAGCUGGAAACAGCAUAGCAAGUUUAAAU AAGGCUAGUCCGUUAUCAACUUGAAAAAGUGGCACCGAGUCGGUGCUUUUUUU |
| 444 | GCTGTGCCTT GGGTGGCTTT | 12 04 | GCUGUGCCUUGGGUGGCUUUGUUUUAAGAGCUAAGCUGGAAACAGCAUAGCAAGUUUAAAU AAGGCUAGUCCGUUAUCAACUUGAAAAAGUGGCACCGAGUCGGUGCUUUUUUU |
| 445 | CTGTGCCTTG GGTGGCTTTG | 12 05 | CUGUGCCUUGGGUGGCUUUGGUUUUAAGAGCUAAGCUGGAAACAGCAUAGCAAGUUUAAAU AAGGCUAGUCCGUUAUCAACUUGAAAAAGUGGCACCGAGUCGGUGCUUUUUUU |
| 446 | TAGCTCCAAA TTCTTTATAA | 12 06 | UAGCUCCAAAUUCUUUAUAAGUUUUAAGAGCUAAGCUGGAAACAGCAUAGCAAGUUUAAAU AAGGCUAGUCCGUUAUCAACUUGAAAAAGUGGCACCGAGUCGGUGCUUUUUUU |
| 447 | GTAGCTCCAA ATTCTTTATA | 12 07 | GUAGCUCCAAAUUCUUUAUAGUUUUAAGAGCUAAGCUGGAAACAGCAUAGCAAGUUUAAAU AAGGCUAGUCCGUUAUCAACUUGAAAAAGUGGCACCGAGUCGGUGCUUUUUUU |
| 448 | TAAAGAATTT GGAGCTACTG | 12 08 | UAAAGAAUUUGGAGCUACUGGUUUUAAGAGCUAAGCUGGAAACAGCAUAGCAAGUUUAAAU AAGGCUAGUCCGUUAUCAACUUGAAAAAGUGGCACCGAGUCGGUGCUUUUUUU |
| 449 | ATGACTCTAG CTACCTGGGT | 12 09 | AUGACUCUAGCUACCUGGGUGUUUUAAGAGCUAAGCUGGAAACAGCAUAGCAAGUUUAAAU AAGGCUAGUCCGUUAUCAACUUGAAAAAGUGGCACCGAGUCGGUGCUUUUUUU |
| 450 | CACATTTCTT GTCTCACTTT | 12 10 | CACAUUUCUUGUCUCACUUUGUUUUAAGAGCUAAGCUGGAAACAGCAUAGCAAGUUUAAAU AAGGCUAGUCCGUUAUCAACUUGAAAAAGUGGCACCGAGUCGGUGCUUUUUUU |
| 451 | TAGTTTCCGG AAGTGTTGAT | 12 11 | UAGUUUCCGGAAGUGUUGAUGUUUUAAGAGCUAAGCUGGAAACAGCAUAGCAAGUUUAAAU AAGGCUAGUCCGUUAUCAACUUGAAAAAGUGGCACCGAGUCGGUGCUUUUUUU |
| 452 | CGTCTAACAA CAGTAGTTTC | 12 12 | CGUCUAACAACAGUAGUUUCGUUUUAAGAGCUAAGCUGGAAACAGCAUAGCAAGUUUAAAU AAGGCUAGUCCGUUAUCAACUUGAAAAAGUGGCACCGAGUCGGUGCUUUUUUU |
| 453 | ACTACTGTTG TTAGACGACG | 12 13 | ACUACUGUUGUUAGACGACGGUUUUAAGAGCUAAGCUGGAAACAGCAUAGCAAGUUUAAAU AAGGCUAGUCCGUUAUCAACUUGAAAAAGUGGCACCGAGUCGGUGCUUUUUUU |
| 454 | CTGTTGTTAG ACGACGAGGC | 12 14 | CUGUUGUUAGACGACGAGGCGUUUUAAGAGCUAAGCUGGAAACAGCAUAGCAAGUUUAAAU AAGGCUAGUCCGUUAUCAACUUGAAAAAGUGGCACCGAGUCGGUGCUUUUUUU |
| 455 | CGAGGGAGTT CTTCTTCTAG | 12 15 | CGAGGGAGUUCUUCUUCUAGGUUUUAAGAGCUAAGCUGGAAACAGCAUAGCAAGUUUAAAU AAGGCUAGUCCGUUAUCAACUUGAAAAAGUGGCACCGAGUCGGUGCUUUUUUU |
| 456 | GCGAGGGAGT TCTTCTTCTA | 12 16 | GCGAGGGAGUUCUUCUUCUAGUUUUAAGAGCUAAGCUGGAAACAGCAUAGCAAGUUUAAAU AAGGCUAGUCCGUUAUCAACUUGAAAAAGUGGCACCGAGUCGGUGCUUUUUUU |
| 457 | GGCGAGGGAG TTCTTCTTCT | 12 17 | GGCGAGGGAGUUCUUCUUCUGUUUUAAGAGCUAAGCUGGAAACAGCAUAGCAAGUUUAAAU AAGGCUAGUCCGUUAUCAACUUGAAAAAGUGGCACCGAGUCGGUGCUUUUUUU |
| 458 | CTCCCTCGCC TCGCAGACGA | 12 18 | CUCCCUCGCCUCGCAGACGAGUUUUAAGAGCUAAGCUGGAAACAGCAUAGCAAGUUUAAAU AAGGCUAGUCCGUUAUCAACUUGAAAAAGUGGCACCGAGUCGGUGCUUUUUUU |
| 459 | GACCTTCGTC TGCGAGGCGA | 12 19 | GACCUUCGUCUGCGAGGCGAGUUUUAAGAGCUAAGCUGGAAACAGCAUAGCAAGUUUAAAU AAGGCUAGUCCGUUAUCAACUUGAAAAAGUGGCACCGAGUCGGUGCUUUUUUU |
| 460 | AGACCTTCGT CTGCGAGGCG | 12 20 | AGACCUUCGUCUGCGAGGCGGUUUUAAGAGCUAAGCUGGAAACAGCAUAGCAAGUUUAAAU AAGGCUAGUCCGUUAUCAACUUGAAAAAGUGGCACCGAGUCGGUGCUUUUUUU |
| 461 | GATTGAGACC TTCGTCTGCG | 12 21 | GAUUGAGACCUUCGUCUGCGGUUUUAAGAGCUAAGCUGGAAACAGCAUAGCAAGUUUAAAU AAGGCUAGUCCGUUAUCAACUUGAAAAAGUGGCACCGAGUCGGUGCUUUUUUU |

TABLE 12-continued

Exemplary gRNA sequences

| SEQ IDs | Target domain sequence | SEQ IDs | gRNA sequence |
|---|---|---|---|
| 462 | GATTGAGATC TTCTGCGACG | 12 22 | GAUUGAGAUCUUCUGCGACGGUUUUAAGAGCUAAGCUGGAAACAGCAUAGCAAGUUUAAAU AAGGCUAGUCCGUUAUCAACUUGAAAAAGUGGCACCGAGUCGGUGCUUUUUU |
| 463 | GTCGCAGAAG ATCTCAATCT | 12 23 | GUCGCAGAAGAUCUCAAUCUGUUUUAAGAGCUAAGCUGGAAACAGCAUAGCAAGUUUAAAU AAGGCUAGUCCGUUAUCAACUUGAAAAAGUGGCACCGAGUCGGUGCUUUUUU |
| 464 | TCGCAGAAGA TCTCAATCTC | 12 24 | UCGCAGAAGAUCUCAAUCUCGUUUUAAGAGCUAAGCUGGAAACAGCAUAGCAAGUUUAAAU AAGGCUAGUCCGUUAUCAACUUGAAAAAGUGGCACCGAGUCGGUGCUUUUUU |
| 465 | ATATGGTGAC CCACAAAATG | 12 25 | AUAUGGUGACCCACAAAAUGGUUUUAAGAGCUAAGCUGGAAACAGCAUAGCAAGUUUAAAU AAGGCUAGUCCGUUAUCAACUUGAAAAAGUGGCACCGAGUCGGUGCUUUUUU |
| 466 | TTTGTGGGTC ACCATATTCT | 12 26 | UUUGUGGGUCACCAUAUUCUGUUUUAAGAGCUAAGCUGGAAACAGCAUAGCAAGUUUAAAU AAGGCUAGUCCGUUAUCAACUUGAAAAAGUGGCACCGAGUCGGUGCUUUUUU |
| 467 | TTGTGGGTCA CCATATTCTT | 12 27 | UUGUGGGUCACCAUAUUCUUGUUUUAAGAGCUAAGCUGGAAACAGCAUAGCAAGUUUAAAU AAGGCUAGUCCGUUAUCAACUUGAAAAAGUGGCACCGAGUCGGUGCUUUUUU |
| 468 | GCTGGATCCA ACTGGTGGTC | 12 28 | GCUGGAUCCAACUGGUGGUCGUUUUAAGAGCUAAGCUGGAAACAGCAUAGCAAGUUUAAAU AAGGCUAGUCCGUUAUCAACUUGAAAAAGUGGCACCGAGUCGGUGCUUUUUU |
| 469 | CACCCCAAAA GGCCTCCGTG | 12 29 | CACCCCAAAAGGCCUCCGUGGUUUUAAGAGCUAAGCUGGAAACAGCAUAGCAAGUUUAAAU AAGGCUAGUCCGUUAUCAACUUGAAAAAGUGGCACCGAGUCGGUGCUUUUUU |
| 470 | CCTTTTGGGG TGGAGCCCTC | 12 30 | CCUUUUGGGGUGGAGCCCUCGUUUUAAGAGCUAAGCUGGAAACAGCAUAGCAAGUUUAAAU AAGGCUAGUCCGUUAUCAACUUGAAAAAGUGGCACCGAGUCGGUGCUUUUUU |
| 471 | CCTGAGGGCT CCACCCCAAA | 12 31 | CCUGAGGGCUCCACCCCAAAGUUUUAAGAGCUAAGCUGGAAACAGCAUAGCAAGUUUAAAU AAGGCUAGUCCGUUAUCAACUUGAAAAAGUGGCACCGAGUCGGUGCUUUUUU |
| 472 | GGGGTGGAGC CCTCAGGCTC | 12 32 | GGGGUGGAGCCCUCAGGCUCGUUUUAAGAGCUAAGCUGGAAACAGCAUAGCAAGUUUAAAU AAGGCUAGUCCGUUAUCAACUUGAAAAAGUGGCACCGAGUCGGUGCUUUUUU |
| 473 | GGGTGGAGCC CTCAGGCTCA | 12 33 | GGGUGGAGCCCUCAGGCUCAGUUUUAAGAGCUAAGCUGGAAACAGCAUAGCAAGUUUAAAU AAGGCUAGUCCGUUAUCAACUUGAAAAAGUGGCACCGAGUCGGUGCUUUUUU |
| 474 | CGATTGGTGG AGGCAGGAGG | 12 34 | CGAUUGGUGGAGGCAGGAGGGUUUUAAGAGCUAAGCUGGAAACAGCAUAGCAAGUUUAAAU AAGGCUAGUCCGUUAUCAACUUGAAAAAGUGGCACCGAGUCGGUGCUUUUUU |
| 475 | CTCATCCTCA GGCCATGCAG | 12 35 | CUCAUCCUCAGGCCAUGCAGGUUUUAAGAGCUAAGCUGGAAACAGCAUAGCAAGUUUAAAU AAGGCUAGUCCGUUAUCAACUUGAAAAAGUGGCACCGAGUCGGUGCUUUUUU |

TABLE 13

Exemplary target domain sequences and effect on HbeAg and HbsAg expression

| SEQ IDs | Associated guide RNA name (if applicable) | Target domain sequence | HbeAg (% expression of non targeting control) | HbsAg (% expression of non targeting control) |
|---|---|---|---|---|
| 334 | gRNA#001 | CTGAACTGGAGCCACCAGCA | 27.77203753 | 23.4507853 |
| 335 | gRNA#002 | CCTGAACTGGAGCCACCAGC | 41.3794605 | 42.3814023 |
| 333 | | CCTGCTGGTGGCTCCAGTTC | 65.36067834 | 43.2303179 |
| 336 | | CCTCGAGAAGATTGACGATA | 82.8943107 | 72.648219 |
| 337 | | TCGTCAATCTTCTCGAGGAT | 45.82985382 | 59.7223204 |
| 338 | | CGTCAATCTTCTCGAGGATT | 70.38176383 | 73.1313979 |
| 339 | | GTCAATCTTCTCGAGGATTG | 51.92713248 | 54.330978 |
| 340 | | AACATGGAGAACATCACATC | 79.31612772 | 80.8981286 |
| 341 | | AACATCACATCAGGATTCCT | 41.40633262 | 37.5509299 |
| 342 | | CTAGACTCTGCGGTATTGTG | 48.56267424 | 41.5330827 |
| 345 | gRNA#003 | CACCACGAGTCTAGACTCTG | 44.43853541 | 40.8553881 |
| 343 | | TACCGCAGAGTCTAGACTCG | 49.18078863 | 56.151898 |
| 344 | | CGCAGAGTCTAGACTCGTGG | 52.41583101 | 57.2264647 |
| 346 | | TGGACTTCTCTCAATTTTCT | 49.58564481 | 51.1350719 |
| 347 | | GGACTTCTCTCAATTTTCTA | 76.16671739 | 79.1684976 |
| 348 | | GACTTCTCTCAATTTTCTAG | 49.79317156 | 54.1540479 |
| 349 | | ACTTCTCTCAATTTTCTAGG | 69.66968253 | 77.4650531 |

TABLE 13-continued

Exemplary target domain sequences and effect on HbeAg and HbsAg expression

| SEQ IDs | Associated guide RNA name (if applicable) | Target domain sequence | HbeAg (% expression of non targeting control) | HbsAg (% expression of non targeting control) |
|---|---|---|---|---|
| 350 | | CGAATTTTGGCCAAGACACA | 53.53282063 | 54.0024954 |
| 371 | gRNA#004 | CACAGAAAGGCCTTGTAAGT | 42.35590319 | 41.6928086 |
| 370 | | CACTTTCTCGCCAACTTACA | 53.25960148 | 55.120666 |
| 373 | gRNA#005 | GGGCAACGGGGTAAAGGTTC | 36.54111842 | 42.8120918 |
| 375 | gRNA#006 | GTTGCCGGGCAACGGGGTAA | 41.20322042 | 38.1885911 |
| 377 | | CTGGCCGTTGCCGGGCAACG | 57.27834882 | 60.830473 |
| 372 | | TGAACCTTTACCCCGTTGCC | 48.16509881 | 60.952804 |
| 378 | | CCTGGCCGTTGCCGGGCAAC | 56.34234102 | 65.50842 |
| 379 | | ACCTGGCCGTTGCCGGGCAA | 54.10829257 | 53.324749 |
| 374 | | TTTACCCCGTTGCCCGGCAA | 56.72089131 | 62.6906255 |
| 380 | | GCACAGACCTGGCCGTTGCC | 42.46818432 | 47.3720079 |
| 381 | | GGCACAGACCTGGCCGTTGC | 72.65381719 | 77.2400091 |
| 376 | | CCCGTTGCCCGGCAACGGCC | 50.93018919 | 61.086777 |
| 382 | | GCAAACACTTGGCACAGACC | 57.0196485 | 69.491449 |
| 383 | | GGGTTGCGTCAGCAAACACT | 49.73518831 | 54.7510029 |
| 384 | | TTTGCTGACGCAACCCCCAC | 41.79724731 | 50.0362297 |
| 385 | | CTGACGCAACCCCCACTGGC | 36.90727137 | 36.8247762 |
| 386 | | TGACGCAACCCCCACTGGCT | 46.49501492 | 59.6959921 |
| 387 | | GACGCAACCCCCACTGGCTG | 40.09200943 | 51.4756937 |
| 388 | | AACCCCCACTGGCTGGGGCT | 61.82883278 | 79.8761795 |
| 390 | gRNA#007 | TCCGCAGTATGGATCGGCAG | 26.33655968 | 33.7255842 |
| 391 | gRNA#008 | AGGAGTTCCGCAGTATGGAT | 28.49512897 | 40.080391 |
| 389 | gRNA#009 | TCCTCTGCCGATCCATACTG | 28.45399116 | 42.735093 |
| 392 | | CGGCTAGGAGTTCCGCAGTA | 56.5241517 | 66.9060644 |
| 393 | gRNA#010 | TGCGAGCAAAACAAGCGGCT | 41.5479747 | 40.5350018 |
| 395 | | CCTGCTGCGAGCAAAACAAG | 36.4525077 | 50.516964 |
| 394 | | CCGCTTGTTTTGCTCGCAGC | 108.4014077 | 90.5082399 |
| 396 | | TGTTTTGCTCGCAGCAGGTC | 68.78508191 | 75.7537996 |
| 397 | | GCAGCACAGCCTAGCAGCCA | 78.73231487 | 68.3785588 |
| 398 | | TGCTAGGCTGTGCTGCCAAC | 59.52249922 | 69.0333267 |
| 401 | | CGTCCCGCGCAGGATCCAGT | 52.51634701 | 49.5876502 |
| 399 | | GCTGCCAACTGGATCCTGCG | 75.81794218 | 89.0162904 |
| 400 | | CTGCCAACTGGATCCTGCGC | 77.79441236 | 73.9461516 |
| 402 | | AAACAAAGGACGTCCCGCGC | 67.52500576 | 72.6685954 |
| 404 | | CGCCGACGGGACGTAAACAA | 77.77475148 | 70.288774 |
| 403 | | GTCCTTTGTTTACGTCCCGT | 94.99070926 | 103.867949 |
| 406 | | AGGTGCGCCCCGTGGTCGGT | 68.80565242 | 65.4335257 |
| 407 | | AGAGAGGTGCGCCCCGTGGT | 42.18514493 | 55.1199635 |
| 408 | | GTAAAGAGAGGTGCGCCCCG | 53.39922155 | 55.7151401 |
| 410 | | CGGGGAGTCCGCGTAAAGAG | 52.63946411 | 66.9249801 |
| 409 | | GGGGCGCACCTCTCTTTACG | 72.81702761 | 66.4993545 |
| 411 | gRNA#011 | CAGATGAGAAGGCACAGACG | 32.31425506 | 44.762352 |
| 413 | | GGCAGATGAGAAGGCACAGA | 59.89738685 | 59.5785052 |
| 415 | | ACACGGTCCGGCAGATGAGA | 41.29188182 | 52.515655 |
| 412 | | GTCTGTGCCTTCTCATCTGC | 70.71073836 | 72.0049046 |
| 416 | | GAAGCGAAGTGCACACGGTC | 31.51588976 | 59.2847924 |
| 417 | | GAGGTGAAGCGAAGTGCACA | 53.23795933 | 54.7085711 |
| 419 | | GGTCTCCATCGCGACGTGCA | 98.80315853 | 94.871871 |
| 418 | | CTTCACCTCTGCACGTCGCA | 76.66072308 | 76.4195077 |
| 421 | | GTCCTCTTATGTAAGACCTT | 50.06169791 | 63.8903663 |
| 422 | | AGTCCTCTTATGTAAGACCT | 54.84793515 | 62.0058784 |
| 420 | | TGCCCAAGGTCTTACATAAG | 65.64906417 | 79.7359246 |
| 423 | | GTCTTACATAAGAGGACTCT | 65.0201597 | 62.5458243 |
| 424 | | AATGTCAACGACCGACCTTG | 53.64938718 | 65.5805852 |
| 425 | | TTTGAAGTATGCCTCAAGGT | 68.9199506 | 80.763234 |
| 426 | gRNA#012 | AGTCTTTGAAGTATGCCTCA | 30.45840615 | 47.6679105 |
| 427 | | AAGACTGTTTGTTTAAAGAC | 75.19137394 | 74.1370789 |
| 428 | | AGACTGTTTGTTTAAAGACT | 66.21290133 | 75.2309845 |
| 429 | | CTGTTTGTTTAAAGACTGGG | 63.52924235 | 72.0972239 |
| 430 | | GTTTAAAGACTGGGAGGAGT | 52.01423199 | 66.8961386 |
| 431 | | TCTTTGTACTAGGAGGCTGT | 51.48581844 | 68.9533809 |
| 432 | | AGGAGGCTGTAGGCATAAAT | 37.69681736 | 56.2655965 |
| 433 | | GTGAAAAAGTTGCATGGTGC | 82.88524703 | 98.0043703 |
| 434 | | GCAGAGGTGAAAAAGTTGCA | 31.73533955 | 53.6210823 |

TABLE 13-continued

Exemplary target domain sequences and effect on HbeAg and HbsAg expression

| SEQ IDs | Associated guide RNA name (if applicable) | Target domain sequence | HbeAg (% expression of non targeting control) | HbsAg (% expression of non targeting control) |
|---|---|---|---|---|
| 435 | gRNA#013 | AACAAGAGATGATTAGGCAG | 30.51551968 | 43.8402184 |
| 436 | gRNA#014 | GACATGAACAAGAGATGATT | 15.37394867 | 25.9017005 |
| 437 | | AGCTTGGAGGCTTGAACAGT | 84.06388656 | 100.433196 |
| 441 | gRNA#015 | CCACCCAAGGCACAGCTTGG | 22.57628478 | 29.4502561 |
| 443 | | AAGCCACCCAAGGCACAGCT | 38.69686132 | 57.447646 |
| 438 | | CAAGCCTCCAAGCTGTGCCT | 57.03790348 | 55.3144232 |
| 439 | | AAGCCTCCAAGCTGTGCCTT | 101.2197916 | 108.433992 |
| 442 | | AGCTGTGCCTTGGGTGGCTT | 62.50798441 | 75.5245296 |
| 444 | | GCTGTGCCTTGGGTGGCTTT | 63.60985011 | 68.2127614 |
| 445 | | CTGTGCCTTGGGTGGCTTTG | 58.80930094 | 60.2093595 |
| 446 | | TAGCTCCAAATTCTTTATAA | 81.50792369 | 102.062484 |
| 447 | | GTAGCTCCAAATTCTTTATA | 57.5300482 | 84.4089935 |
| 448 | | TAAAGAATTTGGAGCTACTG | 55.34840957 | 67.1682598 |
| 449 | | ATGACTCTAGCTACCTGGGT | 70.72899714 | 69.314819 |
| 450 | | CACATTTCTTGTCTCACTTT | 135.7647935 | 119.430868 |
| 451 | | TAGTTTCCGGAAGTGTTGAT | 52.38647155 | 59.8621336 |
| 452 | | CGTCTAACAACAGTAGTTTC | 84.81350809 | 79.1119745 |
| 453 | | ACTACTGTTGTTAGACGACG | 50.34753433 | 57.5139945 |
| 454 | | CTGTTGTTAGACGACGAGGC | 47.03375963 | 53.0434947 |
| 455 | | CGAGGGAGTTCTTCTTCTAG | 36.81318989 | 50.1844755 |
| 456 | | GCGAGGGAGTTCTTCTTCTA | 68.04429109 | 71.2738682 |
| 457 | gRNA#016 | GGCGAGGGAGTTCTTCTTCT | 35.40374342 | 49.4263836 |
| 459 | | GACCTTCGTCTGCGAGGCGA | 28.35732375 | 53.108582 |
| 460 | | AGACCTTCGTCTGCGAGGCG | 41.45363172 | 58.2048965 |
| 461 | | GATTGAGACCTTCGTCTGCG | 63.13599738 | 73.3793991 |
| 458 | | CTCCCTCGCCTCGCAGACGA | 41.73812486 | 56.4066766 |
| 462 | | GATTGAGATCTTCTGCGACG | 134.1434937 | 133.039909 |
| 463 | | GTCGCAGAAGATCTCAATCT | 44.87633493 | 58.0732445 |
| 464 | | TCGCAGAAGATCTCAATCTC | 70.59684886 | 75.0458487 |
| 465 | gRNA#017 | ATATGGTGACCCACAAAATG | 41.36374656 | 46.043276 |
| 466 | | TTTGTGGGTCACCATATTCT | 66.33644682 | 65.6466534 |
| 467 | gRNA#018 | TTGTGGGTCACCATATTCTT | 48.06595023 | 41.7714626 |
| 468 | | GCTGGATCCAACTGGTGGTC | 65.83430344 | 69.3357339 |
| 469 | | CACCCCAAAAGGCCTCCGTG | 21.63462413 | 23.5507547 |
| 471 | gRNA#019 | CCTGAGGGCTCCACCCCAAA | 45.40727826 | 44.6869573 |
| 470 | | CCTTTTGGGGTGGAGCCCTC | 50.06807456 | 31.73417 |
| 472 | | GGGGTGGAGCCCTCAGGCTC | 64.29444481 | 64.1755302 |
| 473 | | GGGTGGAGCCCTCAGGCTCA | 44.19826805 | 53.1051257 |
| 474 | | CGATTGGTGGAGGCAGGAGG | 65.52555289 | 60.9306557 |
| 475 | gRNA#020 | CTCATCCTCAGGCCATGCAG | 35.40063237 | 17.5286587 |

Figure 5A:
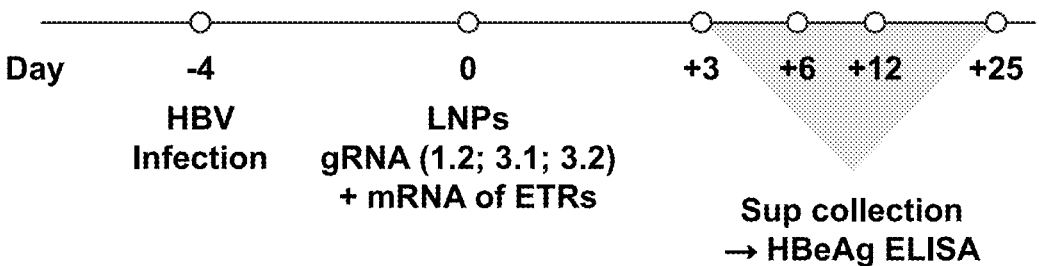
FIG. 5A is a diagram describing the experimental timeline for testing different CRISPR-based epigenetic repressors in a HepG2-NTCP infection model (see, e.g., Methods Mol Biol. 2017; 1540:1-14).
Figure 5B:
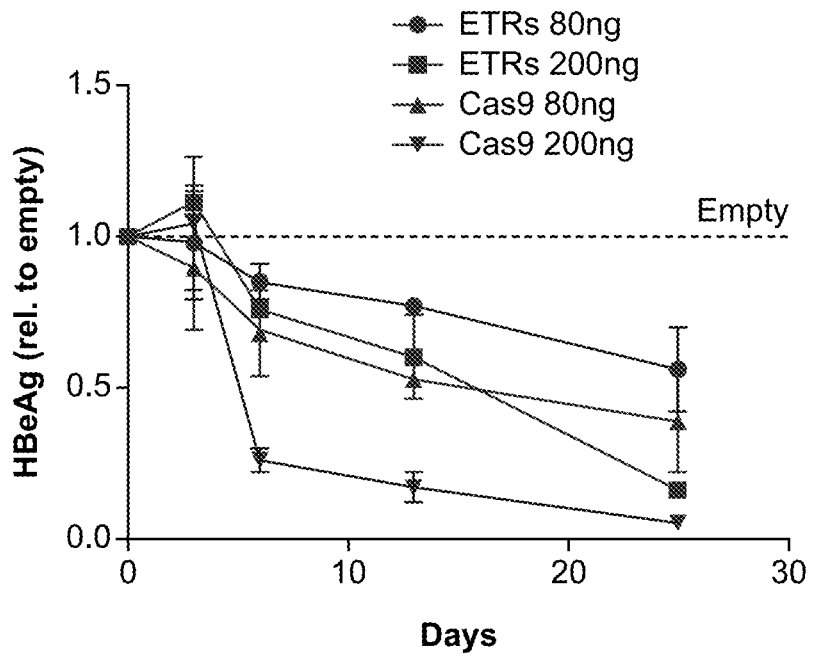
FIG. 5B is a diagram showing the expression of HBe antigen (via ELISA) at different times after treatment of HBV-infected Hep2G-NTCT cells with different doses of CRISPR-based epigenetic repressors (ETRs), or with different doses of Cas9 nuclease targeting HBV (Cas9), plotted normalized to the expression value of HBe antigen measured for a negative control (empty).
Figure 6:
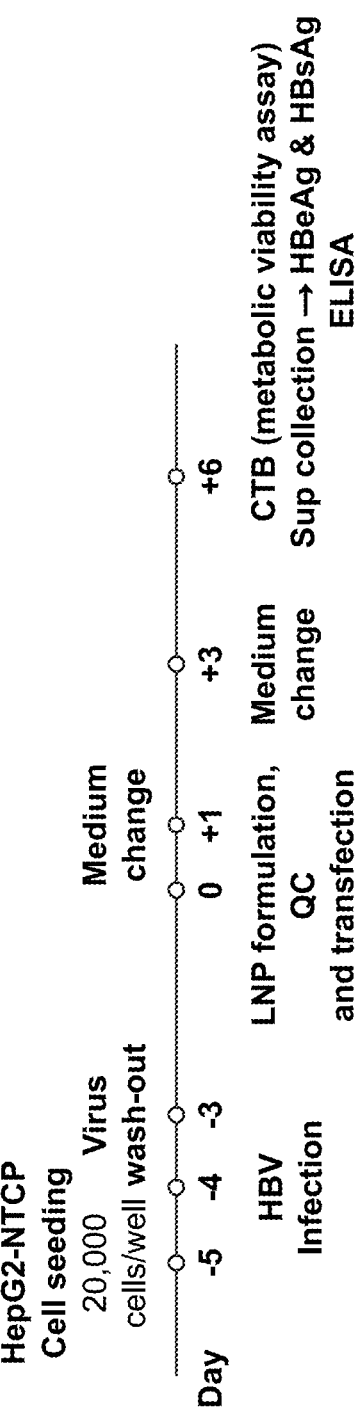
FIG. 6 is a diagram describing the experimental timeline for a guide RNA screen testing different CRISPR-based epigenetic repressor systems in a HepG2-NTCP infection model with ELISA readout for HBe and HBs antigens at day 6.
Figure 7:
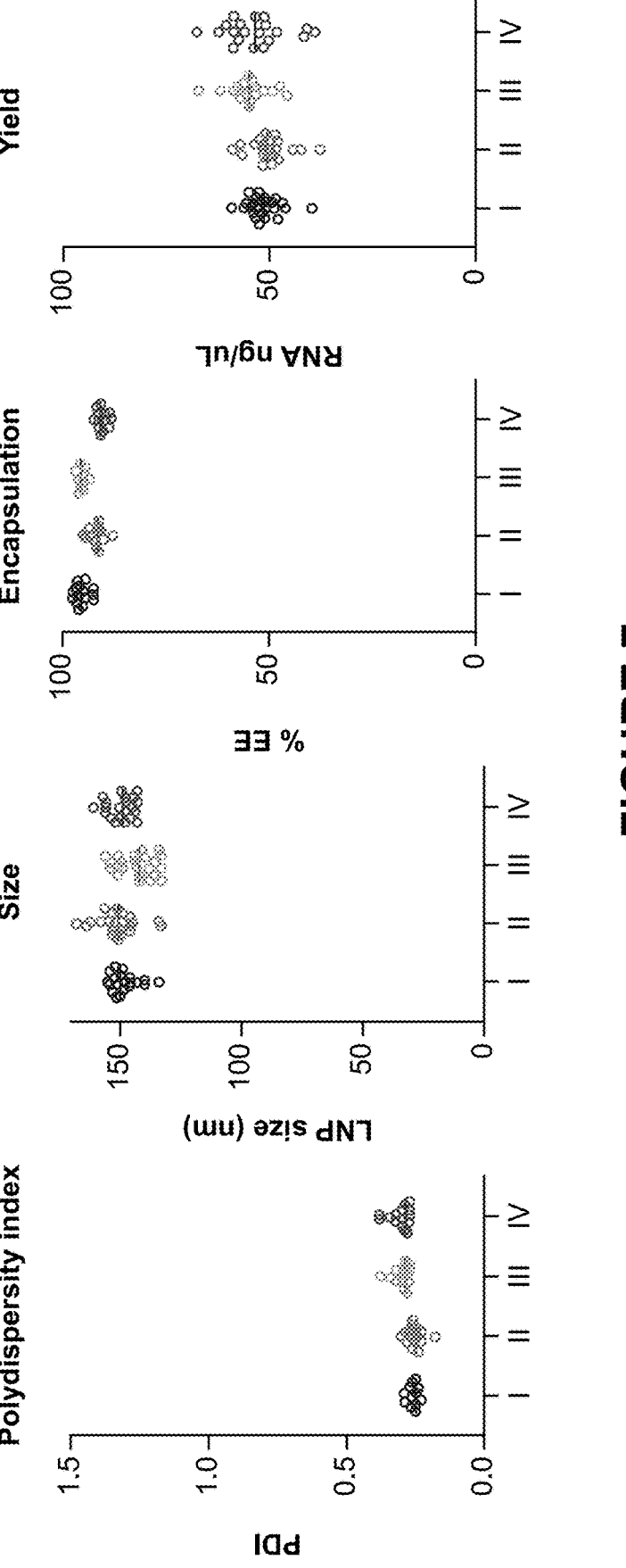
FIG. 7 is a diagram showing QC results from different LNP batches used in the guide screen.
Figure 8:
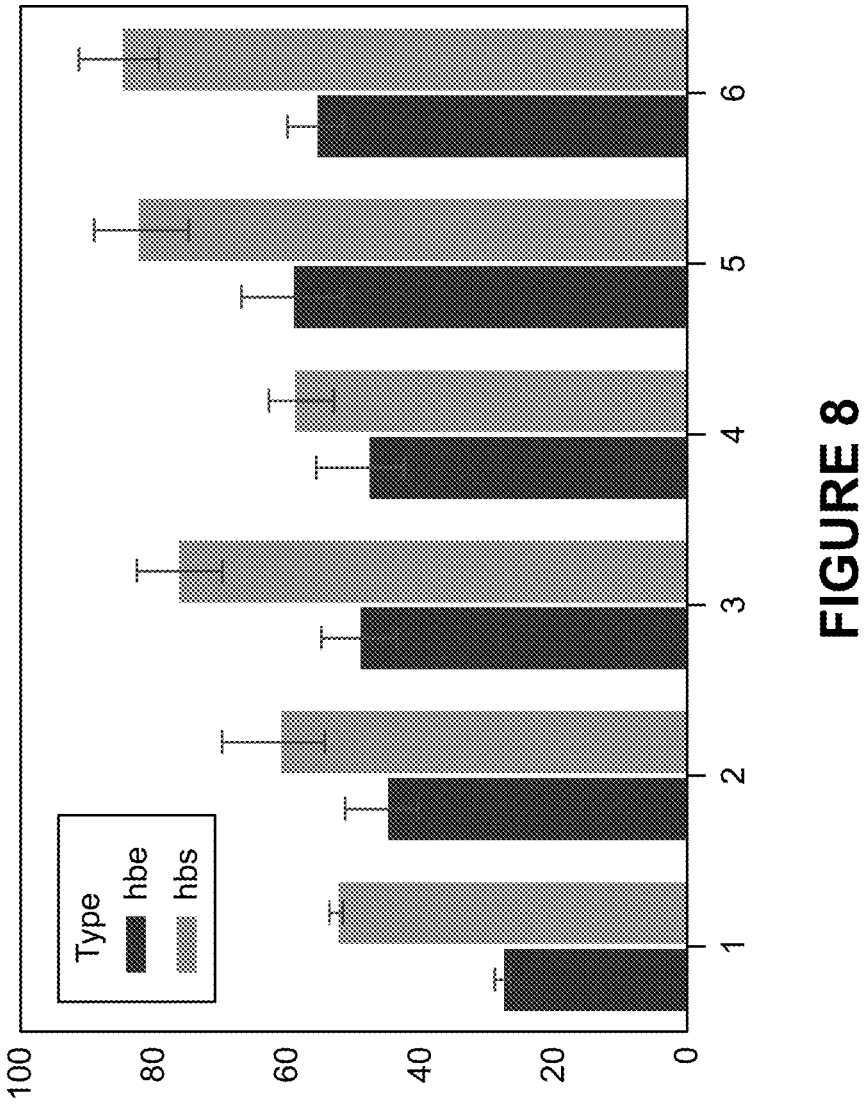
FIG. 8 is a bar graph showing the expression of HBe and HBs for an exemplary CRISPR-based epigenetic repressor (#3.2), calculated as the percentage of the expression of the respective antigen measured for a non-targeting control.
Figure 9:
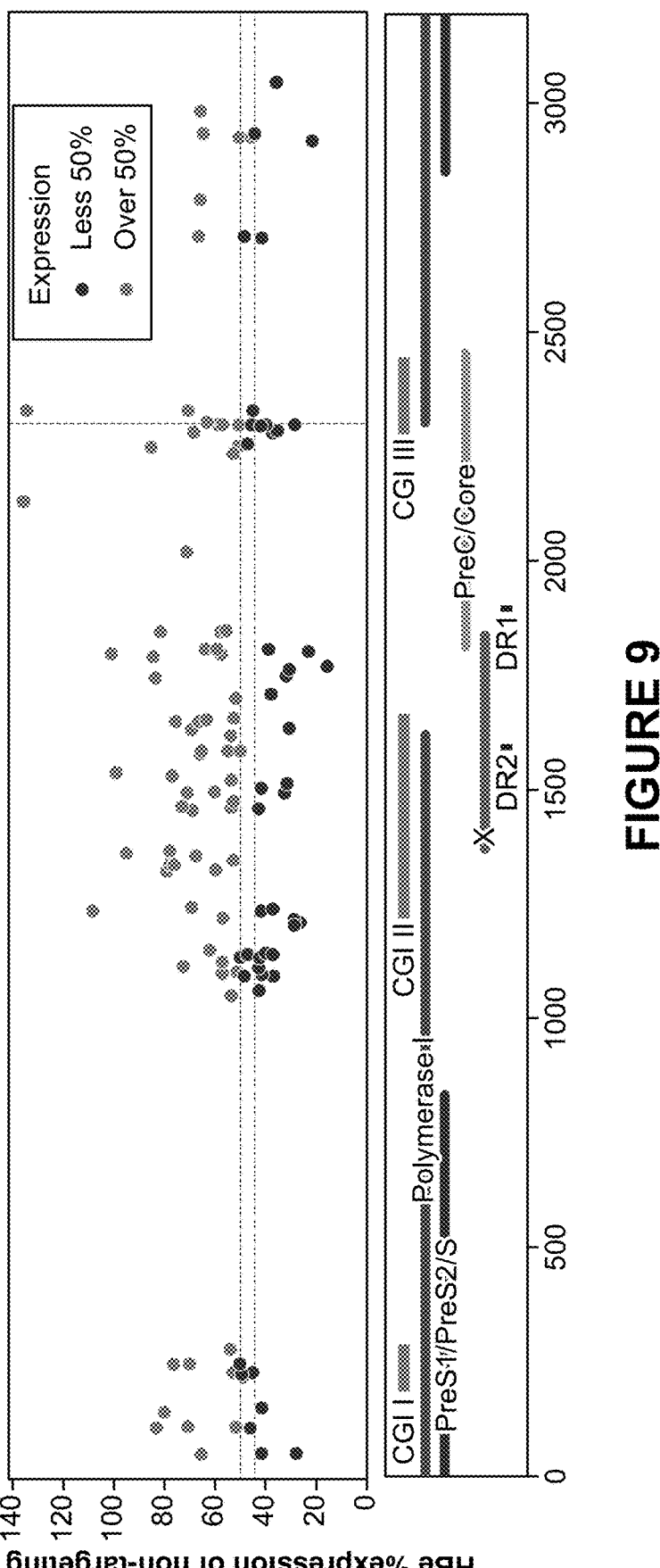
FIG. 9 is a diagram showing HBe expression values measured in the guide RNA screen for different guides (calculated as a percentage of the expression of HBe measured for a non-targeting control). Each guide/repressor combination is represented by a dot. A 50% repression cutoff is shown as a horizontal line. The position of the respective guide RNA within the HBV genome (shown at the bottom of the graph) is mapped on the X-axis. The position and the measured modulation of HBe expression for exemplary guide RNA #3.2 is indicated by red lines.
Figure 10:
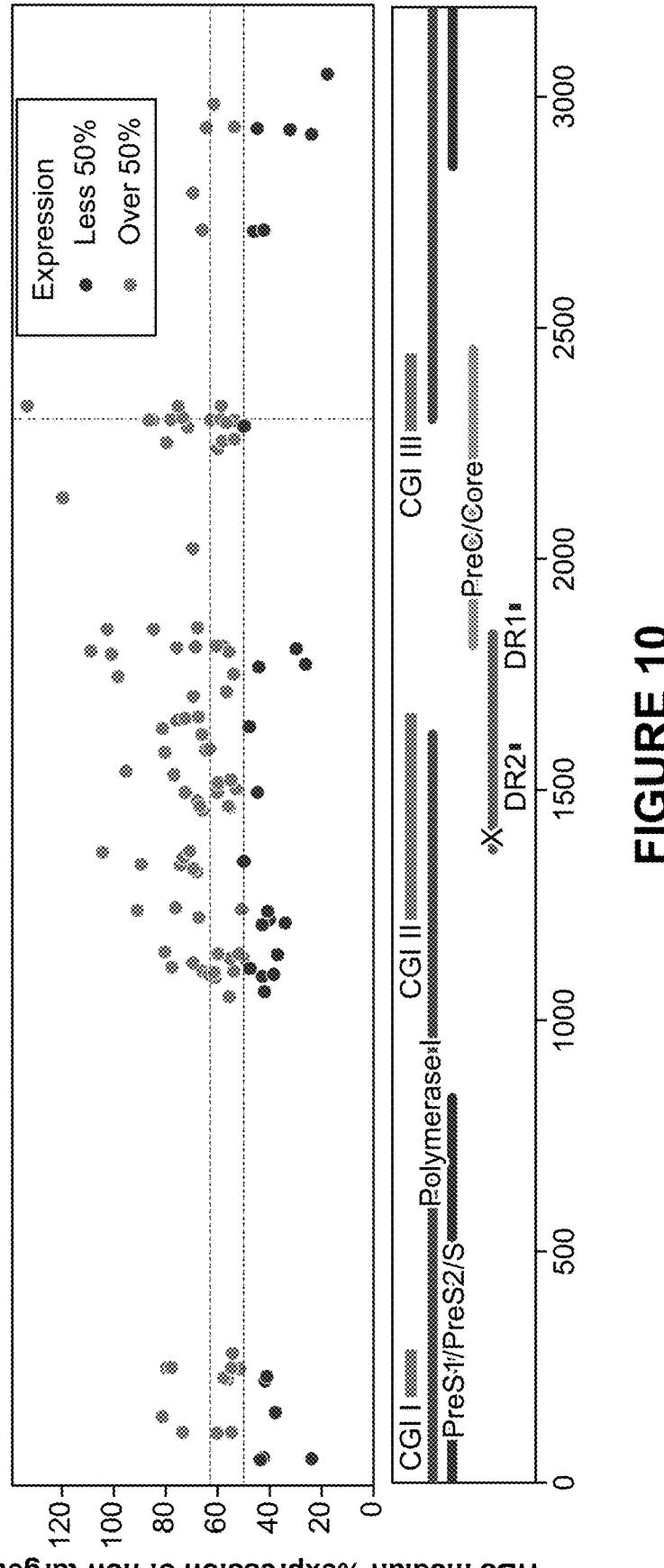
FIG. 10 is a diagram showing HBs expression values measured in the guide RNA screen for different guides (calculated as a percentage of the expression of HBs measured for a non-targeting control). Each guide/repressor combination is represented by a dot. A 50% repression cutoff is shown as a horizontal line. The position of the respective guide RNA within the HBV genome (shown at the bottom of the graph) is mapped on the X-axis. The position and the measured modulation of HBs expression for exemplary guide RNA #3.2 is indicated by red lines.
Figure 11:
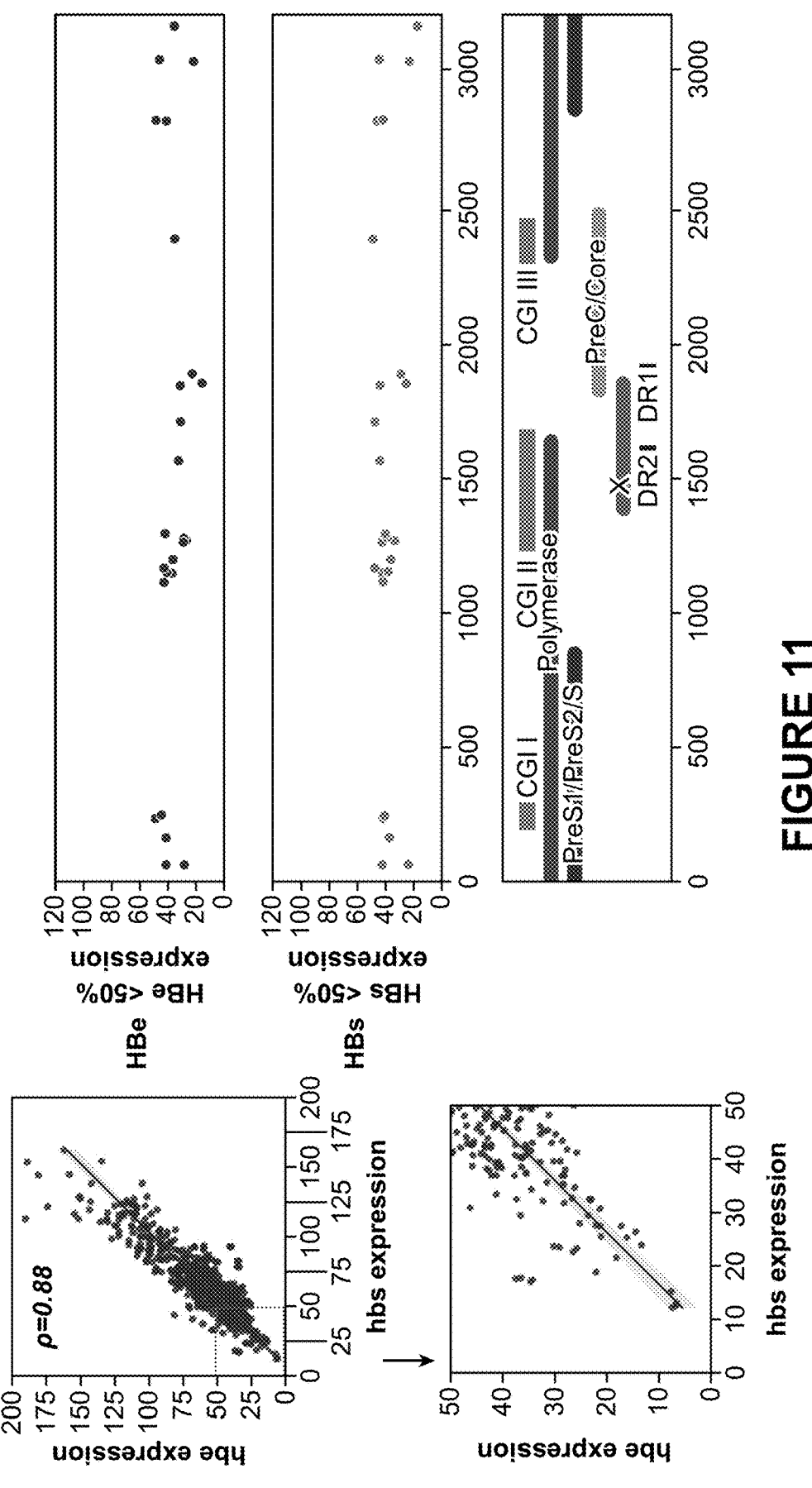
FIG. 11 is a diagram showing a correlation between HBs and HBe expression for the guides tested. The graph on the right shows HBe and HBs repression efficiencies for 25 exemplary guides.

In vitro silencing was observed in an HepG2-NTCP infection model with gRNAs targeting CpG islands with ETRs (FIG. 5A-FIG. 5B). A primary screen was conducted using LNPs of quality within expected parameters and a pilot experiment with a single guide (FIG. 6-FIG. 8). Results demonstrated that 48 gRNAs showed less than 50% expression of HBeAg at day 6 compared to non-targeting control (FIG. 9) and 28 gRNAs showed less than 50% expression of HBsAg at day 6 compared to non-targeting control (FIG. 10). HBsAg and HBeAg expression was positively correlated as shown in FIG. 11.

Example 4: Zinc Finger Repressors for Silencing HBV

Zinc finger repressors targeting epigenetic target sites identified in the HBV genome were designed. Table 1 above provides amino acid sequences of zinc finger and its corresponding motif sequences and target sequences of the zinc finger.

Zinc finger repressors described in Table 1 are tested in an HBV infection model, e.g., in HepG2 cells as described herein, and efficient repression of HBV is confirmed for the zinc finger repressors provided in Table 1.

Example 5: Further In Vitro Evaluation of gRNAs

A CRISPR-Off single construct encoding PLA002, consisting of KRAB, DNMT3A, DNMT3L, and dCas9, was used in combination with one or more of the designed sgRNAs for the in vitro assays described in this example.

Figures 12A, 12B:
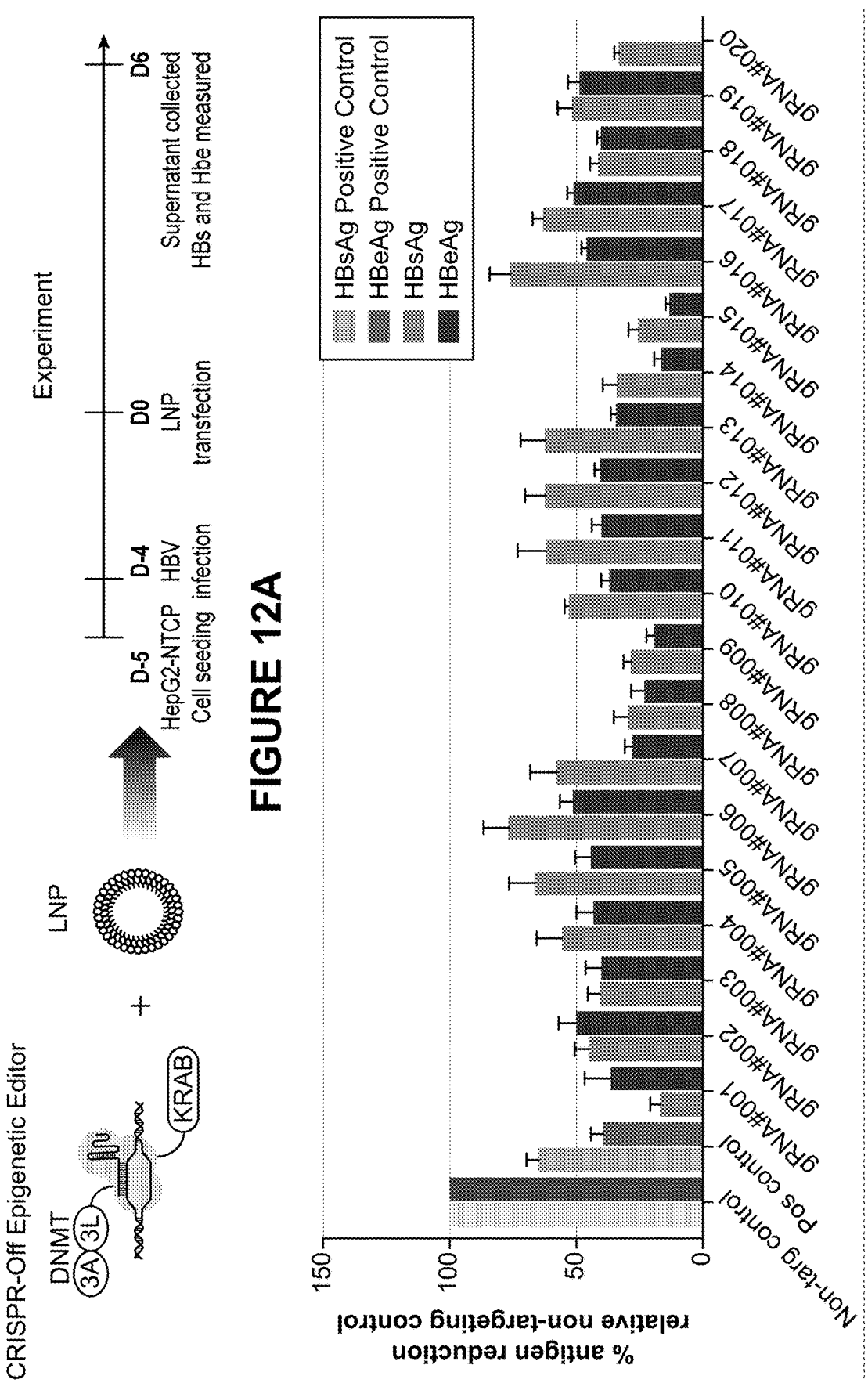
FIG. 12A is a diagram describing the experimental timeline for a guide RNA assay testing CRISPR-off single construct epigenetic editor in combination with individual exemplary gRNAs in a HepG2-NTCP infection model with ELISA readout for HBe and HBs antigens at day 6.
FIG. 12B is a graph summarizing the percentage reduction in HBV antigens at day 6 relative to non-targeting control.

HepG2-NTCP cells were infected with HBV for 4 days, following procedures similar as those in Example 3, and were then transfected with CRISPR-off construct and individual exemplary gRNAs (as indicated in Table 13) formulated in a research-grade LNP. At Day 6 post-transfection HBsAg and HBeAg protein expression in the supernatant was evaluated by ELISA, as depicted in FIG. 12A. Results from this experiment are shown in FIG. 12B. All of the tested gRNAs led to reduction of HBsAg and HBeAg levels in the supernatant. Positive control used in this experiment is a gRNA against HBV genome that was previously shown to reduce antigens ~50%.

Figures 13A, 13B:
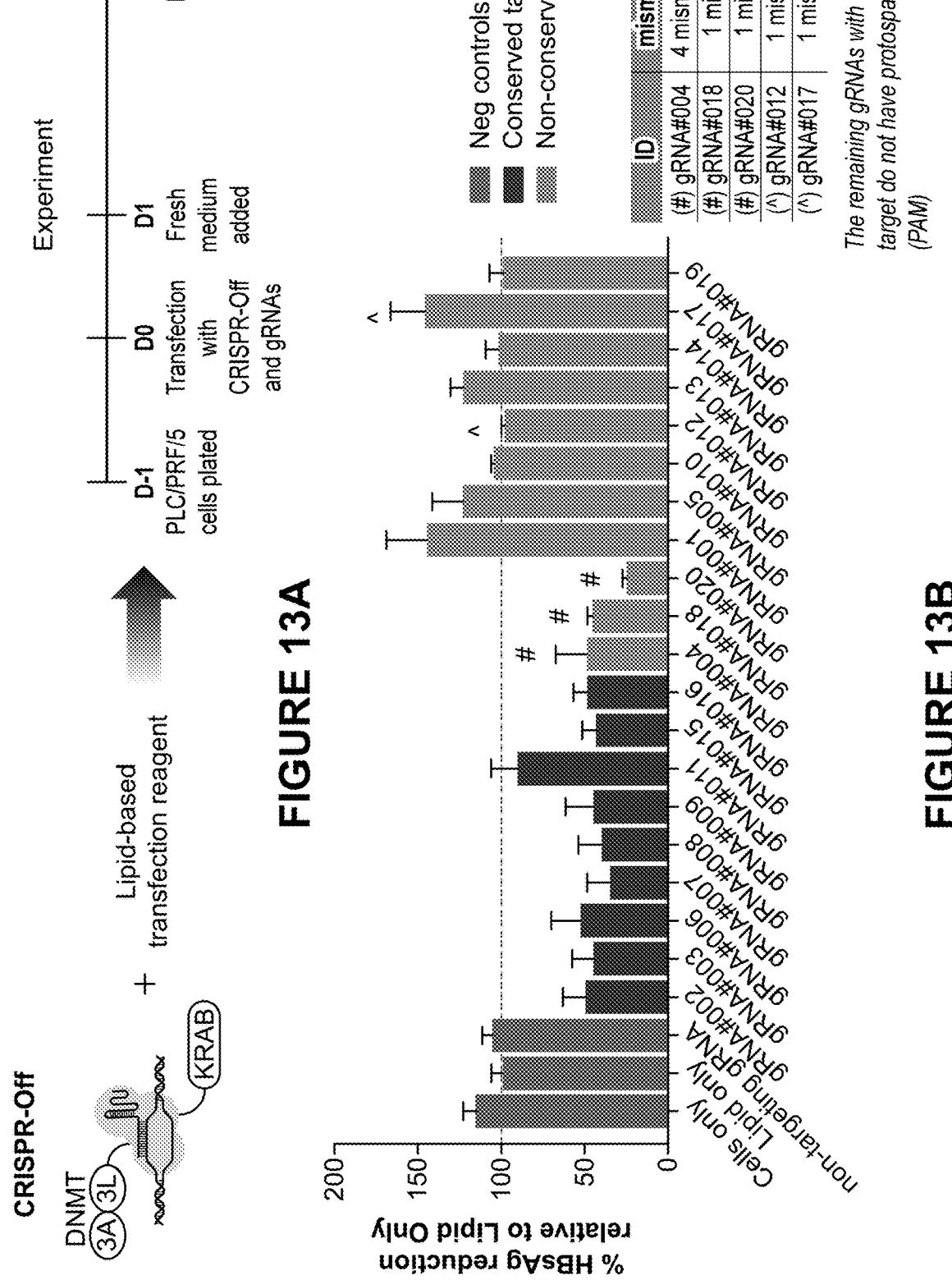
FIG. 13A is a diagram describing the experimental timeline for a guide RNA assay testing CRISPR-off single construct epigenetic editor in combination with individual exemplary gRNAs in a PLC/PRF/5 cell model with ELISA readout for HBs antigen at day 4.
FIG. 13B is a graph summarizing the percentage reduction in HBs antigen at day 4 relative to non-targeting control.

In another experiment, the integrated HBV cell line, PLC/PRF/5, was used to evaluate activity of gRNAs. The PLC/PRF/5 cells were transfected with CRISPR-off (PLA002) and individual gRNAs using a commercial lipid-based transfection reagent. As depicted in FIG. 13A, four days after transfection HBsAg protein expression in the supernatant was evaluated by ELISA. Results from this experiment are shown in FIG. 13B. Target conservation was evaluated in silico and target conservation was defined as 100% gRNA-DNA match.

Figures 14A, 14B:
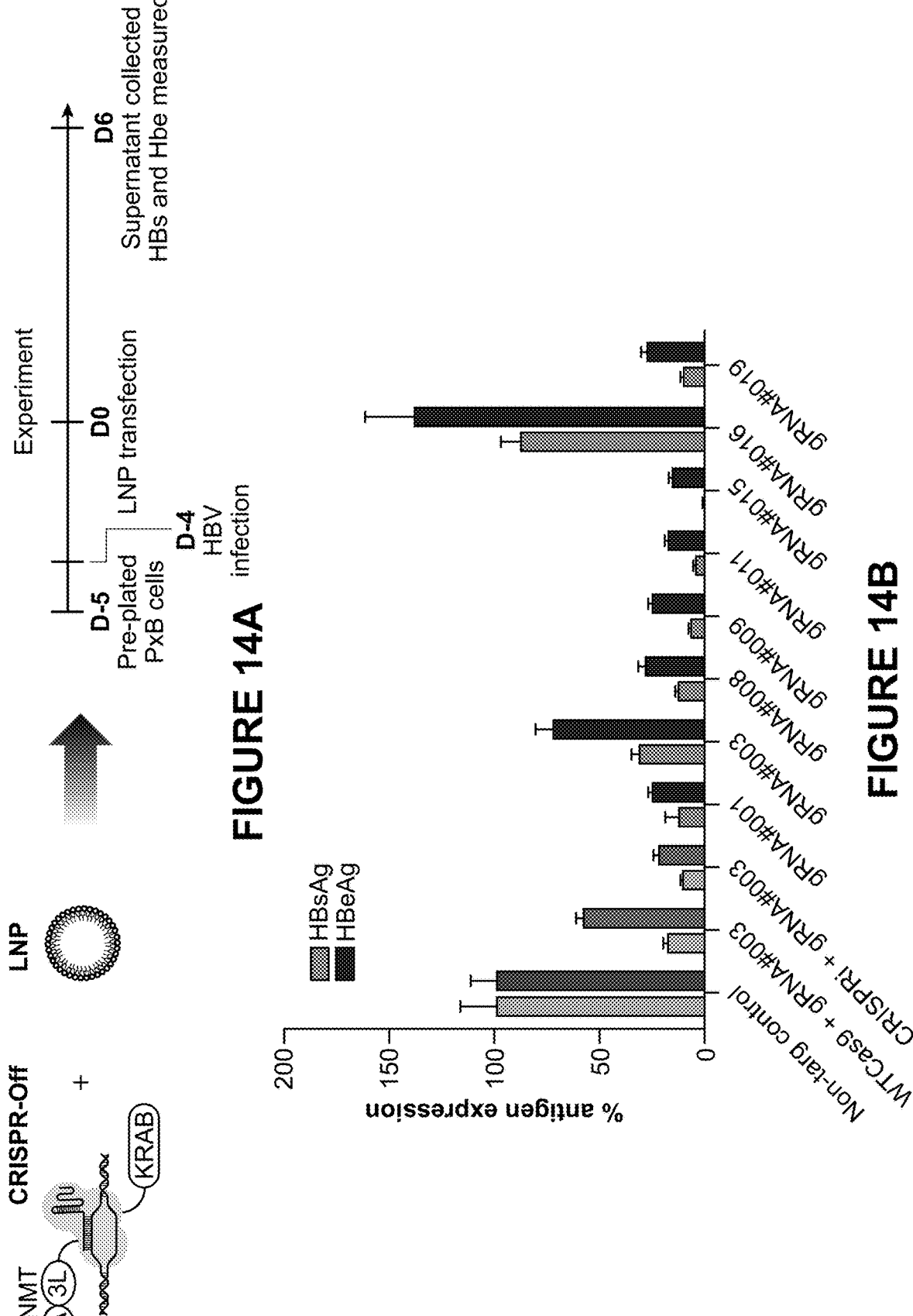
FIG. 14A is a diagram describing the experimental timeline for a guide RNA assay testing CRISPR-off single construct epigenetic editor in combination with individual exemplary gRNAs in a PXB cell model with ELISA readout for HBe and HBs antigens at day 6.
FIG. 14B is a graph summarizing the percentage reduction in HBV antigens at day 6 relative to non-targeting control.
Figure 14C:
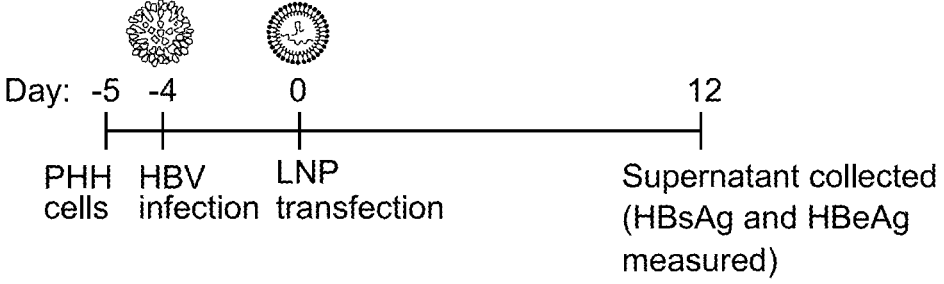
FIG. 14C is a diagram describing the experimental timeline for a guide RNA assay testing CRISPR-off single construct epigenetic editor in combination with individual exemplary gRNAs in a PXB cell model with ELISA readout for HBe and HBs antigens at day 12.
Figure 14D:
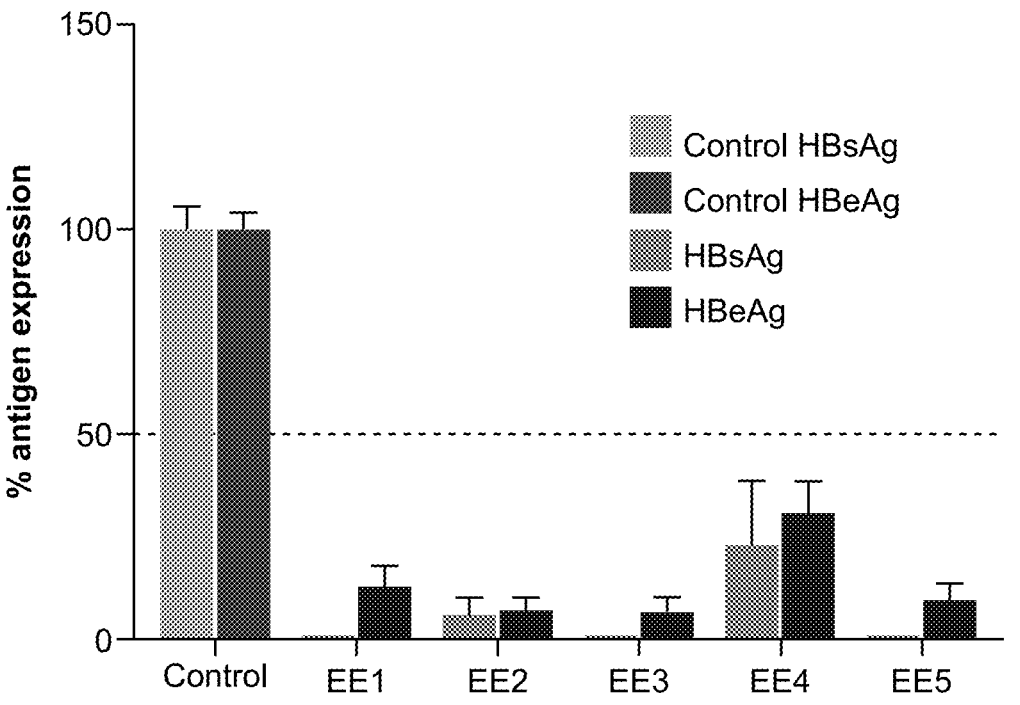
FIG. 14D is a graph summarizing the percentage reduction in HBV antigens at day 12 relative to non-targeting control. Bars represent mean±SEM; N=5. EE1=PLA002 and gRNA #007, EE2=PLA002 and gRNA #008, EE3=PLA002 and gRNA #009, EE4=PLA002 and gRNA #015, and EE5=PLA002 and gRNA #011.

In a further experiment, primary human hepatocytes (PHH) derived from humanized mice were infected with HBV for 4 days and then transfected with CRISPR-off (PLA002) and individual gRNAs formulated in a research-grade LNP, GenVoy LNPs. As depicted in FIG. 14A, at Day 6 post-infection HBsAg and HBeAg protein expression in the supernatant was evaluated by ELISA. Results from this experiment are shown in FIG. 14B. Positive control used in this experiment is an HBV gRNA that was previously shown to reduce antigens ~50%. The data suggested strong in vitro silencing by certain gRNAs at Day 6 after transfection. In a second PHH experiment, depicted in FIG. 14C, post-infection HBsAg and HBeAg protein expression in the supernatant was evaluated by ELISA at Day 12 after delivery of 100 ng of payload (1:1 effector to guide RNA ratio) in research-grade LNPs. Epigenetic editors repress HBsAg and HBeAg secretion in HBV infected PHH cells at this time point, as well. Results are shown in FIG. 14D. Sequences of the exemplary gRNAs that were tested in this example are listed in Table 13.

Example 6: In Vivo Silencing of HBV in HBV Rodent Models

Two different HBV rodent models were tested in this study. As shown in FIG. 15, in one set of experiments, a non-transgenic model of persistent HBV infection in immunocompetent mice was used, which was established by administering an adeno-associated viral vector (AAV) that contains HBV Genotype D DNA into the mice. The administration of the AAV-HBV vector resulted in expression of hepatitis B surface antigen (HBsAg), hepatitis B e antigen (HBeAg), and high levels of serum HBV DNA in the mice. In another set of experiments, a transgenic mouse model of persistent HBV infection was used, whose genome was engineered to integrate HBV Genotype A DNA, resulting in expression of HBsAg and HBeAg, and circulating viral DNA in the mice.

Both mouse models were used to test 6 different treatment groups as shown in FIG. 15. At certain times (such as 7, 14, 28, and 35 days) after single administration of 3 mg/kg of the LNPs that were loaded with the CRISPR-off construct and respective gRNAs, WT-Cas9 construct and gRNA, or control vehicle, mouse serum was extracted for analysis of HBsAg, HBeAg, and HBV DNA. Later the mice were sacrificed, and their livers were collected for further analysis.

Figure 16:
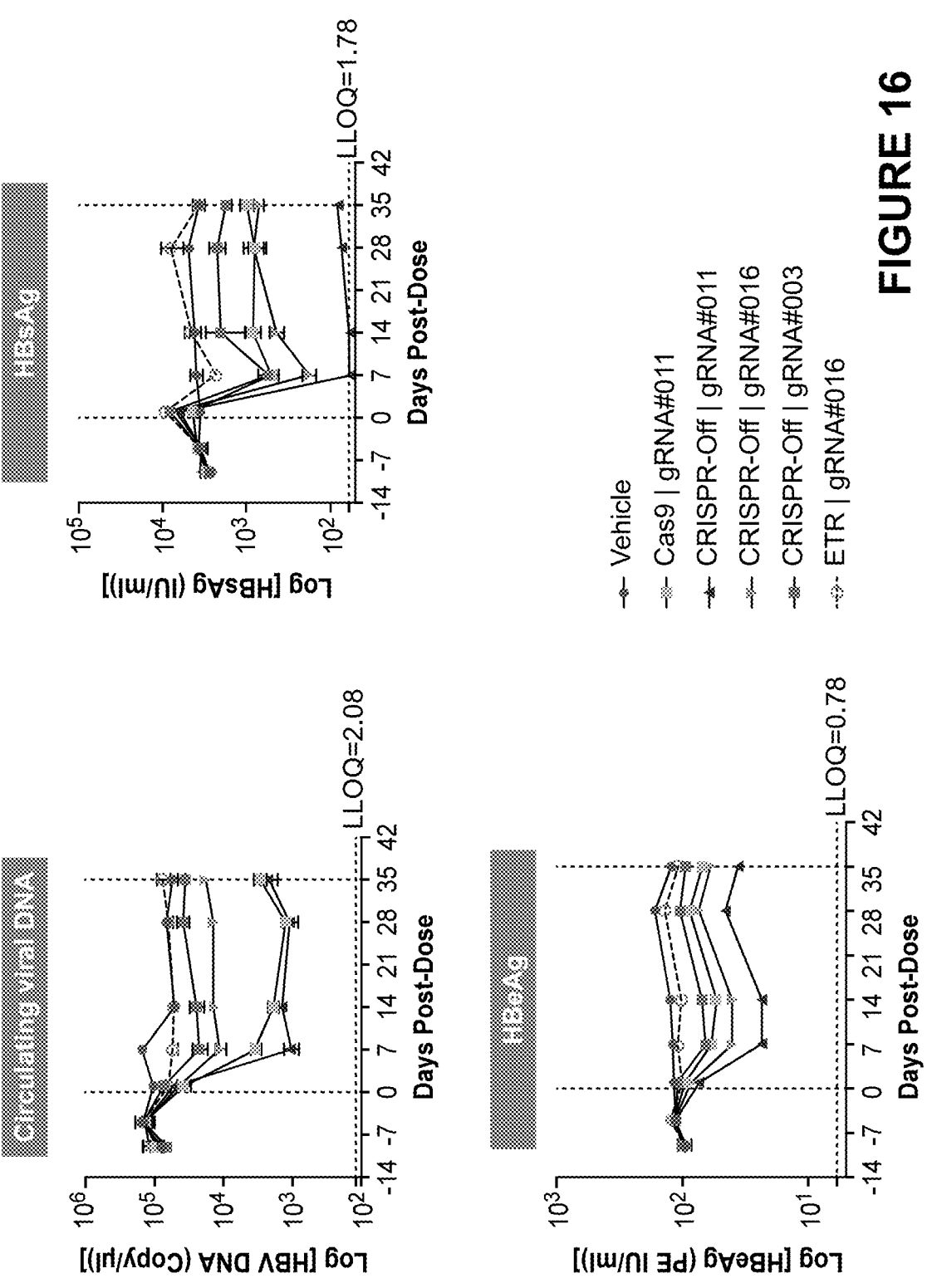
FIG. 16 shows time course graphs summarizing the level of scrum HBV DNA, HBs and HBe antigens in transgenic mouse HBV model before and after single administration of an epigenetic editor (CRISPR-off with gRNA or ETR with gRNA), Cas9 with gRNA, or control vehicle at day 0.

As shown in FIG. 16, in transgenic mouse model, durable (~1 month) and efficacious (~2 Log) DNA and HBsAg reduction was observed with CRIPSR-Off/gRNA #011 treatment. And compared to Cas9 cutter, CRISPR-Off, when administered in combination with gRNA #011, showed similar circulating viral DNA reduction, but superior HBsAg and HBeAg reduction.

Figure 17:
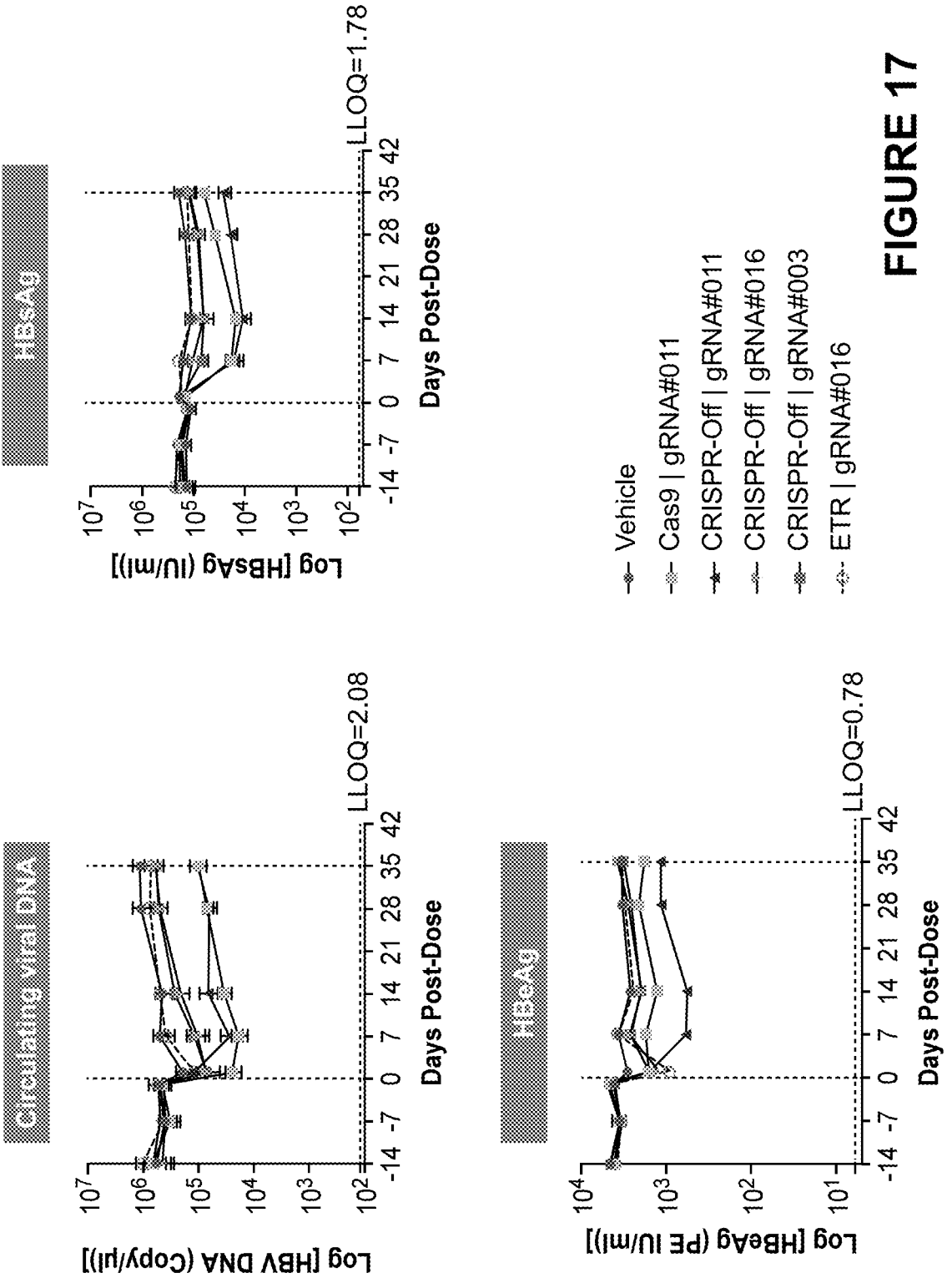
FIG. 17 shows time course graphs summarizing the level of scrum HBV DNA, HBs and HBe antigens in AAV-HBV mouse model before and after single administration of an epigenetic editor (CRISPR-off with gRNA or ETR with gRNA), Cas9 with gRNA, or control vehicle at day 0.

Reduction of HBV markers in AAV-HBV model was also observed with administration of certain exemplary constructs. As shown in FIG. 17, overall results in AAV8-HBV model are similar to the Tg-HBV mouse model. About 1 log DNA and HBsAg antigen reduction was observed with administration of CRISPR-Off and gRNA #011.

Figure 18A:
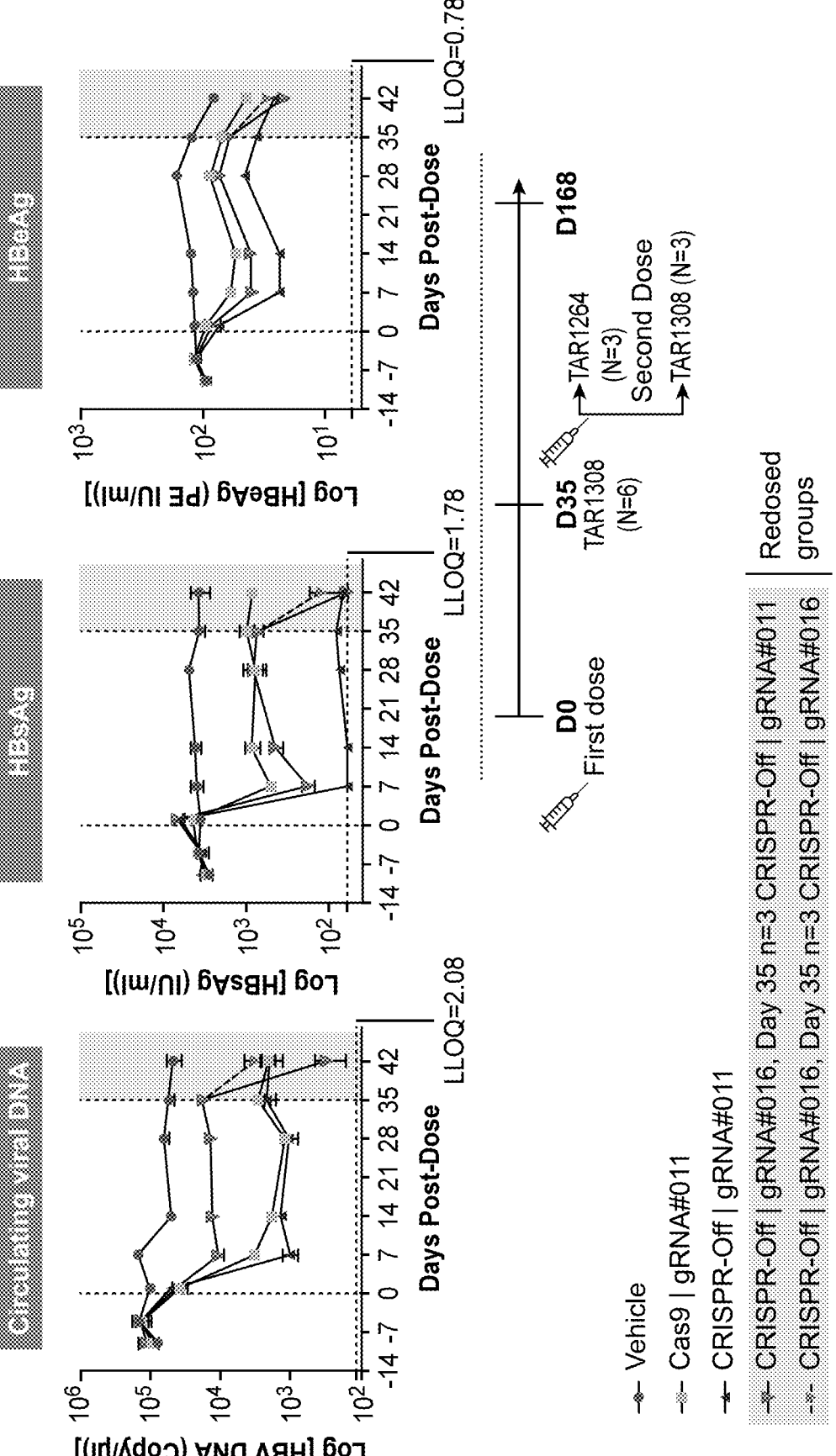
FIG. 18A shows time course graphs summarizing the level of scrum HBV DNA, HBs and HBe antigens in transgenic mouse HBV model, and a schematic of the timeline for the experiment. All mice received a single administration of an epigenetic editor (CRISPR-off with gRNA or ETR with gRNA), Cas9 with gRNA, or control vehicle at day 0, and some mice received a designated redosing at day 35.

Effects of redosing of certain exemplary constructs were also tested. In the same experiments as above, among the six transgenic mice receiving administration of "CRISPR-off+ gRNA #016" (CRISPR-off construct and gRNA gRNA #016), three were administered with a dose of "CRISPR-off+gRNA #016" on Day 35, and the other three were administered with "CRISPR-off+gRNA #011" on Day 35. As shown in FIG. 18A, redosing either with a less effective gRNA (gRNA #016 in this case) or with a more effective gRNA (gRNA #011 in this case) enhanced the silencing of all HBV marker, as shown by reduction of circulating HBV DNA, HBsAg, and HBeAg on Day 42. Redosing the gRNA #016-treated group with gRNA #011 (more effective gRNA) resulted in a more substantial reduction than redosing with gRNA #016 (less effective gRNA).

Single-dose experiments were continued to 168 days, as shown in FIG. 18B. Results show durable and progressive reduction of viral antigens achieving −2.7 log DNA and −2.8 log HBsAg more than five months after single administration of an epigenetic editor (CRISPR-off with gRNA #011). Five out of six animals tested had undetectable HBV DNA and HBsAg 168 days after a single dose of an epigenetic editor.

Figure 19:
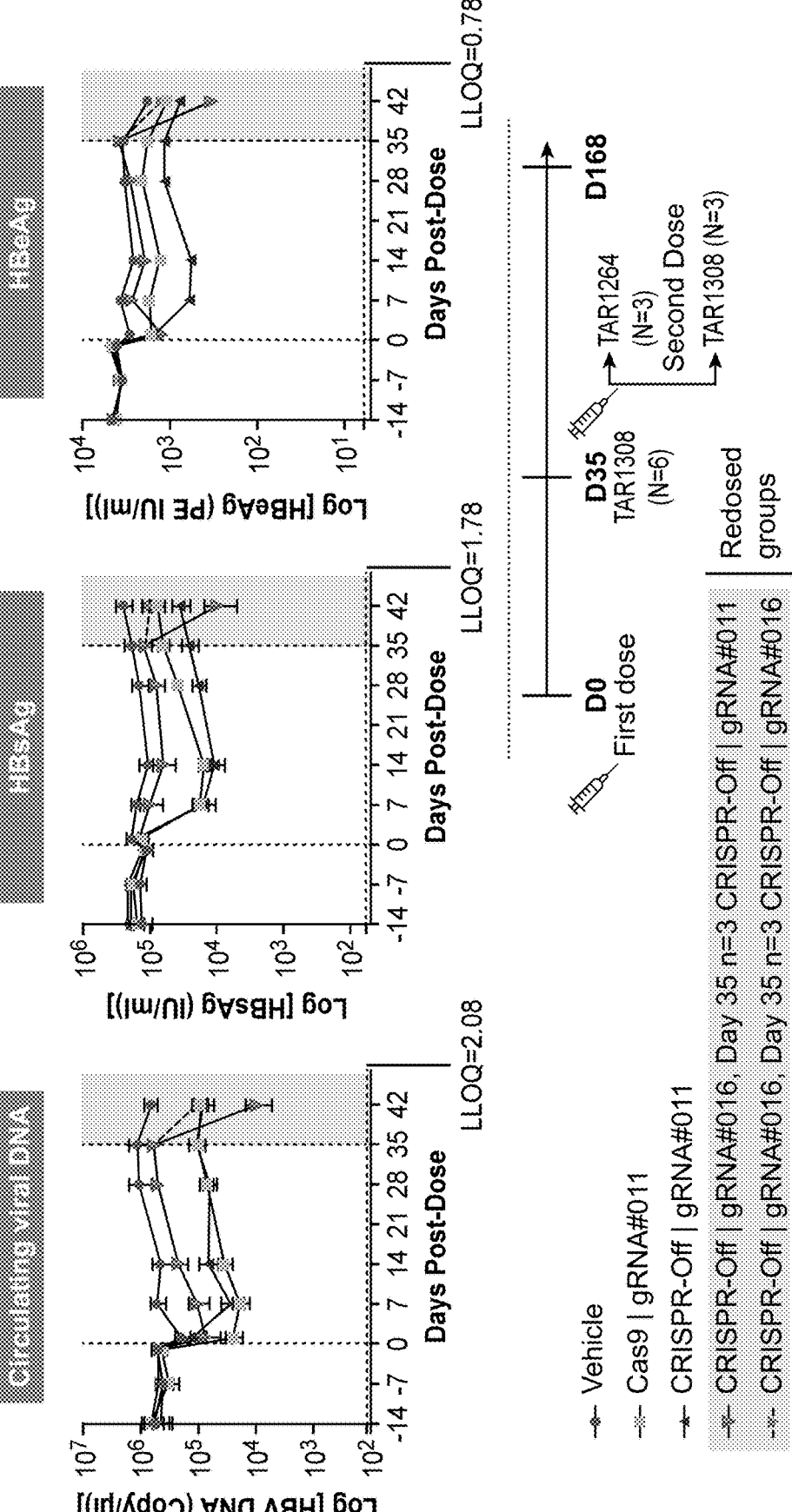
FIG. 19 shows time course graphs summarizing the level of serum HBV DNA, HBs and HBe antigens in AAV-HBV mouse model, and a schematic of the timeline for the experiment. All mice received a single administration of an epigenetic editor (CRISPR-off with gRNA or ETR with gRNA), Cas9 with gRNA, or control vehicle at day 0, and some mice received a designated redosing at day 35.

Redosing experiments were also conducted in AAV-HBV mouse model, as shown in FIG. 19. Dosing with two different gRNAs (gRNA #016 and gRNA #011) further decreased all HBV markers. These data suggest of a potential enhanced activity when two HBV regions are targeted.

Sequences of the exemplary gRNAs that were tested in this example are listed in Table 13.

Example 7: Evaluation of ZFP in HepG2-NTCP Cells

In this example, ZF-off single constructs encoding a fusion protein consisting of KRAB, DNMT3A, DNMT3L, and an exemplary zinc finger motif of choice, were tested. Sequences of the exemplary zinc fingers that were tested in this example are listed in Table 18, as are sequences for plasmids yielding a subset of the ZF-off single construct fusion proteins.

Figures 20A, 20B:
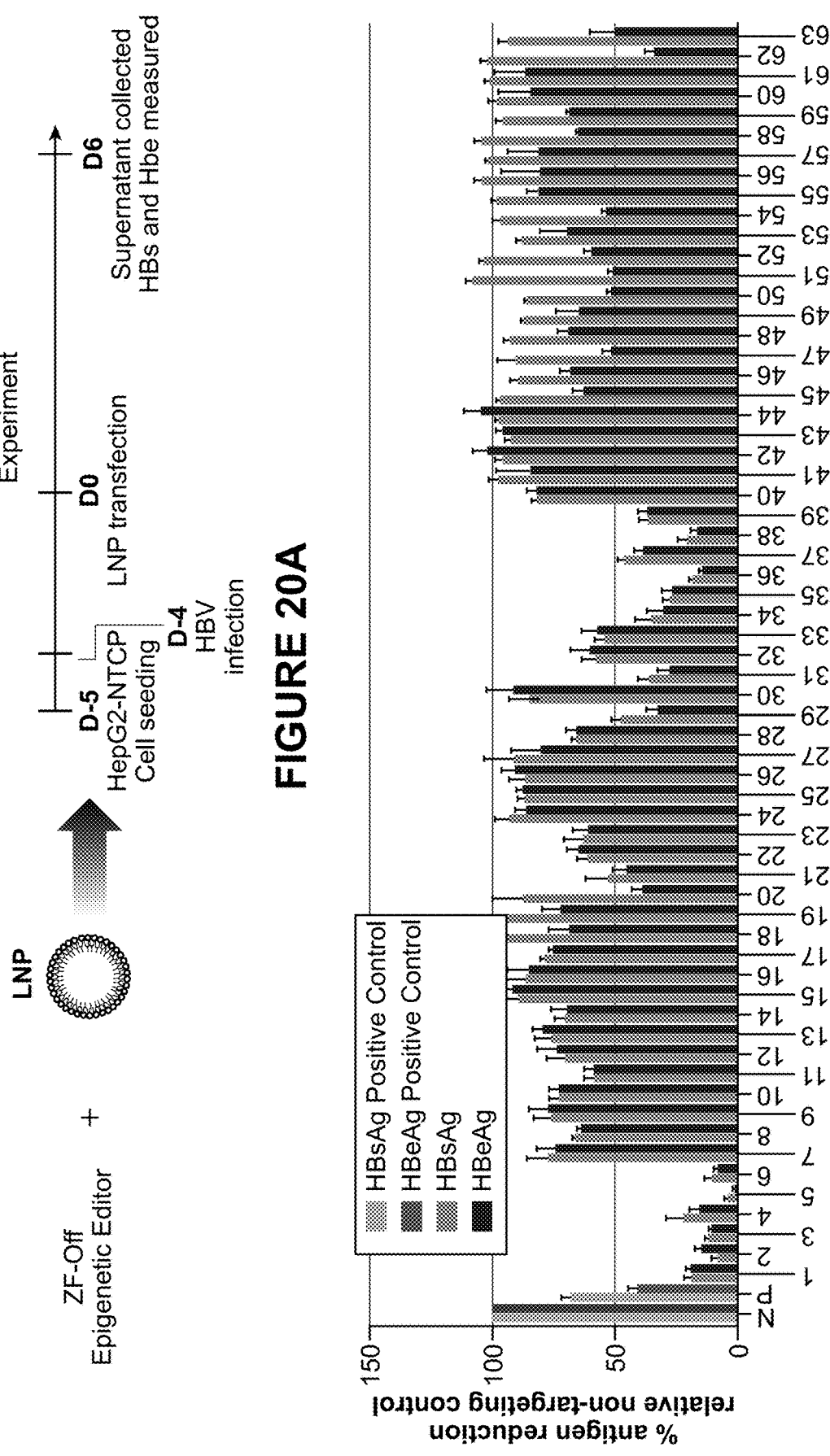
FIG. 20A is a diagram describing the experimental time-line for a zinc finger assay testing ZF-off single construct epigenetic editor that contains individual exemplary zinc finger motif in a HepG2-NTCP infection model with ELISA readout for HBe and HBs antigens at day 6.
FIG. 20B is a graph summarizing the percentage reduction in HBV antigens at day 6 relative to non-targeting control. "N" denotes non-targeting control, "P" denotes the positive control, and the individual numbers on the x-axis denote exemplary constructs tested in the experiment, for instance, "1" represents "mRNA0001" construct, and "20" represents "mRNA0020" construct.
Figure 21A:
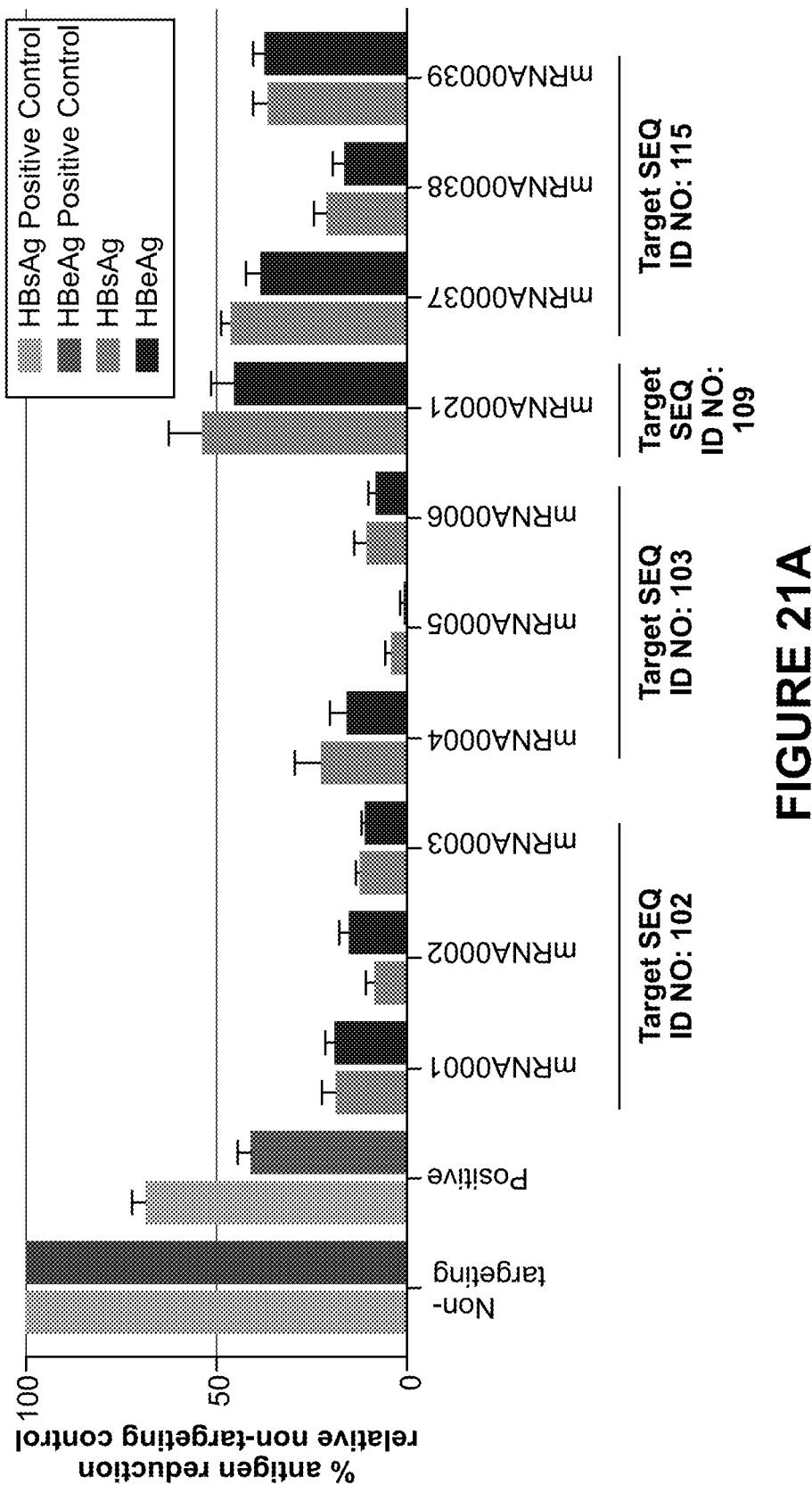
FIG. 21A is a graph summarizing the results of top ten ZF-off constructs from FIG. 20B.
Figure 21B:
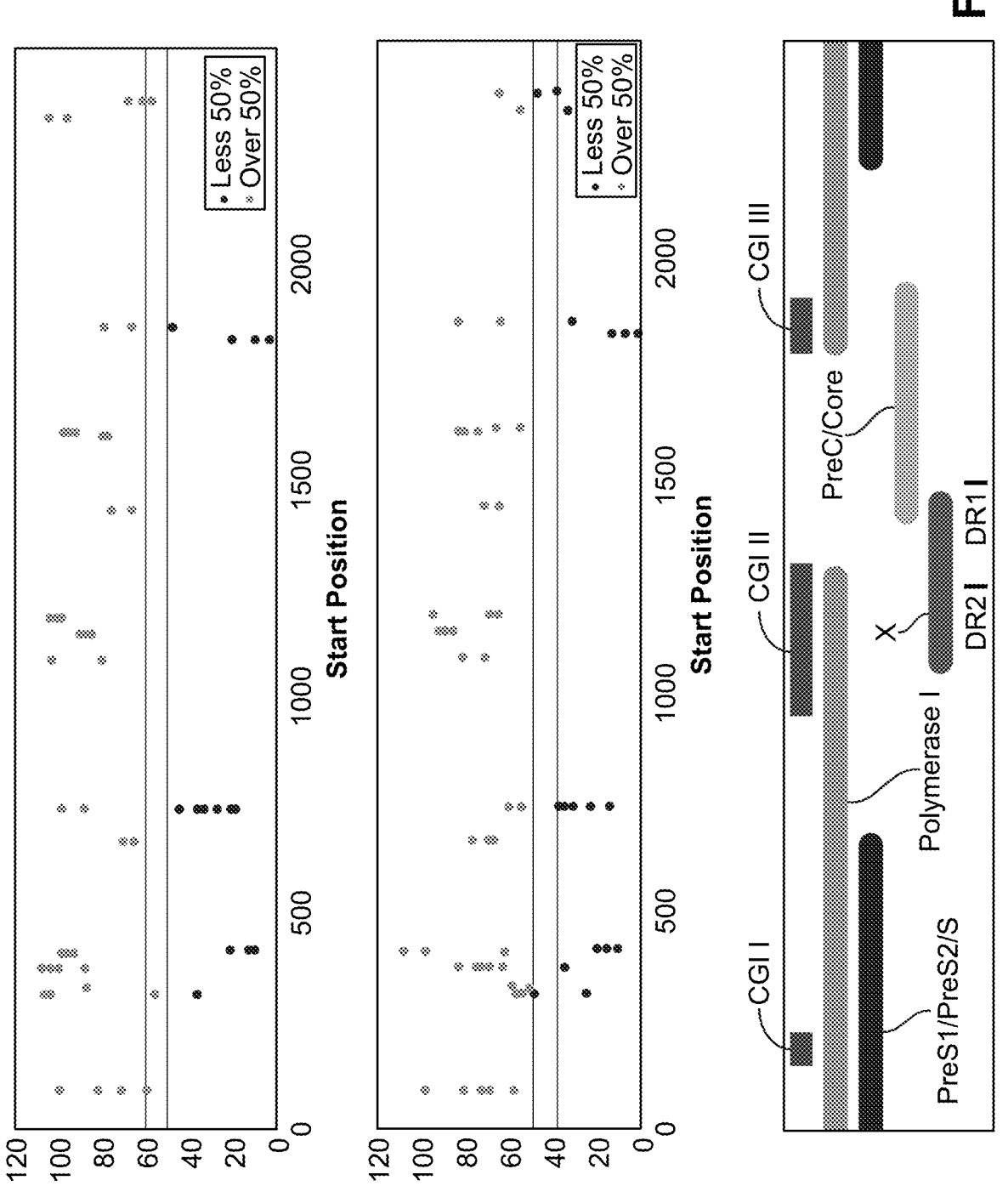
FIG. 21B is a diagram showing HBsAg (top) and HBeAg (middle) expression values measured in the ZF-off screen (calculated as a percentage of the expression of HBsAg or HBeAg—top and middle, respectively—measured for a non-targeting control). Each ZF-off construct is represented by a dot. 50% and 60% repression cutoffs are shown as horizontal lines. The position of the respective guide RNA within the HBV genome (bottom) is mapped on the X-axis.

Certain exemplary ZF-off constructs were formulated in a research-grade LNP. HepG2-NTCP cells were infected with HBV for 4 days and then transfected with the ZF-off loaded LNPs. As depicted in FIG. 20A, at Day 6 post-infection HBsAg and HBeAg protein expression in the supernatant was evaluated by ELISA. FIG. 20B shows the results as measured by percentage reduction in HBV antigens as compared to non-targeting control. Positive control used in this experiment is a HBV gRNA previously shown to reduce antigens ~50%. FIG. 21A shows the results of the top ten ZF-off constructs that lead to the most reduction in HBV antigens. FIG. 21B shows the results for all constructs in the screen.

Table 14 and 15 below show the raw data from these experiments, listed with the mRNA number yielding the zinc finger motif.

TABLE 14

| % HBsAg expression relative to non-targeting control | | | | | | | |
| --- | --- | --- | --- | --- | --- | --- | --- |
| Trial# | 1 | 2 | 3 | 4 | 5 | 6 | 7 | 8 |
| Non-targ control | 100 | 100 | 100 | 100 | | | | |
| Pos control | 54 | 59 | 68 | 61 | 75 | 79 | 65 | 86 |
| mRNA0001 | 10 | 19 | 25 | 23 | | | | |
| mRNA0002 | 12 | 2 | 8 | 12 | | | | |
| mRNA0003 | 10 | 11 | 14 | 15 | | | | |
| mRNA0004 | 10 | 28 | 13 | 39 | | | | |
| mRNA0005 | 3 | 5 | 1 | 8 | | | | |
| mRNA0006 | 4 | 12 | 8 | 19 | | | | |
| mRNA0007 | 97 | 86 | 60 | 66 | | | | |
| mRNA0008 | 68 | 69 | 65 | 64 | | | | |
| mRNA0009 | 65 | 67 | 74 | 98 | | | | |
| mRNA0010 | 84 | 69 | 66 | 73 | | | | |
| mRNA0011 | 67 | 50 | 60 | 59 | | | | |
| mRNA0012 | 59 | 61 | 70 | 92 | | | | |
| mRNA0013 | 97 | 70 | 66 | 71 | | | | |
| mRNA0014 | 60 | 81 | 66 | 74 | | | | |
| mRNA0015 | 81 | 73 | 77 | 129 | | | | |
| mRNA0016 | 120 | 78 | 71 | 77 | | | | |
| mRNA0017 | 75 | 77 | 82 | 82 | | | | |
| mRNA0018 | 78 | 84 | 93 | 131 | | | | |
| mRNA0019 | 107 | 107 | 77 | 100 | | | | |
| mRNA0020 | 77 | 99 | 60 | 116 | | | | |
| mRNA0021 | 32 | 49 | 68 | 66 | | | | |
| mRNA0022 | 71 | 66 | 51 | 56 | | | | |
| mRNA0023 | 65 | 71 | 76 | 41 | | | | |
| mRNA0024 | 109 | 89 | 86 | 92 | | | | |
| mRNA0025 | 86 | 92 | 90 | 82 | | | | |
| mRNA0026 | 77 | 88 | 81 | 104 | | | | |
| mRNA0027 | 128 | 77 | 80 | 81 | | | | |
| mRNA0028 | 71 | 67 | 59 | 66 | | | | |
| mRNA0029 | 48 | 47 | 40 | 57 | | | | |
| mRNA0030 | 109 | 82 | 76 | 75 | | | | |
| mRNA0031 | 46 | 32 | 41 | 27 | | | | |
| mRNA0032 | 50 | 59 | 52 | 73 | | | | |
| mRNA0033 | 61 | 62 | 46 | 50 | | | | |
| mRNA0034 | 51 | 24 | 41 | 25 | | | | |
| mRNA0035 | 30 | 25 | 24 | 34 | | | | |
| mRNA0036 | 16 | 22 | 19 | 19 | | | | |
| mRNA0037 | 54 | 43 | 42 | 46 | | | | |
| mRNA0038 | 19 | 23 | 13 | 29 | | | | |
| mRNA0039 | 28 | 46 | 37 | 36 | | | | |
| mRNA0040 | 88 | 78 | 83 | 80 | | | | |
| mRNA0041 | 103 | 92 | 100 | | | | | |
| mRNA0042 | 99 | 91 | 99 | | | | | |
| mRNA0043 | 93 | 89 | 97 | | | | | |
| mRNA0044 | 98 | 100 | 95 | | | | | |
| mRNA0045 | 100 | 96 | 95 | | | | | |
| mRNA0046 | 94 | 83 | 92 | | | | | |
| mRNA0047 | 97 | 77 | 99 | | | | | |
| mRNA0048 | 96 | 94 | 90 | | | | | |
| mRNA0049 | 88 | 87 | 89 | | | | | |
| mRNA0050 | 87 | 87 | 85 | | | | | |
| mRNA0051 | 106 | 104 | 114 | | | | | |
| mRNA0052 | 104 | 101 | 107 | | | | | |
| mRNA0053 | 88 | 86 | 92 | | | | | |
| mRNA0054 | 98 | 102 | 91 | | | | | |
| mRNA0055 | 101 | 96 | 100 | | | | | |
| mRNA0056 | 99 | 107 | 108 | | | | | |
| mRNA0057 | 101 | 102 | 104 | | | | | |
| mRNA0058 | 110 | 104 | 102 | | | | | |
| mRNA0059 | 100 | 91 | 98 | | | | | |
| mRNA0060 | 94 | 103 | 100 | | | | | |
| mRNA0061 | 104 | 96 | 103 | | | | | |
| mRNA0062 | 106 | 98 | 104 | | | | | |
| mRNA0063 | 96 | 86 | 99 | | | | | |

TABLE 15

| % HBeAg expression relative to non-targeting control | | | | | | | |
| --- | --- | --- | --- | --- | --- | --- | --- |
| Trial# | 100 | 100 | 100 | 100 | | | | |
| Non-targ control | 100 | 100 | 100 | 100 | | | | |
| Pos control | 26 | 36 | 41 | 53 | 43 | 43 | 34 | 54 |
| mRNA0001 | 12 | 19 | 22 | 23 | | | | |
| mRNA0002 | 15 | 8 | 17 | 20 | | | | |
| mRNA0003 | 11 | 9 | 13 | 12 | | | | |
| mRNA0004 | 10 | 17 | 9 | 27 | | | | |
| mRNA0005 | 1 | 1 | -1 | 3 | | | | |
| mRNA0006 | 5 | 8 | 7 | 13 | | | | |
| mRNA0007 | 95 | 78 | 59 | 65 | | | | |
| mRNA0008 | 64 | 67 | 60 | 65 | | | | |
| mRNA0009 | 65 | 64 | 81 | 98 | | | | |
| mRNA0010 | 84 | 68 | 69 | 70 | | | | |
| mRNA0011 | 65 | 51 | 51 | 67 | | | | |
| mRNA0012 | 64 | 61 | 74 | 96 | | | | |
| mRNA0013 | 92 | 74 | 73 | 79 | | | | |
| mRNA0014 | 58 | 85 | 58 | 76 | | | | |
| mRNA0015 | 82 | 83 | 78 | 124 | | | | |
| mRNA0016 | 108 | 81 | 72 | 80 | | | | |
| mRNA0017 | 72 | 77 | 72 | 80 | | | | |
| mRNA0018 | 55 | 55 | 71 | 93 | | | | |
| mRNA0019 | 71 | 79 | 51 | 87 | | | | |
| mRNA0020 | 34 | 36 | 32 | 52 | | | | |
| mRNA0021 | 32 | 40 | 55 | 55 | | | | |
| mRNA0022 | 77 | 64 | 53 | 65 | | | | |
| mRNA0023 | 60 | 69 | 72 | 43 | | | | |
| mRNA0024 | 98 | 76 | 87 | 84 | | | | |
| mRNA0025 | 91 | 86 | 82 | 92 | | | | |
| mRNA0026 | 78 | 97 | 87 | 102 | | | | |
| mRNA0027 | 117 | 62 | 68 | 74 | | | | |
| mRNA0028 | 75 | 59 | 58 | 71 | | | | |
| mRNA0029 | 31 | 32 | 22 | 45 | | | | |
| mRNA0030 | 124 | 86 | 79 | 77 | | | | |
| mRNA0031 | 42 | 23 | 27 | 20 | | | | |
| mRNA0032 | 46 | 57 | 57 | 82 | | | | |
| mRNA0033 | 56 | 51 | 44 | 76 | | | | |
| mRNA0034 | 42 | 21 | 41 | 18 | | | | |
| mRNA0035 | 22 | 22 | 24 | 39 | | | | |
| mRNA0036 | 13 | 17 | 16 | 13 | | | | |
| mRNA0037 | 50 | 35 | 34 | 35 | | | | |
| mRNA0038 | 12 | 16 | 13 | 25 | | | | |
| mRNA0039 | 29 | 45 | 39 | 36 | | | | |
| mRNA0040 | 93 | 73 | 80 | 82 | | | | |
| mRNA0041 | 80 | 63 | 111 | | | | | |
| mRNA0042 | 114 | 94 | 98 | | | | | |
| mRNA0043 | 98 | 91 | 99 | | | | | |
| mRNA0044 | 91 | 115 | 108 | | | | | |
| mRNA0045 | 71 | 55 | 62 | | | | | |
| mRNA0046 | 76 | 66 | 63 | | | | | |
| mRNA0047 | 55 | 55 | 45 | | | | | |
| mRNA0048 | 66 | 63 | 78 | | | | | |
| mRNA0049 | 83 | 59 | 52 | | | | | |
| mRNA0050 | 51 | 55 | 49 | | | | | |
| mRNA0051 | 55 | 49 | 49 | | | | | |
| mRNA0052 | 56 | 57 | 66 | | | | | |
| mRNA0053 | 92 | 60 | 57 | | | | | |
| mRNA0054 | 50 | 55 | 56 | | | | | |
| mRNA0055 | 83 | 88 | 74 | | | | | |
| mRNA0056 | 61 | 69 | 112 | | | | | |
| mRNA0057 | 106 | 73 | 65 | | | | | |
| mRNA0058 | 66 | 65 | 65 | | | | | |
| mRNA0059 | 69 | 66 | 71 | | | | | |
| mRNA0060 | 59 | 94 | 101 | | | | | |
| mRNA0061 | 111 | 81 | 68 | | | | | |
| mRNA0062 | 28 | 33 | 41 | | | | | |
| mRNA0063 | 65 | 55 | 31 | | | | | |

Example 8. Dose Response Testing of Viral
Antigens in HepG2-NTCP Cells

Figure 22:
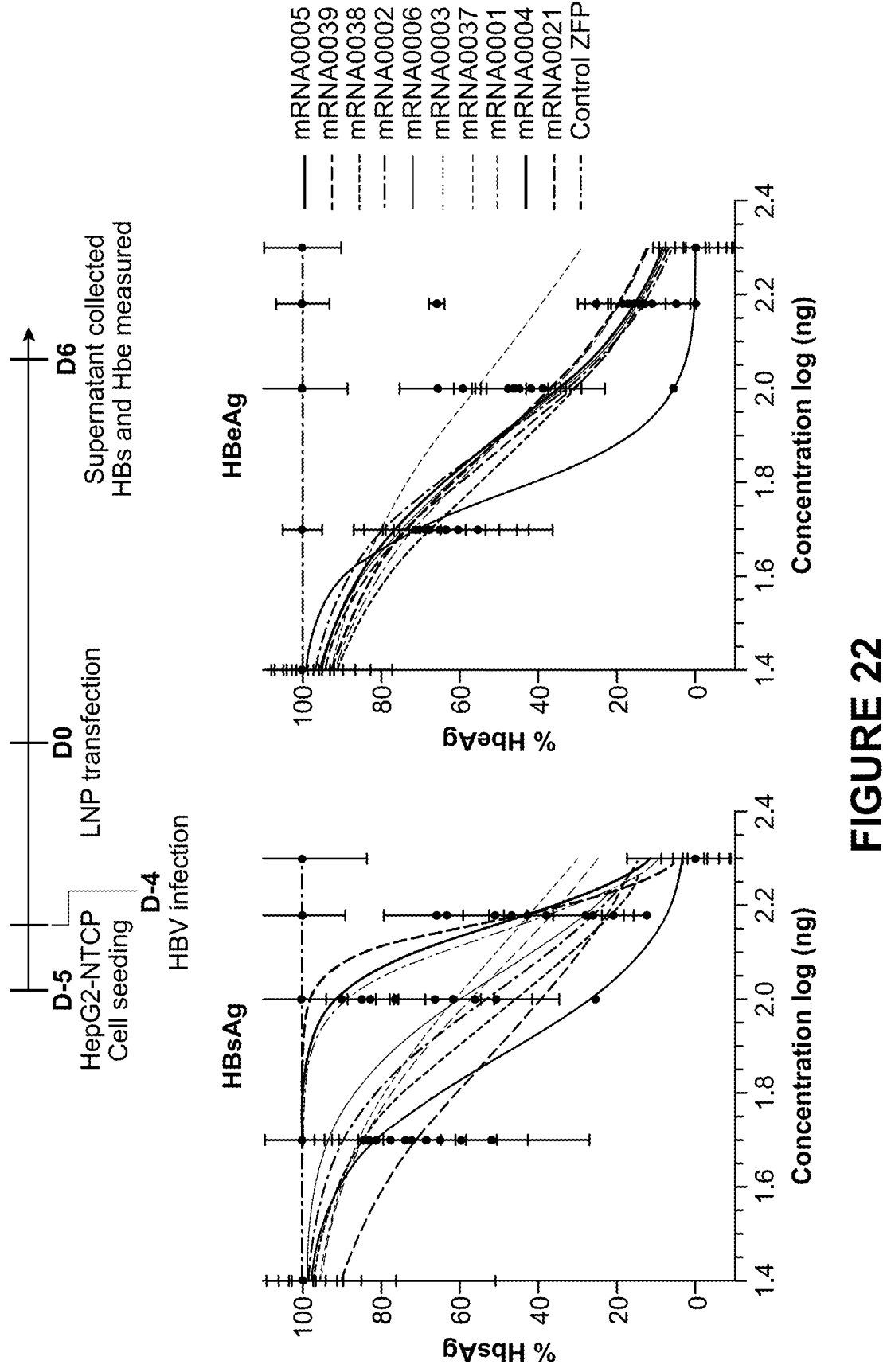
FIG. 22 is an experimental timeline for testing dose response (top) and two graphs showing dose response of % HbsAg (bottom left) and % HbeAg (bottom right) in HepG2-NTCP cells upon administration of ZF fusion proteins. The mRNA corresponding to the ZF motif for each fusion protein is indicated.

In this example, top ZF fusion proteins were tested in 5-point dose response assay for HBsAg and HBeAg. The 5 dosage points were 200 ng, 150 ng, 100 ng, 50 ng, and 25 ng. Experimental schematic and results are shown in FIG. 22.

Example 9. Testing for Durable Repression of HBsAg in HepG2.2.15 Cells

Figures 23A, 23B:
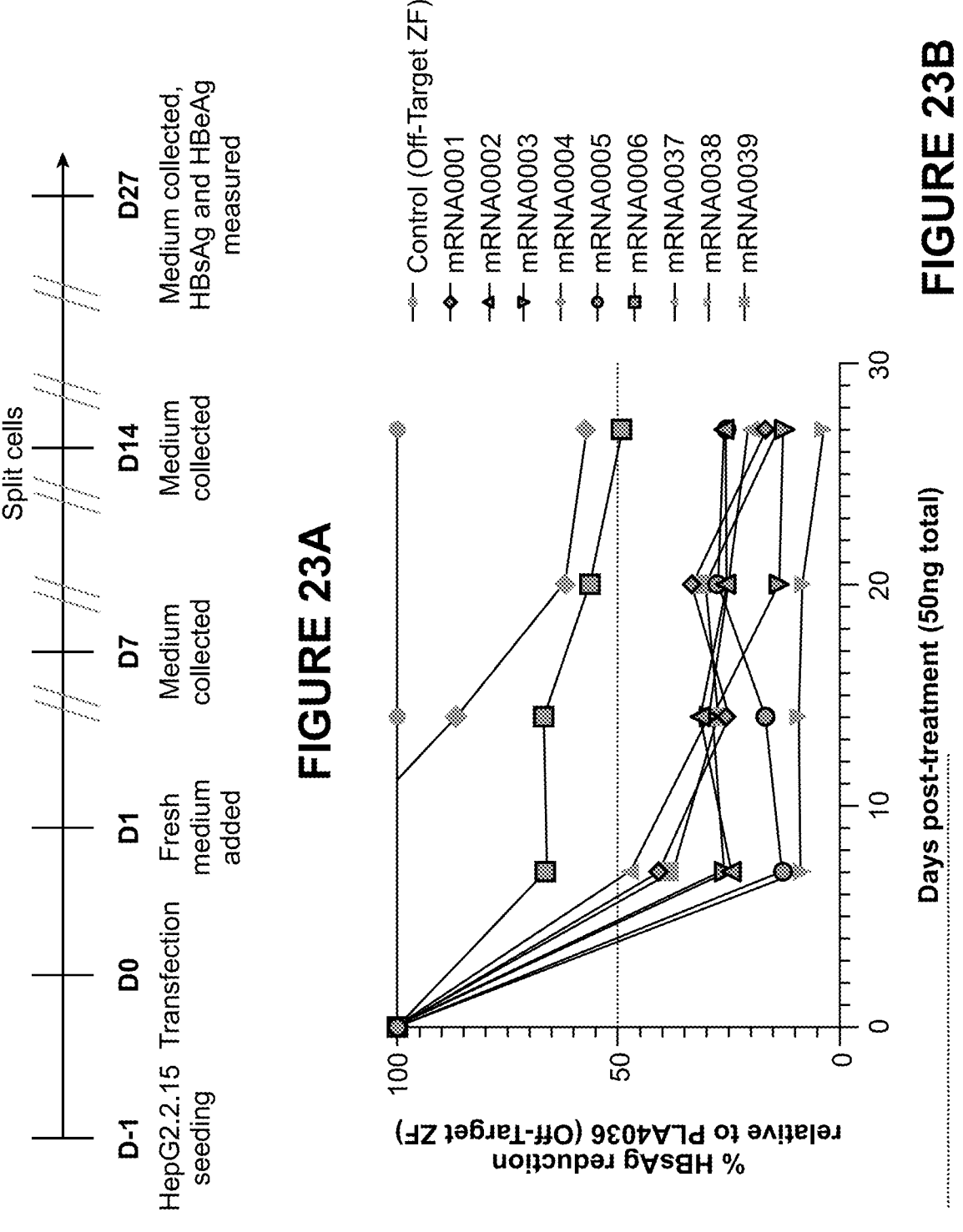
FIGS. 23A-23C show an experimental timeline for testing durable silencing of HBsAg (FIG. 23A), a graph showing the durability of HBsAg silencing by ZF fusion proteins (FIG. 23B), and a graph showing the durability of HBsAg silencing by CRISPR-off fusion proteins with guide RNAs (FIG. 23C) in an integrated cell line. The mRNA corresponding to the ZF motif for each fusion protein is indicated. Error bars represent mean+/–SEM.
Figure 23C:
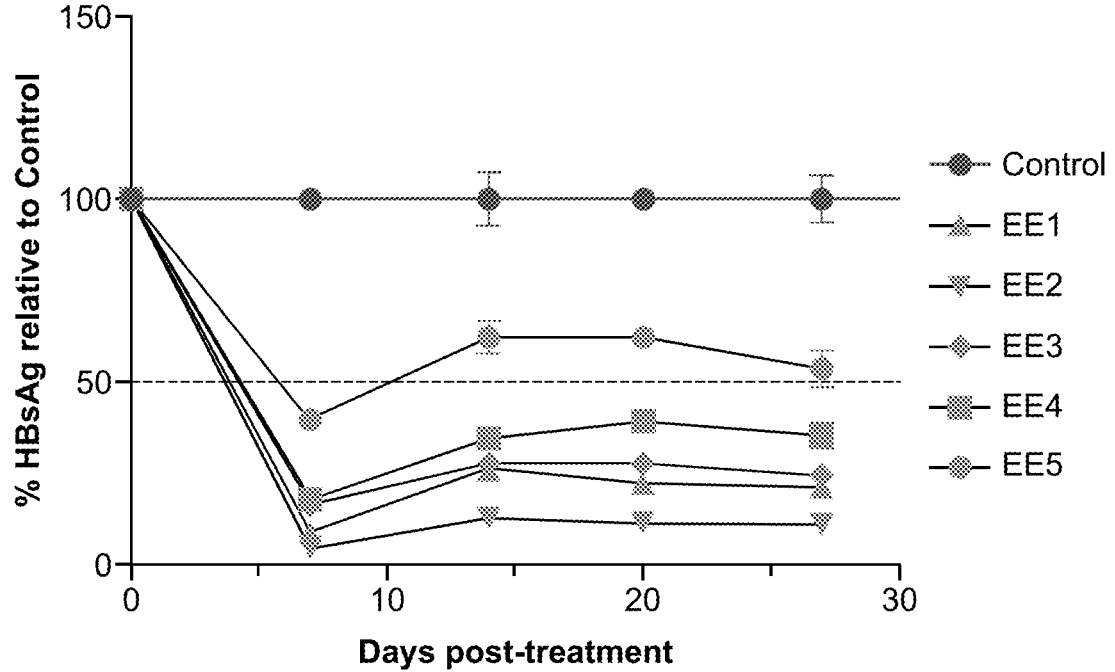

In this example, top ZF and CRISPR-off fusion proteins with guide RNAs were tested for durable repression of HBsAg. Active ZFPs and CRISPR-off editors showed durable silencing through Day 27 with 50 ng treatment. Experimental schematic and results are shown in FIGS. 23A-23C.

Example 10. Testing of Silencing of HBsAg in a Second Model for Int-HBV

Figure 24:
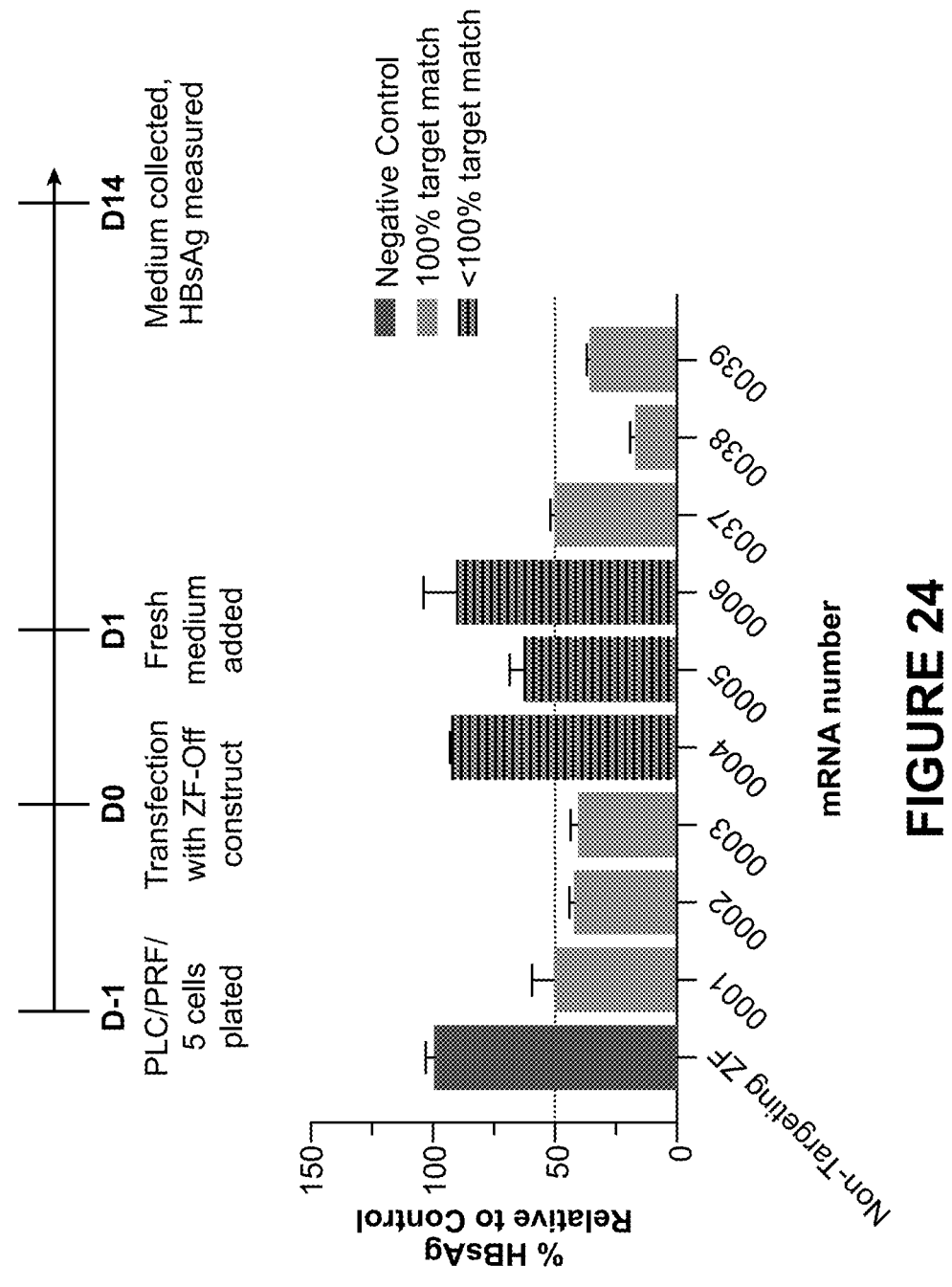
FIG. 24 is an experimental timeline for testing HBsAg silencing in a PLC/PRF/5 in vitro model (top) and a graph showing % HBsAg relative to control on Day 14 after administration of ZF fusion proteins. The mRNA corresponding to the ZF motif for each fusion protein is indicated. Information about the % match to target for each construct is also indicated.
Figure 25A:
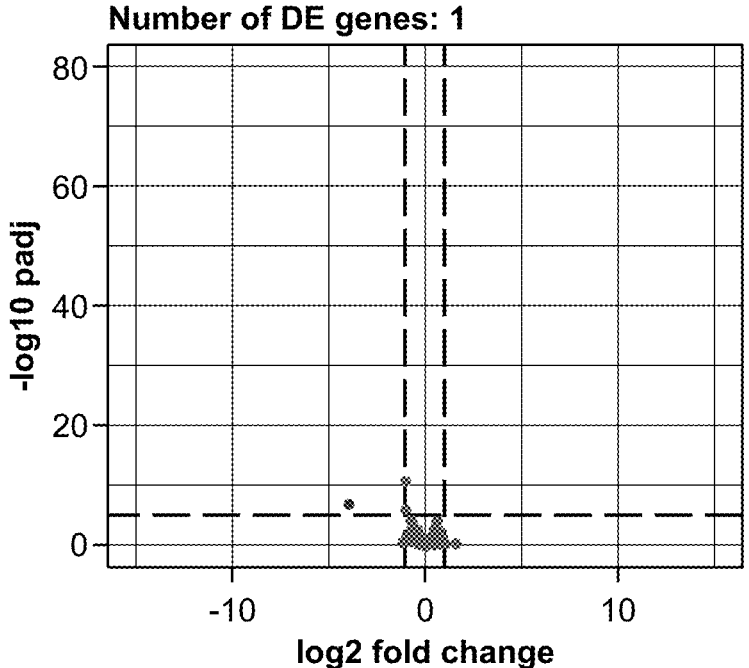
FIG. 25A is a volcano plot showing differentially expressed (DE) genes for an exemplary ZF specificity assay. DE genes are shown with dots.
Figure 25B:
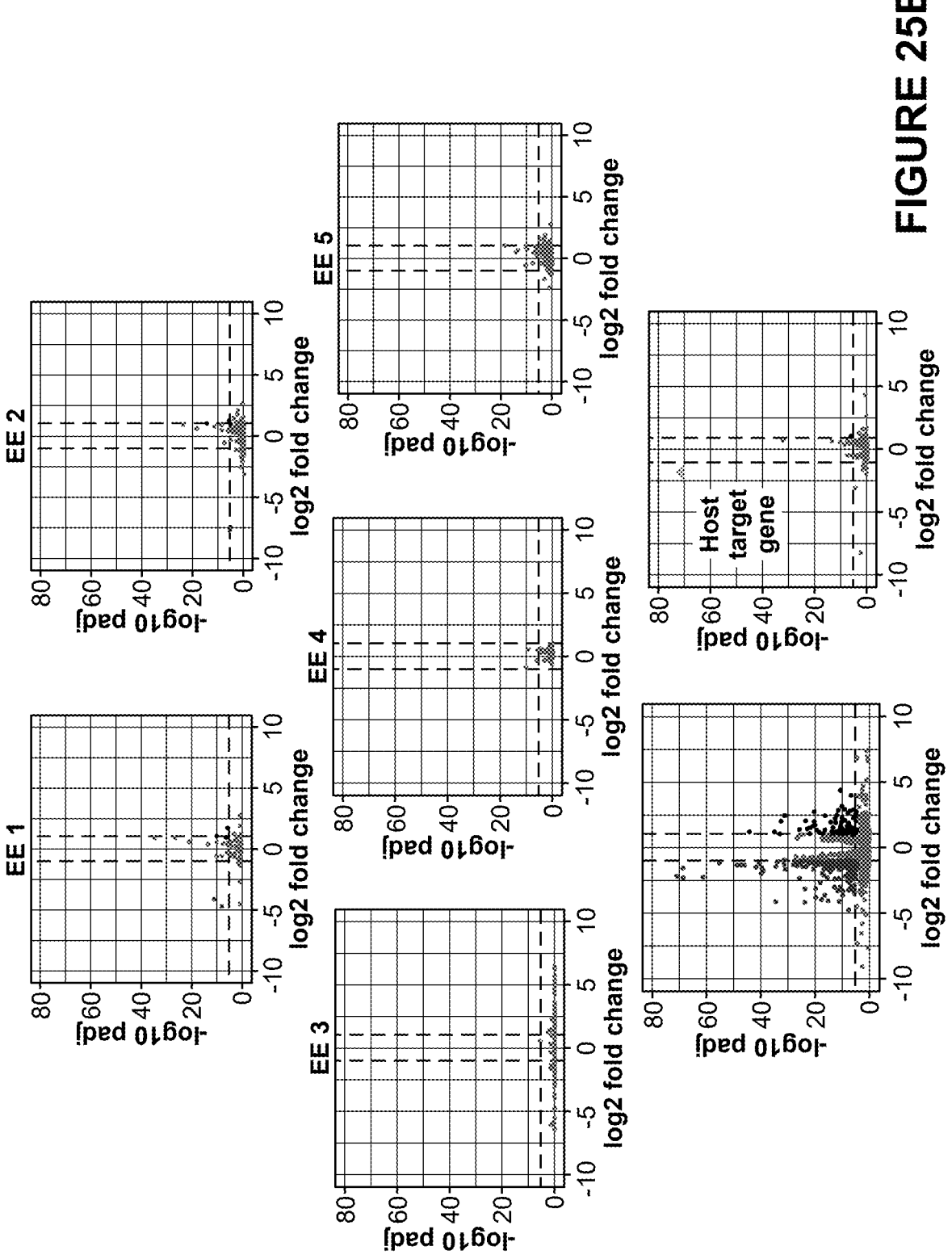
FIG. 25B is a volcano plot showing DE for CRISPR-off and gRNA epigenetic editors. Points represent genes with their change in expression (x-axis) and statistical significance of that change (y-axis).
Figure 25C:
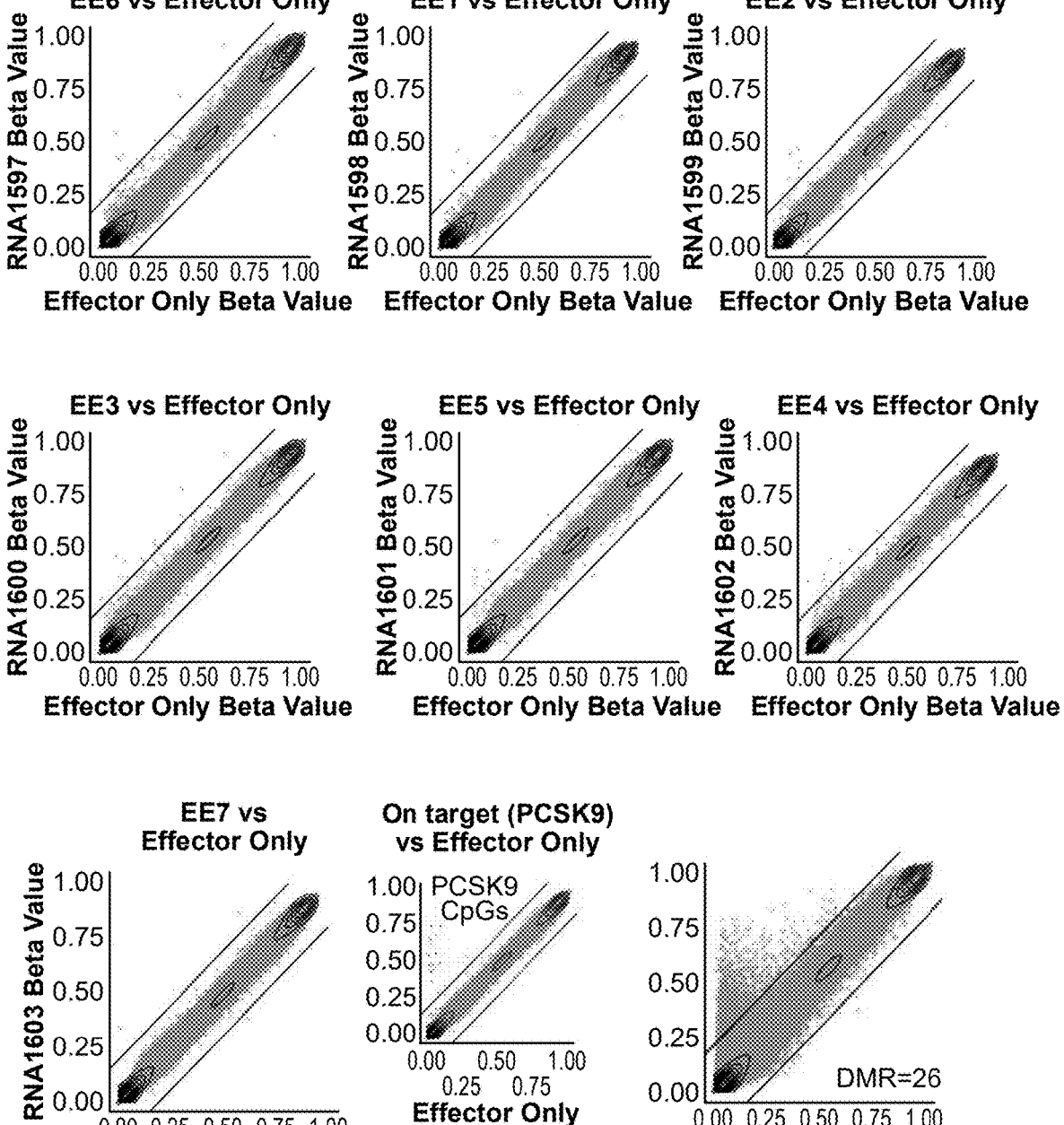

In this example, top ZF fusion proteins were tested for repression of HBsAg in PLC/PRF/5 cells. A subset of the ZFPs silenced HBsAg in this second model. Experimental schematic and results are shown in FIG. 24. 1. Testing ZF Fusion Proteins and CRISPR-off with guide RNAs for Specificity In this example, ZF fusion proteins targeting HBV exhibiting significant silencing were profiled for specificity in HepG2-NTCP at day 19. All comparisons were performed against a non-targeting ZFP control. An exemplary result for the ZF fusion protein with mRNA0001 zinc finger motif is shown in FIG. 25A. CRISPR-off with guide RNAs were similarly profiled. HepG2-NTCP cells were transfected with 100 ng of total payload using Gen Voy™ LNP at a 1:1 gRNA:effector ratio. Cells were split every 3-4 days and collected at day 15 post-treatment for specificity assessments, including RNA-seq and methylation array. DESeq2 was used to identify differential gene expression. As shown in FIG. 25B, little to no changes were observed above chosen thresholds (absolute [log 2 [fold change]]>1 and −log 10 [adjusted p-value]>5) as expected for effectors targeting HBV DNA. For methylation array, the Infinium MethylationEPIC v2.0 array was used, and DMRs were identified using Bumphunter. EE3, EE4, and EE5 had a result of DMR=0. Results are shown in FIGS. 25C-25D.

Example 11. In Vivo Analysis of ZF-Off Constructs

Figure 27:
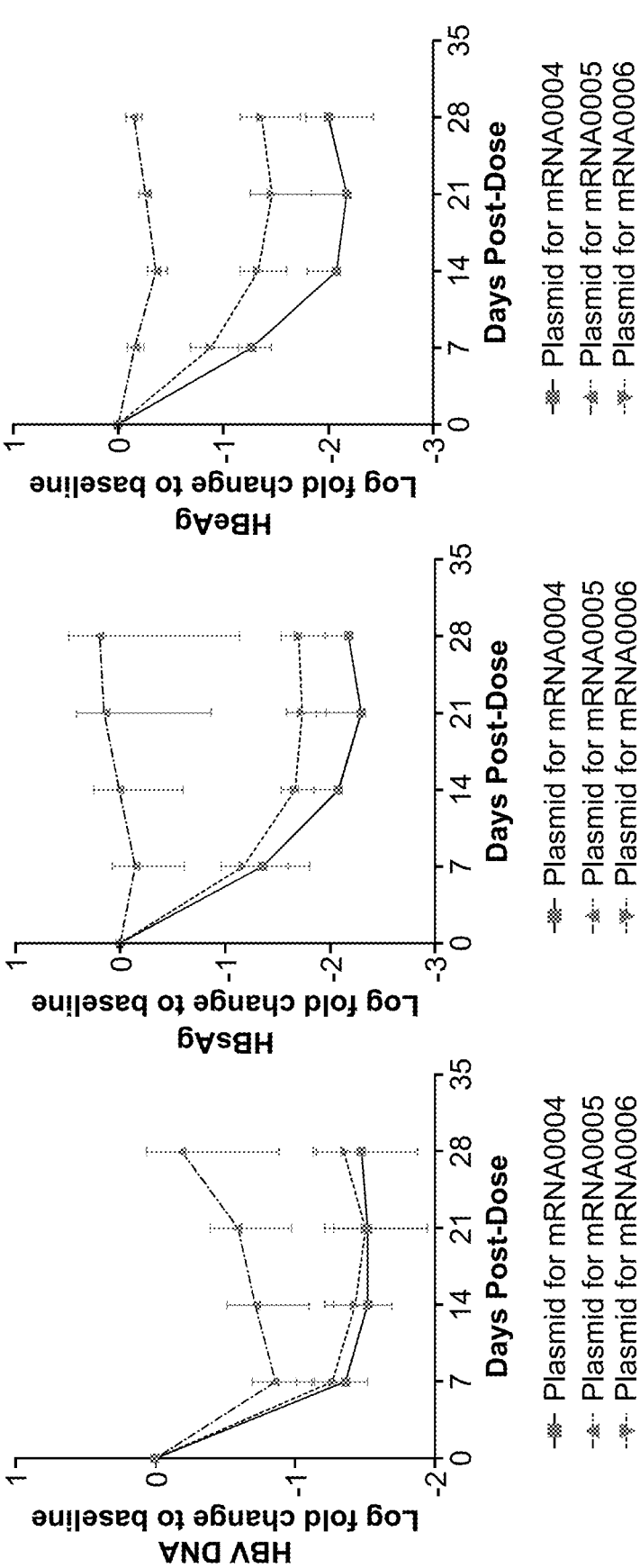
FIG. 27 shows graphs showing log fold change, relative to baseline, for HBV DNA (left), HBsAg (middle), and HBeAg (right) in plasma of mice treated with the plasmids indicated in the experiment shown in FIG. 26.

Ten ZF-Off constructs as well as vehicle-only and CRISPR-Off controls were administered to AAV-HBV mice at 1 mg/kg as shown in the schematic in FIG. 26. Table 16 shows the zinc finger motifs for each experimental group; the corresponding plasmid from Table 18, comprising the nucleic acid encoding the ZF-Off construct, was administered. Plasma from the mice was tested at Days 7, 14, 21, and 28 post dose for HBV DNA, HBsAg, and HBeAg. The livers were collected for further analysis. Results are shown in FIG. 27. The ZF-Off construct with the ZF motif from mRNA0004 showed more than a 1.5 log reduction in HBV DNA, a >2 log reduction in HSbsAg, and a >2 log reduction of HBeAg, all sustained up to 28 days from the dose.

TABLE 16

Experimental groups for in vivo testing of ZF-Off constructs.

| Group | ZF motif in construct administered | N |
| --- | --- | --- |
| 1 | mRNA0001 | 6 |
| 2 | mRNA0002 | 6 |
| 3 | mRNA0003 | 6 |
| 4 | mRNA0005 | 6 |
| 5 | mRNA0006 | 6 |
| 6 | mRNA0038 | 6 |

TABLE 16-continued

Experimental groups for in vivo testing of ZF-Off constructs.

| Group | ZF motif in construct administered | N |
| --- | --- | --- |
| 7 | mRNA0004 | 6 |
| 8 | mRNA0039 | 6 |
| 9 | mRNA0021 | 6 |
| 10 | mRNA0037 | 6 |

Example 12. Zinc Finger Protein Multiplexing Study in an AAV-HBV and Tg-HBV Mouse Model AAV-HBV mice are injected with a single administration at 0.5 mg/kg of one, two, or three ZF fusion proteins, delivered as mRNA, in LNPs (schematic, FIG. 28) in accordance with Table 17. HBV DNA, HBsAg, and HBeAg are assayed in plasma at one or more time points, and the mouse liver is collected for further analysis.

TABLE 17

Multiplexing sample groups.

| Group | ZF_Off-1 | ZF_Off-2 | ZF_Off-3 |
| --- | --- | --- | --- |
| 1 | mRNA0004 | mRNA0021 | — |
| 2 | mRNA0004 | mRNA0003 | — |
| 3 | mRNA0004 | mRNA0038 | — |
| 4 | mRNA0004 | mRNA0021 | mRNA0003 |
| 5 | mRNA0004 | mRNA0038 | mRNA0003 |
| 6 | mRNA0004 | mRNA0021 | mRNA0038 |
| 7 | mRNA0004 | mRNA0001 | — |
| 8 | mRNA0004 | mRNA0039 | — |
| 9 | mRNA0004 | — | — |
| 10 | Vehicle | — | — |

Example 13. Dose Response for CRISPR-Off Constructs in an AAV In Vivo Model

Figure 29:
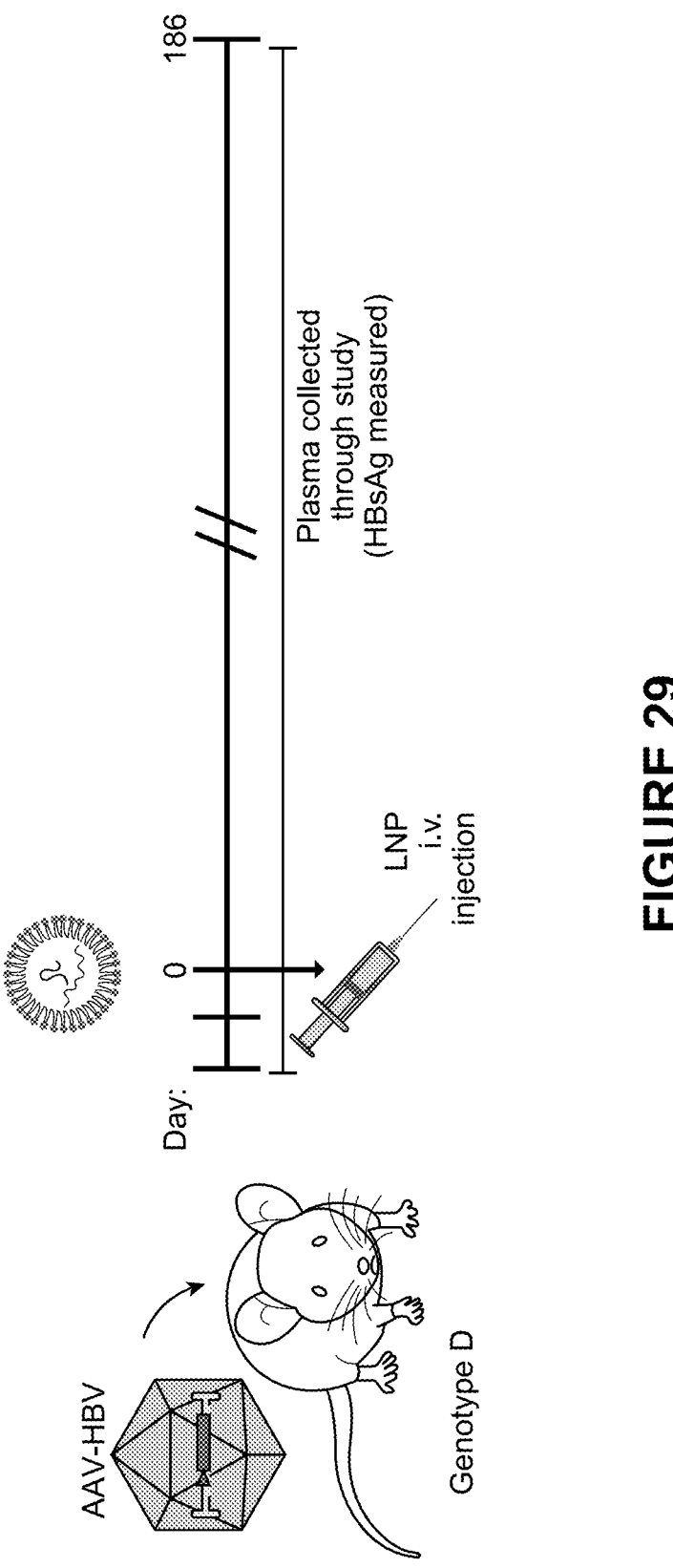
FIG. 29 is a schematic for a dose response experiment using CRISPR-Off in an AAV-HBV in vivo model.
Figure 30:
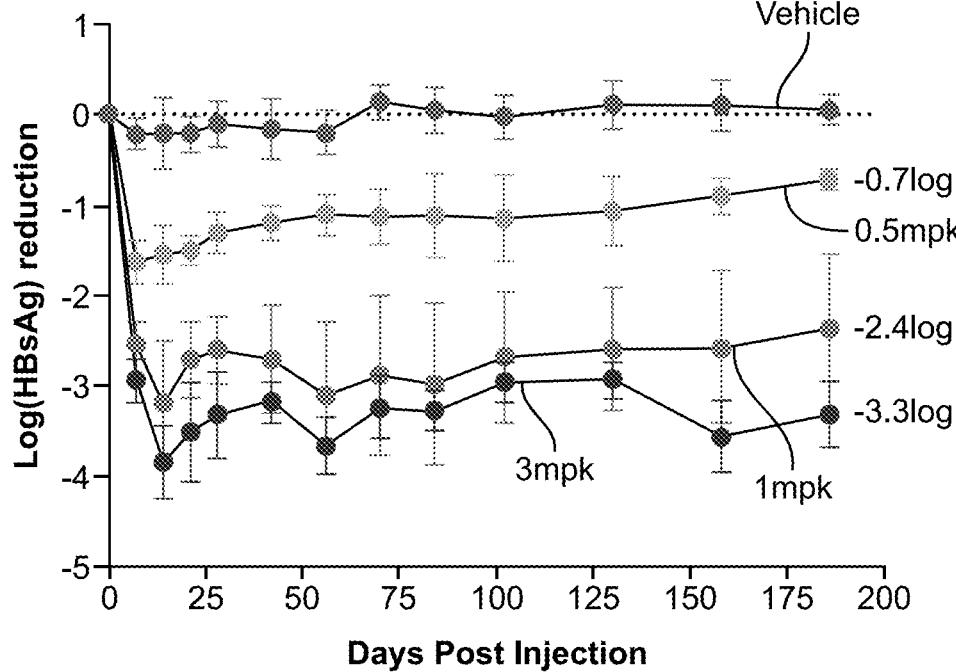
FIG. 30 is a line graph of plasma HBsAg levels for a dose response experiment using CRISPR-Off in an AAV-HBV in vivo model.

A single dose of CRISPR-Off (SEQ ID NO: 1248) mRNA with guide RNA #008 as well as vehicle-only control was tested via 1:1 mRNA:guide RNA administration to AAV-HBV mice at 0.5 mg/kg, 1 mg/kg, or 3 mg/kg in LNPs as shown in the schematic in FIG. 29. Plasma from the mice was tested for HBsAg at thirteen time points through 186 days after injection. Results are shown in FIG. 30. The highest dose administered showed an approximately 3.3 log reduction in HBsAg, sustained through 186 days after the dose.

Example 14. Dose Response for CRISPR Off Constructs in Tg In Vivo Model

Figure 31:
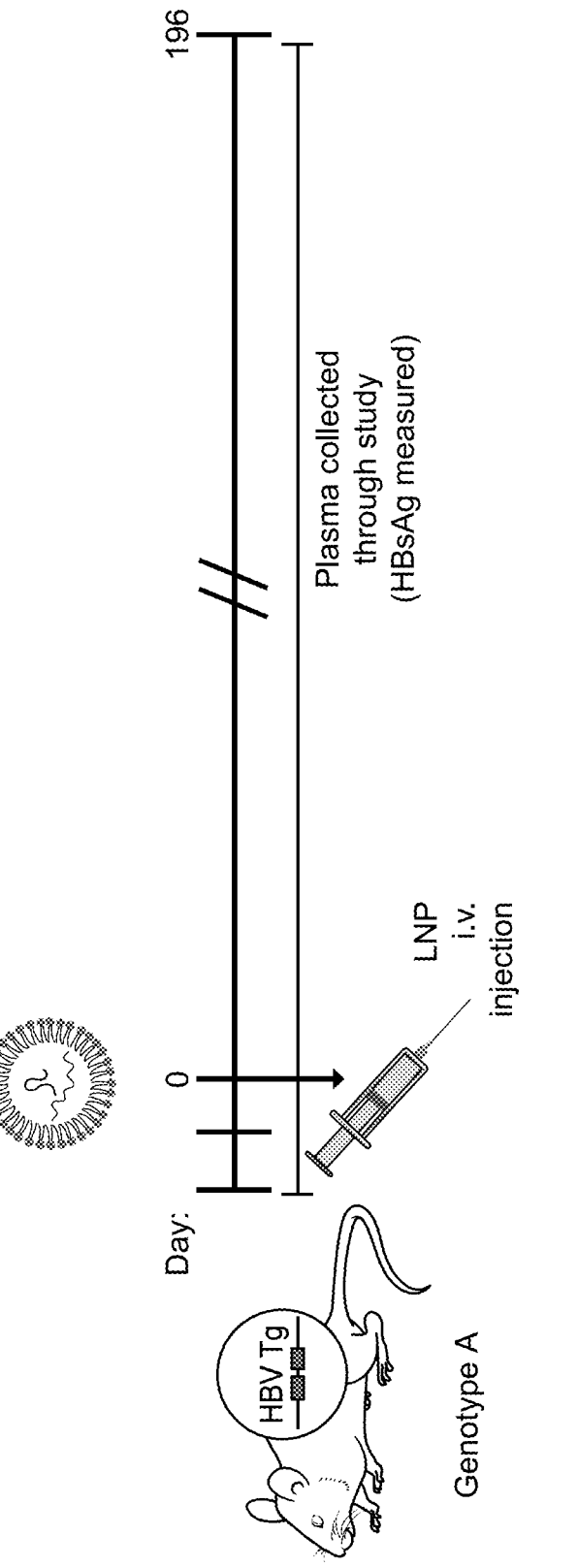
FIG. 31 is a schematic for a dose response experiment using CRISPR-Off in a Tg-HBV in vivo model.
Figure 32:
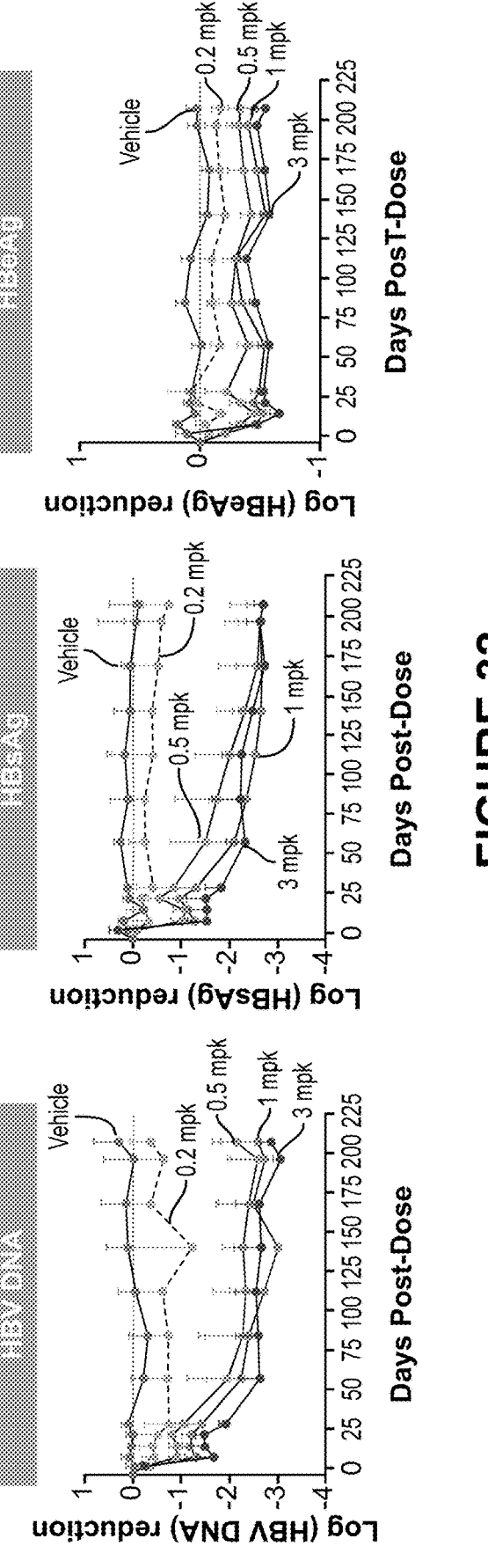
FIG. 32 shows line graphs of plasma HBV DNA, HBsAg, and HBeAg levels for a dose response experiment using CRISPR-Off in a Tg-HBV in vivo model.

A single dose of CRISPR-Off (SEQ ID NO: 1248) mRNA with guide RNA #008 as well as vehicle-only control was tested via 1:1 mRNA:guide RNA administration to Tg-HBV mice at 0.5 mg/kg, 1 mg/kg, or 3 mg/kg in LNPs as shown in the schematic in FIG. 31. Plasma from the mice was tested for HBsAg at thirteen time points through 186 days after injection. Results are shown in FIG. 32. The highest dose administered showed an approximately 2.6 log reduction in HBsAg, sustained through 196 days after the dose.

Figure 33:
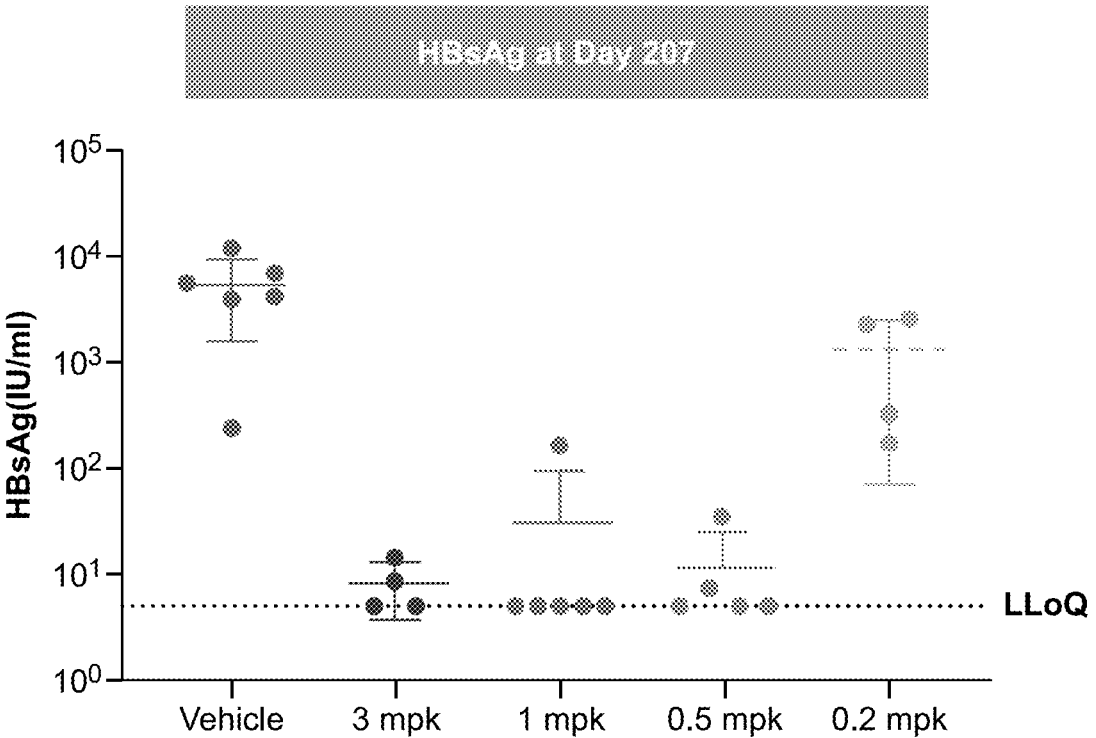
FIG. 33 is a dot plot of HBsAg levels of individual mice at the 207 day time point of a dose response experiment using CRISPR-Off in a Tg-HBV in vivo model.

A second dose response experiment in Tg-HBV model using CRISPR-Off (SEQ ID NO: 1248) mRNA with guide RNA #008 formulated in LNPs was conducted, with administrations at 0.2 mg/kg, 0.5 mg/kg, 1 mg/kg, or 3 mg/kg of 1:1 mRNA:guide RNA. A vehicle-only control was also used. In this experiment, plasma was tested for HBV DNA, HBsAg, and HBeAg at 13 time points through 207 days after injection. Results are shown in FIG. 32. The HBsAg results for individual mice at the final time point of 207 days after injection are plotted in FIG. 33. All of the mice in the 0.5 mg/kg, 1 mg/kg, and 3 mg/kg group had reduced HBsAg at Day 207 as compared to vehicle only control. Alanine transaminase (ALT) level in the mice was also tested at 207 days and found to be comparable to that of healthy untreated mice for all treatment groups.

Example 15. Guide RNA Testing in AAV-HBV Mice

Figure 34:
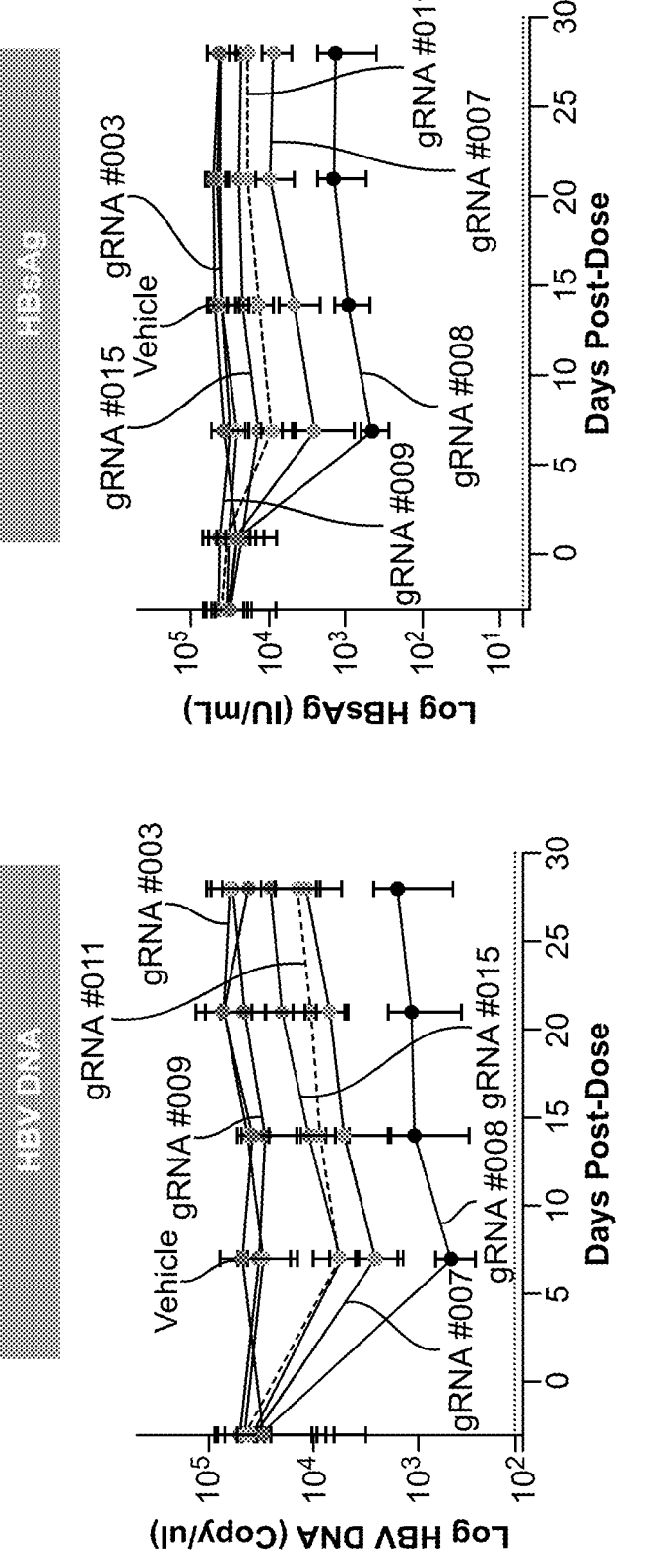
FIG. 34 shows line graphs of HBV-DNA and HBsAg in plasma in AAV mice treated with CRISPR-Off mRNA with various single guide RNAs. n=5 for each guide RNA treatment group; n=4 for vehicle-only control.

Six guide RNAs were tested for relative efficacy using CRISPR-Off (SEQ ID NO: 1248) in a 28-day, single-dose study. CRISPR-Off construct mRNA and one of gRNA #003, gRNA #007, gRNA #008, gRNA #009, gRNA #011, and gRNA #015 was delivered at 1:1 mRNA:guide RNA at 1 mg/kg. Controls included vehicle only, CRISPRi with gRNA #008 (not shown), and wild type Cas9 with gRNA #011 (not shown). HBV DNA and HBsAg was measured over 28 days. Results are shown in FIG. 34. Most of the single guide treatments tested in this experiment resulted in decreased HBV DNA and HBsAg versus vehicle only control.

Figure 35A:
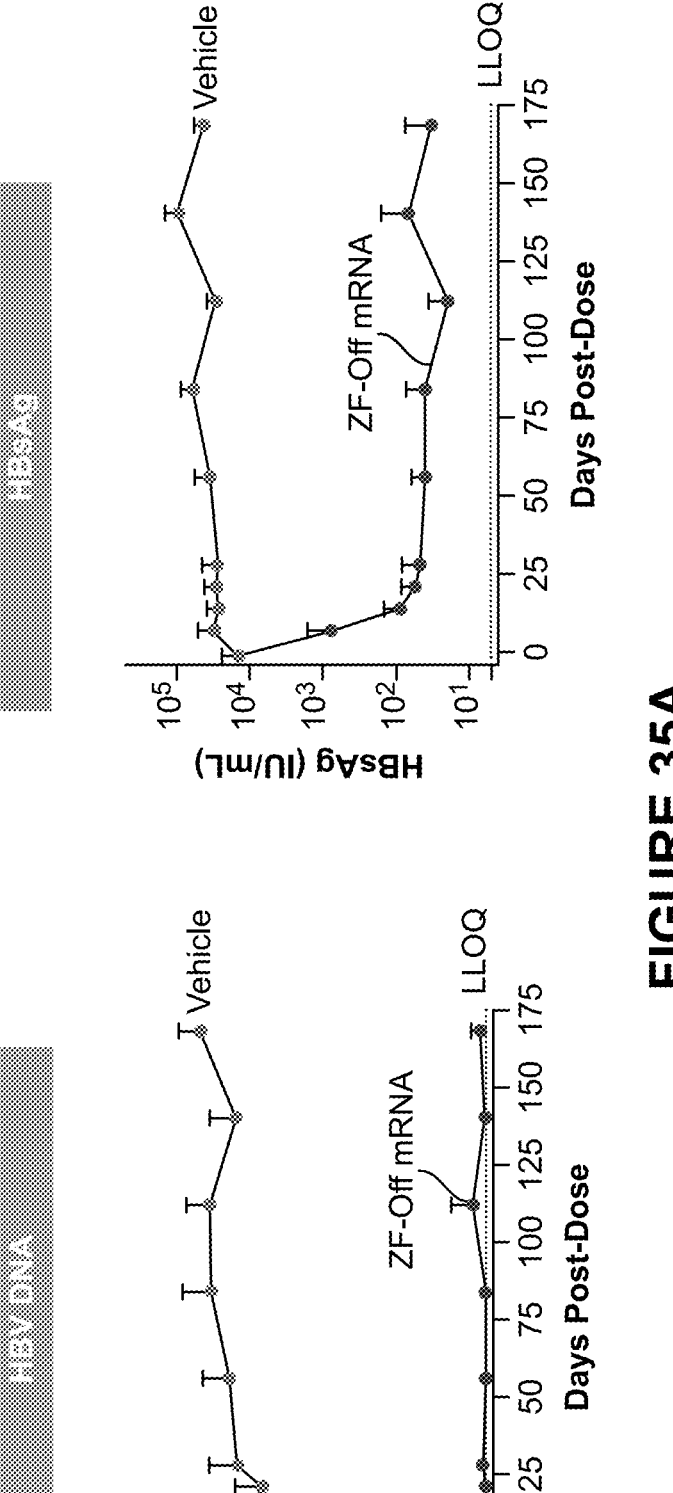
FIG. 35A shows line graphs of HBV-DNA and HBsAg in plasma in AAV mice treated with a single dose of ZF-Off mRNA.

Example 16. Durability Study for ZF-Off in AAV-HBV In Vivo Model: Single and Re-Dose Mice were injected with a single dose ZF-Off construct (SEQ ID NO: 36) mRNA at 1 mg/kg in LNPs. HBV DNA and HBsAg were measured from plasma over a period of 168 days. Results are shown in FIG. 35A. The treatment resulted in a sustained reduction of greater than 2 log in HBV DNA and similar sustained reduction in HBsAg.

Figure 35B:
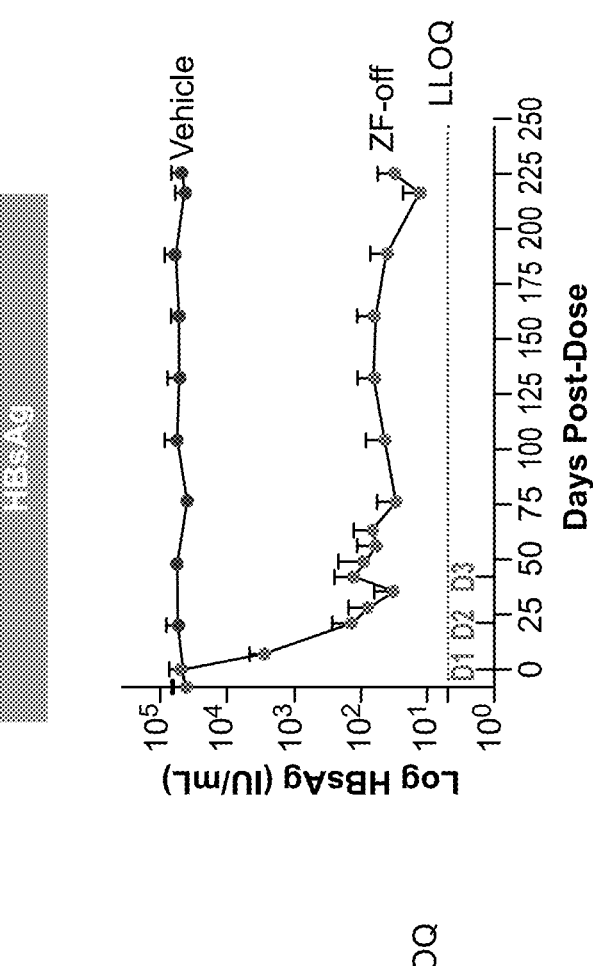
FIG. 35B shows line graphs of HBV-DNA and HBsAg in plasma in AAV mice treated with multiple doses of ZF-Off mRNA.

In another study, mice were injected with the ZF-Off construct (SEQ ID NO: 36) mRNA at 1 mg/kg for three doses: Day 0, Day 21, and Day 42. HBV DNA and HBsAg were measured from plasma over a period of 225 days. Results are shown in FIG. 35B. Results were similar to those of the previous single-dose experiment and in this experiment sustained over 225 days.

Example 17. Re-Dosing Studies for CRISPR-Off in AAV-HBV In Vivo Model

Figure 36:
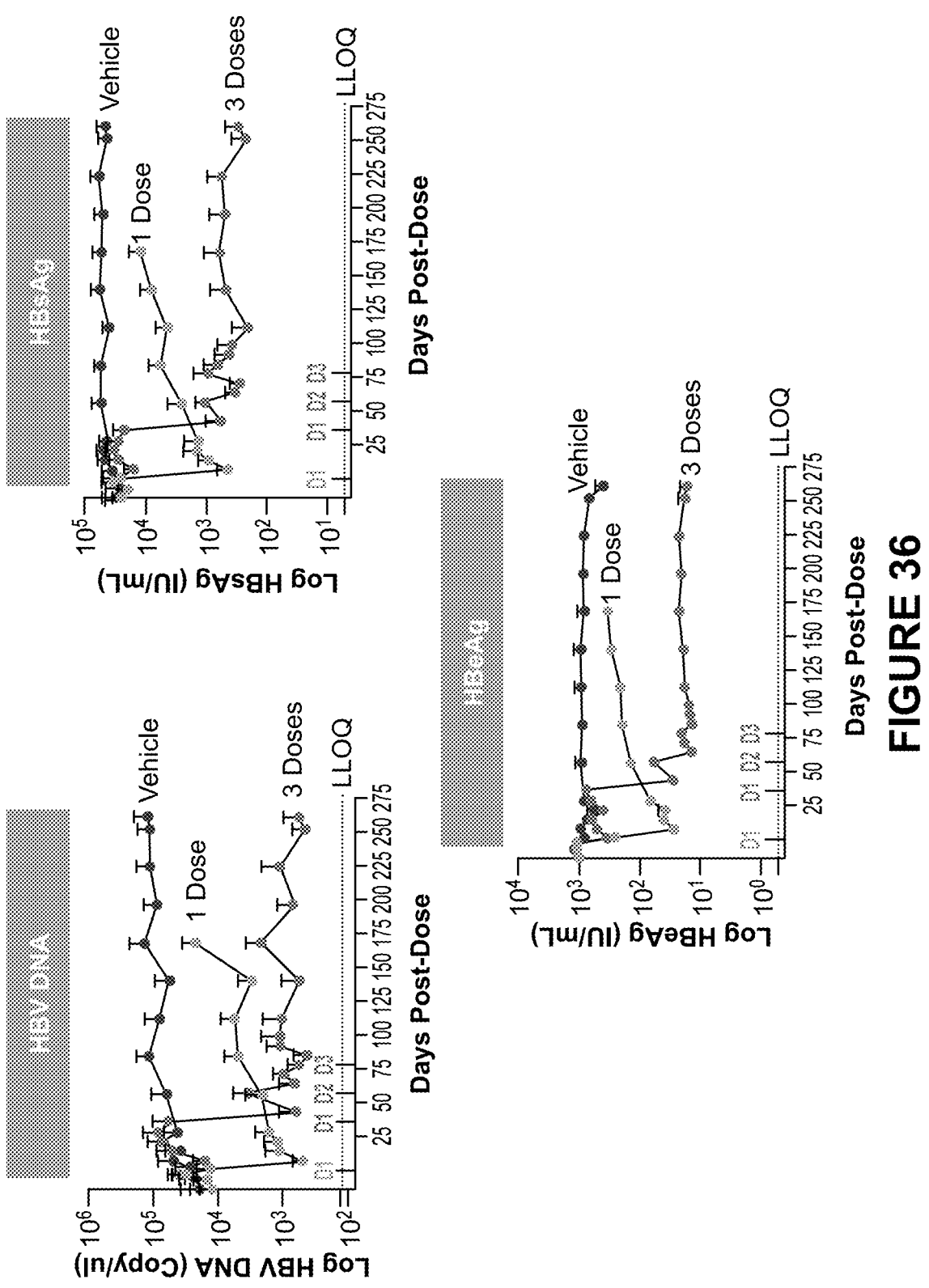
FIG. 36 shows line graphs of HBV-DNA, HBsAg, and HBeAg in plasma in AAV mice treated with single versus multiple doses of 1 mg/kg CRISPR-Off mRNA with guide RNA.

AAV-HBV mice were dosed with either a single dose or three doses, all at 1 mg/kg in LNPs, of CRISPR-Off (SEQ ID NO: 1248) mRNA with gRNA #008 at a 1:1 ratio of mRNA:guide RNA. For the single dose condition, the dose was administered at Day 0. For the three-dose condition, the doses were administered at Day 36, Day 57, and Day 78. A vehicle-only control was also administered. Plasma measurements of HBV DNA, HBsAg, and HBeAg were taken through Day 168 for the single-dose condition, and through Day 261 for both the three-dose condition and the vehicle control. Results are shown in FIG. 36. Re-dosing with CRISPR-Off further improved and sustained the durability of the modulation of these HBV biomarkers.

Figure 37:
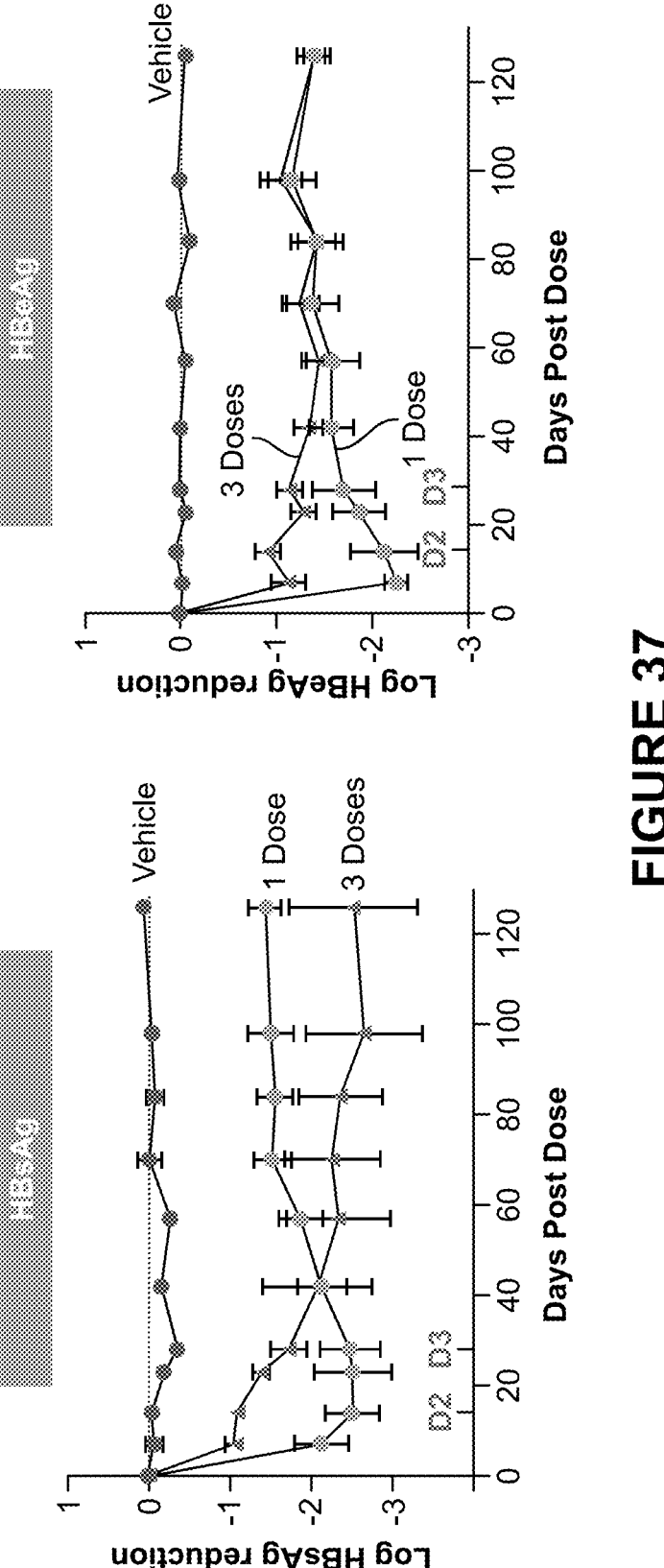
FIG. 37 shows line graphs of HBV-DNA and HBsAg in plasma in AAV mice treated with a single bolus dose of 3 mg/kg versus three doses of 1 mg/kg CRISPR-Off mRNA with guide RNA.

In another study, AAV-HBV mice were dosed with either a single dose of CRISPR-Off (SEQ ID NO: 1248) mRNA with gRNA #008 with an updated modification pattern (SEQ ID NO: 1249) (1:1 ratio mRNA:guide RNA) in LNPs at 3 mg/kg, or three doses of the same epigenetic editor, each at 1 mg/kg. Both groups received a dose at Day 0, and the three-dose group also received a dose at Day 14 and at Day 28. A vehicle-only control was also administered. HBsAg and HBeAg were measured from plasma through 126 days. Results are shown in FIG. 37. Near-additive pharmacology was demonstrated with the repeat dosing.

Figure 38:
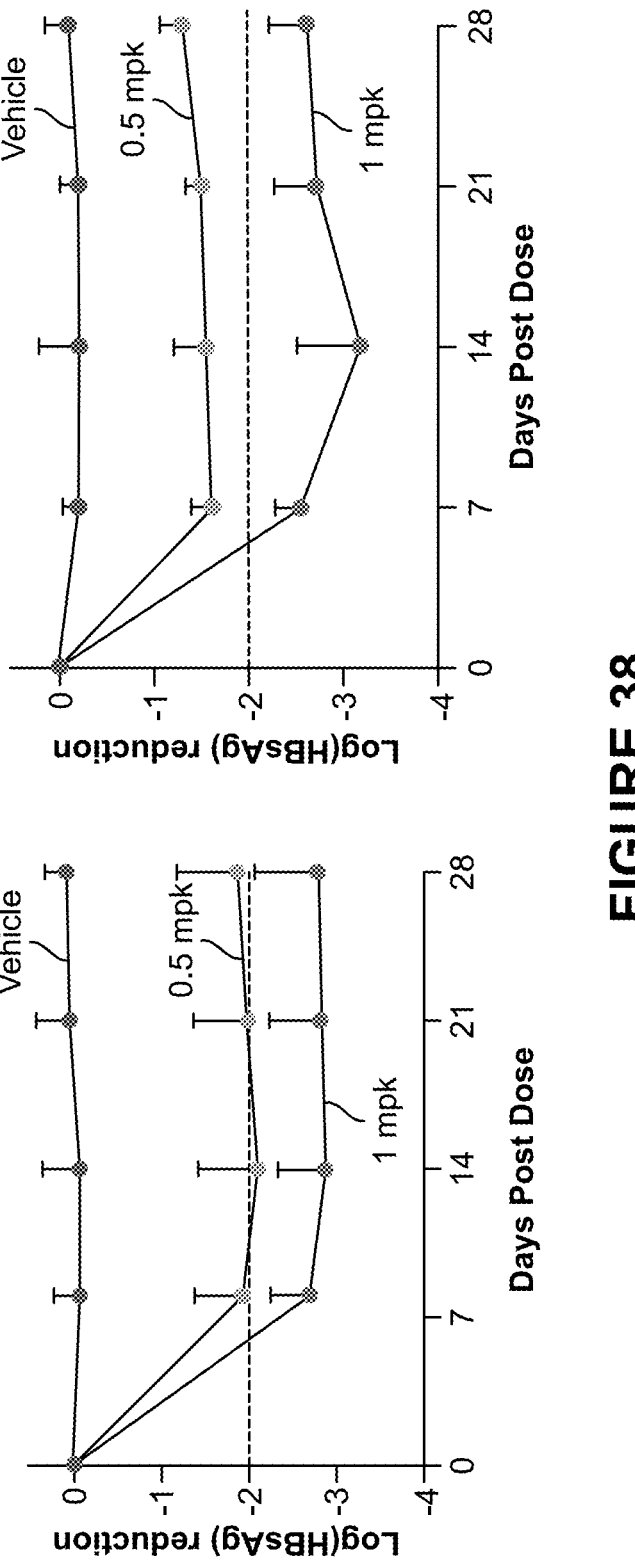
FIG. 38 shows line graphs of HBsAg in plasma in response to treatment with two different CRISPR-Off effectors (left, SEQ ID NO: 1248; right, SEQ ID NO: 1252) delivered via mRNA in combination with the same guide RNA.

Example 18. Testing CRISPR-Off and Guide RNA Modifications in an AAV-HBV In Vivo Model AAV-HBV mice were dosed with a single dose of either CRISPR-Off (SEQ ID NO: 1248) mRNA with gRNA #008 or an updated CRISPR-Off variant (SEQ ID NO: 1252) mRNA with gRNA #008 with an updated modification pattern (SEQ ID NO: 1249), with a 1:1 ratio of mRNA to guide RNA at either 0.5 mg/kg or 1 mg/kg, delivered in LNPs. A vehicle only control was also administered. HBsAg was measured in plasma over 28 days. Results are shown in FIG. 38. The updated CRISPR-Off variant with guide RNA modifications demonstrated 1.5× potency over the previous lead epigenetic editor.

Example 19. Methylation Studies for CRISPR-Off with Various Guide RNAs

Figure 39A:
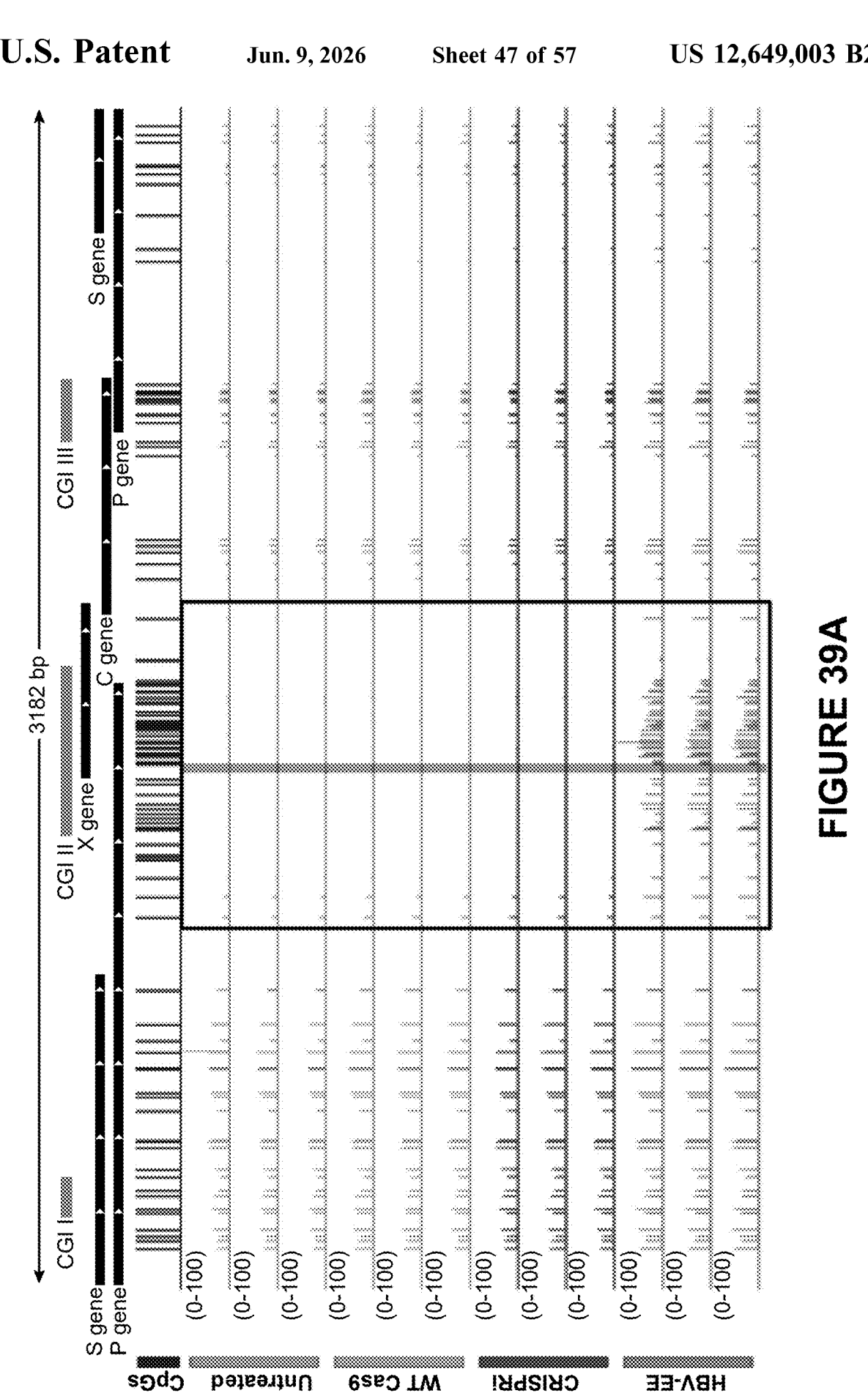
FIGS. 39A-39G show methylation of the HBV genome upon treatment with CRISPR-Off with various single guide RNAs versus wild type Cas9, CRISPRi, and non-targeting controls. The box in FIG. 39A represents the region 500 bp both upstream and downstream of the target site. The arrows indicate the position of the target sequence for the guide RNA used in the depicted experiment.
Figure 39B:
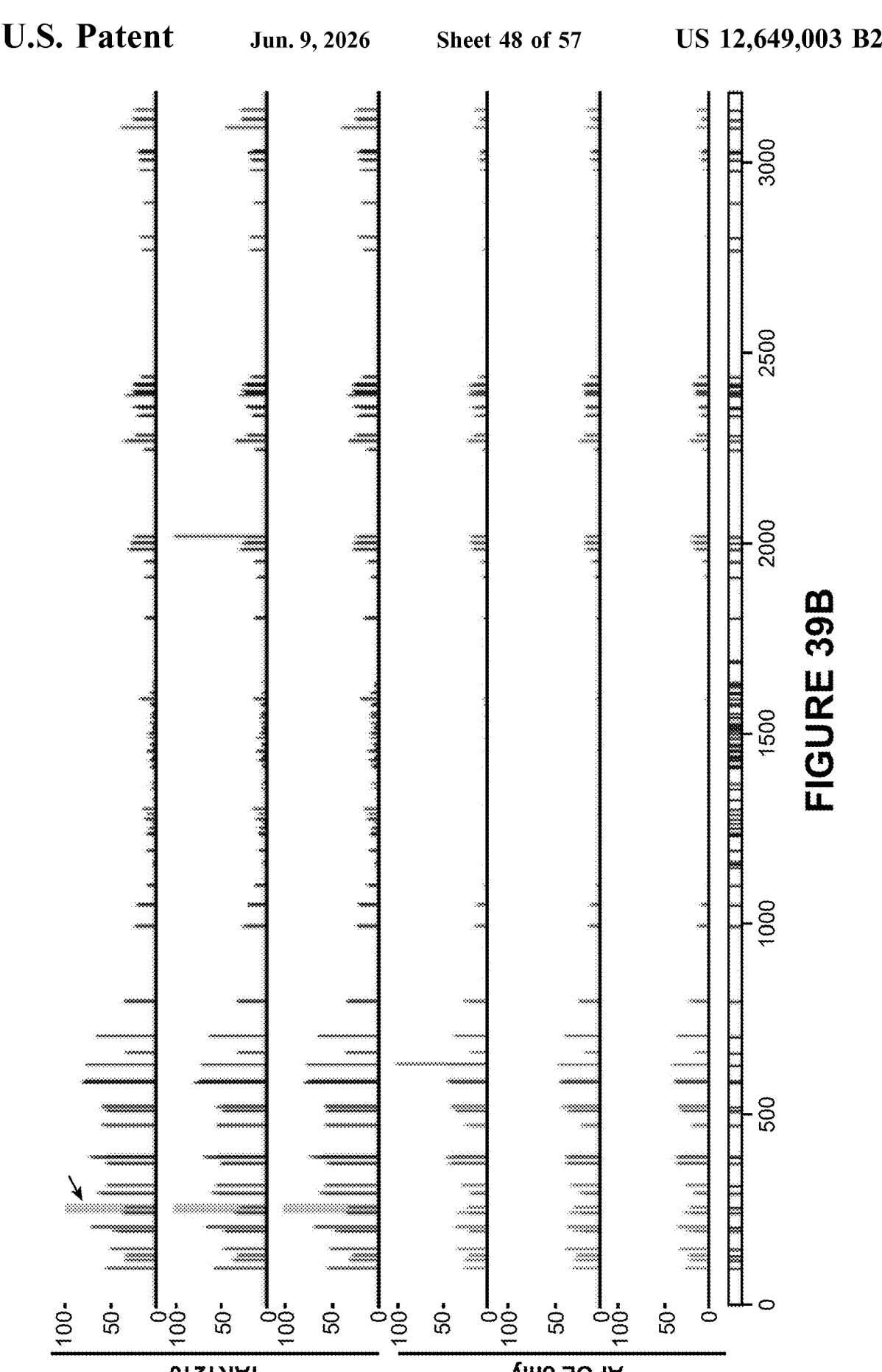
Figure 39C:
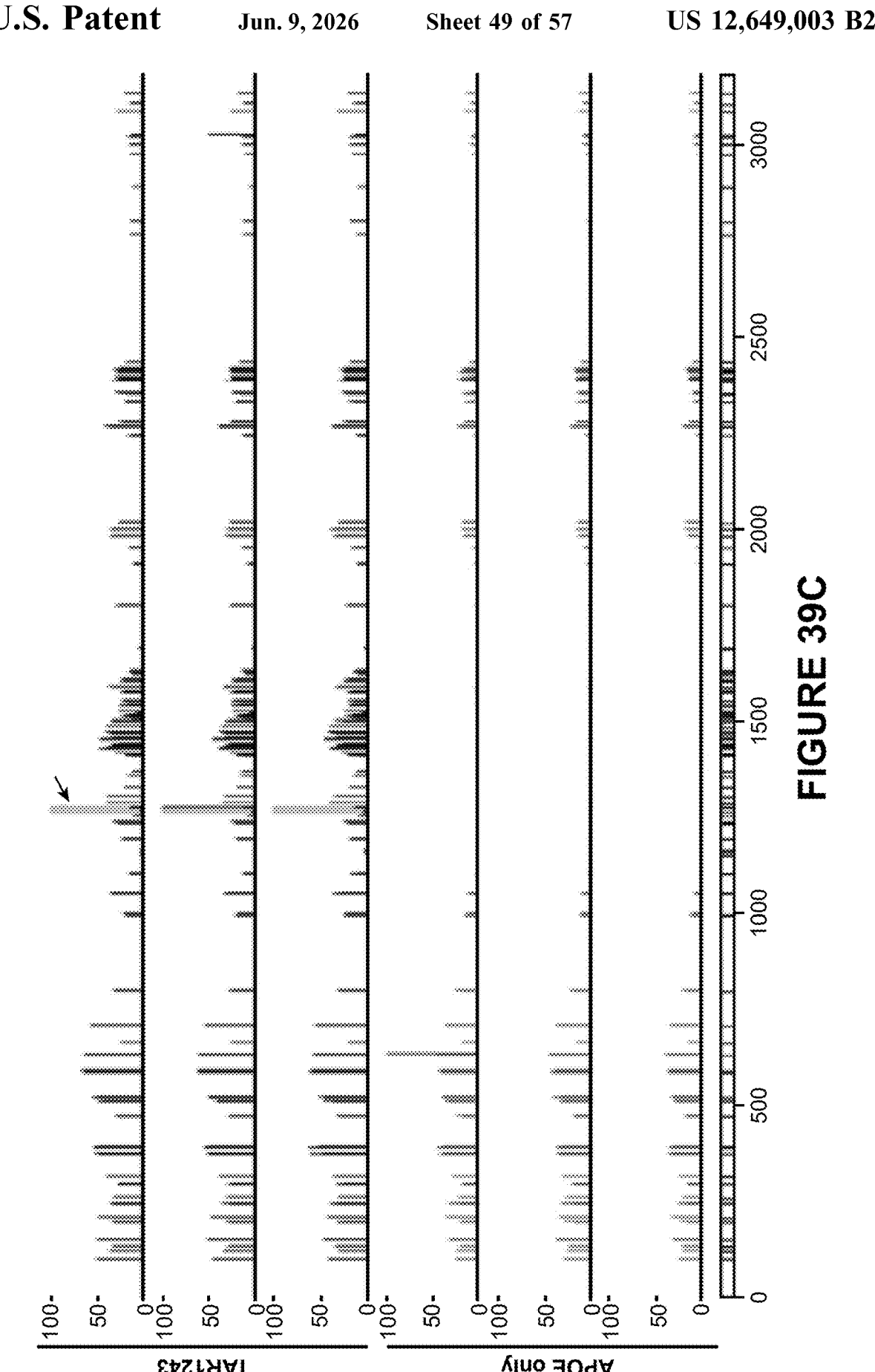
Figure 39D:
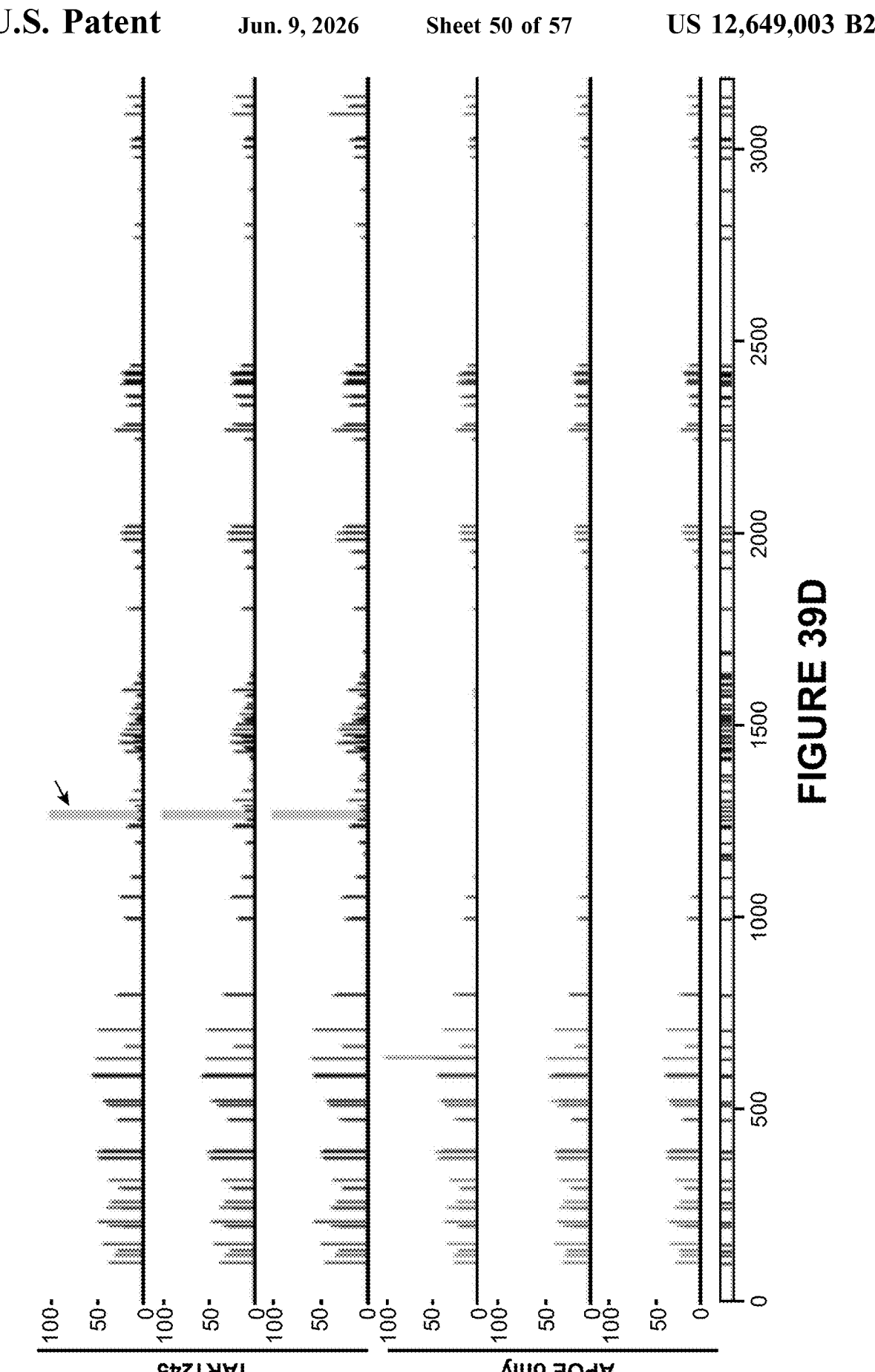
Figure 39E:
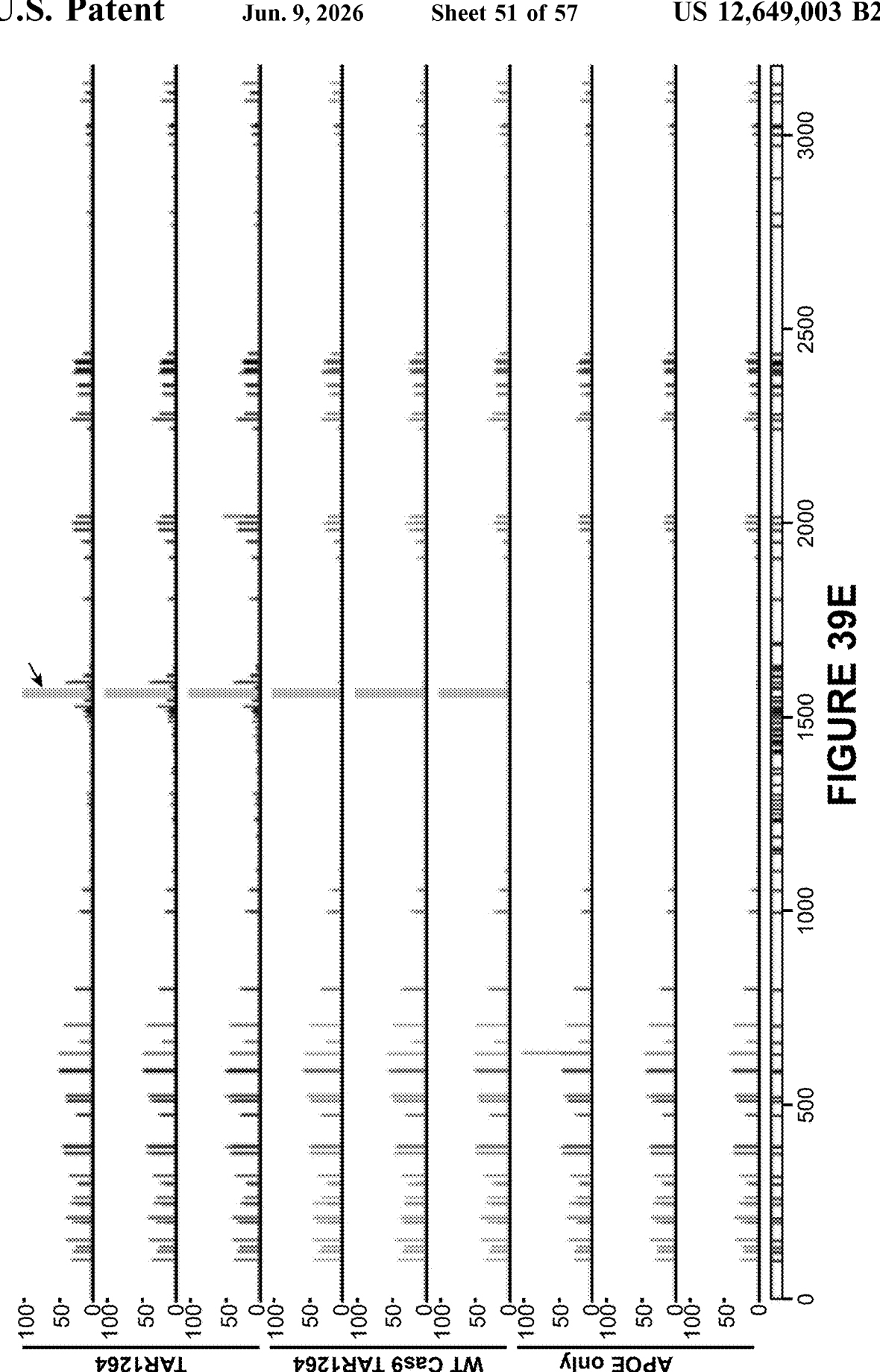
Figure 39F:
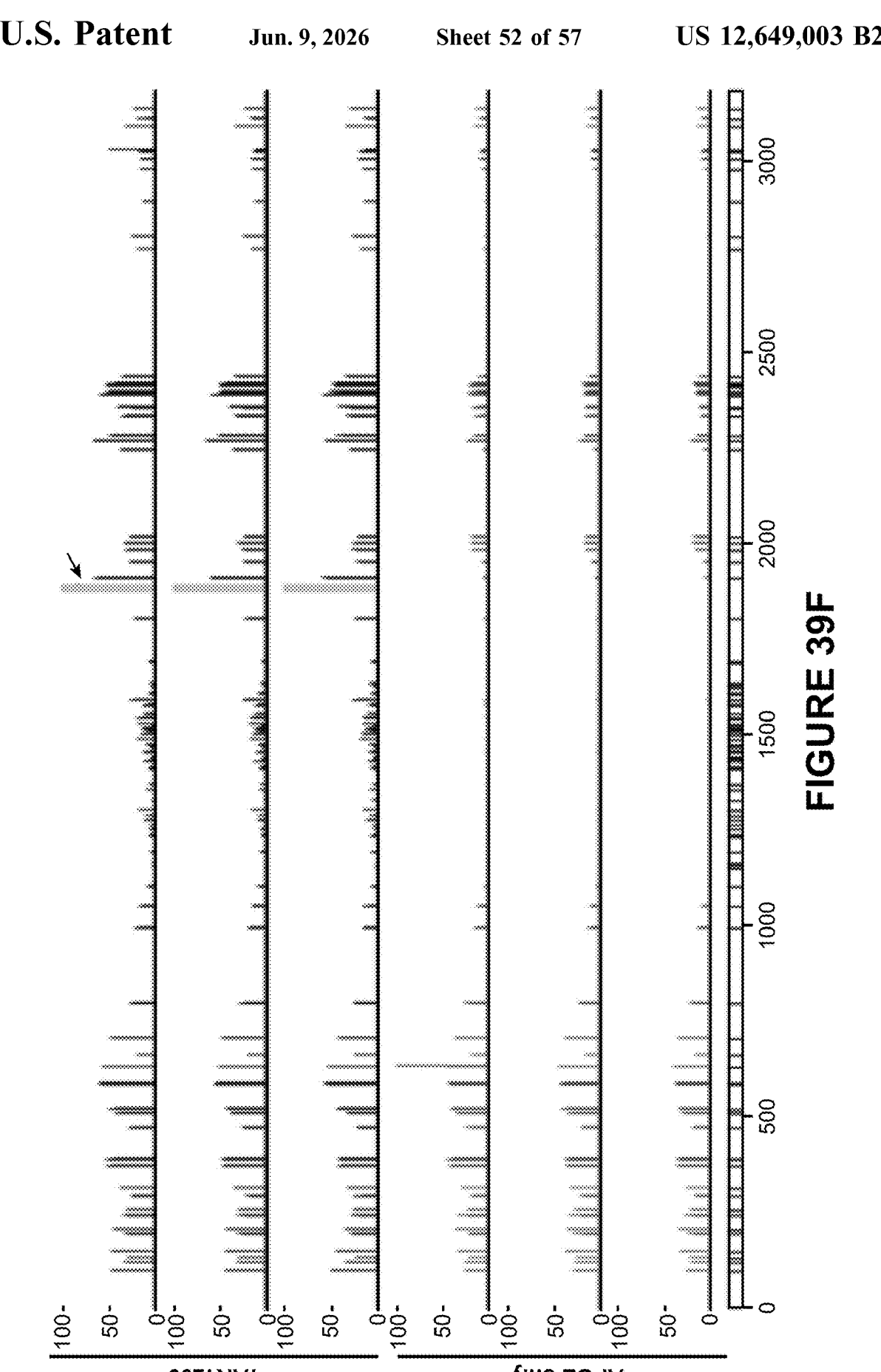
Figure 39G:
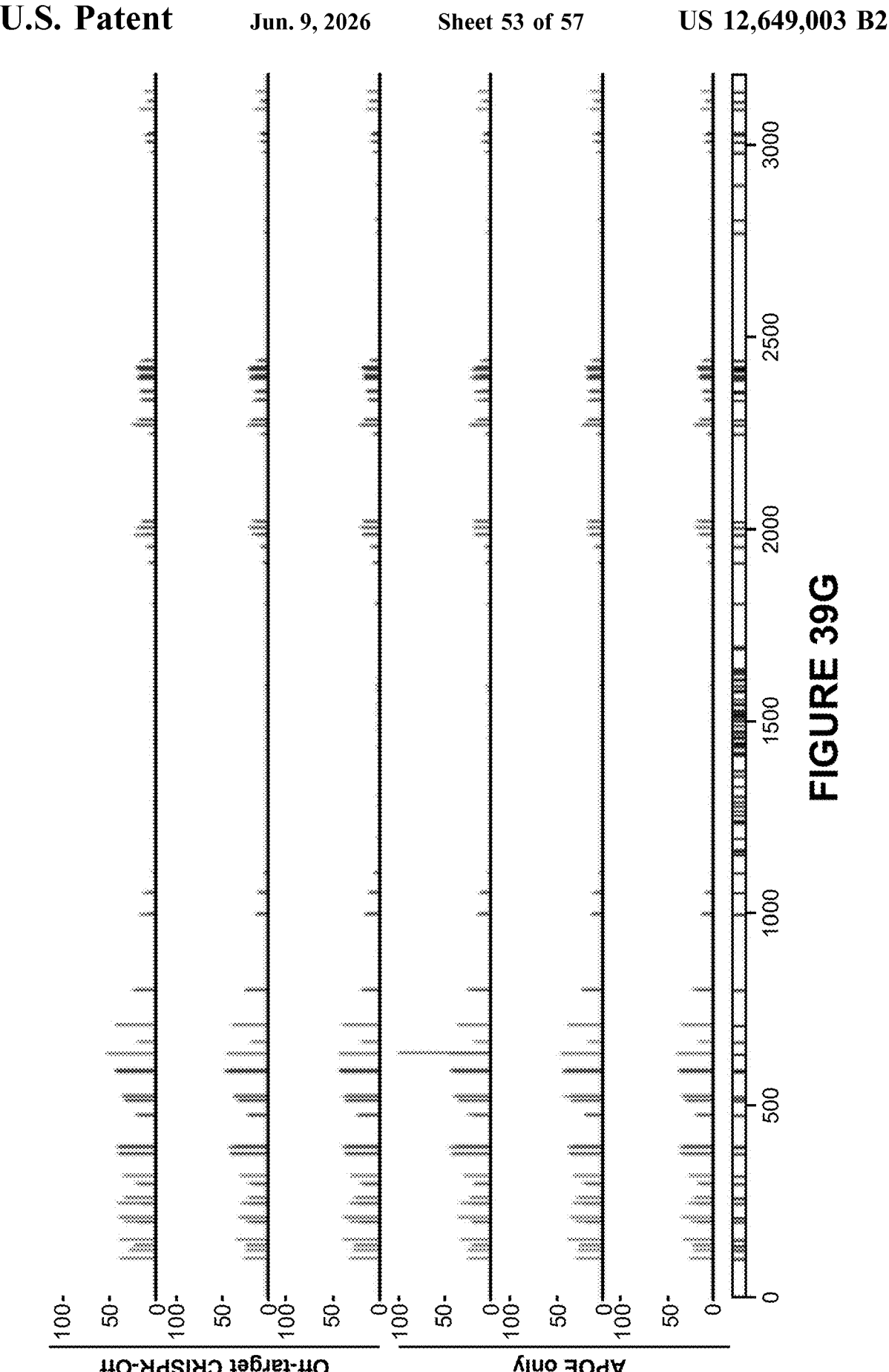

HepG2.2.15 cells were dosed at 1 nanogram (ng)/microliter (100 ng) of 1:1 CRISPR-Off (SEQ ID NO: 1248) mRNA with various single guide RNAs in LNPs with commercial apolipoprotein E (to aid LNP entry). Methylation profiles were performed on the HBV genome samples as well as controls: for gRNA #008, untreated samples and treated with CRISPRi and wild type Cas9. For other gRNAs tested, an untreated sample (APOE only) was used as a control. Results for gRNA #008, gRNA #003, gRNA #007, gRNA #009, gRNA #011, and gRNA #015 are shown in FIGS. 39A, 39B, 39C, 39D, 39E, and 39F, respectively. A control for the application of an off-target PCSK9 guide RNA is shown in FIG. 39G.

Example 20. Specificity Studies for CRISPR-Off and ZF Off

Figure 40:
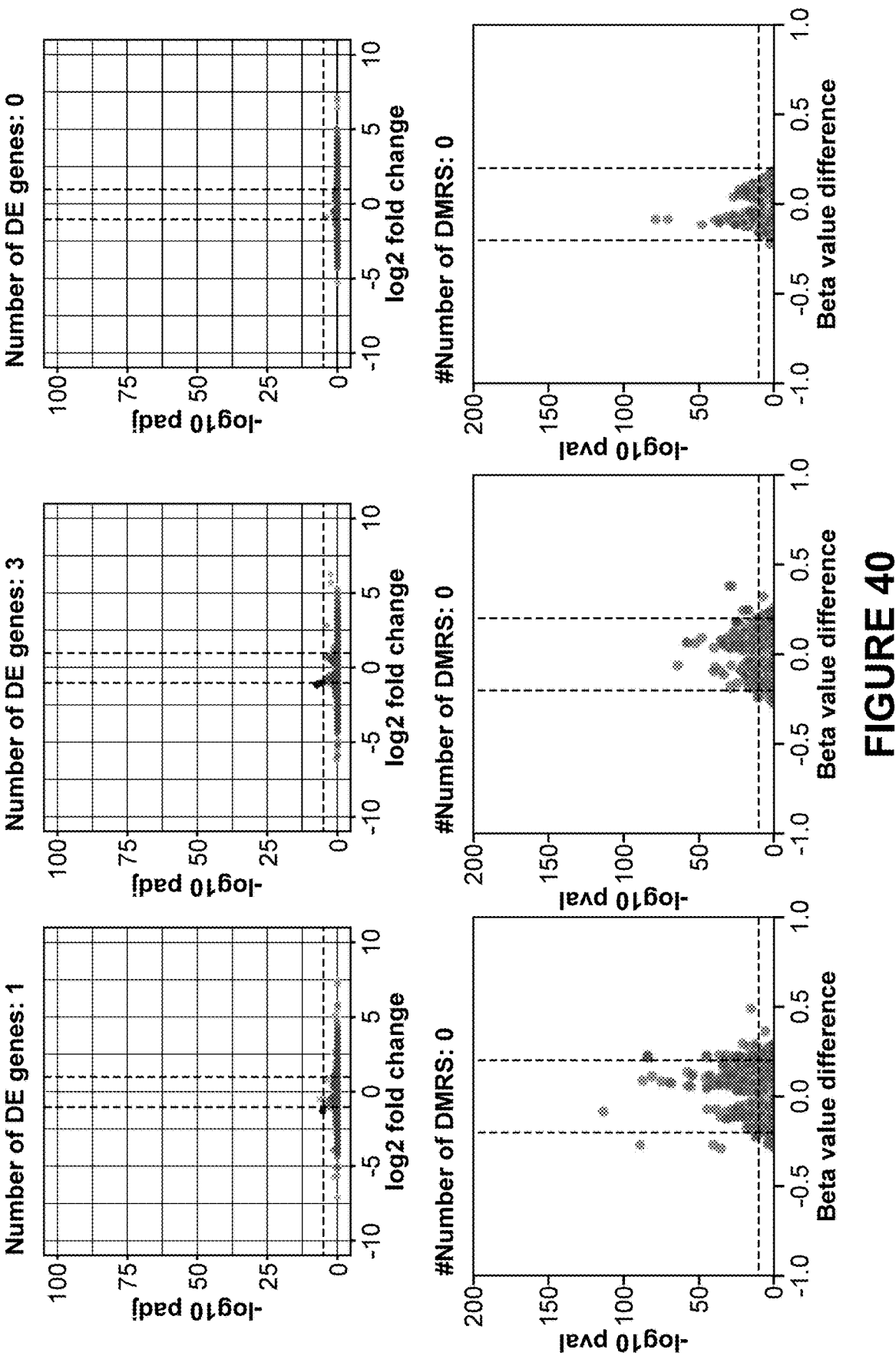
FIG. 40 shows volcano plots of RNA-Seq (top) and methylation (bottom) experiments at Day 14 after treatment in HepG2.2.15 cells treated with ZF-Off (left, SEQ ID NO: 36; center, SEQ ID NO: 73) and CRISPR-Off (right, SEQ ID NO: 1248) constructs (delivered as mRNA) targeting HBV. DE, differentially expressed. DMR: differentially methylated region.
Figure 41:
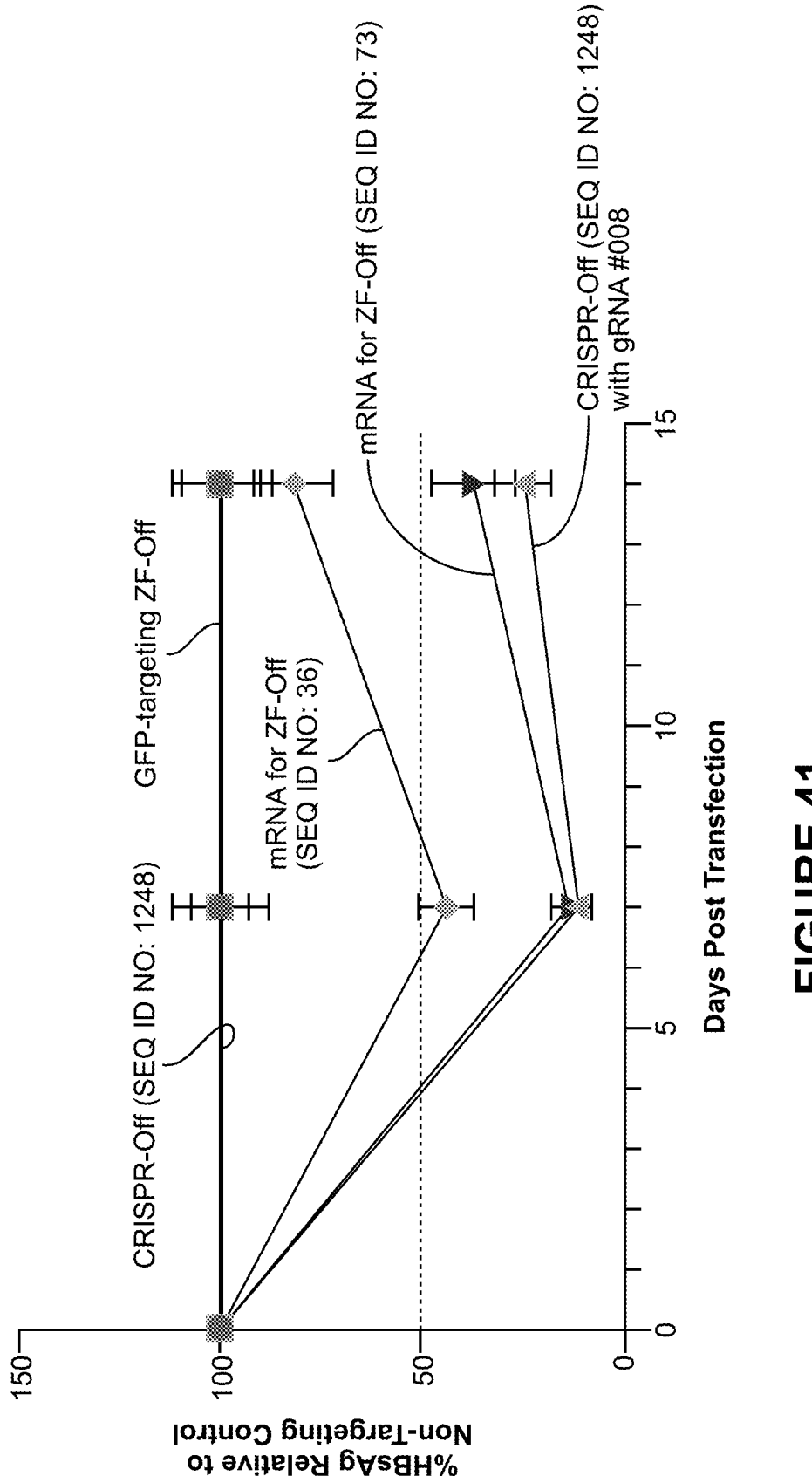
FIG. 41 shows HBsAg levels over 14 days for the cells treated for the RNA-Seq and methylation plots in FIG. 40.

HepG2.2.15 cells were transfected with either ZF-Off (SEQ ID NOs: 36 and 73) mRNA or CRISPR-Off (SEQ ID NO: 1248) mRNA with gRNA #008 in research-grade LNPs. RNA-Seq was conducted to determine differentially expressed genes (DEGs), and the Twist panel was used to determine differentially methylated regions (DMRs) at CpG-enriched sites. Differentially expressed genes (DEG) and differentially methylated regions (DMR) are defined based on literature reviews, software recommendations, sequencing depth and controls DEGs are genes that have >=2-fold change and with adjusted p-value <=1e-05. DMRs are defined as regions with a minimum of 10 CpGs, with 5× coverage, p-value of <=1e-10 and min average change in methylation (beta)>=20%. Results are shown in FIG. 40. Silencing data for same samples was also obtained. Results are shown in FIG. 41.

Example 21. Dose Response of Guide RNAs In Vitro

Figure 42:
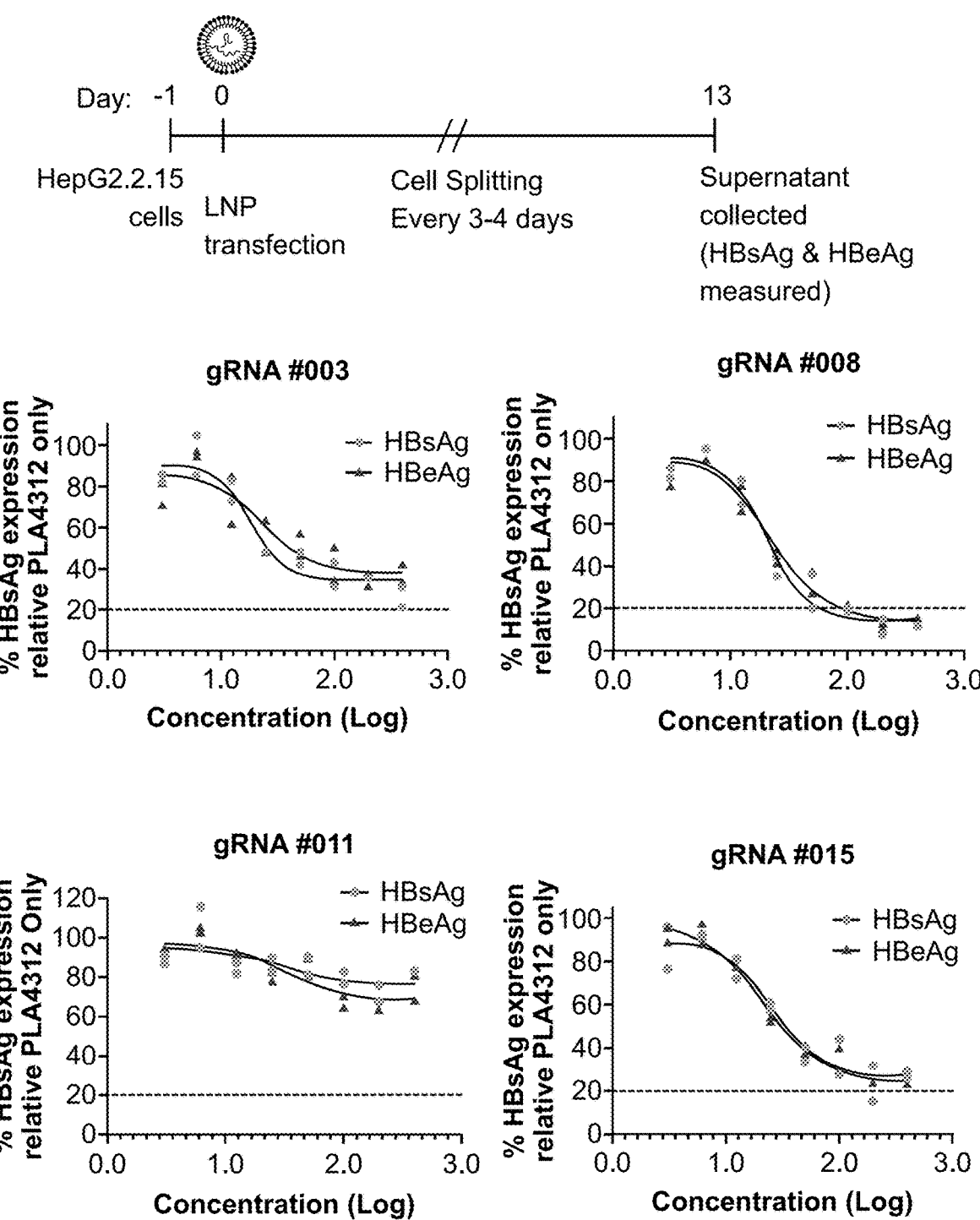
FIG. 42 shows a schematic (top) and dose curves (bottom) for CRISPR-Off dose curve experiments in HepG2.2.15 cells using various single guide RNAs and measuring HBsAg and HBeAg.

An 8-point dose-response (two-fold dilution with from 4 ng/μL (400 ng) to 0.031 ng/μL (3.1 ng)) was generated using HepG2.2.15 cells treated with LNPs with CRISPR-Off effector (SEQ ID NO: 1248), delivered as mRNA, and each of four gRNAs co-formulated in a 1:1 ratio. HBsAg and HBeAg were measured over six days. Results are shown in FIG. 42.

Example 22. Dose Response of CRISPR-Off Variant In Vitro

Figure 43:
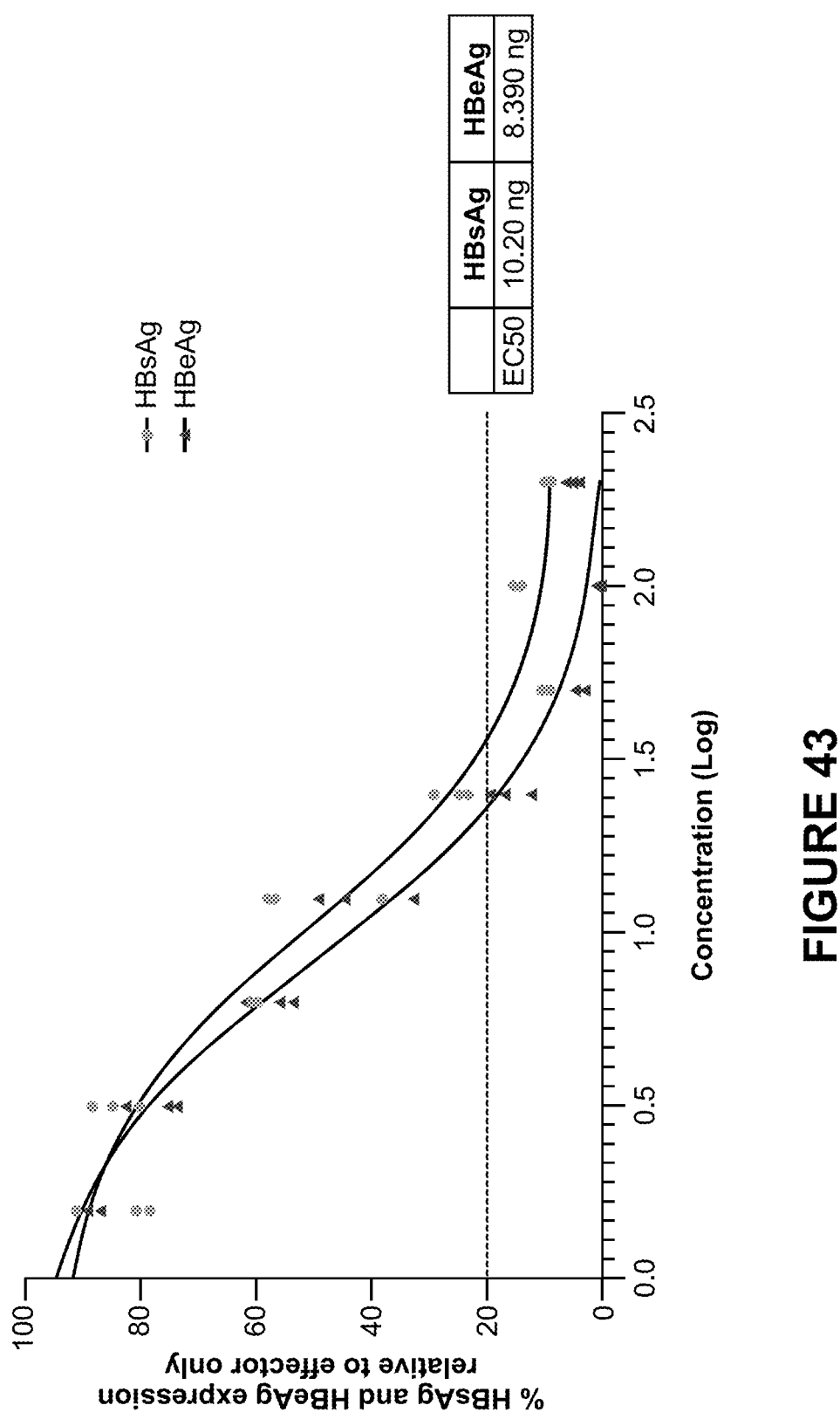
FIG. 43 shows dose curves for a CRISPR-Off variant, delivered with guide RNA, in HepG2.2.15 cells measuring HBsAg and HBeAg.

HepG2.2.15 cells transfected via Messenger Max with CRISPR-Off effector (SEQ ID NO: 1252), delivered as mRNA, and gRNA #008 with updated modification pattern (SEQ ID NO: 1249) was used to generate a 9-point dose-response (200-0.8 ng) curve. HBsAg and HBeAg were measured over 6 days. Results are shown in FIG. 43.

Example 23. Multiplexing Study in AAV-HBV and Tg-HBV Mouse Models

AAV-HBV and Tg-HBV mice are injected with a single administration at 0.5 mg/kg of one, two, three, or four guide RNAs targeting regions listed in Table 12 and Table 13 with CRISPR-Off (SEQ ID NO: 1248 or 1252) mRNA formulated in LNPs.

Amongst others, the following gRNAs are combined: (1) gRNA #008 and gRNA #011; (2) gRNA #008 and gRNA #003; (3) gRNA #008 and gRNA #015; (4) gRNA #008, gRNA #011, and gRNA #015; (6) gRNA #008, gRNA #011, and gRNA #003. Treatment with a single guide RNA, e.g., gRNA #008 or gRNA #011 serves as a positive control, and treatment with vehicle or with a non-targeting guide as a negative control.

One or more of HBV DNA, HBsAg, and HBeAg are assayed in plasma of the mice at one or more time points after administration, and the mouse liver is collected for further analysis. Combinations of multiple guides yield silencing at least as robust as treatment with single guides. In some cases, more robust silencing with multiple guides as compared to treatment with a single guide is observed.

Example 24. Testing mRNA:Guide RNA Ratios In Vivo

AAV-HBV mice are treated with CRISPR-Off effector (SEQ ID NO: 1252) mRNA with guide RNA (SEQ ID NO: 1249) in ratios including 1:1, 1:1.5, 2:1, 1:2, and 1:3 mRNA:guide RNA formulated into LNPs and administered at 0.5 mg/kg. 5 or 6 mice per study group are used. An optimized ratio of effector and guide RNA is identified that results in durable reduction of one or more HBV biomarkers, e.g., plasma level measurements of HBV DNA, HBsAg, and HBeAg of greater than 2 log below the observed control plasma level.

Example 25. Combination Treatment with Epigenetic Editor In Vivo

Tg-HBV mice are dosed with Entecavir (ETV) at 0.1 mg/kg for 14 days followed by CRISPR-Off with guide RNA at 1 mg/kg in a single intravenous dose. HBV DNA and HBsAg are measured in plasma for 112 days. HBV DNA levels drop after ETV treatment and there is slight synergism in the CRISPR-Off with guide with ETV group. After ETV withdrawal, the CRISPR-Off with guide maintains sustained reduction of DNA comparable to a group treated with CRISPR-Off and guide RNA alone. The addition of ETV does not affect HBsAg.

Example 26. Stable HBV Silencing Via Epigenetic Editing in Non-Transgenic Mouse Model of Persistent HBV Infection A non-transgenic model of persistent HBV infection (AAV-HBV) in immunocompetent mice was used, which was established by administering an adeno-associated viral vector (AAV) that contains HBV Genotype D DNA into the mice. The administration of the AAV-HBV vector resulted in expression of hepatitis B surface antigen (HBsAg), hepatitis B e antigen (HBeAg), and high levels of serum HBV DNA in the mice.

The CRISPR-off and ZF-off constructs are tested. Constructs are delivered via IV administration of mRNA/gRNA (CRISPR-Off) or mRNA (ZF-Off) formulated into a lipid nanoparticle (LNP) at 2.5 mg/kg and 0.5 mg/kg for CRISPR-Off and ZF-Off, respectively. Some constructs are formulated in LNP compositions as described in PCT/US2014/070882, US20220402862A1, and/or US20230203480A1. A subset of the mice are re-dosed at two weeks after the first dose; a second subset are re-dosed at one month after the first dose. The readouts are circulating viral DNA, HBsAg, and HBeAg, tested using mouse plasma at one or more time points (such as 7, 14, 28, and 35 days). A durable and significant reduction in the levels of one or more of HBV DNA, HBsAg, and HBeAg is observed for some constructs.

Longer-term durability is tested over three to six months using the HBV DNA, HBsAg, and HBeAg markers. Progressive and durable reduction in one or more of these markers is seen with delivery of some constructs. The mice are sacrificed and livers are collected for further analysis, and durable silencing is confirmed by at least 2 log reduction of HBsAg and HBV DNA.

Example 27: Stable HBV Silencing Via Epigenetic Editing in Transgenic Mice Expressing Viral HBV DNA A transgenic mouse model of persistent HBV infection (Tg-HBV) was used, whose genome was engineered to integrate HBV Genotype A DNA, resulting in expression of HBsAg and HBeAg, and circulating viral DNA in the mice.

The CRISPR-off and ZF-off constructs are tested. Constructs are delivered via IV administration of mRNA/gRNA (CRISPR-Off) or mRNA (ZF-Off) formulated into LNP at 2.5 mg/kg and 0.5 mg/kg for CRISPR-Off and ZF-Off, respectively. Some constructs are formulated in LNP compositions as described in US20220402862A1, and/or US20230203480A1. A subset of the mice are re-dosed at two weeks after the first dose; a second subset are re-dosed at one month after the first dose. The readouts are circulating viral DNA, HBsAg, and HBeAg, tested using mouse plasma at one or more time points (such as 7, 14, 28, and 35 days). A durable and significant reduction in the levels of one or more of HBV DNA, HBsAg, and HBeAg is observed for some constructs.

Longer-term durability is tested over three to six months using the HBV DNA, HBsAg, and HBeAg markers. Progressive and durable reduction in one or more of these markers is seen with delivery of some constructs. The mice are sacrificed and livers are collected for further analysis, and durable silencing is confirmed by at least 2 log reduction of HBsAg and HBV DNA.

Sequences

The SEQ ID NOs (SEQ) of nucleotide (nt) and amino acid (aa) sequences described in the present disclosure are listed in Table 18 below.

TABLE 18

| | | Sequence listing. | | |
| --- | --- | --- |

| SEQ | Description | Sequence |
| --- | --- | --- |
| 1 | *S. pyogenes* WT Cas9 Sequence (nt) | ATGGATAAGAAATACTCAATAGGCTTAGATATCGGCACAAATAGCGTCGGATGG GCGGTGATCACTGATGAATATAAGGTTCCGTCTAAAAAGTTCAAGGTTCTGGGA AATACAGACCGCCACAGTATCAAAAAAAATCTTATAGGGGCTCTTTTATTTGAC AGTGGAGAGACAGCGGAAGCGACTCGTCTCAAACGGACAGCTCGTAGAAGGTAT ACACGTCGGAAGAATCGTATTTGTTATCTACAGGAGATTTTTTCAAATGAGATG GCGAAAGTAGATGATAGTTTCTTTCATCGACTTGAAGAGTCTTTTTTGGTGGAA GAAGACAAGAAGCATGAACGTCATCCTATTTTTGGAAATATAGTAGATGAAGTT GCTTATCATGAGAAATATCCAACTATCTATCATCTGCGAAAAAAATTGGTAGAT TCTACTGATAAAGCGGATTTGCGCTTAATCTATTTGGCCTTAGCGCATATGATT AAGTTTCGTGGTCATTTTTTGATTGAGGGAGATTTAAATCCTGATAATAGTGAT GTGGACAAACTATTTATCCAGTTGGTACAAACCTACAATCAATTATTTGAAGAA AACCCTATTAACGCAAGTGGAGTAGATGCTAAAGCGATTCTTTCTGCACGATTG AGTAAATCAAGACGATTAGAAAATCTCATTGCTCAGCTCCCCGGTGAGAAGAAA AATGGCTTATTTGGGAATCTCATTGCTTTGTCATTGGGTTTGACCCCTAATTTT AAATCAAATTTTGATTTGGCAGAAGATGCTAAATTACAGCTTTCAAAAGATACT TACGATGATGATTTAGATAATTTATTGGCGCAAATTGGAGATCAATATGCTGAT TTGTTTTTGGCAGCTAAGAATTTATCAGATGCTATTTTACTTTCAGATATCCTA AGAGTAAATACTGAAATAACTAAGGCTCCCCTATCAGCTTCAATGATTAAACGC TACGATGAACATCATCAAGACTTGACTCTTTTAAAAGCTTTAGTTCGACAACAA CTTCCAGAAAAGTATAAAGAAATCTTTTTTGATCAATCAAAAAACGGATATGCA GGTTATATTGATGGGGGAGCTAGCCAAGAAGAATTTTATAAATTTATCAAACCA ATTTTAGAAAAAATGGATGGTACTGAGGAATTATTGGTGAAACTAAATCGTGAA GATTTGCTGCGCAAGCAACGGACCTTTGACAACGGCTCTATTCCCCATCAAATT CACTTGGGTGAGCTGCATGCTATTTTGAGAAGACAAGAAGACTTTTATCCATTT TTAAAAGACAATCGTGAGAAGATTGAAAAAATCTTGACTTTTCGAATTCCTTAT TATGTTGGTCCATTGGCGCGTGGCAATAGTCGTTTTGCATGGATGACTCGGAAG TCTGAAGAAACAATTACCCCATGGAATTTTGAAGAAGTTGTCGATAAAGGTGCT TCAGCTCAATCATTTATTGAACGCATGACAAACTTTGATAAAAATCTTCCAAAT GAAAAAGTACTACCAAAACATAGTTTGCTTTATGAGTATTTTACGGTTTATAAC GAATTGACAAAGGTCAAATATGTTACTGAAGGAATGCGAAAACCAGCATTTCTT TCAGGTGAACAGAAGAAAGCCATTGTTGATTTACTCTTCAAAACAAATCGAAAA GTAACCGTTAAGCAATTAAAAGAAGATTATTTCAAAAAAATAGAATGTTTTGAT AGTGTTGAAATTTCAGGAGTTGAAGATAGATTTAATGCTTCATTAGGTACCTAC CATGATTTGCTAAAAATTATTAAAGATAAAGATTTTTTGGATAATGAAGAAAAT GAAGATATCTTAGAGGATATTGTTTTAACATTGACCTTATTTGAAGATAGGGAG ATGATTGAGGAAAGACTTAAAACATATGCTCACCTCTTTGATGATAAGGTGATG AAACAGCTTAAACGTCGCCGTTATACTGGTTGGGGACGTTTGTCTCGAAAATTG ATTAATGGTATTAGGGATAAGCAATCTGGCAAAACAATATTAGATTTTTTGAAA TCAGATGGTTTTGCCAATCGCAATTTTATGCAGCTGATCCATGATGATAGTTTG ACATTTAAAGAAGACATTCAAAAAGCACAAGTGTCTGGACAAGGCGATAGTTTA CATGAACATATTGCAAATTTAGCTGGTAGCCCTGCTATTAAAAAAGGTATTTTA CAGACTGTAAAAGTTGTTGATGAATTGGTCAAAGTAATGGGGCGGCATAAGCCA GAAAATATCGTTATTGAAATGGCACGTGAAAATCAGACAACTCAAAAGGGCCAG AAAAATTCGCGAGAGCGTATGAAACGAATCGAAGAAGGTATCAAAGAATTAGGA AGTCAGATTCTTAAAGAGCATCCTGTTGAAAATACTCAATTGCAAAATGAAAAG CTCTATCTCTATTATCTCCAAAATGGAAGAGACATGTATGTGGACCAAGAATTA GATATTAATCGTTTAAGTGATTATGATGTCGATCACATTGTTCCACAAAGTTTC CTTAAAGACGATTCAATAGACAATAAGGTCTTAACGCGTTCTGATAAAAATCGT GGTAAATCGGATAACGTTCCAAGTGAAGAAGTAGTCAAAAAGATGAAAAACTAT TGGAGACAACTTCTAAACGCCAAGTTAATCACTCAACGTAAGTTTGATAATTTA ACGAAAGCTGAACGTGGAGGTTTGAGTGAACTTGATAAAGCTGGTTTTATCAAA CGCCAATTGGTTGAAACTCGCCAAATCACTAAGCATGTGGCACAAATTTTGGAT AGTCGCATGAATACTAAATACGATGAAAATGATAAACTTATTCGAGAGGTTAAA GTGATTACCTTAAAATCTAAATTAGTTTCTGACTTCCGAAAAGATTTCCAATTC TATAAAGTACGTGAGATTAACAATTACCATCATGCCCATGATGCGTATCTAAAT GCCGTCGTTGGAACTGCTTTGATTAAGAAATATCCAAAACTTGAATCGGAGTTT GTCTATGGTGATTATAAAGTTTATGATGTTCGTAAAATGATTGCTAAGTCTGAG CAAGAAATAGGCAAAGCAACCGCAAAATATTTCTTTTACTCTAATATCATGAAC TTCTTCAAAACAGAAATTACACTTGCAAATGGAGAGATTCGCAAACGCCCTCTA ATCGAACTAATGGGGAAACTGGAGAAATTGTCTGGGATAAAGGGCGAGATTTT GCCACAGTGCGCAAAGTATTGTCCATGCCCCAAGTCAATATTGTCAAGAAAACA GAAGTACAGACAGGCGGATTCTCCAAGGAGTCAATTTTACCAAAAAGAAATTCG GACAAGCTTATTGCTCGTAAAAAAGACTGGGATCCAAAAAAATATGGTGGTTTT GATAGTCCAACGGTAGCTTATTCAGTCCTAGTGGTTGCTAAGGTGGAAAAAGGG AAATCGAAGAAGTTAAAATCCGTTAAAGAGTTACTAGGGATCACAATTATGGAA AGAAGTTCCTTTGAAAAAAATCCGATTGACTTTTTAGAAGCTAAAGGATATAAG GAAGTTAAAAAAGACTTAATCATTAAACTACCTAAATATAGTCTTTTTGAGTTA GAAAACGGTCGTAAACGGATGCTGGCTAGTGCCGGAGAATTACAAAAAGGAAAT GAGCTGGCTCTGCCAAGCAAATATGTGAATTTTTTATATTTAGCTAGTCATTAT GAAAAGTTGAAGGGGTAGTCCAGAAGATAACGAACAAAAACAATTGTTTGTGGAG |

TABLE 18-continued

Sequence listing.

| SEQ | Description | Sequence |
|---|---|---|
| | | CAGCATAAGCATTATTTAGATGAGATTATTGAGCAAATCAGTGAATTTTCTAAG<br>CGTGTTATTTTAGCAGATGCCAATTTAGATAAAGTTCTTAGTGCATATAACAAA<br>CATAGAGACAAACCAATACGTGAACAAGCAGAAAATATTATTCATTTATTTACG<br>TTGACGAATCTTGGAGCTCCCGCTGCTTTTAAATATTTTGATACAACAATTGAT<br>CGTAAACGATATACGTCTACAAAAGAAGTTTTAGATGCCACTCTTATCCATCAA<br>TCCATCACTGGTCTTTATGAAACACGCATTGATTTGAGTCAGCTAGGAGGTGAC<br>TGA |
| 2 | *S. pyogenes* WT<br>Cas9 Sequence<br>(aa) | MDKKYSIGLDIGTNSVGWAVITDEYKVPSKKFKVLGNTDRHSIKKNLIGALLFD<br>SGETAEATRLKRTARRRYTRRKNRICYLQEIFSNEMAKVDDSFFHRLEESFLVE<br>EDKKHERHPIFGNIVDEVAYHEKYPTIYHLRKKLVDSTDKADLRLIYLALAHMI<br>KFRGHFLIEGDLNPDNSDVDKLFIQLVQTYNQLFEENPINASGVDAKAILSARL<br>SKSRRLENLIAQLPGEKKNGLFGNLIALSLGLTPNFKSNFDLAEDAKLQLSKDT<br>YDDDLDNLLAQIGDQYADLFLAAKNLSDAILLSDILRVNTEITKAPLSASMIKR<br>YDEHHQDLTLLKALVRQQLPEKYKEIFFDQSKNGYAGYIDGGASQEEFYKFIKP<br>ILEKMDGTEELLVKLNREDLLRKQRTFDNGSIPHQIHLGELHAILRRQEDFYPF<br>LKDNREKIEKILTFRIPYYVGPLARGNSRFAWMTRKSEETITPWNFEEVVDKGA<br>SAQSFIERMTNFDKNLPNEKVLPKHSLLYEYFTVYNELTKVKYVTEGMRKPAFL<br>SGEQKKAIVDLLFKTNRKVTVKQLKEDYFKKIECFDSVEISGVEDRFNASLGTY<br>HDLLKIIKDKDFLDNEENEDILEDIVLTLTLFEDREMIEERLKTYAHLFDDKVM<br>KQLKRRRYTGWGRLSRKLINGIRDKQSGKTILDFLKSDGFANRNFMQLIHDDSL<br>TFKEDIQKAQVSGQGDSLHEHIANLAGSPAIKKGILQTVKVVDELVKVMGRHKP<br>ENIVIEMARENQTTQKGQKNSRERMKRIEEGIKELGSQILKEHPVENTQLQNEK<br>LYLYYLQNGRDMYVDQELDINRLSDYDVDHIVPQSFLKDDSIDNKVLTRSDKNR<br>GKSDNVPSEEVVKKMKNYWRQLLNAKLITQRKFDNLTKAERGGLSELDKAGFIK<br>RQLVETRQITKHVAQILDSRMNTKYDENDKLIREVKVITLKSKLVSDFRKDFQF<br>YKVREINNYHHAHDAYLNAVVGTALIKKYPKLESEFVYGDYKVYDVRKMIAKSE<br>QEIGKATAKYFFYSNIMNFFKTEITLANGEIRKRPLIETNGETGEIVWDKGRDF<br>ATVRKVLSMPQVNIVKKTEVQTGGFSKESILPKRNSDKLIARKKDWDPKKYGGF<br>DSPTVAYSVLVVAKVEKGKSKKLKSVKELLGITIMERSSFEKNPIDFLEAKGYK<br>EVKKDLIIKLPKYSLFELENGRKRMLASAGELQKGNELALPSKYVNFLYLASHY<br>EKLKGSPEDNEQKQLFVEQHKHYLDEIIEQISEFSKRVILADANLDKVLSAYNK<br>HRDKPIREQAENIIHLFTLTNLGAPAAFKYFDTTIDRKRYTSTKEVLDATLIHQ<br>SITGLYETRIDLSQLGGD |
| 3 | SaCas9 | MKRNYILGLDIGITSVGYGIIDYETRDVIDAGVRLFKEANVENNEGRRSKRGAR<br>RLKRRRRHRIQRVKKLLFDYNLLTDHSELSGINPYEARVKGLSQKLSEEEFSAA<br>LLHLAKRRGVHNVNEVEEDTGNELSTKEQISRNSKALEEKYVAELQLERLKKDG<br>EVRGSINRFKTSDYVKEAKQLLKVQKAYHQLDQSFIDTYIDLLETRRTYYEGPG<br>EGSPFGWKDIKEWYEMLMGHCTYFPEELRSVKYAYNADLYNALNDLNNLVITRD<br>ENEKLEYYEKFQIIENVFKQKKKPTLKQIAKEILVNEEDIKGYRVTSTGKPEFT<br>NLKVYHDIKDITARKEIIENAELLDQIAKILTIYQSSEDIQEELTNLNSELTQE<br>EIEQISNLKGYTGTHNLSLKAINLILDELWHTNDNQIAIFNRLKLVPKKVDLSQ<br>QKEIPTTLVDDFILSPVVKRSFIQSIKVINAIIKKYGLPNDIIIELAREKNSKD<br>AQKMINEMQKRNRQTNERIEEIIRTTGKENAKYLIEKIKLHDMQEGKCLYSLEA<br>IPLEDLLNNPFNYEVDHIIPRSVSFDNSFNNKVLVKQEENSKKGNRTPFQYLSS<br>SDSKISYETFKKHILNLAKGKGRISKTKKEYLLEERDINRFSVQKDFINRNLVD<br>TRYATRGLMNLLRSYFRVNNLDVKVKSINGGFTSFLRRKWKFKKERNKGYKHHA<br>EDALIIANADFIFKEWKKLDKAKKVMENQMFEEKQAESMPEIETEQEYKEIFIT<br>PHQIKHIKDFKDYKYSHRVDKKPNRELINDTLYSTRKDDKGNTLIVNNLNGLYD<br>KDNDKLKKLINKSPEKLLMYHHDPQTYQKLKLIMEQYGDEKNPLYKYYEETGNY<br>LTKYSKKDNGPVIKKIKYYGNKLNAHLDITDDYPNSRNKVVKLSLKPYREDVYL<br>DNGVYKFVTVKNLDVIKKENYYEVNSKCYEEAKKLKKISNQAEFIASFYNNDLI<br>KINGELYRVIGVNNDLLNRIEVNMIDITYREYLENMNDKRPPRIIKTIASKTQS<br>IKKYSTDILGNLYEVKSKKHPQIIKKG |
| 4 | *F. novicida* WT<br>Cpf1 | MSIYQEFVNKYSLSKTLRFELIPQGKTLENIKARGLILDDEKRAKDYKKAKQII<br>DKYHQFFIEEILSSVCISEDLLQNYSDVYFKLKKSDDDNLQKDFKSAKDTIKKQ<br>ISEYIKDSEKFKNLFNQNLIDAKKGQESDLILWLKQSKDNGIELFKANSDITDI<br>DEALEIIKSFKGWTTYFKGFHENRKNVYSSNDIPTSIIYRIVDDNLPKFLENKA<br>KYESLKDKAPEAINYEQIKKDLAEELTFDIDYKTSEVNQRVFSLDEVFEIANEN<br>NYLNQSGITKFNTIIGGKFVNGENTKRKGINEYINLYSQQINDKTLKKYKMSVL<br>FKQILSDTESKSFVIDKLEDDSDVVTTMQSFYEQIAAPKTVEEKSIKETLSLLF<br>DDLKAQKLDLSKIYFKNDKSLTDLSQQVEDDYSVIGTAVLEYITQQIAPKNLDN<br>PSKKEQELIAKKTEKAKYLSLETIKLALEEFNKHRDIDKQCRFEEILANFAAIP<br>MIFDEIAQNKDNLAQISIKYQNQGKKDLLQASAEDDVKAIKDLLDQTNNLLHKL<br>KIPHISQSEDKANILDKDEHFYLVFEECYFELANIVPLYNKIRNYITQKPYSDE<br>KFKLNFENSTLANGWDKNKEPDNTAILFIKDDKYYLGVMNKKNNKIFDDKAIKE<br>NKGEGYKKIVYKLLPGANKMLPKVFFSAKSIKFYNPSEDILRIRNHSTHTKNGS<br>PQKGYEKFEFNIEDCRKFIDFYKQSISKHPEWKDFGFRFSDTQRYNSIDEFYRE<br>VENQGYKLTFENISESYIDSVVNQGKLYLFQIYNKDFSAYSKGRPNLHTLYWKA<br>LFDERNLQDVVYKLNGEAELFYRKQSIPKKITHPAKEAIANKNKDNPKKESVFE<br>YDLIKDKRFTEDKFFFHCPITINFKSSGANKENDEINLLLKEKANDVHILSIDR<br>GERHLAYYTLVDGKGNIIKQDTFNIIGNDRMKTNYHDKLAAIEKDRDSARKDWK<br>KINNIKEMKEGYLSQVVHEIAKLVIEYNAIVVFEDLNFGFKRGRFKVEKQVYQK<br>LEKMLIEKLNYLVFKDNEFDKTGGVLRAYQLTAPFETFKKMGKQTGIIYYVPAG |

TABLE 18-continued

Sequence listing.

| SEQ | Description | Sequence |
|---|---|---|
| | | FTSKICPVTGFVNQLYPKYESVSKSQEFFSKFDKICYNLDKGYFEFSFDYKNFG<br>DKAAKGKWTIASFGSRLINFRNSDKNHNWDTREVYPTKELEKLLKDYSIEYGHG<br>ECIKAAICGESDKKFFAKLTSVLNTILQMRNSKTGTELDYLISPVADVNGNFFD<br>SRQAPKNMPQDADANGAYHIGLKGLMLLGRIKNNQEGKKLNLVIKNEEYFEFVQ<br>NRNN |
| 5 | CasX | MEKRINKIRKKLSADNATKPVSRSGPMKTLLVRVMTDDLKKRLEKRRKKPEVMP<br>QVISNNAANNLRMLLDDYTKMKEAILQVYWQEFKDDHVGLMCKFAQPASKKIDQ<br>NKLKPEMDEKGNLTTAGFACSQCGQPLFVYKLEQVSEKGKAYTNYFGRCNVAEH<br>EKLILLAQLKPEKDSDEAVTYSLGKFGQRALDFYSIHVTKESTHPVKPLAQIAG<br>NRYASGPVGKALSDACMGTIASFLSKYQDIIIEHQKVVKGNQKRLESLRELAGK<br>ENLEYPSVTLPPQPHTKEGVDAYNEVIARVRMWVNLNLWQKLKLSRDDAKPLLR<br>LKGFPSFPVVERRENEVDWWNTINEVKKLIDAKRDMGRVFWSGVTAEKRNTILE<br>GYNYLPNENDHKKREGSLENPKKPAKRQFGDLLLYLEKKYAGDWGKVEDEAWER<br>IDKKIAGLTSHIEREEARNAEDAQSKAVLTDWLRAKASFVLERLKEMDEKEFYA<br>CEIQLQKWYGDLRGNPFAVEAENRVVDISGFSIGSDGHSIQYRNLLAWKYLENG<br>KREFYLLMNYGKKGRIRFTDGTDIKKSGKWQGLLYGGGKAKVIDLTFDPDDEQL<br>IILPLAFGTRQGREFIWNDLLSLETGLIKLANGRVIEKTIYNKKIGRDEPALFV<br>ALTFERREVVDPSNIKPVNLIGVDRGENIPAVIALTDPEGCPLPEFKDSSGGPT<br>DILRIGEGYKEKQRAIQAAKEVEQRRAGGYSRKFASKSRNLADDMVRNSARDLF<br>YHAVTHDAVLVFENLSRGFGRQGKRTFMTERQYTKMEDWLTAKLAYEGLTSKTY<br>LSKTLAQYTSKTCSNCGFTITTADYDGMLVRLKKTSDGWATTLNNKELKAEGQI<br>TYYNRYKRQTVEKELSAELDRLSEESGNNDISKWTKGRRDEALFLLKKRFSHRP<br>VQEQFVCLDCGHEVHADEQAALNIARSWLFLNSNSTEFKSYKSGKQPFVGAWQA<br>FYKRRLKEVWKPNA |
| 6 | CasY | MRKKLFKGYILHNKRLVYTGKAAIRSIKYPLVAPNKTALNNLSEKIIYDYEHLF<br>GPLNVASYARNSNRYSLVDFWIDSLRAGVIWQSKSTSLIDLISKLEGSKSPSEK<br>IFEQIDFELKNKLDKEQFKDIILLNTGIRSSSNVRSLRGRFLKCFKEEFRDTEE<br>VIACVDKWSKDLIVEGKSILVSKQFLYWEEEFGIKIFPHFKDNHDLPKLTFFVE<br>PSLEFSPHLPLANCLERLKKFDISRESLLGLDNNFSAFSNYFNELENLLSRGEI<br>KKIVTAVLAVSKSWENEPELEKRLHFLSEKAKLLGYPKLTSSWADYRMIIGGKI<br>KSWHSNYTEQLIKVREDLKKHQIALDKLQEDLKKVVDSSLREQIEAQREALLPL<br>LDTMLKEKDFSDDLELYRFILSDFKSLLNGSYQRYIQTEEERKEDRDVTKKYKD<br>LYSNLRNIPRFFGESKKEQFNKFINKSLPTIDVGLKILEDIRNALETVSVRKPP<br>SITEEYVTKQLEKLSRKYKINAFNSNRFKQITEQVLRKYNNGELPKISEVFYRY<br>PRESHVAIRILPVKISNPRKDISYLLDKYQISPDWKNSNPGEVVDLIEIYKLTL<br>GWLLSCNKDFSMDFSSYDLKLFPEAASLIKNFGSCLSGYYLSKMIFNCITSEIK<br>GMITLYTRDKFVVRYVTQMIGSNQKFPLLCLVGEKQTKNFSRNWGVLIEEKGDL<br>GEEKNQEKCLIFKDKTDFAKAKEVEIFKNNIWRIRTSKYQIQFLNRLFKKTKEW<br>DLMNLVLSEPSLVLEEEWGVSWDKDKLLPLLKKEKSCEERLYYSLPLNLVPATD<br>YKEQSAEIEQRNTYLGLDVGEFGVAYAVVRIVRDRIELLSWGFLKDPALRKIRE<br>RVQDMKKKQVMAVFSSSSTAVARVREMAIHSLRNQIHSIALAYKAKIIYEISIS<br>NFETGGNRMAKIYRSIKVSDVYRESGADTLVSEMIWGKKNKQMGNHISSYATSY<br>TCCNCARTPFELVIDNDKEYEKGGDEFIFNVGDEKKVRGFLQKSLLGKTIKGKE<br>VLKSIKEYARPPIREVLLEGEDVEQLLKRRGNSYIYRCPFCGYKTDADIQAALN<br>IACRGYISDNAKDAVKEGERKLDYILEVRKLWEKNGAVLRSAKFL |
| 7 | CasPhi | MADTPTLFTQFLRHHLPGQRFRKDILKQAGRILANKGEDATIAFLRGKSEESPP<br>DFQPPVKCPIIACSRPLTEWPIYQASVAIQGYVYGQSLAEFEASDPGCSKDGLL<br>GWFDKTGVCTDYFSVQGLNLIFQNARKRYIGVQTKVTNRNEKRHKKLKRINAKR<br>IAEGLPELTSDEPESALDETGHLIDPPGLNTNIYCYQQVSPKPLALSEVNQLPT<br>AYAGYSTSGDDPIQPMVTKDRLSISKGQPGYIPEHQRALLSQKKHRRMRGYGLK<br>ARALLVIVRIQDDWAVIDLRSLLRNAYWRRIVQTKEPSTITKLLKLVTGDPVLD<br>ATRMVATFTYKPGIVQVRSAKCLKNKQGSKLFSERYLNETVSVTSIDLGSNNLV<br>AVATYRLVNGNTPELLQRFTLPSHLVKDFERYKQAHDTLEDSIQKTAVASLPQG<br>QQTEIRMWSMYGFREAQERVCQELGLADGSIPWNVMTATSTILTDLFLARGGDP<br>KKCMFTSEPKKKKNSKQVLYKIRDRAWAKMYRTLLSKETREAWNKALWGLKRGS<br>PDYARLSKRKEELARRCVNYTISTAEKRAQCGRTIVALEDLNIGFFHGRGKQEP<br>GWVGLFTRKKENRWLMQALHKAFLELAHHRGYHVIEVNPAYTSQTCPVCRHCDP<br>DNRDQHNREAFHCIGCGFRGNADLDVATHNIAMVAITGESLKRARGSVASKTPQ<br>PLAAE |
| 8 | Cas12f1 (Cas14a) | MIKVYRYEIVKPLDLDWKEFGTILRQLQQETRFALNKATQLAWEWMGFSSDYKD<br>NHGEYPKSKDILGYTNVHGYAYHTIKTKAYRLNSGNLSQTIKRATDRFKAYQKE<br>ILRGDMSIPSYKRDIPLDLIKENISVNRMNHGDYIASLSLLSNPAKQEMNVKRK<br>ISVIIIVRGAGKTIMDRILSGEYQVSASQIIHDDRKNKWYLNISYDFEPQTRVL<br>DLNKIMGIDLGVAVAVYMAFQHTPARYKLEGGEIENFRRQVESRRISMLRQGKY<br>AGGARGGHGRDKRIKPIEQLRDKIANFRDTTNHRYSRYIVDMAIKEGCGTIQME<br>DLTNIRDIGSRFLQNWTYYDLQQKIIYKAEEAGIKVIKIDPQYTSQRCSECGNI<br>DSGNRIGQAIFKCRACGYEANADYNAARNIAIPNIDKIIAESIKSGGS |
| 9 | Cas12f2 (Cas14b) | NAMIAQKTIKIKLNPTKEQIIKLNSIIEEYIKVSNFTAKKIAEIQESFTDSGLT<br>QGTCSECGKEKTYRKYHLLKKDNKLFCITCYKRKYSQFTLQKVEFQNKTGLRNV<br>AKLPKTYYTNAIRFASDTFSGFDEIIKKKQNRLNSIQNRLNFWKELLYNPSNRN<br>EIKIKVVKYAPKTDTREHPHYYSEAEIKGRIKRLEKQLKKFKMPKYPEFTSETI |

TABLE 18-continued

| Sequence listing. | | |
| --- | --- | --- |
| SEQ | Description | Sequence |

|  |  | SLQRELYSWKNPDELKISSITDKNESMNYYGKEYLKRYIDLINSQTPQILLEKE<br>NNSFYLCFPITKNIEMPKIDDTFEPVGIDWGITRNIAVVSILDSKTKKPKFVKF<br>YSAGYILGKRKHYKSLRKHFGQKKRQDKINKLGTKEDRFIDSNIHKLAFLIVKE<br>IRNHSNKPIILMENITDNREEAEKSMRQNILLHSVKSRLQNYIAYKALWNNIPT<br>NLVKPEHTSQICNRCGHQDRENRPKGSKLFKCVKCNYMSNADFNASINIARKFY<br>IGEYEPFYKDNEKMKSGVNSISM |
| 10 | Cas12f3 (Cas14c) | MEVQKTVMKTLSLRILRPLYSQEIEKEIKEEEKERRKQAGGTGELDGGFYKKLE<br>KKHSEMFSFDRLNLLLNQLQREIAKVYNHAISELYIATIAQGNKSNKHYISSIV<br>YNRAYGYFYNAYIALGICSKVEANFRSNELLTQQSALPTAKSDNFPIVLHKQKG<br>AEGEDGGFRISTEGSDLIFEIPIPFYEYNGENRKEPYKWVKKGGQKPVLKLILS<br>TFRRQRNKGWAKDEGTDAEIRKVTEGKYQVSQIEINRGKKLGEHQKWFANFSIE<br>QPIYERKPNRSIVGGLDVGIRSPLVCAINNSFSRYSVDSNDVEKFSKQVFAFRR<br>RLLSKNSLKRKHGHAAHKLEPITEMTEKNDKFRKKIIERWAKEVTNFFVKNQVG<br>IVQIEDLSTMKDREDHFFNQYLRGFWPYYQMQTLIENKLKEYGIEVKRVQAKYT<br>SQLCSNPNCRYWNNYENFEYRKVNKFPKFKCEKCNLEISADYNAARNLSTPDIE<br>KFVAKATKGINLPEK |
| 11 | C2c8 | MKVLEFKIHPTEEQVSKIDQSLAACKLLWNLSIALKEESKQRYYRKKHKFDEFS<br>PEIWGLSYSGHYDEKEFKTLKDKEKKLLIGNPCCKIAYFKKTSNGKEYTPLNSI<br>PIRRFMNAENIDKDAVNYLNRKKLAFYFRENTAKFIGEIETEFKKGFFKSVIKP<br>AYDAAKKGIRGIPRFKGRRDKVETLVNGQPETIKIKSNGVIVSSKIGLLKIRGL<br>DRLQGKAPRMAKITRKATGYYLQLTIETDDTIYKESDKCVGLDMGAVAIFTDDL<br>GRQSEAKRYAKIQKKRLNRLQRQASRQKDNSNNQRKTYAKLARVHEKIARQRKG<br>RNAQLAHKITSEYQSVILEDLNLKNMTAAAKPKEREDGDGYKQNGKKRKSGLNK<br>ALLDNAIGQLRTFIENKANERGRKIIRVNPKHTSQTCPNCGNIDKANRVSQSKF<br>KCVSCGYEAHADQNAAANILIRGLRDEFLRAIGSLYKFPVSMIGKYPGLAGEFT<br>PDLDANQESIGDAPIENAEHSISKQMKQEGNRTPTQPENGSQSLIFLSAPPQPC<br>GDSHGTNNPKALPNKASKRSSKKPRGAIPENPDQLTIWDLLD |
| 12 | dSpCas9 | MDKKYSIGLAIGTNSVGWAVITDEYKVPSKKFKVLGNTDRHSIKKNLIGALLED<br>SGETAEATRLKRTARRRYTRRKNRICYLQEIFSNEMAKVDDSFFHRLEESFLVE<br>EDKKHERHPIFGNIVDEVAYHEKYPTIYHLRKKLVDSTDKADLRLIYLALAHMI<br>KFRGHFLIEGDLNPDNSDVDKLFIQLVQTYNQLFEENPINASGVDAKAILSARL<br>SKSRRLENLIAQLPGEKKNGLFGNLIALSLGLTPNFKSNFDLAEDAKLQLSKDT<br>YDDDLDNLLAQIGDQYADLFLAAKNLSDAILLSDILRVNTEITKAPLSASMIKR<br>YDEHHQDLTLLKALVRQQLPEKYKEIFFDQSKNGYAGYIDGGASQEEFYKFIKP<br>ILEKMDGTEELLVKLNREDLLRKQRTFDNGSIPHQIHLGELHAILRRQEDFYPF<br>LKDNREKIEKILTFRIPYYVGPLARGNSRFAWMTRKSEETITPWNFEEVVDKGA<br>SAQSFIERMTNFDKNLPNEKVLPKHSLLYEYFTVYNELTKVKYVTEGMRKPAFL<br>SGEQKKAIVDLLFKTNRKVTVKQLKEDYFKKIECFDSVEISGVEDRENASLGTY<br>HDLLKIIKDKDFLDNEENEDILEDIVLTLTLFEDREMIEERLKTYAHLEDDKVM<br>KQLKRRRYTGWGRLSRKLINGIRDKQSGKTILDFLKSDGFANRNFMQLIHDDSL<br>TFKEDIQKAQVSGQGDSLHEHIANLAGSPAIKKGILQTVKVVDELVKVMGRHKP<br>ENIVIEMARENQTTQKGQKNSRERMKRIEEGIKELGSQILKEHPVENTQLQNEK<br>LYLYYLQNGRDMYVDQELDINRLSDYDVDAIVPQSFLKDDSIDNKVLTRSDKNR<br>GKSDNVPSEEVVKKMKNYWRQLLNAKLITQRKFDNLTKAERGGLSELDKAGFIK<br>RQLVETRQITKHVAQILDSRMNTKYDENDKLIREVKVITLKSKLVSDFRKDFQF<br>YKVREINNYHHAHDAYLNAVVGTALIKKYPKLESEFVYGDYKVYDVRKMIAKSE<br>QEIGKATAKYFFYSNIMNFFKTEITLANGEIRKRPLIETNGETGEIVWDKGRDF<br>ATVRKVLSMPQVNIVKKTEVQTGGFSKESILPKRNSDKLIARKKDWDPKKYGGF<br>DSPTVAYSVLVVAKVEKGKSKKLKSVKELLGITIMERSSFEKNPIDFLEAKGYK<br>EVKKDLIIKLPKYSLFELENGRKRMLASAGELQKGNELALPSKYVNFLYLASHY<br>EKLKGSPEDNEQKQLFVEQHKHYLDEIIEQISEFSKRVILADANLDKVLSAYNK<br>HRDKPIREQAENIIHLFTLTNLGAPAAFKYFDTTIDRKRYTSTKEVLDATLIHQ<br>SITGLYETRIDLSQLGGD |
| 13 | dSaCas9 | MKRNYILGLAIGITSVGYGIIDYETRDVIDAGVRLFKEANVENNEGRRSKRGAR<br>RLKRRRRHRIQRVKKLLFDYNLLTDHSELSGINPYEARVKGLSQKLSEEEFSAA<br>LLHLAKRRGVHNVNEVEEDTGNELSTKEQISRNSKALEEKYVAELQLERLKKDG<br>EVRGSINRFKTSDYVKEAKQLLKVQKAYHQLDQSFIDTYIDLLETRRTYYEGPG<br>EGSPFGWKDIKEWYEMLMGHCTYFPEELRSVKYAYNADLYNALNDLNNLVITRD<br>ENEKLEYYEKFQIIENVFKQKKKPTLKQIAKEILVNEEDIKGYRVTSTGKPEFT<br>NLKVYHDIKDITARKEIIENAELLDQIAKILTIYQSSEDIQEELTNLNSELTQE<br>EIEQISNLKGYTGTHNLSLKAINLILDELWHTNDNQIAIFNRLKLVPKKVDLSQ<br>QKEIPTTLVDDFILSPVVKRSFIQSIKVINAIIKKYGLPNDIIIELAREKNSKD<br>AQKMINEMQKRNRQTNERIEEIIRTTGKENAKYLIEKIKLHDMQEGKCLYSLEA<br>IPLEDLLNNPFNYEVDHIIPRSVSFDNSFNNKVLVKQEEASKKGNRTPFQYLSS<br>SDSKISYETFKKHILNLAKGKGRISKTKKEYLLEERDINRFSVQKDFINRNLVD<br>TRYATRGLMNLLRSYFRVNNLDVKVKSINGGFTSFLRRKWKFKKERNKGYKHHA<br>EDALIIANADFIFKEWKKLDKAKKVMENQMFEEKQAESMPEIETEQEYKEIFIT<br>PHQIKHIKDFKDYKYSHRVDKKPNRELINDTLYSTRKDDKGNTLIVNNLNGLYD<br>KDNDKLKKLINKSPEKLLMYHHDPQTYQKLKLIMEQYGDEKNPLYKYYEETGNY |

TABLE 18-continued

Sequence listing.

| SEQ | Description | Sequence |
|---|---|---|
| | | LTKYSKKDNGPVIKKIKYYGNKLNAHLDITDDYPNSRNKVVKLSLKPYRFDVYL |
| | | DNGVYKFVTVKNLDVIKKENYYEVNSKCYEEAKKLKKISNQAEFIASFYNNDLI |
| | | KINGELYRVIGVNNDLLNRIEVNMIDITYREYLENMNDKRPPRIIKTIASKTQS |
| | | IKKYSTDILGNLYEVKSKKHPQIIKKG |
| 14 | inactive FnCpf1 | MSIYQEFVNKYSLSKTLRFELIPQGKTLENIKARGLILDDEKRAKDYKKAKQII |
| | | DKYHQFFIEEILSSVCISEDLLQNYSDVYFKLKKSDDDNLQKDFKSAKDTIKKQ |
| | | ISEYIKDSEKFKNLFNQNLIDAKKGQESDLILWLKQSKDNGIELFKANSDITDI |
| | | DEALEIIKSFKGWTTYFKGFHENRKNVYSSNDIPTSIIYRIVDDNLPKFLENKA |
| | | KYESLKDKAPEAINYEQIKKDLAEELTFDIDYKTSEVNQRVESLDEVFEIANEN |
| | | NYLNQSGITKFNTIIGGKFVNGENTKRKGINEYINLYSQQINDKTLKKYKMSVL |
| | | FKQILSDTESKSFVIDKLEDDSDVVTTMQSFYEQIAAFKTVEEKSIKETLSLLF |
| | | DDLKAQKLDLSKIYFKNDKSLTDLSQQVEDDYSVIGTAVLEYITQQIAPKNLDN |
| | | PSKKEQELIAKKTEKAKYLSLETIKLALEEFNKHRDIDKQCRFEEILANFAAIP |
| | | MIFDEIAQNKDNLAQISIKYQNQGKKDLLQASAEDDVKAIKDLLDQTNNLLHKL |
| | | KIFHISQSEDKANILDKDEHFYLVFEECYFELANIVPLYNKIRNYITQKPYSDE |
| | | KFKLNFENSTLANGWDKNKEPDNTAILFIKDDKYYLGVMNKKNNKIFDDKAIKE |
| | | NKGEGYKKIVYKLLPGANKMLPKVFFSAKSIKFYNPSEDILRIRNHSTHTKNGS |
| | | PQKGYEKFEFNIEDCRKFIDFYKQSISKHPEWKDFGFRFSDTQRYNSIDEFYRE |
| | | VENQGYKLTFENISESYIDSVVNQGKLYLFQIYNKDFSAYSKGRPNLHTLYWKA |
| | | LFDERNLQDVVYKLNGEAELFYRKQSIPKKITHPAKEAIANKNKDNPKKESVFE |
| | | YDLIKDKRFTEDKFFFHCPITINFKSSGANKENDEINLLLKEKANDVHILSIAR |
| | | GERHLAYYTLVDGKGNIIKQDTFNIIGNDRMKTNYHDKLAAIEKDRDSARKDWK |
| | | KINNIKEMKEGYLSQVVHEIAKLVIEYNAIVVFEDLNFGFKRGRFKVEKQVYQK |
| | | LEKMLIEKLNYLVFKDNEFDKTGGVLRAYQLTAPFETFKKMGKQTGIIYYVPAG |
| | | FTSKICPVTGFVNQLYPKYESVSKSQEFFSKFDKICYNLDKGYFEFSFDYKNFG |
| | | DKAAKGKWTIASFGSRLINFRNSDKNHNWDTREVYPTKELEKLLKDYSIEYGHG |
| | | ECIKAAICGESDKKFFAKLTSVLNTILQMRNSKTGTELDYLISPVADVNGNFFD |
| | | SRQAPKNMPQDADANGAYHIGLKGLMLLGRIKNNQEGKKLNLVIKNEEYFEFVQ |
| | | NRNN |
| 15 | dNmeCas9 | MAAFKPNSINYILGLAIGIASVGWAMVEIDEEENPIRLIDLGVRVFERAEVPKT |
| | | GDSLAMARRLARSVRRLTRRRAHRLLRTRRLLKREGVLQAANFDENGLIKSLPN |
| | | TPWQLRAAALDRKLTPLEWSAVLLHLIKHRGYLSQRKNEGETADKELGALLKGV |
| | | AGNAHALQTGDFRTPAELALNKFEKESGHIRNQRSDYSHTFSRKDLQAELILLE |
| | | EKQKEFGNPHVSGGLKEGIETLLMTQRPALSGDAVQKMLGHCTFEPAEPKAAKN |
| | | TYTAERFIWLTKLNNLRILEQGSERPLTDTERATLMDEPYRKSKLTYAQARKLL |
| | | GLEDTAFFKGLRYGKDNAEASTLMEMKAYHAISRALEKEGLKDKKSPLNLSPEL |
| | | QDEIGTAFSLFKTDEDITGRLKDRIQPEILEALLKHISFDKFVQISLKALRRIV |
| | | PLMEQGKRYDEACAEIYGDHYGKKNTEEKIYLPPIPADEIRNPVVLRALSQARK |
| | | VINGVVRRYGSPARIHIETAREVGKSFKDRKEIEKRQEENRKDREKAAAKFREY |
| | | FPNFVGEPKSKDILKLRLYEQQHGKCLYSGKEINLGRLNEKGYVEIDAALPFSR |
| | | TWDDSFNNKVLVLGSENQNKGNQTPYEYENGKDNSREWQEFKARVETSRFPRSK |
| | | KQRILLQKFDEDGFKERNLNDTRYVNRFLCQFVADRMRLTGKGKKRVFASNGQI |
| | | TNLLRGFWGLRKVRAENDRHHALDAVVVACSTVAMQQKITRFVRYKEMNAFDGK |
| | | TIDKETGEVLHQKTHFPQPWEFFAQEVMIRVFGKPDGKPEFEEADTLEKLRTLL |
| | | AEKLSSRPEAVHEYVTPLFVSRAPNRKMSGQGHMETVKSAKRLDEGVSVLRVPL |
| | | TQLKLKDLEKMVNREREPKLYEALKARLEAHKDDPAKAFAEPPFYKYDKAGNRTQ |
| | | QVKAVRVEQVQKTGVWVRNHNGIADNATMVRVDVFEKGDKYYLVPIYSWQVAKG |
| | | ILPDRAVVQGKDEEDWQLIDDSENFKFSLHPNDLVEVITKKARMFGYFASCHRG |
| | | TGNINIRIHDLDHKIGKNGILEGIGVKTALSFQKYQIDELGKEIRPCRLKKRPP |
| | | VR |
| 16 | dCjCas9 | MARILAFAIGISSIGWAFSENDELKDCGVRIFTKVENPKTGESLALPRRLARSA |
| | | RKRLARRKARLNHLKHLIANEFKLNYEDYQSFDESLAKAYKGSLISPYELRFRA |
| | | LNELLSKQDFARVILHIAKRRGYDDIKNSDDKEKGAILKAIKQNEEKLANYQSV |
| | | GEYLYKEYFQKFKENSKEFTNVRNKKESYERCIAQSFLKDELKLIFKKQREFGF |
| | | SFSKKFEEEVLSVAFYKRALKDFSHLVGNCSFFTDEKRAPKNSPLAFMFVALTR |
| | | IINLLNNLKNTEGILYTKDDLNALLNEVLKNGTLTYKQTKKLLGLSDDYEFKGE |
| | | KGTYFIEFKKYKEFIKALGEHNLSQDDLNEIAKDITLIKDEIKLKKALAKYDLN |
| | | QNQIDSLSKLEFKDHLNISFKALKLVTPLMLEGKKYDEACNELNLKVAINEDKK |
| | | DFLPAFNETYYKDEVTNPVVLRAIKEYRKVLNALLKKYGKVHKINIELAREVGK |
| | | NHSQRAKIEKEQNENYKAKKDAELECEKLGLKINSKNILKLRLFKEQKEFCAYS |
| | | GEKIKISDLQDEKMLEIDAIYPYSRSFDDSYMNKVLVFTKQNQEKLNQTPFEAF |
| | | GNDSAKWQKIEVLAKNLPTKKQKRILDKNYKDKEQKNFKDRNLNDTRYIARLVL |
| | | NYTKDYLDFLPLSDDENTKLNDTQKGSKVHVEAKSGMLTSALRHTWGFSAKDRN |
| | | NHLHHAIDAVIIAYANNSIVKAFSDFKKEQESNSAELYAKKISELDYKNKRKFF |
| | | EPFSGFRQKVLDKIDEIFVSKPERKKPSGALHEETFRKEEEFYQSYGGKEGVLK |
| | | ALELGKIRKVNGKIVKNGDMFRVDIFKHKKTNKFYAVPIYTMDFALKVLPNKAV |
| | | ARSKKGEIKDWILMDENYEFCFSLYKDSLILIQTKDMQEPEFVYYNAFTSSTVS |
| | | LIVSKHDNKFETLSKNQKILFKNANEKEVIAKSIGIQNLKVFEKYIVSALGEVT |
| | | KAEFRQREDFKK |
| 17 | dSt1Cas9 | MGSDLVLGLAIGIGSVGVGILNKVTGEIIHKNSRIFPAAQAENNLVRRTNRQGR |
| | | RLARRKKHRRVRLNRLFEESGLITDFTKISINLNPYQLRVKGLTDELSNEELFI |
| | | ALKNMVKHRGISYLDDASDDGNSSVGDYAQIVKENSKQLETKTPGQIQLERYQT |

TABLE 18-continued

Sequence listing.

| SEQ | Description | Sequence |
|---|---|---|
| | | YGQLRGDFTVEKDGKKHRLINVFPTSAYRSEALRILQTQQEFNPQITDEFINRY<br>LEILTGKRKYYHGPGNEKSRTDYGRYRTSGETLDNIFGILIGKCTFYPDEFRAA<br>KASYTAQEFNLLNDLNNLTVPTETKKLSKEQKNQIINYVKNEKAMGPAKLFKYI<br>AKLLSCDVADIKGYRIDKSGKAEIHTFEAYRKMKTLETLDIEQMDRETLDKLAY<br>VLTLNTEREGIQEALEHEFADGSFSQKQVDELVQFRKANSSIFGKGWHNFSVKL<br>MMELIPELYETSEEQMTILTRLGKQKTTSSSNKTKYIDEKLLTEEIYNPVVAKS<br>VRQAIKIVNAAIKEYGDFDNIVIEMARETNEDDEKKAIQKIQKANKDEKDAAML<br>KAANQYNGKAELPHSVFHGHKQLATKIRLWHQQGERCLYTGKTISIHDLINNSN<br>QFEVDAILPLSITFDDSLANKVLVYATANQEKGQRTPYQALDSMDDAWSFRELK<br>AFVRESKTLSNKKKEYLLTEEDISKFDVRKKFIERNLVDTRYASRVVLNALQEH<br>FRAHKIDTKVSVVRGQFTSQLRRHWGIEKTRDTYHHHAVDALIIAASSQLNLWK<br>KQKNTLVSYSEDQLLDIETGELISDDEYKESVFKAPYQHFVDTLKSKEFEDSIL<br>FSYQVDSKFNRKISDATIYATRQAKVGKDKADETYVLGKIKDIYTQDGYDAFMK<br>IYKKDKSKFLMYRHDPQTFEKVIEPILENYPNKQINEKGKEVPCNPFLKYKEEH<br>GYIRKYSKKGNGPEIKSLKYYDSKLGNHIDITPKDSNNKVVLQSVSPWRADVYF<br>NKTTGKYEILGLKYADLQFEKGTGTYKISQEKYNDIKKKEGVDSDSEFKFTLYK<br>NDLLLVKDTETKEQQLFRFLSRTMPKQKHYVELKPYDKQKFEGGEALIKVLGNV<br>ANSGQCKKGLGKSNISIYKVRTDVLGNQHIIKNEGDKPKLDE |
| 18 | dSt3Cas9 | MTKPYSIGLAIGTNSVGWAVITDNYKVPSKKMKVLGNTSKKYIKKNLLGVLLED<br>SGITAEGRRLKRTARRRYTRRRNRILYLQEIFSTEMATLDDAFFQRLDDSFLVP<br>DDKRDSKYPIFGNLVEEKVYHDEFPTIYHLRKYLADSTKKADLRLVYLALAHMI<br>KYRGHFLIEGEFNSKNNDIQKNFQDFLDTYNAIFESDLSLENSKQLEEIVKDKI<br>SKLEKKDRILKLFPGEKNSGIFSEFLKLIVGNQADERKCENLDEKASLHFSKES<br>YDEDLETLLGYIGDDYSDVFLKAKKLYDAILLSGELTVTDNETEAPLSSAMIKR<br>YNEHKEDLALLKEYIRNISLKTYNEVEKDDTKNGYAGYIDGKTNQEDFYVYLKN<br>LLAEFEGADYFLEKIDREDFLRKQRTFDNGSIPYQIHLQEMRAILDKQAKFYPF<br>LAKNKERIEKILTFRIPYYVGPLARGNSDFAWSIRKRNEKITPWNFEDVIDKES<br>SAEAFINRMTSFDLYLPEEKVLPKHSLLYETFNVYNELTKVRFIAESMRDYQFL<br>DSKQKKDIVRLYFKDKRKVTDKDIIEYLHAIYGYDGIELKGIEKQFNSSLSTYH<br>DLLNIIINDKEFLDDSSNEAIIEEIIHTLTIFEDREMIKQRLSKFENIFDKSVLK<br>KLSRRHYTGWGKLSAKLINGIRDEKSGNTILDYLIDDGISNRNFMQLIHDDALS<br>FKKKIQKAQIIGDEDKGNIKEVVKSLPGSPAIKKGILQSIKIVDELVKVMGGRK<br>PESIVVEMARENQYTNQGKSNSQQRLKRLEKSLKELGSKILKENIPAKLSKIDN<br>NALQNDRLYLYYLQNGKDMYTGDDLDIDRLSNYDIDHIIPQAFLKDNSIDNKVL<br>VSSASARGKSDDFPSLEVVKKRKTFWYQLLKSKLISQRKFDNLTKAERGGLLPE<br>DKAGFIQRQLVETRQITKHVARLLDEKENNKKDENNRAVRTVKIITLKSTLVSQ<br>FRKDFELYKVREINDFHHAHDAYLNAVIASALLKKYPKLEPEFVYGDYPKYNSF<br>RERKSATEKVYFYSNIMNIFKKSISLADGRVIERPLIEVNEETGESVWNKESDL<br>ATVRRVLSYPQVNVVKKVEEQNHGLDRGKPKGLFNANLSSKPKPNSNENLVGAK<br>EYLDPKKYGGYAGISNSFAVLVKGTIEKGAKKKITNVLEFQGISILDRINYRKD<br>KLNFLLEKGYKDIELIIELPKYSLFELSDGSRRMLASILSTNNKRGEIHKGNQI<br>FLSQKFVKLLYHAKRISNTINENHRKYVENHKKEFEELFYYILEFNENYVGAKK<br>NGKLLNSAFQSWQNHSIDELCSSFIGPTGSERKGLFELTSRGSAADFEFLGVKI<br>PRYRDYTPSSLLKDATLIHQSVTGLYETRIDLAKLGEG |
| 19 | dLbCpf1 | MSKLEKFTNCYSLSKTLRFKAIPVGKTQENIDNKRLLVEDEKRAEDYKGVKKLL<br>DRYYLSFINDVLHSIKLKNLNNYISLFRKKTRTEKENKELENLEINLRKEIAKA<br>FKGNEGYKSLFKKDIIETILPEFLDDKDEIALVNSFNGFTTAFTGFFDNRENMF<br>SEEAKSTSIAFRCINENLTRYISNMDIFEKVDAIFDKHEVQEIKEKILNSDYDV<br>EDFFEGEFFNFVLTQEGIDVYNAIIGGFVTESGEKIKGLNEYINLYNQKTKQKL<br>PKFKPLYKQVLSDRESLSFYGEGYTSDEEVLEVERNTLNKNSEIFSSIKKLEKL<br>FKNFDEYSSAGIFVKNGPAISTISKDIFGEWNVIRDKWNAEYDDIHLKKKAVVT<br>EKYEDDRRKSFKKIGSFSLEQLQEYADADLSVVEKLKEIIIQKVDEIYKVYGSS<br>EKLFDADFVLEKSLKKNDAVVAIMKDLLDSVKSFENYIKAFFGEGKETNRDESF<br>YGDPVLAYDILLKVDHIYDAIRNYVTQKPYSKDKFKLYFQNPQFMGGWDKDKET<br>DYRATILRYGSKYYLAIMDKKYAKCLQKIDKDDVNGNYEKINYKLLPGPNKMLP<br>KVFFSKKWMAYYNPSEDIQKIYKNGTFKKGDMENLNDCHKLIDFFKDSISRYPK<br>WSNAYDENESETEKYKDIAGFYREVEEQGYKVSFESASKKEVDKLVEEGKLYMF<br>QIYNKDFSDKSHGTPNLHTMYFKLLFDENNHGQIRLSGGAELFMRRASLKKEEL<br>VVHPANSPIANKNPDNPKKTTTLSYDVYKDKRFSEDQYELHIPIAINKCPKNIF<br>KINTEVRVLLKHDDNPYVIGIARGERNLLYIVVVDGKGNIVEQYSLNEIINNFN<br>GIRIKTDYHSLLDKKEKERFEARQNWTSIENIKELKAGYISQVVHKICELVEKY<br>DAVIALEDLNSGFKNSRVKVEKQVYQKFEKMLIDKLNYMVDKKSNPCATGGALK<br>GYQITNKFESFKSMSTQNGFIFYIPAWLTSKIDPSTGFVNLLKTKYTSIADSKK<br>FISSFDRIMYVPEEDLFEFALDYKNFSRTDADYIKKWKLYSYGNRIRIFRNPKK<br>NNVFDWEEVCLTSAYKELFNKYGINYQQGDIRALLCEQSDKAFYSSFMALMSLM<br>LQMRNSITGRTDVDFLISPVKNSDGIFYDSRNYEAQENAILPKNADANGAYNIA<br>RKVLWAIGQFKKAEDEKLDKVKIAISNKEWLEYAQTSVKH |
| 20 | inactive AsCpf1 | MTQFEGFTNLYQVSKTLRFELIPQGKTLKHIQEQGFIEEDKARNDHYKELKPII<br>DRIYKTYADQCLQLVQLDWENLSAAIDSYRKEKTEETRNALIEEQATYRNAIHD<br>YFIGRTDNLTDAINKRHAEIYKGLFKAELFNGKVLKQLGTVTTTEHENALLRSF<br>DKFTTYFSGFYENRKNVFSAEDISTAIPHRIVQDNFPKFKENCHIFTRLITAVP<br>SLREHFENVKKAIGIFVSTSIEEVFSFPPYNQLLTQTQIDLYNQLLGGISREAG<br>TEKIKGLNEVLNLAIQKNDETAHIIASLPHRFIPLFKQILSDRNTLSFILEEFK |

TABLE 18-continued

Sequence listing.

| SEQ | Description | Sequence |
|-----|-------------|----------|
| | | SDEEVIQSFCKYKTLLRNENVLETAEALFNELNSIDLTHIFISHKKLETISSAL |
| | | CDHWDTLRNALYERRISELTGKITKSAKEKVQRSLKHEDINLQEIISAAGKELS |
| | | EAFKQKTSEILSHAHAALDQPLPTTLKKQEEKEILKSQLDSLLGLYHLLDWFAV |
| | | DESNEVDPEFSARLTGIKLEMEPSLSFYNKARNYATKKPYSVEKFKLNFQMPTL |
| | | ASGWDVNKEKNNGAILFVKNGLYYLGIMPKQKGRYKALSFEPTEKTSEGFDKMY |
| | | YDYFPDAAKMIPKCSTQLKAVTAHFQTHTTPILLSNNFIEPLEITKEIYDLNNP |
| | | EKEPKKFQTAYAKKTGDQKGYREALCKWIDFTRDELSKYTKTTSIDLSSLRPSS |
| | | QYKDLGEYYAELNPLLYHISFQRIAEKEIMDAVETGKLYLFQIYNKDFAKGHHG |
| | | KPNLHTLYWTGLFSPENLAKTSIKLNGQAELFYRPKSRMKRMAHRLGEKMLNKK |
| | | LKDQKTPIPDTLYQELYDYVNHRLSHDLSDEARALLPNVITKEVSHEIIKDRRF |
| | | TSDKFFFHVPITLNYQAANSPSKENQRVNAYLKEHPETPIIGIARGERNLIYIT |
| | | VIDSTGKILEQRSLNTIQQFDYQKKLDNREKERVAARQAWSVVGTIKDLKQGYL |
| | | SQVIHEIVDLMIHYQAVVVLENLNFGFKSKRTGIAEKAVYQQFEKMLIDKLNCL |
| | | VLKDYPAEKVGGVLNPYQLTDQFTSFAKMGTQSGFLFYVPAPYTSKIDPLTGFV |
| | | DPFVWKTIKNHESRKHFLEGFDFLHYDVKTGDFILHFKMNRNLSFQRGLPGFMP |
| | | AWDIVFEKNETQFDAKGTPFIAGKRIVPVIENHRFTGRYRDLYPANELIALLEE |
| | | KGIVFRDGSNILPKLLENDDSHAIDTMVALIRSVLQMRNSNAATGEDYINSPVR |
| | | DLNGVCFDSRFQNPEWPMDADANGAYHIALKGQLLLNHLKESKDLKLQNGISNQ |
| | | DWLAYIQELRN |
| 21 | inactive enAsCpf1 | MTQFEGFTNLYQVSKTLRFELIPQGKTLKHIQEQGFIEEDKARNDHYKELKPII |
| | | DRIYKTYADQCLQLVQLDWENLSAAIDSYRKEKTEETRNALIEEQATYRNAIHD |
| | | YFIGRTDNLTDAINKRHAEIYKGLFKAELFNGKVLKQLGTVTTTEHENALLRSF |
| | | DKFTTYFSGFYRNRKNVFSAEDISTAIPHRIVQDNFPKFKENCHIFTRLITAVP |
| | | SLREHFENVKKAIGIFVSTSIEEVFSFPFYNQLLTQTQIDLYNQLLGGISREAG |
| | | TEKIKGLNEVLNLAIQKNDETAHIIASLPHRFIPLFKQILSDRNTLSFILEEFK |
| | | SDEEVIQSFCKYKTLLRNENVLETAEALFNELNSIDLTHIFISHKKLETISSAL |
| | | CDHWDTLRNALYERRISELTGKITKSAKEKVQRSLKHEDINLQEIISAAGKELS |
| | | EAFKQKTSEILSHAHAALDQPLPTTLKKQEEKEILKSQLDSLLGLYHLLDWFAV |
| | | DESNEVDPEFSARLTGIKLEMEPSLSFYNKARNYATKKPYSVEKFKLNFQMPTL |
| | | ARGWDVNREKNNGAILFVKNGLYYLGIMPKQKGRYKALSFEPTEKTSEGFDKMY |
| | | YDYFPDAAKMIPKCSTQLKAVTAHFQTHTTPILLSNNFIEPLEITKEIYDLNNP |
| | | EKEPKKFQTAYAKKTGDQKGYREALCKWIDFTRDFLSKYTKTTSIDLSSLRPSS |
| | | QYKDLGEYYAELNPLLYHISFQRIAEKEIMDAVETGKLYLFQIYNKDFAKGHHG |
| | | KPNLHTLYWTGLFSPENLAKTSIKLNGQAELFYRPKSRMKRMAHRLGEKMLNKK |
| | | LKDQKTPIPDTLYQELYDYVNHRLSHDLSDEARALLPNVITKEVSHEIIKDRRF |
| | | TSDKFFFHVPITLNYQAANSPSKENQRVNAYLKEHPETPIIGIARGERNLIYIT |
| | | VIDSTGKILEQRSLNTIQQFDYQKKLDNREKERVAARQAWSVVGTIKDLKQGYL |
| | | SQVIHEIVDLMIHYQAVVVLENLNFGFKSKRTGIAEKAVYQQFEKMLIDKLNCL |
| | | VLKDYPAEKVGGVLNPYQLTDQFTSFAKMGTQSGFLFYVPAPYTSKIDPLTGFV |
| | | DPFVWKTIKNHESRKHFLEGFDFLHYDVKTGDFILHFKMNRNLSFQRGLPGFMP |
| | | AWDIVFEKNETQFDAKGTPFIAGKRIVPVIENHRFTGRYRDLYPANELIALLEE |
| | | KGIVFRDGSNILPKLLENDDSHAIDTMVALIRSVLQMRNSNAATGEDYINSPVR |
| | | DLNGVCFDSRFQNPEWPMDADANGAYHIALKGQLLLNHLKESKDLKLQNGISNQ |
| | | DWLAYIQELRN |
| 22 | inactive HFAsCpf1 | MTQFEGFTNLYQVSKTLRFELIPQGKTLKHIQEQGFIEEDKARNDHYKELKPII |
| | | DRIYKTYADQCLQLVQLDWENLSAAIDSYRKEKTEETRNALIEEQATYRNAIHD |
| | | YFIGRTDNLTDAINKRHAEIYKGLFKAELFNGKVLKQLGTVTTTEHENALLRSF |
| | | DKFTTYFSGFYRNRKNVFSAEDISTAIPHRIVQDNFPKFKENCHIFTRLITAVP |
| | | SLREHFENVKKAIGIFVSTSIEEVFSFPFYNQLLTQTQIDLYNQLLGGISREAG |
| | | TEKIKGLNEVLALAIQKNDETAHIIASLPHRFIPLFKQILSDRNTLSFILEEFK |
| | | SDEEVIQSFCKYKTLLRNENVLETAEALFNELNSIDLTHIFISHKKLETISSAL |
| | | CDHWDTLRNALYERRISELTGKITKSAKEKVQRSLKHEDINLQEIISAAGKELS |
| | | EAFKQKTSEILSHAHAALDQPLPTTLKKQEEKEILKSQLDSLLGLYHLLDWFAV |
| | | DESNEVDPEFSARLTGIKLEMEPSLSFYNKARNYATKKPYSVEKFKLNFQMPTL |
| | | ARGWDVNREKNNGAILFVKNGLYYLGIMPKQKGRYKALSFEPTEKTSEGFDKMY |
| | | YDYFPDAAKMIPKCSTQLKAVTAHFQTHTTPILLSNNFIEPLEITKEIYDLNNP |
| | | EKEPKKFQTAYAKKTGDQKGYREALCKWIDFTRDFLSKYTKTTSIDLSSLRPSS |
| | | QYKDLGEYYAELNPLLYHISFQRIAEKEIMDAVETGKLYLFQIYNKDFAKGHHG |
| | | KPNLHTLYWTGLFSPENLAKTSIKLNGQAELFYRPKSRMKRMAHRLGEKMLNKK |
| | | LKDQKTPIPDTLYQELYDYVNHRLSHDLSDEARALLPNVITKEVSHEIIKDRRF |
| | | TSDKFFFHVPITLNYQAANSPSKFNQRVNAYLKEHPETPIIGIARGERNLIYIT |
| | | VIDSTGKILEQRSLNTIQQFDYQKKLDNREKERVAARQAWSVVGTIKDLKQGYL |
| | | SQVIHEIVDLMIHYQAVVVLENLNFGFKSKRTGIAEKAVYQQFEKMLIDKLNCL |
| | | VLKDYPAEKVGGVLNPYQLTDQFTSFAKMGTQSGFLFYVPAPYTSKIDPLTGFV |
| | | DPFVWKTIKNHESRKHFLEGFDFLHYDVKTGDFILHFKMNRNLSFQRGLPGEMP |
| | | AWDIVFEKNETQFDAKGTPFIAGKRIVPVIENHRFTGRYRDLYPANELIALLEE |
| | | KGIVFRDGSNILPKLLENDDSHAIDTMVALIRSVLQMRNSNAATGEDYINSPVR |
| | | DLNGVCFDSRFQNPEWPMDADANGAYHIALKGQLLLNHLKESKDLKLQNGISNQ |
| | | DWLAYIQELRN |
| 23 | inactive RVRAsCpf1 | MTQFEGFTNLYQVSKTLRFELIPQGKTLKHIQEQGFIEEDKARNDHYKELKPII |
| | | DRIYKTYADQCLQLVQLDWENLSAAIDSYRKEKTEETRNALIEEQATYRNAIHD |
| | | YFIGRTDNLTDAINKRHAEIYKGLFKAELFNGKVLKQLGTVTTTEHENALLRSF |
| | | DKFTTYFSGFYENRKNVFSAEDISTAIPHRIVQDNFPKFKENCHIFTRLITAVP |

TABLE 18-continued

Sequence listing.

| SEQ | Description | Sequence |
|---|---|---|
| | | SLREHFENVKKAIGIFVSTSIEEVFSFPPFYNQLLTQTQIDLYNQLLGGISREAG<br>TEKIKGLNEVLNLAIQKNDETAHIIASLPHRFIPLFKQILSDRNTLSFILEEFK<br>SDEEVIQSFCKYKTLLRNENVLETAEALFNELNSIDLTHIFISHKKLETISSAL<br>CDHWDTLRNALYERRISELTGKITKSAKEKVQRSLKHEDINLQEIISAAGKELS<br>EAFKQKTSEILSHAHAALDQPLPTTLKKQEEKEILKSQLDSLLGLYHLLDWFAV<br>DESNEVDPEFSARLTGIKLEMEPSLSFYNKARNYATKKPYSVEKFKLNFQMPTL<br>ARGWDVNVEKNRGAILFVKNGLYYLGIMPKQKGRYKALSFEPTEKTSEGFDKMY<br>YDYFPDAAKMIPKCSTQLKAVTAHFQTHTTPILLSNNFIEPLEITKEIYDLNNP<br>EKEPKKFQTAYAKKTGDQKGYREALCKWIDFTRDFLSKYTKTTSIDLSSLRPSS<br>QYKDLGEYYAELNPLLYHISFQRIAEKEIMDAVETGKLYLFQIYNKDFAKGHHG<br>KPNLHTLYWTGLFSPENLAKTSIKLNGQAELFYRPKSRMKRMAHRLGEKMLNKK<br>LKDQKTPIPDTLYQELYDYVNHRLSHDLSDEARALLPNVITKEVSHEIIKDRRF<br>TSDKFFFHVPITLNYQAANSPSKFNQRVNAYLKEHPETPIIGIARGERNLIYIT<br>VIDSTGKILEQRSLNTIQQFDYQKKLDNREKERVAARQAWSVVGTIKDLKQGYL<br>SQVIHEIVDLMIHYQAVVVLENLNFGFKSKRTGIAEKAVYQQFEKMLIDKLNCL<br>VLKDYPAEKVGGVLNPYQLTDQFTSFAKMGTQSGFLFYVPAPYTSKIDPLTGFV<br>DPFVWKTIKNHESRKHFLEGFDFLHYDVKTGDFILHFKMNRNLSFQRGLPGEMP<br>AWDIVFEKNETQFDAKGTPFIAGKRIVPVIENHRFTGRYRDLYPANELIALLEE<br>KGIVFRDGSNILPKLLENDDSHAIDTMVALIRSVLQMRNSNAATGEDYINSPVR<br>DLNGVCFDSRFQNPEWPMDADANGAYHIALKGQLLLNHLKESKDLKLQNGISNQ<br>DWLAYIQELRN |
| 24 | inactive<br>RRAsCpf1 | MTQFEGFTNLYQVSKTLRFELIPQGKTLKHIQEQGFIEEDKARNDHYKELKPII<br>DRIYKTYADQCLQLVQLDWENLSAAIDSYRKEKTEETRNALIEEQATYRNAIHD<br>YFIGRTDNLTDAINKRHAEIYKGLFKAELFNGKVLKQLGTVTTTEHENALLRSF<br>DKFTTYFSGFYENRKNVESAEDISTAIPHRIVQDNFPKFKENCHIFTRLITAVP<br>SLREHFENVKKAIGIFVSTSIEEVFSFPPFYNQLLTQTQIDLYNQLLGGISREAG<br>TEKIKGLNEVLNLAIQKNDETAHIIASLPHRFIPLFKQILSDRNTLSFILEEFK<br>SDEEVIQSFCKYKTLLRNENVLETAEALFNELNSIDLTHIFISHKKLETISSAL<br>CDHWDTLRNALYERRISELTGKITKSAKEKVQRSLKHEDINLQEIISAAGKELS<br>EAFKQKTSEILSHAHAALDQPLPTTLKKQEEKEILKSQLDSLLGLYHLLDWFAV<br>DESNEVDPEFSARLTGIKLEMEPSLSFYNKARNYATKKPYSVEKFKLNFQMPTL<br>ARGWDVNVEKNNGAILFVKNGLYYLGIMPKQKGRYKALSFEPTEKTSEGEDKMY<br>YDYFPDAAKMIPRCSTQLKAVTAHFQTHTTPILLSNNFIEPLEITKEIYDLNNP<br>EKEPKKFQTAYAKKTGDQKGYREALCKWIDFTRDFLSKYTKTTSIDLSSLRPSS<br>QYKDLGEYYAELNPLLYHISFQRIAEKEIMDAVETGKLYLFQIYNKDFAKGHHG<br>KPNLHTLYWTGLFSPENLAKTSIKLNGQAELFYRPKSRMKRMAHRLGEKMLNKK<br>LKDQKTPIPDTLYQELYDYVNHRLSHDLSDEARALLPNVITKEVSHEIIKDRRF<br>TSDKFFFHVPITLNYQAANSPSKENQRVNAYLKEHPETPIIGIARGERNLIYIT<br>VIDSTGKILEQRSLNTIQQFDYQKKLDNREKERVAARQAWSVVGTIKDLKQGYL<br>SQVIHEIVDLMIHYQAVVVLENLNFGFKSKRTGIAEKAVYQQFEKMLIDKLNCL<br>VLKDYPAEKVGGVLNPYQLTDQFTSFAKMGTQSGFLFYVPAPYTSKIDPLTGFV<br>DPFVWKTIKNHESRKHFLEGFDFLHYDVKTGDFILHFKMNRNLSFQRGLPGFMP<br>AWDIVFEKNETQFDAKGTPFIAGKRIVPVIENHRFTGRYRDLYPANELIALLEE<br>KGIVFRDGSNILPKLLENDDSHAIDTMVALIRSVLQMRNSNAATGEDYINSPVR<br>DLNGVCFDSRFQNPEWPMDADANGAYHIALKGQLLLNHLKESKDLKLQNGISNQ<br>DWLAYIQELRN |
| 25 | dCasX | MEKRINKIRKKLSADNATKPVSRSGPMKTLLVRVMTDDLKKRLEKRRKKPEVMP<br>QVISNNAANNLRMLLDDYTKMKEAILQVYWQEFKDDHVGLMCKFAQPASKKIDQ<br>NKLKPEMDEKGNLTTAGFACSQCGQPLFVYKLEQVSEKGKAYTNYFGRCNVAEH<br>EKLILLAQLKPEKDSDEAVTYSLGKFGQRALDFYSIHVTKESTHPVKPLAQIAG<br>NRYASGPVGKALSDACMGTIASFLSKYQDIIIEHQKVVKGNQKRLESLRELAGK<br>ENLEYPSVTLPPQPHTKEGVDAYNEVIARVRMWVNLNLWQKLKLSRDDAKPLLR<br>LKGFPSFPVVERRENEVDWWNTINEVKKLIDAKRDMGRVFWSGVTAEKRNTILE<br>GYNYLPNENDHKKREGSLENPKKPAKRQFGDLLLYLEKKYAGDWGKVEDEAWER<br>IDKKIAGLTSHIEREEARNAEDAQSKAVLTDWLRAKASFVLERLKEMDEKEFYA<br>CEIQLQKWYGDLRGNPFAVEAENRVVDISGFSIGSDGHSIQYRNLLAWKYLENG<br>KREFYLLMNYGKKGRIRFTDGTDIKKSGKWQGLLYGGGKAKVIDLTFDPDDEQL<br>IILPLAFGTRQGREFIWNDLLSLETGLIKLANGRVIEKTIYNKKIGRDEPALFV<br>ALTFERREVVDPSNIKPVNLIGVARGENIPAVIALTDPEGCPLPEFKDSSGGPT<br>DILRIGEGYKEKQRAIQAAKEVEQRRAGGYSRKFASKSRNLADDMVRNSARDLF<br>YHAVTHDAVLVFANLSRGFGRQGKRTFMTERQYTKMEDWLTAKLAYEGLTSKTY<br>LSKTLAQYTSKTCSNCGFTITTADYDGMLVRLKKTSDGWATTLNNKELKAEGQI<br>TYYNRYKRQTVEKELSAELDRLSEESGNNDISKWTKGRRDEALFLLKKRFSHRP<br>VQEQFVCLDCGHEVHAAEQAALNIARSWLFLNSNSTEFKSYKSGKQPFVGAWQA<br>FYKRRLKEVWKPNA |
| 26 | dCasPhi | MPKPAVESEFSKVLKKHFPGERFRSSYMKRGGKILAAQGEEAVVAYLQGKSEEE<br>PPNFQPPAKCHVVTKSRDFAEWPIMKASEAIQRYIYALSTTERAACKPGKSSES<br>HAAWFAATGVSNHGYSHVQGLNLIFDHTLGRYDGVLKVQLRNEKARARLESIN<br>ASRADEGLPEIKAEEEEVATNETGHLLQPPGINPSFYVYQTISPQAYRPRDEIV<br>LPPEYAGYVRDPNAPIPLGVVRNRCDIQKGCPGYIPEWQREAGTAISPKTGKAV<br>TVPGLSPKKNKRMRRYWRSEKEKAQDALLVTVRIGTDWVVIDVRGLLRNARWRT<br>IAPKDISLNALLDLFTGDPVIDVRRNIVTFTYTLDACGTYARKWTLKGKQTKAT<br>LDKLTATQTVALVAIALGQTNPISAGISRVTQENGALQCEPLDRFTLPDDLLKD |

TABLE 18-continued

Sequence listing.

| SEQ | Description | Sequence |
|---|---|---|
| | | ISAYRIAWDRNEEELRARSVEALPEAQQAEVRALDGVSKETARTQLCADFGLDP |
| | | KRLPWDKMSSNTTFISEALLSNSVSRDQVFFTPAPKKGAKKKAPVEVMRKDRTW |
| | | ARAYKPRLSVEAQKLKNEALWALKRTSPEYLKLSRRKEELCRRSINYVIEKTRR |
| | | RTQCQIVIPVIEDLNVRFFHGSGKRLPGWDNFFTAKKENRWFIQGLHKAFSDLR |
| | | THRSFYVFEVRPERTSITCPKCGHCEVGNRDGEAFQCLSCGKTCNADLDVATHN |
| | | LTQVALTGKTMPKREEPRDAQGTAPARKTKKASKSKAPPAEREDQTPAQEPSQT |
| | | S |
| 27 | inactive VRER SpCas9 | MDKKYSIGLAIGTNSVGWAVITDEYKVPSKKFKVLGNTDRHSIKKNLIGALLED |
| | | SGETAEATRLKRTARRRYTRRKNRICYLQEIFSNEMAKVDDSFFHRLEESFLVE |
| | | EDKKHERHPIFGNIVDEVAYHEKYPTIYHLRKKLVDSTDKADLRLIYLALAHMI |
| | | KFRGHFLIEGDLNPDNSDVDKLFIQLVQTYNQLFEENPINASGVDAKAILSARL |
| | | SKSRRLENLIAQLPGEKKNGLFGNLIALSLGLTPNFKSNFDLAEDAKLQLSKDT |
| | | YDDDLDNLLAQIGDQYADLFLAAKNLSDAILLSDILRVNTEITKAPLSASMIKR |
| | | YDEHHQDLTLLKALVRQQLPEKYKEIFFDQSKNGYAGYIDGGASQEEFYKFIKP |
| | | ILEKMDGTEELLVKLNREDLLRKQRTFDNGSIPHQIHLGELHAILRRQEDFYPF |
| | | LKDNREKIEKILTFRIPYYVGPLARGNSRFAWMTRKSEETITPWNFEEVVDKGA |
| | | SAQSFIERMTNFDKNLPNEKVLPKHSLLYEYFTVYNELTKVKYVTEGMRKPAFL |
| | | SGEQKKAIVDLLFKTNRKVTVKQLKEDYFKKIECFDSVEISGVEDRENASLGTY |
| | | HDLLKIIKDKDELDNEENEDILEDIVLTLTLFEDREMIEERLKTYAHLEDDKVM |
| | | KQLKRRRYTGWGRLSRKLINGIRDKQSGKTILDFLKSDGFANRNFMQLIHDDSL |
| | | TFKEDIQKAQVSGQGDSLHEHIANLAGSPAIKKGILQTVKVVDELVKVMGRHKP |
| | | ENIVIEMARENQTTQKGQKNSRERMKRIEEGIKELGSQILKEHPVENTQLQNEK |
| | | LYLYYLQNGRDMYVDQELDINRLSDYDVDAIVPQSFLKDDSIDNKVLTRSDKNR |
| | | GKSDNVPSEEVVKKMKNYWRQLLNAKLITQRKFDNLTKAERGGLSELDKAGFIK |
| | | RQLVETRQITKHVAQILDSRMNTKYDENDKLIREVKVITLKSKLVSDFRKDFQF |
| | | YKVREINNYHHAHDAYLNAVVGTALIKKYPKLESEFVYGDYKVYDVRKMIAKSE |
| | | QEIGKATAKYFFYSNIMNFFKTEITLANGEIRKRPLIETNGETGEIVWDKGRDF |
| | | ATVRKVLSMPQVNIVKKTEVQTGGFSKESILPKRNSDKLIARKKDWDPKKYGGF |
| | | VSPTVAYSVLVVAKVEKGKSKKLKSVKELLGITIMERSSFEKNPIDFLEAKGYK |
| | | EVKKDLIIKLPKYSLFELENGRKRMLASARELQKGNELALPSKYVNFLYLASHY |
| | | EKLKGSPEDNEQKQLFVEQHKHYLDEIIEQISEFSKRVILADANLDKVLSAYNK |
| | | HRDKPIREQAENIIHLFTLTNLGAPAAFKYFDTTIDRKEYRSTKEVLDATLIHQ |
| | | SITGLYETRIDLSQLGGD |
| 28 | inactive EQR SpCas9 | MDKKYSIGLAIGTNSVGWAVITDEYKVPSKKFKVLGNTDRHSIKKNLIGALLED |
| | | SGETAEATRLKRTARRRYTRRKNRICYLQEIFSNEMAKVDDSFFHRLEESFLVE |
| | | EDKKHERHPIFGNIVDEVAYHEKYPTIYHLRKKLVDSTDKADLRLIYLALAHMI |
| | | KFRGHFLIEGDLNPDNSDVDKLFIQLVQTYNQLFEENPINASGVDAKAILSARL |
| | | SKSRRLENLIAQLPGEKKNGLFGNLIALSLGLTPNFKSNEDLAEDAKLQLSKDT |
| | | YDDDLDNLLAQIGDQYADLFLAAKNLSDAILLSDILRVNTEITKAPLSASMIKR |
| | | YDEHHQDLTLLKALVRQQLPEKYKEIFFDQSKNGYAGYIDGGASQEEFYKFIKP |
| | | ILEKMDGTEELLVKLNREDLLRKQRTFDNGSIPHQIHLGELHAILRRQEDFYPF |
| | | LKDNREKIEKILTFRIPYYVGPLARGNSRFAWMTRKSEETITPWNFEEVVDKGA |
| | | SAQSFIERMTNFDKNLPNEKVLPKHSLLYEYFTVYNELTKVKYVTEGMRKPAFL |
| | | SGEQKKAIVDLLFKTNRKVTVKQLKEDYFKKIECFDSVEISGVEDRNASLGTY |
| | | HDLLKIIKDKDFLDNEENEDILEDIVLTLTLFEDREMIEERLKTYAHLFDDKVM |
| | | KQLKRRRYTGWGRLSRKLINGIRDKQSGKTILDFLKSDGFANRNFMQLIHDDSL |
| | | TFKEDIQKAQVSGQGDSLHEHIANLAGSPAIKKGILQTVKVVDELVKVMGRHKP |
| | | ENIVIEMARENQTTQKGQKNSRERMKRIEEGIKELGSQILKEHPVENTQLQNEK |
| | | LYLYYLQNGRDMYVDQELDINRLSDYDVDAIVPQSFLKDDSIDNKVLTRSDKNR |
| | | GKSDNVPSEEVVKKMKNYWRQLLNAKLITQRKFDNLTKAERGGLSELDKAGFIK |
| | | RQLVETRQITKHVAQILDSRMNTKYDENDKLIREVKVITLKSKLVSDFRKDFQF |
| | | YKVREINNYHHAHDAYLNAVVGTALIKKYPKLESEFVYGDYKVYDVRKMIAKSE |
| | | QEIGKATAKYFFYSNIMNFFKTEITLANGEIRKRPLIETNGETGEIVWDKGRDF |
| | | ATVRKVLSMPQVNIVKKTEVQTGGFSKESILPKRNSDKLIARKKDWDPKKYGGF |
| | | ESPTVAYSVLVVAKVEKGKSKKLKSVKELLGITIMERSSFEKNPIDFLEAKGYK |
| | | EVKKDLIIKLPKYSLFELENGRKRMLASAGELQKGNELALPSKYVNFLYLASHY |
| | | EKLKGSPEDNEQKQLFVEQHKHYLDEIIEQISEFSKRVILADANLDKVLSAYNK |
| | | HRDKPIREQAENIIHLFTLTNLGAPAAFKYFDTTIDRKQYRSTKEVLDATLIHQ |
| | | SITGLYETRIDLSQLGGD |
| 29 | inactive VQR SpCas9 | MDKKYSIGLAIGTNSVGWAVITDEYKVPSKKFKVLGNTDRHSIKKNLIGALLED |
| | | SGETAEATRLKRTARRRYTRRKNRICYLQEIFSNEMAKVDDSFFHRLEESFLVE |
| | | EDKKHERHPIFGNIVDEVAYHEKYPTIYHLRKKLVDSTDKADLRLIYLALAHMI |
| | | KFRGHFLIEGDLNPDNSDVDKLFIQLVQTYNQLFEENPINASGVDAKAILSARL |
| | | SKSRRLENLIAQLPGEKKNGLFGNLIALSLGLTPNFKSNEDLAEDAKLQLSKDT |
| | | YDDDLDNLLAQIGDQYADLFLAAKNLSDAILLSDILRVNTEITKAPLSASMIKR |
| | | YDEHHQDLTLLKALVRQQLPEKYKEIFFDQSKNGYAGYIDGGASQEEFYKFIKP |
| | | ILEKMDGTEELLVKLNREDLLRKQRTFDNGSIPHQIHLGELHAILRRQEDFYPF |
| | | LKDNREKIEKILTFRIPYYVGPLARGNSRFAWMTRKSEETITPWNFEEVVDKGA |
| | | SAQSFIERMTNFDKNLPNEKVLPKHSLLYEYFTVYNELTKVKYVTEGMRKPAFL |
| | | SGEQKKAIVDLLFKTNRKVTVKQLKEDYFKKIECFDSVEISGVEDRNASLGTY |
| | | HDLLKIIKDKDFLDNEENEDILEDIVLTLTLFEDREMIEERLKTYAHLEDDKVM |
| | | KQLKRRRYTGWGRLSRKLINGIRDKQSGKTILDFLKSDGFANRNFMQLIHDDSL |
| | | TFKEDIQKAQVSGQGDSLHEHIANLAGSPAIKKGILQTVKVVDELVKVMGRHKP |

TABLE 18-continued

Sequence listing.

| SEQ | Description | Sequence |
|-----|-------------|----------|
| | | ENIVIEMARENQTTQKGQKNSRERMKRIEEGIKELGSQILKEHPVENTQLQNEK<br>LYLYYLQNGRDMYVDQELDINRLSDYDVDAIVPQSFLKDDSIDNKVLTRSDKNR<br>GKSDNVPSEEVVKKMKNYWRQLLNAKLITQRKFDNLTKAERGGLSELDKAGFIK<br>RQLVETRQITKHVAQILDSRMNTKYDENDKLIREVKVITLKSKLVSDFRKDFQF<br>YKVREINNYHHAHDAYLNAVVGTALIKKYPKLESEFVYGDYKVYDVRKMIAKSE<br>QEIGKATAKYFFYSNIMNFFKTEITLANGEIRKRPLIETNGETGEIVWDKGRDF<br>ATVRKVLSMPQVNIVKKTEVQTGGFSKESILPKRNSDKLIARKKDWDPKKYGGF<br>VSPTVAYSVLVVAKVEKGKSKKLKSVKELLGITIMERSSFEKNPIDFLEAKGYK<br>EVKKDLIIKLPKYSLFELENGRKRMLASAGELQKGNELALPSKYVNFLYLASHY<br>EKLKGSPEDNEQKQLFVEQHKHYLDEIIEQISEFSKRVILADANLDKVLSAYNK<br>HRDKPIREQAENIIHLFTLTNLGAPAAFKYFDTTIDRKQYRSTKEVLDATLIHQ<br>SITGLYETRIDLSQLGGD |
| 30 | inactive SPG<br>SpCas9 | MDKKYSIGLAIGTNSVGWAVITDEYKVPSKKFKVLGNTDRHSIKKNLIGALLFD<br>SGETAEATRLKRTARRRYTRRKNRICYLQEIFSNEMAKVDDSFFHRLEESELVE<br>EDKKHERHPIFGNIVDEVAYHEKYPTIYHLRKKLVDSTDKADLRLIYLALAHMI<br>KFRGHFLIEGDLNPDNSDVDKLFIQLVQTYNQLFEENPINASGVDAKAILSARL<br>SKSRRLENLIAQLPGEKKNGLFGNLIALSLGLTPNFKSNFDLAEDAKLQLSKDT<br>YDDDLDNLLAQIGDQYADLFLAAKNLSDAILLSDILRVNTEITKAPLSASMIKR<br>YDEHHQDLTLLKALVRQQLPEKYKEIFFDQSKNGYAGYIDGGASQEEFYKFIKP<br>ILEKMDGTEELLVKLNREDLLRKQRTFDNGSIPHQIHLGELHAILRRQEDFYPF<br>LKDNREKIEKILTFRIPYYVGPLARGNSRFAWMTRKSEETITPWNFEEVVDKGA<br>SAQSFIERMTNFDKNLPNEKVLPKHSLLYEYFTVYNELTKVKYVTEGMRKPAFL<br>SGEQKKAIVDLLFKTNRKVTVKQLKEDYFKKIECFDSVEISGVEDRENASLGTY<br>HDLLKIIKDKDFLDNEENEDILEDIVLTLTLFEDREMIEERLKTYAHLFDDDKVM<br>KQLKRRRYTGWGRLSRKLINGIRDKQSGKTILDFLKSDGFANRNFMQLIHDDSL<br>TFKEDIQKAQVSGQGDSLHEHIANLAGSPAIKKGILQTVKVVDELVKVMGRHKP<br>ENIVIEMARENQTTQKGQKNSRERMKRIEEGIKELGSQILKEHPVENTQLQNEK<br>LYLYYLQNGRDMYVDQELDINRLSDYDVDAIVPQSFLKDDSIDNKVLTRSDKNR<br>GKSDNVPSEEVVKKMKNYWRQLLNAKLITQRKFDNLTKAERGGLSELDKAGFIK<br>RQLVETRQITKHVAQILDSRMNTKYDENDKLIREVKVITLKSKLVSDERKDFQF<br>YKVREINNYHHAHDAYLNAVVGTALIKKYPKLESEFVYGDYKVYDVRKMIAKSE<br>QEIGKATAKYFFYSNIMNFFKTEITLANGEIRKRPLIETNGETGEIVWDKGRDF<br>ATVRKVLSMPQVNIVKKTEVQTGGFSKESILPKRNSDKLIARKKDWDPKKYGGF<br>LWPTVAYSVLVVAKVEKGKSKKLKSVKELLGITIMERSSFEKNPIDFLEAKGYK<br>EVKKDLIIKLPKYSLFELENGRKRMLASAKQLQKGNELALPSKYVNFLYLASHY<br>EKLKGSPEDNEQKQLFVEQHKHYLDEIIEQISEFSKRVILADANLDKVLSAYNK<br>HRDKPIREQAENIIHLFTLTNLGAPAAFKYEDTTIDRKQYRSTKEVLDATLIHQ<br>SITGLYETRIDLSQLGGD |
| 31 | inactive SpRY<br>Cas9 | MDKKYSIGLAIGTNSVGWAVITDEYKVPSKKFKVLGNTDRHSIKKNLIGALLFD<br>SGETAERTRLKRTARRRYTRRKNRICYLQEIFSNEMAKVDDSFFHRLEESELVE<br>EDKKHERHPIFGNIVDEVAYHEKYPTIYHLRKKLVDSTDKADLRLIYLALAHMI<br>KFRGHFLIEGDLNPDNSDVDKLFIQLVQTYNQLFEENPINASGVDAKAILSARL<br>SKSRRLENLIAQLPGEKKNGLFGNLIALSLGLTPNFKSNEDLAEDAKLQLSKDT<br>YDDDLDNLLAQIGDQYADLFLAAKNLSDAILLSDILRVNTEITKAPLSASMIKR<br>YDEHHQDLTLLKALVRQQLPEKYKEIFFDQSKNGYAGYIDGGASQEEFYKFIKP<br>ILEKMDGTEELLVKLNREDLLRKQRTFDNGSIPHQIHLGELHAILRRQEDFYPF<br>LKDNREKIEKILTFRIPYYVGPLARGNSRFAWMTRKSEETITPWNFEEVVDKGA<br>SAQSFIERMTNFDKNLPNEKVLPKHSLLYEYFTVYNELTKVKYVTEGMRKPAFL<br>SGEQKKAIVDLLFKTNRKVTVKQLKEDYFKKIECFDSVEISGVEDRENASLGTY<br>HDLLKIIKDKDFLDNEENEDILEDIVLTLTLFEDREMIEERLKTYAHLEDDDKVM<br>KQLKRRRYTGWGRLSRKLINGIRDKQSGKTILDFLKSDGFANRNFMQLIHDDSL<br>TFKEDIQKAQVSGQGDSLHEHIANLAGSPAIKKGILQTVKVVDELVKVMGRHKP<br>ENIVIEMARENQTTQKGQKNSRERMKRIEEGIKELGSQILKEHPVENTQLQNEK<br>LYLYYLQNGRDMYVDQELDINRLSDYDVDAIVPQSFLKDDSIDNKVLTRSDKNR<br>GKSDNVPSEEVVKKMKNYWRQLLNAKLITQRKFDNLTKAERGGLSELDKAGFIK<br>RQLVETRQITKHVAQILDSRMNTKYDENDKLIREVKVITLKSKLVSDFRKDFQF<br>YKVREINNYHHAHDAYLNAVVGTALIKKYPKLESEFVYGDYKVYDVRKMIAKSE<br>QEIGKATAKYFFYSNIMNFFKTEITLANGEIRKRPLIETNGETGEIVWDKGRDF<br>ATVRKVLSMPQVNIVKKTEVQTGGFSKESIRPKRNSDKLIARKKDWDPKKYGGF<br>LWPTVAYSVLVVAKVEKGKSKKLKSVKELLGITIMERSSFEKNPIDFLEAKGYK<br>EVKKDLIIKLPKYSLFELENGRKRMLASAKQLQKGNELALPSKYVNFLYLASHY<br>EKLKGSPEDNEQKQLFVEQHKHYLDEIIEQISEFSKRVILADANLDKVLSAYNK<br>HRDKPIREQAENIIHLFTLTRLGAPRAFKYFDTTIDPKQYRSTKEVLDATLIHQ<br>SITGLYETRIDLSQLGGD |
| 32 | inactive KKH<br>dSaCas9 | MKRNYILGLAIGITSVGYGIIDYETRDVIDAGVRLFKEANVENNEGRRSKRGAR<br>RLKRRRHRIQRVKKLLFDYNLLTDHSELSGINPYEARVKGLSQKLSEEEFSAA<br>LLHLAKRRGVHNVNEVEEDTGNELSTKEQISRNSKALEEKYVAELQLERLKKDG<br>EVRGSINRFKTSDYVKEAKQLLKVQKAYHQLDQSFIDTYIDLLETRRTYYEGPG<br>EGSPFGWKDIKEWYEMLMGHCTYFPEELRSVKYAYNADLYNALNDLNNLVITRD<br>ENEKLEYYEKFQIIENVFKQKKKPTLKQIAKEILVNEEDIKGYRVTSTGKPEFT<br>NLKVYHDIKDITARKEIIENAELLDQIAKILTIYQSSEDIQEELTNLNSELTQE<br>EIEQISNLKGYTGTHNLSLKAINLILDELWHTNDNQIAIFNRLKLVPKKVDLSQ<br>QKEIPTTLVDDFILSPVVKRSFIQSIKVINAIIKKYGLPNDIIIELAREKNSKD |

TABLE 18-continued

Sequence listing.

| SEQ | Description | Sequence |
| --- | --- | --- |
| | | AQKMINEMQKRNRQTNERIEEIIRTTGKENAKYLIEKIKLHDMQEGKCLYSLEA<br>IPLEDLLNNPFNYEVDHIIPRSVSFDNSFNNKVLVKQEEASKKGNRTPFQYLSS<br>SDSKISYETFKKHILNLAKGKGRISKTKKEYLLEERDINRFSVQKDFINRNLVD<br>TRYATRGLMNLLRSYFRVNNLDVKVKSINGGFTSFLRRKWKFKKERNKGYKHHA<br>EDALIIANADFIFKEWKKLDKAKKVMENQMFEEKQAESMPEIETEQEYKEIFIT<br>PHQIKHIKDFKDYKYSHRVDKKPNRKLINDTLYSTRKDDKGNTLIVNNLNGLYD<br>KDNDKLKKLINKSPEKLLMYHHDPQTYQKLKLIMEQYGDEKNPLYKYYEETGNY<br>LTKYSKKDNGPVIKKIKYYGNKLNAHLDITDDYPNSRNKVVKLSLKPYRFDVYL<br>DNGVYKFVTVKNLDVIKKENYYEVNSKCYEEAKKLKKISNQAEFIASFYKNDLI<br>KINGELYRVIGVNNDLLNRIEVNMIDITYREYLENMNDKRPPHIIKTIASKTQS<br>IKKYSTDILGNLYEVKSKKHPQIIKKG |
| 33 | mRNA0001 | SRPGERPFQCRICMRNFSKKFNLLQHTRTHTGEKPFQCRICMRNFSRQDNLNSH<br>LRTHTGSQKPFQCRICMRNFSRSHNLKLHTRTHTGEKPFQCRICMRNFSQSTTL<br>KRHLRTHTGSQKPFQCRICMRNFSRNTNLTRHTRTHTGEKPFQCRICMRNFSIK<br>HNLARHLRTHLRGS |
| 34 | mRNA0002 | SRPGERPFQCRICMRNFSKKENLLQHTRTHTGEKPFQCRICMRNFSRKDYLISH<br>LRTHTGSQKPFQCRICMRNFSRSHNLKLHTRTHTGEKPFQCRICMRNFSQSTTL<br>KRHLRTHTGSQKPFQCRICMRNFSRQDNLGRHLRTHTGEKPFQCRICMRNFSVV<br>NNLNRHLKTHLRGS |
| 35 | mRNA0003 | SRPGERPFQCRICMRNFSKKENLLQHTRTHTGEKPFQCRICMRNFSRKDYLISH<br>LRTHTGSQKPFQCRICMRNFSRSHNLRLHTRTHTGEKPFQCRICMRNFSQSTTL<br>KRHLRTHTGSQKPFQCRICMRNFSRQDNLGRHLRTHTGEKPFQCRICMRNFSVV<br>NNLNRHLKTHLRGS |
| 36 | mRNA0004 | SRPGERPFQCRICMRNFSRRHILDRHTRTHTGEKPFQCRICMRNFSRQDNLGRH<br>LRTHTGSQKPFQCRICMRNFSQSTTLKRHLRTHTGEKPFQCRICMRNFSRRDGL<br>AGHLKTHTGSQKPFQCRICMRNFSVHHNLVRHLRTHTGEKPFQCRICMRNFSIS<br>HNLARHLKTHLRGS |
| 37 | mRNA0005 | SRPGERPFQCRICMRNFSRREVLENHLRTHTGEKPFQCRICMRNFSRRDNLNRH<br>LKTHTGSQKPFQCRICMRNFSQSTTLKRHLRTHTGEKPFQCRICMRNFSRRDGL<br>AGHLKTHTGSQKPFQCRICMRNFSVHHNLVRHLRTHTGEKPFQCRICMRNFSIS<br>HNLARHLKTHLRGS |
| 38 | mRNA0006 | SRPGERPFQCRICMRNFSRRAVLDRHTRTHTGEKPFQCRICMRNFSRQDNLGRH<br>LRTHTGSQKPFQCRICMRNFSQSTTLKRHLRTHTGEKPFQCRICMRNFSRRDGL<br>AGHLKTHTGSQKPFQCRICMRNFSVHHNLVRHLRTHTGEKPFQCRICMRNFSIS<br>HNLARHLKTHLRGS |
| 39 | mRNA0064 | SRPGERPFQCRICMRNFSRQEHLVRHLRTHTGEKPFQCRICMRNFSEGGNLMRH<br>LKTHTGSQKPFQCRICMRNFSSDRRDLDHTRTHTGEKPFQCRICMRNFSSFQSY<br>LEHLRTHTGSQKPFQCRICMRNFSRPNHLAIHTRTHTGEKPFQCRICMRNFSQS<br>PHLKRHLRTHLRGS |
| 40 | mRNA0007 | SRPGERPFQCRICMRNFSRREHLVRHLRTHTGEKPFQCRICMRNFSDPSNLQRH<br>LKTHTGSQKPFQCRICMRNFSSDRRDLDHTRTHTGEKPFQCRICMRNFSSFQSY<br>LEHLRTHTGSQKPFQCRICMRNFSRPNHLAIHTRTHTGEKPFQCRICMRNFSQS<br>PHLKRHLRTHLRGS |
| 41 | mRNA0008 | SRPGERPFQCRICMRNFSRREHLVRHLRTHTGEKPFQCRICMRNFSDMGNLGRH<br>LKTHTGSQKPFQCRICMRNFSSDRRDLDHTRTHTGEKPFQCRICMRNFSSFQSY<br>LEHLRTHTGSQKPFQCRICMRNFSRPNHLAIHTRTHTGEKPFQCRICMRNFSQS<br>PHLKRHLRTHLRGS |
| 42 | mRNA0009 | SRPGERPFQCRICMRNFSKKDHLHRHTRTHTGEKPFQCRICMRNFSQKEILTRH<br>LRTHTGSQKPFQCRICMRNFSQSAHLKRHLRTHTGEKPFQCRICMRNFSETGSL<br>RRHLKTHTGGGGSQKPFQCRICMRNFSQSHSLKSHLRTHTGEKPFQCRICMRNF<br>SESGHLKRHLKTHLRGS |
| 43 | mRNA0010 | SRPGERPFQCRICMRNFSKKDHLHRHTRTHTGEKPFQCRICMRNFSQKEILTRH<br>LRTHTGSQKPFQCRICMRNFSQSAHLKRHLRTHTGEKPFQCRICMRNFSDRTPL<br>NRHLKTHTGGGGSQKPFQCRICMRNFSQSHSLKSHLRTHTGEKPFQCRICMRNF<br>SESGHLKRHLKTHLRGS |
| 44 | mRNA0011 | SRPGERPFQCRICMRNFSKTDHLARHTRTHTGEKPFQCRICMRNFSQKEILTRH<br>LRTHTGSQKPFQCRICMRNFSQSAHLKRHLRTHTGEKPFQCRICMRNFSETGSL<br>RRHLKTHTGGGGSQKPFQCRICMRNFSQKHHLVTHLRTHTGEKPFQCRICMRNF<br>SENSKLRRHLKTHLRGS |
| 45 | mRNA0012 | SRPGERPFQCRICMRNFSQAGNLVRHLRTHTGEKPFQCRICMRNFSQNSHLRRH<br>LKTHTGGGGSQKPFQCRICMRNFSDLSTLRRHTRTHTGEKPFQCRICMRNFSQN<br>EHLKVHLRTHTGSQKPFQCRICMRNFSGGTALRMHTRTHTGEKPFQCRICMRNF<br>SQRSSLVRHLRTHLRGS |

TABLE 18-continued

Sequence listing.

| SEQ | Description | Sequence |
|---|---|---|
| 46 | mRNA0013 | SRPGERPFQCRICMRNFSQRGNLQRHLRTHTGEKPFQCRICMRNFSQTTHLSRH<br>LKTHTGGGGSQKPFQCRICMRNFSDGSTLRRHTRTHTGEKPFQCRICMRNFSQK<br>THLAVHLRTHTGSQKPFQCRICMRNFSGGTALRMHTRTHTGEKPFQCRICMRNF<br>SQRSSLVRHLRTHLRGS |
| 47 | mRNA0014 | SRPGERPFQCRICMRNFSQRGNLQRHLRTHTGEKPFQCRICMRNFSQTTHLSRH<br>LKTHTGGGGSQKPFQCRICMRNFSDLSTLRRHTRTHTGEKPFQCRICMRNFSQN<br>EHLKVHLRTHTGSQKPFQCRICMRNFSGGSALSMHTRTHTGEKPFQCRICMRNF<br>SQRSSLVRHLRTHLRGS |
| 48 | mRNA0015 | SRPGERPFQCRICMRNFSDRGNLTRHLRTHTGEKPFQCRICMRNFSQARSLRAH<br>LKTHTGGGGSQKPFQCRICMRNFSEKASLIKHTRTHTGEKPFQCRICMRNFSDH<br>SSLKRHLRTHTGSQKPFQCRICMRNFSRRFILSRHTRTHTGEKPFQCRICMRNF<br>SRNDSLKCHLRTHLRGS |
| 49 | mRNA0016 | SRPGERPFQCRICMRNFSDRGNLTRHLRTHTGEKPFQCRICMRNFSQARSLRAH<br>LKTHTGGGGSQKPFQCRICMRNFSDKSSLRKHTRTHTGEKPFQCRICMRNFSDH<br>SSLKRHLRTHTGSQKPFQCRICMRNFSRNFILQRHTRTHTGEKPFQCRICMRNF<br>SRNDTLIIHLRTHLRGS |
| 50 | mRNA0017 | SRPGERPFQCRICMRNFSDRGNLTRHLRTHTGEKPFQCRICMRNFSQARSLRAH<br>LKTHTGGGGSQKPFQCRICMRNFSCNGSLKKHTRTHTGEKPFQCRICMRNFSDH<br>SSLKRHLRTHTGSQKPFQCRICMRNFSRNFILQRHTRTHTGEKPFQCRICMRNF<br>SRNDTLIIHLRTHLRGS |
| 51 | mRNA0018 | SRPGERPFQCRICMRNFSRTDTLARHLRTHTGEKPFQCRICMRNFSRTDSLPRH<br>LKTHTGGGGSQKPFQCRICMRNFSDHSSLKRHLRTHTGEKPFQCRICMRNFSQP<br>HGLAHHLKTHTGSQKPFQCRICMRNFSQSAHLKRHLRTHTGEKPFQCRICMRNF<br>SVGNSLSRHLKTHLRGS |
| 52 | mRNA0019 | SRPGERPFQCRICMRNFSRTDTLARHLRTHTGEKPFQCRICMRNFSRTDSLPRH<br>LKTHTGGGGSQKPFQCRICMRNFSDHSSLKRHLRTHTGEKPFQCRICMRNFSQP<br>HGLRHHLKTHTGSQKPFQCRICMRNFSQSAHLKRHLRTHTGEKPFQCRICMRNF<br>SVGNSLSRHLKTHLRGS |
| 53 | mRNA0020 | SRPGERPFQCRICMRNFSRTDTLARHLRTHTGEKPFQCRICMRNFSRLDMLARH<br>LKTHTGGGGSQKPFQCRICMRNFSDHSSLKRHLRTHTGEKPFQCRICMRNFSQP<br>HGLSTHLKTHTGSQKPFQCRICMRNFSQQAHLVRHTRTHTGEKPFQCRICMRNF<br>SVHESLKRHLRTHLRGS |
| 54 | mRNA0021 | SRPGERPFQCRICMRNFSRADNLGRHLRTHTGEKPFQCRICMRNFSRNTHLSYH<br>LKTHTGSQKPFQCRICMRNFSRGDGLRRHLRTHTGEKPFQCRICMRNFSRRDNL<br>NRHLKTHTGSQKPFQCRICMRNFSRARNLTLHTRTHTGEKPFQCRICMRNFSDP<br>SSLKRHLRTHLRGS |
| 55 | mRNA0022 | SRPGERPFQCRICMRNFSRADNLGRHLRTHTGEKPFQCRICMRNFSRNTHLSYH<br>LKTHTGSQKPFQCRICMRNFSRKLGLLRHTRTHTGEKPFQCRICMRNFSRQDNL<br>GRHLRTHTGSQKPFQCRICMRNFSRARNLTLHTRTHTGEKPFQCRICMRNFSDP<br>SSLKRHLRTHLRGS |
| 56 | mRNA0023 | SRPGERPFQCRICMRNFSRADNLGRHLRTHTGEKPFQCRICMRNFSRNTHLSYH<br>LKTHTGSQKPFQCRICMRNFSRKLGLLRHTRTHTGEKPFQCRICMRNFSRQDNL<br>GRHLRTHTGSQKPFQCRICMRNFSRRRNLQLHTRTHTGEKPFQCRICMRNFSDH<br>SSLKRHLRTHLRGS |
| 57 | mRNA0024 | SRPGERPFQCRICMRNFSQQSSLLRHTRTHTGEKPFQCRICMRNFSRREHLVRH<br>LRTHTGSQKPFQCRICMRNFSGLTALRTHTRTHTGEKPFQCRICMRNFSERAKL<br>IRHLRTHTGGGGSQKPFQCRICMRNFSAKRDLDRHTRTHTGEKPFQCRICMRNF<br>SVNSSLTRHLRTHLRGS |
| 58 | mRNA0025 | SRPGERPFQCRICMRNFSQQSSLLRHTRTHTGEKPFQCRICMRNFSRREHLVRH<br>LRTHTGSQKPFQCRICMRNFSGLTALRTHTRTHTGEKPFQCRICMRNFSERAKL<br>IRHLRTHTGGGGSQKPFQCRICMRNFSLRKDLVRHTRTHTGEKPFQCRICMRNF<br>SVRHSLTRHLRTHLRGS |
| 59 | mRNA0026 | SRPGERPFQCRICMRNFSQASALSRHTRTHTGEKPFQCRICMRNFSRREHLVRH<br>LRTHTGSQKPFQCRICMRNFSGLTALRTHTRTHTGEKPFQCRICMRNFSERAKL<br>IRHLRTHTGGGGSQKPFQCRICMRNFSAKRDLDRHTRTHTGEKPFQCRICMRNF<br>SVNSSLTRHLRTHLRGS |
| 60 | mRNA0061 | SRPGERPFQCRICMRNFSRGRNLEMHTRTHTGEKPFQCRICMRNFSDSSVLRRH<br>LRTHTGGGGSQKPFQCRICMRNFSQNANLKRHTRTHTGEKPFQCRICMRNFSQK<br>HHLAVHLRTHTGSQKPFQCRICMRNFSQRSNLARHLRTHTGEKPFQCRICMRNF<br>SQKVHLEAHLKTHLRGS |

TABLE 18-continued

Sequence listing.

| SEQ | Description | Sequence |
|---|---|---|
| 61 | mRNA0027 | SRPGERPFQCRICMRNFSRRRNLDVHTRTHTGEKPFQCRICMRNFSDSSVLRRH<br>LRTHTGGGGSQKPFQCRICMRNFSQNANLKRHTRTHTGEKPFQCRICMRNFSQK<br>HHLAVHLRTHTGSQKPFQCRICMRNFSQRSNLARHLRTHTGEKPFQCRICMRNF<br>SQKVHLEAHLKTHLRGS |
| 62 | mRNA0065 | SRPGERPFQCRICMRNFSRGRNLAIHTRTHTGEKPFQCRICMRNFSDSSVLRRH<br>LRTHTGGGGSQKPFQCRICMRNFSLKSNLHRHTRTHTGEKPFQCRICMRNFSLK<br>QHLVVHLRTHTGSQKPFQCRICMRNFSLKTNLARHTRTHTGEKPFQCRICMRNF<br>SQKCHLKAHLRTHLRGS |
| 63 | mRNA0028 | SRPGERPFQCRICMRNFSDGSNLRRHLRTHTGEKPFQCRICMRNFSRIDNLDGH<br>LKTHTGSQKPFQCRICMRNFSQRRYLVEHTRTHTGEKPFQCRICMRNFSQQTNL<br>ARHLRTHTGGGGSQKPFQCRICMRNFSQRSDLTRHLRTHTGEKPFQCRICMRNF<br>SRGDNLNRHLKTHLRGS |
| 64 | mRNA0029 | SRPGERPFQCRICMRNFSDPSNLQRHLRTHTGEKPFQCRICMRNFSRRDNLPKH<br>LKTHTGSQKPFQCRICMRNFSTTFNLRVHTRTHTGEKPFQCRICMRNFSQTQNL<br>TRHLRTHTGGGGSQKPFQCRICMRNFSHKETLNRHLRTHTGEKPFQCRICMRNF<br>SREDNLGRHLKTHLRGS |
| 65 | mRNA0030 | SRPGERPFQCRICMRNFSDPSNLQRHLRTHTGEKPFQCRICMRNFSRRDNLPKH<br>LKTHTGSQKPFQCRICMRNFSQRRYLVEHTRTHTGEKPFQCRICMRNFSQQTNL<br>ARHLRTHTGGGGSQKPFQCRICMRNFSQRSDLTRHLRTHTGEKPFQCRICMRNF<br>SRGDNLNRHLKTHLRGS |
| 66 | mRNA0031 | SRPGERPFQCRICMRNFSQQTNLTRHLRTHTGEKPFQCRICMRNFSANRTLVHH<br>LKTHTGSQKPFQCRICMRNFSEEANLRRHTRTHTGEKPFQCRICMRNFSRGEHL<br>TRHLRTHTGSQKPFQCRICMRNFSTNSSLTRHLRTHTGEKPFQCRICMRNFSRI<br>DNLIRHLKTHLRGS |
| 67 | mRNA0032 | SRPGERPFQCRICMRNFSQQTNLTRHLRTHTGEKPFQCRICMRNFSANRTLVHH<br>LKTHTGSQKPFQCRICMRNFSEEANLRRHTRTHTGEKPFQCRICMRNFSRREHL<br>VRHLRTHTGSQKPFQCRICMRNFSMTSSLRRHTRTHTGEKPFQCRICMRNFSRQ<br>DNLGRHLRTHLRGS |
| 68 | mRNA0033 | SRPGERPFQCRICMRNFSQQTNLTRHLRTHTGEKPFQCRICMRNFSANRTLVHH<br>LKTHTGSQKPFQCRICMRNFSEEANLRRHTRTHTGEKPFQCRICMRNFSRGEHL<br>TRHLRTHTGSQKPFQCRICMRNFSMTSSLRRHTRTHTGEKPFQCRICMRNFSRQ<br>DNLGRHLRTHLRGS |
| 69 | mRNA0034 | SRPGERPFQCRICMRNFSRATHLTRHTRTHTGEKPFQCRICMRNFSRADVLKGH<br>LRTHTGSQKPFQCRICMRNFSQRSSLVRHLRTHTGEKPFQCRICMRNFSRKDAL<br>HVHLKTHTGSQKPFQCRICMRNFSVHHNLVRHLRTHTGEKPFQCRICMRNFSIS<br>HNLARHLKTHLRGS |
| 70 | mRNA0035 | SRPGERPFQCRICMRNFSRATHLTRHTRTHTGEKPFQCRICMRNFSRADVLKGH<br>LRTHTGSQKPFQCRICMRNFSQSSSLVRHLRTHTGEKPFQCRICMRNFSRKERL<br>ATHLKTHTGSQKPFQCRICMRNFSVRHNLTRHLRTHTGEKPFQCRICMRNFSIS<br>HNLARHLKTHLRGS |
| 71 | mRNA0036 | SRPGERPFQCRICMRNFSKKDHLHRHTRTHTGEKPFQCRICMRNFSRKESLTVH<br>LRTHTGSQKPFQCRICMRNFSQSSSLVRHLRTHTGEKPFQCRICMRNFSRKERL<br>ATHLKTHTGSQKPFQCRICMRNFSVHHNLVRHLRTHTGEKPFQCRICMRNFSIS<br>HNLARHLKTHLRGS |
| 72 | mRNA0037 | SRPGERPFQCRICMRNFSRVDHLHRHLRTHTGEKPFQCRICMRNFSRREHLSGH<br>LKTHTGGGGSQKPFQCRICMRNFSQSSSLVRHLRTHTGEKPFQCRICMRNFSRK<br>ERLATHLKTHTGSQKPFQCRICMRNFSVAHNLTRHLRTHTGEKPFQCRICMRNF<br>SISHNLARHLKTHLRGS |
| 73 | mRNA0038 | SRPGERPFQCRICMRNFSRKHHLGRHTRTHTGEKPFQCRICMRNFSRREHLTIH<br>LRTHTGGGGSQKPFQCRICMRNFSQSSSLVRHLRTHTGEKPFQCRICMRNFSRK<br>ERLATHLKTHTGSQKPFQCRICMRNFSVAHNLTRHLRTHTGEKPFQCRICMRNF<br>SISHNLARHLKTHLRGS |
| 74 | mRNA0039 | SRPGERPFQCRICMRNFSRVDHLHRHLRTHTGEKPFQCRICMRNFSRSDHLSLH<br>LKTHTGGGGSQKPFQCRICMRNFSQSSSLVRHLRTHTGEKPFQCRICMRNFSRK<br>ERLATHLKTHTGSQKPFQCRICMRNFSVAHNLTRHLRTHTGEKPFQCRICMRNF<br>SISHNLARHLKTHLRGS |
| 75 | mRNA0040 | SRPGERPFQCRICMRNFSKTDHLARHTRTHTGEKPFQCRICMRNFSQKEILTRH<br>LRTHTGSQKPFQCRICMRNFSQSAHLKRHLRTHTGEKPFQCRICMRNFSETGSL<br>RRHLKTHTGSQKPFQCRICMRNFSQSSSLVRHLRTHTGEKPFQCRICMRNFSQT<br>NTLGRHLKTHLRGS |

TABLE 18-continued

Sequence listing.

| SEQ | Description | Sequence |
|---|---|---|
| 76 | mRNA0041 | SRPGERPFQCRICMRNFSKKDHLHRHTRTHTGEKPFQCRICMRNFSQKEILTRH<br>LRTHTGSQKPFQCRICMRNFSQSAHLKRHLRTHTGEKPFQCRICMRNFSETGSL<br>RRHLKTHTGSQKPFQCRICMRNFSQSSSLVRHLRTHTGEKPFQCRICMRNFSQG<br>GTLRRHLKTHLRGS |
| 77 | mRNA0042 | SRPGERPFQCRICMRNFSKKDHLHRHTRTHTGEKPFQCRICMRNFSQKEILTRH<br>LRTHTGSQKPFQCRICMRNFSQSAHLKRHLRTHTGEKPFQCRICMRNFSDPTSL<br>NRHLKTHTGSQKPFQCRICMRNFSQSSSLVRHLRTHTGEKPFQCRICMRNFSQT<br>NTLGRHLKTHLRGS |
| 78 | mRNA0043 | SRPGERPFQCRICMRNFSQQTNLTRHLRTHTGEKPFQCRICMRNFSVGGNLARH<br>LKTHTGSQKPFQCRICMRNFSKRYNLYQHTRTHTGEKPFQCRICMRNFSRQDNL<br>NTHLRTHTGSQKPFQCRICMRNFSRSHNLKLHTRTHTGEKPFQCRICMRNFSQS<br>TTLKRHLRTHLRGS |
| 79 | mRNA0044 | SRPGERPFQCRICMRNFSQQTNLTRHLRTHTGEKPFQCRICMRNFSVGGNLSRH<br>LKTHTGSQKPFQCRICMRNFSKRYNLYQHTRTHTGEKPFQCRICMRNFSRQDNL<br>NTHLRTHTGSQKPFQCRICMRNFSRSHNLRLHTRTHTGEKPFQCRICMRNFSQS<br>TTLKRHLRTHLRGS |
| 80 | mRNA0045 | SRPGERPFQCRICMRNFSQQTNLTRHLRTHTGEKPFQCRICMRNFSVGGNLSRH<br>LKTHTGSQKPFQCRICMRNFSKKENLLQHTRTHTGEKPFQCRICMRNFSRRDNL<br>KSHLRTHTGSQKPFQCRICMRNFSRSHNLKLHTRTHTGEKPFQCRICMRNFSQS<br>TTLKRHLRTHLRGS |
| 81 | mRNA0046 | SRPGERPFQCRICMRNFSDKSSLRKHTRTHTGEKPFQCRICMRNFSDHSSLKRH<br>LRTHTGSQKPFQCRICMRNFSRNFILQRHTRTHTGEKPFQCRICMRNFSRNDTL<br>IIHLRTHTGGGGSQKPFQCRICMRNFSTSTLLKRHTRTHTGEKPFQCRICMRNF<br>SLKEHLTRHLRTHLRGS |
| 82 | mRNA0047 | SRPGERPFQCRICMRNFSCNGSLKKHTRTHTGEKPFQCRICMRNFSDHSSLKRH<br>LRTHTGSQKPFQCRICMRNFSRNFILARHTRTHTGEKPFQCRICMRNFSRQDIL<br>VVHLRTHTGGGGSQKPFQCRICMRNFSHKSSLTRHLRTHTGEKPFQCRICMRNF<br>SESGHLKRHLKTHLRGS |
| 83 | mRNA0048 | SRPGERPFQCRICMRNFSCNGSLKKHTRTHTGEKPFQCRICMRNFSDHSSLKRH<br>LRTHTGSQKPFQCRICMRNFSRNFILARHTRTHTGEKPFQCRICMRNFSRQDIL<br>VVHLRTHTGGGGSQKPFQCRICMRNFSTSTLLKRHTRTHTGEKPFQCRICMRNF<br>SLKEHLTRHLRTHLRGS |
| 84 | mRNA0049 | SRPGERPFQCRICMRNFSTNNNLARHTRTHTGEKPFQCRICMRNFSRTDSLTLH<br>LRTHTGSQKPFQCRICMRNFSQREHLTTHLRTHTGEKPFQCRICMRNFSRRDNL<br>NRHLKTHTGSQKPFQCRICMRNFSRRQKLTIHTRTHTGEKPFQCRICMRNFSHK<br>SSLTRHLRTHLRGS |
| 85 | mRNA0050 | SRPGERPFQCRICMRNFSTNNNLARHTRTHTGEKPFQCRICMRNFSRTDSLTLH<br>LRTHTGSQKPFQCRICMRNFSQREHLTTHLRTHTGEKPFQCRICMRNFSRGDNL<br>KRHLKTHTGSQKPFQCRICMRNFSRRQKLTIHTRTHTGEKPFQCRICMRNFSHK<br>SSLTRHLRTHLRGS |
| 86 | mRNA0066 | SRPGERPFQCRICMRNFSTNNNLARHTRTHTGEKPFQCRICMRNFSRTDSLTLH<br>LRTHTGSQKPFQCRICMRNFSQREHLNGHLRTHTGEKPFQCRICMRNFSRGDNL<br>ARHLKTHTGSQKPFQCRICMRNFSRRQKLTIHTRTHTGEKPFQCRICMRNFSHK<br>SSLTRHLRTHLRGS |
| 87 | mRNA0051 | SRPGERPFQCRICMRNFSQQTNLTRHLRTHTGEKPFQCRICMRNFSANRTLVHH<br>LKTHTGSQKPFQCRICMRNFSDPANLRRHTRTHTGEKPFQCRICMRNFSRQEHL<br>VRHLRTHTGGGGSQKPFQCRICMRNFSMKHHLGRHLRTHTGEKPFQCRICMRNF<br>SQNSHLRRHLKTHLRGS |
| 88 | mRNA0052 | SRPGERPFQCRICMRNFSQQTNLTRHLRTHTGEKPFQCRICMRNFSANRTLVHH<br>LKTHTGSQKPFQCRICMRNFSEEANLRRHTRTHTGEKPFQCRICMRNFSRREHL<br>VRHLRTHTGGGGSQKPFQCRICMRNFSMKHHLGRHLRTHTGEKPFQCRICMRNF<br>SQNSHLRRHLKTHLRGS |
| 89 | mRNA0067 | SRPGERPFQCRICMRNFSQQTNLTRHLRTHTGEKPFQCRICMRNFSANRTLVHH<br>LKTHTGSQKPFQCRICMRNFSDPANLRRHTRTHTGEKPFQCRICMRNFSRQEHL<br>VRHLRTHTGGGGSQKPFQCRICMRNFSLKQHLVRHLRTHTGEKPFQCRICMRNF<br>SQGGHLARHLKTHLRGS |
| 90 | mRNA0068 | SRPGERPFQCRICMRNFSRNTHLARHTRTHTGEKPFQCRICMRNFSRADVLKGH<br>LRTHTGSQKPFQCRICMRNFSQRSSLVRHLRTHTGEKPFQCRICMRNFSRKDAL<br>HVHLKTHTGGGGSQKPFQCRICMRNFSQNEHLKVHLRTHTGEKPFQCRICMRNF<br>SQNSHLRRHLKTHLRGS |

TABLE 18-continued

| Sequence listing. | | |
|---|---|---|
| SEQ | Description | Sequence |
| 91 | mRNA0053 | SRPGERPFQCRICMRNFSRNTHLARHTRTHTGEKPFQCRICMRNFSRADVLKGH LRTHTGSQKPFQCRICMRNFSQSSSLVRHLRTHTGEKPFQCRICMRNFSRKERL ATHLKTHTGGGGSQKPFQCRICMRNFSQKTHLAVHLRTHTGEKPFQCRICMRNF SQGGHLKRHLKTHLRGS |
| 92 | mRNA0054 | SRPGERPFQCRICMRNFSRNTHLARHTRTHTGEKPFQCRICMRNFSRADVLKGH LRTHTGSQKPFQCRICMRNFSQSSSLVRHLRTHTGEKPFQCRICMRNFSRKERL ATHLKTHTGGGGSQKPFQCRICMRNFSQKTHLAVHLRTHTGEKPFQCRICMRNE SQNSHLRRHLKTHLRGS |
| 93 | mRNA0055 | SRPGERPFQCRICMRNFSHKSSLTRHLRTHTGEKPFQCRICMRNFSESGHLKRH LKTHTGSQKPFQCRICMRNFSRRRNLTLHTRTHTGEKPFQCRICMRNFSDRSSL KRHLRTHTGSQKPFQCRICMRNFSQPHSLAVHLRTHTGEKPFQCRICMRNFSQK PHLSRHLKTHLRGS |
| 94 | mRNA0056 | SRPGERPFQCRICMRNFSHKSSLTRHLRTHTGEKPFQCRICMRNFSEGGHLKRH LKTHTGSQKPFQCRICMRNFSRRRNLQLHTRTHTGEKPFQCRICMRNFSDHSSL KRHLRTHTGSQKPFQCRICMRNFSRRQHLQYHTRTHTGEKPFQCRICMRNFSQS AHLKRHLRTHLRGS |
| 95 | mRNA0057 | SRPGERPFQCRICMRNFSHKSSLTRHLRTHTGEKPFQCRICMRNFSEGGHLKRH LKTHTGSQKPFQCRICMRNFSRRRNLTLHTRTHTGEKPFQCRICMRNFSDRSSL KRHLRTHTGSQKPFQCRICMRNFSRRQHLQYHTRTHTGEKPFQCRICMRNFSQS AHLKRHLRTHLRGS |
| 96 | mRNA0058 | SRPGERPFQCRICMRNFSGHTALRNHTRTHTGEKPFQCRICMRNFSQSGTLHRH LRTHTGGGGSQKPFQCRICMRNFSDHSSLKRHLRTHTGEKPFQCRICMRNFSAM RSLMGHLKTHTGSQKPFQCRICMRNFSRRSRLVRHTRTHTGEKPFQCRICMRNF SRGEHLTRHLRTHLRGS |
| 97 | mRNA0059 | SRPGERPFQCRICMRNFSGHTALRNHTRTHTGEKPFQCRICMRNFSQSTTLKRH LRTHTGGGGSQKPFQCRICMRNFSDHSSLKRHLRTHTGEKPFQCRICMRNFSQQ RSLVGHLKTHTGSQKPFQCRICMRNFSEAHHLSRHLRTHTGEKPFQCRICMRNF SRTEHLARHLKTHLRGS |
| 98 | mRNA0060 | SRPGERPFQCRICMRNFSGHTALRNHTRTHTGEKPFQCRICMRNFSQSTTLKRH LRTHTGGGGSQKPFQCRICMRNFSDHSSLKRHLRTHTGEKPFQCRICMRNFSAM RSLMGHLKTHTGSQKPFQCRICMRNFSRQSRLQRHTRTHTGEKPFQCRICMRNF SRREHLVRHLRTHLRGS |
| 99 | mRNA0062 | SRPGERPFQCRICMRNFSQGETLKRHLRTHTGEKPFQCRICMRNFSRADNLRRH LKTHTGSQKPFQCRICMRNFSDKANLTRHLRTHTGEKPFQCRICMRNFSDQGNL IRHLKTHTGGGGSQKPFQCRICMRNFSHRHVLINHTRTHTGEKPFQCRICMRNF STNSSLTRHLRTHLRGS |
| 100 | mRNA0063 | SRPGERPFQCRICMRNFSQGETLKRHLRTHTGEKPFQCRICMRNFSRADNLRRH LKTHTGSQKPFQCRICMRNFSDSSNLRRHLRTHTGEKPFQCRICMRNFSDQGNL IRHLKTHTGGGGSQKPFQCRICMRNFSHKSSLTRHLRTHTGEKPFQCRICMRNE SIRTSLKRHLKTHLRGS |
| 101 | mRNA0069 | SRPGERPFQCRICMRNFSQGETLKRHLRTHTGEKPFQCRICMRNFSRADNLRRH LKTHTGSQKPFQCRICMRNFSEQGNLLRHLRTHTGEKPFQCRICMRNFSDGGNL GRHLKTHTGGGGSQKPFQCRICMRNFSHRHVLINHTRTHTGEKPFQCRICMRNF STNSSLTRHLRTHLRGS |
| 102 | HBV target sequence | GATGAGGCATAGCAGCAG |
| 103 | HBV target sequence | GATGATTAGGCAGAGGTG |
| 104 | HBV target sequence | GGATTCAGCGCCGACGGG |
| 105 | HBV target sequence | GGCAGTAGTCGGAACAGGG |
| 106 | HBV target sequence | GTAAACTGAGCCAGGAGAA |
| 107 | HBV target sequence | ACGGTGGTCTCCATGCGAC |
| 108 | HBV target sequence | GCTGGATGTGTCTGCGGCG |

TABLE 18-continued

Sequence listing.

| SEQ | Description | Sequence |
|---|---|---|
| 109 | HBV target sequence | GTCTGCGAGGCGAGGGAG |
| 110 | HBV target sequence | GTTGCCGGGCAACGGGGTA |
| 111 | HBV target sequence | CGAGAAAGTGAAAGCCTGC |
| 112 | HBV target sequence | GAGGCTTGAACAGTAGGAC |
| 113 | HBV target sequence | GAGGTTGGGGACTGCGAA |
| 114 | HBV target sequence | GATGATGTGGTATTGGGG |
| 115 | HBV target sequence | GATGATGTGGTATTGGGGG |
| 116 | HBV target sequence | GCAGTAGTCGGAACAGGG |
| 117 | HBV target sequence | GCATAGCAGCAGGATGAA |
| 118 | HBV target sequence | GGCGTTCACGGTGGTCTCC |
| 119 | HBV target sequence | GTTGGTGAGTGATTGGAG |
| 120 | HBV target sequence | GGAGGTTGGGGACTGCGAA |
| 121 | HBV target sequence | GGATGATGTGGTATTGGGG |
| 122 | HBV target sequence | GGATGTGTCTGCGGCGTT |
| 123 | HBV target sequence | GGGGGTTGCGTCAGCAAAC |
| 124 | HBV target sequence | GTTGTTAGACGACGAGGCA |
| 125 | F1 | KKENLLQ |
| 126 | F1 | RRHILDR |
| 127 | F1 | RREVLEN |
| 128 | F1 | RRAVLDR |
| 129 | F1 | RQEHLVR |
| 130 | F1 | RREHLVR |
| 131 | F1 | KKDHLHR |
| 132 | F1 | KTDHLAR |
| 133 | F1 | QAGNLVR |
| 134 | F1 | QRGNLQR |
| 135 | F1 | DRGNLTR |
| 136 | F1 | RTDTLAR |
| 137 | F1 | RADNLGR |
| 138 | F1 | QQSSLLR |

TABLE 18-continued

Sequence listing.

| SEQ | Description | Sequence |
|---|---|---|
| 139 | F1 | QASALSR |
| 140 | F1 | RGRNLEM |
| 141 | F1 | RRRNLDV |
| 142 | F1 | RGRNLAI |
| 143 | F1 | DGSNLRR |
| 144 | F1 | DPSNLQR |
| 145 | F1 | QQTNLTR |
| 146 | F1 | RATHLTR |
| 147 | F1 | RVDHLHR |
| 148 | F1 | RKHHLGR |
| 149 | F1 | DKSSLRK |
| 150 | F1 | CNGSLKK |
| 151 | F1 | TNNNLAR |
| 152 | F1 | RNTHLAR |
| 153 | F1 | HKSSLTR |
| 154 | F1 | GHTALRN |
| 155 | F1 | QGETLKR |
| 156 | F2 | RQDNLNS |
| 157 | F2 | RKDYLIS |
| 158 | F2 | RQDNLGR |
| 159 | F2 | RRDNLNR |
| 160 | F2 | EGGNLMR |
| 161 | F2 | DPSNLQR |
| 162 | F2 | DMGNLGR |
| 163 | F2 | QKEILTR |
| 164 | F2 | QNSHLRR |
| 165 | F2 | QTTHLSR |
| 166 | F2 | QARSLRA |
| 167 | F2 | RTDSLPR |
| 168 | F2 | RLDMLAR |
| 169 | F2 | RNTHLSY |
| 170 | F2 | RREHLVR |
| 171 | F2 | DSSVLRR |
| 172 | F2 | RIDNLDG |
| 173 | F2 | RRDNLPK |
| 174 | F2 | ANRTLVH |
| 175 | F2 | RADVLKG |
| 176 | F2 | RKESLTV |

TABLE 18-continued

| SEQ | Description | Sequence |
|---|---|---|
| 177 | F2 | RREHLSG |
| 178 | F2 | RREHLTI |
| 179 | F2 | RSDHLSL |
| 180 | F2 | VGGNLAR |
| 181 | F2 | VGGNLSR |
| 182 | F2 | DHSSLKR |
| 183 | F2 | RTDSLTL |
| 184 | F2 | ESGHLKR |
| 185 | F2 | EGGHLKR |
| 186 | F2 | QSGTLHR |
| 187 | F2 | QSTTLKR |
| 188 | F2 | RADNLRR |
| 189 | F3 | RSHNLKL |
| 190 | F3 | RSHNLRL |
| 191 | F3 | QSTTLKR |
| 192 | F3 | SDRRDLD |
| 193 | F3 | QSAHLKR |
| 194 | F3 | DLSTLRR |
| 195 | F3 | DGSTLRR |
| 196 | F3 | EKASLIK |
| 197 | F3 | DKSSLRK |
| 198 | F3 | CNGSLKK |
| 199 | F3 | DHSSLKR |
| 200 | F3 | RGDGLRR |
| 201 | F3 | RKLGLLR |
| 202 | F3 | GLTALRT |
| 203 | F3 | QNANLKR |
| 204 | F3 | LKSNLHR |
| 205 | F3 | QRRYLVE |
| 206 | F3 | TTFNLRV |
| 207 | F3 | EEANLRR |
| 208 | F3 | QRSSLVR |
| 209 | F3 | QSSSLVR |
| 210 | F3 | KRYNLYQ |
| 211 | F3 | KKENLLQ |
| 212 | F3 | RNFILQR |
| 213 | F3 | RNFILAR |
| 214 | F3 | QREHLTT |

US 12,649,003 B2

225                                                                                          226

TABLE 18-continued

Sequence listing.

| SEQ | Description | Sequence |
|-----|-------------|----------|
| 215 | F3 | QREHLNG |
| 216 | F3 | DPANLRR |
| 217 | F3 | RRRNLTL |
| 218 | F3 | RRRNLQL |
| 219 | F3 | DKANLTR |
| 220 | F3 | DSSNLRR |
| 221 | F3 | EQGNLLR |
| 222 | F4 | QSTTLKR |
| 223 | F4 | RRDGLAG |
| 224 | F4 | SFQSYLE |
| 225 | F4 | ETGSLRR |
| 226 | F4 | DRTPLNR |
| 227 | F4 | QNEHLKV |
| 228 | F4 | QKTHLAV |
| 229 | F4 | DHSSLKR |
| 230 | F4 | QPHGLAH |
| 231 | F4 | QPHGLRH |
| 232 | F4 | QPHGLST |
| 233 | F4 | RRDNLNR |
| 234 | F4 | RQDNLGR |
| 235 | F4 | ERAKLIR |
| 236 | F4 | QKHHLAV |
| 237 | F4 | LKQHLVV |
| 238 | F4 | QQTNLAR |
| 239 | F4 | QTQNLTR |
| 240 | F4 | RGEHLTR |
| 241 | F4 | RREHLVR |
| 242 | F4 | RKDALHV |
| 243 | F4 | RKERLAT |
| 244 | F4 | DPTSLNR |
| 245 | F4 | RQDNLNT |
| 246 | F4 | RRDNLKS |
| 247 | F4 | RNDTLII |
| 248 | F4 | RQDILVV |
| 249 | F4 | RGDNLKR |
| 250 | F4 | RGDNLAR |
| 251 | F4 | RQEHLVR |
| 252 | F4 | DRSSLKR |

TABLE 18-continued

| Sequence listing. | | |
| --- | --- | --- |
| SEQ | Description | Sequence |
| 253 | F4 | AMRSLMG |
| 254 | F4 | QQRSLVG |
| 255 | F4 | DQGNLIR |
| 256 | F4 | DGGNLGR |
| 257 | F5 | RNTNLTR |
| 258 | F5 | RQDNLGR |
| 259 | F5 | VHHNLVR |
| 260 | F5 | RPNHLAI |
| 261 | F5 | QSHSLKS |
| 262 | F5 | QKHHLVT |
| 263 | F5 | GGTALRM |
| 264 | F5 | GGSALSM |
| 265 | F5 | RRFILSR |
| 266 | F5 | RNFILQR |
| 267 | F5 | QSAHLKR |
| 268 | F5 | QQAHLVR |
| 269 | F5 | RARNLTL |
| 270 | F5 | RRRNLQL |
| 271 | F5 | AKRDLDR |
| 272 | F5 | LRKDLVR |
| 273 | F5 | QRSNLAR |
| 274 | F5 | LKTNLAR |
| 275 | F5 | QRSDLTR |
| 276 | F5 | HKETLNR |
| 277 | F5 | TNSSLTR |
| 278 | F5 | MTSSLRR |
| 279 | F5 | VRHNLTR |
| 280 | F5 | VAHNLTR |
| 281 | F5 | QSSSLVR |
| 282 | F5 | RSHNLKL |
| 283 | F5 | RSHNLRL |
| 284 | F5 | TSTLLKR |
| 285 | F5 | HKSSLTR |
| 286 | F5 | RRQKLTI |
| 287 | F5 | MKHHLGR |
| 288 | F5 | LKQHLVR |
| 289 | F5 | QNEHLKV |
| 290 | F5 | QKTHLAV |

TABLE 18-continued

| SEQ | Description | Sequence |
|---|---|---|
| 291 | F5 | QPHSLAV |
| 292 | F5 | RRQHLQY |
| 293 | F5 | RRSRLVR |
| 294 | F5 | EAHHLSR |
| 295 | F5 | RQSRLQR |
| 296 | F5 | HRHVLIN |
| 297 | F6 | IKHNLAR |
| 298 | F6 | VVNNLNR |
| 299 | F6 | ISHNLAR |
| 300 | F6 | QSPHLKR |
| 301 | F6 | ESGHLKR |
| 302 | F6 | ENSKLRR |
| 303 | F6 | QRSSLVR |
| 304 | F6 | RNDSLKC |
| 305 | F6 | RNDTLII |
| 306 | F6 | VGNSLSR |
| 307 | F6 | VHESLKR |
| 308 | F6 | DPSSLKR |
| 309 | F6 | DHSSLKR |
| 310 | F6 | VNSSLTR |
| 311 | F6 | VRHSLTR |
| 312 | F6 | QKVHLEA |
| 313 | F6 | QKCHLKA |
| 314 | F6 | RGDNLNR |
| 315 | F6 | REDNLGR |
| 316 | F6 | RIDNLIR |
| 317 | F6 | RQDNLGR |
| 318 | F6 | QTNTLGR |
| 319 | F6 | QGGTLRR |
| 320 | F6 | QSTTLKR |
| 321 | F6 | LKEHLTR |
| 322 | F6 | HKSSLTR |
| 323 | F6 | QNSHLRR |
| 324 | F6 | QGGHLAR |
| 325 | F6 | QGGHLKR |
| 326 | F6 | QKPHLSR |
| 327 | F6 | QSAHLKR |
| 328 | F6 | RGEHLTR |

TABLE 18-continued

| | Sequence listing. | |
|---|---|---|
| SEQ | Description | Sequence |
| 329 | F6 | RTEHLAR |
| 330 | F6 | RREHLVR |
| 331 | F6 | TNSSLTR |
| 332 | F6 | IRTSLKR |
| 327 | F6 | QSAHLKR |
| 328 | F6 | RGEHLTR |
| 329 | F6 | RTEHLAR |
| 330 | F6 | RREHLVR |
| 331 | F6 | TNSSLTR |
| 332 | F6 | IRTSLKR |
| 495 | ZIM3 | MNNSQGRVTFEDVTVNFTQGEWQRLNPEQRNLYRDVMLENYSNLVSVGQGETTK PDVILRLEQGKEPWLEEEEVLGSGRAEKNGDIGGQIWKPKDVKESL |
| 496 | ZNF436 | MAATLLMAGSQAPVTFEDMAMYLTREEWRPLDAAQRDLYRDVMQENYGNVVSLD FEIRSENEVNPKQEISEDVQFGTTSERPAENAEENPESEEGFESGDRSERQW |
| 497 | ZNF257 | MLENYRNLVFLGIAVSKPDLITCLEQGKEPCNMKRHEMVAKPPVMCSHIAEDLC PERDIKYFFQKVILRRYDKCEHENLQLRKGCKSVDECKVCK |
| 498 | ZNF675 | MGLLTFRDVAIEFSLEEWQCLDTAQRNLYKNVILENYRNLVFLGIAVSKQDLIT CLEQEKEPLTVKRHEMVNEPPVMCSHFAQEFWPEQNIKDSF |
| 499 | ZNF490 | MLQMQNSEHHGQSIKTQTDSISLEDVAVNFTLEEWALLDPGQRNIYRDVMRATF KNLACIGEKWKDQDIEDEHKNQGRNLRSPMVEALCENKEDCPCGKSTSQIPDLN TNLETPTG |
| 500 | ZNF320 | MALSQGLLTFRDVAIEFSQEEWKCLDPAQRTLYRDVMLENYRNLVSLDISSKCM MNTLSSTGQGNTEVIHTGTLQRQASYHIGAFCSQEIEKDIHDFVFQ |
| 501 | ZNF331 | MAQGLVTFADVAIDFSQEEWACLNSAQRDLYWDVMLENYSNLVSLDLESAYENK SLPTKKNIHEIRASKRNSDRRSKSLGRNWICEGTLERPQRSRGR |
| 502 | ZNF816 | MLREEATKKSKEKEPGMALPQGRLTFRDVAIEFSLEEWKCLNPAQRALYRAVML ENYRNLEFVDSSLKSMMEFSSTRHSITGEVIHTGTLQRHKSHHIGDFCFPEMKK DIHHFEFQWQ |
| 503 | ZNF680 | MPGPPGSLEMGPLTFRDVAIEFSLEEWQCLDTAQRNLYRKVMFENYRNLVELGI AVSKPHLITCLEQGKEPWNRKRQEMVAKPPVIYSHFTEDLWPEHSIKDSF |
| 504 | ZNF41 | MSPPWSPALAAEGRGSSCEASVSFEDVTVDFSKEEWQHLDPAQRRLYWDVTLEN YSHLLSVGYQIPKSEAAFKLEQGEGPWMLEGEAPHQSCSGEAIGKMQQQGIPGG IFFHC |
| 505 | ZNF189 | MASPSPPPESKEEWDYLDPAQRSLYKDVMMENYGNLVSLDVLNRDKDEEPTVKQ EIEEIEEEVEPQGVIVTRIKSEIDQDPMGRETFELVGRLDKQRGIFLWEIPRES L |
| 506 | ZNF528 | MALTQGPLKFMDVAIEFSQEEWKCLDPAQRTLYRDVMLENYRNLVSLGICLPDL SVTSMLEQKRDPWTLQSEEKIANDPDGRECIKGVNTERSSKLGSN |
| 507 | ZNF543 | MAASAQVSVTFEDVAVTFTQEEWGQLDAAQRTLYQEVMLETCGLLMSLGCPLFK PELIYQLDHRQELWMATKDLSQSSYPGDNTKPKTTEPTFSHLALPE |
| 508 | ZNF554 | MFSQEERMAAGYLPRWSQELVTFEDVSMDFSQEEWELLEPAQKNLYREVMLENY RNVVSLEALKNQCTDVGIKEGPLSPAQTSQVTSLSSWTGYLLFQPVASSHLEQR EALWIEEKGTPQASCSDWMTVLRNQDSTYKKVALQE |
| 509 | ZNF140 | MSQGSVTFRDVAIDFSQEEWKWLQPAQRDLYRCVMLENYGHLVSLGLSISKPDV VSLLEQGKEPWLGKREVKRDLFSVSESSGEIKDFSPKNVIYDD |
| 510 | ZNF610 | MEEAQKRKAKESGMALPQGRLTFMDVAIEFSQEEWKSLDPGQRALYRDVMLENY RNLVFLGRSCVLGSNAENKPIKNQLGLTLESHLSELQLFQAGRKIYRSNQVEKF TNHR |
| 511 | ZNF264 | MAAAVLTDRAQVSVTFDDVAVTFTKEEWGQLDLAQRTLYQEVMLENCGLLVSLG CPVPKAELICHLEHGQEPWTRKEDLSQDTCPGDKGKPKTTEPTTCEPALSE |

TABLE 18-continued

Sequence listing.

| SEQ | Description | Sequence |
|---|---|---|
| 512 | ZNF350 | MIQAQESITLEDVAVDFTWEEWQLLGAAQKDLYRDVMLENYSNLVAVGYQASKP<br>DALFKLEQGEQLWTIEDGIHSGACSDIWKVDHVLERLQSESLVNR |
| 513 | ZNF8 | MEGVAGVMSVGPPAARLQEPVTFRDVAVDFTQEEWGQLDPTQRILYRDVMLETE<br>GHLLSIGPELPKPEVISQLEQGTELWVAERGTTQGCHPAWEPRSESQASRKEEG<br>LPEE |
| 514 | ZNF582 | MSLGSELFRDVAIVFSQEEWQWLAPAQRDLYRDVMLETYSNLVSLGLAVSKPDV<br>ISFLEQGKEPWMVERVVSGGLCPVLESRYDTKELFPKQHVYEV |
| 515 | ZNF30 | MAHKYVGLQYHGSVTFEDVAIAFSQQEWESLDSSQRGLYRDVMLENYRNLVSMA<br>GHSRSKPHVIALLEQWKEPEVTVRKDGRRWCTDLQLEDDTIGCKEMPTSEN |
| 516 | ZNF324 | MAFEDVAVYFSQEEWGLLDTAQRALYRRVMLDNFALVASLGLSTSRPRVVIQLE<br>RGEEPWVPSGTDTTLSRTTYRRRNPGSWSLTEDRDVSG |
| 517 | ZNF98 | MLENYRNLVFVGIAASKPDLITCLEQGKEPWNVKRHEMVTEPPVVYSYFAQDLW<br>PKQGKKNYFQKVILRTYKKCGRENLQLRKYCKSMDECKVHKECYNGLNQC |
| 518 | ZNF669 | MHFRRPDPCREPLASPIQDSVAFEDVAVNFTQEEWALLDSSQKNLYREVMQETC<br>RNLASVGSQWKDQNIEDHFEKPGKDIRNHIVQRLCESKEDGQYGEVVSQIPNLD<br>LNENISTGLKPCECSICGK |
| 519 | ZNF677 | MALSQGLFTFKDVAIEFSQEEWECLDPAQRALYRDVMLENYRNLLSLDEDNIPP<br>EDDISVGFTSKGLSPKENNKEELYHLVILERKESHGINNFDLKEVWENMPKFDS<br>LW |
| 520 | ZNF596 | MTFEDIIVDFTQEEWALLDTSQRKLFQDVMLENISHLVSIGKQLCKSVVLSQLE<br>QVEKLSTQRISLLQGREVGIKHQEIPFIHHIYQKGTSTISTMRS |
| 521 | ZNF214 | MAVTFEDVTIIFTWEEWKFLDSSQKRLYREVMWENYTNVMSVENWNESYKSQEE<br>KFRYLEYENFSYWQGWWNAGAQMYENQNYGETVQGTDSKDLTQQDRSQC |
| 522 | ZNF37A | MITSQGSVSFRDVTVGFTQEEWQHLDPAQRTLYRDVMLENYSHLVSVGYCIPKP<br>EVILKLEKGEEPWILEEKFPSQSHLELINTSRNYSIMKENEENKG |
| 523 | ZNF34 | MFEDVAVYLSREEWGRLGPAQRGLYRDVMLETYGNLVSLGVGPAGPKPGVISQL<br>ERGDEPWVLDVQGTSGKEHLRVNSPALGTRTEYKELTSQETFGEEDPQGSEPVE<br>ACDHIS |
| 524 | ZNF250 | METYGNVVSLGLPGSKPDIISQLERGEDPWVLDRKGAKKSQGLWSDYSDNLKYD<br>HTTACTQQDSLSCPWECETKGESQNTDLSPKPLISEQTVILGKTPLGRIDQENN<br>ETKQ |
| 525 | ZNF547 | MAEMNPAQGHVVFEDVAIYFSQEEWGHLDEAQRLLYRDVMLENLALLSSLGCCH<br>GAEDEEAPLEPGVSVGVSQVMAPKPCLSTQNTQPCETCSSLLKDILRL |
| 526 | ZNF273 | MLDNYRNLVFLGIAVSKPDLITCLEQGKEPCNMKRHAMVAKPPVVCSHFAQDLW<br>PKQGLKDS |
| 527 | ZNF354A | MAAGQREARPQVSLTFEDVAVLFTRDEWRKLAPSQRNLYRDVMLENYRNLVSLG<br>LPFTKPKVISLLQQGEDPWEVEKDGSGVSSLGSKSSHKTTKSTQTQDSSFQ |
| 528 | ZFP82 | MALRSVMFSDVSIDFSPEEWEYLDLEQKDLYRDVMLENYSNLVSLGCFISKPDV<br>ISSLEQGKEPWKVVRKGRRQYPDLETKYETKKLSLENDIYEIN |
| 529 | ZNF224 | MTTFKEAMTFKDVAVVFTEEELGLLDLAQRKLYRDVMLENFRNLLSVGHQAFHR<br>DTFHFLREEKIWMMKTAIQREGNSGDKIQTEMETVSEAGTHQEW |
| 530 | ZNF33A | MFQVEQKSQESVSFKDVTVGFTQEEWQHLDPSQRALYRDVMLENYSNLVSVGYC<br>VHKPEVIFRLQQGEEPWKQEEEFPSQSFPEVWTADHLKERSQENQSKHL |
| 531 | ZNF45 | MTKSKEAVTFKDVAVVFSEEELQLLDLAQRKLYRDVMLENFRNVVSVGHQSTPD<br>GLPQLEREEKLWMMKMATQRDNSSGAKNLKEMETLQEVGLRYLP |
| 532 | ZNF175 | MSQKPQVLGPEKQDGSCEASVSFEDVTVDFSREEWQQLDPAQRCLYRDVMLELY<br>SHLFAVGYHIPNPEVIFRMLKEKEPRVEEAEVSHQRCQEREFGLEIPQKEISKK<br>ASFQ |
| 533 | ZNF595 | MELVTFRDVAIEFSPEEWKCLDPAQQNLYRDVMLENYRNLVSLGFVISNPDLVT<br>CLEQIKEPCNLKIHETAAKPPAICSPFSQDLSPVQGIEDSF |
| 534 | ZNF184 | MSTLLQGGHNLLSSASFQESVTFKDVIVDFTQEEWKQLDPGQRDLFRDVTLENY<br>THLVSIGLQVSKPDVISQLEQGTEPWIMEPSIPVGTCADWETRLENSVSAPEPD<br>ISEE |

TABLE 18-continued

Sequence listing.

| SEQ | Description | Sequence |
|---|---|---|
| 535 | ZNF419 | MDPAQVPVAADLLTDHEEGYVTFEDVAVYFSQEEWRLLDDAQRLLYRNVMLENF<br>TLLASLGLASSKTHEITQLESWEEPFMPAWEVVTSAIPRGCWHGAEAEEAPEQI<br>ASVG |
| 536 | ZFP28-1 | MKKLEAVGTGIEPKAMSQGLVTFGDVAVDFSQEEWEWINPIQRNLYRKVMLENY<br>RNLASLGLCVSKPDVISSLEQGKEPWTVKRKMTRAWCPDLKAVWKIKELPLKKD<br>FCEG |
| 537 | ZFP28-2 | MSLLGEHWDYDALFETQPGLVTIKNLAVDFRQQLHPAQKNFCKNGIWENNSDLG<br>SAGHCVAKPDLVSLLEQEKEPWMVKRELTGSLFSGQRSVHETQELFPKQDSYAE |
| 538 | ZNF18 | MLALAASQPARLEERLIRDRDLGASLLPAAPQEQWRQLDSTQKEQYWDLILETY<br>GKMVSGAGISHPKSDLTNSIEFGEELAGIYLHVNEKIPRPTCIGDRQENDKENL<br>NLENH |
| 539 | ZNF213 | MEGRPGETTDTCFVSGVHGPVALGDIPFYFSREEWGTLDPAQRDLFWDIKRENS<br>RNTTLGFGLKGQSEKSLLQEMVPVVPGQTGSDVTVSWSPEEAEAWESENRPRAA<br>LGPVVGARRGRPPTRRRQFRDLA |
| 540 | ZNF394 | MVAVVRALQRALDGTSSQGMVTFEDTAVSLTWEEWERLDPARRDFCRESAQKDS<br>GSTVPPSLESRVENKELIPMQQILEEAEPQGGQLQEAFQGKRPLFSKCGSTHEDR<br>VEKQSGDP |
| 541 | ZFP1 | MNKSQGSVSFTDVTVDFTQEEWEQLDPSQRILYMDVMLENYSNLLSVEVWKADD<br>QMERDHRNPDEQARQFLILKNQTPIEERGDLFGKALNLNTDFVSLRQVPYKYDL<br>YEKTL |
| 542 | ZFP14 | MAHGSVTFRDVAIDFSQEEWEFLDPAQRDLYRDVMWENYSNFISLGPSISKPDV<br>ITLLDEERKEPGMVVREGTRRYCPDLESRYRTNTLSPEKDIYEIYSFQWDIMER |
| 543 | ZNF416 | MAAAVLRDSTSVPVTAEAKLMGFTQGCVTFEDVAIYFSQEEWGLLDEAQRLLYR<br>DVMLENFALITALVCWHGMEDEETPEQSVSVEGVPQVRTPEASPSTQKIQSCDM<br>CVPFLTDILHLTDLPGQELYLTGACAVFHQDQK |
| 544 | ZNF557 | MLPPTAASQREGHTEGGELVNELLKSWLKGLVTFEDVAVEFTQEEWALLDPAQR<br>TLYRDVMLENCRNLASLGNQVDKPRLISQLEQEDKVMTEERGILSGTCPDVENP<br>FKAKGLTPKLHVFRKEQSRNMKMER |
| 545 | ZNF566 | MAQESVMFSDVSVDFSQEEWECLNDDQRDLYRDVMLENYSNLVSMGHSISKPNV<br>ISYLEQGKEPWLADRELTRGQWPVLESRCETKKLFLKKEIYEIESTQWEIMEK |
| 546 | ZNF729 | MPGAPGSLEMGPLTFRDVTIEFSLEEWQCLDTVQQNLYRDVMLENYRNLVFLGM<br>AVFKPDLITCLKQGKEPWNMKRHEMVTKPPVMRSHFTQDLWPDQSTKDSFQEVI<br>LRTYAR |
| 547 | ZIM2 | MAGSQFPDFKHLGTFLVFEELVTFEDVLVDFSPEELSSLSAAQRNLYREVMLEN<br>YRNLVSLGHQFSKPDIISRLEEEESYAMETDSRHTVICQGE |
| 548 | ZNF254 | MPGPPRSLEMGLLTFRDVAIEFSLEEWQHLDIAQQNLYRNVMLENYRNLAFLGI<br>AVSKPDLITCLEQGKEPWNMKRHE |
| 549 | ZNF764 | MAPPLAPLPPRDPNGAGPEWREPGAVSFADVAVYFCREEWGCLRPAQRALYRDV<br>MRETYGHLSALGIGGNKPALISWVEEEAELWGPAAQDPE |
| 550 | ZNF785 | MGPPLAPRPAHVPGEAGPRRTRESRPGAVSFADVAVYFSPEEWECLRPAQRALY<br>RDVMRETFGHLGALGFSVPKPAFISWVEGEVEAWSPEAQDPDGESS |
| 551 | ZNF10 (KOX1) | MDAKSLTAWSRTLVTFKDVFVDFTREEWKLLDTAQQIVYRNVMLENYKNLVSLG<br>YQLTKPDVILRLEKGEEPWLVEREIHQETHPDSETAFEIKSSVSSRSIFKDKQS<br>CDIKMEGMARNDLWYLSLEEVWKCRDQLDKYQENPERHLRQVAPTQKKVLTQER<br>VSESGKYGGNCLLPAQLVLREYFHKRDSHTKSLKHDLVLNGHQDSCASNSNECG<br>QTFCQNIHLIQFARTHTGDKSYKCPDNDNSLTHGSSLGISKGIHREKPYECKEC<br>GKFFSWRSNLTRHQLIHTGEKPYECKECGKSFSRSSHLIGHQKTHTGEEPYECK<br>ECGKSFSWFSHLVTHQRTHTGDKLYTCNQCGKSFVHSSRLIRHQRTHTGEKPYE<br>CPECGKSFRQSTHLILHQRTHVRVRPYECNECGKSYSQRSHLVVHHRIHTGLKP<br>FECKDCGKCFSRSSHLYSHQRTHTGEKPYECHDCGKSFSQSSALIVHQRIHTGE<br>KPYECCQCGKAFIRKNDLIKHQRIHVGEETYKCNQCGIIFSQNSPFIVHQIAHT<br>GEQFLTCNQCGTALVNTSNLIGYQTNHIRENAY |
| 552 | CBX5<br>(chromoshadow<br>domain) | MGKKTKRTADSSSSEDEEYVVEKVLDRRVVKGQVEYLLKWKGFSEEHNTWEPE<br>KNLDCPELISEFMKKYKKMKEGENNKPREKSESNKRKSNFSNSADDIKSKKKRE<br>QSNDIARGFERGLEPEKIIGATDSCGDLMFLMKWKDTDEADLVLAKEANVKCPQ<br>IVIAFYEERLTWHAYPEDAENKEKETAKS |

TABLE 18-continued

Sequence listing.

| SEQ | Description | Sequence |
|---|---|---|
| 553 | RYBP (YAF2_RYBP component of PRC1) | MTMGDKKSPTRPKRQAKPAADEGFWDCSVCTFRNSAEAFKCSICDVRKGTSTRK PRINSQLVAQQVAQQYATPPPPKKEKKEKVEKQDKEKPEKDKEISPSVTKKNTN KKTKPKSDILKDPPSEANSIQSANATTKTSETNHTSRPRLKNVDRSTAQQLAVT VGNVTVIITDFKEKTRSSSTSSSTVTSSAGSEQQNQSSSGSESTDKGSSRSSTP KGDMSAVNDESF |
| 554 | YAF2 (YAF2_RYBP component of PRC1) | MGDKKSPTRPKRQPKPSSDEGYWDCSVCTFRNSAEAFKCMMCDVRKGTSTRKPR PVSQLVAQQVTQQFVPPTQSKKEKKDKVEKEKSEKETTSKKNSHKKTRPRLKNV DRSSAQHLEVTVGDLTVIITDFKEKTKSPPASSAASADQHSQSGSSSDNTERGM SRSSSPRGEASSLNGESH |
| 555 | MGA (component of PRC1.6) | MEEKQQIILANQDGGTVAGAAPTFFVILKQPGNGKTDQGILVTNQDACALASSV SSPVKSKGKICLPADCTVGGITVTLDNNSMWNEFYHRSTEMILTKQGRRMFPYC RYWITGLDSNLKYILVMDISPVDNHRYKWNGRWWEPSGKAEPHVLGRVFIHPES PSTGHYWMHQPVSFYKLKLTNNTLDQEGHIILHSMHRYLPRLHLVPAEKAVEVI QLNGPGVHTFTFPQTEFFAVTAYQNIQITQLKIDYNPFAKGERDDGLNNKPQRD GKQKNSSDQEGNNISSSSGHRVRLTEGQGSEIQPGDLDPLSRGHETSGKGLEKT SLNIKRDFLGFMDTDSALSEVPQLKQEISECLIASSFEDDSRVASPLDQNGSEN VVIKEEPLDDYDYELGECPEGVTVKQEETDEETDVYSNSDDDPILEKQLKRHNK VDNPEADHLSSKWLPSSPSGVAKAKMFKLDTGKMPVVYLEPCAVTRSTVKISEL PDNMLSTSRKDKSSMLAELEYLPTYIENSNETAFCLGKESENGLRKHSPDLRVV QKYPLLKEPQWKYPDISDSISTERILDDSKDSVGDSLSGKEDLGRKRTTMLKIA TAAKVVNANQNASPNVPGKRGRPRKLKLCKAGRPPKNTGKSLISTKNTPVSPGS TFPDVKPDLEDVDGVLFVSFESKEALDIHAVDGTTEESSSLQASTTNDSGYRAR ISQLEKELIEDLKTLRHKQVIHPGLQEVGLKLNSVDPTMSIDLKYLGVQLPLAP ATSFPFWNLTGTNPASPDAGFPFVSRTGKTNDFTKIKGWRGKFHSASASRNEGG NSESSLKNRSAFCSDKLDEYLENEGKLMETSMGFSSNAPTSPVVYQLPTKSTSY VRTLDSVLKKQSTISPSTSYSLKPHSVPPVSRKAKSQNRQATFSGRTKSSYKSI LPYPVSPKQKYSHVILGDKVTKNSSGIISENQANNFVVPTLDENIFPKQISLRQ AQQQQQQQGSRPPGLSKSQVKLMDLEDCALWEGKPRTYITEERADVSLTTLLT AQASLKTKPIHTIIRKRAPPCNNDFCRLGCVCSSLALEKRQPAHCRRPDCMFGC TCLKRKVVLVKGGSKTKHFQRKAAHRDPVFYDTLGEEAREEEEGIREEEEQLKE KKKRKKLEYTICETEPEQPVRHYPLWVKVEGEVDPEPVYIPTPSVIEPMKPLLL PQPEVLSPTVKGKLLTGIKSPRSYTPKPNPVIREEDKDPVYLYFESMMTCARVR VYERKKEDQRQPSSSSSPSPSFQQQTSCHSSPENHNNAKEPDSEQQPLKQLTCD LEDDSDKLQEKSWKSSCNEGESSSTSYMHQRSPGGPTKLIEIISDCNWEEDRNK ILSILSQHINSNMPQSLKVGSFIIELASQRKSRGEKNPPVYSSRVKISMPSCQD QDDMAEKSGSETPDGPLSPGKMEDISPVQTDALDSVRERLHGGKGLPFYAGLSP AGKLVAYKRKPSSSTSGLIQVASNAKVAASRKPRTLLPSTSNSKMASSSGTATN RPGKNLKAFVPAKRPIAARPSPGGVFTQFVMSKVGALQQKIPGVSTPQTLAGTQ KFSIRPSPVMVVTPVVSSEPVQVCSPVTAAVTTTTPQVFLENTTAVTPMTAISD VETKETTYSSGATTTGVVEVSETNTSTSVTSTQSTATVNLTKTTGITTPVASVA FPKSLVASPSTITLPVASTASTSLVVVTAAASSSMVTTPTSSLGSVPIILSGIN GSPPVSQRPENAAQIPVATPQVSPNTVKRAGPRLLLIPVQQGSPTLRPVSNTQL QGHRMVLQPVRSPSGMNLFRHPNGQIVQLLPLHQLRGSNTQPNLQPVMERNPGS VMGIRLPAPSKPSETPPSSTSSSAFSVMNPVIQAVGSSSAVNVITQAPSLLSSG ASFVSQAGTLTLRISPPEPQSFASKTGSETKITYSSGGQPVGTASLIPLQSGSF ALLQLPGGQKPVPSSILQHVASLQMKRESQNPDQKDETNSIKREQETKKVLQSEG EAVDPEANVIKQNSGAATSEETLNDSLEDRGDHLDEECLPEEGCATVKPSEHSC ITGSHTDQDYKDVNEEYGARNRKSSKEKVAVLEVRTISEKASNKTVQNLSKVQH QKLGDVKVEQQKGFDNPEENSSEFPVTFKEESKFELSGSKVMEQQSNLQPEAKE KECGDSLEKDRERWRKHLKGPLTRKCVGASQECKKEADEQLIKETKTCQENSDV FQQEQGISDLLGKSGITEDARVLKTECDSWSRISNPSAFSIVPRRAAKSSRGNG HFQGHLLLPGEQIQPKQEKKGGRSSADFTVLDLEEDDEDDNEKTDDSIDEIVDV VSDYQSEEVDDVEKNNCVEYIEDDEEHVDIETVEELSEEINVAHLKTTAAHTQS FKQPSCTHISADEKAAERSRKAPPIPLKLKPDYWSDKLQKEAEAFAYYRRTHTA NERRRRGEMRDLFEKLKITLGLLHSSKVSKSLILTRAFSEIQGLTDQADKLIGQ KNLLTRKRNILIRKVSSLSGKTEEVVLKKLEYIYAKQQALEAQKRKKKMGSDEF DISPRISKQQEGSSASSVDLGQMFINNRRGKPLILSRKKDQATENTSPLNTPHT SANLVMTPQGQLLTLKGPLFSGPVVAVSPDLLESDLKPQVAGSAVALPENDDLF MMPRIVNVTSLATEGGLVDMGGSKYPHEVPDSKPSDHLKDTVRNEDNSLEDKGR ISSRGNRDGRVTLGPTQVFLANKDSGYPQIVDVSNMQKAQEFLPKKISGDMRGI QYKWKESESRGERVKSKDSSFHKLKMKDLKDSSIEMELRKVTSAIEEAALDSSE LLTNMEDEDDTDETLTSLLNEIAFLNQQLNDDSVGLAELPSSMDTEFPGDARRA FISKVPPGSRATFQVEHLGTGLKELPDVQGESDSISPLLLHLEDDDFSENEKQL AEPASEPDVLKIVIDSEIKDSLLSNKKAIDGGKNTSGLPAEPESVSSPPTLHMK TGLENSNSTDTLWRPMPKLAPLGLKVANPSSDADGQSLKVMPCLAPIAAKVGSV GHKMNLTGNDQEGRESKVMPTLAPVVAKLGNSGASPSSAGK |
| 556 | CBX1 (chromoshadow) | MGKKQNKKKVEEVLEEEEEYVVEKVLDRRVVKGKVEYLLKWKGFSDEDNTWEP EENLDCPDLIAEFLQSQKTAHETDKSEGGKRKADSDSEDKGEESKPKKKKEESE KPRGFARGLEPERIIGATDSSGELMFLMKWKNSDEADLVPAKEANVKCPQVVIS FYEERLTWHSYPSEDDDKKDDKN |

TABLE 18-continued

Sequence listing.

| SEQ | Description | Sequence |
|---|---|---|
| 557 | SCMH1 (SAM_1/SPM) | MLVCYSVLACEILWDLPCSIMGSPLGHFTWDKYLKETCSVPAPVHCFKQSYTPP<br>SNEFKISMKLEAQDPRNTTSTCIATVVGLTGARLRLRLDGSDNKNDFWRLVDSA<br>EIQPIGNCEKNGGMLQPPLGFRLNASSWPMFLLKTLNGAEMAPIRIFHKEPPSP<br>SHNFFKMGMKLEAVDRKNPHFICPATIGEVRGSEVLVTFDGWRGAFDYWCRFDS<br>RDIFPVGWCSLTGDNLQPPGTKVVIPKNPYPASDVNTEKPSIHSSTKTVLEHQP<br>GQRGRKPGKKRGRTPKTLISHPISAPSKTAEPLKFPKKRGPKPGSKRKPRTLLN<br>PPPASPTTSTPEPDTSTVPQDAATIPSSAMQAPTVCIYLNKNGSTGPHLDKKKV<br>QQLPDHFGPARASVVLQQAVQACIDCAYHQKTVFSFLKQGHGGEVISAVEDREQ<br>HTLNLPAVNSITYVLRFLEKLCHNLRSDNLFGNQPFTQTHLSLTAIEYSHSHDR<br>YLPGETFVLGNSLARSLEPHSDSMDSASNPTNLVSTSQRHRPLLSSCGLPPSTA<br>SAVRRLCSRGVLKGSNERRDMESFWKLNRSPGSDRYLESRDASRLSGRDPSSWT<br>VEDVMQFVREADPQLGPHADLFRKHEIDGKALLLLRSDMMMKYMGLKLGPALKL<br>SYHIDRLKQGKF |
| 558 | MPP8 (Chromodomain) | MEQVAEGARVTAVPVSAADSTEELAEVEEGVGVVGEDNDAAARGAEAFGDSEED<br>GEDVFEVEKILDMKTEGGKVLYKVRWKGYTSDDDTWEPEIHLEDCKEVLLEFRK<br>KIAENKAKAVRKDIQRLSLNNDIFEANSDSDQQSETKEDTSPKKKKKKLRQREE<br>KSPDDLKKKKAKAGKLKDKSKPDLESSLESLVEDLRTKKRISEAKEELKESKKP<br>KKDEVKETKELKKVKKGEIRDLKTKTREDPKENRKTKKEKFVESQVESESSVLN<br>DSPPFPEDDSEGLHSDSREEKQNTKSARERAGQDMGLEHGFEKPLDSAMSAEEDT<br>DVRGRRKKKTPRKAEDTRENRKLENKNAFLEKKTVPKKQRNQDRSKSAAELEKL<br>MPVSAQTPKGRRLSGEERGLWSTDSAEEDKETKRNESKEKYQKRHDSDKEEKGR<br>KEPKGLKTLKEIRNAFDLFKLTPEEKNDVSENNRKREEIPLDFKTIDDHKTKEN<br>KQSLKERRNTRDETDTWAYIAAEGDQEVLDSVCQADENSDGRQQILSLGMDLQL<br>EWMKLEDFQKHLDGKDENFAATDAIPSNVLRDAVKNGDYITVKVALNSNEEYNL<br>DQEDSSGMTLVMLAAAGGQDDLLRLLITKGAKVNGRQKNGTTALIHAAEKNELT<br>TVAILLEAGAFVNVQQSNGETALMKACKRGNSDIVRLVIECGADCNILSKHQNS<br>ALHFAKQSNNVLVYDLLKNHLETLSRVAEETIKDYFEARLALLEPVFPIACHRL<br>CEGPDFSTDFNYKPPQNIPEGSGILLFIFHANFLGKEVIARLCGPCSVQAVVLN<br>DKFQLPVFLDSHFVYSFSPVAGPNKLFIRLTEAPSAKVKLLIGAYRVQLQ |
| 559 | SUMO3 (Rad60-SLD) | MSEEKPKEGVKTENDHINLKVAGQDGSVVQFKIKRHTPLSKLMKAYCERQGLSM<br>RQIRFRFDGQPINETDTPAQLEMEDEDTIDVFQQQTGGVPESSLAGHSF |
| 560 | HERC2 (Cyt-b5) | MPSESFCLAAQARLDSKWLKTDIQLAFTRDGLCGLWNEMVKDGEIVYTGTESTQ<br>NGELPPPRKDDSVEPSGTKKEDLNDKEKKDEEETPAPIYRAKSILDSWVWGKQPD<br>VNELKECLSVLVKEQQALAVQSATTTLSALRLKQRLVILERYFIALNRTVFQEN<br>VKVKWKSSGISLPPVDKKSSRPAGKGVEGLARVGSRAALSFAFAFLRRAWRSGE<br>DADLCSELLQESLDALRALPEASLFDESTVSSVWLEVVERATRFLRSVVTGDVH<br>GTPATKGPGSIPLQDQHLALAILLELAVQRGTLSQMLSAILLLLQLWDSGAQET<br>DNERSAQGTSAPLLPLLQRFQSIICRKDAPHSEGDMHLLSGPLSPNESFLRYLT<br>LPQDNELAIDLRQTAVVVMAHLDRLATPCMPPLCSSPTSHKGSLQEVIGWGLIG<br>WKYYANVIGPIQCEGLANLGVTQIACAEKRFLILSRNGRVYTQAYNSDTLAPQL<br>VQGLASRNIVKIAAHSDGHHYLALAATGEVYSWGCGDGGRLGHGDTVPLEEPKV<br>ISAFSGKQAGKHVVHIACGSTYSAAITAEGELYTWGRGNYGRLGHGSSEDEAIP<br>MLVAGLKGLKVIDVACGSGDAQTLAVTENGQVWSWGDGDYGKLGRGGSDGCKTP<br>KLIEKLQDLDVVKVRCGSQFSIALTKDGQVYSWGKGDNQRLGHGTEEHVRYPKL<br>LEGLQGKKVIDVAAGSTHCLALTEDSEVHSWGSNDQCHFDTLRVTKPEPAALP<br>GLDTKHIVGIACGPAQSFAWSSCSEWSIGLRVPFVVDICSMTFEQLDLLLRQVS<br>EGMDGSADWPPPQEKECVAVATLNLLRLQLHAAISHQVDPEFLGLGLGSILLNS<br>LKQTVVTLASSAGVLSTVQSAAQAVLQSGWSVLLPTAEERARALSALLPCAVSG<br>NEVNISPGRRFMIDLLVGSLMADGGLESALHAAITAEIQDIEAKKEAQKEKEID<br>EQEANASTFHRSRTPLDKDLINTGICESSGKQCLPLVQLIQQLLRNIASQTVAR<br>LKDVARRISSCLDFEQHSRERSASLDLLLRFQRLLISKLYPGESIGQTSDISSP<br>ELMGVGSLLKKYTALLCTHIGDILPVAASIASTSWRHFAEVAYIVEGDFTGVLL<br>PELVVSIVLLLSKNAGLMQEAGAVPLLGGLLEHLDRENHLAPGKERDDHEELAW<br>PGIMESFFTGQNCRNNEEVTLIRKADLENHNKDGGFWTVIDGKVYDIKDFQTQS<br>LTGNSILAQFAGEDPVVALEAALQFEDTRESMHAFCVGQYLEPDQEIVTIPDLG<br>SLSSPLIDTERNLGLLLGLHASYLAMSTPLSPVEIECAKWLQSSIFSGGLQTSQ<br>IHYSYNEEKDEDHCSSPGGTPASKSRLCSHRRALGDHSQAFLQAIADNNIQDHN<br>VKDFLCQIERYCRQCHLTTPIMFPPEHPVEEVGRLLLCCLLKHEDLGHVALSLV<br>HAGALGIEQVKHRTLPKSVVDVCRVVYQAKCSLIKTHQEQGRSYKEVCAPVIER<br>LRFLFNELRPAVCNDLSIMSKFKLLSSLPRWRRIAQKIIRERRKKRVPKKPEST<br>DDEEKIGNEESDLEEACILPHSPINVDKRPIAIKSPKDKWQPLLSTVTGVHKYK<br>WLKQNVQGLYPQSPLLSTIAEFALKEEPVDVEKMRKCLLKQLERAEVRLEGIDT<br>ILKLASKNFLLPSVQYAMFCGWQRLIPEGIDIGEPLTDCLKDVDLIPPENRMLL<br>EVTFGKLYAWAVQNIRNVLMDASAKFKELGIQPVPLQTITNENPSGPSLGTIPQ<br>ARFLLVMLSMLTLQHGANNLDLLLNSGMLALTQTALRLIGPSCDNVEEDMNASA<br>QGASATVLEETRKETAPVQLPVSGPELAAMMKIGTRVMRGVDWKWGDQDGPPPG<br>LGRVIGELGEDGWIRVQWDTGSTNSYRMGKEGKYDLKLAELPAAAQPSAEDSDT<br>EDDSEAEQTERNIHPTAMMFTSTINLLQTLCLSAGVHAEIMQSEATKTLCGLLR<br>MLVESGTTDKTSSPNRLVYREQHRSWCTLGFVRSIALTPQVCGALSSPQWITLL<br>MKVVEGHAPFTATSLQRQILAVHLLQAVLPSWDKTERARDMKCLVEKLFDFLGS<br>LLTTCSSDVPLLRESTLRRRRVRPQASLTATHSSTLAEEVVALLRTLHSLTQWN<br>GLINKYINSQLRSITHSFVGRPSEGAQLEDYFPDSENPEVGGLMAVLAVIGGID<br>GRLRLGGQVMHDEFGEGTVTRITPKGKITVQFSDMRTCRVCPLNQLKPLPAVAF |

TABLE 18-continued

Sequence listing.

| SEQ | Description | Sequence |
|-----|-------------|----------|
| | | NVNNLPFTEPMLSVWAQLVNLAGSKLEKHKIKKSTKQAFAGQVDLDLLRCQQLK<br>LYILKAGRALLSHQDKLRQILSQPAVQETGTVHTDDGAVVSPDLGDMSPEGPQP<br>PMILLQQLLASATQPSPVKAIFDKQELEAAALAVCQCLAVESTHPSSPGFEDCS<br>SSEATTPVAVQHIRPARVKRRKQSPVPALPIVVQLMEMGESRRNIEFALKSLTG<br>ASGNASSLPGVEALVGWLLDHSDIQVTELSDADTVSDEYSDEEVVEDVDDAAYS<br>MSTGAVVTESQTYKKRADFLSNDDYAVYVRENIQVGMMVRCCRAYEEVCEGDVG<br>KVIKLDRDGLHDLNVQCDWQQKGGTYWVRYIHVELIGYPPPSSSSHIKIGDKVR<br>VKASVTTPKYKWGSVTHQSVGVVKAFSANGKDIIVDFPQQSHWTGLLSEMELVP<br>SIHPGVTCDGCQMFPINGSRFKCRNCDDFDFCETCFKTKKHNTRHTFGRINEPG<br>QSAVFCGRSGKQLKRCHSSQPGMLLDSWSRMVKSLNVSSSVNQASRLIDGSEPC<br>WQSSGSQGKHWIRLEIFPDVLVHRLKMIVDPADSSYMPSLVVVSGGNSLNNLIE<br>LKTININPSDTTVPLLNDCTEYHRYIEIAIKQCRSSGIDCKIHGLILLGRIRAE<br>EEDLAAVPPLASDNEEEEDEKGNSGSLIRKKAAGLESAATIRTKVFVWGLNDKD<br>QLGGLKGSKIKVPSFSETLSALNVVQVAGGSKSLFAVTVEGKVYACGEATNGRL<br>GLGISSGTVPIPRQITALSSYVVKKVAVHSGGRHATALTVDGKVFSWGEGDDGK<br>LGHFSRMNCDKPRLIEALKTKRIRDIACGSSHSAALTSSGELYTWGLGEYGRLG<br>HGDNTTQLKPKMVKVLLGHRVIQVACGSRDAQTLALTDEGLVFSWGDGDFGKLG<br>RGGSEGCNIPQNIERLNGQGVCQIECGAQFSLALTKSGVVWTWGKGDYFRLGHG<br>SDVHVRKPQVVEGLRGKKIVHVAVGALHCLAVTDSGQVYAWGDNDHGQQGNGTT<br>TVNRKPTLVQGLEGQKITRVACGSSHSVAWTTVDVATPSVHEPVLFQTARDPLG<br>ASYLGVPSDADSSAASNKISGASNSKPNRPSLAKILLSLDGNLAKQQALSHILT<br>ALQIMYARDAVVGALMPAAMIAPVECPSFSSAAPSDASAMASPMNGEECMLAVD<br>IEDRLSPNPWQEKREIVSSEDAVTPSAVTPSAPSASARPFIPVTDDLGAASIIA<br>ETMTKTKEDVESQNKAAGPEPQALDEFTSLLIADDTRVVVDLLKLSVCSRAGDR<br>GRDVLSAVLSGMGTAYPQVADMLLELCVTELEDVATDSQSGRLSSQPVVVESSH<br>PYTDDTSTSGTVKIPGAEGLRVEFDRQCSTERRHDPLTVMDGVNRIVSVRSGRE<br>WSDWSSELRIPGDELKWKFISDGSVNGWGWRFTVYPIMPAAGPKELLSDRCVLS<br>CPSMDLVTCLLDERLNLASNRSIVPRLAASLAACAQLSALAASHRMWALQRLRK<br>LLTTEFGQSININRLLGENDGETRALSFTGSALAALVKGLPEALQRQFEYEDPI<br>VRGGKQLLHSPFFKVLVALACDLELDTLPCCAETHKWAWFRRYCMASRVAVALD<br>KRTPLPRLFLDEVAKKIRELMADSENMDVLHESHDIFKREQDEQLVQWMNRRPD<br>DWTLSAGGSGTIYGWGHNHRGQLGGIEGAKVKVPTPCEALATLRPVQLIGGEQT<br>LFAVTADGKLYATGYGAGGRLGIGGTESVSTPTLLESIQHVFIKKVAVNSGGKH<br>CLALSSEGEVYSWGEAEDGKLGHGNRSPCDRPRVIESLRGIEVVDVAAGGAHSA<br>CVTAAGDLYTWGKGRYGRLGHSDSEDQLKPKLVEALQGHRVVDIACGSGDAQTL<br>CLTDDDTVWSWGDGDYGKLGRGGSDGCKVPMKIDSLTGLGVVKVECGSQFSVAL<br>TKSGAVYTWGKGDYHRLGHGSDDHVRRPRQVQGLQGKKVIAIATGSLHCVCCTE<br>DGEVYTWGDNDEGQLGDGTTNAIQRPRLVAALQGKKVNRVACGSAHTLAWSTSK<br>PASAGKLPAQVPMEYNHLQEIPIIALRNRLLLLHHLSELFCPCIPMFDLEGSLD<br>ETGLGPSVGFDTLRGILISQGKEAAFRKVVQATMVRDRQHGPVVELNRIQVKRS<br>RSKGGLAGPDGTKSVFGQMCAKMSSFGPDSLLLPHRVWKVKFVGESVDDCGGGY<br>SESIAEICEELQNGLTPLLIVTPNGRDESGANRDCYLLSPAARAPVHSSMFREL<br>GVLLGIAIRTGSPLSLNLAEPVWKQLAGMSLTIADLSEVDKDFIPGLMYIRDNE<br>ATSEEFEAMSLPFTVPSASGQDIQLSSKHTHITLDNRAEYVRLAINYRLHEFDE<br>QVAAVREGMARVVPVPLLSLFTGYELETMVCGSPDIPLHLLKSVATYKGIEPSA<br>SLIQWFWEVMESESNTERSLFLRFVWGRTRLPRTIADERGRDFVIQVLDKYNPP<br>DHFLPESYTCFFLLKLPRYSCKQVLEEKLKYAIHFCKSIDTDDYARIALTGEPA<br>ADDSSDDSDNEDVDSFASDSTQDYLTGH |
| 561 | BIN1 (SH3_9) | MAEMGSKGVTAGKIASNVQKKLTRAQEKVLQKLGKADETKDEQFEQCVQNENKQ<br>LTEGTRLQKDLRTYLASVKAMHEASKKLNECLQEVYEPDWPGRDEANKIAENND<br>LLWMDYHQKLVDQALLTMDTYLGQFPDIKSRIAKRGRKLVDYDSARHHYESLQT<br>AKKKDEAKIAKPVSLLEKAAPQWCQGKLQAHLVAQTNLLRNQAEEELIKAQKVF<br>EEMNVDLQEELPSLWNSRVGFYVNTFQSIAGLEENFHKEMSKLNQNLNDVLVGL<br>EKQHGSNTFTVKAQPSDNAPAKGNKSPSPPDGSPAATPEIRVNHEPEPAGGATP<br>GATLPKSPSQLRKGPPVPPPPKHTPSKEVKQEQILSLFEDTFVPEISVTTPSQF<br>EAPGPFSEQASLLDLDFDPLPPVTSPVKAPTPSGQSIPWDLWEPTESPAGSLPS<br>GEPSAAEGTFAVSWPSQTAEPGPAQPAEASEVAGGTQPAAGAQEPGETAASEAA<br>SSSLPAVVVETFPATVNGTVEGGSGAGRLDLPPGFMFKVQAQHDYTATDTDELQ<br>LKAGDVVLVIPFQNPEEQDEGWLMGVKESDWNQHKELEKCRGVFPENFTERVP |
| 562 | PCGF2 (RING<br>finger protein<br>domain) | MHRTTRIKITELNPHLMCALCGGYFIDATTIVECLHSFCKTCIVRYLETNKYCP<br>MCDVQVHKTRPLLSIRSDKTLQDIVYKLVPGLFKDEMKRRRDFYAAYPLTEVPN<br>GSNEDRGEVLEQEKGALSDDEIVSLSIEFYEGARDRDEKKGPLENGDGDKEKTG<br>VRFLRCPAAMTVMHLAKFLRNKMDVPSKYKVEVLYEDEPLKEYYTLMDIAYIYP<br>WRRNGPLPLKYRVQPACKRLTLATVPTPSEGTNTSGASECESVSDKAPSPATLP<br>ATSSSLPSPATPSHGSPSSHGPPATHPTSPTPPSTASGATTAANGGSLNCLQTP<br>SSTSRGRKMTVNGAPVPPLT |
| 563 | TOX (HMG box) | MDVRFYPPPAQPAAAPDAPCLGPSPCLDPYYCNKFDGENMYMSMTEPSQDYVPA<br>SQSYPGPSLESEDFNIPPITPPSLPDHSLVHLNEVESGYHSLCHPMNHNGLLPF<br>HPQNMDLPEITVSNMLGQDGTLLSNSISVMPDIRNPEGTQYSSHPQMAAMRPRG<br>QPADIRQQPGMMPHGQLTTINQSQLSAQLGLNMGGSNVPHNSPSPPGSKSATPS<br>PSSSVHEDEGDDTSKINGGEKRPASDMGKKPKTPKKKKKKDPNEPQKPVSAYAL<br>FFRDTQAAIKGQNPNATFGEVSKIVASMWDGLGEEQKQVYKKKTEAAKKEYLKQ<br>LAAYRASLVSKSYSEPVDVKTSQPPQLINSKPSVFHGPSQAHSALYLSSHYHQQ |

TABLE 18-continued

Sequence listing.

| SEQ | Description | Sequence |
|---|---|---|
| | | PGMNPHLTAMHPSLPRNIAPKPNNQMPVTVSIANMAVSPPPPLQISPPLHQHLN<br>MQQHQPLTMQQPLGNQLPMQVQSALHSPTMQQGFTLQPDYQTIINPTSTAAQVV<br>TQAMEYVRSGCRNPPPQPVDWNNDYCSSGGMQRDKALYLT |
| 564 | FOXA1 (HNF3A C-terminal domain) | MLGTVKMEGHETSDWNSYYADTQEAYSSVPVSNMNSGLGSMNSMNTYMTMNTMT<br>TSGNMTPASFNMSYANPGLGAGLSPGAVAGMPGGSAGAMNSMTAAGVTAMGTAL<br>SPSGMGAMGAQQAASMNGLGPYAAAMNPCMSPMAYAPSNLGRSRAGGGGDAKTF<br>KRSYPHAKPPYSYISLITMAIQQAPSKMLTLSEIYQWIMDLFPYYRQNQQRWQN<br>SIRHSLSENDCFVKVARSPDKPGKGSYWTLHPDSGNMFENGCYLRRQKRFKCEK<br>QPGAGGGGGSGSGGSGAKGGPESRKDPSGASNPSADSPLHRGVHGKTGQLEGAP<br>APGPAASPQTLDHSGATATGGASELKTPASSTAPPISSGPGALASVPASHPAHG<br>LAPHESQLHLKGDPHYSENHPFSINNLMSSSEQQHKLDFKAYEQALQYSPYGST<br>LPASLPLGSASVTTRSPIEPSALEPAYYQGVYSRPVLNTS |
| 565 | FOXA2 (HNF3B C-terminal domain) | MLGAVKMEGHEPSDWSSYYAEPEGYSSVSNMNAGLGMNGMNTYMSMSAAAMGSG<br>SGNMSAGSMNMSSYVGAGMSPSLAGMSPGAGAMAGMGGSAGAAGVAGMGPHLSP<br>SLSPLGGQAAGAMGGLAPYANMNSMSPMYGQAGLSRARDPKTYRRSYTHAKPPY<br>SYISLITMAIQQSPNKMLTLSEIYQWIMDLFPFYRQNQQRWQNSIRHSLSENDC<br>FLKVPRSPDKPGKGSFWTLHPDSGNMFENGCYLRRQKRFKCEKQLALKEAAGAA<br>GSGKKAAAGAQASQAQLGEAAGPASETPAGTESPHSSASPCQEHKRGGLGELKG<br>TPAAALSPPEPAPSPGQQQQAAAHLLGPPHHPGLPPEAHLKPEHHYAFNHPFSI<br>NNLMSSEQQHHHSHHHHQPHKMDLKAYEQVMHYPGYGSPMPGSLAMGPVTNKTG<br>LDASPLAADTSYYQGVYSRPIMNSS |
| 566 | IRF2BP1 (IRF-2BP1_2 N-terminal domain) | MASVQASRRQWCYLCDLPKMPWAMVWDESEAVCRGCVNFEGADRIELLIDAARQ<br>LKRSHVLPEGRSPGPPALKHPATKDLAAAAAQGPQLPPPQAQPQPSGTGGGVSG<br>QDRYDRATSSGRLPLPSPALEYTLGSRLANGLGREEAVAEGARRALLGSMPGLM<br>PPGLLAAAVSGLGSRGLTLAPGLSPARPLFGSDFEKEKQQRNADCLAELNEAMR<br>GRAEEWHGRPKAVREQLLALSACAPFNVREKKDHGLVGRVFAFDATARPPGYEF<br>ELKLFTEYPCGSGNVYAGVLAVARQMFHDALREPGKALASSGFKYLEYERRHGS<br>GEWRQLGELLTDGVRSFREPAPAEALPQQYPEPAPAALCGPPPRAPSRNLAPTP<br>RRRKASPEPEGEAAGKMTTEEQQQRHWVAPGGPYSAETPGVPSPIAALKNVAEA<br>LGHSPKDPGGGGGPVRAGGASPAASSTAQPPTQHRLVARNGEAEVSPTAGAEAV<br>SGGGSGTGATPGAPLCCTLCRERLEDTHFVQCPSVPGHKFCFPCSREFIKAQGP<br>AGEVYCPSGDKCPLVGSSVPWAFMQGEIATILAGDIKVKKERDP |
| 567 | IRF2BP2 (IRF-2BP1_2 N-terminal domain) | MAAAVAVAAASRRQSCYLCDLPRMPWAMIWDFTEPVCRGCVNYEGADRVEFVIE<br>TARQLKRAHGCFPEGRSPPGAAASAAAKPPPLSAKDILLQQQQQLGHGGPEAAP<br>RAPQALERYPLAAAAERPPRLGSDFGSSRPAASLAQPPTPQPPPVNGILVPNGF<br>SKLEEPPELNRQSPNPRRGHAVPPTLVPLMNGSATPLPTALGLGGRAAASLAAV<br>SGTAAASLGSAQPTDLGAHKRPASVSSSAAVEHEQREAAAKEKQPPPPAHRGPA<br>DSLSTAAGAAELSAEGAGKSRGSGEQDWVNRPKTVRDTLLALHQHGHSGPFESK<br>FKKEPALTAGRLLGFEANGANGSKAVARTARKRKPSPEPEGEVGPPKINGEAQP<br>WLSTSTEGLKIPMTPTSSFVSPPPPTASPHSNRTTPPEAAQNGQSPMAALILVA<br>DNAGGSHASKDANQVHSTTRRNSNSPPSPSSMNQRRLGPREVGGQGAGNTGGLE<br>PVHPASLPDSSLATSAPLCCTLCHERLEDTHFVQCPSVPSHKFCFPCSRQSIKQ<br>QGASGEVYCPSGEKCPLVGSNVPWAFMQGEIATILAGDVKVKKERDS |
| 568 | IRF2BPL IRF-2BP1_2 N-terminal domain | MSAAQVSSSRRQSCYLCDLPRMPWAMIWDFSEPVCRGCVNYEGADRIEFVIETA<br>RQLKRAHGCFQDGRSPGPPPPVGVKTVALSAKEAAAAAAAAAAAAAAAAAQQQQQQ<br>QQLNHVDGSSKPAVLAAPSGLERYGLSAAAAAAAAAA<br>AAVEQRSRFEYPPPPVSLGSSSHTARLPNGLGGPNGFPKPTPEEGPPELNRQSP<br>NSSSAAASVASRRGTHGGLVTGLPNPGGGGGPQLTVPPNLLPQTLLNGPASAAV<br>LPPPPPHALGSRGPPTPAPPGAPGGPACLGGTPGVSATSSSASSSTSSSVAEVG<br>VGAGGKRPGSVSSTDQERELKEKQRNAEALAELSESLRNRAEEWASKPKMVRDT<br>LLTLAGCTPYEVRFKKDHSLLGRVFAFDAVSKPGMDYELKLFIEYPTGSGNVYS<br>SASGVAKQMYQDCMKDFGRGLSSGFKYLEYEKKHGSGDWRLLGDLLPEAVRFFK<br>EGVPGADMLPQPYLDASCPMLPTALVSLSRAPSAPPGTGALPPAAPSGRGAAAS<br>LRKRKASPEPPDSAEGALKLGEEQQRQQWMANQSEALKLTMSAGGFAAPGHAAG<br>GPPPPPPPLGPHSNRTTPPESAPQNGPSPMAALMSVADTLGTAHSPKDGSSVHS<br>TTASARRNSSSPVSPASVPGQRRLASRNGDLNLQVAPPPPSAHPGMDQVHPQNI<br>PDSPMANSGPLCCTICHERLEDTHFVQCPSVPSHKFCFPCSRESIKAQGATGEV<br>YCPSGEKCPLVGSNVPWAFMQGEIATILAGDVKVKKERDP |
| 569 | HOXA13 (homeodomain) | MTASVLLHPRWIEPTVMFLYDNGGGLVADELNKNMEGAAAAAAAAAAAAAAAGAG<br>GGGFPHPAAAAAGGNFSVAAAAAAAAAAAAANQCRNLMAHPAPLAPGAASAYSSA<br>PGEAPPSAAAAAAAAAAAAAAAAAASSSGGPGPAGPAGAEAAKQCSPCSAAAQS<br>SSGPAALPYGYFGSGYYPCARMGPHPNAIKSCAQPASAAAAAAFADKYMDTAGP<br>AAEEFSSRAKEFAFYHQGYAAGPYHHHQPMPGYLDMPVVPGLGGPGESRHEPLG<br>LPMESYQPWALPNGWNGQMYCPKEQAQPPHLWKSTLPDVVSHPSDASSYRRGRK<br>KRVPYTKVQLKELEREYATNKFITKDKRRRISATTNLSERQVTIWFQNRRVKEK<br>KVINKLKTTS |
| 570 | HOXB13 (homeodomain) | MEPGNYATLDGAKDIEGLLGAGGGRNLVAHSPLTSHPAAPTLMPAVNYAPLDLP<br>GSAEPPKQCHPCPGVPQGTSPAPVPYGYFGGGYYSCRVSRSSLKPCAQAATLAA<br>YPAETPTAGEEYPSRPTEFAFYPGYPGTYQPMASYLDVSVVQTLGAPGEPRHDS |

Sequence listing.

| SEQ | Description | Sequence |
|---|---|---|
| | | LLPVDSYQSWALAGGWNSQMCCQGEQNPPGPFWKAAFADSSGQHPPDACAFRRG RKKRIPYSKGQLRELEREYAANKFITKDKRRKISAATSLSERQITIWFQNRRVK EKKVLAKVKNSATP |
| 571 | HOXC13 (homeodomain) | MTTSLLLHPRWPESLMYVYEDSAAESGIGGGGGGGGGGGTGGAGGGCSGASPGKA PSMDGLGSSCPASHCRDLLPHPVLGRPPAPLGAPQGAVYTDIPAPEAARQCAPP PAPPTSSSATLGYGYPFGGSYYGCRLSHNVNLQQKPCAYHPGDKYPEPSGALPG DDLSSRAKEFAFYPSFASSYQAMPGYLDVSVVPGISGHPEPRHDALIPVEGYQH WALSNGWDSQVYCSKEQSQSAHLWKSPFPDVVPLQPEVSSYRRGRKKRVPYTKV QLKELEKEYAASKFITKEKRRRISATTNLSERQVTIWFQNRRVKEKKVVSKSKA PHLHST |
| 572 | HOXA11 (homeodomain) | MDFDERGPCSSNMYLPSCTYYVSGPDFSSLPSFLPQTPSSRPMTYSYSSNLPQV QPVREVTFREYAIEPATKWHPRGNLAHCYSAEELVHRDCLQAPSAAGVPGDVLA KSSANVYHHPTPAVSSNFYSTVGRNGVLPQAFDQFFETAYGTPENLASSDYPGD KSAEKGPPAATATSAAAAAAATGAPATSSSDSGGGGGCRETAAAAEEKERRRRP ESSSSPESSSGHTEDKAGGSSGQRTRKKRCPYTKYQIRELEREFFFSVYINKEK RLQLSRMLNLTDRQVKIWFQNRRMKEKKINRDRLQYYSANPLL |
| 573 | HOXC11 (homeodomain) | MFNSVNLGNFCSPSRKERGADFGERGSCASNLYLPSCTYYMPEFSTVSSFLPQA PSRQISYPYSAQVPPVREVSYGLEPSGKWHHRNSYSSCYAAADELMHRECLPPS TVTEILMKNEGSYGGHHHPSAPHATPAGFYSSVNKNSVLPQAFDRFEDNAYCGG GDPPAEPPCSGKGEAKGEPEAPPASGLASRAEAGAEAEAEEENTNPSSSGSAHS VAKEPAKGAAPNAPRTRKKRCPYSKFQIRELEREFFENVYINKEKRLQLSRMLN LTDRQVKIWFQNRRMKEKKLSRDRLQYFSGNPLL |
| 574 | HOXC10 (homeodomain) | MTCPRNVTPNSYAEPLAAPGGGERYSRSAGMYMQSGSDENCGVMRGCGLAPSLS KRDEGSSPSLALNTYPSYLSQLDSWGDPKAAYRLEQPVGRPLSSCSYPPSVKEE NVCCMYSAEKRAKSGPEAALYSHPLPESCLGEHEVPVPSYYRASPSYSALDKTP HCSGANDFEAPFEQRASLNPRAEHLESPQLGGKVSFPETPKSDSQTPSPNEIKT EQSLAGPKGSPSESEKERAKAADSSPDTSDNEAKEEIKAENTTGNWLTAKSGRK KRCPYTKHQTLELEKEFLENMYLTRERRLEISKTINLTDRQVKIWFQNRRMKLK KMNRENRIRELTSNENFT |
| 575 | HOXA10 (homeodomain) | MSARKGYLLPSPNYPTTMSCSESPAANSFLVDSLISSGRGEAGGGGGGGAGGGGG GGYYAHGGVYLPPAADLPYGLQSCGLFPTLGGKRNEAASPGSGGGGGGGLGPGAH GYGPSPIDLWLDAPRSCRMEPPDGPPPPPQQQPPPPPQPPQPAPQATSCSFAQN IKEESSYCLYDSADKCPKVSATAAELAPFPRGPPPDGCALGTSSGVPVPGYERL SQAYGTAKGYGSGGGGAQQLGAGPFPAQPPGRGFDLPPALASGSADAARKERAL DSPPPPTLACGSGGGSQGDEEAHASSSAAEELSPAPSESSKASPEKDSLGNSKG ENAANWLTAKSGRKKRCPYTKHQTLELEKEFLENMYLTRERRLEISRSVHLTDR QVKIWFQNRRMKLKKMNRENRIRELTANENFS |
| 576 | HOXB9 (homeodomain) | MSISGTLSSYYVDSIISHESEDAPPAKFPSGQYASSRQPGHAEHLEFPSCSFQP KAPVFGASWAPLSPHASGSLPSVYHPYIQPQGVPPAESRYLRTWLEPAPRGEAA PGQGQAAVKAEPLLGAPGELLKQGTPEYSLETSAGREAVLSNQRPGYGDNKICE GSEDKERPDQTNPSANWLHARSSRKKRCPYTKYQTLELEKEFLENMYLTRDRRH EVARLLNLSERQVKIWFQNRRMKMKKMNKEQGKE |
| 577 | HOXA9 (homeodomain) | MATTGALGNYYVDSFLLGADAADELSVGRYAPGTLGQPPRQAATLAEHPDFSPC SFQSKATVEGASWNPVHAAGANAVPAAVYHHHHHHPYVHPQAPVAAAAPDGRYM RSWLEPTPGALSFAGLPSSRPYGIKPEPLSARRGDCPTLDTHTLSLTDYACGSP PVDREKQPSEGAFSENNAENESGGDKPPIDPNNPAANWLHARSTRKKRCPYTKH QTLELEKEFLFNMYLTRDRRYEVARLLNLTERQVKIWFQNRRMKMKKINKDRAK DE |
| 578 | ZFP28_HUMAN | NKKLEAVGTGIEPKAMSQGLVTFGDVAVDFSQEEWEWLNPIQRNLYRKVMLENY RNLASLGLCVSKPDVISSLEQGKEPW |
| 579 | ZN334_HUMAN | KMKKFQIPVSFQDLTVNFTQEEWQQLDPAQRLLYRDVMLENYSNLVSVGYHVSK PDVIFKLEQGEEPWIVEEFSNQNYPD |
| 580 | ZN568_HUMAN | CSQESALSEEEEDTTRPLETVTFKDVAVDLTQEEWEQMKPAQRNLYRDVMLENY SNLVTVGCQVTKPDVIFKLEQEEEPW |
| 581 | ZN37A_HUMAN | ITSQGSVSFRDVTVGFTQEEWQHLDPAQRTLYRDVMLENYSHLVSVGYCIPKPE VILKLEKGEEPWILEEKFPSQSHLEL |
| 582 | ZN181_HUMAN | PQVTFNDVAIDFTHEEWGWLSSAQRDLYKDVMVQNYENLVSVAGLSVTKPYVIT LLEDGKEPWMMEKKLSKGMIPDWESR |
| 583 | ZN510_HUMAN | PLRFSTLFQEQQKMNISQASVSFKDVTIEFTQEEWQQMAPVQKNLYRDVMLENY SNLVSVGYCCFKPEVIFKLEQGEEPW |
| 584 | ZN862_HUMAN | QDPSAEGLSEEVPVVFEELPVVFEDVAVYFTREEWGMLDKRQKELYRDVMRMNY ELLASLGPAAAKPDLISKLERRAAPW |

TABLE 18-continued

Sequence listing.

| SEQ | Description | Sequence |
|---|---|---|
| 585 | ZN140_HUMAN | SQGSVTFRDVAIDFSQEEWKWLQPAQRDLYRCVMLENYGHLVSLGLSISKPDVV<br>SLLEQGKEPWLGKREVKRDLFSVSES |
| 586 | ZN208_HUMAN | GSLTFRDVAIEFSLEEWQCLDTAQQNLYRNVMLENYRNLVFLGIAAFKPDLIIF<br>LEEGKESWNMKRHEMVEESPVICSHF |
| 587 | ZN248_HUMAN | NKSQEQVSFKDVCVDFTQEEWYLLDPAQKILYRDVILENYSNLVSVGYCITKPE<br>VIFKIEQGEEPWILEKGFPSQCHPER |
| 588 | ZN571_HUMAN | PHLLVTFRDVAIDFSQEEWECLDPAQRDLYRDVMLENYSNLISLDLESSCVTKK<br>LSPEKEIYEMESLQWENMGKRINHHL |
| 589 | ZN699_HUMAN | EEERKTAELQKNRIQDSVVFEDVAVDFTQEEWALLDLAQRNLYRDVMLENFQNL<br>ASLGYPLHTPHLISQWEQEEDLQTVK |
| 590 | ZN726_HUMAN | GLLTFRDVAIEFSLEEWQCLDTAQKNLYRNVMLENYRNLAFLGIAVSKPDLIIC<br>LEKEKEPWNMKRDEMVDEPPGICPHF |
| 591 | ZIK1_HUMAN | RAPTQVTVSPETHMDLTKGCVTFEDIAIYFSQDEWGLLDEAQRLLYLEVMLENF<br>ALVASLGCGHGTEDEETPSDQNVSVG |
| 592 | ZNF2_HUMAN | AAVSPTTRCQESVTFEDVAVVFTDEEWSRLVPIQRDLYKEVMLENYNSIVSLGL<br>PVPQPDVIFQLKRGDKPWMVDLHGSE |
| 593 | Z705F_HUMAN | HSLEKVTFEDVAIDFTQEEWDMMDTSKRKLYRDVMLENISHLVSLGYQISKSYI<br>ILQLEQGKELWREGRVFLQDQNPDRE |
| 594 | ZNF14_HUMAN | DSVSFEDVAVNFTLEEWALLDSSQKKLYEDVMQETFKNLVCLGKKWEDQDIEDD<br>HRNQGKNRRCHMVERLCESRRGSKCG |
| 595 | ZN471_HUMAN | NVEVVKVMPQDLVTFKDVAIDESQEEWQWMNPAQKRLYRSMMLENYQSLVSLGL<br>CISKPYVISLLEQGREPWEMTSEMTR |
| 596 | ZN624_HUMAN | TQPDEDLHLQAEETQLVKESVTFKDVAIDFTLEEWRLMDPTQRNLHKDVMLENY<br>RNLVSLGLAVSKPDMISHLENGKGPW |
| 597 | ZNF84_HUMAN | TMLQESFSFDDLSVDFTQKEWQLLDPSQKNLYKDVMLENYSSLVSLGYEVMKPD<br>VIFKLEQGEEPWVGDGEIPSSDSPEV |
| 598 | ZNF7_HUMAN | EVVTFGDVAVHFSREEWQCLDPGQRALYREVMLENHSSVAGLAGFLVFKPELIS<br>RLEQGEEPWVLDLQGAEGTEAPRTSK |
| 599 | ZN891_HUMAN | RNAEEERMIAVFLTTWLQEPMTFKDVAVEFTQEEWMMLDSAQRSLYRDVMLENY<br>RNLTSVEYQLYRLTVISPLDQEEIRN |
| 600 | ZN337_HUMAN | GPQGARRQAFLAFGDVTVDFTQKEWRLLSPAQRALYREVTLENYSHLVSLGILH<br>SKPELIRRLEQGEVPWGEERRRRPGP |
| 601 | Z705G_HUMAN | HSLKKLTFEDVAIDFTQEEWAMMDTSKRKLYRDVMLENISHLVSLGYQISKSYI<br>ILQLEQGKELWREGRVFLQDQNPNRE |
| 602 | ZN529_HUMAN | MPEVEFPDQFFTVLTMDHELVTLRDVVINFSQEEWEYLDSAQRNLYWDVMMENY<br>SNLLSLDLESRNETKHLSVGKDIIQN |
| 603 | ZN729_HUMAN | PGAPGSLEMGPLTFRDVTIEFSLEEWQCLDTVQQNLYRDVMLENYRNLVFLGMA<br>VFKPDLITCLKQGKEPWNMKRHEMVT |
| 604 | ZN419_HUMAN | RDPAQVPVAADLLTDHEEGYVTFEDVAVYFSQEEWRLLDDAQRLLYRNVMLENF<br>TLLASLGLASSKTHEITQLESWEEPF |
| 605 | Z705A_HUMAN | HSLKKVTFEDVAIDFTQEEWAMMDTSKRKLYRDVMLENISHLVSLGYQISKSYI<br>ILQLEQGKELWREGREFLQDQNPDRE |
| 606 | ZNF45_HUMAN | TKSKEAVTFKDVAVVFSEEELQLLDLAQRKLYRDVMLENFRNVVSVGHQSTPDG<br>LPQLEREEKLWMMKMATQRDNSSGAK |
| 607 | ZN302_HUMAN | SQVTFSDVAIDFSHEEWACLDSAQRDLYKDVMVQNYENLVSVGLSVTKPYVIML<br>LEDGKEPWMMEKKLSKAYPFPLSHSV |
| 608 | ZN486_HUMAN | PGPLRSLEMESLQFRDVAVEFSLEEWHCLDTAQQNLYRDVMLENYRHLVFLGII<br>VSKPDLITCLEQGIKPLTMKRHEMIA |
| 609 | ZN621_HUMAN | LQTTWPQESVTFEDVAVYFTQNQWASLDPAQRALYGEVMLENYANVASLVAFPF<br>PKPALISHLERGEAPWGPDPWDTEIL |

TABLE 18-continued

Sequence listing.

| SEQ | Description | Sequence |
|---|---|---|
| 610 | ZN688_HUMAN | APLLAPRPGETRPGCRKPGTVSFADVAVYFSPEEWGCLRPAQRALYRDVMQETY GHLGALGFPGPKPALISWMEQESEAW |
| 611 | ZN33A_HUMAN | NKVEQKSQESVSFKDVTVGFTQEEWQHLDPSQRALYRDVMLENYSNLVSVGYCV HKPEVIFRLQQGEEPWKQEEEFPSQS |
| 612 | ZN554_HUMAN | CFSQEERMAAGYLPRWSQELVTFEDVSMDFSQEEWELLEPAQKNLYREVMLENY RNVVSLEALKNQCTDVGIKEGPLSPA |
| 613 | ZN878_HUMAN | DSVAFEDVAVNFTQEEWALLDPSQKNLYREVMQETLRNLTSIGKKWNNQYIEDE HQNPRRNLRRLIGERLSESKESHQHG |
| 614 | ZN772_HUMAN | MGPAQVPMNSEVIVDPIQGQVNFEDVFVYFSQEEWVLLDEAQRLLYRDVMLENF ALMASLGHTSFMSHIVASLVMGSEPW |
| 615 | ZN224_HUMAN | TTFKEAMTFKDVAVVFTEEELGLLDLAQRKLYRDVMLENFRNLLSVGHQAFHRD TFHFLREEKIWMMKTAIQREGNSGDK |
| 616 | ZN184_HUMAN | DSTLLQGGHNLLSSASFQEAVTFKDVIVDFTQEEWKQLDPGQRDLFRDVTLENY THLVSIGLQVSKPDVISQLEQGTEPW |
| 617 | ZN544_HUMAN | EARSMLVPPQASVCFEDVAMAFTQEEWEQLDLAQRTLYREVTLETWEHIVSLGL FLSKSDVISQLEQEEDLCRAEQEAPR |
| 618 | ZNF57_HUMAN | DSVVFEDVAVDFTLEEWALLDSAQRDLYRDVMLETFRNLASVDDGTQFKANGSV SLQDMYGQEKSKEQTIPNFTGNNSCA |
| 619 | ZN283_HUMAN | EESHGALISSCNSRTMTDGLVTFRDVAIDFSQEEWECLDPAQRDLYVDVMLENY SNLVSLDLESKTYETKKIFSENDIFE |
| 620 | ZN549_HUMAN | VITPQIPMVTEEFVKPSQGHVTFEDIAVYFSQEEWGLLDEAQRCLYHDVMLENF SLMASVGCLHGIEAEEAPSEQTLSAQ |
| 621 | ZN211_HUMAN | VQLRPQTRMATALRDPASGSVTFEDVAVYFSWEEWDLLDEAQKHLYFDVMLENF ALTSSLGCWCGVEHEETPSEQRISGE |
| 622 | ZN615_HUMAN | MQAQESLTLEDVAVDFTWEEWQFLSPAQKDLYRDVMLENYSNLVAVGYQASKPD ALSKLERGEETCTTEDEIYSRICSEI |
| 623 | ZN253_HUMAN | GPLQFRDVAIEFSLEEWHCLDTAQRNLYRDVMLENYRNLVFLGIVVSKPDLVTC LEQGKKPLTMERHEMIAKPPVMSSHF |
| 624 | ZN226_HUMAN | NMFKEAVTFKDVAVAFTEEELGLLGPAQRKLYRDVMVENFRNLLSVGHPPFKQD VSPIERNEQLWIMTTATRRQGNLGEK |
| 625 | ZN730_HUMAN | GALTFRDVAIEFSLEEWQCLDTEQQNLYRNVMLDNYRNLVFLGIAVSKPDLITC LEQEKEPWNLKTHDMVAKPPVICSHI |
| 626 | Z585A_HUMAN | SPQKSSALAPEDHGSSYEGSVSFRDVAIDESREEWRHLDPSQRNLYRDVMLETY SHLLSVGYQVPEAEVVMLEQGKEPWA |
| 627 | ZN732_HUMAN | ELLTFRDVAIEFSPEEWKCLDPAQQNLYRDVMLENYRNLISLGVAISNPDLVIY LEQRKEPYKVKIHETVAKHPAVCSHF |
| 628 | ZN681_HUMAN | EPLKFRDVAIEFSLEEWQCLDTIQQNLYRNVMLENYRNLVFLGIVVSKPDLITC LEQEKEPWTRKRHRMVAEPPVICSHF |
| 629 | ZN667_HUMAN | PSARGKSKSKAPITFGDLAIYFSQEEWEWLSPIQKDLYEDVMLENYRNLVSLGL SFRRPNVITLLEKGKAPWMVEPVRRR |
| 630 | ZN649_HUMAN | TKAQESLTLEDVAVDFTWEEWQFLSPAQKDLYRDVMLENYSNLVSVGYQAGKPD ALTKLEQGEPLWTLEDEIHSPAHPEI |
| 631 | ZN470_HUMAN | SQEEVEVAGIKLCKAMSLGSVTFTDVAIDFSQDEWEWLNLAQRSLYKKVMLENY RNLVSVGLCISKPDVISLLEQEKDPW |
| 632 | ZN484_HUMAN | TKSLESVSFKDVTVDFSRDEWQQLDLAQKSLYREVMLENYFNLISVGCQVPKPE VIFSLEQEEPCMLDGEIPSQSRPDGD |
| 633 | ZN431_HUMAN | SGCPGAERNLLVYSYFEKETLTFRDVAIEFSLEEWECLNPAQQNLYMNVMLENY KNLVFLGVAVSKQDPVTCLEQEKEPW |
| 634 | ZN382_HUMAN | PLQGSVSFKDVTVDFTQEEWQQLDPAQKALYRDVMLENYCHFVSVGFHMAKPDM IRKLEQGEELWTQRIFPSYSYLEEDG |

TABLE 18-continued

Sequence listing.

| SEQ | Description | Sequence |
|---|---|---|
| 635 | ZN254_HUMAN | PGPPRSLEMGLLTFRDVAIEFSLEEWQHLDIAQQNLYRNVMLENYRNLAFLGIA<br>VSKPDLITCLEQGKEPWNMKRHEMVD |
| 636 | ZN124_HUMAN | SGHPGSWEMNSVAFEDVAVNFTQEEWALLDPSQKNLYRDVMQETFRNLASIGNK<br>GEDQSIEDQYKNSSRNLRHIISHSGN |
| 637 | ZN607_HUMAN | SYGSITFGDVAIDFSHQEWEYLSLVQKTLYQEVMMENYDNLVSLAGHSVSKPDL<br>ITLLEQGKEPWMIVREETRGECTDLD |
| 638 | ZN317_HUMAN | DLFVCSGLEPHTPSVGSQESVTFQDVAVDFTEKEWPLLDSSQRKLYKDVMLENY<br>SNLTSLGYQVGKPSLISHLEQEEEPR |
| 639 | ZN620_HUMAN | FQTAWRQEPVTFEDVAVYFTQNEWASLDSVQRALYREVMLENYANVASLAFPFT<br>TPVLVSQLEQGELPWGLDPWEPMGRE |
| 640 | ZN141_HUMAN | ELLTFRDVAIEFSPEEWKCLDPDQQNLYRDVMLENYRNLVSLGVAISNPDLVTC<br>LEQRKEPYNVKIHKIVARPPAMCSHF |
| 641 | ZN584_HUMAN | AGEAEAQLDPSLQGLVMFEDVTVYFSREEWGLLNVTQKGLYRDVMLENFALVSS<br>LGLAPSRSPVFTQLEDDEQSWVPSWV |
| 642 | ZN540_HUMAN | AHALVTFRDVAIDFSQKEWECLDTTQRKLYRDVMLENYNNLVSLGYSGSKPDVI<br>TLLEQGKEPCVVARDVTGRQCPGLLS |
| 643 | ZN75D_HUMAN | KRIKHWKMASKLILPESLSLLTFEDVAVYFSEEEWQLLNPLEKTLYNDVMQDIY<br>ETVISLGLKLKNDTGNDHPISVSTSE |
| 644 | ZN555_HUMAN | DSVVFEDVAVDFTLEEWALLDSAQRDLYRDVMLETFQNLASVDDETQFKASGSV<br>SQQDIYGEKIPKESKIATFTRNVSWA |
| 645 | ZN658_HUMAN | NMSQASVSFQDVTVEFTREEWQHLGPVERTLYRDVMLENYSHLISVGYCITKPK<br>VISKLEKGEEPWSLEDEFLNQRYPGY |
| 646 | ZN684_HUMAN | ISFQESVTFQDVAVDFTAEEWQLLDCAERTLYWDVMLENYRNLISVGCPITKTK<br>VILKVEQGQEPWMVEGANPHESSPES |
| 647 | RBAK_HUMAN | NTLQGPVSFKDVAVDFTQEEWQQLDPDEKITYRDVMLENYSHLVSVGYDTTKPN<br>VIIKLEQGEEPWIMGGEFPCQHSPEA |
| 648 | ZN829_HUMAN | HPEEEERMHDELLQAVSKGPVMFRDVSIDFSQEEWECLDADQMNLYKEVMLENF<br>SNLVSVGLSNSKPAVISLLEQGKEPW |
| 649 | ZN582_HUMAN | SLGSELFRDVAIVFSQEEWQWLAPAQRDLYRDVMLETYSNLVSLGLAVSKPDVI<br>SFLEQGKEPWMVERVVSGGLCPVLES |
| 650 | ZN112_HUMAN | TKFQEMVTFKDVAVVFTEEELGLLDSVQRKLYRDVMLENFRNLLLVAHQPFKPD<br>LISQLEREEKLLMVETETPRDGCSGR |
| 651 | ZN716_HUMAN | AKRPGPPGSREMGLLTFRDIAIEFSLAEWQCLDHAQQNLYRDVMLENYRNLVSL<br>GIAVSKPDLITCLEQNKEPQNIKRNE |
| 652 | HKR1_HUMAN | TCMVHRQTMSCSGAGGITAFVAFRDVAVYFTQEEWRLLSPAQRTLHREVMLETY<br>NHLVSLEIPSSKPKLIAQLERGEAPW |
| 653 | ZN350_HUMAN | IQAQESITLEDVAVDFTWEEWQLLGAAQKDLYRDVMLENYSNLVAVGYQASKPD<br>ALFKLEQGEQLWTIEDGIHSGACSDI |
| 654 | ZN480_HUMAN | AQKRRKRKAKESGMALPQGHLTFRDVAIEFSQAEWKCLDPAQRALYKDVMLENY<br>RNLVSLGISLPDLNINSMLEQRREPW |
| 655 | ZN416_HUMAN | DSTSVPVTAEAKLMGFTQGCVTFEDVAIYFSQEEWGLLDEAQRLLYRDVMLENF<br>ALITALVCWHGMEDEETPEQSVSVEG |
| 656 | ZNF92_HUMAN | GPLTFRDVKIEFSLEEWQCLDTAQRNLYRDVMLENYRNLVFLGIAVSKPDLITW<br>LEQGKEPWNLKRHEMVDKTPVMCSHF |
| 657 | ZN100_HUMAN | SGCPGAERSLLVQSYFEKGPLTFRDVAIEFSLEEWQCLDSAQQGLYRKVMLENY<br>RNLVFLAGIALTKPDLITCLEQGKEP |
| 658 | ZN736_HUMAN | GVLTFRDVAVEFSPEEWECLDSAQQRLYRDVMLENYGNLVSLGLAIFKPDLMTC<br>LEQRKEPWKVKRQEAVAKHPAGSFHF |
| 659 | ZNF74_HUMAN | KENLEDISGWGLPEARSKESVSFKDVAVDFTQEEWGQLDSPQRALYRDVMLENY<br>QNLLALGPPLHKPDVISHLERGEEPW |

TABLE 18-continued

Sequence listing.

| SEQ | Description | Sequence |
| --- | --- | --- |
| 660 | CBX1_HUMAN | EESEKPRGFARGLEPERIIGATDSSGELMFLMKWKNSDEADLVPAKEANVKCPQ<br>VVISFYEERLTWHSYPSEDDDKKDDK |
| 661 | ZN443_HUMAN | ASVALEDVAVNFTREEWALLGPCQKNLYKDVMQETIRNLDCVVMKWKDQNIEDQ<br>YRYPRKNLRCRMLERFVESKDGTQCG |
| 662 | ZN195_HUMAN | TLLTFRDVAIEFSLEEWKCLDLAQQNLYRDVMLENYRNLFSVGLTVCKPGLITC<br>LEQRKEPWNVKRQEAADGHPEMGFHH |
| 663 | ZN530_HUMAN | AAALRAPTQQVFVAFEDVAIYFSQEEWELLDEMQRLLYRDVMLENFAVMASLGC<br>WCGAVDEGTPSAESVSVEELSQGRTP |
| 664 | ZN782_HUMAN | NTFQASVSFQDVTVEFSQEEWQHMGPVERTLYRDVMLENYSHLVSVGYCFTKPE<br>LIFTLEQGEDPWLLEKEKGFLSRNSP |
| 665 | ZN791_HUMAN | DSVAFEDVSVSFSQEEWALLAPSQKKLYRDVMQETFKNLASIGEKWEDPNVEDQ<br>HKNQGRNLRSHTGERLCEGKEGSQCA |
| 666 | ZN331_HUMAN | AQGLVTFADVAIDFSQEEWACLNSAQRDLYWDVMLENYSNLVSLDLESAYENKS<br>LPTEKNIHEIRASKRNSDRRSKSLGR |
| 667 | Z354C_HUMAN | AVDLLSAQEPVTFRDVAVFFSQDEWLHLDSAQRALYREVMLENYSSLVSLGIPF<br>SMPKLIHQLQQGEDPCMVEREVPSDT |
| 668 | ZN157_HUMAN | SPQRFPALIPGEPGRSFEGSVSFEDVAVDFTRQEWHRLDPAQRTMHKDVMLETY<br>SNLASVGLCVAKPEMIFKLERGEELW |
| 669 | ZN727_HUMAN | RVLTFRDVAVEFSPEEWECLDSAQQRLYRDVMLENYGNLESLGLAIFKPDLITY<br>LEQRKEPWNARRQKTVAKHPAGSLHF |
| 670 | ZN550_HUMAN | AETKDAAQMLVTFKDVAVTFTREEWRQLDLAQRTLYREVMLETCGLLVSLGHRV<br>PKPELVHLLEHGQELWIVKRGLSHAT |
| 671 | ZN793_HUMAN | IEYQIPVSFKDVVVGFTQEEWHRLSPAQRALYRDVMLETYSNLVSVGYEGTKPD<br>VILRLEQEEAPWIGEAACPGCHCWED |
| 672 | ZN235_HUMAN | TKFQEAVTFKDVAVAFTEEELGLLDSAQRKLYRDVMLENFRNLVSVGHQSFKPD<br>MISQLEREEKLWMKELQTQRGKHSGD |
| 673 | ZNF8_HUMAN | DEGVAGVMSVGPPAARLQEPVTFRDVAVDFTQEEWGQLDPTQRILYRDVMLETF<br>GHLLSIGPELPKPEVISQLEQGTELW |
| 674 | ZN724_HUMAN | GPLTFMDVAIEFSVEEWQCLDTAQQNLYRNVMLENYRNLVFLGIAVSKPDLITC<br>LEQGKEPWNMERHEMVAKPPGMCCYF |
| 675 | ZN573_HUMAN | HQVGLIRSYNSKTMTCFQELVTFRDVAIDFSRQEWEYLDPNQRDLYRDVMLENY<br>RNLVSLGGHSISKPVVVDLLERGKEP |
| 676 | ZN577_HUMAN | NATIVMSVRREQGSSSGEGSLSFEDVAVGFTREEWQFLDQSQKVLYKEVMLENY<br>INLVSIGYRGTKPDSLFKLEQGEPPG |
| 677 | ZN789_HUMAN | FPPARGKELLSFEDVAMYFTREEWGHLNWGQKDLYRDVMLENYRNMVLLGFQFP<br>KPEMICQLENWDEQWILDLPRTGNRK |
| 678 | ZN718_HUMAN | ELLTFKDVAIEFSPEEWKCLDTSQQNLYRDVMLENYRNLVSLGVSISNPDLVTS<br>LEQRKEPYNLKIHETAARPPAVCSHF |
| 679 | ZN300_HUMAN | MKSQGLVSFKDVAVDFTQEEWQQLDPSQRTLYRDVMLENYSHLVSMGYPVSKPD<br>VISKLEQGEEPWIIKGDISNWIYPDE |
| 680 | ZN383_HUMAN | AEGSVMFSDVSIDFSQEEWDCLDPVQRDLYRDVMLENYGNLVSMGLYTPKPQVI<br>SLLEQGKEPWMVGRELTRGLCSDLES |
| 681 | ZN429_HUMAN | GPLTFTDVAIEFSLEEWQCLDTAQQNLYRNVMLENYRNLVFLGIAVSKPDLITC<br>LEKEKEPCKMKRHEMVDEPPVVCSHF |
| 682 | ZN677_HUMAN | ALSQGLFTFKDVAIEFSQEEWECLDPAQRALYRDVMLENYRNLLSLDEDNIPPE<br>DDISVGFTSKGLSPKENNKEELYHLV |
| 683 | ZN850_HUMAN | NMEGLVMFQDLSIDFSQEEWECLDAAQKDLYRDVMMENYSSLVSLGLSIPKPDV<br>ISLLEQGKEPWMVSRDVLGGWCRDSE |
| 684 | ZN454_HUMAN | AVSHLPTMVQESVTFKDVAILFTQEEWGQLSPAQRALYRDVMLENYSNLVSLGL<br>LGPKPDTFSQLEKREVWMPEDTPGGF |

TABLE 18-continued

Sequence listing.

| SEQ | Description | Sequence |
|---|---|---|
| 685 | ZN257_HUMAN | GPLTIRDVTVEFSLEEWHCLDTAQQNLYRDVMLENYRNLVFLGIAVSKPDLITC<br>LEQGKEPCNMKRHEMVAKPPVMCSHI |
| 686 | ZN264_HUMAN | AAAVLTDRAQVSVTFDDVAVTFTKEEWGQLDLAQRTLYQEVMLENCGLLVSLGC<br>PVPKAELICHLEHGQEPWTRKEDLSQ |
| 687 | ZFP82_HUMAN | ALRSVMFSDVSIDFSPEEWEYLDLEQKDLYRDVMLENYSNLVSLGCFISKPDVI<br>SSLEQGKEPWKVVRKGRRQYPDLETK |
| 688 | ZFP14_HUMAN | AHGSVTFRDVAIDFSQEEWEFLDPAQRDLYRDVMWENYSNFISLGPSISKPDVI<br>TLLDEERKEPGMVVREGTRRYCPDLE |
| 689 | ZN485_HUMAN | APRAQIQGPLTFGDVAVAFTRIEWRHLDAAQRALYRDVMLENYGNLVSVGLLSS<br>KPKLITQLEQGAEPWTEVREAPSGTH |
| 690 | ZN737_HUMAN | GPLQFRDVAIEFSLEEWHCLDTAQRNLYRNVMLENYRNLVFLGIVVSKPDLITC<br>LEQGKKPLTMKKHEMVANPSVTCSHF |
| 691 | ZNF44_HUMAN | TLPRGQPEVLEWGLPKDQDSVAFEDVAVNFTHEEWALLGPSQKNLYRDVMRETI<br>RNLNCIGMKWENQNIDDQHQNLRRNP |
| 692 | ZN596_HUMAN | PSPDSMTFEDIIVDFTQEEWALLDTSQRKLFQDVMLENISHLVSIGKQLCKSVV<br>LSQLEQVEKLSTQRISLLQGREVGIK |
| 693 | ZN565_HUMAN | EESREIRAGQIVLKAMAQGLVTFRDVAIEFSLEEWKCLEPAQRDLYREVTLENF<br>GHLASLGLSISKPDVVSLLEQGKEPW |
| 694 | ZN543_HUMAN | AASAQVSVTFEDVAVTFTQEEWGQLDAAQRTLYQEVMLETCGLLMSLGCPLFKP<br>ELIYQLDHRQELWMATKDLSQSSYPG |
| 695 | ZFP69_HUMAN | RESLEDEVTPGLPTAESQELLTFKDISIDFTQEEWGQLAPAHQNLYREVMLENY<br>SNLVSVGYQLSKPSVISQLEKGEEPW |
| 696 | SUMO1_HUMAN | EGEYIKLKVIGQDSSEIHFKVKMTTHLKKLKESYCQRQGVPMNSLRFLFEGQRI<br>ADNHTPKELGMEEEDVIEVYQEQTGG |
| 697 | ZNF12_HUMAN | NKSLGPVSFKDVAVDFTQEEWQQLDPEQKITYRDVMLENYSNLVSVGYHIIKPD<br>VISKLEQGEEPWIVEGEFLLQSYPDE |
| 698 | ZN169_HUMAN | SPGLLTTRKEALMAFRDVAVAFTQKEWKLLSSAQRTLYREVMLENYSHLVSLGI<br>AFSKPKLIEQLEQGDEPWREENEHLL |
| 699 | ZN433_HUMAN | MFQDSVAFEDVAVTFTQEEWALLDPSQKNLCRDVMQETFRNLASIGKKWKPQNI<br>YVEYENLRRNLRIVGERLFESKEGHQ |
| 700 | SUMO3_HUMAN | ENDHINLKVAGQDGSVVQFKIKRHTPLSKLMKAYCERQGLSMRQIRFREDGQPI<br>NETDTPAQLEMEDEDTIDVEQQQTGG |
| 701 | ZNF98_HUMAN | PGPLGSLEMGVLTFRDVALEFSLEEWQCLDTAQQNLYRNVMLENYRNLVFVGIA<br>ASKPDLITCLEQGKEPWNVKRHEMVT |
| 702 | ZN175_HUMAN | LSQKPQVLGPEKQDGSCEASVSFEDVTVDFSREEWQQLDPAQRCLYRDVMLELY<br>SHLFAVGYHIPNPEVIFRMLKEKEPR |
| 703 | ZN347_HUMAN | ALTQGQVTFRDVAIEFSQEEWTCLDPAQRTLYRDVMLENYRNLASLGISCFDLS<br>IISMLEQGKEPFTLESQVQIAGNPDG |
| 704 | ZNF25_HUMAN | NKFQGPVTLKDVIVEFTKEEWKLLTPAQRTLYKDVMLENYSHLVSVGYHVNKPN<br>AVFKLKQGKEPWILEVEFPHRGFPED |
| 705 | ZN519_HUMAN | ELLTFRDVAIEFSPEEWKCLDPAQQNLYRDVMLENYRNLVSLAVYSYYNQGILP<br>EQGIQDSFKKATLGRYGSCGLENICL |
| 706 | Z585B_HUMAN | SPQKSSALAPEDHGSSYEGSVSFRDVAIDFSREEWRHLDLSQRNLYRDVMLETY<br>SHLLSVGYQVPKPEVVMLEQGKEPWA |
| 707 | ZIM3_HUMAN | NNSQGRVTFEDVTVNFTQGEWQRLNPEQRNLYRDVMLENYSNLVSVGQGETTKP<br>DVILRLEQGKEPWLEEEEVLGSGRAE |
| 708 | ZN517_HUMAN | AMALPMPGPQEAVVFEDVAVYFTRIEWSCLAPDQQALYRDVMLENYGNLASLGF<br>LVAKPALISLLEQGEEPGALILQVAE |
| 709 | ZN846_HUMAN | DSSQHLVTFEDVAVDFTQEEWTLLDQAQRDLYRDVMLENYKNLIILAGSELFKR<br>SLMSGLEQMEELRTGVTGVLQELDLQ |

TABLE 18-continued

Sequence listing.

| SEQ | Description | Sequence |
|-----|-------------|----------|
| 710 | ZN230_HUMAN | TTFKEAVTFKDVAVFFTEEELGLLDPAQRKLYQDVMLENFTNLLSVGHQPFHPF<br>HFLREEKFWMMETATQREGNSGGKTI |
| 711 | ZNF66_HUMAN | GPLQFRDVAIEFSLEEWHCLDMAQRNLYRDVMLENYRNLVFLGIVVSKPDLITH<br>LEQGKKPSTMQRHEMVANPSVLCSHF |
| 712 | ZFP1_HUMAN | NKSQGSVSFTDVTVDFTQEEWEQLDPSQRILYMDVMLENYSNLLSVEVWKADDQ<br>MERDHRNPDEQARQFLILKNQTPIEE |
| 713 | ZN713_HUMAN | EEEEMNDGSQMVRSQESLTFQDVAVDFTREEWDQLYPAQKNLYRDVMLENYRNL<br>VALGYQLCKPEVIAQLELEEEWVIER |
| 714 | ZN816_HUMAN | EEATKKSKEKEPGMALPQGRLTFRDVAIEFSLEEWKCLNPAQRALYRAVMLENY<br>RNLEFVDSSLKSMMEFSSTRHSITGE |
| 715 | ZN426_HUMAN | EKTPAGRIVADCLTDCYQDSVTFDDVAVDFTQEEWTLLDSTQRSLYSDVMLENY<br>KNLATVGGQIIKPSLISWLEQEESRT |
| 716 | ZN674_HUMAN | AMSQESLTFKDVFVDFTLEEWQQLDSAQKNLYRDVMLENYSHLVSVGHLVGKPD<br>VIFRLGPGDESWMADGGTPVRTCAGE |
| 717 | ZN627_HUMAN | DSVAFEDVAVNFTLEEWALLDPSQKNLYRDVMRETFRNLASVGKQWEDQNIEDP<br>FKIPRRNISHIPERLCESKEGGQGEE |
| 718 | ZNF20_HUMAN | MFQDSVAFEDVAVSFTQEEWALLDPSQKNLYRDVMQETFKNLTSVGKTWKVQNI<br>EDEYKNPRRNLSLMREKLCESKESHH |
| 719 | Z587B_HUMAN | AVVATLRLSAQGTVTFEDVAVKFTQEEWNLLSEAQRCLYRDVTLENLALMSSLG<br>CWCGVEDEAAPSKQSIYIQRETQVRT |
| 720 | ZN316_HUMAN | EEEEEDEDEDDLLTAGCQELVTFEDVAVYFSLEEWERLEADQRGLYQEVMQENY<br>GILVSLGYPIPKPDLIFRLEQGEEPW |
| 721 | ZN233_HUMAN | TKFQEMVTFKDVAVVFTREELGLLDLAQRKLYQDVMLENFRNLLSVGYQPFKLD<br>VILQLGKEDKLRMMETEIQGDGCSGH |
| 722 | ZN611_HUMAN | EEAAQKRKGKEPGMALPQGRLTFRDVAIEFSLAEWKCLNPSQRALYREVMLENY<br>RNLEAVDISSKCMMKEVLSTGQGNTE |
| 723 | ZN556_HUMAN | DTVVFEDVVVDFTLEEWALLNPAQRKLYRDVMLETFKHLASVDNEAQLKASGSI<br>SQQDTSGEKLSLKQKIEKFTRKNIWA |
| 724 | ZN234_HUMAN | TTFKEGLTFKDVAVVFTEEELGLLDPVQRNLYQDVMLENFRNLLSVGHHPFKHD<br>VFLLEKEKKLDIMKTATQRKGKSADK |
| 725 | ZN560_HUMAN | SALQQEFWKIQTSNGIQMDLVTFDSVAVEFTQEEWTLLDPAQRNLYSDVMLENY<br>KNLSSVGYQLFKPSLISWLEEEEELS |
| 726 | ZNF77_HUMAN | DCVIFEEVAVNFTPEEWALLDHAQRSLYRDVMLETCRNLASLDCYIYVRTSGSS<br>SQRDVFGNGISNDEEIVKFTGSDSWS |
| 727 | ZN682_HUMAN | ELLTFRDVTIEFSLEEWEFLNPAQQSLYRKVMLENYRNLVSLGLTVSKPELISR<br>LEQRQEPWNVKRHETIAKPPAMSSHY |
| 728 | ZN614_HUMAN | IKTQESLTLEDVAVEFSWEEWQLLDTAQKNLYRDVMVENYNHLVSLGYQTSKPD<br>VLSKLAHGQEPWTTDAKIQNKNCPGI |
| 729 | ZN785_HUMAN | PAHVPGEAGPRRTRESRPGAVSFADVAVYFSPEEWECLRPAQRALYRDVMRETF<br>GHLGALGFSVPKPAFISWVEGEVEAW |
| 730 | ZN445_HUMAN | GCPGDQVTPTRSLTAQLQETMTFKDVEVTFSQDEWGWLDSAQRNLYRDVMLENY<br>RNMASLVGPFTKPALISWLEAREPWG |
| 731 | ZFP30_HUMAN | ARDLVMFRDVAVDFSQEEWECLNSYQRNLYRDVILENYSNLVSLAGCSISKPDV<br>ITLLEQGKEPWMVVRDEKRRWTLDLE |
| 732 | ZN225_HUMAN | TTLKEAVTFKDVAVVFTEEELRLLDLAQRKLYREVMLENFRNLLSVGHQSLHRD<br>TFHFLKEEKFWMMETATQREGNLGGK |
| 733 | ZN551_HUMAN | SPPSPRSSMAAVALRDSAQGMTFEDVAIYFSQEEWELLDESQRFLYCDVMLENF<br>AHVTSLGYCHGMENEAIASEQSVSIQ |
| 734 | ZN610_HUMAN | DEEAQKRKAKESGMALPQGRLTFMDVAIEFSQEEWKSLDPGQRALYRDVMLENY<br>RNLVFLGICLPDLSIISMLKQRREPL |

TABLE 18-continued

Sequence listing.

| SEQ | Description | Sequence |
|---|---|---|
| 735 | ZN528_HUMAN | ALTQGPLKFMDVAIEFSQEEWKCLDPAQRTLYRDVMLENYRNLVSLGICLPDLS VTSMLEQKRDPWTLQSEEKIANDPDG |
| 736 | ZN284_HUMAN | TMFKEAVTFKDVAVVFTEEELGLLDVSQRKLYRDVMLENFRNLLSVGHQLSHRD TFHFQREEKFWIMETATQREGNSGGK |
| 737 | ZN418_HUMAN | QGTVAFEDVAVNFSQEEWSLLSEVQRCLYHDVMLENWVLISSLGCWCGSEDEEA PSKKSISIQRVSQVSTPGAGVSPKKA |
| 738 | MPP8_HUMAN | AEAFGDSEEDGEDVFEVEKILDMKTEGGKVLYKVRWKGYTSDDDTWEPEIHLED CKEVLLEFRKKIAENKAKAVRKDIQR |
| 739 | ZN490_HUMAN | VLQMQNSEHHGQSIKTQTDSISLEDVAVNFTLEEWALLDPGQRNIYRDVMRATE KNLACIGEKWKDQDIEDEHKNQGRNL |
| 740 | ZN805_HUMAN | AMALTDPAQVSVTFDDVAVTFTQEEWGQLDLAQRTLYQEVMLENCGLLVSLGCP VPRPELIYHLEHGQEPWTRKEDLSQG |
| 741 | Z780B_HUMAN | VHGSVTFRDVAIDFSQEEWECLQPDQRTLYRDVMLENYSHLISLGSSISKPDVI TLLEQEKEPWIVVSKETSRWYPDLES |
| 742 | ZN763_HUMAN | DPVACEDVAVNFTQEEWALLDISQRKLYREVMLETFRNLTSIGKKWKDQNIEYE YQNPRRNFRSLIEGNVNEIKEDSHCG |
| 743 | ZN285_HUMAN | IKFQERVTFKDVAVVFTKEELALLDKAQINLYQDVMLENFRNLMLVRDGIKNNI LNLQAKGLSYLSQEVLHCWQIWKQRI |
| 744 | ZNF85_HUMAN | GPLTFRDVAIEFSLKEWQCLDTAQRNLYRNVMLENYRNLVFLGITVSKPDLITC LEQGKEAWSMKRHEIMVAKPTVMCSH |
| 745 | ZN223_HUMAN | TMSKEAVTFKDVAVVFTEEELGLLDLAQRKLYRDVMLENFRNLLSVGHQPFHRD TFHFLREEKFWMMDIATQREGNSGGK |
| 746 | ZNF90_HUMAN | GPLEFRDVAIEFSLEEWHCLDTAQQNLYRDVMLENYRHLVFLGIVVTKPDLITC LEQGKKPFTVKRHEMIAKSPVMCFHF |
| 747 | ZN557_HUMAN | GHTEGGELVNELLKSWLKGLVTFEDVAVEFTQEEWALLDPAQRTLYRDVMLENC RNLASLGNQVDKPRLISQLEQEDKVM |
| 748 | ZN425_HUMAN | AEPASVTVTFDDVALYFSEQEWEILEKWQKQMYKQEMKTNYETLDSLGYAFSKP DLITWMEQGRMLLISEQGCLDKTRRT |
| 749 | ZN229_HUMAN | HSQASAISQDREEKIMSQEPLSFKDVAVVFTEEELELLDSTQRQLYQDVMQENF RNLLSVGERNPLGDKNGKDTEYIQDE |
| 750 | ZN606_HUMAN | GSLEEGRRATGLPAAQVQEPVTFKDVAVDFTQEEWGQLDLVQRTLYRDVMLETY GHLLSVGNQIAKPEVISLLEQGEEPW |
| 751 | ZN155_HUMAN | TTFKEAVTFKDVAVVFTEEELGLLDPAQRKLYRDVMLENFRNLLSVGHQPFHQD TCHFLREEKFWMMGTATQREGNSGGK |
| 752 | ZN222_HUMAN | AKLYEAVTFKDVAVIFTEEELGLLDPAQRKLYRDVMLENFRNLLSVGGKIQTEM ETVPEAGTHEEFSCKQIWEQIASDLT |
| 753 | ZN442_HUMAN | RSDLFLPDSQTNEERKQYDSVAFEDVAVNFTQEEWALLGPSQKSLYRDVMWETI RNLDCIGMKWEDTNIEDQHRNPRRSL |
| 754 | ZNF91_HUMAN | PGTPGSLEMGLLTFRDVAIEFSPEEWQCLDTAQQNLYRNVMLENYRNLAFLGIA LSKPDLITYLEQGKEPWNMKQHEMVD |
| 755 | ZN135_HUMAN | TPGVRVSTDPEQVTFEDVVVGFSQEEWGQLKPAQRTLYRDVMLDTFRLLVSVGH WLPKPNVISLLEQEAELWAVESRLPQ |
| 756 | ZN778_HUMAN | EQTQAAGMVAGWLINCYQDAVTFDDVAVDFTQEEWTLLDPSQRDLYRDVMLENY ENLASVEWRLKTKGPALRQDRSWFRA |
| 757 | RYBP_HUMAN | PSEANSIQSANATTKTSETNHTSRPRLKNVDRSTAQQLAVTVGNVTVIITDFKE KTRSSSTSSSTVTSSAGSEQQNQSSS |
| 758 | ZN534_HUMAN | ALTQGQLSFSDVAIEFSQEEWKCLDPGQKALYRDVMLENYRNLVSLGEDNVRPE ACICSGICLPDLSVTSMLEQKRDPWT |
| 759 | ZN586_HUMAN | AAAAALRAPAQSSVTFEDVAVNESLEEWSLLNEAQRCLYRDVMLETLTLISSLG CWHGGEDEAAPSKQSTCIHIYKDQGG |

TABLE 18-continued

Sequence listing.

| SEQ | Description | Sequence |
| --- | --- | --- |
| 760 | ZN567_HUMAN | AQGSVSFNDVTVDFTQEEWQHLDHAQKTLYMDVMLENYCHLISVGCHMTKPDVI LKLERGEEPWTSFAGHTCLEENWKAE |
| 761 | ZN440_HUMAN | DPVAFKDVAVNFTQEEWALLDISQRKLYREVMLETFRNLTSLGKRWKDQNIEYE HQNPRRNFRSLIEEKVNEIKDDSHCG |
| 762 | ZN583_HUMAN | SKDLVTFGDVAVNFSQEEWEWLNPAQRNLYRKVMLENYRSLVSLGVSVSKPDVI SLLEQGKEPWMVKKEGTRGPCPDWEY |
| 763 | ZN441_HUMAN | DSVAFEDVAINFTCEEWALLGPSQKSLYRDVMQETIRNLDCIGMIWQNHDIEED QYKDLRRNLRCHMVERACEIKDNSQC |
| 764 | ZNF43_HUMAN | GPLTEMDVAIEFCLEEWQCLDIAQQNLYRNVMLENYRNLVFLGIAVSKPDLITC LEQEKEPWEPMRRHEMVAKPPVMCSH |
| 765 | CBX5_HUMAN | QSNDIARGFERGLEPEKIIGATDSCGDLMFLMKWKDTDEADLVLAKEANVKCPQ IVIAFYEERLTWHAYPEDAENKEKET |
| 766 | ZN589_HUMAN | ALPAKDSAWPWEEKPRYLGPVTFEDVAVLFTEAEWKRLSLEQRNLYKEVMLENL RNLVSLAESKPEVHTCPSCPLAFGSQ |
| 767 | ZNF10_HUMAN | DAKSLTAWSRTLVTFKDVFVDFTREEWKLLDTAQQIVYRNVMLENYKNLVSLGY QLTKPDVILRLEKGEEPWLVEREIHQ |
| 768 | ZN563_HUMAN | DAVAFEDVAVNFTQEEWALLGPSQKNLYRYVMQETIRNLDCIRMIWEEQNTEDQ YKNPRRNLRCHMVERFSESKDSSQCG |
| 769 | ZN561_HUMAN | EKTKVERMVEDYLASGYQDSVTFDDVAVDFTPEEWALLDTTEKYLYRDVMLENY MNLASVEWEIQPRTKRSSLQQGELKN |
| 770 | ZN136_HUMAN | DSVAFEDVDVNFTQEEWALLDPSQKNLYRDVMWETMRNLASIGKKWKDQNIKDH YKHRGRNLRSHMLERLYQTKDGSQRG |
| 771 | ZN630_HUMAN | IESQEPVTFEDVAVDFTQEEWQQLNPAQKTLHRDVMLETYNHLVSVGCSGIKPD VIFKLEHGKDPWIIESELSRWIYPDR |
| 772 | ZN527_HUMAN | AVGLCKAMSQGLVTFRDVALDFSQEEWEWLKPSQKDLYRDVMLENYRNLVWLGL SISKPNMISLLEQGKEPWMVERKMSQ |
| 773 | ZN333_HUMAN | DKVEEEAMAPGLPTACSQEPVTFADVAVVFTPEEWVELDSTQRSLYRDVMLENY RNLASVADQLCKPNALSYLEERGEQW |
| 774 | Z324B_HUMAN | TFEDVAVYFSQEEWGLLDTAQRALYRHVMLENFTLVTSLGLSTSRPRVVIQLER GEEPWVPSGKDMTLARNTYGRLNSGS |
| 775 | ZN786_HUMAN | AEPPRLPLTFEDVAIYFSEQEWQDLEAWQKELYKHVMRSNYETLVSLDDGLPKP ELISWIEHGGEPFRKWRESQKSGNII |
| 776 | ZN709_HUMAN | DSVVFEDVAVNFTQEEWALLGPSQKKLYRDVMQETFVNLASIGENWEEKNIEDH KNQGRKLRSHMVERLCERKEGSQFGE |
| 777 | ZN792_HUMAN | AAAALRDPAQGCVTFEDVTIYFSQEEWVLLDEAQRLLYCDVMLENFALIASLGL ISFRSHIVSQLEMGKEPWVPDSVDMT |
| 778 | ZN599_HUMAN | AAPALALVSFEDVVVTFTGEEWGHLDLAQRTLYQEVMLETCRLLVSLGHPVPKP ELIYLLEHGQELWTVKRGLSQSTCAG |
| 779 | ZN613_HUMAN | IKSQESLTLEDVAVEFTWEEWQLLGPAQKDLYRDVMLENYSNLVSVGYQASKPD ALFKLEQGEPWTVENEIHSQICPEIK |
| 780 | ZF69B_HUMAN | GESLESRVTLGSLTAESQELLTFKDVSVDFTQEEWGQLAPAHRNLYREVMLENY GNLVSVGCQLSKPGVISQLEKGEEPW |
| 781 | ZN799_HUMAN | ASVALEDVAVNFTREEWALLGPCQKNLYKDVMQETIRNLDCVGMKWKDQNIEDQ YRYPRKNLRCRMLERFVESKDGTQCG |
| 782 | ZN569_HUMAN | TESQGTVTFKDVAIDFTQEEWKRLDPAQRKLYRNVMLENYNNLITVGYPFTKPD VIFKLEQEEEPWVMEEEVLRRHWQGE |
| 783 | ZN564_HUMAN | DSVASEDVAVNFTLEEWALLDPSQKKLYRDVMRETFRNLACVGKKWEDQSIEDW YKNQGRILRNHMEEGLSESKEYDQCG |
| 784 | ZN546_HUMAN | EETQGELTSSCGSKTMANVSLAFRDVSIDLSQEEWECLDAVQRDLYKDVMLENY SNLVALGYTIPKPDVITLLEQEKEPW |

TABLE 18-continued

| SEQ | Description | Sequence |
|---|---|---|
| | | Sequence listing. |
| 785 | ZFP92_HUMAN | AAILLTTRPKVPVSFEDVSVYFTKTEWKLLDLRQKVLYKRVMLENYSHLVSLGF SFSKPHLISQLERGEGPWVADIPRTW |
| 786 | YAF2_HUMAN | KDKVEKEKSEKETTSKKNSHKKTRPRLKNVDRSSAQHLEVTVGDLTVIITDFKE KTKSPPASSAASADQHSQSGSSSDNT |
| 787 | ZN723_HUMAN | GPLTFTDVAIKFSLEEWQFLDTAQQNLYRDVMLENYRNLVFLGVGVSKPDLITC LEQGKEPWNMKRHKMVAKPPVVCSHF |
| 788 | ZNF34_HUMAN | RKPNPQAMAALFLSAPPQAEVTFEDVAVYLSREEWGRLGPAQRGLYRDVMLETY GNLVSLGVGPAGPKPGVISQLERGDE |
| 789 | ZN439_HUMAN | LSLSPILLYTCEMFQDPVAFKDVAVNFTQEEWALLDISQKNLYREVMLETFWNL TSIGKKWKDQNIEYEYQNPRRNFRSV |
| 790 | ZFP57_HUMAN | AAGEPRSLLFFQKPVTFEDVAVNFTQEEWDCLDASQRVLYQDVMSETFKNLTSV ARIFLHKPELITKLEQEEEQWRETRV |
| 791 | ZNF19_HUMAN | AAMPLKAQYQEMVTFEDVAVHFTKTEWTGLSPAQRALYRSVMLENFGNLTALGY PVPKPALISLLERGDMAWGLEAQDDP |
| 792 | ZN404_HUMAN | ARVPLTFSDVAIDFSQEEWEYLNSDQRDLYRDVMLENYTNLVSLDFNFTTESNK LSSEKRNYEVNAYHQETWKRNKTENL |
| 793 | ZN274_HUMAN | ASRLPTAWSCEPVTFEDVTLGFTPEEWGLLDLKQKSLYREVMLENYRNLVSVEH QLSKPDVVSQLEEAEDFWPVERGIPQ |
| 794 | CBX3_HUMAN | SKKKRDAADKPRGFARGLDPERIIGATDSSGELMFLMKWKDSDEADLVLAKEAN MKCPQIVIAFYEERLTWHSCPEDEAQ |
| 795 | ZNF30_HUMAN | AHKYVGLQYHGSVTFEDVAIAFSQQEWESLDSSQRGLYRDVMLENYRNLVSMGH SRSKPHVIALLEQWKEPEVTVRKDGR |
| 796 | ZN250_HUMAN | AAARLLPVPAGPQPLSFQAKLTFEDVAVLLSQDEWDRLCPAQRGLYRNVMMETY GNVVSLGLPGSKPDIISQLERGEDPW |
| 797 | ZN570_HUMAN | AVGLLKAMYQELVTFRDVAVDFSQEEWDCLDSSQRHLYSNVMLENYRILVSLGL CFSKPSVILLLEQGKAPWMVKRELTK |
| 798 | ZN675_HUMAN | GLLTFRDVAIEFSLEEWQCLDTAQRNLYKNVILENYRNLVFLGIAVSKQDLITC LEQEKEPLTVKRHEMVNEPPVMCSHF |
| 799 | ZN695_HUMAN | GLLAFRDVALEFSPEEWECLDPAQRSLYRDVMLENYRNLISLGEDSFNMQFLFH SLAMSKPELIICLEARKEPWNVNTEK |
| 800 | ZN548_HUMAN | NLTEGRVVFEDVAIYFSQEEWGHLDEAQRLLYRDVMLENLALLSSLGSWHGAED EEAPSQQGFSVGVSEVTASKPCLSSQ |
| 801 | ZN132_HUMAN | GPAQHTSWPCGSAVPTLKSMVTFEDVAVYFSQEEWELLDAAQRHLYHSVMLENL ELVTSLGSWHGVEGEGAHPKQNVSVE |
| 802 | ZN738_HUMAN | SGYPGAERNLLEYSYFEKGPLTFRDVVIEFSQEEWQCLDTAQQDLYRKVMLENF RNLVFLGIDVSKPDLITCLEQGKDPW |
| 803 | ZN420_HUMAN | ARKLVMFRDVAIDFSQEEWECLDSAQRDLYRDVMLENYSNLVSLDLPSRCASKD LSPEKNTYETELSQWEMSDRLENCDL |
| 804 | ZN626_HUMAN | GPLQFRDVAIEFSLEEWHCLDTAQRNLYRNVMLENYSNLVFLGITVSKPDLITC LEQGRKPLTMKRNEMIAKPSVMCSHF |
| 805 | ZN559_HUMAN | VAGWLTNYSQDSVTFEDVAVDFTQEEWTLLDQTQRNLYRDVMLENYKNLVAVDW ESHINTKWSAPQQNFLQGKTSSVVEM |
| 806 | ZN460_HUMAN | AAAWMAPAQESVTFEDVAVTFTQEEWGQLDVTQRALYVEVMLETCGLLVALGDS TKPETVEPIPSHLALPEEVSLQEQLA |
| 807 | ZN268_HUMAN | VLEWLFISQEQPKITKSWGPLSFMDVFVDFTWEEWQLLDPAQKCLYRSVMLENY SNLVSLGYQHTKPDIIFKLEQGEELC |
| 808 | ZN304_HUMAN | AAAVLMDRVQSCVTFEDVFVYFSREEWELLEEAQRFLYRDVMLENFALVATLGF WCEAEHEAPSEQSVSVEGVSQVRTAE |
| 809 | ZIM2_HUMAN | AGSQFPDFKHLGTFLVFEELVTFEDVLVDESPEELSSLSAAQRNLYREVMLENY RNLVSLGHQFSKPDIISRLEEEESYA |

TABLE 18-continued

| | Sequence listing. | |
|---|---|---|
| SEQ | Description | Sequence |
| 810 | ZN605_HUMAN | IQSQISFEDVAVDFTLEEWQLLNPTQKNLYRDVMLENYSNLVFLEVWLDNPKMW LRDNQDNLKSMERGHKYDVFGKIFNS |
| 811 | ZN844_HUMAN | DLVAFEDVAVNFTQEEWSLLDPSQKNLYREVMQETLRNLASIGEKWKDQNIEDQ YKNPRNNLRSLLGERVDENTEENHCG |
| 812 | SUMO5_HUMAN | KDEDIKLRVIGQDSSEIHFKVKMTTPLKKLKKSYCQRQGVPVNSLRFLFEGQRI ADNHTPEELGMEEEDVIEVYQEQIGG |
| 813 | ZN101_HUMAN | DSVAFEDVAVNFTQEEWALLSPSQKNLYRDVTLETFRNLASVGIQWKDQDIENL YQNLGIKLRSLVERLCGRKEGNEHRE |
| 814 | ZN783_HUMAN | RNFWILRLPPGSKGEAPKVPVTFDDVAVYFSELEWGKLEDWQKELYKHVMRGNY ETLVSLDYAISKPDILTRIERGEEPC |
| 815 | ZN417_HUMAN | AAAAPRRPTQQGTVTFEDVAVNFSQEEWCLLSEAQRCLYRDVMLENLALISSLG CWCGSKDEEAPCKQRISVQRESQSRT |
| 816 | ZN182_HUMAN | SGEDSGSFYSWQKAKREQGLVTFEDVAVDFTQEEWQYLNPPQRTLYRDVMLETY SNLVFVGQQVTKPNLILKLEVEECPA |
| 817 | ZN823_HUMAN | DSVAFEDVAVNFTQEEWALLGPSQKSLYRNVMQETIRNLDCIEMKWEDQNIGDQ CQNAKRNLRSHTCEIKDDSQCGETFG |
| 818 | ZN177_HUMAN | AAGWLTTWSQNSVTFQEVAVDFSQEEWALLDPAQKNLYKDVMLENFRNLASVGY QLCRHSLISKVDQEQLKTDERGILQG |
| 819 | ZN197_HUMAN | ENPRNQLMALMLLTAQPQELVMFEEVSVCFTSEEWACLGPIQRALYWDVMLENY GNVTSLEWETMTENEEVTSKPSSSQR |
| 820 | ZN717_HUMAN | LETYNSLVSLQELVSFEEVAVHFTWEEWQDLDDAQRTLYRDVMLETYSSLVSLG HCITKPEMIFKLEQGAEPWIVEETPN |
| 821 | ZN669_HUMAN | RHFRRPEPCREPLASPIQDSVAFEDVAVNFTQEEWALLDSSQKNLYREVMQETC RNLASVGSQWKDQNIEDHFEKPGKDI |
| 822 | ZN256_HUMAN | AAAELTAPAQGIVTFEDVAVYFSWKEWGLLDEAQKCLYHDVMLENLTLTTSLGG SGAGDEEAPYQQSTSPQRVSQVRIPK |
| 823 | ZN251_HUMAN | AATFQLPGHQEMPLTFQDVAVYFSQAEGRQLGPQQRALYRDVMLENYGNVASLG FPVPKPELISQLEQGKELWVLNLLGA |
| 824 | CBX4_HUMAN | RSEAGEPPSSLQVKPETPASAAVAVAAAAPTTTAEKPPAEAQDEPAESLSEFK PFFGNIIITDVTANCLTVTFKEYVTV |
| 825 | PCGF2_HUMAN | HRTTRIKITELNPHLMCALCGGYFIDATTIVECLHSFCKTCIVRYLETNKYCPM CDVQVHKTRPLLSIRSDKTLQDIVYK |
| 826 | CDY2_HUMAN | ASQEFEVEAIVDKRQDKNGNTQYLVRWKGYDKQDDTWEPEQHLMNCEKCVHDEN RRQTEKQKKLTWTTTSRIFSNNARRR |
| 827 | CDYL2_HUMAN | ASGDLYEVERIVDKRKNKKGKWEYLIRWKGYGSTEDTWEPEHHLLHCEEFIDEF NGLHMSKDKRIKSGKQSSTSKLLRDS |
| 828 | HERC2_HUMAN | TLIRKADLENHNKDGGFWTVIDGKVYDIKDFQTQSLTGNSILAQFAGEDPVVAL EAALQFEDTRESMHAFCVGQYLEPDQ |
| 829 | ZN562_HUMAN | EKTKIGTMVEDHRSNSYQDSVTFDDVAVEFTPEEWALLDTTQKYLYRDVMLENY MNLASVDFFFCLTSEWEIQPRTKRSS |
| 830 | ZN461_HUMAN | AHELVMERDVAIDVSQEEWECLNPAQRNLYKEVMLENYSNLVSLGLSVSKPAVI SSLEQGKEPWMVVREETGRWCPGTWK |
| 831 | Z324A_HUMAN | AFEDVAVYFSQEEWGLLDTAQRALYRRVMLDNFALVASLGLSTSRPRVVIQLER GEEPWVPSGTDTTLSRTTYRRRNPGS |
| 832 | ZN766_HUMAN | AQLRRGHLTFRDVAIEFSQEEWKCLDPVQKALYRDVMLENYRNLVSLGICLPDL SIISMMKQRTEPWTVENEMKVAKNPD |
| 833 | ID2_HUMAN | SDHSLGISRSKTPVDDPMSLLYNMNDCYSKLKELVPSIPQNKKVSKMEILQHVI DYILDLQIALDSHPTIVSLHHQRPGQ |
| 834 | TOX_HUMAN | KDPNEPQKPVSAYALFFRDTQAAIKGQNPNATFGEVSKIVASMWDGLGEEQKQV YKKKTEAAKKEYLKQLAAYRASLVSK |

TABLE 18-continued

| | | Sequence listing. | |
|---|---|---|
| SEQ | Description | Sequence |
| 835 | ZN274_HUMAN | QEEKQEDAAICPVTVLPEEPVTFQDVAVDFSREEWGLLGPTQRTEYRDVMLETF<br>GHLVSVGWETTLENKELAPNSDIPEE |
| 836 | SCMH1_HUMAN | DASRLSGRDPSSWTVEDVMQFVREADPQLGPHADLFRKHEIDGKALLLLRSDMM<br>MKYMGLKLGPALKLSYHIDRLKQGKF |
| 837 | ZN214_HUMAN | AVTFEDVTIIFTWEEWKFLDSSQKRLYREVMWENYTNVMSVENWNESYKSQEEK<br>FRYLEYENFSYWQGWWNAGAQMYENQ |
| 838 | CBX7_HUMAN | ELSAIGEQVFAVESIRKKRVRKGKVEYLVKWKGWPPKYSTWEPEEHILDPRLVM<br>AYEEKEERDRASGYRKRGPKPKRLLL |
| 839 | ID1_HUMAN | GGAGARLPALLDEQQVNVLLYDMNGCYSRLKELVPTLPQNRKVSKVEILQHVID<br>YIRDLQLELNSESEVGTPGGRGLPVR |
| 840 | CREM_HUMAN | VVMAASPGSLHSPQQLAEEATRKRELRLMKNREAAKECRRRKKEYVKCLESRVA<br>VLEVQNKKLIEELETLKDICSPKTDY |
| 841 | SCX_HUMAN | GGGPGGGRPGREPRQRHTANARERDRTNSVNTAFTALRTLIPTEPADRKLSKIET<br>LRLASSYISHLGNVLLAGEACGDGQP |
| 842 | ASCL1_HUMAN | SGFGYSLPQQQPAAVARRNERERNRVKLVNLGFATLREHVPNGAANKKMSKVET<br>LRSAVEYIRALQQLLDEHDAVSAAFQ |
| 843 | ZN764_HUMAN | APLPPRDPNGAGPEWREPGAVSFADVAVYFCREEWGCLRPAQRALYRDVMRETY<br>GHLSALGIGGNKPALISWVEEEAELW |
| 844 | SCML2_HUMAN | KQGFSKDPSTWSVDEVIQFMKHTDPQISGPLADLFRQHEIDGKALFLLKSDVMM<br>KYMGLKLGPALKLCYYIEKLKEGKYS |
| 845 | TWST1_HUMAN | SGGGSPQSYEELQTQRVMANVRERQRTQSLNEAFAALRKIIPTLPSDKLSKIQT<br>LKLAARYIDFLYQVLQSDELDSKMAS |
| 846 | CREB1_HUMAN | IAPGVVMASSPALPTQPAEEAARKREVRLMKNREAARECRRKKKEYVKCLENRV<br>AVLENQNKTLIEELKALKDLYCHKSD |
| 847 | TERF1_HUMAN | SRIPVSKSQPVTPEKHRARKRQAWLWEEDKNLRSGVRKYGEGNWSKILLHYKEN<br>NRTSVMLKDRWRTMKKLKLISSDSED |
| 848 | ID3_HUMAN | SLAIARGRGKGPAAEEPLSLLDDMNHCYSRLRELVPGVPRGTQLSQVEILQRVI<br>DYILDLQVVLAEPAPGPPDGPHLPIQ |
| 849 | CBX8_HUMAN | GSGPPSSGGGLYRDMGAQGGRPSLIARIPVARILGDPEEESWSPSLTNLEKVVV<br>TDVTSNFLTVTIKESNTDQGFFKEKR |
| 850 | CBX4_HUMAN | ELPAVGEHVFAVESIEKKRIRKGRVEYLVKWRGWSPKYNTWEPEENILDPRLLI<br>AFQNRERQEQLMGYRKRGPKPKPLVV |
| 851 | GSX1_HUMAN | VDSSSNQLPSSKRMRTAFTSTQLLELEREFASNMYLSRLRRIEIATYLNLSEKQ<br>VKIWFQNRRVKHKKEGKGSNHRGGGG |
| 852 | NKX22_HUMAN | TPGGGGDAGKKRKRRVLFSKAQTYELERRFRQQRYLSAPEREHLASLIRLTPTQ<br>VKIWFQNHRYKMKRARAEKGMEVTPL |
| 853 | ATF1_HUMAN | QTVVMTSPVTLTSQTTKTDDPQLKREIRLMKNREAARECRRKKKEYVKCLENRV<br>AVLENQNKTLIEELKTLKDLYSNKSV |
| 854 | TWST2_HUMAN | KGSPSAQSFEELQSQRILANVRERQRTQSLNEAFAALRKIIPTLPSDKLSKIQT<br>LKLAARYIDFLYQVLQSDEMDNKMTS |
| 855 | ZNF17_HUMAN | NLTEDYMVFEDVAIHFSQEEWGILNDVQRHLHSDVMLENFALLSSVGCWHGAKD<br>EEAPSKQCVSVGVSQVTTLKPALSTQ |
| 856 | TOX3_HUMAN | KDPNEPQKPVSAYALFFRDTQAAIKGQNPNATFGEVSKIVASMWDSLGEEQKQV<br>YKRKTEAAKKEYLKALAAYRASLVSK |
| 857 | TOX4_HUMAN | KDPNEPQKPVSAYALFFRDTQAAIKGQNPNATFGEVSKIVASMWDSLGEEQKQV<br>YKRKTEAAKKEYLKALAAYKDNQECQ |
| 858 | ZMYM3_HUMAN | LDGSTWDFCSEDCKSKYLLWYCKAARCHACKRQGKLLETIHWRGQIRHFCNQQC<br>LLRFYSQQNQPNLDTQSGPESLLNSQ |

TABLE 18-continued

| SEQ | Description | Sequence |
|---|---|---|
| 859 | 12BP1_HUMAN | ASVQASRRQWCYLCDLPKMPWAMVWDESEAVCRGCVNFEGADRIELLIDAARQL<br>KRSHVLPEGRSPGPPALKHPATKDLA |
| 860 | RHXF1_HUMAN | MEGPQPENMQPRTRRTKFTLLQVEELESVFRHTQYPDVPTRRELAENLGVTEDK<br>VRVWFKNKRARCRRHQRELMLANELR |
| 861 | SSX2_HUMAN | PKIMPKKPAEEGNDSEEVPEASGPQNDGKELCPPGKPTTSEKIHERSGPKRGEH<br>AWTHRLRERKQLVIYEEISDPEEDDE |
| 862 | 12BPL_HUMAN | SAAQVSSSRRQSCYLCDLPRMPWAMIWDFSEPVCRGCVNYEGADRIEFVIETAR<br>QLKRAHGCFQDGRSPGPPPPVGVKTV |
| 863 | ZN680_HUMAN | PGPPGSLEMGPLTFRDVAIEFSLEEWQCLDTAQRNLYRKVMFENYRNLVFLGIA<br>VSKPHLITCLEQGKEPWNRKRQEMVA |
| 864 | CBX1_HUMAN | NKKKVEEVLEEEEEYVVEKVLDRRVVKGKVEYLLKWKGFSDEDNTWEPEENLD<br>CPDLIAEFLQSQKTAHETDKSEGGKR |
| 865 | TRI68_HUMAN | LANVVEKVRLLRLHPGMGLKGDLCERHGEKLKMFCKEDVLIMCEACSQSPEHEA<br>HSVVPMEDVAWEYKWELHEALEHLKK |
| 866 | HXA13_HUMAN | VVSHPSDASSYRRGRKKRVPYTKVQLKELEREYATNKFITKDKRRRISATTNLS<br>ERQVTIWFQNRRVKEKKVINKLKTTS |
| 867 | PHC3_HUMAN | ENSDLLPVAQTEPSIWTVDDVWAFIHSLPGCQDIADEFRAQEIDGQALLLLKED<br>HLMSAMNIKLGPALKICARINSLKES |
| 868 | TCF24_HUMAN | AGPGGGSRSGSGRPAAANAARERSRVQTLRHAFLELQRTLPSVPPDTKLSKLDV<br>LLLATTYIAHLTRSLQDDAEAPADAG |
| 869 | CBX3_HUMAN | QNGKSKKVEEAEPEEFVVEKVLDRRVVNGKVEYFLKWKGFTDADNTWEPEENLD<br>CPELIEAFLNSQKAGKEKDGTKRKSL |
| 870 | HXB13_HUMAN | QHPPDACAFRRGRKKRIPYSKGQLRELEREYAANKFITKDKRRKISAATSLSER<br>QITIWFQNRRVKEKKVLAKVKNSATP |
| 871 | HEY1_HUMAN | SMSPTTSSQILARKRRRGIIEKRRRDRINNSLSELRRLVPSAFEKQGSAKLEKA<br>EILQMTVDHLKMLHTAGGKGYFDAHA |
| 872 | PHC2_HUMAN | LVGMGHHFLPSEPTKWNVEDVYEFIRSLPGCQEIAEEFRAQEIDGQALLLLKED<br>HLMSAMNIKLGPALKIYARISMLKDS |
| 873 | ZNF81_HUMAN | PANEDAPQPGEHGSACEVSVSFEDVTVDFSREEWQQLDSTQRRLYQDVMLENYS<br>HLLSVGFEVPKPEVIFKLEQGEGPWT |
| 874 | FIGLA_HUMAN | GYSSTENLQLVLERRRVANAKERERIKNLNRGFARLKALVPFLPQSRKPSKVDI<br>LKGATEYIQVLSDLLEGAKDSKKQDP |
| 875 | SAM11_HUMAN | EEAPAPEDVTKWTVDDVCSFVGGLSGCGEYTRVFREQGIDGETLPLLTEEHLLT<br>NMGLKLGPALKIRAQVARRLGRVFYV |
| 876 | KMT2B_HUMAN | GGTLAHTPRRSLPSHHGKKMRMARCGHCRGCLRVQDCGSCVNCLDKPKFGGPNT<br>KKQCCVYRKCDKIEARKMERLAKKGR |
| 877 | HEY2_HUMAN | LNSPTTTSQIMARKKRRGIIEKRRRDRINNSLSELRRLVPTAFEKQGSAKLEKA<br>EILQMTVDHLKMLQATGGKGYFDAHA |
| 878 | JDP2_HUMAN | QPVKSELDEEEERRKRRREKNKVAAARCRNKKKERTEFLQRESERLELMNAELK<br>TQIEELKQERQQLILMLNRHRPTCIV |
| 879 | HXC13_HUMAN | LQPEVSSYRRGRKKRVPYTKVQLKELEKEYAASKFITKEKRRRISATTNLSERQ<br>VTIWFQNRRVKEKKVVSKSKAPHLHS |
| 880 | ASCL4_HUMAN | LPVPLDSAFEPAFLRKRNERERQRVRCVNEGYARLRDHLPRELADKRLSKVETL<br>RAAIDYIKHLQELLERQAWGLEGAAG |
| 881 | HHEX_HUMAN | SPFLQRPLHKRKGGQVRESNDQTIELEKKFETQKYLSPPERKRLAKMLQLSERQ<br>VKTWFQNRRAKWRRLKQENPQSNKKE |
| 882 | HERC2_HUMAN | IAIATGSLHCVCCTEDGEVYTWGDNDEGQLGDGTTNAIQRPRLVAALQGKKVNR<br>VACGSAHTLAWSTSKPASAGKLPAQV |

TABLE 18-continued

Sequence listing.

| SEQ | Description | Sequence |
|-----|-------------|----------|
| 883 | GSX2_HUMAN | GGSDASQVPNGKRMRTAFTSTQLLELEREFSSNMYLSRLRRIEIATYLNLSEKQ VKIWFQNRRVKHKKEGKGTQRNSHAG |
| 884 | BIN1_HUMAN | RLDLPPGFMFKVQAQHDYTATDTDELQLKAGDVVLVIPFQNPEEQDEGWLMGVK ESDWNQHKELEKCRGVFPENFTERVP |
| 885 | ETV7_HUMAN | GICKLPGRLRIQPALWSREDVLHWLRWAEQEYSLPCTAEHGFEMNGRALCILTK DDFRHRAPSSGDVLYELLQYIKTQRR |
| 886 | ASCL3_HUMAN | PNYRGCEYSYGPAFTRKRNERERQRVKCVNEGYAQLRHHLPEEYLEKRLSKVET LRAAIKYINYLQSLLYPDKAETKNNP |
| 887 | PHC1_HUMAN | LHGINPVFLSSNPSRWSVEEVYEFIASLQGCQEIAEEFRSQEIDGQALLLLKEE HLMSAMNIKLGPALKICAKINVLKET |
| 888 | OTP_HUMAN | QAGQQQGQQKQKRHRTRFTPAQLNELERSFAKTHYPDIFMREELALRIGLTESR VQVWFQNRRAKWKKRKKTTNVFRAPG |
| 889 | 12BP2_HUMAN | AAAVAVAAASRRQSCYLCDLPRMPWAMIWDFTEPVCRGCVNYEGADRVEFVIET ARQLKRAHGCFPEGRSPPGAAASAAA |
| 890 | VGLL2_HUMAN | FSSQTPASIKEEEGSPEKERPPEAEYINSRCVLFTYFQGDISSVVDEHFSRALS QPSSYSPSCTSSKAPRSSGPWRDCSF |
| 891 | HXA11_HUMAN | DKAGGSSGQRTRKKRCPYTKYQIRELEREFFFSVYINKEKRLQLSRMLNLTDRQ VKIWFQNRRMKEKKINRDRLQYYSAN |
| 892 | PDLI4_HUMAN | GAPLSGLQGLPECTRCGHGIVGTIVKARDKLYHPECFMCSDCGLNLKQRGYFFL DERLYCESHAKARVKPPEGYDVVAVY |
| 893 | ASCL2_HUMAN | RRPATAETGGGAAAVARRNERERNRVKLVNLGFQALRQHVPHGGASKKLSKVET LRSAVEYIRALQRLLAEHDAVRNALA |
| 894 | CDX4_HUMAN | TVQVTGKTRTKEKYRVVYTDHQRLELEKEFHCNRYITIQRKSELAVNLGLSERQ VKIWFQNRRAKERKMIKKKISQFENS |
| 895 | ZN860_HUMAN | EEAAQKRKEKEPGMALPQGHLTFRDVAIEFSLEEWKCLDPTQRALYRAMMLENY RNLHSVDISSKCMMKKESSTAQGNTE |
| 896 | LMBL4_HUMAN | DIRASQVARWTVDEVAEFVQSLLGCEEHAKCFKKEQIDGKAFLLLTQTDIVKVM KIKLGPALKIYNSILMFRHSQELPEE |
| 897 | PDIP3_HUMAN | LSPLEGTKMTVNNLHPRVTEEDIVELFCVCGALKRARLVHPGVAEVVFVKKDDA ITAYKKYNNRCLDGQPMKCNLHMNGN |
| 898 | NKX25_HUMAN | DNAERPRARRRRKPRVLESQAQVYELERRFKQQRYLSAPERDQLASVLKLTSTQ VKIWFQNRRYKCKRQRQDQTLELVGL |
| 899 | CEBPB_HUMAN | SQVKSAKKTVDKHSDEYKIRRERNNIAVRKSRDKAKMRNLETQHKVLELTAEN ERLQKKVEQLSRELSTLRNLFKQLPE |
| 900 | ISL1_HUMAN | KRDYIRLYGIKCAKCSIGFSKNDFVMRARSKVYHIECFRCVACSRQLIPGDEFA LREDGLFCRADHDVVERASLGAGDPL |
| 901 | CDX2_HUMAN | SLGSQVKTRTKDKYRVVYTDHQRLELEKEFHYSRYITIRRKAELAATLGLSERQ VKIWFQNRRAKERKINKKKLQQQQQQ |
| 902 | PROP1_HUMAN | QGGQRGRPHSRRRHRTTFSPVQLEQLESAFGRNQYPDIWARESLARDTGLSEAR IQVWFQNRRAKQRKQERSLLQPLAHL |
| 903 | SIN3B_HUMAN | DALTYLDQVKIRFGSDPATYNGFLEIMKEFKSQSIDTPGVIRRVSQLFHEHPDL IVGFNAFLPLGYRIDIPKNGKLNIQS |
| 904 | SMBT1_HUMAN | RLHLDSNPLKWSVADVVRFIRSTDCAPLARIFLDQEIDGQALLLLTLPTVQECM DLKLGPAIKLCHHIERIKFAFYEQFA |
| 905 | HXC11_HUMAN | AKGAAPNAPRTRKKRCPYSKFQIRELEREFFENVYINKEKRLQLSRMLNLTDRQ VKIWFQNRRMKEKKLSRDRLQYFSGN |
| 906 | HXC10_HUMAN | TTGNWLTAKSGRKKRCPYTKHQTLELEKEFLENMYLTRERRLEISKTINLTDRQ VKIWFQNRRMKLKKMNRENRIRELTS |
| 907 | PRS6A_HUMAN | YLVSNVIELLDVDPNDQEEDGANIDLDSQRKGKCAVIKTSTRQTYFLPVIGLVD AEKLKPGDLVGVNKDSYLILETLPTE |

TABLE 18-continued

| SEQ | Description | Sequence |
|-----|-------------|----------|
| 908 | VSX1_HUMAN | KASPTLGKRKKRRHRTVFTAHQLEELEKAFSEAHYPDVYAREMLAVKTELPEDR IQVWFQNRRAKWRKREKRWGGSSVMA |
| 909 | NKX23_HUMAN | EESERPKPRSRRKPRVLFSQAQVFELERRFKQQRYLSAPEREHLASSLKLTSTQ VKIWFQNRRYKCKRQRQDKSLELGAH |
| 910 | MTG16_HUMAN | VVPGSRQEEVIDHKLTEREWAEEWKHLNNLLNCIMDMVEKTRRSLTVLRRCQEA DREELNHWARRYSDAEDTKKGPAPAA |
| 911 | HMX3_HUMAN | ESPEKKPACRKKKTRTVFSRSQVFQLESTFDMKRYLSSSERAGLAASLHLTETQ VKIWFQNRRNKWKRQLAAELEAANLS |
| 912 | HMX1_HUMAN | RGGVGVGGGRKKKTRTVFSRSQVFQLESTFDLKRYLSSAERAGLAASLQLTETQ VKIWFQNRRNKWKRQLAAELEAASLS |
| 913 | KIF22_HUMAN | ELLAHGRQKILDLLNEGSARDLRSLQRIGPKKAQLIVGWRELHGPFSQVEDLER VEGITGKQMESFLKANILGLAAGQRC |
| 914 | CSTF2_HUMAN | ESPYGETISPEDAPESISKAVASLPPEQMFELMKQMKLCVQNSPQEARNMLLQN PQLAYALLQAQVVMRIVDPEIALKIL |
| 915 | CEBPE_HUMAN | AGPLHKGKKAVNKDSLEYRLRRERNNIAVRKSRDKAKRRILETQQKVLEYMAEN ERLRSRVEQLTQELDTLRNLFRQIPE |
| 916 | DLX2_HUMAN | IRIVNGKPKKVRKPRTIYSSFQLAALQRRFQKTQYLALPERAELAASLGLTQTQ VKIWFQNRRSKFKKMWKSGEIPSEQH |
| 917 | ZMYM3_HUMAN | TVYQFCSPSCWTKFQRTSPEGGIHLSCHYCHSLFSGKPEVLDWQDQVFQFCCRD CCEDFKRLRGVVSQCEHCRQEKLLHE |
| 918 | PPARG_HUMAN | TMVDTEMPFWPTNFGISSVDLSVMEDHSHSFDIKPFTTVDESSISTPHYEDIPF TRTDPVVADYKYDLKLQEYQSAIKVE |
| 919 | PRIC1_HUMAN | GRHHAELLKPRCSACDEIIFADECTEAEGRHWHMKHFCCLECETVLGGQRYIMK DGRPFCCGCFESLYAEYCETCGEHIG |
| 920 | UNC4_HUMAN | DPDKESPGCKRRRTRTNFTGWQLEELEKAFNESHYPDVEMREALALRLDLVESR VQVWFQNRRAKWRKKENTKKGPGRPA |
| 921 | BARX2_HUMAN | TEQPTPRQKKPRRSRTIFTELQLMGLEKKFQKQKYLSTPDRLDLAQSLGLTQLQ VKTWYQNRRMKWKKMVLKGGQEAPTK |
| 922 | ALX3_HUMAN | SMELAKNKSKKRRNRTTFSTFQLEELEKVFQKTHYPDVYAREQLALRTDLTEAR VQVWFQNRRAKWRKRERYGKIQEGRN |
| 923 | TCF15_HUMAN | GGGGGAGPVVVVRQRQAANARERDRTQSVNTAFTALRTLIPTEPVDRKLSKIET VRLASSYIAHLANVLLLGDSADDGQP |
| 924 | TERA_HUMAN | IDDTVEGITGNLFEVYLKPYFLEAYRPIRKGDIFLVRGGMRAVEFKVVETDPSP YCIVAPDTVIHCEGEPIKREDEEESL |
| 925 | VSX2_HUMAN | SALNQTKKRKKRRHRTIFTSYQLEELEKAFNEAHYPDVYAREMLAMKTELPEDR IQVWFQNRRAKWRKREKCWGRSSVMA |
| 926 | HXD12_HUMAN | DGLPWGAAPGRARKKRKPYTKQQIAELENEFLVNEFINRQKRKELSNRLNLSDQ QVKIWFQNRRMKKKRVVLREQALALY |
| 927 | CDX1_HUMAN | GGGGSGKTRTKDKYRVVYTDHQRLELEKEFHYSRYITIRRKSELAANLGLTERQ VKIWFQNRRAKERKVNKKQQQQQPP |
| 928 | TCF23_HUMAN | TRAGGLALGRSEASPENAARERSRVRTLRQAFLALQAALPAVPPDTKLSKLDVL VLAASYIAHLTRTLGHELPGPAWPPF |
| 929 | ALX1_HUMAN | KCDSNVSSSKKRRHRTTFTSLQLEELEKVFQKTHYPDVYVREQLALRTELTEAR VQVWFQNRRAKWRKRERYGQIQQAKS |
| 930 | HXA10_HUMAN | NAANWLTAKSGRKKRCPYTKHQTLELEKEFLENMYLTRERRLEISRSVHLTDRQ VKIWFQNRRMKLKKMNRENRIRELTA |
| 931 | RX_HUMAN | LSEEEQPKKKHRRNRTTFTTYQLHELERAFEKSHYPDVYSREELAGKVNLPEVR VQVWFQNRRAKWRRQEKLEVSSMKLQ |
| 932 | CXXC5_HUMAN | HMAGLAEYPMQGELASAISSGKKKKRKRCGMCAPCRRRINCEQCSSCRNRKTGHQ ICKFRKCEELKKKPSAALEKVMLPTG |

TABLE 18-continued

Sequence listing.

| SEQ | Description | Sequence |
|---|---|---|
| 933 | SCML1_HUMAN | SITKHPSTWSVEAVVLFLKQTDPLALCPLVDLERSHEIDGKALLLLTSDVLLKH<br>LGVKLGTAVKLCYYIDRLKQGKCFEN |
| 934 | NFIL3_HUMAN | ACRRKREFIPDEKKDAMYWEKRRKNNEAAKRSREKRRLNDLVLENKLIALGEEN<br>ATLKAELLSLKLKFGLISSTAYAQEI |
| 935 | DLX6_HUMAN | EIRFNGKGKKIRKPRTIYSSLQLQALNHRFQQTQYLALPERAELAASLGLTQTQ<br>VKIWFQNKRSKFKKLLKQGSNPHESD |
| 936 | MTG8_HUMAN | GLHGTRQEEMIDHRLTDREWAEEWKHLDHLLNCIMDMVEKTRRSLTVLRRCQEA<br>DREELNYWIRRYSDAEDLKKGGGSSS |
| 937 | CBX8_HUMAN | ELSAVGERVFAAEALLKRRIRKGRMEYLVKWKGWSQKYSTWEPEENILDARLLA<br>AFEEREREMELYGPKKRGPKPKTELL |
| 938 | CEBPD_HUMAN | AREKSAGKRGPDRGSPEYRQRRERNNIAVRKSRDKAKRRNQEMQQKLVELSAEN<br>EKLHQRVEQLTRDLAGLRQFFKQLPS |
| 939 | SEC13_HUMAN | SGGCDNLIKLWKEEEDGQWKEEQKLEAHSDWVRDVAWAPSIGLPTSTIASCSQD<br>GRVFIWTCDDASSNTWSPKLLHKEND |
| 940 | FIP1_HUMAN | VKGVDLDAPGSINGVPLLEVDLDSFEDKPWRKPGADLSDYFNYGFNEDTWKAYC<br>EKQKRIRMGLEVIPVTSTTNKITAED |
| 941 | ALX4_HUMAN | KADSESNKGKKRRNRTTFTSYQLEELEKVFQKTHYPDVYAREQLAMRTDLTEAR<br>VQVWFQNRRAKWRKRERFGQMQQVRT |
| 942 | LHX3_HUMAN | TAKQREAEATAKRPRTTITAKQLETLKSAYNTSPKPARHVREQLSSETGLDMRV<br>VQVWFQNRRAKEKRLKKDAGRQRWGQ |
| 943 | PRIC2_HUMAN | GRHHAECLKPRCAACDEIIFADECTEAEGRHWHMKHFCCFECETVLGGQRYIMK<br>EGRPYCCHCFESLYAEYCDTCAQHIG |
| 944 | MAGI3_HUMAN | IIGGDRPDEFLQVKNVLKDGPAAQDGKIAPGDVIVDINGNCVLGHTHADVVQMF<br>QLVPVNQYVNLTLCRGYPLPDDSEDP |
| 945 | NELL1_HUMAN | CCPECDTRVTSQCLDQNGHKLYRSGDNWTHSCQQCRCLEGEVDCWPLTCPNLSC<br>EYTAILEGECCPRCVSDPCLADNITY |
| 946 | PRRX1_HUMAN | LNSEEKKKRKQRRNRTTFNSSQLQALERVFERTHYPDAFVREDLARRVNLTEAR<br>VQVWFQNRRAKERRNERAMLANKNAS |
| 947 | MTG8R_HUMAN | GLNGGYQDELVDHRLTEREWADEWKHLDHALNCIMEMVEKTRRSMAVLRRCQES<br>DREELNYWKRRYNENTELRKTGTELV |
| 948 | RAX2_HUMAN | GPGEEAPKKKHRRNRTTFTTYQLHQLERAFEASHYPDVYSREELAAKVHLPEVR<br>VQVWFQNRRAKWRRQERLESGSGAVA |
| 949 | DLX3_HUMAN | VRMVNGKPKKVRKPRTIYSSYQLAALQRRFQKAQYLALPERAELAAQLGLTQTQ<br>VKIWFQNRRSKFKKLYKNGEVPLEHS |
| 950 | DLX1_HUMAN | EVRFNGKGKKIRKPRTIYSSLQLQALNRRFQQTQYLALPERAELAASLGLTQTQ<br>VKIWFQNKRSKFKKLMKQGGAALEGS |
| 951 | NKX26_HUMAN | GRSEQPKARQRRKPRVLFSQAQVLALERRFKQQRYLSAPEREHLASALQLTSTQ<br>VKIWFQNRRYKCKRQRQDKSLELAGH |
| 952 | NAB1_HUMAN | LPRTLGELQLYRILQKANLLSYFDAFIQQGGDDVQQLCEAGEEEFLEIMALVGM<br>ASKPLHVRRLQKALRDWVTNPGLENQ |
| 953 | SAMD7_HUMAN | NLSLDEDIQKWTVDDVHSFIRSLPGCSDYAQVFKDHAIDGETLPLLTEEHLRGT<br>MGLKLGPALKIQSQVSQHVGSMFYKK |
| 954 | PITX3_HUMAN | SPEDGSLKKKQRRQRTHFTSQQLQELEATFQRNRYPDMSTREEIAVWTNLTEAR<br>VRVWFKNRRAKWRKRERSQQAELCKG |
| 955 | WDR5_HUMAN | SNLLVSASDDKTLKIWDVSSGKCLKTLKGHSNYVFCCNFNPQSNLIVSGSFDES<br>VRIWDVKTGKCLKTLPAHSDPVSAVH |
| 956 | MEOX2_HUMAN | GNYKSEVNSKPRKERTAFTKEQIRELEAEFAHHNYLTRLRRYEIAVNLDLTERQ<br>VKVWFQNRRMKWKRVKGGQQGAAARE |

TABLE 18-continued

Sequence listing.

| SEQ | Description | Sequence |
|---|---|---|
| 957 | NAB2_HUMAN | LPRTLGELQLYRVLQRANLLSYYETFIQQGGDDVQQLCEAGEEEFLEIMALVGM ATKPLHVRRLQKALREWATNPGLFSQ |
| 958 | DHX8_HUMAN | PEEPTIGDIYNGKVTSIMQFGCFVQLEGLRKRWEGLVHISELRREGRVANVADV VSKGQRVKVKVLSFTGTKTSLSMKDV |
| 959 | FOXA2_HUMAN | YAFNHPFSINNLMSSEQQHHSHHHHQPHKMDLKAYEQVMHYPGYGSPMPGSLA MGPVTNKTGLDASPLAADTSYYQGVY |
| 960 | CBX6_HUMAN | TAAAGPAPPTAPEPAGASSEPEAGDWRPEMSPCSNVVVTDVTSNLLTVTIKEFC NPEDFEKVAAGVAGAAGGGGSIGASK |
| 961 | EMX2_HUMAN | FLLHNALARKPKRIRTAFSPSQLLRLEHAFEKNHYVVGAERKQLAHSLSLTETQ VKVWFQNRRTKFKRQKLEEEGSDSQQ |
| 962 | CPSF6_HUMAN | KRIALYIGNLTWWTTDEDLTEAVHSLGVNDILEIKFFENRANGQSKGFALVGVG SEASSKKLMDLLPKRELHGQNPVVTP |
| 963 | HXC12_HUMAN | SGAPWYPINSRSRKKRKPYSKLQLAELEGEFLVNEFITRQRRRELSDRINLSDQ QVKIWFQNRRMKKKRLLLREQALSFF |
| 964 | KDM4B_HUMAN | SDNLYPESITSRDCVQLGPPSEGELVELRWTDGNLYKAKFISSVTSHIYQVEFE DGSQLTVKRGDIFTLEEELPKRVRSR |
| 965 | LMBL3_HUMAN | GIPASKVSKWSTDEVSEFIQSLPGCEEHGKVFKDEQIDGEAFLLMTQTDIVKIM SIKLGPALKIFNSILMFKAAEKNSHN |
| 966 | PHX2A_HUMAN | EPSGLHEKRKQRRIRTTFTSAQLKELERVFAETHYPDIYTREELALKIDLTEAR VQVWFQNRRAKFRKQERAASAKGAAG |
| 967 | EMX1_HUMAN | LLLHGPFARKPKRIRTAFSPSQLLRLERAFEKNHYVVGAERKQLAGSLSLSETQ VKVWFQNRRTKYKRQKLEEEGPESEQ |
| 968 | NC2B_HUMAN | SSGNDDDLTIPRAAINKMIKETLPNVRVANDARELVVNCCTEFIHLISSEANEI CNKSEKKTISPEHVIQALESLGFGSY |
| 969 | DLX4_HUMAN | ERRPQAPAKKLRKPRTIYSSLQLQHLNQRFQHTQYLALPERAQLAAQLGLTQTQ VKIWFQNKRSKYKKLLKQNSGGQEGD |
| 970 | SRY_HUMAN | NVQDRVKRPMNAFIVWSRDQRRKMALENPRMRNSEISKQLGYQWKMLTEAEKWP FFQEAQKLQAMHREKYPNYKYRPRRK |
| 971 | ZN777_HUMAN | EITRLAVWAAVQAVERKLEAQAMRLLTLEGRTGTNEKKIADCEKTAVEFANHLE SKWVVLGTLLQEYGLLQRRLENMENL |
| 972 | NELL1_HUMAN | CEKDIDECSEGIIECHNHSRCVNLPGWYHCECRSGFHDDGTYSLSGESCIDIDE CALRTHTCWNDSACINLAGGFDCLCP |
| 973 | ZN398_HUMAN | AAISLWTVVAAVQAIERKVEIHSRRLLHLEGRTGTAEKKLASCEKTVTELGNQL EGKWAVLGTLLQEYGLLQRRLENLEN |
| 974 | GATA3_HUMAN | GQNRPLIKPKRRLSAARRAGTSCANCQTTTTTLWRRNANGDPVCNACGLYYKLH NINRPLTMKKEGIQTRNRKMSSKSKK |
| 975 | BSH_HUMAN | HAELPGKHCRRRKARTVFSDSQLSGLEKRFEIQRYLSTPERVELATALSLSETQ VKTWFQNRRMKHKKQLRKSQDEPKAP |
| 976 | SF3B4_HUMAN | QDATVYVGGLDEKVSEPLLWELFLQAGPVVNTHMPKDRVTGQHQGYGFVEFLSE EDADYAIKIMNMIKLYGKPIRVNKAS |
| 977 | TEAD1_HUMAN | PIDNDAEGVWSPDIEQSFQEALAIYPPCGRRKIILSDEGKMYGRNELIARYIKL RTGKTRTRKQVSSHIQVLARRKSRDF |
| 978 | TEAD3_HUMAN | GLDNDAEGVWSPDIEQSFQEALAIYPPCGRRKIILSDEGKMYGRNELIARYIKL RTGKTRTRKQVSSHIQVLARKKVREY |
| 979 | RGAP1_HUMAN | DSVGTPQSNGGMRLHDFVSKTVIKPESCVPCGKRIKFGKLSLKCRDCRVVSHPE CRDRCPLPCIPTLIGTPVKIGEGMLA |
| 980 | PHF1_HUMAN | SAPHSMTASSSSVSSPSPGLPRRSAPPSPLCRSLSPGTGGGVRGGVGYLSRGDP VRVLARRVRPDGSVQYLVEWGGGGIF |
| 981 | FOXA1_HUMAN | GDPHYSFNHPFSINNLMSSEQQHKLDFKAYEQALQYSPYGSTLPASLPLGSAS VTTRSPIEPSALEPAYYQGVYSRPVL |

TABLE 18-continued

Sequence listing.

| SEQ | Description | Sequence |
|-----|-------------|----------|
| 982 | GATA2_HUMAN | GQNRPLIKPKRRLSAARRAGTCCANCQTTTTTLWRRNANGDPVCNACGLYYKLH NVNRPLTMKKEGIQTRNRKMSNKSKK |
| 983 | FOXO3_HUMAN | DSLSGSSLYSTSANLPVMGHEKFPSDLDLDMENGSLECDMESIIRSELMDADGL DENFDSLISTQNVVGLNVGNFTGAKQ |
| 984 | ZN212_HUMAN | TEISLWTVVAAIQAVEKKMESQAARLQSLEGRTGTAEKKLADCEKMAVEFGNQL EGKWAVLGTLLQEYGLLQRRLENVEN |
| 985 | IRX4_HUMAN | MDSGTRRKNATRETTSTLKAWLQEHRKNPYPTKGEKIMLAIITKMTLTQVSTWF ANARRRLKKENKMTWPPRNKCADEKR |
| 986 | ZBED6_HUMAN | NIEKQIYLPSTRAKTSIVWHFFHVDPQYTWRAICNLCEKSVSRGKPGSHLGTST LQRHLQARHSPHWTRANKFGVASGEE |
| 987 | LHX4_HUMAN | AKQNDDSEAGAKRPRTTITAKQLETLKNAYKNSPKPARHVREQLSSETGLDMRV VQVWFQNRRAKEKRLKKDAGRHRWGQ |
| 988 | SIN3A_HUMAN | DALSYLDQVKLQFGSQPQVYNDFLDIMKEFKSQSIDTPGVISRVSQLFKGHPDL IMGFNTFLPPGYKIEVQTNDMVNVTT |
| 989 | RBBP7_HUMAN | DDHTVCLWDINAGPKEGKIVDAKAIFTGHSAVVEDVAWHLLHESLFGSVADDQK LMIWDTRSNTTSKPSHLVDAHTAEVN |
| 990 | NKX61_HUMAN | GSILLDKDGKRKHTRPTFSGQQIFALEKTFEQTKYLAGPERARLAYSLGMTESQ VKVWFQNRRTKWRKKHAAEMATAKKK |
| 991 | TRI68_HUMAN | DPTALVEAIVEEVACPICMTFLREPMSIDCGHSFCHSCLSGLWEIPGESQNWGY TCPLCRAPVQPRNLRPNWQLANVVEK |
| 992 | R51A1_HUMAN | QSLPKKVSLSSDTTRKPLEIRSPSAESKKPKWVPPAASGGSRSSSSPLVVVSVK SPNQSLRLGLSRLARVKPLHPNATST |
| 993 | MB3L1_HUMAN | AKSSQRKQRDCVNQCKSKPGLSTSIPLRMSSYTFKRPVTRITPHPGNEVRYHQW EESLEKPQQVCWQRRLQGLQAYSSAG |
| 994 | DLX5_HUMAN | VRMVNGKPKKVRKPRTIYSSFQLAALQRRFQKTQYLALPERAELAASLGLTQTQ VKIWFQNKRSKIKKIMKNGEMPPEHS |
| 995 | NOTC1_HUMAN | LQCNNHACGWDGGDCSLNFNDPWKNCTQSLQCWKYFSDGHCDSQCNSAGCLFDG FDCQRAEGQCNPLYDQYCKDHFSDGH |
| 996 | TERF2_HUMAN | ETWVEEDELFQVQAAPDEDSTTNITKKQKWTVEESEWVKAGVQKYGEGNWAAIS KNYPFVNRTAVMIKDRWRTMKRLGMN |
| 997 | ZN282_HUMAN | AEISLWTVVAAIQAVERKVDAQASQLLNLEGRTGTAEKKLADCEKTAVEFGNHM ESKWAVLGTLLQEYGLLQRRLENLEN |
| 998 | RGS12_HUMAN | LEKRTLFRLDLVPINRSVGLKAKPTKPVTEVLRPVVARYGLDLSGLLVRLSGEK EPLDLGAPISSLDGQRVVLEEKDPSR |
| 999 | ZN840_HUMAN | PNCLSSSMQLPHGGGRHQELVRFRDVAVVESPEEWDHLTPEQRNLYKDVMLDNC KYLASLGNWTYKAHVMSSLKQGKEPW |
| 1000 | SPI2B_HUMAN | DDYKEGDLRIMPESSESPPTEREPGGVVDGLIGKHVEYTKEDGSKRIGMVIHQV EAKPSVYFIKFDDDFHIYVYDLVKKS |
| 1001 | PAX7_HUMAN | SEPDLPLKRKQRRSRTTFTAEQLEELEKAFERTHYPDIYTREELAQRTKLTEAR VQVWFSNRRARWRKQAGANQLAAFNH |
| 1002 | NKX62_HUMAN | AGGVLDKDGKKKHSRPTFSGQQIFALEKTFEQTKYLAGPERARLAYSLGMTESQ VKVWFQNRRTKWRKRHAVEMASAKKK |
| 1003 | ASXL2_HUMAN | DVMSFSVTVTTIPASQAMNPSSHGQTIPVQAFSEENSIEGTPSKCYCRLKAMIM CKGCGAFCHDDCIGPSKLCVSCLVVR |
| 1004 | FOXO1_HUMAN | GGYSSVSSCNGYGRMGLLHQEKLPSDLDGMFIERLDCDMESIIRNDLMDGDTLD FNFDNVLPNQSFPHSVKTTTHSWVSG |
| 1005 | GATA3_HUMAN | GGSPTGFGCKSRPKARSSTGRECVNCGATSTPLWRRDGTGHYLCNACGLYHKMN GQNRPLIKPKRRLSAARRAGTSCANC |
| 1006 | GATA1_HUMAN | GQNRPLIRPKKRLIVSKRAGTQCTNCQTTTTTLWRRNASGDPVCNACGLYYKLH QVNRPLTMRKDGIQTRNRKASGKGKK |

TABLE 18-continued

Sequence listing.

| SEQ | Description | Sequence |
|---|---|---|
| 1007 | ZMYM5_HUMAN | PVALLRKQNFQPTAQQQLTKPAKITCANCKKPLQKGQTAYQRKGSAHLFCSTTC<br>LSSFSHKRTQNTRSIICKKDASTKKA |
| 1008 | ZN783_HUMAN | TEITLWTVVAAIQALEKKVDSCLTRLLTLEGRTGTAEKKLADCEKTAVEFGNQL<br>EGKWAVLGTLLQEYGLLQRRLENVEN |
| 1009 | SPI2B_HUMAN | KKQRGRPSSQPRRNIVGCRISHGWKEGDEPITQWKGTVLDQVPINPSLYLVKYD<br>GIDCVYGLELHRDERVLSLKILSDRV |
| 1010 | LRP1_HUMAN | WTCDLDDDCGDRSDESASCAYPTCFPLTQFTCNNGRCININWRCDNDNDCGDNS<br>DEAGCSHSCSSTQFKCNSGRCIPEHW |
| 1011 | MIXL1_HUMAN | PKGAAAPSASQRRKRTSFSAEQLQLLELVFRRTRYPDIHLRERLAALTLLPESR<br>IQVWFQNRRAKSRRQSGKSFQPLARP |
| 1012 | SGT1_HUMAN | KIKYDWYQTESQVVITLMIKNVQKNDVNVEFSEKELSALVKLPSGEDYNLKLEL<br>LHPIIPEQSTFKVLSTKIEIKLKKPE |
| 1013 | LMCD1_HUMAN | DPSKEVEYVCELCKGAAPPDSPVVYSDRAGYNKQWHPTCFVCAKCSEPLVDLIY<br>FWKDGAPWCGRHYCESLRPRCSGCDE |
| 1014 | CEBPA_HUMAN | GSGAGKAKKSVDKNSNEYRVRRERNNIAVRKSRDKAKQRNVETQQKVLELTSDN<br>DRLRKRVEQLSRELDTLRGIFRQLPE |
| 1015 | GATA2_HUMAN | GPASSFTPKQRSKARSCSEGRECVNCGATATPLWRRDGTGHYLCNACGLYHKMN<br>GQNRPLIKPKRRLSAARRAGTCCANC |
| 1016 | SOX14_HUMAN | KPSDHIKRPMNAFMVWSRGQRRKMAQENPKMHNSEISKRLGAEWKLLSEAEKRP<br>YIDEAKRLRAQHMKEHPDYKYRPRRK |
| 1017 | WTIP_HUMAN | LYSGFQQTADKCSVCGHLIMEMILQALGKSYHPGCFRCSVCNECLDGVPFTVDV<br>ENNIYCVRDYHTVFAPKCASCARPIL |
| 1018 | PRP19_HUMAN | HPSQDLVFSASPDATIRIWSVPNASCVQVVRAHESAVTGLSLHATGDYLLSSSD<br>DQYWAFSDIQTGRVLTKVTDETSGCS |
| 1019 | CBX6_HUMAN | ELSAVGERVFAAESIIKRRIRKGRIEYLVKWKGWAIKYSTWEPEENILDSRLIA<br>AFEQKERERELYGPKKRGPKPKTELL |
| 1020 | NKX11_HUMAN | RTGSDSKSGKPRRARTAFTYEQLVALENKFKATRYLSVCERLNLALSLSLTETQ<br>VKIWFQNRRTKWKKQNPGADTSAPTG |
| 1021 | RBBP4_HUMAN | VWDLSKIGEEQSPEDAEDGPPELLFIHGGHTAKISDESWNPNEPWVICSVSEDN<br>IMQVWQMAENIYNDEDPEGSVDPEGQ |
| 1022 | DMRT2_HUMAN | ERCTPAGGGAEPRKLSRTPKCARCRNHGVVSCLKGHKRFCRWRDCQCANCLLVV<br>ERQRVMAAQVALRRQQATEDKKGLSG |
| 1023 | SMCA2_HUMAN | SQPGALIPGDPQAMSQPNRGPSPFSPVQLHQLRAQILAYKMLARGQPLPETLQL<br>AVQGKRTLPGLQQQQQQQQQQQQQQQQ |
| 1024 | ZNF10 | MDAKSLTAWSRTLVTFKDVFVDFTREEWKLLDTAQQIVYRNVMLENYKNLVSLG<br>YQLTKPDVILRLEKGEEPWLVEREIHQETHPDSETAFEIKSSVSSRSIFKDKQS<br>CDIKMEGMARNDLWYLSLEEVWKCRDQLDKYQENPERHLRQVAFTQKKVLTQER<br>VSESGKYGGNCLLPAQLVLREYFHKRDSHTKSLKHDLVLNGHQDSCASNSNECG<br>QTFCQNIHLIQFARTHTGDKSYKCPDNDNSLTHGSSLGISKGIHREKPYECKEC<br>GKFFSWRSNLTRHQLIHTGEKPYECKECGKSFSRSSHLIGHQKTHTGEEPYECK<br>ECGKSFSWFSHLVTHQRTHTGDKLYTCNQCGKSFVHSSRLIRHQRTHTGEKPYE<br>CPECGKSFRQSTHLILHQRTHVRVRPYECNECGKSYSQRSHLVVHHRIHTGLKP<br>FECKDCGKCFSRSSHLYSHQRTHTGEKPYECHDCGKSFSQSSALIVHQRIHTGE<br>KPYECCQCGKAFIRKNDLIKHQRIHVGEETYKCNQCGIIFSQNSPFIVHQIAHT<br>GEQFLTCNQCGTALVNTSNLIGYQTNHIRENAY |
| 1025 | EED_HUMAN | MSEREVSTAPAGTDMPAAKKQKLSSDENSNPDLSGDENDDAVSIESGTNTERPD<br>TPTNTPNAPGRKSWGKGKWKSKKCKYSFKCVNSLKEDHNQPLFGVQFNWHSKEG<br>DPLVFATVGSNRVTLYECHSQGEIRLLQSYVDADADENFYTCAWTYDSNTSHPL<br>LAVAGSRGIIRIINPITMQCIKHYVGHGNAINELKFHPRDPNLLLSVSKDHALR<br>LWNIQTDTLVAIFGGVEGHRDEVLSADYDLLGEKIMSCGMDHSLKLWRINSKRM<br>MNAIKESYDYNPNKTNRPPISQKIHFPDFSTRDIHRNYVDCVRWLGDLILSKSC<br>ENAIVCWKPGKMEDDIDKIKPSESNVTILGRFDYSQCDIWYMRFSMDFWQKMLA<br>LGNQVGKLYVWDLEVEDPHKAKCTTLTHHKCGAAIRQTSFSRDSSILIAVCDDA<br>SIWRWDRLR |
| 1026 | RCOR1_HUMAN | MPAMVEKGPEVSGKRRGRNNAAASASAAAASAAASAACASPAATAASGAAASSA<br>SAAAASAAAAPNNGQNKSLAAAAPNGNSSSNSWEEGSSGSSSDEEHGGGGMRVG<br>PQYQAVVPDFDPAKLARRSQERDNLGMLVWSPNQNLSEAKLDEYIAIAKEKHGY |

TABLE 18-continued

Sequence listing.

| SEQ | Description | Sequence |
|---|---|---|
| | | NMEQALGMLFWHKHNIEKSLADLPNFTPFPDEWTVEDKVLFEQAFSFHGKTFHR |
| | | IQQMLPDKSIASLVKFYYSWKKTRTKTSVMDRHARKQKREREESEDELEEANGN |
| | | NPIDIEVDQNKESKKEVPPTETVPQVKKEKHSTQAKNRAKRKPPKGMFLSQEDV |
| | | EAVSANATAATTVLRQLDMELVSVKRQIQNIKQTNSALKEKLDGGIEPYRLPEV |
| | | IQKCNARWTTEEQLLAVQAIRKYGRDFQAISDVIGNKSVVQVKNFFVNYRRREN |
| | | IDEVLQEWEAEHGKEETNGPSNQKPVKSPDNSIKMPEEEDEAPVLDVRYASAS |
| 1027 | human DNMT1 | MPARTAPARVPTLAVPAISLPDDVRRRLKDLERDSLTEKECVKEKLNLLHEFLQ |
| | | TEIKNQLCDLETKLRKEELSEEGYLAKVKSLLNKDLSLENGAHAYNREVNGRLE |
| | | NGNQARSEARRVGMADANSPPKPLSKPRTPRRSKSDGEAKPEPSPSPRITRKST |
| | | RQTTITSHFAKGPAKRKPQEESERAKSDESIKEEDKDQDEKRRRVTSRERVARP |
| | | LPAEEPERAKSGTRTEKEEERDEKEEKRLRSQTKEPTPKQKLKEEPDREARAGV |
| | | QADEDEDGDEKDEKKHRSQPKDLAAKRRPEEKEPEKVNPQISDEKDEDEKEEKR |
| | | RKTTPKEPTEKKMARAKTVMNSKTHPPKCIQCGQYLDDPLKYGQHPPDAVDEPQ |
| | | MLTNEKLSIFDANESGFESYEALPQHKLTCFSVYCKHGHLCPIDTGLIEKNIEL |
| | | FFSGSAKPIYDDDPSLEGGVNGKNLGPINEWWITGEDGGEKALIGESTSFAEYI |
| | | LMDPSPEYAPIFGLMQEKIYISKIVVEFLQSNSDSTYEDLINKIETTVPPSGLN |
| | | LNRFTEDSLLRHAQFVVEQVESYDEAGDSDEQPIFLTPCMRDLIKLAGVTLGQR |
| | | RAQARRQTIRHSTREKDRGPTKATTTKLVYQIFDTFFAEQIEKDDREDKENAFK |
| | | RRRCGVCEVCQQPECGKCKACKDMVKFGGSGRSKQACQERRCPNMAMKEADDDE |
| | | EVDDNIPEMPSPKKMHQGKKKKQNKNRISWVGEAVKTDGKKSYYKKVCIDAETL |
| | | EVGDCVSVIPDDSSKPLYLARVTALWEDSSNGQMFHAHWFCAGTDTVLGATSDP |
| | | LELFLVDECEDMQLSYIHSKVKVIYKAPSENWAMEGGMDPESLLEGDDGKTYFY |
| | | QLWYDQDYARFESPPKTQPTEDNKFKFCVSCARLAEMRQKEIPRVLEQLEDLDS |
| | | RVLYYSATKNGILYRVGDGVYLPPEAFTENIKLSSPVKRPRKEPVDEDLYPEHY |
| | | RKYSDYIKGSNLDAPEPYRIGRIKEIFCPKKSNGRPNETDIKIRVNKFYRPENT |
| | | HKSTPASYHADINLLYWSDEEAVVDFKAVQGRCTVEYGEDLPECVQVYSMGGPN |
| | | RFYFLEAYNAKSKSFEDPPNHARSPGNKGKGKGKGKGKPKSQACEPSEPEIEIK |
| | | LPKLRTLDVFSGCGGLSEGFHQAGISDTLWAIEMWDPAAQAFRLNNPGSTVFTE |
| | | DCNILLKLVMAGETTNSRGQRLPQKGDVEMLCGGPPCQGESGMNRFNSRTYSKF |
| | | KNSLVVSFLSYCDYYRPRFFLLENVRNFVSFKRSMVLKLTLRCLVRMGYQCTFG |
| | | VLQAGQYGVAQTRRRAIILAAAPGEKLPLFPEPLHVFAPRACQLSVVVDDKKFV |
| | | SNITRLSSGPFRTITVRDTMSDLPEVRNGASALEISYNGEPQSWFQRQLRGAQY |
| | | QPILRDHICKDMSALVAARMRHIPLAPGSDWRDLPNIEVRLSDGTMARKLRYTH |
| | | HDRKNGRSSSGALRGVCSCVEAGKACDPAARQFNTLIPWCLPHTGNRHNHWAGL |
| | | YGRLEWDGFFSTTVTNPEPMGKQGRVLHPEQHRVVSVRECARSQGFPDTYRLFG |
| | | NILDKHRQVGNAVPPPLAKAIGLEIKLCMLAKARESASAKIKEEEAAKD |
| 1028 | human DNMT3A | MPAMPSSGPGDTSSSAAEREEDRKDGEEQEEPRGKEERQEPSTTARKVGRPGRK |
| | | RKHPPVESGDTPKDPAVISKSPSMAQDSGASELLPNGDLEKRSEPQPEEGSPAG |
| | | GQKGGAPAEGEGAAETLPEASRAVENGCCTPKEGRGAPAEAGKEQKETNIESMK |
| | | MEGSRGRLRGGLGWESSLRQRPMPRLTFQAGDPYYISKRKRDEWLARWKREAEK |
| | | KAKVIAGMNAVEENQGPGESQKVEEASPPAVQQPTDPASPTVATTPEPVGSDAG |
| | | DKNATKAGDDEPEYEDGRGFGIGELVWGKLRGFSWWPGRIVSWWMTGRSRAAEG |
| | | TRWVMWFGDGKFSVVCVEKLMPLSSFCSAFHQATYNKQPMYRKAIYEVLQVASS |
| | | RAGKLFPVCHDSDESDTAKAVEVQNKPMIEWALGGFQPSGPKGLEPPEEKNPY |
| | | KEVYTDMWVEPEAAAYAPPPPAKKPRKSTAEKPKVKEIIDERTRERLVYEVRQK |
| | | CRNIEDICISCGSLNVTLEHPLFVGGMCQNCKNCFLECAYQYDDDGYQSYCTIC |
| | | CGGREVLMCGNNNCCRCFCVECVDLLVGPGAAQAAIKEDPWNCYMCGHKGTYGL |
| | | LRRREDWPSRLQMFFANNHDQEFDPPKVYPPVPAEKRKPIRVLSLEDGIATGLL |
| | | VLKDLGIQVDRYIASEVCEDSITVGMVRHQGKIMYVGDVRSVTQKHIQEWGPED |
| | | LVIGGSPCNDLSIVNPARKGLYEGTGRLFFEFYRLLHDARPKEGDDRPFFWLFE |
| | | NVVAMGVSDKRDISRFLESNPVMIDAKEVSAAHRARYFWGNLPGMNRPLASTVN |
| | | DKLELQECLEHGRIAKFSKVRTITTRSNSIKQGKDQHPPVEMNEKEDILWCTEM |
| | | ERVFGFPVHYTDVSNMSRLARQRLLGRSWSVPVIRHLFAPLKEYFACV |
| 1029 | human DNMT3A catalytic domain | NHDQEFDPPKVYPPVPAEKRKPIRVLSLEDGIATGLLVLKDLGIQVDRYIASEV |
| | | CEDSITVGMVRHQGKIMYVGDVRSVTQKHIQEWGPFDLVIGGSPCNDLSIVNPA |
| | | RKGLYEGTGRLFFEFYRLLHDARPKEGDDRPFFWLFENVVAMGVSDKRDISREL |
| | | ESNPVMIDAKEVSAAHRARYFWGNLPGMNRPLASTVNDKLELQECLEHGRIAKF |
| | | SKVRTITTRSNSIKQGKDQHPVFMNEKEDILWCTEMERVFGFPVHYTDVSNMS |
| | | RLARQRLLGRSWSVPVIRHLFAPLKEYFACV |
| 1030 | human DNMT3B | MKGDTRHLNGEEDAGGREDSILVNGACSDQSSDSPPILEAIRTPEIRGRRSSSR |
| | | LSKREVSSLLSYTQDLTGDGDGEDGDGSDTPVMPKLFRETRTRSESPAVRTRNN |
| | | NSVSSRERHRPSPRSTRGRQGRNHVDESPVEFPATRSLRRRATASAGTPWPSPP |
| | | SSYLTIDLTDDTEDTHGTPQSSSTPYARLAQDSQQGGMESPQVEADSGDGDSSE |
| | | YQDGKEFGIGDLVWGKIKGFSWWPAMVVSWKATSKRQAMSGMRWVQWFGDGKFS |
| | | EVSADKLVALGLFSQHFNLATENKLVSYRKAMYHALEKARVRAGKTFPSSPGDS |
| | | LEDQLKPMLEWAHGGFKPTGIEGLKPNNTQPVVNKSKVRRAGSRKLESRKYENK |
| | | TRRRTADDSATSDYCPAPKRLKTNCYNNGKDRGDEDQSREQMASDVANNKSSLE |
| | | DGCLSCGRKNPVSFHPLFEGGLCQTCRDRFLELFYMYDDDGYQSYCTVCCEGRE |
| | | LLLCSNTSCCRCFCVECLEVLVGTGTAAEAKLQEPWSCYMCLPQRCHGVLRRRK |
| | | DWNVRLQAFFTSDTGLEYEAPKLYPAIPAARRRPIRVLSLEDGIATGYLVLKEL |
| | | GIKVGKYVASEVCEESIAVGTVKHEGNIKYVNDVRNITKKNIEEWGPFDLVIGG |
| | | SPCNDLSNVNPARKGLYEGTGRLFFEFYHLLNYSRPKEGDDRPFFWMFENVVAM |

TABLE 18-continued

Sequence listing.

| SEQ | Description | Sequence |
|---|---|---|
| | | KVGDKRDISRFLECNPVMIDAIKVSAAHRARYFWGNLPGMNRPVIASKNDKLEL<br>QDCLEYNRIAKLKKVQTITTKSNSIKQGKNQLFPVVMNGKEDVLWCTELERIFG<br>FPVHYTDVSNMGRGARQKLLGRSWSVPVIRHLFAPLKDYFACE |
| 1031 | mouse DNMT3C | MRGGSRHLSNEEDVSGCEDCIIISGTCSDQSSDPKTVPLTQVLEAVCTVENRGC<br>RTSSQPSKRKASSLISYVQDLTGDGDEDRDGEVGGSSGSGTPVMPQLFCETRIP<br>SKTPAPLSWQANTSASTPWLSPASPYPIIDLTDEDVIPQSISTPSVDWSQDSHQ<br>EGMDTTQVDAESRDGGNIEYQVSADKLLLSQSCILAAFYKLVPYRESTYRTLEK<br>ARVRAGKACPSSPGESLEDQLKPMLEWAHGGFKPTGIEGLKPNKKQPENKSRRR<br>TTNDPAASESSPPKRLKTNSYGGKDRGEDEESREQMASDVTNNKGNLEDHCLSC<br>GRKDPVSFHPLFEGGLCQSCRDRFLELFYMYDEDGYQSYCTVCCEGRELLLCSN<br>TSCCRCFCVECLEVLVGAGTAEDVKLQEPWSCYMCLPQRCHGVLRRRKDWNMRL<br>QDFFTTDPDLEEFEPPKLYPAIPAAKRRPIRVLSLEDGIATGYLVLKELGIKVE<br>KYIASEVCAESIAVGTVKHEGQIKYVDDIRNITKEHIDEWGPFDLVIGGSPCND<br>LSCVNPVRKGLFEGTGRLFFEFYRLLNYSCPEEEDDRPPFWMFENVVAMEVGDK<br>RDISRFLECNPVMIDAIKVSAAHRARYFWGNLPGMNRPVMASKNDKLELQDCLE<br>FSRTAKLKKVQTITTKSNSIRQGKNQLFPVVMNGKDDVLWCTELERIFGFPEHY<br>TDVSNMGRGARQKLLGRSWSVPVIRHLFAPLKDHFACE |
| 1032 | human DNMT3L | MAAIPALDPEAEPSMDVILVGSSELSSSVSPGTGRDLIAYEVKANQRNIEDICI<br>CCGSLQVHTQHPLFEGGICAPCKDKFLDALFLYDDDGYQSYCSICCSGETLLIC<br>GNPDCTRCYCFECVDSLVGPGTSGKVHAMSNWVCYLCLPSSRSGLLQRRRKWRS<br>QLKAFYDRESENPLEMFETVPVWRRQPVRVLSLFEDIKKELTSLGFLESGSDPG<br>QLKHVVDVTDTVRKDVEEWGPFDLVYGATPPLGHTCDRPPSWYLFQFHRLLQYA<br>RPKPGSPRPFFWMFVDNLVLNKEDLDVASRFLEMEPVTIPDVHGGSLQNAVRVW<br>SNIPAIRSSRHWALVSEEELSLLAQNKQSSKLAAKWPTKLVKNCFLPLREYFKY<br>FSTELTSSL |
| 1033 | human DNMT3L<br>catalytic domain | NPLEMFETVPVWRRQPVRVLSLFEDIKKELTSLGFLESGSDPGQLKHVVDVTDT<br>VRKDVEEWGPFDLVYGATPPLGHTCDRPPSWYLFQFHRLLQYARPKPGSPRPFF<br>WMFVDNLVLNKEDLDVASRFLEMEPVTIPDVHGGSLQNAVRVWSNIPAIRSRHW<br>ALVSEEELSLLAQNKQSSKLAAKWPTKLVKNCFLPLREYFKYFSTELTSSL |
| 1034 | mouse DNMT3L | MGSRETPSSCSKTLETLDLETSDSSSPDADSPLEEQWLKSSPALKEDSVDVVLE<br>DCKEPLSPSSPPTGREMIRYEVKVNRRSIEDICLCCGTLQVYTRHPLFEGGLCA<br>PCKDKFLESLFLYDDDGHQSYCTICCSGGTLFICESPDCTRCYCFECVDILVGP<br>GTSERINAMACWVCFLCLPFSRSGLLQRRKRWRHQLKAFHDQEGAGPMEIYKTV<br>SAWKRQPVRVLSLFRNIDKVLKSLGFLESGSGSGGGTLKYVEDVTNVVRRDVEK<br>WGPFDLVYGSTQPLGSSCDRCPGWYMFQFHRILQYALPRQESQRPFFWIFMDNL<br>LLTEDDQETTTRFLQTEAVTLQDVRGRDYQNAMRVWSNIPGLKSKHAPLTPKEE<br>EYLQAQVRSRSKLDAPKVDLLVKNCLLPLREYFKYFSQNSLPL |
| 1035 | mouse DNMT3L<br>catalytic domain | GPMEIYKTVSAWKRQPVRVLSLERNIDKVLKSLGFLESGSGSGGGTLKYVEDVT<br>NVVRRDVEKWGPFDLVYGSTQPLGSSCDRCPGWYMFQFHRILQYALPRQESQRP<br>FFWIFMDNLLLTEDDQETTTRFLQTEAVTLQDVRGRDYQNAMRVWSNIPGLKSK<br>HAPLTPKEEEYLQAQVRSRSKLDAPKVDLLVKNCLLPLREYFKYFSQNSLPL |
| 1036 | human TRDMT1<br>(DNMT2) | MEPLRVLELYSGVGGMHHALRESCIPAQVVAAIDVNTVANEVVKYNFPHTQLLA<br>KTIEGITLEEFDRLSFDMILMSPPCQPFTRIGRQGDMTDSRTNSFLHILDILPR<br>LQKLPKYILLENVKGFEVSSTRDLLIQTIENCGFQYQEFLLSPTSLGIPNSRLR<br>YFLIAKLQSEPLPFQAPGQVLMEFPKIESVHPQKYAMDVENKIQEKNVEPNISE<br>DGSIQCSGKDAILFKLETAEEIHRKNQQDSDLSVKMLKDFLEDDTDVNQYLLPP<br>KSLLRYALLLDIVQPTCRRSVCFTKGYGSYIEGTGSVLQTAEDVQVENIYKSLT<br>NLSQEEQITKLLILKLRYFTPKEIANLLGFPPEFGFPEKITVKQRYRLLGNSLN<br>VHVVAKLIKILYE |
| 1037 | *M. penetrans*<br>M MpeI | MNSNKDKIKVIKVFEAFAGIGSQFKALKNIARSKNWEIQHSGMVEWFVDAIVSY<br>VAIHSKNFNPKIEQLDKDILSISNDSKMPISEYGIKKINNTIKASYLNYAKKHF<br>NNLFDIKKVNKDNFPKNIDIFTYSFPCQDLSVQGLQKGIDKELNTRSGLLWEIE<br>RILEEIKNSFSKEEMPKYLLMENVKNLLSHKNKKNYNTWLKQLEKFGYKSKTYL<br>LNSKNFDNCQNRERVFCLSIRDDYLEKTGFKFKELEKVKNPPKKIKDILVDSSN<br>YKYLNLNKYETTTPRETKSNIISRSLKNYTTENSENYVYNINGIGPTLTASGAN<br>SRIKIETQQGVRYLTPLECFKYMQFDVNDFKKVQSTNLISENKMIYIAGNSIPV<br>KILEAIENTLEFVNNEE |
| 1038 | *S. monobiae*<br>M SssI | MSKVENKTKKLRVFEAFAGIGAQRKALEKVRKDEYEIVGLAEWYVPAIVMYQAI<br>HNNFHTKLEYKSVSREEMIDYLENKTLSWNSKNPVSNGYWKRKKDDELKIIYNA<br>IKLSEKEGNIFDIRDLYKRTLKNIDLLTYSFPCQDLSQQGIQKGMKRGSGTRSG<br>LLWEIERALDSTEKNDLPKYLLMENVGALLHKKNEEELNQWKQKLESLGYQNSI<br>EVLNAADFGSSQARRRVFMISTLNEFVELPKGDKKPKSIKKVLNKIVSEKDILN<br>NLLKYNLTEFKKTKSNINKASLIGYSKENSEGYVVDPEPTGPTLTASGANSRIK<br>IKDGSNIRKMNSDETFLYIGFDSQDGKRVNEIEFLTENQKIFVCGNSISVEVLE<br>AIIDKIGG |
| 1039 | *H. parainfluenzae*<br>M HpaII | MKDVLDDNLLEEPAAQYSLFEPESNPNLREKFTFIDLFAGIGGFRIAMQNLGGK<br>CIFSSEWDEQAQKTYEANFGDLPYGDITLEETKAFIPEKFDILCAGFPCQAFSI |

TABLE 18-continued

Sequence listing.

| SEQ | Description | Sequence |
|---|---|---|
| | | AGKRGGFEDTRGTLFFDVAEIIRRHQPKAFFLENVKGLKNHDKGRTLKTILNVL<br>REDLGYFVPEPAIVNAKNFGVPQNRERIYIVGFHKSTGVNSFSYPEPLDKIVTF<br>ADIREEKTVPTKYYLSTQYIDTLRKHKERHESKGNGFGYEIIPDDGIANAIVVG<br>GMGRERNLVIDHRITDFTPTTNIKGEVNREGIRKMTPREWARLQGFPDSYVIPV<br>SDASAYKQFGNSVAVPAIQATGKKILEKLGNLYD |
| 1040 | *A. luteus*<br>M AluI | MSKANAKYSFVDLFAGIGGFHAALAATGGVCEYAVEIDREAAAVYERNWNKPAL<br>GDITDDANDEGVTLRGYDGPIDVLTGGFPCQPFSKSGAQHGMAETRGTLFWNIA<br>RIIEEREPTVLILENVRNLVGPRHRHEWLTIIETLRFFGYEVSGAPAIFSPHLL<br>PAWMGGTPQVRERVFITATLVPERMRDERIPRTETGEIDAEAIGPKPVATMNDR<br>FPIKKGGTELFHPGDRKSGWNLLTSGIIREGDPEPSNVDLRLTETETLWIDAWD<br>DLESTIRRATGRPLEGFPYWADSWTDFRELSRLVVIRGFQAPEREVVGDRKRYV<br>ARTDMPEGFVPASVTRPAIDETLPAWKQSHLRRNYDFFERHFAEVVAWAYRWGV<br>YTDLFPASRRKLEWQAQDAPRLWDTVMHFRPSGIRAKRPTYLPALVAITQTSIV<br>GPLERRLSPRETARLQGLPEWFDFGEQRAAATYKQMGNGVNVGVVRHILREHVR<br>RDRALLKLTPAGQRIINAVLADEPDATVGALGAAE |
| 1041 | *H. aegyptius*<br>M HaeIII | MNLISLFSGAGGLDLGFQKAGFRIICANEYDKSIWKTYESNHSAKLIKGDISKI<br>SSDEFPKCDGIIGGPPCQSWSEGGSLRGIDDPRGKLFYEYIRILKQKKPIFFLA<br>ENVKGMMAQRHNKAVQEFIQEFDNAGYDVHIILLNANDYGVAQDRKRVFYIGER<br>KELNINYLPPIPHLIKPTFKDVIWDLKDNPIPALDKNKTNGNKCIYPNHEYFIG<br>SYSTIFMSRNRVRQWNEPAFTVQASGRQCQLHPQAPVMLKVSKNLNKFVEGKEH<br>LYRRLTVRECARVQGFPDDFIFHYESLNDGYKMIGNAVPVNLAYEIAKTIKSAL<br>EICKGN |
| 1042 | *H. haemolyticus*<br>M HhaI | MIEIKDKQLTGLRFIDLFAGLGGFRLALESCGAECVYSNEWDKYAQEVYEMNFG<br>EKPEGDITQVNEKTIPDHDILCAGFPCQAFSISGKQKGFEDSRGTLFFDIARIV<br>REKKPKVVFMENVKNFASHDNGNTLEVVKNTMNELDYSFHAKVLNALDYGIPQK<br>RERIYMICFRNDLNIQNFQFPKPFELNTFVKDLLLPDSEVEHLVIDRKDLVMTN<br>QEIEQTTPKTVRLGIVGKGGQGERIYSTRGIAITLSAYGGGIFAKTGGYLVNGK<br>TRKLHPRECARVMGYPDSYKVHPSTSQAYKQFGNSVVINVLQYIAYNIGSSLNF<br>KPY |
| 1043 | *Moraxella*<br>M MspI | MKPEILKLIRSKLDLTQKQASEIIEVSDKTWQQWESGKTEMHPAYYSFLQEKLK<br>DKINFEELSAQKTLQKKIFDKYNQNQITKNAEELAEITHIEERKDAYSSDFKFI<br>DLFSGIGGIRQSFEVNGGKCVFSSEIDPFAKFTYYTNFGVVPFGDITKVEATTI<br>PQHDILCAGFPCQPFSHIGKREGFEHPTQGTMFHEIVRIIETKKTPVLFLENVP<br>GLINHDDGNTLKVIIETLEDMGYKVHHTVLDASHFGIPQKRKRFYLVAFLNQNI<br>HFEFPKPPMISKDIGEVLESDVTGYSISEHLQKSYLFKKDDGKPSLIDKNTTGA<br>VKTLVSTYHKIQRLTGTFVKDGETGIRLLTTNECKAIMGFPKDFVIPVSRTQMY<br>RQMGNSVVVPVVTKIAEQISLALKTVNQQSPQENFELELV |
| 1044 | *Ascobolus* Masc1 | MSERRYEAGMTVALHEGSFLKIQRVYIRQYHADNRREHMLVGPLFRRTKYLKAL<br>SKKVNEVAIVHESIHVPVQDVIGVRELIITNRPFPECRKGDEHTGRLVCRWVYN<br>LDERAKGREYKKQRYIRRITEAEADPEYRVEDRVLRRRWFQEGYIGDEISYKEH<br>GNGDIVDIRSESPLQVLDGWGGDLVDLENGEETSIPGPCRSASSYGRLMKPPLA<br>QAADSNTSRKYTFGDTFCGGGGVSLGARQAGLEVKWAFDMNPNAGANYRRNEPN<br>TDFFLAEAEQFIQLSVGISQHVDILHLSPPCQTFSRAHTIAGKNDENNEASFFA<br>VVNLIKAVRPRLFTVEETDGIMDRQSRQFIDTALMGITELGYSFRICVLNAIEY<br>GVCQNRKRLIIIGAAPGEELPPFPLPTHQDFFSKDPRRDLLPAVTLDDALSTIT<br>PESTDHHLNHVWQPAEWKTPYDAHRPFKNAIRAGGGEYDIYPDGRRKFTVRELA<br>CIQGFPDEYEFVGTLTDKRRIIGNAVPPPLSAAIMSTLRQWMTEKDFERME |
| 1045 | *Arabidopsis* MET1 | MVENGAKAAKRKKRPLPEIQEVEDVPRTRRPRRAAACTSFKEKSIRVCEKSATI<br>EVKKQQIVEEEFLALRLTALETDVEDRPTRRLNDFVLFDSDGVPQPLEMLEIHD<br>IFVSGAILPSDVCTDKEKEKGVRCTSFGRVEHWSISGYEDGSPVIWISTELADY<br>DCRKPAASYRKVYDYFYEKARASVAVYKKLSKSSGGDPDIGLEELLAAVVRSMS<br>SGSKYFSSGAAIIDFVISQGDFIYNQLAGLDETAKKHESSYVEIPVLVALREKS<br>SKIDKPLQRERNPSNGVRIKEVSQVAESEALTSDQLVDGTDDDRRYAILLQDEE<br>NRKSMQQPRKNSSSGSASNMFYIKINEDEIANDYPLPSYYKTSEEETDELILYD<br>ASYEVQSEHLPHRMLHNWALYNSDLRFISLELLPMKQCDDIDVNIFGSGVVTDD<br>NGSWISLNDPDSGSQSHDPDGMCIFLSQIKEWMIEFGSDDIISISIRTDVAWYR<br>LGKPSKLYAPWWKPVLKTARVGISILTFLRVESRVARLSFADVTKRLSGLQAND<br>KAYISSDPLAVERYLVVHGQIILQLFAVYPDDNVKRCPFVVGLASKLEDRHHTK<br>WIIKKKKISLKELNLNPRAGMAPVASKRKAMQATTTRLVNRIWGEFYSNYSPED<br>PLQATAAENGEDEVEEEGGNGEEEVEEEGENGLTEDTVPEPVEVQKPHTPKKIR<br>GSSGKREIKWDGESLGKTSAGEPLYQQALVGGEMVAVGGAVTLEVDDPDEMPAI<br>YFVEYMFESTDHCKMLHGRFLQRGSMTVLGNAANERELFLTNECMTTQLKDIKG<br>VASFEIRSRPWGHQYRKKNITADKLDWARALERKVKDLPTEYYCKSLYSPERGG<br>FFSLPLSDIGRSSGFCTSCKIREDEEKRSTIKLNVSKTGFFINGIEYSVEDFVY<br>VNPDSIGGLKEGSKTSFKSGRNIGLRAYVVCQLLEIVPKESRKADLGSFDVKVR<br>RFYRPEDVSAEKAYASDIQELYFSQDTVVLPPGALEGKCEVRKKSDMPLSREYP<br>ISDHIFFCDLFFDTSKGSLKQLPANMKPKFSTIKDDTLLRKKKGKGVESEIESE<br>IVKPVEPPKEIRLATLDIFAGCGGLSHGLKKAGVSDAKWAIEYEEPAGQAFKQN<br>HPESTVFVDNCNVILRAIMEKGGDQDDCVSTTEANELAAKLTEEQKSTLPLPGQ<br>VDFINGGPPCQGFSGMNRFNQSSWSKVQCEMILAFLSFADYFRPRYELLENVRT |

TABLE 18-continued

Sequence listing.

| SEQ | Description | Sequence |
|---|---|---|
| | | FVSFNKGQTFQLTLASLLEMGYQVRFGILEAGAYGVSQSRKRAFIWAAAPEEVL<br>PEWPEPMHVFGVPKLKISLSQGLHYAAVRSTALGAPFRPITVRDTIGDLPSVEN<br>GDSRTNKEYKEVAVSWFQKEIRGNTIALTDHICKAMNELNLIRCKLIPTRPGAD<br>WHDLPKRKVTLSDGRVEEMIPFCLPNTAERHNGWKGLYGRLDWQGNFPTSVTDP<br>QPMGKVGMCFHPEQHRILTVRECARSQGFPDSYEFAGNINHKHRQIGNAVPPPL<br>AFALGRKLKEALHLKKSPQHQP |
| 1046 | *Ascobolus* Masc2 | MELTPELSGVSTDLGGGGSIFAHWRMKEESPAPTEILDDLNVLEWEKTTRDYSK<br>EDLRIADQLFSIEDEHQSLPFETADAEDGTPTEEEEEKELPMRTLDNFVLYDAS<br>DLELAALDLIGTELNIHAVGTVGPIYTEGEEDEQEDEDEDVSPPVRTGTQATSA<br>SVTQMTVELYIRNIVQYEFCFNDDGTVETWIQTTNAHYKLLQPAKCYTSLYRPV<br>NDCLNVITAIITLAPESTTMSLKDLLKVMDDKAQAVSYEEVERMSEFIVQHLDQ<br>WMETAPKKKSKLIEKSKVYIDLNNLAGIDMVSGVRPPPVRRVTGRSSAPKKRIV<br>RNMNDAVLLHQNETTVTNWIHQLSAGMFGRALNVLGAETADVENLTCDPASAKF<br>VVPQRRLHKRLKWETRGHIPVSEEEYKHIYQGKKYAKFFEAVRAVDESKLTIKL<br>GDLVYVLDQDPKVTQTQFATAGREGRKKGAEKEKIQVRFGRVLSIRQPDSNSKD<br>AQNVFIHVQWLVLGCDTILQEMASRRELFLTDSCDTVFADVIYGVAKLTPLGAK<br>DIPTVEFHESMATMMGENEFFVRFKYNYQDGSFTDLKDVDAEQIGTLQPRVNTH<br>RNPGYCSNCRIKYDNERTGDKWIYENDTEGEPRLERSSKGWCIYAQEFVYLQPV<br>EKQPGTTFRVGYISEINKSSVIVELLARVDDDDKSGHISYSDPRHLYFTGTDIK<br>VTFDKIIRKCFVFHDSGDQKAKAPLMYGTLQRDLYYYRYEKRKGKAELVPVREI<br>RSIHEQTLNDWESRTQIERHGAVSGKKLKGLDIFAGCGGLTLGLDLSGAVDTKW<br>DIEFAPSAANTLALNFPDAQVENQCANVLLSRAIQSEDEGSLDIEYDLQGRVLP<br>DLPKKGEVDFIYGGPPCQGFSGVNRYKKGNDIKNSLVATFLSYVDHYKPRFVLL<br>ENVKGLITTKLGNSKNAEGKWEGGISNGVVKFIYRTLISMNYQCRIGLVQSGEY<br>GVPQSRPRVIFLAARMGERLPDLPEPMHAFEVLDSQYALPHIKRYHTTQNGVAP<br>LPRITIGEAVSDLPKFQYANPGVWPRHDPYSSAKAQPSDKTIEKFSVSKATSFV<br>GYLLQPYHSRPQSEFQRRLRTKLVPSDEPAEKTSLLTTKLVTAHVTRLENKETT<br>QRIVCVPMWPGADHRSLPKEMRPWCLVDPNSQAEKHRFWPGLFGRLGMEDFEST<br>ALTDVQPCGKQGKVLHPTQRRVYTVRELARAQGFPDWFAFTDGDADSGLGGVKK<br>WHRNIGNAVPVPLGEQIGRCIGYSVWWKDDMIAQLREDGADEDEEMIDGNDQWV<br>EELNTQMAADMPGLPLLVTHLLNLCVYRRLYGPNAKEFLPARVYDKKLEGGRRR<br>LVWAML |
| 1047 | *Neurospora* Dim2 | MDSPDRSHGGMFIDVPAETMGFQEDYLDMFASVLSQGLAKEGDYAHHQPLPAGK<br>EECLEPIAVATTITPSPDDPQLQLQLELEQQFQTESGLNGVDPAPAPESEDEAD<br>LPDGFSDESPDDDPVVQRSKHITVDLPVSTLINPRSTFQRIDENDNLVPPPQST<br>PERVAVEDLLKAAKAAGKNKEDYIEFELHDENFYVNYAYHPQEMRPIQLVATKV<br>LHDKYYFDGVLKYGNTKHYVTGMQVLELPVGNYGASLHSVKGQIWVRSKHNAKK<br>EIYYLLKKPAFEYQRYYQPFLWIADLGKHVVDYCTRMVERKREVTLGCFKSDFI<br>QWASKAHGKSKAFQNWRAQHPSDDFRTSVAANIGYIWKEINGVAGAKRAAGDQL<br>FRELMIVKPGQYFRQEVPPGPVVTEGDRTVAATIVTPYIKECFGHMILGKVLRL<br>AGEDAEKEKEVKLAKRLKIENKNATKADTKDDMKNDTATESLPTPLRSLPVQVL<br>EATPIESDIVSIVSSDLPPSENNPPPLTNGSVKPKAKANPKPKPSTQPLHAAHV<br>KYLSQELVNKIKVGDVISTPRDDSSNTDTKWKPTDTDDHRWFGLVQRVHTAKTK<br>SSGRGLNSKSFDVIWFYRPEDTPCCAMKYKWRNELFLSNHCTCQEGHHARVKGN<br>EVLAVHPVDWFGTPESNKGEFFVRQLYESEQRRWITLQKDHLTCYHNQPPKPPT<br>APYKPGDTVLATLSPSDKFSDPYEVVEYFTQGEKETAFVRLRKLLRRRKVDRQD<br>APANELVYTEDLVDVRAERIVGKCIMRCFRPDERVPSPYDRGGTGNMFFITHRQ<br>DHGRCVPLDTLPPTLRQGFNPLGNLGKPKLRGMDLYCGGGNFGRGLEEGGVVEM<br>RWANDIWDKAIHTYMANTPDPNKTNPFLGSVDDLLRLALEGKFSDNVPRPGEVD<br>FIAAGSPCPGFSLLTQDKKVLNQVKNQSLVASFASFVDFYRPKYGVLENVSGIV<br>QTFVNRKQDVLSQLFCALVGMGYQAQLILGDAWAHGAPQSRERVFLYFAAPGLP<br>LPDPPLPSHSHYRVKNRNIGFLCNGESYVQRSFIPTAFKFVSAGEGTADLPKIG<br>DGKPDACVRFPDHRLASGITPYIRAQYACIPTHPYGMNFIKAWNNGNGVMSKSD<br>RDLFPSEGKTRTSDASVGWKRLNPKTLFPTVTTTSNPSDARMGPGLHWDEDRPY<br>TVQEMRRAQGYLDEEVLVGRTTDQWKLVGNSVSRHMALAIGLKFREAWLGTLYD<br>ESAVVATATATATTAAAVGVTVPVMEEPGIGTTESSRPSRSPVHTAVDLDDSKS<br>ERSRSTTPATVLSTSSAAGDGSANAAGLEDDDNDDMEMMEVTRKRSSPAVDEEG<br>MRPSKVQKVEVTVASPASRRSSRQASRNPTASPSSKASKATTHEAPAPEELESD<br>AESYSETYDKEGFDGDYHSGHEDQYSEEDEEEEYAEPETMTVNGMTIVKL |
| 1048 | *Drosophila* dDnmt2 | MVFRVLELFSGIGGMHYAFNYAQLDGQIVAALDVNTVANAVYAHNYGSNLVKTR<br>NIQSLSVKEVTKLQANMLLMSPPCQPHTRQGLQRDTEDKRSDALTHLCGLIPEC<br>QELEYILMENVKGFESSQARNQFIESLERSGFHWREFILTPTQFNVPNTRYRYY<br>CIARKGADFPFAGGKIWEEMPGAIAQNQGLSQIAEIVEENVSPDFLVPDDVLTK<br>RVLVMDIIHPAQSRSMCFTKGYTHYTEGTGSAYTPLSEDESHRIFELVKEIDTS<br>NQDASKSEKILQQRLDLLHQVRLRYFTPREVARLMSFPENFEFPPETTNRQKYR<br>LLGNSINVKVVGELIKLLTIK |

TABLE 18-continued

Sequence listing.

| SEQ | Description | Sequence |
|---|---|---|
| 1049 | *S. pombe* Pmt1 | MLSTKRLRVLELYSGIGGMHYALNLANIPADIVCAIDINPQANEIYNLNHGKLA<br>KHMDISTLTAKDFDAFDCKLWTMSPSCQPFTRIGNRKDILDPRSQAFLNILNVL<br>PHVNNLPEYILIENVQGFEESKAAEECRKVLRNCGYNLIEGILSPNQFNIPNSR<br>SRWYGLARLNFKGEWSIDDVFQFSEVAQKEGEVKRIRDYLEIERDWSSYMVLES<br>VLNKWGHQFDIVKPDSSSCCCFTRGYTHLVQGAGSILQMSDHENTHEQFERNRM<br>ALQLRYFTAREVARLMGFPESLEWSKSNVTEKCMYRLLGNSINVKVVSYLISLL<br>LEPLNF |
| 1050 | *Arabidopsis* DRM1 | MVMSHIFLISQIQEVEHGDSDDVNWNTDDDELAIDNFQFSPSPVHISATSPNSI<br>QNRISDETVASFVEMGFSTQMIARAIEETAGANMEPMMILETLFNYSASTEASS<br>SKSKVINHFIAMGFPEEHVIKAMQEHGDEDVGEITNALLTYAEVDKLRESEDMN<br>ININDDDDDNLYSLSSDDEEDELNNSSNEDRILQALIKMGYLREDAAIAIERCG<br>EDASMEEVVDFICAAQMARQFDEIYAEPDKKELMNNNKKRRTYTETPRKPNTDQ<br>LISLPKEMIGFGVPNHPGLMMHRPVPIPDIARGPPFFYYENVAMTPKGVWAKIS<br>SHLYDIVPEFVDSKHFCAAARKRGYIHNLPIQNRFQIQPPQHNTIQEAFPLTKR<br>WWPSWDGRTKLNCLLTCIASSRLTEKIREALERYDGETPLDVQKWVMYECKKWN<br>LVWVGKNKLAPLDADEMEKLLGFPRDHTRGGGISTTDRYKSLGNSFQVDTVAYH<br>LSVLKPLFPNGINVLSLFTGIGGGEVALHRLQIKMNVVVSVEISDANRNILRSF<br>WEQTNQKGILREFKDVQKLDDNTIERLMDEYGGFDLVIGGSPCNNLAGGNRHHR<br>VGLGGEHSSLFFDYCRILEAVRRKARHMRR |
| 1051 | *Arabadopsis* DRM2 | MVIWNNDDDDFLEIDNFQSSPRSSPIHAMQCRVENLAGVAVTTSSLSSPTETTD<br>LVQMGFSDEVFATLFDMGFPVEMISRAIKETGPNVETSVIIDTISKYSSDCEAG<br>SSKSKAIDHFLAMGFDEEKVVKAIQEHGEDNMEAIANALLSCPEAKKLPAAVEE<br>EDGIDWSSSDDDTNYTDMLNSDDEKDPNSNENGSKIRSLVKMGFSELEASLAVE<br>RCGENVDIAELTDELCAAQMAREFSEFYTEHEEQKPRHNIKKRRFESKGEPRSS<br>VDDEPIRLPNPMIGFGVPNEPGLITHRSLPELARGPPFFYYENVALTPKGVWET<br>ISRHLFEIPPEFVDSKYFCVAARKRGYIHNLPINNRFQIQPPPKYTIHDAFPLS<br>KRWWPEWDKRTKLNCILTCTGSAQLTNRIRVALEPYNEEPEPPKHVQRYVIDQC<br>KKWNLVWVGKNKAAPLEPDEMESILGFPKNHTRGGGMSRTERFKSLGNSFQVDT<br>VAYHLSVLKPIFPHGINVLSLFTGIGGGEVALHRLQIKMKLVVSVEISKVNRNI<br>LKDFWEQTNQTGELIEFSDIQHLTNDTIEGLMEKYGGFDLVIGGSPCNNLAGGN<br>RVSRVGLEGDQSSLFFEYCRILEVVRARMRGS |
| 1052 | *Arabadopsis* CMT1 | MAARNKQKKRAEPESDLCFAGKPMSVVESTIRWPHRYQSKKTKLQAPTKKPANK<br>GGKKEDEEIIKQAKCHFDKALVDGVLINLNDDVYVTGLPGKLKFIAKVIELFEA<br>DDGVPYCRFRWYYRPEDTLIERFSHLVQPKRVFLSNDENDNPLTCIWSKVNIAK<br>VPLPKITSRIEQRVIPPCDYYYDMKYEVPYLNFTSADDGSDASSSLSSDSALNC<br>FENLHKDEKFLLDLYSGCGAMSTGFCMGASISGVKLITKWSVDINKFACDSLKL<br>NHPETEVRNEAAEDFLALLKEWKRLCEKFSLVSSTEPVESISELEDEEVEENDD<br>IDEASTGAELEPGEFEVEKFLGIMFGDPQGTGEKTLQLMVRWKGYNSSYDTWEP<br>YSGLGNCKEKLKEYVIDGFKSHLLPLPGTVYTVCGGPPCQGISGYNRYRNNEAP<br>LEDQKNQQLLVFLDIIDFLKPNYVLMENVVDLLRFSKGFLARHAVASFVAMNYQ<br>TRLGMMAAGSYGLPQLRNRVFLWAAQPSEKLPPYPLPTHEVAKKENTPKEFKDL<br>QVGRIQMEFLKLDNALTLADAISDLPPVTNYVANDVMDYNDAAPKTEFENFISL<br>KRSETLLPAFGGDPTRRLFDHQPLVLGDDDLERVSYIPKQKGANYRDMPGVLVH<br>NNKAEINPRFRAKLKSGKNVVPAYAISFIKGKSKKPFGRLWGDEIVNTVVTRAE<br>PHNQCVIHPMQNRVLSVRENARLQGFPDCYKLCGTIKEKYIQVGNAVAVPVGVA<br>LGYAFGMASQGLTDDEPVIKLPFKYPECMQAKDQI |
| 1053 | *Arabadopsis* CMT2 | MLSPAKCESEEAQAPLDLHSSSRSEPECLSLVLWCPNPEEAAPSSTRELIKLPD<br>NGEMSLRRSTTLNCNSPEENGGEGRVSQRKSSRGKSQPLLMLTNGCQLRRSPRF<br>RALHANFDNVCSVPVTKGGVSQRKFSRGKSQPLLTLTNGCQLRRSPRFRAVDGN<br>FDSVCSVPVTGKFGSRKRKSNSALDKKESSDSEGLTFKDIAVIAKSLEMEIISE<br>CQYKNNVAEGRSRLQDPAKRKVDSDTLLYSSINSSKQSLGSNKRMRRSQREMKG<br>TENEGEENLGKSKGKGMSLASCSFRRSTRLSGTVETGNTETLNRRKDCGPALCG<br>AEQVRGTERLVQISKKDHCCEAMKKCEGDGLVSSKQELLVFPSGCIKKTVNGCR<br>DRTLGKPRSSGLNTDDIHTSSLKISKNDTSNGLTMTTALVEQDAMESLLQGKTS<br>ACGAADKGKTREMHVNSTVIYLSDSDEPSSIEYLNGDNLTQVESGSALSSGGNE<br>GIVSLDLNNPTKSTKRKGKRVTRTAVQEQNKRSICFFIGEPLSCEEAQERWRWR<br>YELKERKSKSRGQQSEDDEDKIVANVECHYSQAKVDGHTFSLGDFAYIKGEEEE<br>THVGQIVEFFKTTDGESYPRVQWFYRATDTIMERQATNHDKRRLFYSTVMNDNP<br>VDCLISKVTVLQVSPRVGLKPNSIKSDYYFDMEYCVEYSTFQTLRNPKTSENKL<br>ECCADVVPTESTESILKKKSFSGELPVLDLYSGCGGMSTGLSLGAKISGVDVVT<br>KWAVDQNTAACKSLKLNHPNTQVRNDAAGDFLQLLKEWDKLCKRYVENNDQRTD<br>TLRSVNSTKETSGSSSSSDDDSDSEEYEVEKLVDICFGDHDKTGKNGLKFKVHW<br>KGYRSDEDTWELAEELSNCQDAIREFVTSGFKSKILPLPGRVGVICGGPPCQGI<br>SGYNRHRNVDSPLNDERNQQIIVEMDIVEYLKPSYVLMENVVDILRMDKGSLGR<br>YALSRLVNMRYQARLGIMTAGCYGLSQFRSRVFMWGAVPNKNLPPFPLPTHDVI<br>VRYGLPLEFERNVVAYAEGQPRKLEKALVLKDAISDLPHVSNDEDREKLPYESL<br>PKTDFQRYIRSTKRDLTGSAIDNCNKRTMLLHDHRPFHINEDDYARVCQIPKRK<br>GANFRDLPGLIVRNNTVCRDPSMEPVILPSGKPLVPGYVFTFQQGKSKRPFARL<br>WWDETVPTVLTVPTCHSQALLHPEQDRVLTIRESARLQGFPDYFQFCGTIKERY<br>CQIGNAVAVSVSRALGYSLGMAFRGLARDEHLIKLPQNFSHSTYPQLQETIPH |

TABLE 18-continued

Sequence listing.

| SEQ | Description | Sequence |
|---|---|---|
| 1054 | *Arabadopsis* CMT3 | MAPKRKRPATKDDTTKSIPKPKKRAPKRAKTVKEEPVTVVEEGEKHVARFLDEP IPESEAKSTWPDRYKPIEVQPPKASSRKKTKDDEKVEIIRARCHYRRAIVDERQ IYELNDDAYVQSGEGKDPFICKIIEMFEGANGKLYFTARWFYRPSDTVMKEFEI LIKKKRVFFSEIQDTNELGLLEKKLNILMIPLNENTKETIPATENCDFFCDMNY FLPYDTFEAIQQETMMAISESSTISSDTDIREGAAAISEIGECSQETEGHKKAT LLDLYSGCGAMSTGLCMGAQLSGLNLVTKWAVDMNAHACKSLQHNHPETNVRNM TAEDFLFLLKEWEKLCIHFSLRNSPNSEEYANLHGLNNVEDNEDVSEESENEDD GEVFTVDKIVGISFGVPKKLLKRGLYLKVRWLNYDDSHDTWEPIEGLSNCRGKI EEFVKLGYKSGILPLPGGVDVVCGGPPCQGISGHNRFRNLLDPLEDQKNKQLLV YMNIVEYLKPKFVLMENVVDMLKMAKGYLARFAVGRLLQMNYQVRNGMMAAGAY GLAQFRLRFFLWGALPSEIIPQFPLPTHDLVHRGNIVKEFQGNIVAYDEGHTVK LADKLLLKDVISDLPAVANSEKRDEITYDKDPTTPFQKFIRLRKDEASGSQSKS KSKKHVLYDHHPLNLNINDYERVCQVPKRKGANFRDFPGVIVGPGNVVKLEEGK ERVKLESGKTLVPDYALTYVDGKSCKPFGRLWWDEIVPTVVTRAEPHNQVIIHP EQNRVLSIRENARLQGFPDDYKLFGPPKQKYIQVGNAVAVPVAKALGYALGTAF QGLAVGKDPLLTLPEGFAFMKPTLPSELA |
| 1055 | *Neurospora* Rid | MAEQNPFVIDDEDDVIQIHDEEEVEEEVAEVIDITEDDIEPSELDRAFGSRPKE ETLPSLLLRDQGFIVRPGMTVELKAPIGRFAISFVRVNSIVKVRQAHVNNVTIR GHGFTRAKEMNGMLPKQLNECCLVASIDTRDPRP |
| 1056 | *E. coli* strain 12 hsdM | MNNNDLVAKLWKLCDNLRDGGVSYQNYVNELASLLFLKMCKETGQEAEYLPEGY RWDDLKSRIGQEQLQFYRKMLVHLGEDDKKLVQAVFHNVSTTITEPKQITALVS NMDSLDWYNGAHGKSRDDFGDMYEGLLQKNANETKSGAGQYFTPRPLIKTIIHL LKPQPREVVQDPAAGTAGFLIEADRYVKSQTNDLDDLDGDTQDFQIHRAFIGLE LVPGTRRLALMNCLLHDIEGNLDHGGAIRLGNTLGSDGENLPKAHIVATNPPFG SAAGTNITRTFVHPTSNKQLCFMQHIIETLHPGGRAAVVVPDNVLFEGGKGTDI RRDLMDKCHLHTILRLPTGIFYAQGVKTNVLFFTKGTVANPNQDKNCTDDVWVY DLRTNMPSFGKRTPFTDEHLQPFERVYGEDPHGLSPRTEGEWSENAEETEVADS EENKNTDQHLATSRWRKFSREWIRTAKSDSLDISWLKDKDSIDADSLPEPDVLA AEAMGELVQALSELDALMRELGASDEADLQRQLLEEAFGGVKE |
| 1057 | *E. coli* strain 12 hsdS | MSAGKLPEGWVIAPVSTVTTLIRGVTYKKEQAINYLKDDYLPLIRANNIQNGKF DTTDLVFVPKNLVKESQKISPEDIVIAMSSGSKSVVGKSAHQHLPFECSFGAFC GVLRPEKLIFSGFIAHFTKSSLYRNKISSLSAGANINNIKPASFDLINIPIPPL AEQKIIAEKLDTLLAQVDSTKARFEQIPQILKRFRQAVLGGAVNGKLTEKWRNF EPQHSVFKKLNFESILTELRNGLSSKPNESGVGHPILRISSVRAGHVDQNDIRE LECSESELNRHKLQDGDLLFTRYNGSLEFVGVCGLLKKLQHQNLLYPDKLIRAR LTKDALPEYIEIFFSSPSARNAMMNCVKTTSGQKGISGKDIKSQVVLLPPVKEQ AEIVRRVEQLFAYADTIEKQVNNALARVNNLTQSILAKAFRGELTAQWRAENPD LISGENSAAALLEKIKAERAASGGKKASRKKS |
| 1058 | *T. aquaticus* M TaqI | MGLPPLLSLPSNSAPRSLGRVETPPEVVDFMVSLAEAPRGGRVLEPACAHGPFL RAFREAHGTAYRFVGVEIDPKALDLPPWAEGILADFLLWEPGEAFDLILGNPPY GIVGEASKYPIHVFKAVKDLYKKAFSTWKGKYNLYGAFLEKAVRLLKPGGVLVF VVPATWLVLEDFALLREFLAREGKTSVYYLGEVFPQKKVSAVVIRFQKSGKGLS LWDTQESESGFTPILWAEYPHWEGEIIRFETEETRKLEISGMPLGDLFHIRFAA RSPEFKKHPAVRKEPGPGLVPVLTGRNLKPGWVDYEKNHSGLWMPKERAKELRD FYATPHLVVAHTKGTRVVAAWDERAYPWREEFHLLPKEGVRLDPSSLVQWLNSE AMQKHVRTLYRDFVPHLTLRMLERLPVRREYGEHTSPESARNF |
| 1059 | *E. coli* M EcoDam | MKKNRAFLKWAGGKYPLLDDIKRHLPKGECLVEPFVGAGSVFLNTDFSRYILAD INSDLISLYNIVKMRTDEYVQAARELFVPETNCAEVYYQFREEFNKSQDPFRRA VLFLYLNRYGYNGLCRYNLRGEFNVPFGRYKKPYFPEAELYHFAEKAQNAFFYC ESYADSMARADDASVVYCDPPYAPLSATANFTAYHTNSFTLEQQAHLAEIAEGL VERHIPVLISNHDTMLTREWYQRAKLHVVKVRRSISSNGGTRKKVDELLALYKP GVVSPAKK |
| 1060 | *C. crescentus* M CcrMI | MKFGPETIIHGDCIEQMNALPEKSVDLIFADPPYNLQLGGDLLRPDNSKVDAVD DHWDQFESFAAYDKFTREWLKAARRVLKDDGAIWVIGSYHNIFRVGVAVQDLGF WILNDIVWRKSNPMPNFKGTRFANAHETLIWASKSQNAKRYTFNYDALKMANDE VQMRSDWTIPLCTGEERIKGADGQKAHPTQKPEALLYRVILSTTKPGDVILDPF FGVGTTGAAAKRLGRKFIGIEREAEYLEHAKARIAKVVPIAPEDLDVMGSKRAE PRVPFGTIVEAGLLSPGDTLYCSKGTHVAKVRPDGSITVGDLSGSIHKIGALVQ SAPACNGWTYWHFKTDAGLAPIDVLRAQVRAGMN |

TABLE 18-continued

Sequence listing.

| SEQ | Description | Sequence |
|-----|-------------|----------|
| 1061 | *C. difficile* CamA | MDDISQDNFLLSKEYENSLDVDTKKASGIYYTPKIIVDYIVKKTLKNHDIIKNP<br>YPRILDISCGCGNFLLEVYDILYDLFEENIYELKKKYDENYWTVDNIHRHILNY<br>CIYGADIDEKAISILKDSLTNKKVVNDLDESDIKINLFCCDSLKKKWRYKEDYI<br>VGNPPYIGHKKLEKKYKKFLLEKYSEVYKDKADLYFCFYKKIIDILKQGGIGSV<br>ITPRYFLESLSGKDLREYIKSNVNVQEIVDFLGANIFKNIGVSSCILTFDKKKT<br>KETYIDVFKIKNEDICINKFETLEELLKSSKFEHFNINQRLLSDEWILVNKDDE<br>TFYNKIQEKCKYSLEDIAISFQGIITGCDKAFILSKDDVKLNLVDDKFLKCWIK<br>SKNINKYIVDKSEYRLIYSNDIDNENTNKRILDEIIGLYKTKLENRRECKSGIR<br>KWYELQWGREKLFFERKKIMYPYKSNENRFAIDYDNNFSSADVYSFFIKEEYLD<br>KFSYEYLVGILNSSVYDKYFKITAKKMSKNIYDYYPNKVMKIRIFRDNNYEEIE<br>NLSKQIISILLNKSIDKGKVEKLQIKMDNLIMDSLGI |
| 1062 | KAP1 | MAASAAAASAAAASAASGSPGPGEGSAGGEKRSTAPSAAASASASAAAASSPAGG<br>GAEALELLEHCGVCRERLRPEREPRLLPCLHSACSACLGPAAPAAANSSGDGGA<br>AGDGTVVDCPVCKQQCFSKDIVENYFMRDSGSKAATDAQDANQCCTSCEDNAPA<br>TSYCVECSEPLCETCVEAHQRVKYTKDHTVRSTGPAKSRDGERTVYCNVHKHEP<br>LVLFCESCDTLTCRDCQLNAHKDHQYQFLEDAVRNQRKLLASLVKRLGDKHATL<br>QKSTKEVRSSIRQVSDVQKRVQVDVKMAILQIMKELNKRGRVLVNDAQKVTEGQ<br>QERLERQHWTMTKIQKHQEHILRFASWALESDNNTALLLSKKLIYFQLHRALKM<br>IVDPVEPHGEMKFQWDLNAWTKSAEAFGKIVAERPGTNSTGPAPMAPPRAPGPL<br>SKQGSGSSQPMEVQEGYGFGSGDDPYSSAEPHVSGVKRSRSGEGEVSGLMRKVP<br>RVSLERLDLDLTADSQPPVFKVFPGSTTEDYNLIVIERGAAAAATGQPGTAPAG<br>TPGAPPLAGMAIVKEEETEAAIGAPPTATEGPETKPVLMALAEGPGAEGPRLAS<br>PSGSTSSGLEVVAPEGTSAPGGGPGTLDDSATICRVCQKPGDLVMCNQCEFCFH<br>LDCHLPALQDVPGEEWSCSLCHVLPDLKEEDGSLSLDGADSTGVVAKLSPANQR<br>KCERVLLALFCHEPCRPLHQLATDSTFSLDQPGGTLDLTLIRARLQEKLSPPYS<br>SPQEFAQDVGRMFKQFNKLTEDKADVQSIIGLQRFFETRMNEAFGDTKFSAVLV<br>EPPPMSLPGAGLSSQELSGGPGDGP |
| 1063 | MECP2 | MVAGMLGLREEKSEDQDLQGLKDKPLKFKKVKKDKKEEKEGKHEPVQPSAHHSA<br>EPAEAGKAETSEGSGSAPAVPEASASPKQRRSIIRDRGPMYDDPTLPEGWTRKL<br>KQRKSGRSAGKYDVYLINPQGKAFRSKVELIAYFEKVGDTSLDPNDFDFTVTGR<br>GSPSRREQKPPKKPKSPKAPGTGRGRGRPKGSGTTRPKAATSEGVQVKRVLEKS<br>PGKLLVKMPFQTSPGGKAEGGGATTSTQVMVIKRPGRKRKAEADPQAIPKKRGR<br>KPGSVVAAAAEAKKKAVKESSIRSVQETVLPIKKRKTRETVSIEVKEVVKPLL<br>VSTLGEKSGKGLKTCKSPGRKSKESSPKGRSSSASSPPKKEHHHHHHSESPKA<br>PVPLLPPLPPPPPEPESSEDPTSPPEPQDLSSSVCKEEKMPRGGSLESDGCPKE<br>PAKTQPAVATAATAAEKYKHRGEGERKDIVSSSMPRPNREEPVDSRTPVTERVS |
| 1064 | linker | SGSETPGTSESATPES |
| 1065 | linker | SGGS |
| 1066 | linker | SGGSSGSETPGTSESATPESSGGS |
| 1067 | linker | SGGSSGGSSGSETPGTSESATPESSGGSSGGS |
| 1068 | linker | GGSGGSPGSPAGSPTSTEEGTSESATPESGPGTSTEPSEGSAPGSPAGSPTSTE<br>EGTSTEPSEGSAPGTSTEPSEGSAPGTSESATPESGPGSEPATSGGSGGS |
| 1069 | XTEN linker<br>(XTEN16) | SGSETPGTSESATPES |
| 1070 | XTEN linker | SGGSSGGSSGSETPGTSESATPES |
| 1071 | XTEN linker | SGGSSGGSSGSETPGTSESATPESSGGSSGGSSGGSSGGS |
| 1072 | XTEN linker | SGGSSGGSSGSETPGTSESATPESSGGSSGGSSGGSSGGSSGSETPGTSESATP<br>ESSGGSSGGS |
| 1073 | XTEN linker | PGSPAGSPTSTEEGTSESATPESGPGTSTEPSEGSAPGSPAGSPTSTEEGTSTE<br>PSEGSAPGTSTEPSEGSAPGTSESATPESGPGSEPATS |
| 1074 | NLS | PKKKRKV |
| 1075 | NLS | AVKRPAATKKAGQAKKKKLD |
| 1076 | NLS | MSRRRKANPTKLSENAKKLAKEVEN |
| 1077 | NLS | PAAKRVKLD |

TABLE 18-continued

Sequence listing.

| SEQ | Description | Sequence |
|---|---|---|
| 1078 | NLS | KLKIKRPVK |
| 1079 | NLS | MDSLLMNRRKFLYQFKNVRWAKGRRETYLC |
| 1092 | XTEN linker (XTEN80) | GGPSSGAPPPSGGSPAGSPTSTEEGTSESATPESGPGTSTEPSEGSAPGSPAGS PTSTEEGTSTEPSEGSAPGTSTEPSE |
| 1236 | Plasmid for fusion protein with mRNA001 | CGTCGATCGACGGATCGGGAGATCTCCCGATCCCCTATGGTGCACTCTCAGTAC AATCTGCTCTGATGCCGCATAGTTAAGCCAGTATCTGCTCCCTGCTTGTGTGTT GGAGGTCGCTGAGTAGTGCGCGAGCAAAATTTAAGCTACAACAAGGCAAGGCTT GACCGACAATTGCATGAAGAATCTGCTTAGGGTTAGGCGTTTTGCGCTGCTTCG CGATGTACGGGCCAGATATACGCGTTGACATTGATTATTGACTAGTTATTAATA GTAATCAATTACGGGGTCATTAGTTCATAGCCCATATATGGAGTTCCGCGTTAC ATAACTTACGGTAAATGGCCCGCCTGGCTGACCGCCCAACGACCCCCGCCCATT GACGTCAATAATGACGTATGTTCCCATAGTAACGCCAATAGGGACTTTCCATTG ACGTCAATGGGTGGAGTATTTACGGTAAACTGCCCACTTGGCAGTACATCAAGT GTATCATATGCCAAGTACGCCCCCTATTGACGTCAATGACGGTAAATGGCCCGC CTGGCATTATGCCCAGTACATGACCTTATGGGACTTTCCTACTTGGCAGTACAT CTACGTATTAGTCATCGCTATTACCATGGTGATGCGGTTTTGGCAGTACATCAA TGGGCGTGGATAGCGGTTTGACTCACGGGGATTTCCAAGTCTCCACCCCATTGA CGTCAATGGGAGTTTGTTTTGGCACCAAAATCAACGGGACTTTCCAAAATGTCG TAACAACTCCGCCCCATTGACGCAAATGGGCGGTAGGCGTGTACGGTGGGAGGT CTATATAAGCAGAGCTCTCTGGCTAACTAGAGAACCCACTGCTTACTGGCTTAT CGAAATTAATACGACTCACTATAAGGAGACCCAAGCTACCGGTGCCACCATGTA CCCATACGATGTTCCAGATTACGCTTCGCCGAAGAAAAAGCGCAAGGTCAATCA CGATCAGGAGTTCGACCCCCCTAAGGTGTACCCACCAGTGCCTGCAGAGAAGAG GAAGCCAATCCGGGTGCTGAGCCTGTTTGATGGCATCGCCACCGGCCTGCTGGT GCTGAAGGATCTGGGCATCCAGGTGGACCGGTACATCGCCTCCGAGGTGTGCGA GGATTCTATCACCGTGTGCCATGGTGCGCCACCAGGGCAAGATCATGTATGTGG GCGACGTGCGGTCCGTGACACAGAAGCACATCCAGGAGTGGGGCCCATTCGATCT GGTGATCGGCGGCAGCCCCTGTAATGACCTGTCCATCGTGAACCCTGCAAGGAA GGGACTGTACGAGGGAACCGGCCGGCTGTTCTTTGAGTTTTATAGACTGCTGCA CGACGCCAGGCCTAAGGAGGGCGACGATAGACCATTCTTTTGGCTGTTCGAGAA TGTGGTGGCTATGGGCGTGAGCGATAAGAGGGACATCTCCAGGTTTCTGGAGTC TAACCCCGTGATGATCGATGCAAAGGAGGTGTCCGCCGCACACAGAGCCAGGTA TTTCTGGGGCAATCTGCCAGGAATGAACAGGCCACTGGCAAGCACCGTGAATGA CAAGCTGGAGCTGCAGGAGTGCCTGGAGCACGGAAGGATCGCCAAGTTTTCCAA GGTGCGCACAATCACCACACGGAGCAATTCCATCAAGCAGGGCAAGGATCAGCA CTTCCCCGTGTTCATGAACGAGAAGGAGGACATCCTGTGGTGTACCGAGATGGA GAGAGTGTTCGGCTTTCCAGTGCACTACACAGACGTGTCTAACATGAGCAGGCT GGCAAGGCAGCGGCTGCTGGGCAGATCTTGGAGCGTGCCCGTGATCAGGCACCT GTTCGCCCCTCTGAAGGAGTATTTTGCCTGCGTGAGCAGCGGCAACTCCAATGC CAACAGCCGGGGCGCCCTCTTTCAGCTCCGGATTGGTGCCTCTGAGCCTGAGGGG CTCCCACATGGCAGCAATCCCCGCCCTGGACCCCGAGGCCGAGCCTAGCATGGA CGTGATCCTGGTGGGCTCTAGCGAGCTGTCCTCTAGCGTGTCTCCAGGAACCGG AAGGGATCTGATCGCATACGAGGTGAAGGCCAATCAGCGGAACATCGAGGACAT CTGTATCTGCTGTGGCAGCCTGCAGGTGCACACACAGCACCCACTGTTCGAGGG AGGAATCTGCGCACCCTGTAAGGATAAGTTCCTGGACGCCCTGTTTCTGTACGA CGATGACGGCTACCAGTCCTATTGCTCTATCTGCTGTTCCGGCGAGACCCTGCT GATCTGCGGCAATCAGATTGTACAAGGTGCTATTGTTTTGAGTGCGTGGACTC TCTGGTGGGACCAGGCACCAGCGGAAAGGTGCACGCCATGTCCAACTGGGTGTG CTACCTGTGCCTGCCATCCTCTCGCAGCGGACTGCTGCAGCGGAGAAGGAAGTG GAGATCCCAGCTGAAGGCCTTCTATGATAGGGAGTCTGAGAACCCCCTGGAGAT GTTTGAGACCGTGCCAGTGTGGCGCCGGCCGGCCGTGAGGGTGCTGAGCCTGTT CGAGGATATCAAGAAGGAGCTGACATCCCTGGGCTTTCTGGAGTCCGGCTCTGA CCCCGGACAGCTGAAGCACGTGGTGGATGTGACCGACACAGTGCGGAAGGATGT GGAGGAGTGGGGCCCTTTCGACCTGGTGTACGGAGCAACCCCTCCACTGGGACA CACATGCGACAGACCCCCTTCTTGGTACCTGTTCCAGTTTCACCGCCTGCTGCA GTATGCAAGGCCAAAGCCAGGCAGCCCTAGACCATTCTTTTGGATGTTCGTGGA TAATCTGGTGCTGAACAAGGAGGATCTGGACGTGGCCAGCAGGTTTCTGGAGAT GGAGCCAGTGACCATCCCAGACGTGCACGGCGGCTCCCTGCAGAATGCCGTGCG CGTGTGGTCTAACATCCCTGCCATCAGAAGCAGGCACTGGGCACTGGTGAGCGA GGAGGAGCTGTCCCTGCTGGCCCAGAATAAGCAGAGCAGCAAGCTGGCCGCCAA GTGGCCTACAAAGCTGGTGAAGAACTGCTTCCTGCCACTGCGGGAGTACTTCAA GTATTTTTCCACCGAGCTGACATCTAGCCTGGGAGGACCCTCCTCTGGCGCCCC ACCACCTAGCGGCGGCTCCCCTGCCGGCTCTCCAACCAGCACAGAGGAGGGCAC CAGCGAGTCCGCCACACCAGAGTCTGGACCTGGCACCAGCACAGAGCCATCCGA GGGCTCTGCCCCAGGCTCTCCTGCAGGCAGCCCTACCTCCACCGAAGAGGGCAC CAGCACAGAGCCTTCTGAGGGCAGCGCCCCAGGCACCTCTACAGAGCCAAGCGA GCTCGAGTCCCGGCCAGGGGAACGGCCCTTCCAGTGTCGGATCTGCATGAGAAA CTTTTCAAAGAAGTTCAATCTCCTTCAGCATACCCGGACCCACACTGGAGAGAA ACCCTTTCAGTGCAGGATATGTATGCGGAATTTTTCCCGGCAAGATAATTTGAA TTCCCATTTGAGAACACATACCGGGAGTCAGAAGCCTTTCCAATGCCGGATTTG CATGAGGAACTTCTCCCGAAGCCATAATTTGAAACTCCATACTAGAACACATAC AGGCGAGAAGCCATTCCAGTGTAGGATCTGCATGCGCAATTTTAGCCAATCAAC CACTCTTAAACGCCATCTGAGAACGCATACAGGTAGTCAGAAGCCTTTTCAGTG |

US 12,649,003 B2

TABLE 18-continued

Sequence listing.

| SEQ | Description | Sequence |
|---|---|---|
| | | CAGGATCTGCATGAGGAATTTTAGTCGCAACACGAACTTGACTAGACACACAAG<br>AACGCATACTGGAGAGAAGCCCTTTCAGTGTAGGATTTGTATGCGGAACTTCAG<br>CATTAAACACAACCTGGCAAGGCATCTGAGGACTCATTTGCGCGGGTCTAGCCC<br>CAAGAAGAAGAGAAAGGTGGGAGTCGACGGATCCAGCGGCTCCGAGACCCCAGG<br>CACATCTGAGAGCGCCACCCCTGAGTCCCGGACCCTGGTGACATTCAAGGACGT<br>GTTCGTGGACTTCACCCGGGAGGAGTGGAAGCTGCTGGACACAGCCCAGCAGAT<br>CGTGTACAGGAACGTGATGCTGGAGAACTATAAGAATCTGGTGTCTCTGGGCTA<br>CCAGCTGACAAAGCCAGATGTGATCCTGCGGCTGGAGAAGGGAGAGGAGCCCTG<br>GCTGGTGTAGTCTAGAAATCAACCTCTGGATTACAAAATTTGTGAAAGATTGAC<br>TGGTATTCTTAACTATGTTGCTCCTTTTACGCTATGTGGATACGCTGCTTTAAT<br>GCCTTTGTATCATGCTATTGCTTCCCGTATGGCTTTCATTTTCTCCTCCTTGTA<br>TAAATCCTGGTTGCTGTCTCTTTATGAGGAGTTGTGGCCCGTTGTCAGGCAACG<br>TGGCGTGGTGTGCACTGTGTTTGCTGACGCAACCCCCACTGGTTGGGGCATTGC<br>CACCACCTGTCAGCTCCTTTCCGGGACTTTCGCTTTCCCCCTCCCTATTGCCAC<br>GGCGGAACTCATCGCCGCCTGCCTTGCCCGCTGCTGGACAGGGGCTCGGCTGTT<br>GGGCACTGACAATTCCGTGGTGTTGTCGGGGAAATCATCGTCCTTTCCTTGGCT<br>GCTCGCCTGTGTTGCCACCTGGATTCTGCGCGGGACGTCCTTCTGCTACGTCCC<br>TTCGGCCCTCAATCCAGCGGACCTTCCTTCCCGCGGCCTGCTGCCGGCTCTGCG<br>GCCTCTTCCGCGTCTTCGCCTTCGCCCTCAGCGAGTCGGATCTCCCTTTGGGC<br>CGCCTCCCCGCCTGTTAATTAAAAAAAAAAAAAAAAAAAAAAAAAAAAAAAAA<br>AAAAAAAAAAAAAAAAAAAACTAGTGGCGCCTGATGCGGTATTTTCTCCTTACGCA<br>TCTGTGCGGTATTTCACACCGCATAATCCAGCACAGTGGCGGCCCGTTTAAACC<br>CGCTGATCAGCCTCGACTGTGCCTTCTAGTTGCCAGCCATCTGTTGTTTGCCCC<br>TCCCCCGTGCCTTCCTTGACCCTGGAAGGTGCCACTCCCACTGTCCTTTCCTAA<br>TAAAATGAGGAAATTGCATCGCATTGTCTGAGTAGGTGTCATTCTATTCTGGGG<br>GGTGGGGTGGGGCAGGACAGCAAGGGGGAGGATTGGGAAGACAATAGCAGGCAT<br>GCTGGGGATGCGGTGGGCTCTATGGCTTCTGAGGCGGAAAGAACCAGCTGCATT<br>AATGAATCGGCCAACGCGCGGGGAGAGGCGGTTTGCGTATTGGGCGCTCTTCCG<br>CTTCCTCGCTCACTGACTCGCTGCGCTCGGTCGTTCGGCTGCGGCGAGCGGTAT<br>CAGCTCACTCAAAGGCGGTAATACGGTTATCCACAGAATCAGGGGATAACGCAG<br>GAAAGAACATGTGAGCAAAAGGCCAGCAAAAGGCCAGGAACCGTAAAAAGGCCG<br>CGTTGCTGGCGTTTTTCCATAGGCTCCGCCCCCCTGACGAGCATCACAAAAATC<br>GACGCTCAAGTCAGAGGTGGCGAAACCCGACAGGACTATAAAGATACCAGGCGT<br>TTCCCCCTGGAAGCTCCCTCGTGCGCTCTCCTGTTCCGACCCTGCCGCTTACCG<br>GATACCTGTCCGCCTTTCTCCCTTCGGGAAGCGTGGCGCTTTCTCATAGCTCAC<br>GCTGTAGGTATCTCAGTTCGGTGTAGGTCGTTCGCTCCAAGCTGGGCTGTGTGC<br>ACGAACCCCCCGTTCAGCCCGACCGCTGCGCCTTATCCGGTAACTATCGTCTTG<br>AGTCCAACCCGGTAAGACACGACTTATCGCCACTGGCAGCAGCCACTGGTAACA<br>GGATTAGCAGAGCGAGGTATGTAGGCGGTGCTACAGAGTTCTTGAAGTGGTGGC<br>CTAACTACGGCTACACTAGAAGAACAGTATTTGGTATCTGCGCTCTGCTGAAGC<br>CAGTTACCTTCGGAAAAAGAGTTGGTAGCTCTTGATCCGGCAAACAAACCACCG<br>CTGGTAGCGGTTTTTTTGTTTGCAAGCAGCAGATTACGCGCAGAAAAAAAGGAT<br>CTCAAGAAGATCCTTTGATCTTTTCTACGGGGTCTGACGCTCAGTGGAACGAAA<br>ACTCACGTTAAGGGATTTTGGTCATGAGATTATCAAAAAGGATCTTCACCTAGA<br>TCCTTTTAAATTAAAAATGAAGTTTTAAATCAATCTAAAGTATATATGAGTAAA<br>CTTGGTCTGACAGTTACCAATGCTTAATCAGTGAGGCACCTATCTCAGCGATCT<br>GTCTATTTCGTTCATCCATAGTTGCCTGACTCCCCGTCGTGTAGATAACTACGA<br>TACGGGAGGGCTTACCATCTGGCCCCAGTGCTGCAATGATACCGCGAGACCCAC<br>GCTCACCGGCTCCAGATTTATCAGCAATAAACCAGCCAGCCGGAAGGGCCGAGC<br>GCAGAAGTGGTCCTGCAACTTTATCCGCCTCCATCCAGTCTATTAATTGTTGCC<br>GGGAAGCTAGAGTAAGTAGTTCGCCAGTTAATAGTTTGCGCAACGTTGTTGCCA<br>TTGCTACAGGCATCGTGGTGTCACGCTCGTCGTTTGGTATGGCTTCATTCAGCT<br>CCGGTTCCCAACGATCAAGGCGAGTTACATGATCCCCCATGTTGTGCAAAAAAG<br>CGGTTAGCTCCTTCGGTCCTCCGATCGTTGTCAGAAGTAAGTTGGCCGCAGTGT<br>TATCACTCATGGTTATGGCAGCACTGCATAATTCTCTTACTGTCATGCCATCCG<br>TAAGATGCTTTTCTGTGACTGGTGAGTACTCAACCAAGTCATTCTGAGAATAGT<br>GTATGCGGCGACCGAGTTGCTCTTGCCCGGCGTCAATACGGGATAATACCGCGC<br>CACATAGCAGAACTTTAAAAGTGCTCATCATTGGAAAACGTTCTTCGGGGCGAA<br>AACTCTCAAGGATCTTACCGCTGTTGAGATCCAGTTCGATGTAACCCACTCGTG<br>CACCCAACTGATCTTCAGCATCTTTTACTTTCACCAGCGTTTCTGGGTGAGCAA<br>AAACAGGAAGGCAAAATGCCGCAAAAAAGGGAATAAGGGCGACACGGAAATGTT<br>GAATACTCATACTCTTCCTTTTTCAATATTATTGAAGCATTTATCAGGGTTATT<br>GTCTCATGAGCGGATACATATTTGAATGTATTTAGAAAAATAAACAAATAGGGG<br>TTCCGCGCACATTTCCCCGAAAGTGCCACCTGA |
| 1237 | Plasmid for fusion protein with mRNA002 | CGTCGATCGACGGATCGGGAGATCTCCCGATCCCCTATGGTGCACTCTCAGTAC<br>AATCTGCTCTGATGCCGGCATAGTTAAGCCAGTATCTGCTCCCTGCTTGTGTGTT<br>GGAGGTCGCTGAGTAGTGCGCGAGCAAAATTTAAGCTACAACAAGGCAAGGCTT<br>GACCGACAATTGCATGAAGAATCTGCTTAGGGTTAGGCGTTTTGCGCTGCTTCG<br>CGATGTACGGGCCAGATATACGCGTTGACATTGATTATTGACTAGTTATTAATA<br>GTAATCAATTACGGGGTCATTAGTTCATAGCCCATATATGGAGTTCCGCGTTAC<br>ATAACTTACGGTAAATGGCCCGCCTGGCTGACCGCCCAACGACCCCCGCCCATT<br>GACGTCAATAATGACGTATGTTCCCATAGTAACGCCAATAGGGACTTTCCATTG<br>ACGTCAATGGGTGGAGTATTTACGGTAAACTGCCCACTTGGCAGTACATCAAGT<br>GTATCATATGCCAAGTACGCCCCCTATTGACGTCAATGACGGTAAATGGCCCGC<br>CTGGCATTATGCCCAGTACATGACCTTATGGGACTTTCCTACTTGGCAGTACAT |

TABLE 18-continued

Sequence listing.

| SEQ | Description | Sequence |
|-----|-------------|----------|
| | | CTACGTATTAGTCATCGCTATTACCATGGTGATGCGGTTTTGGCAGTACATCAA |
| | | TGGGCGTGGATAGCGGTTTGACTCACGGGGATTTCCAAGTCTCCACCCCATTGA |
| | | CGTCAATGGGAGTTTGTTTTGGCACCAAAATCAACGGGACTTTCCAAAATGTCG |
| | | TAACAACTCCGCCCCATTGACGCAAATGGGCGGTAGGCGTGTACGGTGGGAGGT |
| | | CTATATAAGCAGAGCTCTCTGGCTAACTAGAGAACCCACTGCTTACTGGCTTAT |
| | | CGAAATTAATACGACTCACTATAAGGAGACCCAAGCTACCGGTGCCACCATGTA |
| | | CCCATACGATGTTCCAGATTACGCTTCGCCGAAGAAAAAGCGCAAGGTCAATCA |
| | | CGATCAGGAGTTCGACCCCCCTAAGGTGTACCCACCAGTGCCTGCAGAGAAGAG |
| | | GAAGCCAATCCGGGTGCTGAGCCTGTTTGATGGCATCGCCACCGGCCTGCTGGT |
| | | GCTGAAGGATCTGGGCATCCAGGTGGACCGGTACATCGCCTCCGAGGTGTGCGA |
| | | GGATTCTATCACCGTGGGCATGGTGCGCCACCAGGGCAAGATCATGTATGTGGG |
| | | CGACGTGCGGTCCGTGACACAGAAGCACATCCAGGAGTGGGGCCCATTCGATCT |
| | | GGTGATCGGCGGCAGCCCCTGTAATGACCTGTCCATCGTGAACCCTGCAAGGAA |
| | | GGGACTGTACGAGGGAACCGGCCGGCTGTTCTTTGAGTTTTATAGACTGCTGCA |
| | | CGACGCCAGGCCTAAGGAGGGCGACGATAGACCATTCTTTTGGCTGTTCGAGAA |
| | | TGTGGTGGCTATGGGCGTGAGCGATAAGAGGGACATCTCCAGGTTTCTGGAGTC |
| | | TAACCCCGTGATGATCGATGCAAAGGAGGTGTCCGCCGCACACAGAGCCAGGTA |
| | | TTTCTGGGGCAATCTGCCAGGAATGAACAGGCCACTGGCAAGCACCGTGAATGA |
| | | CAAGCTGGAGCTGCAGGAGTGCCTGGAGCACGGAAGGATCGCCAAGTTTTCCAA |
| | | GGTGCGCACAATCACCACACGGAGCAATTCCATCAAGCAGGGCAAGGATCAGCA |
| | | CTTCCCCGTGTTCATGAACGAGAAGGAGGACATCCTGTGGTGTACCGAGATGGA |
| | | GAGAGTGTTCGGCTTTCCAGTGCACTACACAGACGTGTCTAACATGAGCAGGCT |
| | | GGCAAGGCAGCGGCTGCTGGGCAGATCTTGGAGCGTGCCCGTGATCAGGCACCT |
| | | GTTCGCCCCTCTGAAGGAGTATTTTGCCTGCGTGAGCAGCGGCAACTCCAATGC |
| | | CAACAGCCGGGGCCCCTCTTTCAGCTCCGGATTGGTGCCTCTGAGCCTGAGGGG |
| | | CTCCCACATGGCAGCAATCCCCGCCCTGGACCCCGAGGCCGAGCCTAGCATGGA |
| | | CGTGATCCTGGTGGGCTCTAGCGAGCTGTCCTCTAGCGTGTCTCCAGGAACCGG |
| | | AAGGGATCTGATCGCATACGAGGTGAAGGCCAATCAGCGGAACATCGAGGACAT |
| | | CTGTATCTGCTGTGGCAGCCTGCAGGTGCCACACAGCACCCACTGTTCGAGGG |
| | | AGGAATCTGCGCACCCTGTAAGGATAAGTTCCTGGACGCCCTGTTTCTGTACGA |
| | | CGATGACGGCTACCAGTCCTATTGCTCTATCTGCTGTTCCGGCGAGACCCTGCT |
| | | GATCTGCGGCAATCCAGATTGTACAAGGTGCTATTGTTTTGAGTGCGTGGACTC |
| | | TCTGGTGGGACCAGGCACCAGCGGAAAGGTGCACGCCATGTCCAACTGGGTGTG |
| | | CTACCTGTGCCTGCCATCCTCTCGCAGCGGACTGCTGCAGCGGAGAAGGAAGTG |
| | | GAGATCCCAGCTGAAGGCCTTCTATGATAGGGAGTCTGAGAACCCCCTGGAGAT |
| | | GTTTGAGACCGTGCCAGTGTGGCGCCGGCAGCCCGTGAGGGTGCTGAGCCTGTT |
| | | CGAGGATATCAAGAAGGAGCTGACATCCCTGGGCTTTCTGGAGTCCGGCTCTGA |
| | | CCCCGGACAGCTGAAGCACGTGGTGGATGTGACCGACACAGTGCGGAAGGATGT |
| | | GGAGGAGTGGGGGCCCTTTCGACCTGGTGTACGGAGCAACCCCTCCACTGGGACA |
| | | CACATGCGACAGACCCCCTTCTTGGTACCTGTTCCAGTTTCACCGCCTGCTGCA |
| | | GTATGCAAGGCCAAAGCCAGGCAGCCCTAGACCATTCTTTTGGATGTTCGTGGA |
| | | TAATCTGGTGCTGAACAAGGAGGATCTGGACGTGGCCAGCAGGTTTCTGGAGAT |
| | | GGAGCCAGTGACCATCCCAGACGTGCACGGCGGCTCCCTGCAGAATGCCGTGCG |
| | | CGTGTGGTCTAACATCCCTGCCATCAGAAGCAGGCACTGGGCACTGGTGAGCGA |
| | | GGAGGAGCTGTCCCTGCTGGCCCAGAATAAGCAGAGCAGCAAGCTGGCCGCCAA |
| | | GTGGCCTACAAAGCTGGTGAAGAACTGCTTCCTGCCACTGCGGGAGTACTTCAA |
| | | GTATTTTTCCACCGAGCTGACATCTAGCCTGGGAGGACCCTCCTCTGGCGCCCC |
| | | ACCACCTAGCGGCGGCTCCCCTGCCGGCTCTCCAACCAGCACAGAGGAGGGCAC |
| | | CAGCGAGTCCGCCACACCAGAGTCTGGACCTGGCACCAGCACAGAGCCATCCGA |
| | | GGGCTCTGCCCCAGGCTCTCCTGCAGGCAGCCCTACCTCCACCGAAGAGGGCAC |
| | | CAGCACAGAGCCTTCTGAGGGCAGCGCCCCAGGCACCTCTACAGAGCCAAGCGA |
| | | GCTCGAGTCCCGGCCAGGGGAACGGCCCTTCCAGTGTCGGATCTGCATGAGAAA |
| | | CTTTTCAAAGAAGTTCAATCTGCTTCAGCACACCCGGACCCACACTGGAGAGAA |
| | | ACCCTTTCAGTGCAGGATATGTATGCGGAATTTTTCCCGAAAAGATTACTTGAT |
| | | TAGCCACCTCCGAACACATACCGGGAGTCAGAAGCCTTTCCAATGCCGGATTTG |
| | | CATGAGGAACTTCTCCAGGAGCCACAACCTTAAACTGCACACAAGAACACATAC |
| | | AGGCGAGAAGCCATTCCAGTGTAGGATCTGCATGCGCAATTTTAGCCAATCCAC |
| | | AACATTGAAAAGACATCTTCGGACGCATACAGGTAGTCAGAAGCCTTTTCAGTG |
| | | CAGGATCTGCATGAGGAATTTTAGTCGACAAGATAATCTTGGCCGACATCTTCG |
| | | AACGCATACTGGAGAGAAGCCCTTTCAGTGTAGGATTTGTATGCGGAACTTCAG |
| | | CGTAGTAAACAACTTGAACAGACACTTGAAAACTCATTTGCGCGGGTCTAGCCC |
| | | CAAGAAGAAGAGAAAGGTGGGAGTCGACGGATCCAGCGGCTCCGAGACCCCAGG |
| | | CACATCTGAGAGCGCCACCCCTGAGTCCCGGACCCTGGTGACATTCAAGGACGT |
| | | GTTCGTGGACTTCACCCGGGAGGAGTGGAAGCTGCTGGACACAGCCCAGCAGAT |
| | | CGTGTACAGGAACGTGATGCTGGAGAACTATAAGAATCTGGTGTCTCTGGGCTA |
| | | CCAGCTGACAAAGCCAGATGTGATCCTGCGGCTGGAGAAGGGAGAGGAGCCCTG |
| | | GCTGGTGTAGTCTAGAAATCAACCTCTGGATTACAAAATTTGTGAAAGATTGAC |
| | | TGGTATTCTTAACTATGTTGCTCCTTTTACGCTATGTGGATACGCTGCTTTAAT |
| | | GCCTTTGTATCATGCTATTGCTTCCCGTATGGCTTTCATTTTCTCCTCCTTGTA |
| | | TAAATCCTGGTTGCTGTCTCTTTATGAGGAGTTGTGGCCCGTTGTCAGGCAACG |
| | | TGGCGTGGTGTGCACTGTGTTTGCTGACGCAACCCCCACTGGTTGGGGCATTGC |
| | | CACCACCTGTCAGCTCCTTTCCGGGACTTTCGCTTTCCCCCTCCCTATTGCCAC |
| | | GGCGGAACTCATCGCCGCCTGCCTTGCCCGCTGCTGGACAGGGGCTCGGCTGTT |
| | | GGGCACTGACAATTCCGTGGTGTTGTCGGGGAAATCATCGTCCTTTCCTTGGCT |
| | | GCTCGCCTGTGTTGCCACCTGGATTCTGCGCGGGACGTCCTTCTGCTACGTCCC |
| | | TTCGGCCCTCAATCCAGCGGACCTTCCTTCCCGCGGCCTGCTGCCGGCTCTGCG |

TABLE 18-continued

Sequence listing.

| SEQ | Description | Sequence |
|---|---|---|
| | | GCCTCTTCCGCGTCTTCGCCTTCGCCCTCAGACGAGTCGGATCTCCCTTTGGGC<br>CGCCTCCCCGCCTGTTAATTAAAAAAAAAAAAAAAAAAAAAAAAAAAAAAAAAAAA<br>AAAAAAAAAAAAAAAAAACTAGTGGCGCCTGATGCGGTATTTTCTCCTTACGCA<br>TCTGTGCGGTATTTCACACCGCATAATCCAGCACAGTGGCGGCCCGTTTAAACC<br>CGCTGATCAGCCTCGACTGTGCCTTCTAGTTGCCAGCCATCTGTTGTTTGCCCC<br>TCCCCCGTGCCTTCCTTGACCCTGGAAGGTGCCACTCCCACTGTCCTTTCCTAA<br>TAAAATGAGGAAATTGCATCGCATTGTCTGAGTAGGTGTCATTCTATTCTGGGG<br>GGTGGGGTGGGGCAGGACAGCAAGGGGGAGGATTGGGAAGACAATAGCAGGCAT<br>GCTGGGGATGCGGTGGGCTCTATGGCTTCTGAGGCGGAAAGAACCAGCTGCATT<br>AATGAATCGGCCAACGCGCGGGGAGAGGCGGTTTGCGTATTGGGCGCTCTTCCG<br>CTTCCTCGCTCACTGACTCGCTGCGCTCGGTCGTTCGGCTGCGGCGAGCGGTAT<br>CAGCTCACTCAAAGGCGGTAATACGGTTATCCACAGAATCAGGGGATAACGCAG<br>GAAAGAACATGTGAGCAAAAGGCCAGCAAAAGGCCAGGAACCGTAAAAAGGCCG<br>CGTTGCTGGCGTTTTTCCATAGGCTCCGCCCCCCTGACGAGCATCACAAAAATC<br>GACGCTCAAGTCAGAGGTGGCGAAACCCGACAGGACTATAAAGATACCAGGCGT<br>TTCCCCCTGGAAGCTCCCTCGTGCGCTCTCCTGTTCCGACCCTGCCGCTTACCG<br>GATACCTGTCCGCCTTTCTCCCTTCGGGAAGCGTGGCGCTTTCTCATAGCTCAC<br>GCTGTAGGTATCTCAGTTCGGTGTAGGTCGTTCGCTCCAAGCTGGGCTGTGTGC<br>ACGAACCCCCCGTTCAGCCCGACCGCTGCGCCTTATCCGGTAACTATCGTCTTG<br>AGTCCAACCCGGTAAGACACGACTTATCGCCACTGGCAGCAGCCACTGGTAACA<br>GGATTAGCAGAGCGAGGTATGTAGGCGGTGCTACAGAGTTCTTGAAGTGGTGGC<br>CTAACTACGGCTACACTAGAAGAACAGTATTTGGTATCTGCGCTCTGCTGAAGC<br>CAGTTACCTTCGGAAAAAGAGTTGGTAGCTCTTGATCCGGCAAACAAACCACCG<br>CTGGTAGCGGTTTTTTTGTTTGCAAGCAGCAGATTACGCGCAGAAAAAAAGGAT<br>CTCAAGAAGATCCTTTGATCTTTTCTACGGGGTCTGACGCTCAGTGGAACGAAA<br>ACTCACGTTAAGGGATTTTGGTCATGAGATTATCAAAAAGGATCTTCACCTAGA<br>TCCTTTTAAATTAAAAATGAAGTTTTAAATCAATCTAAAGTATATATGAGTAAA<br>CTTGGTCTGACAGTTACCAATGCTTAATCAGTGAGGCACCTATCTCAGCGATCT<br>GTCTATTTCGTTCATCCATAGTTGCCTGACTCCCCGTCGTGTAGATAACTACGA<br>TACGGGAGGGCTTACCATCTGGCCCCAGTGCTGCAATGATACCGCGAGACCCAC<br>GCTCACCGGCTCCAGATTTATCAGCAATAAACCAGCCAGCCGGAAGGGCCGAGC<br>GCAGAAGTGGTCCTGCAACTTTATCCGCCTCCATCCAGTCTATTAATTGTTGCC<br>GGGAAGCTAGAGTAAGTAGTTCGCCAGTTAATAGTTTGCGCAACGTTGTTGCCA<br>TTGCTACAGGCATCGTGGTGTCACGCTCGTCGTTTGGTATGGCTTCATTCAGCT<br>CCGGTTCCCAACGATCAAGGCGAGTTACATGATCCCCCATGTTGTGCAAAAAAG<br>CGGTTAGCTCCTTCGGTCCTCCGATCGTTGTCAGAAGTAAGTTGGCCGCAGTGT<br>TATCACTCATGGTTATGGCAGCACTGCATAATTCTCTTACTGTCATGCCATCCG<br>TAAGATGCTTTTCTGTGACTGGTGAGTACTCAACCAAGTCATTCTGAGAATAGT<br>GTATGCGGCGACCGAGTTGCTCTTGCCCGGCGTCAATACGGGATAATACCGCGC<br>CACATAGCAGAACTTTAAAAGTGCTCATCATTGGAAAACGTTCTTCGGGGCGAA<br>AACTCTCAAGGATCTTACCGCTGTTGAGATCCAGTTCGATGTAACCCACTCGTG<br>CACCCAACTGATCTTCAGCATCTTTTACTTTCACCAGCGTTTCTGGGTGAGCAA<br>AAACAGGAAGGCAAAATGCCGCAAAAAAGGGAATAAGGGCGACACGGAAATGTT<br>GAATACTCATACTCTTCCTTTTTCAATATTATTGAAGCATTTATCAGGGTTATT<br>GTCTCATGAGCGGATACATATTTGAATGTATTTAGAAAAATAAACAAATAGGGG<br>TTCCGCGCACATTTCCCCGAAAAGTGCCACCTGA |
| 1238 | Plasmid for fusion<br>protein with<br>mRNA0003 | CGTCGATCGACGGATCGGGAGATCTCCCGATCCCCTATGGTGCACTCTCAGTAC<br>AATCTGCTCTGATGCCGCATAGTTAAGCCAGTATCTGCTCCCTGCTTGTGTGTT<br>GGAGGTCGCTGAGTAGTGCGCGAGCAAAATTTAAGCTACAACAAGGCAAGGCTT<br>GACCGACAATTGCATGAAGAATCTGCTTAGGGTTAGGCGTTTTGCGCTGCTTCG<br>CGATGTACGGGCCAGATATACGCGTTGACATTGATTATTGACTAGTTATTAATA<br>GTAATCAATTACGGGGTCATTAGTTCATAGCCCATATATGGAGTTCCGCGTTAC<br>ATAACTTACGGTAAATGGCCCGCCTGGCTGACCGCCCAACGACCCCCGCCCATT<br>GACGTCAATAATGACGTATGTTCCCATAGTAACGCCAATAGGGACTTTCCATTG<br>ACGTCAATGGGTGGAGTATTTACGGTAAACTGCCCACTTGGCAGTACATCAAGT<br>GTATCATATGCCAAGTACGCCCCCTATTGACGTCAATGACGGTAAATGGCCCGC<br>CTGGCATTATGCCCAGTACATGACCTTATGGGACTTTCCTACTTGGCAGTACAT<br>CTACGTATTAGTCATCGCTATTACCATGGTGATGCGGTTTTGGCAGTACATCAA<br>TGGGCGTGGATAGCGGTTTGACTCACGGGGATTTCCAAGTCTCCACCCCATTGA<br>CGTCAATGGGAGTTTGTTTTGGCACCAAAATCAACGGGACTTTCCAAAATGTCG<br>TAACAACTCCGCCCCATTGACGCAAATGGGCGGTAGGCGTGTACGGTGGGAGGT<br>CTATATAAGCAGAGCTCTCTGGCTAACTAGAGAACCCACTGCTTACTGGCTTAT<br>CGAAATTAATACGACTCACTATAAGGAGACCCAAGCTACCGGTGCCACCATGTA<br>CCCATACGATGTTCCAGATTACGCTTCGCCGAAGAAAAAGCGCAAGGTCAATCA<br>CGATCAGGAGTTCGACCCCCCTAAGGTGTACCCACCAGTGCCTGCAGAGAAGAG<br>GAAGCCAATCCGGGTGCTGAGCCTGTTTGATGGCATCGCCACCGGCCTGCTGGT<br>GCTGAAGGATCTGGGCATCCAGGTGGACCGGTACATCGCCTCCGAGGTGTGCGA<br>GGATTCTATCACCGTGGGCATGGTGCGCCACCAGGGCAAGATCATGTATGTGGG<br>CGACGTGCGGTCCGTGACACAGAAGCACATCCAGGAGTGGGGCCCATTCGATCT<br>GGTGATCGGCGGCAGCCCCTGTAATGACCTGTCCATCGTGAACCCTGCAAGGAA<br>GGGACTGTACGAGGGAACCGGCCGGCTGTTCTTTGAGTTTTATAGACTGCTGCA<br>CGACGCCAGGCCTAAGGAGGGCGACGATAGACCATTCTTTTGGCTGTTCGAGAA<br>TGTGGTGGCTATGGGCGTGAGCGATAAGAGGGACATCTCCAGGTTTCTGGAGTC<br>TAACCCCGTGATGATCGATGCAAAGGAGGTGTCCGCGCACACAGAGCCAGGTA<br>TTTCTGGGGCAATCTGCCCAGGAATGAACAGGCCACTGGCAAGCACCGTGAATGA |

TABLE 18-continued

Sequence listing.

| SEQ | Description | Sequence |
|---|---|---|
| | | CAAGCTGGAGCTGCAGGAGTGCCTGGAGCACGGAAGGATCGCCAAGTTTTCCAA |
| | | GGTGCGCACAATCACCACACGGAGCAATTCCATCAAGCAGGGCAAGGATCAGCA |
| | | CTTCCCCGTGTTCATGAACGAGAAGGAGGACATCCTGTGGTGTACCGAGATGGA |
| | | GAGAGTGTTCGGCTTTCCAGTGCACTACACAGACGTGTCTAACATGAGCAGGCT |
| | | GGCAAGGCAGCGGCTGCTGGGCAGATCTTGGAGCGTGCCCGTGATCAGGCACCT |
| | | GTTCGCCCCTCTGAAGGAGTATTTTGCCTGCGTGAGCAGCGGCAACTCCAATGC |
| | | CAACAGCCGGGGCCCCTCTTTCAGCTCCGGATTGGTGCCTCTGAGCCTGAGGGG |
| | | CTCCCACATGGCAGCAATCCCCGCCCTGGACCCCGAGGCCGAGCCTAGCATGGA |
| | | CGTGATCCTGGTGGGCTCTAGCGAGCTGTCCTCTAGCGTGTCTCCAGGAACCGG |
| | | AAGGGATCTGATCGCATACGAGGTGAAGGCCAATCAGCGGAACATCGAGGACAT |
| | | CTGTATCTGCTGTGGCAGCCTGCAGGTGCACACACAGCACCCACTGTTCGAGGG |
| | | AGGAATCTGCGCACCCTGTAAGGATAAGTTCCTGGACGCCCTGTTTCTGTACGA |
| | | CGATGACGGCTACCAGTCCTATTGCTCTATCTGCTGTTCCGGCGAGACCCTGCT |
| | | GATCTGCGGCAATCCAGATTGTACAAGGTGCTATTGTTTTGAGTGCGTGGACTC |
| | | TCTGGTGGGACCAGGCACCAGCGGAAAGGTGCACGCCATGTCCAACTGGGTGTG |
| | | CTACCTGTGCCTGCCATCCTCTCGCAGCGGACTGCTGCAGCGGAGAAGGAAGTG |
| | | GAGATCCCAGCTGAAGGCCTTCTATGATAGGGAGTCTGAGAACCCCCTGGAGAT |
| | | GTTTGAGACCGTGCCAGTGTGGCGCCGGCAGCCCGTGAGGGTGCTGAGCCTGTT |
| | | CGAGGATATCAAGAAGGAGCTGACATCCCTGGGCTTTCTGGAGTCCGGCTCTGA |
| | | CCCCGGACAGCTGAAGCACGTGGTGGATGTGACCGACACAGTGCGGAAGGATGT |
| | | GGAGGAGTGGGGCCCTTTCGACCTGGTGTACGGAGCAACCCCTCCACTGGGACA |
| | | CACATGCGACAGACCCCCTTCTTGGTACCTGTTCCAGTTTCACCGCCTGCTGCA |
| | | GTATGCAAGGCCAAAGCCAGGCAGCCCTAGACCATTCTTTTGGATGTTCGTGGA |
| | | TAATCTGGTGCTGAACAAGGAGGATCTGGACGTGGCCAGCAGGTTTCTGGAGAT |
| | | GGAGCCAGTGACCATCCCAGACGTGCACGGCGGCTCCCTGCAGAATGCCGTGCG |
| | | CGTGTGGTCTAACATCCCTGCCATCAGAAGCAGGCACTGGGCACTGGTGAGCGA |
| | | GGAGGAGCTGTCCCTGCTGGCCCAGAATAAGCAGAGCAGCAAGCTGGCCGCCAA |
| | | GTGGCCTACAAAGCTGGTGAAGAACTGCTTCCTGCCACTGCGGGAGTACTTCAA |
| | | GTATTTTTCCACCGAGCTGACATCTAGCCTGGGGAGGACCCTCCTCTGGCGCCCC |
| | | ACCACCTAGCGGCGGCTCCCCTGCCGGCTCTCCAACCAGCACAGAGGAGGGCAC |
| | | CAGCGAGTCCGCCACACCAGAGTCTGGACCTGGCACCAGCACAGAGCCATCCGA |
| | | GGGCTCTGCCCCAGGCTCTCCTGCAGGCAGCCCTACCTCCACCGAAGAGGGCAC |
| | | CAGCACAGAGCCTTCTGAGGGCAGCGCCCCAGGCACCTCTACAGAGCCAAGCGA |
| | | GCTCGAGTCCCGGCCAGGGGAACGGCCCTTCCAGTGTCGGATCTGCATGAGAAA |
| | | CTTTTCAAAAAAGTTTAACCTTCTCCAACACACACGAACCCACACTGGAGAGAA |
| | | ACCCTTTCAGTGCAGGATATGTATGCGGAATTTTTCCAGAAAAGATTATTTGAT |
| | | CAGTCATCTGCGAACACATACCGGGAGTCAGAAGCCTTTCCAATGCCGGATTTG |
| | | CATGAGGAACTTCTCCAGGAGTCATAACCTCCGGTTGCACACACGCACACATAC |
| | | AGGCGAGAAGCCATTCCAGTGTAGGATCTGCATGCGCAATTTTAGCCAGAGTAC |
| | | GACCCTGAAGAGACATCTGCGGACGCATACAGGTAGTCAGAAGCCTTTTCAGTG |
| | | CAGGATCTGCATGAGGAATTTTAGTCGGCAAGATAATTTGGGGAGACACTTGAG |
| | | AACGCATACTGGAGAGAAGCCCTTTCAGTGTAGGATTTGTATGCGGAACTTCAG |
| | | CGTTGTGAATAATTTGAATCGGCATCTCAAAACTCATTTGCGCGGGTCTAGCCC |
| | | CAAGAAGAAGAGAAAGGTGGGAGTCGACGGATCCAGCGGCTCCGAGACCCCAGG |
| | | CACATCTGAGAGCGCCACCCCTGAGTCCCGGACCCTGGTGACATTCAAGGACGT |
| | | GTTCGTGGACTTCACCCGGGAGGAGTGGAAGCTGCTGGACACAGCCCAGCAGAT |
| | | CGTGTACAGGAACGTGATGCTGGAGAACTATAAGAATCTGGTGTCTCTGGGCTA |
| | | CCAGCTGACAAAGCCAGATGTGATCCTGCGGCTGGAGAAGGGAGAGGAGCCCTG |
| | | GCTGGTGTAGTCTAGAAATCAACCTCTGGATTACAAAATTTGTGAAAGATTGAC |
| | | TGGTATTCTTAACTATGTTGCTCCTTTTACGCTATGTGGATACGCTGCTTTAAT |
| | | GCCTTTGTATCATGCTATTGCTTCCCGTATGGCTTTCATTTTCTCCTCCTTGTA |
| | | TAAATCCTGGTTGCTGTCTCTTTATGAGGAGTTGTGGCCCGTTGTCAGGCAACG |
| | | TGGCGTGGTGTGCACTGTGTTTGCTGACGCAACCCCCACTGGTTGGGGCATTGC |
| | | CACCACCTGTCAGCTCCTTTCCGGGACTTTCGCTTTCCCCCTCCCTATTGCCAC |
| | | GGCGGAACTCATCGCCGCCTGCCTTGCCCGCTGCTGGACAGGGGCTCGGCTGTT |
| | | GGGCACTGACAATTCCGTGGTGTTGTCGGGGAAATCATCGTCCTTTCCTTGGCT |
| | | GCTCGCCTGTGTTGCCACCTGGATTCTGCGCGGGACGTCCTTCTGCTACGTCCC |
| | | TTCGGCCCTCAATCCAGCGGACCTTCCTTCCCGCGGCCTGCTGCCGGCTCTGCG |
| | | GCCTCTTCCGCGTCTTCGCCTTCGCCCTCAGACGAGTCGGATCTCCCTTTGGGC |
| | | CGCCTCCCCGCCTGTTAATTAAAAAAAAAAAAAAAAAAAAAAAAAAAAAAAAAAA |
| | | AAAAAAAAAAAAAAAAAACTAGTGGCGCCTGATGCGGTATTTTCTCCTTACGCA |
| | | TCTGTGCGGTATTTCACACCGCATAATCCAGCACAGTGGCGGCCCGTTTAAACC |
| | | CGCTGATCAGCCTCGACTGTGCCTTCTAGTTGCCAGCCATCTGTTGTTTGCCCC |
| | | TCCCCCGTGCCTTCCTTGACCCTGGAAGGTGCCACTCCCACTGTCCTTTCCTAA |
| | | TAAAATGAGGAAATTGCATCGCATTGTCTGAGTAGGTGTCATTCTATTCTGGGG |
| | | GGTGGGGTGGGGCAGGACAGCAAGGGGGAGGATTGGGAAGACAATAGCAGGCAT |
| | | GCTGGGGATGCGGTGGGCTCTATGGCTTCTGAGGCGGAAAGAACCAGCTGCATT |
| | | AATGAATCGGCCAACGCGCGGGGAGAGGCGGTTTGCGTATTGGGCGCTCTTCCG |
| | | CTTCCTCGCTCACTGACTCGCTGCGCTCGGTCGTTCGGCTGCGGCGAGCGGTAT |
| | | CAGCTCACTCAAAGGCGGTAATACGGTTATCCACAGAATCAGGGGATAACGCAG |
| | | GAAAGAACATGTGAGCAAAAGGCCAGCAAAAGGCCAGGAACCGTAAAAAGGCCG |
| | | CGTTGCTGGCGTTTTTCCATAGGCTCCGCCCCCCTGACGAGCATCACAAAAATC |
| | | GACGCTCAAGTCAGAGGTGGCGAAACCCGACAGGACTATAAAGATACCAGGCGT |
| | | TTCCCCCTGGAAGCTCCCTCGTGCGCTCTCCTGTTCCGACCCTGCCGCTTACCG |
| | | GATACCTGTCCGCCTTTCTCCCTTCGGGAAGCGTGGCGCTTTCTCATAGCTCAC |
| | | GCTGTAGGTATCTCAGTTCGGTGTAGGTCGTTCGCTCCAAGCTGGGCTGTGTGC |

TABLE 18-continued

Sequence listing.

| SEQ | Description | Sequence |
|---|---|---|
| | | ACGAACCCCCCGTTCAGCCCGACCGCTGCGCCTTATCCGGTAACTATCGTCTTG<br>AGTCCAACCCGGTAAGACACGACTTATCGCCACTGGCAGCAGCCACTGGTAACA<br>GGATTAGCAGAGCGAGGTATGTAGGCGGTGCTACAGAGTTCTTGAAGTGGTGGC<br>CTAACTACGGCTACACTAGAAGAACAGTATTTGGTATCTGCGCTCTGCTGAAGC<br>CAGTTACCTTCGGAAAAAGAGTTGGTAGCTCTTGATCCGGCAAACAAACCACCG<br>CTGGTAGCGGTTTTTTTGTTTGCAAGCAGCAGATTACGCGCAGAAAAAAAGGAT<br>CTCAAGAAGATCCTTTGATCTTTTCTACGGGGTCTGACGCTCAGTGGAACGAAA<br>ACTCACGTTAAGGGATTTTGGTCATGAGATTATCAAAAAGGATCTTCACCTAGA<br>TCCTTTTAAATTAAAAATGAAGTTTTAAATCAATCTAAAGTATATATGAGTAAA<br>CTTGGTCTGACAGTTACCAATGCTTAATCAGTGAGGCACCTATCTCAGCGATCT<br>GTCTATTTCGTTCATCCATAGTTGCCTGACTCCCCGTCGTGTAGATAACTACGA<br>TACGGGAGGGCTTACCATCTGGCCCCAGTGCTGCAATGATACCGCGAGACCCAC<br>GCTCACCGGCTCCAGATTTATCAGCAATAAACCAGCCAGCCGGAAGGGCCGAGC<br>GCAGAAGTGGTCCTGCAACTTTATCCGCCTCCATCCAGTCTATTAATTGTTGCC<br>GGGAAGCTAGAGTAAGTAGTTCGCCAGTTAATAGTTTGCGCAACGTTGTTGCCA<br>TTGCTACAGGCATCGTGGTGTCACGCTCGTCGTTTGGTATGGCTTCATTCAGCT<br>CCGGTTCCCAACGATCAAGGCGAGTTACATGATCCCCCATGTTGTGCAAAAAAG<br>CGGTTAGCTCCTTCGGTCCTCCGATCGTTGTCAGAAGTAAGTTGGCCGCAGTGT<br>TATCACTCATGGTTATGGCAGCACTGCATAATTCTCTTACTGTCATGCCATCCG<br>TAAGATGCTTTTCTGTGACTGGTGAGTACTCAACCAAGTCATTCTGAGAATAGT<br>GTATGCGGCGACCGAGTTGCTCTTGCCCGGCGTCAATACGGGATAATACCGCGC<br>CACATAGCAGAACTTTAAAAGTGCTCATCATTGGAAAACGTTCTTCGGGGCGAA<br>AACTCTCAAGGATCTTACCGCTGTTGAGATCCAGTTCGATGTAACCCACTCGTG<br>CACCCAACTGATCTTCAGCATCTTTTACTTTCACCAGCGTTTCTGGGTGAGCAA<br>AAACAGGAAGGCAAAATGCCGCAAAAAAGGGAATAAGGGCGACACGGAAATGTT<br>GAATACTCATACTCTTCCTTTTTCAATATTATTGAAGCATTTATCAGGGTTATT<br>GTCTCATGAGCGGATACATATTTGAATGTATTTAGAAAAATAAACAAATAGGGG<br>TTCCGCGCACATTTCCCCGAAAAGTGCCACCTGA |
| 1239 | Plasmid for fusion<br>protein with<br>mRNA0004 | CGTCGATCGACGGATGGGGAGATCTCCCGATCCCCTATGGTGCACTCTCAGTAC<br>AATCTGCTCTGATGCCGCATAGTTAAGCCAGTATCTGCTCCCTGCTTGTGTGTT<br>GGAGGTCGCTGAGTAGTGCGCGAGCAAAATTTAAGCTACAACAAGGCAAGGCTT<br>GACCGACAATTGCATGAAGAATCTGCTTAGGGTTAGGCGTTTTGCGCTGCTTCG<br>CGATGTACGGGCCAGATATACGCGTTGACATTGATTATTGACTAGTTATTAATA<br>GTAATCAATTACGGGGTCATTAGTTCATAGCCCATATATGGAGTTCCGCGTTAC<br>ATAACTTACGGTAAATGGCCCGCCTGGCTGACCGCCCAACGACCCCCGCCCATT<br>GACGTCAATAATGACGTATGTTCCCATAGTAACGCCAATAGGGACTTTCCATTG<br>ACGTCAATGGGTGGAGTATTTACGGTAAACTGCCCACTTGGCAGTACATCAAGT<br>GTATCATATGCCAAGTACGCCCCCTATTGACGTCAATGACGGTAAATGGCCCGC<br>CTGGCATTATGCCCAGTACATGACCTTATGGGACTTTCCTACTTGGCAGTACAT<br>CTACGTATTAGTCATCGCTATTACCATGGTGATGCGGTTTTGGCAGTACATCAA<br>TGGGCGTGGATAGCGGTTTGACTCACGGGGATTTCCAAGTCTCCACCCCATTGA<br>CGTCAATGGGAGTTTGTTTTGGCACCAAAATCAACGGGACTTTCCAAAATGTCG<br>TAACAACTCCGCCCCATTGACGCAAATGGGCGGTAGGCGTGTACGGTGGGAGGT<br>CTATATAAGCAGAGCTCTCTGGCTAACTAGAGAACCCACTGCTTACTGGCTTAT<br>CGAAATTAATACGACTCACTATAAGGAGACCCAAGCTACCGGTGCCACCATGTA<br>CCCATACGATGTTCCAGATTACGCTTCGCCGAAGAAAAAGCGCAAGGTCAATCA<br>CGATCAGGAGTTCGACCCCCCTAAGGTGTACCCACCAGTGCCTGCAGAGAAGAG<br>GAAGCCAATCCGGGTGCTGAGCCTGTTTGATGGCATCGCCACCGGCCTGCTGGT<br>GCTGAAGGATCTGGGCATCCAGGTGGACCGGTACATCGCCTCCGAGGTGTGCGA<br>GGATTCTATCACCGTGGGCATGGTGCGCCACCAGGGCAAGATCATGTATGTGGG<br>CGACGTGCGGTCCGTGACACAGAAGCACATCCAGGAGTGGGGCCCATTCGATCT<br>GGTGATCGGCGGCAGCCCCTGTAATGACCTGTCCATCGTGAACCCTGCAAGGAA<br>GGGACTGTACGAGGGAACCGGCCGGCTGTTCTTTGAGTTTTATAGACTGCTGCA<br>CGACGCCAGGCCTAAGGAGGGCGACGATAGACCATTCTTTTGGCTGTTCGAGAA<br>TGTGGTGGCTATGGGCGTGAGCGATAAGAGGGACATCTCCAGGTTTCTGGAGTC<br>TAACCCCGTGATGATCGATGCAAAGGAGGTGTCCGCCGCACACAGAGCCAGGTA<br>TTTCTGGGGCAATCTGCCAGGAATGAACAGGCCACTGGCAAGCACCGTGAATGA<br>CAAGCTGGAGCTGCAGGAGTGCCTGGAGCACGGAAGGATCGCCAAGTTTTCCAA<br>GGTGCGCACAATCACCACACGGAGCAATTCCATCAAGCAGGGCAAGGATCAGCA<br>CTTCCCCGTGTTCATGAACGAGAAGGAGGACATCCTGTGGTGTACCGAGATGGA<br>GAGAGTGTTCGGCTTTCCAGTGCACTACACAGACGTGTCTAACATGAGCAGGCT<br>GGCCAAGGCAGCGGCTGCTGGGCAGATCTTGGAGCGTGCCCGTGATCAGGCACCT<br>GTTCGCCCCTCTGAAGGAGTATTTTGCCTGCGTGAGCAGCGGCAACTCCAATGC<br>CAACAGCCGGGGCCCCTCTTTCAGCTCCGGATTGGTGCCTCTGAGCCTGAGGGG<br>CTCCCACATGGCAGCAATCCCCGCCCTGGACCCCGAGGCCGAGCCTAGCATGGA<br>CGTGATCCTGGTGGGCTCTAGCGAGCTGTCCTCTAGCGTGTCTCCAGGAACCGG<br>AAGGGATCTGATCGCATACGAGGTGAAGGCCAATCAGCGGAACATCGAGGACAT<br>CTGTATCTGCTGTGGCAGCCTGCAGGTGCACACACAGCACCCACTGTTCGAGGG<br>AGGAATCTGCGCACCCTGTAAGGATAAGTTCCTGGACGCCCTGTTTCTGTACGA<br>CGATGACGGCTACCAGTCCTATTGCTCTATCTGCTGTTCCGGCGAGACCCTGCT<br>GATCTGCGGCAATCCAGATTGTACAAGGTGCTATTGTTTTGAGTGCGTGGACTC<br>TCTGGTGGGACCAGGCACCAGCGGAAAGGTGCACGCCATGTCCAACTGGGTGTG<br>CTACCTGTGCCTGCCATCCTCTCGCAGCGGACTGCTGCAGCGGGAGAAGGAAGTG<br>GAGATCCCAGCTGAAGGCCTTCTATGATAGGGAGTCTGAGAACCCCCTGGAGAT<br>GTTTGAGACCGTGCCAGTGTGGCGCCGGCAGCCCGTGAGGGTGCTGAGCCTGTT |

TABLE 18-continued

Sequence listing.

| SEQ | Description | Sequence |
|-----|-------------|----------|
| | | CGAGGATATCAAGAAGGAGCTGACATCCCTGGGCTTTCTGGAGTCCGGCTCTGA |
| | | CCCCGGACAGCTGAAGCACGTGGTGGATGTGACCGACACAGTGCGGAAGGATGT |
| | | GGAGGAGTGGGGCCCTTTCGACCTGGTGTACGGAGCAACCCCTCCACTGGGACA |
| | | CACATGCGACAGACCCCCTTCTTGGTACCTGTTCCAGTTTCACCGCCTGCTGCA |
| | | GTATGCAAGGCCAAAGCCAGGCAGCCCTAGACCATTCTTTTGGATGTTCGTGGA |
| | | TAATCTGGTGCTGAACAAGGAGGATCTGGACGTGGCCAGCAGGTTTCTGGAGAT |
| | | GGAGCCAGTGACCATCCCAGACGTGCACGGCGGCTCCCTGCAGAATGCCGTGCG |
| | | CGTGTGGTCTAACATCCCTGCCATCAGAAGCAGGCACTGGGCACTGGTGAGCGA |
| | | GGAGGAGCTGTCCCTGCTGGCCCAGAATAAGCAGAGCAGCAAGCTGGCCGCCAA |
| | | GTGGCCTACAAAGCTGGTGAAGAACTGCTTCCTGCCACTGCGGGAGTACTTCAA |
| | | GTATTTTTCCACCGAGCTGACATCTAGCCTGGGAGGACCCTCCTCTGGCGCCCC |
| | | ACCACCTAGCGGCGGCTCCCCTGCCGGCTCTCCAACCAGCACAGAGGAGGGCAC |
| | | CAGCGAGTCCGCCACACCAGAGTCTGGACCTGGCACCAGCACAGAGCCATCCGA |
| | | GGGCTCTGCCCCAGGCTCTCCTGCAGGCAGCCCTACCTCCACCGAAGAGGGCAC |
| | | CAGCACAGAGCCTTCTGAGGGCAGCGCCCCAGGCACCTCTACAGAGCCAAGCGA |
| | | GCTCGAGTCCCGGCCAGGGGAACGGCCCTTCCAGTGTCGGATCTGCATGAGAAA |
| | | CTTTTCACGACGCCACATTTTGGACAGACATACTCGGACCCACACTGGAGAGAA |
| | | ACCCTTTCAGTGCAGGATATGTATGCGGAATTTTTCCCGCCAGGACAACTTGGG |
| | | GCGGCATCTGCGCACACATACCGGGAGTCAGAAGCCTTTCCAATGCCGGATTTG |
| | | CATGAGGAACTTCTCCCAATCTACCACTCTTAAACGACACTTGCGCACACATAC |
| | | AGGCGAGAAGCCATTCCAGTGTAGGATCTGCATGCGCAATTTTAGCCGCCGGGA |
| | | CGGCCTGGCAGGGCACCTTAAGACGCATACAGGTAGTCAGAAGCCTTTTCAGTG |
| | | CAGGATCTGCATGAGGAATTTTAGTGTTCATCATAACCTCGTTAGGCATCTGAG |
| | | AACGCATACTGGAGAGAAGCCCTTTCAGTGTAGGATTTGTATGCGGAACTTCAG |
| | | CATCAGTCACAATTTGGCGCGGCACCTTAAGACTCATTTGCGCGGGTCTAGCCC |
| | | CAAGAAGAAGAGAAAGGTGGGAGTCGACGGATCCAGCGGCTCCGAGACCCCAGG |
| | | CACATCTGAGAGCGCCACCCCTGAGTCCCGGACCCTGGTGACATTCAAGGACGT |
| | | GTTCGTGGACTTCACCCGGGAGGAGTGGAAGCTGCTGGACACAGCCCAGCAGAT |
| | | CGTGTACAGGAACGTGATGCTGGAGAACTATAAGAATCTGGTGTCTCTGGGCTA |
| | | CCAGCTGACAAAGCCAGATGTGATCCTGCGGCTGGAGAAGGGAGAGGAGCCCTG |
| | | GCTGGTGTAGTCTAGAAATCAACCTCTGGATTACAAAATTTGTGAAAGATTGAC |
| | | TGGTATTCTTAACTATGTTGCTCCTTTTACGCTATGTGGATACGCTGCTTTAAT |
| | | GCCTTTGTATCATGCTATTGCTTCCCGTATGGCTTTCATTTTCTCCTCCTTGTA |
| | | TAAATCCTGGTTGCTGTCTCTTTATGAGGAGTTGTGGCCCGTTGTCAGGCAACG |
| | | TGGCGTGGTGTGCACTGTGTTTGCTGACGCAACCCCCACTGGTTGGGGCATTGC |
| | | CACCACCTGTCAGCTCCTTTCCGGGACTTTCGCTTTCCCCCTCCCTATTGCCAC |
| | | GGCGGAACTCATCGCCGCCTGCCTTGCCCGCTGCTGGACAGGGGCTCGGCTGTT |
| | | GGGCACTGACAATTCCGTGGTGTTGTCGGGGAAATCATCGTCCTTTCCTTGGCT |
| | | GCTCGCCTGTGTTGCCACCTGGATTCTGCGCGGGACGTCCTTCTGCTACGTCCC |
| | | TTCGGCCCTCAATCCAGCGGACCTTCCTTCCCGCGGCCTGCTGCCGGCTCTGCG |
| | | GCCTCTTCCGCGTCTTCGCCTTCGCCCTCAGACGAGTCGGATCTCCCTTTGGGC |
| | | CGCCTCCCCGCCTGTTAATTAAAAAAAAAAAAAAAAAAAAAAAAAAAAAAAAAA |
| | | AAAAAAAAAAAAAAAAAACTAGTGGCGCCTGATGCGGTATTTTCTCCTTACGCA |
| | | TCTGTGCGGTATTTCACACCGCATAATCCAGCACAGTGGCGGCCCGTTTAAACC |
| | | CGCTGATCAGCCTCGACTGTGCCTTCTAGTTGCCAGCCATCTGTTGTTTGCCCC |
| | | TCCCCCGTGCCTTCCTTGACCCTGGAAGGTGCCACTCCCACTGTCCTTTCCTAA |
| | | TAAAATGAGGAAATTGCATCGCATTGTCTGAGTAGGTGTCATTCTATTCTGGGG |
| | | GGTGGGGTGGGGCAGGACAGCAAGGGGGAGGATTGGGAAGACAATAGCAGGCAT |
| | | GCTGGGGATGCGGTGGGCTCTATGGCTTCTGAGGCGGAAAGAACCAGCTGCATT |
| | | AATGAATCGGCCAACGCGCGGGGAGAGGCGGTTTGCGTATTGGGCGCTCTTCCG |
| | | CTTCCTCGCTCACTGACTCGCTGCGCTCGGTCGTTCGGCTGCGGCGAGCGGTAT |
| | | CAGCTCACTCAAAGGCGGTAATACGGTTATCCACAGAATCAGGGGATAACGCAG |
| | | GAAAGAACATGTGAGCAAAAGGCCAGCAAAAGGCCAGGAACCGTAAAAAGGCCG |
| | | CGTTGCTGGCGTTTTTCCATAGGCTCCGCCCCCCTGACGAGCATCACAAAAATC |
| | | GACGCTCAAGTCAGAGGTGGCGAAACCCGACAGGACTATAAAGATACCAGGCGT |
| | | TTCCCCCTGGAAGCTCCCTCGTGCGCTCTCCTGTTCCGACCCTGCCGCTTACCG |
| | | GATACCTGTCCGCCTTTCTCCCTTCGGGAAGCGTGGCGCTTTCTCATAGCTCAC |
| | | GCTGTAGGTATCTCAGTTCGGTGTAGGTCGTTCGCTCCAAGCTGGGCTGTGTGC |
| | | ACGAACCCCCGTTCAGCCCGACCGCTGCGCCTTATCCGGTAACTATCGTCTTG |
| | | AGTCCAACCCGGTAAGACACGACTTATCGCCACTGGCAGCAGCCACTGGTAACA |
| | | GGATTAGCAGAGCGAGGTATGTAGGCGGTGCTACAGAGTTCTTGAAGTGGTGGC |
| | | CTAACTACGGCTACACTAGAAGAACAGTATTTGGTATCTGCGCTCTGCTGAAGC |
| | | CAGTTACCTTCGGAAAAAGAGTTGGTAGCTCTTGATCCGGCAAACAAACCACCG |
| | | CTGGTAGCGGTTTTTTTGTTTGCAAGCAGCAGATTACGCGCAGAAAAAAAGGAT |
| | | CTCAAGAAGATCCTTTGATCTTTTCTACGGGGTCTGACGCTCAGTGGAACGAAA |
| | | ACTCACGTTAAGGGATTTTGGTCATGAGATTATCAAAAAGGATCTTCACCTAGA |
| | | TCCTTTTAAATTAAAAATGAAGTTTTAAATCAATCTAAAGTATATATGAGTAAA |
| | | CTTGGTCTGACAGTTACCAATGCTTAATCAGTGAGGCACCTATCTCAGCGATCT |
| | | GTCTATTTCGTTCATCCATAGTTGCCTGACTCCCCGTCGTGTAGATAACTACGA |
| | | TACGGGAGGGCTTACCATCTGGCCCCAGTGCTGCAATGATACCGCGAGACCCAC |
| | | GCTCACCGGCTCCAGATTTATCAGCAATAAACCAGCCAGCCGGAAGGGCCGAGC |
| | | GCAGAAGTGGTCCTGCAACTTTATCCGCCTCCATCCAGTCTATTAATTGTTGCC |
| | | GGGAAGCTAGAGTAAGTAGTTCGCCAGTTAATAGTTTGCGCAACGTTGTTGCCA |
| | | TTGCTACAGGCATCGTGGTGTCACGCTCGTCGTTTGGTATGGCTTCATTCAGCT |
| | | CCGGTTCCCAACGATCAAGGCGAGTTACATGATCCCCCATGTTGTGCAAAAAAG |
| | | CGGTTAGCTCCTTCGGTCCTCCGATCGTTGTCAGAAGTAAGTTGGCCGCAGTGT |

TABLE 18-continued

Sequence listing.

| SEQ | Description | Sequence |
|---|---|---|
| | | TATCACTCATGGTTATGGCAGCACTGCATAATTCTCTTACTGTCATGCCATCCG<br>TAAGATGCTTTTCTGTGACTGGTGAGTACTCAACCAAGTCATTCTGAGAATAGT<br>GTATGCGGCGACCGAGTTGCTCTTGCCCGGCGTCAATACGGGATAATACCGCGC<br>CACATAGCAGAACTTTAAAAGTGCTCATCATTGGAAAACGTTCTTCGGGGCGAA<br>AACTCTCAAGGATCTTACCGCTGTTGAGATCCAGTTCGATGTAACCCACTCGTG<br>CACCCAACTGATCTTCAGCATCTTTTACTTTCACCAGCGTTTCTGGGTGAGCAA<br>AAACAGGAAGGCAAAATGCCGCAAAAAAGGGAATAAGGGCGACACGGAAATGTT<br>GAATACTCATACTCTTCCTTTTTCAATATTATTGAAGCATTTATCAGGGTTATT<br>GTCTCATGAGCGGATACATATTTGAATGTATTTAGAAAAATAAACAAATAGGGG<br>TTCCGCGCACATTTCCCCGAAAAGTGCCACCTGA |
| 1240 | Plasmid for fusion<br>protein with<br>mRNA0005 | CGTCGATCGACGGATCGGGAGATCTCCCGATCCCCTATGGTGCACTCTCAGTAC<br>AATCTGCTCTGATGCCGCATAGTTAAGCCAGTATCTGCTCCCTGCTTGTGTGTT<br>GGAGGTCGCTGAGTAGTGCGCGAGCAAAATTTAAGCTACAACAAGGCAAGGCTT<br>GACCGACAATTGCATGAAGAATCTGCTTAGGGTTAGGCGTTTTGCGCTGCTTCG<br>CGATGTACGGGCCAGATATACGCGTTGACATTGATTATTGACTAGTTATTAATA<br>GTAATCAATTACGGGGTCATTAGTTCATAGCCCATATATGGAGTTCCGCGTTAC<br>ATAACTTACGGTAAATGGCCCGCCTGGCTGACCGCCCAACGACCCCCGCCCATT<br>GACGTCAATAATGACGTATGTTCCCATAGTAACGCCAATAGGGACTTTCCATTG<br>ACGTCAATGGGTGGAGTATTTACGGTAAACTGCCCACTTGGCAGTACATCAAGT<br>GTATCATATGCCAAGTACGCCCCCTATTGACGTCAATGACGGTAAATGGCCCGC<br>CTGGCATTATGCCCAGTACATGACCTTATGGGACTTTCCTACTTGGCAGTACAT<br>CTACGTATTAGTCATCGCTATTACCATGGTGATGCGGTTTTGGCAGTACATCAA<br>TGGGCGTGGATAGCGGTTTGACTCACGGGGATTTCCAAGTCTCCACCCCATTGA<br>CGTCAATGGGAGTTTGTTTTGGCACCAAAATCAACGGGACTTTCCAAAATGTCG<br>TAACAACTCCGCCCCATTGACGCAAATGGGCGGTAGGCGTGTACGGTGGGAGGT<br>CTATATAAGCAGAGCTCTCTGGCTAACTAGAGAACCCACTGCTTACTGGCTTAT<br>CGAAATTAATACGACTCACTATAAGGAGACCCAAGCTACCGGTGCCACCATGTA<br>CCCATACGATGTTCCAGATTACGCTTCGCCGAAGAAAAAGCGCAAGGTCAATCA<br>CGATCAGGAGTTCGACCCCCCTAAGGTGTACCCACCAGTGCCTGCAGAGAAGAG<br>GAAGCCAATCCGGGTGCTGAGCCTGTTTGATGGCATCGCCACCGGCCTGCTGGT<br>GCTGAAGGATCTGGGCATCCAGGTGGACCGGTACATCGCCTCCGAGGTGTGCGA<br>GGATTCTATCACCGTGGGCATGGTGCGCCACCAGGGCAAGATCATGTATGTGGG<br>CGACGTGCGGTCCGTGACACAGAAGCACATCCAGGAGTGGGGCCCATTCGATCT<br>GGTGATCGGCGGCAGCCCCTGTAATGACCTGTCCATCGTGAACCCTGCAAGGAA<br>GGGACTGTACGAGGGAACCGGCCGGCTGTTCTTTGAGTTTTATAGACTGCTGCA<br>CGACGCCAGGCCTAAGGAGGGCGACGATAGACCATTCTTTTGGCTGTTCGAGAA<br>TGTGGTGGCTATGGGCGTGAGCGATAAGAGGGACATCTCCAGGTTTCTGGAGTC<br>TAACCCCGTGATGATCGATGCAAAGGAGGTGTCCGCCGCACACAGAGCCAGGTA<br>TTTCTGGGGCAATCTGCCCAGGAATGAACAGGCCACTGGCAAGCACCGTGAATGA<br>CAAGCTGGAGCTGCAGGAGTGCCTGGAGCACGGAAGGATCGCCAAGTTTTCCAA<br>GGTGCGCACAATCACCACACGGAGCAATTCCATCAAGCAGGGCAAGGATCAGCA<br>CTTCCCCGTGTTCATGAACGAGAAGGAGGACATCCTGTGGTGTACCGAGATGGA<br>GAGAGTGTTCGGCTTTCCAGTGCACTACACAGACGTGTCTAACATGAGCAGGCT<br>GGCAAGGCAGCGGCTGCTGGGCAGATCTTGGAGCGTGCCCGTGATCAGGCACCT<br>GTTCGCCCCTCTGAAGGAGTATTTTGCCTGCGTGAGCAGCGGCAACTCCAATGC<br>CAACAGCCGGGGCCCCTCTTTCAGCTCCGGATTGGTGCCTCTGAGCCTGAGGGG<br>CTCCCACATGGCAGCAATCCCCGCCCTGGACCCCGAGGCCGAGCCTAGCATGGA<br>CGTGATCCTGGTGGGCTCTAGCGAGCTGTCCTCTAGCGTGTCTCCAGGAACCGG<br>AAGGGATCTGATCGCATACGAGGTGAAGGCCAATCAGCGGAACATCGAGGACAT<br>CTGTATCTGCTGTGGCAGCCTGCAGGTGCACACACAGCACCCACTGTTCGAGGG<br>AGGAATCTGCGCACCCTGTAAGGATAAGTTCCTGGACGCCCTGTTTCTGTACGA<br>CGATGACGGCTACCAGTCCTATTGCTCTATCTGCTGTTCCGGCGAGACCCTGCT<br>GATCTGCGGCAATCCAGATTGTACAAGGTGCTATTGTTTTGAGTGCGTGGACTC<br>TCTGGTGGGACCAGGCACCAGCGGAAAGGTGCACGCCATGTCCAACTGGGTGTG<br>CTACCTGTGCCTGCCATCCTCTCGCAGCGGACTGCTGCAGCGGAGAAGGAAGTG<br>GAGATCCCAGCTGAAGGCCTTCTATGATAGGGAGTCTGAGAACCCCCTGGAGAT<br>GTTTGAGACCGTGCCAGTGTGGCGCCGGCAGCCCGTGAGGGTGCTGAGCCTGTT<br>CGAGGATATCAAGAAGGAGCTGACATCCCTGGGCTTTCTGGAGTCCGGCTCTGA<br>CCCCGGACAGCTGAAGCACGTGGTGGATGTGACCGACACAGTGCGGAAGGATGT<br>GGAGGAGTGGGGCCCTTTCGACCTGGTGTACGGAGCAACCCCTCCACTGGGACA<br>CACATGCGACAGACCCCCTTCTTGGTACCTGTTCCAGTTTCACCGCCTGCTGCA<br>GTATGCAAGGCCAAAGCCAGGCAGCCCTAGACCATTCTTTTGGATGTTCGTGGA<br>TAATCTGGTGCTGAACAAGGAGGATCTGGACGTGGCCAGCAGGTTTCTGGAGAT<br>GGAGCCAGTGACCATCCCAGACGTGCACGGCGGCTCCCTGCAGAATGCCGTGCG<br>CGTGTGGTCTAACATCCCTGCCATCAGAAGCAGGCACTGGGCACTGGTGAGCGA<br>GGAGGAGCTGTCCCTGCTGGCCCAGAATAAGCAGAGCAGCAAGCTGGCCGCCAA<br>GTGGCCTACAAAGCTGGTGAAGAACTGCTTCCTGCCACTGCGGGAGTACTTCAA<br>GTATTTTTCCACCGAGCTGACATCTAGCCTGGGAGGACCCTCCTCTGGCGCCCC<br>ACCACCTAGCGGCGGCTCCCCTGCCGGCTCTCCAACCAGCACAGAGGAGGGCAC<br>CAGCGAGTCCGCCACACCAGAGTCTGGACCTGGCACCAGCACAGAGCCATCCGA<br>GGGCTCTGCCCCAGGCTCTCCTGCAGGCAGCCCTACCTCCACCGAAGAGGGCAC<br>CAGCACAGAGCCTTCTGAGGGCAGCGCCCCAGGCACCTCTACAGAGCCAAGCGA<br>GCTCGAGTCCCGGCCAGGGGAACGGCCCTTCCAGTGTCGGATCTGCATGAGAAA<br>CTTTTCACGCCGGGGAGGTATTGGAAAAACCATTTGCGAACCCACACTGGAGAGAA<br>ACCCTTTCAGTGCAGGATATGTATGCGGAATTTTTTCCCGGCGGGATAATCTCAA |

TABLE 18-continued

Sequence listing.

| SEQ | Description | Sequence |
|-----|-------------|----------|
| | | TCGGCACTTGAAAACACATACCGGGAGTCAGAAGCCTTTCCAATGCCGGATTTG |
| | | CATGAGGAACTTCTCCCAATCCACTACCCTCAAGCGACATCTGCGGACACATAC |
| | | AGGCGAGAAGCCATTCCAGTGTAGGATCTGCATGCGCAATTTTAGCCGAAGGGA |
| | | TGGGCTGGCGGGCCATCTTAAGACGCATACAGGTAGTAGTCAGAAGCCTTTTCAGTG |
| | | CAGGATCTGCATGAGGAATTTTAGTGTCCATCACAACCTGGTCAGACACCTTAG |
| | | GACGCATACTGGAGAGAAGCCCTTTCAGTGTAGGATTTGTATGCGGAACTTCAG |
| | | CATATCACATAACCTTGCCCGACACTTGAAGACTCATTTGCGCGGGTCTAGCCC |
| | | CAAGAAGAAGAGAAAGGTGGGAGTCGACGGATCCAGCGGCTCCGAGACCCCAGG |
| | | CACATCTGAGAGCGCCACCCCTGAGTCCCGGACCCTGGTGACATTCAAGGACGT |
| | | GTTCGTGGACTTCACCCGGGAGGAGTGGAAGCTGCTGGACACAGCCCAGCAGAT |
| | | CGTGTACAGGAACGTGATGCTGGAGAACTATAAGAATCTGGTGTCTCTGGGCTA |
| | | CCAGCTGACAAAGCCAGATGTGATCCTGCGGCTGGAGAAGGGAGAGGAGCCCTG |
| | | GCTGGTGTAGTCTAGAAATCAACCTCTGGATTACAAAATTTGTGAAAGATTGAC |
| | | TGGTATTCTTAACTATGTTGCTCCTTTTACGCTATGTGGATACGCTGCTTTAAT |
| | | GCCTTTGTATCATGCTATTGCTTCCCGTATGGCTTTCATTTTCTCCTCCTTGTA |
| | | TAAATCCTGGTTGCTGTCTCTTTATGAGGAGTTGTGGCCCGTTGTCAGGCAACG |
| | | TGGCGTGGTGTGCACTGTGTTTGCTGACGCAACCCCCACTGGTTGGGGCATTGC |
| | | CACCACCTGTCAGCTCCTTTCCGGGACTTTCGCTTTCCCCCTCCCTATTGCCAC |
| | | GGCGGAACTCATCGCCGCCTGCCTTGCCCGCTGCTGGACAGGGGCTCGGCTGTT |
| | | GGGCACTGACAATTCCGTGGTGTTGTCGGGGAAATCATCGTCCTTTCCTTGGCT |
| | | GCTCGCCTGTGTTGCCACCTGGATTCTGCGCGGGACGTCCTTCTGCTACGTCCC |
| | | TTCGGCCCTCAATCCAGCGGACCTTCCTTCCCGCGGCCTGCTGCCGGCTCTGCG |
| | | GCCTCTTCCGCGTCTTCGCCTTCGCCCTCAGACGAGTCGGATCTCCCTTTGGGC |
| | | CGCCTCCCCGCCTGTTAATTAAAAAAAAAAAAAAAAAAAAAAAAAAAAAAAAAAA |
| | | AAAAAAAAAAAAAAAAAAACTAGTGGCGCCTGATGCGGTATTTTCTCCTTACGCA |
| | | TCTGTGCGGTATTTCACACCGCATAATCCAGCACAGTGGCGGCCCGTTTAAACC |
| | | CGCTGATCAGCCTCGACTGTGCCTTCTAGTTGCCAGCCATCTGTTGTTTGCCCC |
| | | TCCCCCGTGCCTTCCTTGACCCTGGAAGGTGCCACTCCCACTGTCCTTTCCTAA |
| | | TAAAATGAGGAAATTGCATCGCATTGTCTGAGTAGGTGTCATTCTATTCTGGGG |
| | | GGTGGGGTGGGGCAGGACAGCAAGGGGGAGGATTGGGAAGACAATAGCAGGCAT |
| | | GCTGGGGATGCGGTGGGCTCTATGGCTTCTGAGGCGGAAAGAACCAGCTGCATT |
| | | AATGAATCGGCCAACGCGCGGGGAGAGGCGGTTTGCGTATTGGGCGCTCTTCCG |
| | | CTTCCTCGCTCACTGACTCGCTGCGCTCGGTCGTTCGGCTGCGGCGAGCGGTAT |
| | | CAGCTCACTCAAAGGCGGTAATACGGTTATCCACAGAATCAGGGGATAACGCAG |
| | | GAAAGAACATGTGAGCAAAAGGCCAGCAAAAGGCCAGGAACCGTAAAAAGGCCG |
| | | CGTTGCTGGCGTTTTTCCATAGGCTCCGCCCCCCTGACGAGCATCACAAAAATC |
| | | GACGCTCAAGTCAGAGGTGGCGAAACCCGACAGGACTATAAAGATACCAGGCGT |
| | | TTCCCCCTGGAAGCTCCCTCGTGCGCTCTCCTGTTCCGACCCTGCCGCTTACCG |
| | | GATACCTGTCCGCCTTTCTCCCTTCGGGAAGCGTGGCGCTTTCTCATAGCTCAC |
| | | GCTGTAGGTATCTCAGTTCGGTGTAGGTCGTTCGCTCCAAGCTGGGCTGTGTGC |
| | | ACGAACCCCCCGTTCAGCCCGACCGCTGCGCCTTATCCGGTAACTATCGTCTTG |
| | | AGTCCAACCCGGTAAGACACGACTTATCGCCACTGGCAGCAGCCACTGGTAACA |
| | | GGATTAGCAGAGCGAGGTATGTAGGCGGTGCTACAGAGTTCTTGAAGTGGTGGC |
| | | CTAACTACGGCTACACTAGAAGAACAGTATTTGGTATCTGCGCTCTGCTGAAGC |
| | | CAGTTACCTTCGGAAAAAGAGTTGGTAGCTCTTGATCCGGCAAACAAACCACCG |
| | | CTGGTAGCGGTTTTTTTGTTTGCAAGCAGCAGATTACGCGCAGAAAAAAAGGAT |
| | | CTCAAGAAGATCCTTTGATCTTTTCTACGGGGTCTGACGCTCAGTGGAACGAAA |
| | | ACTCACGTTAAGGGATTTTGGTCATGAGATTATCAAAAAGGATCTTCACCTAGA |
| | | TCCTTTTAAATTAAAAATGAAGTTTTAAATCAATCTAAAGTATATATGAGTAAA |
| | | CTTGGTCTGACAGTTACCAATGCTTAATCAGTGAGGCACCTATCTCAGCGATCT |
| | | GTCTATTTCGTTCATCCATAGTTGCCTGACTCCCCGTCGTGTAGATAACTACGA |
| | | TACGGGAGGGCTTACCATCTGGCCCCAGTGCTGCAATGATACCGCGAGACCCAC |
| | | GCTCACCGGCTCCAGATTTATCAGCAATAAACCAGCCAGCCGGAAGGGCCGAGC |
| | | GCAGAAGTGGTCCTGCAACTTTATCCGCCTCCATCCAGTCTATTAATTGTTGCC |
| | | GGGAAGCTAGAGTAAGTAGTTCGCCAGTTAATAGTTTGCGCAACGTTGTTGCCA |
| | | TTGCTACAGGCATCGTGGTGTCACGCTCGTCGTTTGGTATGGCTTCATTCAGCT |
| | | CCGGTTCCCAACGATCAAGGCGAGTTACATGATCCCCCATGTTGTGCAAAAAAG |
| | | CGGTTAGCTCCTTCGGTCCTCCGATCGTTGTCAGAAGTAAGTTGGCCGCAGTGT |
| | | TATCACTCATGGTTATGGCAGCACTGCATAATTCTCTTACTGTCATGCCATCCG |
| | | TAAGATGCTTTTCTGTGACTGGTGAGTACTCAACCAAGTCATTCTGAGAATAGT |
| | | GTATGCGGCGACCGAGTTGCTCTTGCCCGGCGTCAATACGGGATAATACCGCGC |
| | | CACATAGCAGAACTTTAAAAGTGCTCATCATTGGAAAACGTTCTTCGGGGCGAA |
| | | AACTCTCAAGGATCTTACCGCTGTTGAGATCCAGTTCGATGTAACCCACTCGTG |
| | | CACCCAACTGATCTTCAGCATCTTTTACTTTCACCAGCGTTTCTGGGTGAGCAA |
| | | AAACAGGAAGGCAAAATGCCGCAAAAAAGGGAATAAGGGCGACACGGAAATGTT |
| | | GAATACTCATACTCTTCCTTTTTCAATATTATTGAAGCATTTATCAGGGTTATT |
| | | GTCTCATGAGCGGATACATATTTGAATGTATTTAGAAAAATAAACAAATAGGGG |
| | | TTCCGCGCACATTTCCCCGAAAAGTGCCACCTGA |
| 1241 | Plasmid for fusion fusion protein with mRNA0006 | CGTCGATCGACGGATCGGGAGATCTCCCGATCCCCTATGGTGCACTCTCAGTAC |
| | | AATCTGCTCTGATGCCGCATAGTTAAGCCAGTATCTGCTCCCTGCTTGTGTGTT |
| | | GGAGGTCGCTGAGTAGTGCGCGAGCAAAATTTAAGCTACAACAAGGCAAGGCTT |
| | | GACCGACAATTGCATGAAGAATCTGCTTAGGGTTAGGCGTTTTGCGCTGCTTCG |
| | | CGATGTACGGGCCAGATATACGCGTTGACATTGATTATTGACTAGTTATTAATA |
| | | GTAATCAATTACGGGGTCATTAGTTCATAGCCCATATATGGAGTTCCGCGTTAC |
| | | ATAACTTACGGTAAATGGCCCGCCTGGCTGACCGCCCAACGACCCCCGCCCATT |

TABLE 18-continued

| Sequence listing. | | |
| --- | --- | --- |
| SEQ | Description | Sequence |
| | | GACGTCAATAATGACGTATGTTCCCATAGTAACGCCAATAGGGACTTTCCATTG |
| | | ACGTCAATGGGTGGAGTATTTACGGTAAACTGCCCACTTGGCAGTACATCAAGT |
| | | GTATCATATGCCAAGTACGCCCCCTATTGACGTCAATGACGGTAAATGGCCCGC |
| | | CTGGCATTATGCCCAGTACATGACCTTATGGGACTTTCCTACTTGGCAGTACAT |
| | | CTACGTATTAGTCATCGCTATTACCATGGTGATGCGGTTTTGGCAGTACATCAA |
| | | TGGGCGTGGATAGCGGTTTGACTCACGGGGATTTCCAAGTCTCCACCCCATTGA |
| | | CGTCAATGGGAGTTTGTTTTGGCACCAAAATCAACGGGACTTTCCAAAATGTCG |
| | | TAACAACTCCGCCCCATTGACGCAAATGGGCGGTAGGCGTGTACGGTGGGAGGT |
| | | CTATATAAGCAGAGCTCTCTGGCTAACTAGAGAACCCACTGCTTACTGGCTTAT |
| | | CGAAATTAATACGACTCACTATAAGGAGACCCAAGCTACCGGTGCCACCATGTA |
| | | CCCATACGATGTTCCAGATTACGCTTCGCCGAAGAAAAAGCGCAAGGTCAATCA |
| | | CGATCAGGAGTTCGACCCCCCTAAGGTGTACCCACCAGTGCCTGCAGAGAAGAG |
| | | GAAGCCAATCCGGGTGCTGAGCCTGTTTGATGGCATCGCCACCGGCCTGCTGGT |
| | | GCTGAAGGATCTGGGCATCCAGGTGGACCGGTACATCGCCTCCGAGGTGTGCGA |
| | | GGATTCTATCACCGTGGGCATGGTGCGCCACCAGGGCAAGATCATGTATGTGGG |
| | | CGACGTGCGGTCCGTGACACAGAAGCACATCCAGGAGTGGGGCCCATTCGATCT |
| | | GGTGATCGGCGGCAGCCCCTGTAATGACCTGTCCATCGTGAACCCTGCAAGGAA |
| | | GGGACTGTACGAGGGAACCGGCCGGCTGTTCTTTGAGTTTTATAGACTGCTGCA |
| | | CGACGCCAGGCCTAAGGAGGGCGACGATAGACCATTCTTTTGGCTGTTCGAGAA |
| | | TGTGGTGGCTATGGGCGTGAGCGATAAGAGGGACATCTCCAGGTTTCTGGAGTC |
| | | TAACCCCGTGATGATCGATGCAAAGGAGGTGTCCGCCGCACACAGAGCCAGGTA |
| | | TTTCTGGGGCAATCTGCCAGGAATGAACAGGCCACTGGCAAGCACCGTGAATGA |
| | | CAAGCTGGAGCTGCAGGAGTGCCTGGAGCACGGAAGGATCGCCAAGTTTTCCAA |
| | | GGTGCGCACAATCACCACACGGAGCAATTCCATCAAGCAGGGCAAGGATCAGCA |
| | | CTTCCCCGTGTTCATGAACGAGAAGGAGGACATCCTGTGGTGTACCGAGATGGA |
| | | GAGAGTGTTCGGCTTTCCAGTGCACTACACAGACGTGTCTAACATGAGCAGGCT |
| | | GGCAAGGCAGCGGCTGCTGGGCAGATCTTGGAGCGTGCCCGTGATCAGGCACCT |
| | | GTTCGCCCCTCTGAAGGAGTATTTTGCCTGCGTGAGCAGCGGCAACTCCAATGC |
| | | CAACAGCCGGGGCCCCTCTTTCAGCTCCGGATTGGTGCCTCTGAGCCTGAGGGG |
| | | CTCCCACATGGCAGCAATCCCCGCCCTGGACCCCGAGGCCGAGCCTAGCATGGA |
| | | CGTGATCCTGGTGGGCTCTAGCGAGCTGTCCTCTAGCGTGTCTCCAGGAACCGG |
| | | AAGGGATCTGATCGCATACGAGGTGAAGGCCAATCAGCGGAACATCGAGGACAT |
| | | CTGTATCTGCTGTGTGGCAGCCTGCAGGTGCACACACAGCACCCACTGTTCGAGGG |
| | | AGGAATCTGCGCACCCTGTAAGGATAAGTTCCTGGACGCCCTGTTTCTGTACGA |
| | | CGATGACGGCTACCAGTCCTATTGCTCTATCTGCTGTTCCGGCGAGACCCTGCT |
| | | GATCTGCGGCAATCCAGATTGTACAAGGTGCTATTGTTTTGAGTGCGTGGACTC |
| | | TCTGGTGGGACCAGGCACCAGCGGAAAGGTGCACGCCATGTCCAACTGGGTGTG |
| | | CTACCTGTGCCTGCCATCCTCTCGCAGCGGACTGCTGCAGCGGAGAAGGAAGTG |
| | | GAGATCCCAGCTGAAGGCCTTCTATGATAGGGAGTCTGAGAACCCCCTGGAGAT |
| | | GTTTGAGACCGTGCCAGTGTGGCGCCGGCAGCCCGTGAGGGTGCTGAGCCTGTT |
| | | CGAGGATATCAAGAAGGAGCTGACATCCCTGGGCTTTCTGGAGTCCGGCTCTGA |
| | | CCCCGGACAGCTGAAGCACGTGGTGGATGTGACCGACACAGTGCGGAAGGATGT |
| | | GGAGGAGTGGGGGCCCTTTCGACCTGGTGTACGGAGCAACCCCTCCACTGGGACA |
| | | CACATGCGACAGACCCCCTTCTTGGTACCTGTTCCAGTTTCACCGCCTGCTGCA |
| | | GTATGCAAGGCCAAAGCCAGGCAGCCCTAGACCATTCTTTTGGATGTTCGTGGA |
| | | TAATCTGGTGCTGAACAAGGAGGATCTGGACGTGGCCAGCAGGTTTCTGGAGAT |
| | | GGAGCCAGTGACCATCCCAGACGTGCACGGCGGCTCCCTGCAGAATGCCGTGCG |
| | | CGTGTGGTCTAACATCCCTGCCATCAGAAGCAGGCACTGGGCACTGGTGAGCGA |
| | | GGAGGAGCTGTCCCTGCTGGCCCAGAATAAGCAGAGCAGCAAGCTGGCCGCCAA |
| | | GTGGCCTACAAAGCTGGTGAAGAACTGCTTCCTGCCACTGCGGGAGTACTTCAA |
| | | GTATTTTTCCACCGAGCTGACATCTAGCCTGGGAGGACCCTCCTCTGGCGCCCC |
| | | ACCACCTAGCGGCGGCTCCCCTGCCGGCTCTCCAACCAGCACAGAGGAGGGCAC |
| | | CAGCGAGTCCGCCACACCAGAGTCTGGACCTGGCACCAGCACAGAGCCATCCGA |
| | | GGGCTCTGCCCCAGGCTCTCCTGCAGGCAGCCCTACCTCCACCGAAGAGGGCAC |
| | | CAGCACAGAGCCTTCTGAGGGCAGCGCCCCAGGCACCTCTACAGAGCCAAGCGA |
| | | GCTCGAGTCCCGGCCAGGGGAACGGCCCTTCCAGTGTCGGATCTGCATGAGAAA |
| | | CTTTTCACGCAGGGCAGTGTTGGATAGACATACCCGGACCCACACTGGAGAGAA |
| | | ACCCTTTCAGTGCAGGATATGTATGCGGAATTTTTCCCGACAAGATAATCTGGG |
| | | GAGGCATCTGCGGACACATACCGGGAGTCAGAAGCCTTTCCAATGCCGGATTTG |
| | | CATGAGGAACTTCTCCCAATCAACTACCCTGAAGCGACATCTGCGCACACATAC |
| | | AGGCGAGAAGCCATTCCAGTGTAGGATCTGCATGCGCAATTTTAGCCGCCGCGA |
| | | TGGGCTGGCTGGACACCTGAAGACGCATACAGGTAGTCAGAAGCCTTTTCAGTG |
| | | CAGGATCTGCATGAGGAATTTTAGTGTTCATCACAACTTGGTCCGACACCTTCG |
| | | GACGCATACTGGAGAGAAGCCCTTTCAGTGTAGGATTTGTATGCGGAACTTCAG |
| | | CATTTCACACAACCTCGCGCGCCACTTGAAAACTCATTTGCGCGGGTCTAGCCC |
| | | CAAGAAGAAGAGAAAGGTGGGAGTCGACGGATCCAGCGGCTCCGAGACCCCAGG |
| | | CACATCTGAGAGCGCCACCCCTGAGTCCGACCCTGGTGACATTCAAGGACGT |
| | | GTTCGTGGACTTCACCCGGGAGGAGTGGAAGCTGCTGGACACAGCCCAGCAGAT |
| | | CGTGTACAGGAACGTGATGCTGGAGAACTATAAGAATCTGGTGTCTCTGGGCTA |
| | | CCAGCTGACAAAGCCAGATGTGATCCTGCGGCTGGAGAAGGGAGAGGAGCCCTG |
| | | GCTGGTGTAGTCTAGAAATCAACCTCTGGATTACAAAATTTGTGAAAGATTGAC |
| | | TGGTATTCTTAACTATGTTGCTCCTTTTACGCTATGTGGATACGCTGCTTTAAT |
| | | GCCTTTGTATCATGCTATTGCTTCCCGTATGGCTTTCATTTTCTCCTCCTTGTA |
| | | TAAATCCTGGTTGCTGTCTCTTTATGAGGAGTTGTGGCCCGTTGTCAGGCAACG |
| | | TGGCGTGGTGTGCACTGTGTTTGCTGACGCAACCCCCACTGGTTGGGGCATTGC |
| | | CACCACCTGTCAGCTCCTTTCCGGGACTTTCGCTTTCCCCCTCCCTATTGCCAC |

TABLE 18-continued

Sequence listing.

| SEQ | Description | Sequence |
|---|---|---|
| | | GGCGGAACTCATCGCCGCCTGCCTTGCCCGCTGCTGGACAGGGGCTCGGCTGTT<br>GGGCACTGACAATTCCGTGGTGTTGTCGGGGAAATCATCGTCCTTTCCTTGGCT<br>GCTCGCCTGTGTTGCCACCTGGATTCTGCGCGGGACGTCCTTCTGCTACGTCCC<br>TTCGGCCCTCAATCCAGCGGACCTTCCTTCCCGCGGGTCTGCTGCCGGCTCTGCG<br>GCCTCTTCCGCGTCTTCGCCTTCGCCCTCAGACGAGTCGGATCTCCCTTTGGGC<br>CGCCTCCCCGCCTGTTAATTAAAAAAAAAAAAAAAAAAAAAAAAAAAAAAAAAAA<br>AAAAAAAAAAAAAAAAAAACTAGTGGCGCCTGATGCGGTATTTTCTCCTTACGCA<br>TCTGTGCGGTATTTCACACCGCATAATCCAGCACAGTGGCGGCCCGTTTAAACC<br>CGCTGATCAGCCTCGACTGTGCCTTCTAGTTGCCAGCCATCTGTTGTTTGCCCC<br>TCCCCCGTGCCTTCCTTGACCCTGGAAGGTGCCACTCCCACTGTCCTTTCCTAA<br>TAAAATGAGGAAATTGCATCGCATTGTCTGAGTAGGTGTCATTCTATTCTGGGG<br>GGTGGGGTGGGGCAGGACAGCAAGGGGGAGGATTGGGAAGACAATAGCAGGCAT<br>GCTGGGGATGCGGTGGGCTCTATGGCTTCTGAGGCGGAAGAACCAGCTGCATT<br>AATGAATCGGCCAACGCGCGGGGAGAGGCGGTTTGCGTATTGGGCGCTCTTCCG<br>CTTCCTCGCTCACTGACTCGCTGCGCTCGGTCGTTCGGCTGCGGCGAGCGGTAT<br>CAGCTCACTCAAAGGCGGTAATACGGTTATCCACAGAATCAGGGGATAACGCAG<br>GAAAGAACATGTGAGCAAAAGGCCAGCAAAAGGCCAGGAACCGTAAAAAGGCCG<br>CGTTGCTGGCGTTTTTCCATAGGCTCCGCCCCCCTGACGAGCATCACAAAAATC<br>GACGCTCAAGTCAGAGGTGGCGAAACCCGACAGGACTATAAAGATACCAGGCGT<br>TTCCCCCTGGAAGCTCCCTCGTGCGCTCTCCTGTTCCGACCCTGCCGCTTACCG<br>GATACCTGTCCGCCTTTCTCCCTTCGGGAAGCGTGGCGCTTTCTCATAGCTCAC<br>GCTGTAGGTATCTCAGTTCGGTGTAGGTCGTTCGCTCCAAGCTGGGCTGTGTGC<br>ACGAACCCCCCGTTCAGCCCGACCGCTGCGCCTTATCCGGTAACTATCGTCTTG<br>AGTCCAACCCGGTAAGACACGACTTATCGCCACTGGCAGCAGCCACTGGTAACA<br>GGATTAGCAGAGCGAGGTATGTAGGCGGTGCTACAGAGTTCTTGAAGTGGTGGC<br>CTAACTACGGCTACACTAGAAGAACAGTATTTGGTATCTGCGCTCTGCTGAAGC<br>CAGTTACCTTCGGAAAAAGAGTTGGTAGCTCTTGATCCGGCAAACAAACCACCG<br>CTGGTAGCGGTTTTTTTGTTTGCAAGCAGCAGATTACGCGCAGAAAAAAAGGAT<br>CTCAAGAAGATCCTTTGATCTTTTCTACGGGGTCTGACGCTCAGTGGAACGAAA<br>ACTCACGTTAAGGGATTTTGGTCATGAGATTATCAAAAAGGATCTTCACCTAGA<br>TCCTTTTAAATTAAAAATGAAGTTTTAAATCAATCTAAAGTATATATGAGTAAA<br>CTTGGTCTGACAGTTACCAATGCTTAATCAGTGAGGCACCTATCTCAGCGATCT<br>GTCTATTTCGTTCATCCATAGTTGCCTGACTCCCCGTCGTGTAGATAACTACGA<br>TACGGGAGGGCTTACCATCTGGCCCCAGTGCTGCAATGATACCGCGAGACCCAC<br>GCTCACCGGCTCCAGATTTATCAGCAATAAACCAGCCAGCCGGAAGGGCCGAGC<br>GCAGAAGTGGTCCTGCAACTTTATCCGCCTCCATCCAGTCTATTAATTGTTGCC<br>GGGAAGCTAGAGTAAGTAGTTCGCCAGTTAATAGTTTGCGCAACGTTGTTGCCA<br>TTGCTACAGGCATCGTGGTGTCACGCTCGTCGTTTGGTATGGCTTCATTCAGCT<br>CCGGTTCCCAACGATCAAGGCGAGTTACATGATCCCCCATGTTGTGCAAAAAAG<br>CGGTTAGCTCCTTCGGTCCTCCGATCGTTGTCAGAAGTAAGTTGGCCGCAGTGT<br>TATCACTCATGGTTATGGCAGCACTGCATAATTCTCTTACTGTCATGCCATCCG<br>TAAGATGCTTTTCTGTGACTGGTGAGTACTCAACCAAGTCATTCTGAGAATAGT<br>GTATGCGGCGACCGAGTTGCTCTTGCCCGGCGTCAATACGGGATAATACCGCGC<br>CACATAGCAGAACTTTAAAAGTGCTCATCATTGGAAAACGTTCTTCGGGGCGAA<br>AACTCTCAAGGATCTTACCGCTGTTGAGATCCAGTTCGATGTAACCCACTCGTG<br>CACCCAACTGATCTTCAGCATCTTTTACTTTCACCAGCGTTTCTGGGTGAGCAA<br>AAACAGGAAGGCAAAATGCCGCAAAAAAGGGAATAAGGGCGACACGGAAATGTT<br>GAATACTCATACTCTTCCTTTTTCAATATTATTGAAGCATTTATCAGGGTTATT<br>GTCTCATGAGCGGATACATATTTGAATGTATTTAGAAAAATAAACAAATAGGGG<br>TTCCGCGCACATTTCCCCGAAAAGTGCCACCTGA |
| 1242 | Plasmid for fusion protein with mRNA0021 | CGTCGATCGACGGATCGGGAGATCTCCCGATCCCCTATGGTGCACTCTCAGTAC<br>AATCTGCTCTGATGCCGCATAGTTAAGCCAGTATCTGCTCCCTGCTTGTGTGTT<br>GGAGGTCGCTGAGTAGTGCGCGAGCAAAATTTAAGCTACAACAAGGCAAGGCTT<br>GACCGACAATTGCATGAAGAATCTGCTTAGGGTTAGGCGTTTTGCGCTGCTTCG<br>CGATGTACGGGCCAGATATACGCGTTGACATTGATTATTGACTAGTTATTAATA<br>GTAATCAATTACGGGGTCATTAGTTCATAGCCCATATATGGAGTTCCGCGTTAC<br>ATAACTTACGGTAAATGGCCCGCCTGGCTGACCGCCCAACGACCCCCGCCCATT<br>GACGTCAATAATGACGTATGTTCCCATAGTAACGCCAATAGGGACTTTCCATTG<br>ACGTCAATGGGTGGAGTATTTACGGTAAACTGCCCACTTGGCAGTACATCAAGT<br>GTATCATATGCCAAGTACGCCCCCTATTGACGTCAATGACGGTAAATGGCCCGC<br>CTGGCATTATGCCCAGTACATGACCTTATGGGACTTTCCTACTTGGCAGTACAT<br>CTACGTATTAGTCATCGCTATTACCATGGTGATGCGGTTTTGGCAGTACATCAA<br>TGGGCGTGGATAGCGGTTTGACTCACGGGGATTTCCAAGTCTCCACCCCATTGA<br>CGTCAATGGGAGTTTGTTTTGGCACCAAAATCAACGGGACTTTCCAAAATGTCG<br>TAACAACTCCGCCCCATTGACGCAAATGGGCGGTAGGCGTGTACGGTGGGAGGT<br>CTATATAAGCAGAGCTCTCTGGCTAACTAGAGAACCCACTGCTTACTGGCTTAT<br>CGAAATTAATACGACTCACTATAAGGAGACCCAAGCTACCGGTGCCACCATGTA<br>CCCATACGATGTTCCAGATTACGCTTCGCCGAAGAAAAAGCGCAAGGTCAATCA<br>CGATCAGGAGTTCGACCCCCCTAAGGTGTACCCACCAGTGCCTGCAGAGAAGAG<br>GAAGCCAATCCGGGTGCTGAGCCTGTTTGATGGCATCGCCACCGGCCTGCTGGT<br>GCTGAAGGATCTGGGCATCCAGGTGGACCGGTACATCGCCTCCGAGGTGTGCGA<br>GGATTCTATCACCGTGGGCATGGTGCGCCACCAGGGCAAGATCATGTATGTGGG<br>CGACGTGCGGTCCGTGACACAGAAGCACATCCAGGAGTGGGGCCCATTCGATCT<br>GGTGATCGGCGGCAGCCCCTGTAATGACCTGTCCATCGTGAACCCTGCAAGGAA<br>GGGACTGTACGAGGGAACCGGCCGGCTGTTCTTTGAGTTTTATAGACTGCTGCA |

TABLE 18-continued

Sequence listing.

| SEQ | Description | Sequence |
|-----|-------------|----------|
|     |             | CGACGCCAGGCCTAAGGAGGGCGACGATAGACCATTCTTTTGGCTGTTCGAGAA |
|     |             | TGTGGTGGCTATGGGCGTGAGCGATAAGAGGGACATCTCCAGGTTTCTGGAGTC |
|     |             | TAACCCCGTGATGATCGATGCAAAGGAGGTGTCCGCCGCCACACAGAGCCAGGTA |
|     |             | TTTCTGGGGCAATCTGCCAGGAATGAACAGGCCACTGGCAAGCACCGTGAATGA |
|     |             | CAAGCTGGAGCTGCAGGAGTGCCTGGAGCACGGAAGGATCGCCAAGTTTTCCAA |
|     |             | GGTGCGCACAATCACCACACGGAGCAATTCCATCAAGCAGGGCAAGGATCAGCA |
|     |             | CTTCCCCGTGTTCATGAACGAGAAGGAGGACATCCTGTGGTGTACCGAGATGGA |
|     |             | GAGAGTGTTCGGCTTTCCAGTGCACTACACAGACGTGTCTAACATGAGCAGGCT |
|     |             | GGCAAGGCAGCGGCTGCTGGGCAGATCTTGGAGCGTGCCCGTGATCAGGCACCT |
|     |             | GTTCGCCCCTCTGAAGGAGTATTTTGCCTGCGTGAGCAGCGGCAACTCCAATGC |
|     |             | CAACAGCCGGGGCCCCTCTTTCAGCTCCGGATTGGTGCCTCTGAGCCTGAGGGG |
|     |             | CTCCCACATGGCAGCAATCCCCGCCCTGGACCCCGAGGCCGAGCCTAGCATGGA |
|     |             | CGTGATCCTGGTGGGCTCTAGCGAGCTGTCCTCTAGCGTGTCTCCAGGAACCGG |
|     |             | AAGGGATCTGATCGCATACGAGGTGAAGGCCAATCAGCGGAACATCGAGGACAT |
|     |             | CTGTATCTGCTGTGGCAGCCTGCAGGTGCACACACAGCACCCACTGTTCGAGGG |
|     |             | AGGAATCTGCGCACCCTGTAAGGATAAGTTCCTGGACGCCCTGTTTCTGTACGA |
|     |             | CGATGACGGCTACCAGTCCTATTGCTCTATCTGCTGTTCCGGCGAGACCCTGCT |
|     |             | GATCTGCGGCAATCCAGATTGTACAAGGTGCTATTGTTTTGAGTGCGTGGACTC |
|     |             | TCTGGTGGGACCCAGGCACCAGCGGAAAGGTGCACGCCATGTCCAACTGGGTGTG |
|     |             | CTACCTGTGCCTGCCATCCTCTCGCAGCGGACTGCTGCAGCGGAGAAGGAAGTG |
|     |             | GAGATCCCAGCTGAAGGCCTTCTATGATAGGGAGTCTGAGAACCCCCTGGAGAT |
|     |             | GTTTGAGACCGTGCCAGTGTGGCGCCGGCAGCCCGTGAGGGTGCTGAGCCTGTT |
|     |             | CGAGGATATCAAGAAGGAGCTGACATCCCTGGGCTTTCTGGAGTCCGGCTCTGA |
|     |             | CCCCGGACAGCTGAAGCACGTGGTGGATGTGACCGACACAGTGCGGAAGGATGT |
|     |             | GGAGGAGTGGGGCCCTTTCGACCTGGTGTACGGAGCAACCCCTCCACTGGGACA |
|     |             | CACATGCGACAGACCCCCTTCTTGGTACCTGTTCCAGTTTCACCGCCTGCTGCA |
|     |             | GTATGCAAGGCCAAAGCCAGGCAGCCCTAGACCATTCTTTTGGATGTTCGTGGA |
|     |             | TAATCTGGTGCTGAACAAGGAGGATCTGGACGTGGCCAGCAGGTTTCTGGAGAT |
|     |             | GGAGCCAGTGACCATCCCAGACGTGCACGGCGGCTCCCTGCAGAATGCCGTGCG |
|     |             | CGTGTGGTCTAACATCCCTGCCATCAGAAGCAGGCACTGGGCACTGGTGAGCGA |
|     |             | GGAGGAGCTGTCCCTGCTGGCCCAGAATAAGCAGAGCAGCAAGCTGGCCGCCAA |
|     |             | GTGGCCTACAAAGCTGGTGAAGAACTGCTTCCTGCCACTGCGGGAGTACTTCAA |
|     |             | GTATTTTTCCACCGAGCTGACATCTAGCCTGGGGAGGACCCTCCTCTGGCGCCCC |
|     |             | ACCACCTAGCGGCGGCTCCCCTGCCGGCTCTCCAACCAGCACAGAGGAGGGCAC |
|     |             | CAGCGAGTCCGCCACACCAGAGTCTGGACCTGGCACCAGCACAGAGCCATCCGA |
|     |             | GGGCTCTGCCCCCAGGCTCTCCTGCAGGCAGCCCTACCTCCACCGAAGAGGGCAC |
|     |             | CAGCACAGAGCCTTCTGAGGGCAGCGCCCCAGGCACCTCTACAGAGCCAAGCGA |
|     |             | GCTCGAGTCCCGGCCAGGGGAACGGCCCTTCCAGTGTCGGATCTGCATGAGAAA |
|     |             | CTTTTCAAGAGCAGATAATCTGGGTCGGCACCTCCGCACCCACACTGGAGAGAA |
|     |             | ACCCTTTCAGTGCAGGATATGTATGCGGAATTTTTCCCGCAACACGCATCTCAG |
|     |             | TTATCACCTTAAAACACATACCGGGAGTCAGAAGCCTTTCCAATGCCGGATTTG |
|     |             | CATGAGGAACTTCTCCAGGGGCGACGGCTTGAGGCGGCATCTTCGCACACATAC |
|     |             | AGGCGAGAAGCCATTCCAGTGTAGGATCTGCATGCGCAATTTTAGCCGCAGAGA |
|     |             | CAATTTGAACAGACATCTCAAAACGCATACAGGTAGTCAGAAGCCTTTTCAGTG |
|     |             | CAGGATCTGCATGAGGAATTTTAGTCGAGCAAGAAACTTGACGCTGCACACCCG |
|     |             | GACGCATACTGGAGAGAAGCCCTTTCAGTGTAGGATTTGTATGCGGAACTTCAG |
|     |             | CGACCCTTCATCTTTGAAGCGCCATCTTCGCACTCATTTGCGCGGGTCTAGCCC |
|     |             | CAAGAAGAAGAGAAAGGTGGGAGTCGACGGATCCAGCGGCTCCGAGACCCCAGG |
|     |             | CACATCTGAGAGCGCCACCCCTGAGTCCCGGACCCTGGTGACATTCAAGGACGT |
|     |             | GTTCGTGGACTTCACCCGGGAGGAGTGGAAGCTGCTGGACACAGCCCAGCAGAT |
|     |             | CGTGTACAGGAACGTGATGCTGGAGAACTATAAGAATCTGGTGTCTCTGGGCTA |
|     |             | CCAGCTGACAAAGCCAGATGTGATCCTGCGGCTGGAGAAGGGAGAGGAGCCCTG |
|     |             | GCTGGTGTAGTCTAGAAATCAACCTCTGGATTACAAAATTTGTGAAAGATTGAC |
|     |             | TGGTATTCTTAACTATGTTGCTCCTTTTACGCTATGTGGATACGCTGCTTTAAT |
|     |             | GCCTTTGTATCATGCTATTGCTTCCCGTATGGCTTTCATTTTCTCCTCCTTGTA |
|     |             | TAAATCCTGGTTGCTGTCTCTTTATGAGGAGTTGTGGCCCGTTGTCAGGCAACG |
|     |             | TGGCGTGGTGTGCACTGTGTTTGCTGACGCAACCCCCACTGGTTGGGGCATTGC |
|     |             | CACCACCTGTCAGCTCCTTTCCGGGACTTTCGCTTTCCCCCTCCCTATTGCCAC |
|     |             | GGCGGAACTCATCGCCGCCTGCCTTGCCCGCTGCTGGACAGGGGCTCGGCTGTT |
|     |             | GGGCACTGACAATTCCGTGGTGTTGTCGGGGAAATCATCGTCCTTTCCTTGGCT |
|     |             | GCTCGCCTGTGTTGCCACCTGGATTCTGCGCGGGACGTCCTTCTGCTACGTCCC |
|     |             | TTCGGCCCTCAATCCAGCGGACCTTCCTTCCCGCGGCCTGCTGCCGGCTCTGCG |
|     |             | GCCTCTTCCGCGTCTTCGCCTTCGCCCTCAGACGAGTCGGATCTCCCTTTGGGC |
|     |             | CGCCTCCCCGCCTGTTAATTAAAAAAAAAAAAAAAAAAAAAAAAAAAAAAAAAAA |
|     |             | AAAAAAAAAAAAAAAAAACTAGTGGCGCCTGATGCGGTATTTTCTCCTTACGCA |
|     |             | TCTGTGCGGTATTTCACACCGCATAATCCAGCACAGTGGCGGCCCGTTTAAACC |
|     |             | CGCTGATCAGCCTCGACTGTGCCTTCTAGTTGCCAGCCATCTGTTGTTTGCCCC |
|     |             | TCCCCCGTGCCTTCCTTGACCCTGGAAGGTGCCACTCCCACTGTCCTTTCCTAA |
|     |             | TAAAATGAGGAAATTGCATCGCATTGTCTGAGTAGGTGTCATTCTATTCTGGGG |
|     |             | GGTGGGGTGGGGCAGGACAGCAAGGGGGAGGATTGGGAAGACAATAGCAGGCAT |
|     |             | GCTGGGGATGCGGTGGGCTCTATGGCTTCTGAGGCGGAAAGAACCAGCTGCATT |
|     |             | AATGAATCGGCCAACGCGCGGGGAGAGGCGGTTTGCGTATTGGGCGCTCTTCCG |
|     |             | CTTCCTCGCTCACTGACTCGCTGCGCTCGGTCGTTCGGCTGCGGCGAGCGGTAT |
|     |             | CAGCTCACTCAAAGGCGGTAATACGGTTATCCACAGAATCAGGGGATAACGCAG |
|     |             | GAAAGAACATGTGAGCAAAAGGCCAGCAAAAGGCCAGGAACCGTAAAAAGGCCG |
|     |             | CGTTGCTGGCGTTTTTCCATAGGCTCCGCCCCCCTGACGAGCATCACAAAAATC |

TABLE 18-continued

Sequence listing.

| SEQ | Description | Sequence |
|-----|-------------|----------|
| | | GACGCTCAAGTCAGAGGTGGCGAAACCCGACAGGACTATAAAGATACCAGGCGT<br>TTCCCCCTGGAAGCTCCCTCGTGCGCTCTCCTGTTCCGACCCTGCCGCTTACCG<br>GATACCTGTCCGCCTTTCTCCCTTCGGGAAGCGTGGCGCTTTCTCATAGCTCAC<br>GCTGTAGGTATCTCAGTTCGGTGTAGGTCGTTCGCTCCAAGCTGGGCTGTGTGC<br>ACGAACCCCCCGTTCAGCCCGACCGCTGCGCCTTATCCGGTAACTATCGTCTTG<br>AGTCCAACCCGGTAAGACACGACTTATCGCCACTGGCAGCAGCCACTGGTAACA<br>GGATTAGCAGAGCGAGGTATGTAGGCGGTGCTACAGAGTTCTTGAAGTGGTGGC<br>CTAACTACGGCTACACTAGAAGAACAGTATTTGGTATCTGCGCTCTGCTGAAGC<br>CAGTTACCTTCGGAAAAAGAGTTGGTAGCTCTTGATCCGGCAAACAAACCACCG<br>CTGGTAGCGGTTTTTTTGTTTGCAAGCAGCAGATTACGCGCAGAAAAAAAGGAT<br>CTCAAGAAGATCCTTTGATCTTTTCTACGGGGTCTGACGCTCAGTGGAACGAAA<br>ACTCACGTTAAGGGATTTTGGTCATGAGATTATCAAAAAGGATCTTCACCTAGA<br>TCCTTTTAAATTAAAAATGAAGTTTTAAATCAATCTAAAGTATATATGAGTAAA<br>CTTGGTCTGACAGTTACCAATGCTTAATCAGTGAGGCACCTATCTCAGCGATCT<br>GTCTATTTCGTTCATCCATAGTTGCCTGACTCCCCGTCGTGTAGATAACTACGA<br>TACGGGAGGGCTTACCATCTGGCCCCAGTGCTGCAATGATACCGCGAGACCCAC<br>GCTCACCGGCTCCAGATTTATCAGCAATAAACCAGCCAGCCGGAAGGGCCGAGC<br>GCAGAAGTGGTCCTGCAACTTTATCCGCCTCCATCCAGTCTATTAATTGTTGCC<br>GGGAAGCTAGAGTAAGTAGTTCGCCAGTTAATAGTTTGCGCAACGTTGTTGCCA<br>TTGCTACAGGCATCGTGGTGTCACGCTCGTCGTTTGGTATGGCTTCATTCAGCT<br>CCGGTTCCCAACGATCAAGGCGAGTTACATGATCCCCCATGTTGTGCAAAAAAG<br>CGGTTAGCTCCTTCGGTCCTCCGATCGTTGTCAGAAGTAAGTTGGCCGCAGTGT<br>TATCACTCATGGTTATGGCAGCACTGCATAATTCTCTTACTGTCATGCCATCCG<br>TAAGATGCTTTTCTGTGACTGGTGAGTACTCAACCAAGTCATTCTGAGAATAGT<br>GTATGCGGCGACCGAGTTGCTCTTGCCCGGCGTCAATACGGGATAATACCGCGC<br>CACATAGCAGAACTTTAAAAGTGCTCATCATTGGAAAACGTTCTTCGGGGCGAA<br>AACTCTCAAGGATCTTACCGCTGTTGAGATCCAGTTCGATGTAACCCACTCGTG<br>CACCCAACTGATCTTCAGCATCTTTTACTTTCACCAGCGTTTCTGGGTGAGCAA<br>AAACAGGAAGGCAAAATGCCGCAAAAAAGGGAATAAGGGCGACACGGAAATGTT<br>GAATACTCATACTCTTCCTTTTTCAATATTATTGAAGCATTTATCAGGGTTATT<br>GTCTCATGAGCGGATACATATTTGAATGTATTTAGAAAAATAAACAAATAGGGG<br>TTCCGCGCACATTTCCCCGAAAAGTGCCACCTGA |
| 1243 | Plasmid for fusion<br>protein with<br>mRNA0037 | CGTCGATCGACGGATCGGGAGATCTCCCGATCCCCTATGGTGCACTCTCAGTAC<br>AATCTGCTCTGATGCCGCATAGTTAAGCCAGTATCTGCTCCCTGCTTGTGTGTT<br>GGAGGTCGCTGAGTAGTGCGCGAGCAAAATTTAAGCTACAACAAGGCAAGGCTT<br>GACCGACAATTGCATGAAGAATCTGCTTAGGGTTAGGCGTTTTGCGCTGCTTCG<br>CGATGTACGGGCCAGATATACGCGTTGACATTGATTATTGACTAGTTATTAATA<br>GTAATCAATTACGGGGTCATTAGTTCATAGCCCATATATGGAGTTCCGCGTTAC<br>ATAACTTACGGTAAATGGCCCGCCTGGCTGACCGCCCAACGACCCCCGCCCATT<br>GACGTCAATAATGACGTATGTTCCCATAGTAACGCCAATAGGGACTTTCCATTG<br>ACGTCAATGGGTGGAGTATTTACGGTAAACTGCCCACTTGGCAGTACATCAAGT<br>GTATCATATGCCAAGTACGCCCCCTATTGACGTCAATGACGGTAAATGGCCCGC<br>CTGGCATTATGCCCAGTACATGACCTTATGGGACTTTCCTACTTGGCAGTACAT<br>CTACGTATTAGTCATCGCTATTACCATGGTGATGCGGTTTTGGCAGTACATCAA<br>TGGGCGTGGATAGCGGTTTGACTCACGGGGATTTCCAAGTCTCCACCCCATTGA<br>CGTCAATGGGAGTTTGTTTTGGCACCAAAATCAACGGGACTTTCCAAAATGTCG<br>TAACAACTCCGCCCCATTGACGCAAATGGGCGGTAGGCGTGTACGGTGGGAGGT<br>CTATATAAGCAGAGCTCTCTGGCTAACTAGAGAACCCACTGCTTACTGGCTTAT<br>CGAAATTAATACGACTCACTATAAGGAGACCCAAGCTACCGGTGCCACCATGTA<br>CCCATACGATGTTCCAGATTACGCTTCGCCGAAGAAAAAGCGCAAGGTCAATCA<br>CGATCAGGAGTTCGACCCCCCTAAGGTGTACCCACCAGTGCCTGCAGAGAAGAG<br>GAAGCCAATCCGGGTGCTGAGCCTGTTTGATGGCATCGCCACCGGCCTGCTGGT<br>GCTGAAGGATCTGGGCATCCAGGTGGACCGGTACATCGCCTCCGAGGTGTGCGA<br>GGATTCTATCACCGTGGGCATGGTGCGCCACCAGGGCAAGATCATGTATGTGGG<br>CGACGTGCGGTCCGTGACACAGAAGCACATCCAGGAGTGGGGGCCCATTCGATCT<br>GGTGATCGGCGGCAGCCCCTGTAATGACCTGTCCATCGTGAACCCTGCAAGGAA<br>GGGACTGTACGAGGGAACCGGCCGGCTGTTCTTTGAGTTTTATAGACTGCTGCA<br>CGACGCCAGGCCTAAGGAGGGCGACGATAGACCATTCTTTTGGCTGTTCGAGAA<br>TGTGGTGGCTATGGGCGTGAGCGATAAGAGGGACATCTCCAGGTTTCTGGAGTC<br>TAACCCCGTGATGATCGATGCAAAGGAGGTGTCCGCCGCACACAGAGCCAGGTA<br>TTTCTGGGGCAATCTGCCAGGAATGAACAGGCCACTGGCAAGCACCGTGAATGA<br>CAAGCTGGAGCTGCAGGAGTGCCTGGAGCACGGAAGGATCGCCAAGTTTTCCAA<br>GGTGCGCACAATCACCCACGGGAGCAATTCCATCAAGCAGGGCAAGGATCAGCA<br>CTTCCCCGTGTTCATGAACGAGAAGGAGGACATCCTGTGGTGTACCGAGATGGA<br>GAGAGTGTTCGGCTTTCCAGTGCACTACACAGACGTGTCTAACATGAGCAGGCT<br>GGCCAAGGCAGCGGCTGCTGGGCAGATCTTGGAGCGTGCCCGTGATCAGGCACCT<br>GTTCGCCCCTCTGAAGGAGTATTTTGCCTGCGTGAGCAGCGGCAACTCCAATGC<br>CAACAGCCGGGGCCCCTCTTTCAGCTCCGGATTGGTGCCTCTGAGCCTGAGGGG<br>CTCCCACATGGCAGCAATCCCCGCCCTGGACCCCGAGGCCGAGCCTAGCATGGA<br>CGTGATCCTGGTGGGCTCTAGCGAGCTGTCCTCTAGCGTGTCTCCAGGAACCGG<br>AAGGGATCTGATCGCATACGAGGTGAAGGCCAATCAGCGGAACATCGAGGACAT<br>CTGTATCTGCTGTGGCAGCCTGCAGGTGCACACACAGCACCCACTGTTCGAGGG<br>AGGAATCTGCGCACCCTGTAAGGATAAGTTCCTGGACGCCCTGTTTCTGTACGA<br>CGATGACGGCTACCAGTCCTATTGCTCTATCTGCTGTTCCGGCGAGACCCTGCT<br>GATCTGCGGCAATCCAGATTGTACAAGGTGCTATTGTTTTGAGTGCGTGGACTC |

TABLE 18-continued

Sequence listing.

| SEQ | Description | Sequence |
|-----|-------------|----------|
| | | TCTGGTGGGACCAGGCACCAGCGGAAAGGTGCACGCCATGTCCAACTGGGTGTG |
| | | CTACCTGTGCCTGCCATCCTCTCGCAGCGGACTGCTGCAGCGGAGAAGGAAGTG |
| | | GAGATCCCAGCTGAAGGCCTTCTATGATAGGGAGTCTGAGAACCCCCTGGAGAT |
| | | GTTTGAGACCGTGCCAGTGTGGCGCCGGCAGCCCGTGAGGGTGCTGAGCCTGTT |
| | | CGAGGATATCAAGAAGGAGCTGACATCCCTGGGCTTTCTGGAGTCCGGCTCTGA |
| | | CCCCGGACAGCTGAAGCACGTGGTGGATGTGACCGACACAGTGCGGAAGGATGT |
| | | GGAGGAGTGGGGCCCTTTCGACCTGGTGTACGGAGCAACCCCTCCACTGGGACA |
| | | CACATGCGACAGACCCCCTTCTTGGTACCTGTTCCAGTTTCACCGCCTGCTGCA |
| | | GTATGCAAGGCCAAAGCCAGGCAGCCCTAGACCATTCTTTTGGATGTTCGTGGA |
| | | TAATCTGGTGCTGAACAAGGAGGATCTGGACGTGGCCAGCAGGTTTCTGGAGAT |
| | | GGAGCCAGTGACCATCCCAGACGTGCACGGCGGCTCCCTGCAGAATGCCGTGCG |
| | | CGTGTGGTCTAACATCCCTGCCATCAGAAGCAGGCACTGGGCACTGGTGAGCGA |
| | | GGAGGAGCTGTCCCTGCTGGCCCAGAATAAGCAGAGCAGCAAGCTGGCCGCCAA |
| | | GTGGCCTACAAAGCTGGTGAAGAACTGCTTCCTGCCACTGCGGGAGTACTTCAA |
| | | GTATTTTTCCACCGAGCTGACATCTAGCCTGGGAGGACCCTCCTCTGGCGCCCC |
| | | ACCACCTAGCGGCGGCTCCCCTGCCGGCTCTCCAACCAGCACAGAGGAGGGCAC |
| | | CAGCGAGTCCGCCACACCAGAGTCTGGACCTGGCACCAGCACAGAGCCATCCGA |
| | | GGGCTCTGCCCCAGGCTCTCCTGCAGGCAGCCCTACCTCCACCGAAGAGGGCAC |
| | | CAGCACAGAGCCTTCTGAGGGCAGCGCCCCAGGCACCTCTACAGAGCCAAGCGA |
| | | GCTCGAGTCCCGGCCAGGGGAACGGCCCTTCCAGTGTCGGATCTGCATGAGAAA |
| | | CTTTTCAAGAGTGGATCATCTCCATCGACACCTCCGGACCCACACTGGAGAGAA |
| | | ACCCTTTCAGTGCAGGATATGTATGCGGAATTTTTCCCGGAGGGAACATTTGTC |
| | | CGGACATCTCAAGACACATACCGGGGGAGGCGGTAGTCAGAAGCCTTTCCAATG |
| | | CCGGATTTGCATGAGGAACTTCTCCCAAAGTTCCAGCCTCGTCCGCCATCTTCG |
| | | CACACATACAGGCGAGAAGCCATTCCAGTGTAGGATCTGCATGCGCAATTTTAG |
| | | CCGCAAGGAGCGATTGGCAACCCACCTCAAGACGCATACAGGTAGTCAGAAGCC |
| | | TTTTCAGTGCAGGATCTGCATGAGGAATTTTAGTGTCGCACATAACCTCACAAG |
| | | GCATCTGCGCACGCATACTGGAGAGAAGCCCTTTCAGTGTAGGATTTGTATGCG |
| | | GAACTTCAGCATTAGTCATAACCTGGCAAGGCATCTCAAAACTCATTTGCGCGG |
| | | GTCTAGCCCCAAGAAGAAGAGAAAGGTGGGAGTCGACGGATCCAGCGGCTCCGA |
| | | GACCCCAGGCACATCTGAGAGCGCCACCCCTGAGTCCCGGACCCTGGTGACATT |
| | | CAAGGACGTGTTCGTGGACTTCACCCGGGAGGAGTGGAAGCTGCTGGACACAGC |
| | | CCAGCAGATCGTGTACAGGAACGTGATGCTGGAGAACTATAAGAATCTGGTGTC |
| | | TCTGGGCTACCAGCTGACAAAGCCAGATGTGATCCTGCGGCTGGAGAAGGGAGA |
| | | GGAGCCCTGGCTGGTGTAGTCTAGAAATCAACCTCTGGATTACAAAATTTGTGA |
| | | AAGATTGACTGGTATTCTTAACTATGTTGCTCCTTTTACGCTATGTGGATACGC |
| | | TGCTTTAATGCCTTTGTATCATGCTATTGCTTCCCGTATGGCTTTCATTTTCTC |
| | | CTCCTTGTATAAATCCTGGTTGCTGTCTCTTTATGAGGAGTTGTGGCCCGTTGT |
| | | CAGGCAACGTGGCGTGGTGTGCACTGTGTTTGCTGACGCAACCCCCACTGGTTG |
| | | GGGCATTGCCACCACCTGTCAGCTCCTTTCCGGGACTTTCGCTTTCCCCCTCCC |
| | | TATTGCCACGGCGGAACTCATCGCCGCCTGCCTTGCCCGCTGCTGGACAGGGGC |
| | | TCGGCTGTTGGGCACTGACAATTCCGTGGTGTTGTCGGGGAAATCATCGTCCTT |
| | | TCCTTGGCTGCTCGCCTGTGTTGCCACCTGGATTCTGCGCGGGACGTCCTTCTG |
| | | CTACGTCCCTTCGGCCCTCAATCCAGCGGACCTTCCTTCCCGCGGCCTGCTGCC |
| | | GGCTCTGCGGCCTCTTCCGCGTCTTCGCCTTCGCCCTCAGACGAGTCGGATCTC |
| | | CCTTTGGGCCGCCTCCCCGCCTGTTAATTAAAAAAAAAAAAAAAAAAAAAAAAA |
| | | AAAAAAAAAAAAAAAAAAAAAAAAAAAACTAGTGGCGCCTGATGCGGTATTTTCT |
| | | CCTTACGCATCTGTGCGGTATTTCACACCGCATAATCCAGCACAGTGGCGGCCC |
| | | GTTTAAACCCGCTGATCAGCCTCGACTGTGCCTTCTAGTTGCCAGCCATCTGTT |
| | | GTTTGCCCCTCCCCCGTGCCTTCCTTGACCCTGGAAGGTGCCACTCCCACTGTC |
| | | CTTTCCTAATAAAATGAGGAAATTGCATCGCATTGTCTGAGTAGGTGTCATTCT |
| | | ATTCTGGGGGGTGGGGTGGGGCAGGACAGCAAGGGGGAGGATTGGGAAGACAAT |
| | | AGCAGGCATGCTGGGGATGCGGTGGGCTCTATGGCTTCTGAGGCGGAAAGAACC |
| | | AGCTGCATTAATGAATCGGCCAACGCGCGGGGAGAGGCGGTTTGCGTATTGGGC |
| | | GCTCTTCCGCTTCCTCGCTCACTGACTCGCTGCGCTCGGTCGTTCGGCTGCGGC |
| | | GAGCGGTATCAGCTCACTCAAAGGCGGTAATACGGTTATCCACAGAATCAGGGG |
| | | ATAACGCAGGAAAGAACATGTGAGCAAAAGGCCAGCAAAAGGCCAGGAACCGTA |
| | | AAAAGGCCGCGTTGCTGGCGTTTTTCCATAGGCTCCGCCCCCCTGACGAGCATC |
| | | ACAAAAATCGACGCTCAAGTCAGAGGTGGCGAAACCCGACAGGACTATAAAGAT |
| | | ACCAGGCGTTTCCCCCTGGAAGCTCCCTCGTGCGCTCTCCTGTTCCGACCCTGC |
| | | CGCTTACCGGATACCTGTCCGCCTTTCTCCCTTCGGGAAGCGTGGCGCTTTCTC |
| | | ATAGCTCACGCTGTAGGTATCTCAGTTCGGTGTAGGTCGTTCGCTCCAAGCTGG |
| | | GCTGTGTGCACGAACCCCCCGTTCAGCCCGACCGCTGCGCCTTATCCGGTAACT |
| | | ATCGTCTTGAGTCCAACCCGGTAAGACACGACTTATCGCCACTGGCAGCAGCCA |
| | | CTGGTAACAGGATTAGCAGAGCGAGGTATGTAGGCGGTGCTACAGAGTTCTTGA |
| | | AGTGGTGGCCTAACTACGGCTACACTAGAAGAACAGTATTTGGTATCTGCGCTC |
| | | TGCTGAAGCCAGTTACCTTCGGAAAAAGAGTTGGTAGCTCTTGATCCGGCAAAC |
| | | AAACCACCGCTGGTAGCGGTTTTTTTGTTTGCAAGCAGCAGATTACGCGCAGAA |
| | | AAAAAGGATCTCAAGAAGATCCTTTGATCTTTTCTACGGGGTCTGACGCTCAGT |
| | | GGAACGAAAACTCACGTTAAGGGATTTTGGTCATGAGATTATCAAAAAGGATCT |
| | | TCACCTAGATCCTTTTAAATTAAAAATGAAGTTTTAAATCAATCTAAAGTATAT |
| | | ATGAGTAAACTTGGTCTGACAGTTACCAATGCTTAATCAGTGAGGCACCTATCT |
| | | CAGCGATCTGTCTATTTCGTTCATCCATAGTTGCCTGACTCCCCGTCGTGTAGA |
| | | TAACTACGATACGGGAGGGCTTACCATCTGGCCCCAGTGCTGCAATGATACCGC |
| | | GAGACCCACGCTCACCGGCTCCAGATTTATCAGCAATAAACCAGCCAGCCGGAA |
| | | GGGCCGAGCGCAGAAGTGGTCCTGCAACTTTATCCGCCTCCATCCAGTCTATTA |

TABLE 18-continued

Sequence listing.

| SEQ | Description | Sequence |
|-----|-------------|----------|
|  |  | ATTGTTGCCGGGAAGCTAGAGTAAGTAGTTCGCCAGTTAATAGTTTGCGCAACG |
|  |  | TTGTTGCCATTGCTACAGGCATCGTGGTGTCACGCTCGTCGTTTGGTATGGCTT |
|  |  | CATTCAGCTCCGGTTCCCAACGATCAAGGCGAGTTACATGATCCCCCATGTTGT |
|  |  | GCAAAAAAGCGGTTAGCTCCTTCGGTCCTCCGATCGTTGTCAGAAGTAAGTTGG |
|  |  | CCGCAGTGTTATCACTCATGGTTATGGCAGCACTGCATAATTCTCTTACTGTCA |
|  |  | TGCCATCCGTAAGATGCTTTTCTGTGACTGGTGAGTACTCAACCAAGTCATTCT |
|  |  | GAGAATAGTGTATGCGGCGACCGAGTTGCTCTTGCCCGGCGTCAATACGGGATA |
|  |  | ATACCGCGCCACATAGCAGAACTTTAAAAGTGCTCATCATTGGAAAACGTTCTT |
|  |  | CGGGGCGAAAACTCTCAAGGATCTTACCGCTGTTGAGATCCAGTTCGATGTAAC |
|  |  | CCACTCGTGCACCCAACTGATCTTCAGCATCTTTTACTTTCACCAGCGTTTCTG |
|  |  | GGTGAGCAAAAACAGGAAGGCAAATGCCGCAAAAAAGGGAATAAGGGCGACAC |
|  |  | GGAAATGTTGAATACTCATACTCTTCCTTTTTCAATATTATTGAAGCATTTATC |
|  |  | AGGGTTATTGTCTCATGAGCGGATACATATTTGAATGTATTTAGAAAAATAAAC |
|  |  | AAATAGGGGTTCCGCGCACATTTCCCCGAAAAGTGCCACCTGA |
| 1244 | Plasmid for fusion protein with mRNA0038 | CGTCGATCGACGGATCGGGAGATCTCCCGATCCCCTATGGTGCACTCTCAGTAC |
|  |  | AATCTGCTCTGATGCCGCATAGTTAAGCCAGTATCTGCTCCCTGCTTGTGTGTT |
|  |  | GGAGGTCGCTGAGTAGTGCGCGAGCAAAATTTAAGCTACAACAAGGCAAGGCTT |
|  |  | GACCGACAATTGCATGAAGAATCTGCTTAGGGTTAGGCGTTTTGCGCTGCTTCG |
|  |  | CGATGTACGGGCCAGATATACGCGTTGACATTGATTATTGACTAGTTATTAATA |
|  |  | GTAATCAATTACGGGGTCATTAGTTCATAGCCCATATATGGAGTTCCGCGTTAC |
|  |  | ATAACTTACGGTAAATGGCCCGCCTGGCTGACCGCCCAACGACCCCCGCCCATT |
|  |  | GACGTCAATAATGACGTATGTTCCCATAGTAACGCCAATAGGGACTTTCCATTG |
|  |  | ACGTCAATGGGTGGAGTATTTACGGTAAACTGCCCACTTGGCAGTACATCAAGT |
|  |  | GTATCATATGCCAAGTACGCCCCCTATTGACGTCAATGACGGTAAATGGCCCGC |
|  |  | CTGGCATTATGCCCAGTACATGACCTTATGGGACTTTCCTACTTGGCAGTACAT |
|  |  | CTACGTATTAGTCATCGCTATTACCATGGTGATGCGGTTTTGGCAGTACATCAA |
|  |  | TGGGCGTGGATAGCGGTTTGACTCACGGGGATTTCCAAGTCTCCACCCCATTGA |
|  |  | CGTCAATGGGAGTTTGTTTTGGCACCAAAATCAACGGGACTTTCCAAAATGTCG |
|  |  | TAACAACTCCGCCCCATTGACGCAAATGGGCGGTAGGCGTGTACGGTGGGAGGT |
|  |  | CTATATAAGCAGAGCTCTCTGGCTAACTAGAGAACCCACTGCTTACTGGCTTAT |
|  |  | CGAAATTAATACGACTCACTATAAGGAGACCCAAGCTACCGGTGCCACCATGTA |
|  |  | CCCATACGATGTTCCAGATTACGCTTCGCCGAAGAAAAAGCGCAAGGTCAATCA |
|  |  | CGATCAGGAGTTCGACCCCCCTAAGGTGTACCCACCAGTGCCTGCAGAGAAGAG |
|  |  | GAAGCCAATCCGGGTGCTGAGCCTGTTTGATGGCATCGCCACCGGCCTGCTGGT |
|  |  | GCTGAAGGATCTGGGCATCCAGGTGGACCGGTACATCGCCTCCGAGGTGTGCGA |
|  |  | GGATTCTATCACCGTGGGCATGGTGCGCCACCAGGGCAAGATCATGTATGTGGG |
|  |  | CGACGTGCGGTCCGTGACACAGAAGCACATCCAGGAGTGGGGCCCATTCGATCT |
|  |  | GGTGATCGGCGGCAGCCCCTGTAATGACCTGTCCATCGTGAACCCTGCAAGGAA |
|  |  | GGGACTGTACGAGGGAACCGGCCGGCTGTTCTTTGAGTTTTATAGACTGCTGCA |
|  |  | CGACGCCAGGCCTAAGGAGGGCGACGATAGACCATTCTTTTGGCTGTTCGAGAA |
|  |  | TGTGGTGGCTATGGGCGTGAGCGATAAGAGGGACATCTCCAGGTTTCTGGAGTC |
|  |  | TAACCCCGTGATGATCGATGCAAAGGAGGTGTCCGCCGCACACAGAGCCAGGTA |
|  |  | TTTCTGGGGCAATCTGCCAGGAATGAACAGGCCACTGGCAAGCACCGTGAATGA |
|  |  | CAAGCTGGAGCTGCAGGAGTGCCTGGAGCACGGAAGGATCGCCAAGTTTTCCAA |
|  |  | GGTGCGCACAATCACCACACAGGAGCAATTCCATCAAGCAGGGCAAGGATCAGCA |
|  |  | CTTCCCCGTGTTCATGAACGAGAAGGAGGACATCCTGTGGTGTACCGAGATGGA |
|  |  | GAGAGTGTTCGGCTTTCCAGTGCACTACACAGACGTGTCTAACATGAGCAGGCT |
|  |  | GGCAAGGCAGCGGCTGCTGGGCAGATCTTGGAGCGTGCCCGTGATCAGGCACCT |
|  |  | GTTCGCCCCTCTGAAGGAGTATTTGCCTGCGTGAGCAGCGGCAACTCCAATGC |
|  |  | CAACAGCCGGGGCCCCTCTTTCAGCTCCGGATTGGTGCCTCTGAGCCTGAGGGG |
|  |  | CTCCCACATGGCAGCAATCCCCGCCCTGGACCCCGAGGCCGAGCCTAGCATGGA |
|  |  | CGTGATCCTGGTGGGCTCTAGCGAGCTGTCCTCTAGCGTGTCTCCAGGAACCGG |
|  |  | AAGGGATCTGATCGCATACGAGGTGAAGGCCAATCAGCGGAACATCGAGGACAT |
|  |  | CTGTATCTGCTGTGGCAGCCTGCAGGTGCACACACAGCACCCACTGTTCGAGGG |
|  |  | AGGAATCTGCGCACCCTGTAAGGATAAGTTCCTGGACGCCCTGTTTCTGTACGA |
|  |  | CGATGACGGCTACCAGTCCTATTGCTCTATCTGCTGTTCCGGCGAGACCCTGCT |
|  |  | GATCTGCGGCAATCCAGATTGTACAAGGTGCTATTGTTTTGAGTGCGTGGACTC |
|  |  | TCTGGTGGGACCAGGCACCAGGCGGAAAGGTGCACGCCATGTCCAACTGGGTGTG |
|  |  | CTACCTGTGCCTGCCATCCTCTCGCAGCGGACTGCTGCAGCGGAGAAGGAAGTG |
|  |  | GAGATCCCAGCTGAAGGCCTTCTATGATAGGGAGTCTGAGAACCCCCTGGAGAT |
|  |  | GTTTGAGACCGTGCCAGTGTGGCGCCGGCAGCCCGTGAGGGTGCTGAGCCTGTT |
|  |  | CGAGGATATCAAGAAGGAGCTGACATCCTGGGCTTTCTGGAGTCCGGCTCTGA |
|  |  | CCCCGGACAGCTGAAGCACGTGGTGGATGTGACCGACACAGTGCGGAAGGATGT |
|  |  | GGAGGAGTGGGGGCCCTTTCGACCTGGTGTACGGAGCAACCCCTCCACTGGGACA |
|  |  | CACATGCGACAGACCCCCTTCTTGGTACCTGTTCCAGTTTCACCGCCTGCTGCA |
|  |  | GTATGCAAGGCCAAAGCCAGGCAGCCCTAGACCATTCTTTTGGATGTTCGTGGA |
|  |  | TAATCTGGTGCTGAACAAGGAGGATCTGGACGTGGCCAGCAGGTTTCTGGAGAT |
|  |  | GGAGCCAGTGACCATCCCAGACGTGCACGGCGGCTCCCTGCAGAATGCCGTGCG |
|  |  | CGTGTGGTCTAACATCCCTGCCATCAGAAGCAGGCACTGGGCACTGGTGAGCGA |
|  |  | GGAGGAGCTGTCCCTGCTGGCCCAGAATAAGCAGAGCAGCAAGCTGGCCGCCAA |
|  |  | GTGGCCTACAAAGCTGGTGAAGAACTGCTTCCTGCCACTGCGGGAGTACTTCAA |
|  |  | GTATTTTTCCACCGAGCTGACATCTAGCCTGGGAGGACCCTCCTCTGGCGCCCC |
|  |  | ACCACCTAGCGGCGGCTCCCCTGCCGGCTCTCCAACCAGCACAGAGGAGGGCAC |
|  |  | CAGCGAGTCCGCCACACCAGAGTCTGGACCTGGCACCAGCACAGAGCCATCCGA |
|  |  | GGGCTCTGCCCCCAGGCTCTCCTGCAGGCAGCCCTACCTCCACCGAAGAGGGCAC |

TABLE 18-continued

Sequence listing.

| SEQ | Description | Sequence |
|-----|-------------|----------|
| | | CAGCACAGAGCCTTCTGAGGGCAGCGCCCCAGGCACCTCTACAGAGCCAAGCGA<br>GCTCGAGTCCCGGCCAGGGGAACGGCCCTTCCAGTGTCGGATCTGCATGAGAAA<br>CTTTTCACGCAAGCACCACCTTGGGAGACATACCAGAACCCACACTGGAGAGAA<br>ACCCTTTCAGTGCAGGATATGTATGCGGAATTTTTCCCGACGGGAACACCTCAC<br>GATTCATTTGCGGACACATACCGGGGGAGGCGGTAGTCAGAAGCCTTTCCAATG<br>CCGGATTTGCATGAGGAACTTCTCCCAGAGCTCATCTCTCGTGCGGCACCTGCG<br>GACACATACAGGCGAGAAGCCATTCCAGTGTAGGATCTGCATGCGCAATTTTAG<br>CCGGAAGGAGCGATTGGCGACGCACCTGAAAACGCATACAGGTAGTCAGAAGCC<br>TTTTCAGTGCAGGATCTGCATGAGGAATTTTAGTGTAGCCCACAACCTGACTAG<br>GCATTTGAGGACGCATACTGGAGAGAAGCCCTTTCAGTGTAGGATTTGTATGCG<br>GAACTTCAGCATTTCTCACAATCTCGCGCGACATTTGAAAACTCATTTGCGCGG<br>GTCTAGCCCCAAGAAGAAGAGAAAGGTGGGAGTCGACGGATCCAGCGGCTCCGA<br>GACCCCAGGCACATCTGAGAGCGCCACCCCTGAGTCCCGGACCCTGGTGACATT<br>CAAGGACGTGTTCGTGGACTTCACCCGGGAGGAGTGGAAGCTGCTGGACACAGC<br>CCAGCAGATCGTGTACAGGAACGTGATGCTGGAGAACTATAAGAATCTGGTGTC<br>TCTGGGCTACCAGCTGACAAAGCCAGATGTGATCCTGCGGCTGGAGAAGGGAGA<br>GGAGCCCTGGCTGGTGTAGTCTAGAAATCAACCTCTGGATTACAAAATTTGTGA<br>AAGATTGACTGGTATTCTTAACTATGTTGCTCCTTTTACGCTATGTGGATACGC<br>TGCTTTAATGCCTTTGTATCATGCTATTGCTTCCCGTATGGCTTTCATTTTCTC<br>CTCCTTGTATAAATCCTGGTTGCTGTCTCTTTATGAGGAGTTGTGGCCCGTTGT<br>CAGGCAACGTGGCGTGGTGTGCACTGTGTTTGCTGACGCAACCCCCACTGGTTG<br>GGGCATTGCCACCACCTGTCAGCTCCTTTCCGGGACTTTCGCTTTCCCCCTCCC<br>TATTGCCACGGCGGAACTCATCGCCGCCTGCCTTGCCCGCTGCTGGACAGGGGC<br>TCGGCTGTTGGGCACTGACAATTCCGTGGTGTTGTCGGGGAAATCATCGTCCTT<br>TCCTTGGCTGCTCGCCTGTGTTGCCACCTGGATTCTGCGCGGGACGTCCTTCTG<br>CTACGTCCCTTCGGCCCTCAATCCAGCGGACCTTCCTTCCCGCGGCCTGCTGCC<br>GGCTCTGCGGCCTCTTCCGCGTCTTCGCCTTCGCCCTCAGACGAGTCGGATCTC<br>CCTTTGGGCCGCCTCCCCGCCTGTTAATTAAAAAAAAAAAAAAAAAAAAAAAAAA<br>AAAAAAAAAAAAAAAAAAAAAAAAACTAGTGGCGCCTGATGCGGTATTTTCT<br>CCTTACGCATCTGTGCGGTATTTCACACCGCATAATCCAGCACAGTGGCGGCCC<br>GTTTAAACCCGCTGATCAGCCTCGACTGTGCCTTCTAGTTGCCAGCCATCTGTT<br>GTTTGCCCCTCCCCCGTGCCTTCCTTGACCCTGGAAGGTGCCACTCCCACTGTC<br>CTTTCCTAATAAAATGAGGAAATTGCATCGCATTGTCTGAGTAGGTGTCATTCT<br>ATTCTGGGGGGTGGGGTGGGGCAGGACAGCAAGGGGGAGGATTGGGAAGACAAT<br>AGCAGGCATGCTGGGGATGCGGTGGGCTCTATGGCTTCTGAGGCGGAAAGAACC<br>AGCTGCATTAATGAATCGGCCAACGCGCGGGGAGAGGCGGTTTGCGTATTGGGC<br>GCTCTTCCGCTTCCTCGCTCACTGACTCGCTGCGCTCGGTCGTTCGGCTGCGGC<br>GAGCGGTATCAGCTCACTCAAAGGCGGTAATACGGTTATCCACAGAATCAGGGG<br>ATAACGCAGGAAAGAACATGTGAGCAAAAGGCCAGCAAAAGGCCAGGAACCGTA<br>AAAAGGCCGCGTTGCTGGCGTTTTTCCATAGGCTCCGCCCCCCTGACGAGCATC<br>ACAAAAATCGACGCTCAAGTCAGAGGTGGCGAAACCCGACAGGACTATAAAGAT<br>ACCAGGCGTTTCCCCCTGGAAGCTCCCTCGTGCGCTCTCCTGTTCCGACCCTGC<br>CGCTTACCGGATACCTGTCCGCCTTTCTCCCTTCGGGAAGCGTGGCGCTTTCTC<br>ATAGCTCACGCTGTAGGTATCTCAGTTCGGTGTAGGTCGTTCGCTCCAAGCTGG<br>GCTGTGTGCACGAACCCCCCGTTCAGCCCGACCGCTGCGCCTTATCCGGTAACT<br>ATCGTCTTGAGTCCAACCCGGTAAGACACGACTTATCGCCACTGGCAGCAGCCA<br>CTGGTAACAGGATTAGCAGAGCGAGGTATGTAGGCGGTGCTACAGAGTTCTTGA<br>AGTGGTGGCCTAACTACGGCTACACTAGAAGAACAGTATTTGGTATCTGCGCTC<br>TGCTGAAGCCAGTTACCTTCGGAAAAAGAGTTGGTAGCTCTTGATCCGGCAAAC<br>AAACCACCGCTGGTAGCGGTTTTTTTGTTTGCAAGCAGCAGATTACGCGCAGAA<br>AAAAAGGATCTCAAGAAGATCCTTTGATCTTTTCTACGGGGTCTGACGCTCAGT<br>GGAACGAAAACTCACGTTAAGGGATTTTGGTCATGAGATTATCAAAAAGGATCT<br>TCACCTAGATCCTTTTAAATTAAAAATGAAGTTTTAAATCAATCTAAAGTATAT<br>ATGAGTAAACTTGGTCTGACAGTTACCAATGCTTAATCAGTGAGGCACCTATCT<br>CAGCGATCTGTCTATTTCGTTCATCCATAGTTGCCTGACTCCCCGTCGTGTAGA<br>TAACTACGATACGGGAGGGCTTACCATCTGGCCCCAGTGCTGCAATGATACCGC<br>GAGACCCACGCTCACCGGCTCCAGATTTATCAGCAATAAACCAGCCAGCCGGAA<br>GGGCCGAGCGCAGAAGTGGTCCTGCAACTTTATCCGCCTCCATCCAGTCTATTA<br>ATTGTTGCCGGGAAGCTAGAGTAAGTAGTTCGCCAGTTAATAGTTTGCGCAACG<br>TTGTTGCCATTGCTACAGGCATCGTGGTGTCACGCTCGTCGTTTGGTATGGCTT<br>CATTCAGCTCCGGTTCCCAACGATCAAGGCGAGTTACATGATCCCCCATGTTGT<br>GCAAAAAAGCGGTTAGCTCCTTCGGTCCTCCGATCGTTGTCAGAAGTAAGTTGG<br>CCGCAGTGTTATCACTCATGGTTATGGCAGCACTGCATAATTCTCTTACTGTCA<br>TGCCATCCGTAAGATGCTTTTCTGTGACTGGTGAGTACTCAACCAAGTCATTCT<br>GAGAATAGTGTATGCGGCGACCGAGTTGCTCTTGCCCGGCGTCAATACGGGATA<br>ATACCGCGCCACATAGCAGAACTTTAAAAGTGCTCATCATTGGAAAACGTTCTT<br>CGGGGCGAAAACTCTCAAGGATCTTACCGCTGTTGAGATCCAGTTCGATGTAAC<br>CCACTCGTGCACCCAACTGATCTTCAGCATCTTTTACTTTCACCAGCGTTTCTG<br>GGTGAGCAAAAACAGGAAGGCAAAATGCCGCAAAAAAGGGAATAAGGGCGACAC<br>GGAAATGTTGAATACTCATACTCTTCCTTTTTCAATATTATTGAAGCATTTATC<br>AGGGTTATTGTCTCATGAGCGGATACATATTTGAATGTATTTAGAAAAATAAAC<br>AAATAGGGGTTCCGCGCACATTTCCCCGAAAAGTGCCACCTGA |
| 1245 | Plasmid for fusion<br>protein with<br>mRNA0039 | CGTCGATCGACGGATCGGGAGATCTCCCGATCCCCTATGGTGCACTCTCAGTAC<br>AATCTGCTCTGATGCCGCATAGTTAAGCCAGTATCTGCTCCCTGCTTGTGTGTT<br>GGAGGTCGCTGAGTAGTGCGCGAGCAAAATTTAAGCTACAACAAGGCAAGGCTT |

TABLE 18-continued

| Sequence listing. |||
| --- | --- | --- |
| SEQ | Description | Sequence |
| | | GACCGACAATTGCATGAAGAATCTGCTTAGGGTTAGGCGTTTTGCGCTGCTTCG |
| | | CGATGTACGGGCCAGATATACGCGTTGACATTGATTATTGACTAGTTATTAATA |
| | | GTAATCAATTACGGGGTCATTAGTTCATAGCCCATATATGGAGTTCCGCGTTAC |
| | | ATAACTTACGGTAAATGGCCCGCCTGGCTGACCGCCCAACGACCCCCGCCCATT |
| | | GACGTCAATAATGACGTATGTTCCCATAGTAACGCCAATAGGGACTTTCCATTG |
| | | ACGTCAATGGGTGGAGTATTTACGGTAAACTGCCCACTTGGCAGTACATCAAGT |
| | | GTATCATATGCCAAGTACGCCCCCTATTGACGTCAATGACGGTAAATGGCCCGC |
| | | CTGGCATTATGCCCAGTACATGACCTTATGGGACTTTCCTACTTGGCAGTACAT |
| | | CTACGTATTAGTCATCGCTATTACCATGGTGATGCGGTTTTGGCAGTACATCAA |
| | | TGGGCGTGGATAGCGGTTTGACTCACGGGGATTTCCAAGTCTCCACCCCATTGA |
| | | CGTCAATGGGAGTTTGTTTTGGCACCAAAATCAACGGGACTTTCCAAAATGTCG |
| | | TAACAACTCCGCCCCATTGACGCAAATGGGCGGTAGGCGTGTACGGTGGGAGGT |
| | | CTATATAAGCAGAGCTCTCTGGCTAACTAGAGAACCCACTGCTTACTGGCTTAT |
| | | CGAAATTAATACGACTCACTATAAGGAGACCCAAGCTACCGGTGCCACCATGTA |
| | | CCCATACGATGTTCCAGATTACGCTTCGCCGAAGAAAAAGCGCAAGGTCAATCA |
| | | CGATCAGGAGTTCGACCCCCCTAAGGTGTACCCACCAGTGCCTGCAGAGAAGAG |
| | | GAAGCCAATCCGGGTGCTGAGCCTGTTTGATGGCATCGCCACCGGCCTGCTGGT |
| | | GCTGAAGGATCTGGGCATCCAGGTGGACCGGTACATCGCCTCCGAGGTGTGCGA |
| | | GGATTCTATCACCGTGGGCATGGTGCGCCACCAGGGCAAGATCATGTATGTGGG |
| | | CGACGTGCGGTCCGTGACACAGAAGCACATCCAGGAGTGGGGCCCATTCGATCT |
| | | GGTGATCGGCGGCAGCCCCTGTAATGACCTGTCCATCGTGAACCCTGCAAGGAA |
| | | GGGACTGTACGAGGGAACCGGCCGGCTGTTCTTTGAGTTTTATAGACTGCTGCA |
| | | CGACGCCAGGCCTAAGGAGGGCGACGATAGACCATTCTTTTGGCTGTTCGAGAA |
| | | TGTGGTGGCTATGGGCGTGAGCGATAAGAGGGACATCTCCAGGTTTCTGGAGTC |
| | | TAACCCCGTGATGATCGATGCAAAGGAGGTGTCCGCCGCACACAGAGCCAGGTA |
| | | TTTCTGGGGCAATCTGCCAGGAATGAACAGGCCACTGGCAAGCACCGTGAATGA |
| | | CAAGCTGGAGCTGCAGGAGTGCCTGGAGCACGGAAGGATCGCCAAGTTTTCCAA |
| | | GGTGCGCACAATCACCACACGGAGCAATTCCATCAAGCAGGGCAAGGATCAGCA |
| | | CTTCCCCGTGTTCATGAACGAGAAGGAGGACATCCTGTGGTGTACCGAGATGGA |
| | | GAGAGTGTTCGGCTTTCCAGTGCACTACACAGACGTGTCTAACATGAGCAGGCT |
| | | GGCAAGGCAGCGGCTGCTGGGCAGATCTTGGAGCGTGCCCGTGATCAGGCACCT |
| | | GTTCGCCCCTCTGAAGGAGTATTTTGCCTGCGTGAGCAGCGGCAACTCCAATGC |
| | | CAACAGCCGGGGCCCCTCTTTCAGCTCCGGATTGGTGCCTCTGAGCCTGAGGGG |
| | | CTCCCACATGGCAGCAATCCCCGCCCTGGACCCCGAGGCCGAGCCTAGCATGGA |
| | | CGTGATCCTGGTGGGCTCTAGCGAGCTGTCCTCTAGCGTGTCTCCAGGAACCGG |
| | | AAGGGATCTGATCGCATACGAGGTGAAGGCCAATCAGCGGAACATCGAGGACAT |
| | | CTGTATCTGCTGTGGCAGCCTGCAGGTGCACACACAGCACCCACTGTTCGAGGG |
| | | AGGAATCTGCGCACCCTGTAAGGATAAGTTCCTGGACGCCCTGTTTCTGTACGA |
| | | CGATGACGGCTACCAGTCCTATTGCTCTATCTGCTGTTCCGGCGAGACCCTGCT |
| | | GATCTGCGGCAATCCAGATTGTACAAGGTGCTATTGTTTTGAGTGCGTGGACTC |
| | | TCTGGTGGGACCAGGCACCAGCGGAAAGGTGCACGCCATGTCCAACTGGGTGTG |
| | | CTACCTGTGCCTGCCATCCTCTCGCAGCGGACTGCTGCAGCGGAGAAGGAAGTG |
| | | GAGATCCCAGCTGAAGGCCTTCTATGATAGGGAGTCTGAGAACCCCCTGGAGAT |
| | | GTTTGAGACCGTGCCAGTGTGGCGCCGGCAGCCCGTGAGGGTGCTGAGCCTGTT |
| | | CGAGGATATCAAGAAGGAGCTGACATCCCTGGGCTTTCTGGAGTCCGGCTCTGA |
| | | CCCCGGACAGCTGAAGCACGTGGTGGATGTGACCGACACAGTGCGGAAGGATGT |
| | | GGAGGAGTGGGGCCCTTTCGACCTGGTGTACGGGAGCAACCCCTCCACTGGGACA |
| | | CACATGCGACAGACCCCCTTCTTGGTACCTGTTCCAGTTTCACCGCCTGCTGCA |
| | | GTATGCAAGGCCAAAGCCAGGCAGCCCTAGACCATTCTTTTGGATGTTCGTGGA |
| | | TAATCTGGTGCTGAACAAGGAGGATCTGGACGTGGCCAGCAGGTTTCTGGAGAT |
| | | GGAGCCAGTGACCATCCCAGACGTGCACGGCGGCTCCCTGCAGAATGCCGTGCG |
| | | CGTGTGGTCTAACATCCCTGCCATCAGAAGCAGGCACTGGGCACTGGTGAGCGA |
| | | GGAGGAGCTGTCCCTGCTGGCCCAGAATAAGCAGAGCAGCAAGCTGGCCGCCAA |
| | | GTGGCCTACAAAGCTGGTGAAGAACTGCTTCCTGCCACTGCGGGAGTACTTCAA |
| | | GTATTTTTCCACCGAGCTGACATCTAGCCTGGGAGGACCCTCCTCTGGCGCCCC |
| | | ACCACCTAGCGGCGGCTCCCCTGCCGGCTCTCAACCAGCACAGAGGAGGGCAC |
| | | CAGCGAGTCCGCCACACCAGAGTCTGGACCTGGCACCAGCACAGAGCCATCCGA |
| | | GGGCTCTGCCCCAGGCTCTCCTGCAGGCAGCCCTACCTCCACCGAAGAGGGCAC |
| | | CAGCACAGAGCCTTCTGAGGGCAGCGCCCCAGGCACCTCTACAGAGCCAAGCGA |
| | | GCTCGAGTCCCGGCCAGGGGAACGGCCCTTCCAGTGTCGGATCTGCATGAGAAA |
| | | CTTTTCACGAGTCGATCACCTCCACCGCCACCTGCGAACCCACACTGGAGAGAA |
| | | ACCCTTTCAGTGCAGGATATGTATGCGGAATTTTTTCCAGGTCCGACCACCTCAG |
| | | CTTGCACTTGAAGACACATACCGGGGGAGGCGGTAGTCAGAAGCCTTTCCAATG |
| | | CCGGATTTGCATGAGGAACTTCTCCCAATCTAGTTCATTGGTACGACATCTTAG |
| | | GACACATACAGGCGAGAAGCCATTCCAGTGTAGGATCTGCATGCGCAATTTTAG |
| | | CCGAAAAGAGCGGCTGGCGACCCACTTGAAAACGCATACAGGTAGTCAGAAGCC |
| | | TTTTCAGTGCAGGATCTGCATGAGGAATTTTAGTGTAGCGCATAACTTGACACG |
| | | GCACTTGCGCACGCATACTGGAGAGAAGCCCTTTCAGTGTAGGATTTGTATGCG |
| | | GAACTTCAGCATTTCCCATAATCTGGCGCGGCACCTGAAGACTCATTTGCGCGG |
| | | GTCTAGCCCCAAGAAGAAGAGAAAGGTGGGAGTCGACGGATCCAGCGGCTCCGA |
| | | GACCCCCAGGCACATCTGAGAGCGCCACCCTGAGTCCCGGACCCTGGTGACATT |
| | | CAAGGACGTGTTCGTGGACTTCACCCGGGAGGAGTGGAAGCTGCTGGACACAGC |
| | | CCAGCAGATCGTGTACAGGAACGTGATGCTGGAGAACTATAAGAATCTGGTGTC |
| | | TCTGGGCTACCAGCTGACAAAGCCAGATGTGATCCTGCGGCTGGAGAAGGGAGA |
| | | GGAGCCCTGGCTGGTGTAGTCTAGAAATCAACCTCTGGATTACAAAATTTGTGA |
| | | AAGATTGACTGGTATTCTTAACTATGTTGCTCCTTTTACGCTATGTGGATACGC |

TABLE 18-continued

Sequence listing.

| SEQ | Description | Sequence |
|---|---|---|
| | | TGCTTTAATGCCTTTGTATCATGCTATTGCTTCCCGTATGGCTTTCATTTTCTC<br>CTCCTTGTATAAATCCTGGTTGCTGTCTCTTTATGAGGAGTTGTGGCCCGTTGT<br>CAGGCAACGTGGCGTGGTGTGCACTGTGTTTGCTGACGCAACCCCCACTGGTTG<br>GGGCATTGCCACCACCTGTCAGCTCCTTTCCGGGACTTTCGCTTTCCCCCTCCC<br>TATTGCCACGGCGGAACTCATCGCCGCCTGCCTTGCCCGCTGCTGGACAGGGGC<br>TCGGCTGTTGGGCACTGACAATTCCGTGGTGTTGTCGGGGAAATCATCGTCCTT<br>TCCTTGGCTGCTCGCCTGTGTTGCCACCTGGATTCTGCGCGGGACGTCCTTCTG<br>CTACGTCCCTTCGGCCCTCAATCCAGCGGACCTTCCTTCCCGCGGCCTGCTGCC<br>GGCTCTGCGGCCTCTTCCGCGTCTTCGCCTTCGCCCTCAGACGAGTCGGATCTC<br>CCTTTGGGCCGCCTCCCCGCCTGTTAATTAAAAAAAAAAAAAAAAAAAAAAAAA<br>AAAAAAAAAAAAAAAAAAAAAAAAAAAAACTAGTGGCGCCTGATGCGGTATTTTCT<br>CCTTACGCATCTGTGCGGTATTTCACACCGCATAATCCAGCACAGTGGCGGCCC<br>GTTTAAACCCGCTGATCAGCCTCGACTGTGCCTTCTAGTTGCCAGCCATCTGTT<br>GTTTGCCCCTCCCCCGTGCCTTCCTTGACCCTGGAAGGTGCCACTCCCACTGTC<br>CTTTCCTAATAAAATGAGGAAATTGCATCGCATTGTCTGAGTAGGTGTCATTCT<br>ATTCTGGGGGGTGGGGTGGGGCAGGACAGCAAGGGGGAGGATTGGGAAGACAAT<br>AGCAGGCATGCTGGGGATGCGGTGGGCTCTATGGCTTCTGAGGCGGAAAGAACC<br>AGCTGCATTAATGAATCGGCCAACGCGCGGGGAGAGGCGGTTTGCGTATTGGGC<br>GCTCTTCCGCTTCCTCGCTCACTGACTCGCTGCGCTCGGTCGTTCGGCTGCGGC<br>GAGCGGTATCAGCTCACTCAAAGGCGGTAATACGGTTATCCACAGAATCAGGGG<br>ATAACGCAGGAAAGAACATGTGAGCAAAAGGCCAGCAAAAGGCCAGGAACCGTA<br>AAAAGGCCGCGTTGCTGGCGTTTTTCCATAGGCTCCGCCCCCCTGACGAGCATC<br>ACAAAAATCGACGCTCAAGTCAGAGGTGGCGAAACCCGACAGGACTATAAAGAT<br>ACCAGGCGTTTCCCCCTGGAAGCTCCCTCGTGCGCTCTCCTGTTCCGACCCTGC<br>CGCTTACCGGATACCTGTCCGCCTTTCTCCCTTCGGGAAGCGTGGCGCTTTCTC<br>ATAGCTCACGCTGTAGGTATCTCAGTTCGGTGTAGGTCGTTCGCTCCAAGCTGG<br>GCTGTGTGCACGAACCCCCCGTTCAGCCCGACCGCTGCGCCTTATCCGGTAACT<br>ATCGTCTTGAGTCCAACCCGGTAAGACACGACTTATCGCCACTGGCAGCAGCCA<br>CTGGTAACAGGATTAGCAGAGCGAGGTATGTAGGCGGTGCTACAGAGTTCTTGA<br>AGTGGTGGCCTAACTACGGCTACACTAGAAGAACAGTATTTGGTATCTGCGCTC<br>TGCTGAAGCCAGTTACCTTCGGAAAAAGAGTTGGTAGCTCTTGATCCGGCAAAC<br>AAACCACCGCTGGTAGCGGTTTTTTTGTTTGCAAGCAGCAGATTACGCGCAGAA<br>AAAAAGGATCTCAAGAAGATCCTTTGATCTTTTCTACGGGGTCTGACGCTCAGT<br>GGAACGAAAACTCACGTTAAGGGATTTTGGTCATGAGATTATCAAAAAGGATCT<br>TCACCTAGATCCTTTTAAATTAAAAATGAAGTTTTAAATCAATCTAAAGTATAT<br>ATGAGTAAACTTGGTCTGACAGTTACCAATGCTTAATCAGTGAGGCACCTATCT<br>CAGCGATCTGTCTATTTCGTTCATCCATAGTTGCCTGACTCCCCGTCGTGTAGA<br>TAACTACGATACGGGAGGGCTTACCATCTGGCCCCAGTGCTGCAATGATACCGC<br>GAGACCCACGCTCACCGGCTCCAGATTTATCAGCAATAAACCAGCCAGCCGGAA<br>GGGCCGAGCGCAGAAGTGGTCCTGCAACTTTATCCGCCTCCATCCAGTCTATTA<br>ATTGTTGCCGGGAAGCTAGAGTAAGTAGTTCGCCAGTTAATAGTTTGCGCAACG<br>TTGTTGCCATTGCTACAGGCATCGTGGTGTCACGCTCGTCGTTTGGTATGGCTT<br>CATTCAGCTCCGGTTCCCAACGATCAAGGCGAGTTACATGATCCCCCATGTTGT<br>GCAAAAAAGCGGTTAGCTCCTTCGGTCCTCCGATCGTTGTCAGAAGTAAGTTGG<br>CCGCAGTGTTATCACTCATGGTTATGGCAGCACTGCATAATTCTCTTACTGTCA<br>TGCCATCCGTAAGATGCTTTTCTGTGACTGGTGAGTACTCAACCAAGTCATTCT<br>GAGAATAGTGTATGCGGCGACCGAGTTGCTCTTGCCCGGCGTCAATACGGGATA<br>ATACCGCGCCACATAGCAGAACTTTAAAAGTGCTCATCATTGGAAAACGTTCTT<br>CGGGGCGAAAACTCTCAAGGATCTTACCGCTGTTGAGATCCAGTTCGATGTAAC<br>CCACTCGTGCACCCAACTGATCTTCAGCATCTTTTACTTTCACCAGCGTTTCTG<br>GGTGAGCAAAAACAGGAAGGCAAAATGCCGCAAAAAAGGGAATAAGGGCGACAC<br>GGAAATGTTGAATACTCATACTCTTCCTTTTTCAATATTATTGAAGCATTTATC<br>AGGGTTATTGTCTCATGAGCGGATACATATTTGAATGTATTTAGAAAAATAAAC<br>AAATAGGGGTTCCGCGCACATTTCCCCGAAAAGTGCCACCTGA |
| 1246 | Plasmid for<br>expression of<br>CRISPR-Off<br>fusion protein (nt) | GGGCGCTCGAGCAGGTTCAGAAGGAGATCAAAAACCCCCAAGGATCAAACATGC<br>CAAAAAGAAGAGAAAGGTACCGAAGAAAAAAGAAAGGTATACAATCACGATC<br>AGGAGTTCGACCCCCCTAAGGTGTACCCACCAGTGCCTGCAGAGAAGAGGAAGC<br>CAATCCGGGTGCTGAGCCTGTTTGATGGCATCGCCACCGGCCTGCTGGTGCTGA<br>AGGATCTGGGCATCCAGGTGGACCGGTACATCGCCTCCGAGGTGTGCGAGGATT<br>CTATCACCGTGGGCATGGTGCGCCACCAGGGCAAGATCATGTATGTGGGCGACG<br>TGCGGTCCGTGACACAGAAGCACATCCAGGAGTGGGGCCCATTCGATCTGGTGA<br>TCGGCGGCAGCCCCTGTAATGACCTGTCCATCGTGAACCCTGCAAGGAAGGGAC<br>TGTACGAGGGAACCGGCCGGCTGTTCTTTGAGTTTTATAGACTGCTGCACGACG<br>CCAGGCCTAAGGAGGGCGACGATAGACCATTCTTTTGGCTGTTCGAGAATGTGG<br>TGGCTATGGGCGTGAGCGATAAGAGGGACATCTCCAGGTTTCTGGAGTCTAACC<br>CCGTGATGATCGATGCAAAGGAGGTGTCCGCCGCACACAGAGCCAGGTATTTCT<br>GGGGCAATCTGCTCAGGAATGAACAGGCCACTGGCAAGCACCGTGAATGACAAGC<br>TGGAGCTGCAGGAGTGCCTGGAGCACGGAAGGATCGCCAAGTTTTCCAAGGTGC<br>GCACAATCACCACACGGAGCAATTCCATCAAGCAGGGCAAGGATCAGCACTTCC<br>CCGTGTTCATGAACGAGAAGGAGGATCACTCTGTGGTGTACCAGATGGAGAGAG<br>TGTTCGGCTTTCCAGTGCACTACACAGACGTGTCTAACATGAGCAGGCTGGCAA<br>GGCAGCGGCTGCTGGGCAGATCTTGGAGCGTGCCCGTGATCAGGCACCTGTTCG<br>CCCCTCTGAAGGAGTATTTTGCCTGCGTGAGCAGCGGCAACTCCAATGCCAACA<br>GCCGGGGCCCCTCTTTCAGCTCCGGATTGGTGCCTCTGAGCCTGAGGGGCTCCC<br>ACATGGCAGCAATCCCCGCCCTGGACCCCGAGGCCGAGCCTAGCATGGACGTGA |

TABLE 18-continued

| Sequence listing. | | |
| --- | --- | --- |
| SEQ | Description | Sequence |
| | | TCCTGGTGGGCTCTAGCGAGCTGTCCTCTAGCGTGTCTCCAGGAACCGGAAGGG |
| | | ATCTGATCGCATACGAGGTGAAGGCCAATCAGCGGAACATCGAGGACATCTGTA |
| | | TCTGCTGTGGCAGCCTGCAGGTGCACACACAGCACCCACTGTTCGAGGGAGGAA |
| | | TCTGCGCACCCTGTAAGGATAAGTTCCTGGACGCCCTGTTTCTGTACGACGATG |
| | | ACGGCTACCAGTCCTATTGCTCTATCTGCTGTTCCGGCGAGACCCTGCTGATCT |
| | | GCGGCAATCCAGATTGTACAAGGTGCTATTGTTTTGAGTGCGTGGACTCTCTGG |
| | | TGGGACCAGGCACCAGCGGAAAGGTGCACGCCATGTCCAACTGGGTGTGCTACC |
| | | TGTGCCTGCCATCCTCTCGCAGCGGACTGCTGCAGCGGAGAAGGAAGTGGAGAT |
| | | CCCAGCTGAAGGCCTTCTATGATAGGGAGTCTGAGAACCCCCTGGAGATGTTTG |
| | | AGACCGTGCCAGTGTGGCGCCGGCAGCCCGTGAGGGTGCTGAGCCTGTTCGAGG |
| | | ATATCAAGAAGGAGCTGACATCCCTGGGCTTTCTGGAGTCCGGCTCTGACCCCG |
| | | GACAGCTGAAGCACGTGGTGGATGTGACCGACACAGTGCGGAAGGATGTGGAGG |
| | | AGTGGGGCCCTTTCGACCTGGTGTACGGAGCAACCCCTCCACTGGGACACACAT |
| | | GCGACAGACCCCCTTCTTGGTACCTGTTCCAGTTTCACCGCCTGCTGCAGTATG |
| | | CAAGGCCAAAGCCAGGCAGCCCTAGACCATTCTTTTGGATGTTCGTGGATAATC |
| | | TGGTGCTGAACAAGGAGGATCTGGACGTGGCCAGCAGGTTTCTGGAGATGGAGC |
| | | CAGTGACCATCCCAGACGTGCACGGCGGCTCCCTGCAGAATGCCGTGCGCGTGT |
| | | GGTCTAACATCCCTGCCATCAGAAGCAGGCACTGGGCACTGGTGAGCGAGGAGG |
| | | AGCTGTCCCTGCTGGCCCAGAATAAGCAGAGCAGCAAGCTGGCCGCCAAGTGGC |
| | | CTACAAAGCTGGTGAAGAACTGCTTCCTGCCACTGCGGGAGTACTTCAAGTATT |
| | | TTTCCACCGAGCTGACATCTAGCCTGGGGAGGACCCTCCTCTIGGCGCCCCACCAC |
| | | CTAGCGGCGGCTCCCCTGCCGGCTCTCCAACCAGCACAGAGGAGGGCACCAGCG |
| | | AGTCCGCCACACCAGAGTCTGGACCTGGCACCAGCACAGAGCCATCCGAGGGCT |
| | | CTGCCCCAGGCTCTCCTGCAGGCAGCCCTACCTCCACCGAAGAGGGCACCAGCA |
| | | CAGAGCCTTCTGAGGGCAGCGCCCCAGGCACCTCTACAGAGCCAAGCGAGCTCG |
| | | AGGACAAGAAGTACAGCATCGGCCTGGCCATCGGCACCAACTCTGTGGGCTGGG |
| | | CCGTGATCACCGACGAGTACAAGGTGCCCAGCAAGAAATTCAAGGTGCTGGGCA |
| | | ACACCGACCGGCACAGCATCAAGAAGAACCTGATCGGAGCCCTGCTGTTCGACA |
| | | GCGGCGAAACAGCCGAGGCCACCCGGCTGAAGAGAACCGCCAGAAGAAGATACA |
| | | CCAGACGGAAGAACCGGATCTGCTATCTGCAAGAGATCTTCAGCAACGAGATGG |
| | | CCAAGGTGGACGACAGCTTCTTCCACAGACTGGAAGAGTCCTTCCTGGTGGAAG |
| | | AGGATAAGAAGCACGAGCGGCACCCCATCTTCGGCAACATCGTGGACGAGGTGG |
| | | CCTACCACGAGAAGTACCCCACCATCTACCACCTGAGAAAGAAACTGGTGGACA |
| | | GCACCGACAAGGCCGACCTGCGGCTGATCTATCTGGCCCTGGCCCACATGATCA |
| | | AGTTCCGGGGCCACTTCCTGATCGAGGGCGACCTGAACCCCGACAACAGCGACG |
| | | TGGACAAGCTGTTCATCCAGCTGGTGCAGACCTACAACCAGCTGTTCGAGGAAA |
| | | ACCCCATCAACGCCAGCGGCGTGGACGCCAAGGCCATCCTGTCTGCCAGACTGA |
| | | GCAAGAGCAGACGGCTGGAAAATCTGATCGCCCAGCTGCCCGGCGAGAAGAAGA |
| | | ATGGCCTGTTCGGCAACCTGATTGCCCTGAGCCTGGGCCTGACCCCCCAACTTCA |
| | | AGAGCAACTTCGACCTGGCCGAGGATGCCAAACTGCAGCTGAGCAAGGACACCT |
| | | ACGACGACGACCTGGACAACCTGCTGGCCCAGATCGGCGACCAGTACGCCGACC |
| | | TGTTTCTGGCCGCCAAGAACCTGTCCGACGCCATCCTGCTGAGCGACATCCTGA |
| | | GAGTGAACACCGAGATCACCAAGGCCCCCCTGAGCGCCTCTATGATCAAGAGAT |
| | | ACGACGAGCACCACCAGGACCTGACCCTGCTGAAAGCTCTCGTGCGGCAGCAGC |
| | | TGCCTGAGAAGTACAAAGAGATTTTCTTCGACCAGAGCAAGAACGGCTACGCCG |
| | | GCTACATTGACGGCGGAGCCAGCCAGGAAGAGTTCTACAAGTTCATCAAGCCCA |
| | | TCCTGGAAAAGATGGACGGCACCGAGGAACTGCTCGTGAAGCTGAACAGAGAGG |
| | | ACCTGCTGCGGAAGCAGCGGACCTTCGACAACGGCAGCATCCCCCCACCAGATCC |
| | | ACCTGGGAGAGCTGCACGCCATTCTGCGGCGGCAGGAAGATTTTTACCCATTCC |
| | | TGAAGGACAACCGGGAAAAGATCGAGAAGATCCTGACCTTCCGCATCCCCTACT |
| | | ACGTGGGCCCTCTGGCCAGGGGAAACAGCAGATTCGCCTGGATGACCAGAAAGA |
| | | GCGAGGAAACCATCACCCCCTGGAACTTCGAGGAAGTGGTGGACAAGGGCGCTT |
| | | CCGCCCAGAGCTTCATCGAGCGGATGACCAACTTCGATAAGAACCTGCCCAACG |
| | | AGAAGGTGCTGCCCAAGCACAGCCTGCTGTACGAGTACTTCACCGTGTATAACG |
| | | AGCTGACCAAAGTGAAATACGTGACCGAGGGAATGAGAAAGCCCGCCTTCCTGA |
| | | GCGGCGAGCAGAAAAAGGCCATCGTGGACCTGCTGTTCAAGACCAACCGGAAAG |
| | | TGACCGTGAAGCAGCTGAAAGAGGACTACTTCAAGAAAATCGAGTGCTTCGACT |
| | | CCGTGGAAATCTCCGGCGTGGAAGATCGGTTCAACGCCTCCCTGGGCACATACC |
| | | ACGATCTGCTGAAAATTATCAAGGACAAGGACTTCCTGGACAATGAGGAAAACG |
| | | AGGACATTCTGGAAGATATCGTGCTGACCCTGACACTGTTTGAGGACAGAGAGA |
| | | TGATCGAGGAACGGCTGAAAACCTATGCCCACCTGTTCGACGACAAAGTGATGA |
| | | AGCAGCTGAAGCGGCGGAGATACACCGGCTGGGGCAGGCTGAGCCGGAAGCTGA |
| | | TCAACGGCATCCGGGACAAGCAGTCCGGCAAGACAATCCTGGATTTCCTGAAGT |
| | | CCGACGGCTTCGCCAACAGAAACTTCATGCAGCTGATCCACGACGACAGCCTGA |
| | | CCTTTAAAGAGGACATCCAGAAAGCCCAGGTGTCCGGCCAGGGCGATAGCCTGC |
| | | ACGAGCACATTGCCAATCTGGCCGGCAGCCCCGCCATTAAGAAGGGCATCCTGC |
| | | AGACAGTGAAGGTGGTGGACGAGCTCGTGAAAGTGATGGGCCGGCACAAGCCCG |
| | | AGAACATCGTGATCGAAATGGCCAGAGAGAACCAGACCACCCAGAAGGGACAGA. |
| | | AGAACAGCCGCGAGAGAATGAAGCGGATCGAAGAGGGCATCAAAGAGCTGGGCA |
| | | GCCAGATCCTGAAAGAACACCCCGTGGAAAACACCCAGCTGCAGAACGAGAAGC |
| | | TGTACCTGTACTACCTGCAGAATGGGCGGGATATGTACGTGGACCAGGAACTGGA |
| | | ACATCAACCGGCTGTCCGACTACGATGTGGACGCCATCGTGCCTCAGAGCTTTC |
| | | TGAAGGACGACTCCATCGACAACAAGGTGCTGACCAGAAGCGACAAGAACCGGG |
| | | GCAAGAGCGACAACGTGCCCTCCGAAGAGGTCGTGAAGAAGATGAAGAACTACT |
| | | GGCGGCAGCTGCTGAACGCCAAGCTGATTACCCAGAGAAAGTTCGACAATCTGA |
| | | CCAAGGCCGAGAGAGGCGGCCTGAGCGAACTGGATAAGGCCGGCTTCATCAAGA |

TABLE 18-continued

| Sequence listing. | | |
| --- | --- | --- |
| SEQ | Description | Sequence |
| | | GACAGCTGGTGGAAACCCGGCAGATCACAAAGCACGTGGCACAGATCCTGGACT |
| | | CCCGGATGAACACTAAGTACGACGAGAATGACAAGCTGATCCGGGAAGTGAAAG |
| | | TGATCACCCTGAAGTCCAAGCTGGTGTCCGATTTCCGGAAGGATTTCCAGTTTT |
| | | ACAAAGTGCGCGAGATCAACAACTACCACCACGCCCACGACGCCTACCTGAACG |
| | | CCGTCGTGGGAACCGCCCTGATCAAAAAGTACCCTAAGCTGGAAAGCGAGTTCG |
| | | TGTACGGCGACTACAAGGTGTACGACGTGCGGAAGATGATCGCCAAGAGCGAGC |
| | | AGGAAATCGGCAAGGCTACCGCCAAGTACTTCTTCTACAGCAACATCATGAACT |
| | | TTTTCAAGACCGAGATTACCCTGGCCAACGGCGAGATCCGGAAGCGGCCTCTGA |
| | | TCGAGACAAACGGCGAAACCGGGGAGATCGTGTGGGATAAGGGCCGGGATTTTG |
| | | CCACCGTGCGGAAAGTGCTGAGCATGCCCCAAGTGAATATCGTGAAAAAGACCG |
| | | AGGTGCAGACAGGCGGCTTCAGCAAAGAGTCTATCCTGCCCAAGAGGAACAGCG |
| | | ATAAGCTGATCGCCAGAAAGAAGGACTGGGACCCTAAGAAGTACGGCGGCTTCG |
| | | ACAGCCCCACCGTGGCCTATTCTGTGCTGGTGGTGGCCAAAGTGGAAAAGGGCA |
| | | AGTCCAAGAAACTGAAGAGTGTGAAAGAGCTGCTGGGGATCACCATCATGGAAA |
| | | GAAGCAGCTTCGAGAAGAATCCCATCGACTTTCTGGAAGCCAAGGGCTACAAAG |
| | | AAGTGAAAAAGGACCTGATCATCAAGCTGCCTAAGTACTCCCTGTTCGAGCTGG |
| | | AAAACGGCCGGAAGAGAATGCTGGCCTCTGCCGGCGAACTGCAGAAGGGAAACG |
| | | AACTGGCCCTGCCCTCCAAATATGTGAACTTCCTGTACCTGGCCAGCCACTATG |
| | | AGAAGCTGAAGGGCTCCCCCGAGGATAATGAGCAGAAACAGCTGTTTGTGGAAC |
| | | AGCACAAGCACTACCTGGACGAGATCATCGAGCAGATCAGCGAGTTCTCCAAGA |
| | | GAGTGATCCTGGCCGACGCTAATCTGGACAAAGTGCTGTCCGCCTACAACAAGC |
| | | ACCGGGATAAGCCCATCAGAGAGCAGGCCGAGAATATCATCCACCTGTTTACCC |
| | | TGACCAATCTGGGAGCCCCTGCCGCCTTCAAGTACTTTGACACCACCATCGACC |
| | | GGAAGAGGTACACCAGCACCAAAGAGGTGCTGGACGCCACCCTGATCCACCAGA |
| | | GCATCACCGGCCTGTACGAGACACGGATCGACCTGTCTCAGCTGGGAGGCGACA |
| | | GCCCCAAGAAGAAGAGAAAGGTGGGAGTCGACGGATCCAGCGGCTCCGAGACCC |
| | | CAGGCACATCTGAGAGCGCCACCCCTGAGTCCACCGGTATGAACAATTCACAGG |
| | | GGAGAGTGACATTCGAAGACGTGACCGTGAACTTCACCCAGGGAGAATGGCAGC |
| | | GCTTGAACCCAGAACAAAGGAACCTCTATCGGGACGTGATGCTGGAAAACTACT |
| | | CAAATTTGGTGAGCGTTGGGCAGGGTGAGACCACTAAGCCTGACGTGATCCTGA |
| | | GATTGGAACAGGGCAAGGAGCCTTGGCTCGAGGAAGAGGAAGTCCTGGGCTCAG |
| | | GGAGGGCCGAGAAAAACGGTGATATAGGAGGCCAGATATGGAAGCCTAAGGACG |
| | | TCAAGGAGAGCCTGAGCGCTCCCAAGAAGAAAAGGAAGGTCCCAAAGAAAAAAA |
| | | GAAAGGTGTGAGGATCCTGAGTCTAGAAATCAACCTCTGGATTACAAAATTTGT |
| | | GAAAGATTGACTGGTATTCTTAACTATGTTGCTCCTTTTACGCTATGTGGATAC |
| | | GCTGCTTTAATGCCTTTGTATCATGCTATTGCTTCCCGTATGGCTTTCATTTTC |
| | | TCCTCCTTGTATAAATCCTGGTTGCTGTGTCTCTTTATGAGGAGTTGTGGCCCGTT |
| | | GTCAGGCAACGTGGCGTGGTGTGCACTGTGTTTGCTGACGCAACCCCCACTGGT |
| | | TGGGGCATTGCCACCACCTGTCAGCTCCTTTCCGGGACTTTCGCTTTCCCCCTC |
| | | CCTATTGCCACGGCGGAACTCATCGCCGCCTGCCTTGCCCGCTGCTGGACAGGG |
| | | GCTCGGCTGTTGGGCACTGACAATTCCGTGGTGTTGTCGGGGAAATCATCGTCC |
| | | TTTCCTTGGCTGCTCGCCTGTGTTGCCACCTGGATTCTGCGCGGGACGTCCTTC |
| | | TGCTACGTCCCTTCGGCCCTCAATCCAGCGGACCTTCCTTCCCGCGGCCTGCTG |
| | | CCGGCTCTGCGGCCTCTTCCGCGTCTTCGCCTTCGCCCTCAGACGAGTCGGATC |
| | | TCCCTTTGGGCCGCCTCCCCGCCTGTTAATTAAAAAAAAAAAAAAAAAAAAAAAA |
| | | AAAAAAAAAAAAAAAAAAAAAAAAAAAAAAAAAAAAAAAAAAAAAAAAAAAAAAA |
| | | AAAAAAAAAAAAAAAAAAAAAAAAAAGCTTGAAGAGCCTAGTGGCGCCTGATGCGG |
| | | TATTTTCTCCTTACGCATCTGTGCGGTATTTCACACCGCATAATCCAGCACAGT |
| | | GGCGGCCCGTTTAAACCCGCTGATCAGCCTCGACTGTGCCTTCTAGTTGCCAGC |
| | | CATCTGTTGTTTGCCCCTCCCCCGTGCCTTCCTTGACCCTGGAAGGTGCCACTC |
| | | CCACTGTCCTTTCCTAATAAAATGAGGAAATTGCATCGCATTGTCTGAGTAGGT |
| | | GTCATTCTATTCTGGGGGGTGGGGTGGGGCAGGACAGCAAGGGGGAGGATTGGG |
| | | AAGACAATAGCAGGCATGCTGGGGATGCGGTGGGCTCTATGGCTTCTGAGGCGG |
| | | AAAGAACCAGCTGCATTAATGAATCGGCCAACGCGCGGGGAGAGGCGGTTTGCG |
| | | TATTGGGCGCTCTTCCGCTTCCTCGCTCACTGACTCGCTGCGCTCGGTCGTTCG |
| | | GCTGCGGCGAGCGGTATCAGCTCACTCAAAGGCGGTAATACGGTTATCCACAGA |
| | | ATCAGGGGATAACGCAGGAAAGAACATGTGAGCAAAAGGCCAGCAAAAGGCCAG |
| | | GAACCGTAAAAAGGCCGCGTTGCTGGCGTTTTTCCATAGGCTCCGCCCCCCTGA |
| | | CGAGCATCACAAAAATCGACGCTCAAGTCAGAGGTGGCGAAACCCGACAGGACT |
| | | ATAAAGATACCAGGCGTTTCCCCCTGGAAGCTCCCTCGTGCGCTCTCCTGTTCC |
| | | GACCCTGCCGCTTACCGGATACCTGTCCGCCTTTCTCCCTTCGGGAAGCGTGGC |
| | | GCTTTCTCATAGCTCACGCTGTAGGTATCTCAGTTCGGTGTAGGTCGTTCGCTC |
| | | CAAGCTGGGCTGTGTGCACGAACCCCCCGTTCAGCCCGACCGCTGCGCCTTATC |
| | | CGGTAACTATCGTCTTGAGTCCAACCCGGTAAGACACGACTTATCGCCACTGGC |
| | | AGCAGCCACTGGTAACAGGATTAGCAGAGCGAGGTATGTAGGCGGTGCTACAGA |
| | | GTTCTTGAAGTGGTGGCCTAACTACGGCTACACTAGAAGAACAGTATTTGGTAT |
| | | CTGCGCTCTGCTGAAGCCAGTTACCTTCGGAAAAAGAGTTGGTAGCTCTTGATC |
| | | CGGCAAACAAACCACCGCTGGTAGCGGTGGTTTTTTTGTTTGCAAGCAGCAGAT |
| | | TACGCGCAGAAAAAAAGGATCTCAAGAAGATCCTTTGATCTTTTCTACGGGGTC |
| | | TGACGCTCAGTGGAACGAAAACTCACGTTAAGGGATTTTGGTCATGAGATTATC |
| | | AAAAAGGATCTTCACCTAGATCCTTTTAAATTAAAAATGAAGTTTTAAATCAAT |
| | | CTAAAGTATATATGAGTAAACTTGGTCTGACAGTTAGAAAAACTCATCGAGCAT |
| | | CAAATGAAACTGCAATTTATTCATATCAGGATTATCAATACCATATTTTTGAAA |
| | | AAGCCGTTTCTGTAATGAAGGAGAAAACTCACCGAGGCAGTTCCATAGGATGGC |
| | | AAGATCCTGGTATCGGTCTGCGATTCCGACTCGTCCAACATCAATACAACCTAT |
| | | TAATTTCCCCTCGTCAAAAATAAGGTTATCAAGTGAGAAATCACCATGAGTGAC |

TABLE 18-continued

| Sequence listing. | | |
|---|---|---|
| SEQ | Description | Sequence |
| | | GACTGAATCCGGTGAGAATGGCAAAAGTTTATGCATTTCTTTCCAGACTTGTTC<br>AACAGGCCAGCCATTACGCTCGTCATCAAAATCACTCGCATCAACCAAACCGTT<br>ATTCATTCGTGATTGCGCCTGAGCGAAACGAAATACGCGATCGCTGTTAAAAGG<br>ACAATTACAAACAGGAATCGAATGCAACCGGCGCAGGAACACTGCCAGCGCATC<br>AACAATATTTTCACCTGAATCAGGATATTCTTCTAATACCTGGAATGCTGTTTT<br>CCCAGGGATCGCAGTGGTGAGTAACCATGCATCATCAGGAGTACGGATAAAATG<br>CTTGATGGTCGGAAGAGGCATAAATTCCGTCAGCCAGTTTAGTCTGACCATCTC<br>ATCTGTAACATCATTGGCAACGCTACCTTTGCCATGTTTCAGAAACAACTCTGG<br>CGCATCGGGCTTCCCATACAATCGATAGATTGTCGCACCTGATTGCCCGACATT<br>ATCGCGAGCCCATTTATACCCATATAAATCAGCATCCATGTTGGAATTTAATCG<br>CGGCCTAGAGCAAGACGTTTCCCGTTGAATATGGCTCATACTCTTCCTTTTTCA<br>ATATTATTGAAGCATTTATCAGGGTTATTGTCTCATGAGCGGATACATATTTGA<br>ATGTATTTAGAAAAATAAACAAATAGGGGTTCCGCGCACATTTCCCCGAAAAGT<br>GCCACCTGACGTCGATCGACGGATCGGGAGATCTCCCGATCCCCTATGGTGCAC<br>TCTCAGTACAATCTGCTCTGATGCCGCATAGTTAAGCCAGTATCTGCTCCCTGC<br>TTGTGTGTTGGAGGTCGCTGAGTAGTGCGCGAGCAAAATTTAAGCTACAACAAG<br>GCAAGGCTTGACCGACAATTGCATGAAGAATCTGCTTAGGGTTAGGCGTTTTGC<br>GCTGCTTCGCGATGTACGGGCCAGATATACGCGTTGACATTGATTATTGACTAG<br>TTATTAATAGTAATCAATTACGGGGTCATTAGTTCATAGCCCATATATGGAGTT<br>CCGCGTTACATAACTTACGGTAAATGGCCCGCCTGGCTGACCGCCCAACGACCC<br>CCGCCCATTGACGTCAATAATGACGTATGTTCCCATAGTAACGCCAATAGGGAC<br>TTTCCATTGACGTCAATGGGTGGAGTATTTACGGTAAACTGCCCACTTGGCAGT<br>ACATCAAGTGTATCATATGCCAAGTACGCCCCCTATTGACGTCAATGACGGTAA<br>ATGGCCCGCCTGGCATTATGCCCAGTACATGACCTTATGGGACTTTCCTACTTG<br>GCAGTACATCTACGTATTAGTCATCGCTATTACCATGGTGATGCGGTTTTGGCA<br>GTACATCAATGGGCGTGGATAGCGGTTTGACTCACGGGGATTTCCAAGTCTCCA<br>CCCCATTGACGTCAATGGGAGTTTGTTTTGGCACCAAAATCAACGGGACTTTCC<br>AAAATGTCGTAACAACTCCGCCCCATTGACGCAAATGGGGGGTAGGCGTGTACG<br>GTGGGAGGTCTATATAAGCAGAGCTCTCTGGCTAACTAGAGAACCCACTGCTTA<br>CTGGCTTATCGAAATTAATACGACTCACTATAAG |
| 1247 | Coding region of<br>plasmid for<br>expression of<br>CRISPR-Off<br>fusion protein (nt) | ATGCCAAAAAGAAGAGAAAGGTACCGAAGAAAAAAAGAAAGGTATACAATCAC<br>GATCAGGAGTTCGACCCCCCCTAAGGTGTACCCACCAGTGCCTGCAGAGAAGAGG<br>AAGCCAATCCGGGTGCTGAGCCTGTTTGATGGCATCGCCACCGGCCTGCTGGTG<br>CTGAAGGATCTGGGCATCCAGGTGGACCGGTACATCGCCTCCGAGGTGTGCGAG<br>GATTCTATCACCGTGGGCATGGTGCGCCACCAGGGCAAGATCATGTATGTGGGC<br>GACGTGCGGTCCGTGACACAGAAGCACATCCAGGAGTGGGGCCCATTCGATCTG<br>GTGATCGGCGGCAGCCCCTGTAATGACCTGTCCATCGTGAACCCTGCAAGGAAG<br>GGACTGTACGAGGGAACCGGCCGGCTGTTCTTTGAGTTTTATAGACTGCTGCAC<br>GACGCCAGGCCTAAGGAGGGCGACGATAGACCATTCTTTTGGCTGTTCGAGAAT<br>GTGGTGGCTATGGGCGTGAGCGATAAGAGGGACATCTCCAGGTTTCTGGAGTCT<br>AACCCCGTGATGATCGATGCAAAGGAGGTGTCCGCCGCACACAGAGCCAGGTAT<br>TTCTGGGGCAATCTGCCCAGGAATGAACAGGCCACTGGCAAGCACCGTGAATGAC<br>AAGCTGGAGCTGCAGGAGTGCCTGGAGCACGGAAGGATCGCCAAGTTTTCCAAG<br>GTGCGCACAATCACCACACGGAGCAATTCCATCAAGCAGGGCAAGGATCAGCAC<br>TTCCCCGTGTTCATGAACGAGAAGGAGGACATCCTGTGGTGTACCGAGATGGAG<br>AGAGTGTTCGGCTTTCCAGTGCACTACACAGACGTGTCTAACATGAGCAGGCTG<br>GCAAGGCAGCGGCTGCTGGGCAGATCTTGGAGCGTGCCCGTGATCAGGCACCTG<br>TTCGCCCCTCTGAAGGAGTATTTTGCCTGCGTGAGCAGCGGCAACTCCAATGCC<br>AACAGCCGGGGCCCCTCTTTCAGCTCCGGATTGGTGCCTCTGAGCCTGAGGGGC<br>TCCCACATGGCAGCAATCCCCGCCCTGGACCCCGAGGCCGAGCCTAGCATGGAC<br>GTGATCCTGGTGGGCTCTAGCGAGCTGTCCTCTAGCGTGTCTCCAGGAACCGGA<br>AGGGATCTGATCGCATACGAGGTGAAGGCCAATCAGCGGAACATCGAGGACATC<br>TGTATCTGCTGTGTGGCAGCCTGCAGGTGCACACACAGCACCCACTGTTCGAGGGA<br>GGAATCTGCGCACCCTGTAAGGATAAGTTCCTGGACGCCCTGTTTCTGTACGAC<br>GATGACGGCTACCAGTCCTATTGCTCTATCTGCTGTTCCGGCGAGACCCTGCTG<br>ATCTGCGGCAATCCAGATTGTACAAGGTGCTATTGTTTTGAGTGCGTGGACTCT<br>CTGGTGGGACCAGGCACCAGCGGAAAGGTGCACGCCATGTCCAACTGGGTGTGC<br>TACCTGTGCTGCCATCCTCTCGCAGCGGACTGCTGCAGCGGAGAAGGAAGTGG<br>AGATCCCAGCTGAAGGCCTTCTATGATAGGGAGTCTGAGAACCCCCTGGAGATG<br>TTTGAGACCGTGCCAGTGTGGCGCCGGCAGCCCGTGAGGGTGCTGAGCCTGTTC<br>GAGGATATCAAGAAGGAGCTGACATCCCTGGGCTTTCTGGAGTCCGGCTCTGAC<br>CCCGGACAGCTGAAGCACGTGGTGGATGTGACCGACACAGTGCGGAAGGATGTG<br>GAGGAGTGGGGCCCTTTCGACCTGGTGTACGGAGCAACCCCTCCACTGGGACAC<br>ACATGCGACAGACCCCCTTCTTGGTACCTGTTCCAGTTTCACCGCCTGCTGCAG<br>TATGCAAGGCCAAAGCCAGGCAGCCCTAGACCATTCTTTTGGATGTTCGTGGAT<br>AATCTGGTGCTGAACAAGGAGGATCTGGACGTGGCCAGCAGGTTTCTGGAGATG<br>GAGCCAGTGACCATCCCAGACGTGCACGGCGGCTCCCTGCAGAATGCCGTGCGC<br>GTGTGGTCTAACATCCCTGCCATCAGAAGCAGGCACTGGGCACTGGTGAGCGAG<br>GAGGAGCTGTCCCTGCTGGCCCAGAATAAGCAGAGCAGCAAGCTGGCCGCCAAG<br>TGGCCTACAAAGCTGGTGAAGAACTGCTTCCTGCCACTGCGGGAGTACTTCAAG<br>TATTTTTCCACCGAGCTGACATCTAGCCTGGGAGGACCCTCCTCTGGCGCCCCA<br>CCACCTAGCGGCGGCTCCCCTGCCGGCTCTCCAACCAGCACAGAGGAGGGCACC<br>AGCGAGTCCGCCACACCAGAGTCTGGACCTGGCACCAGCACAGAGCCATCCGAG<br>GGCTCTGCCCCAGGCTCTCCTGCAGGCAGCCCTACCTCCACCGAAGAGGGCACC<br>AGCACAGAGCCTTCTGAGGGCAGCGCCCCAGGCACCTCTACAGAGCCAAGCGAG |

TABLE 18-continued

Sequence listing.

| SEQ | Description | Sequence |
|---|---|---|
| | | CTCGAGGACAAGAAGTACAGCATCGGCCTGGCCATCGGCACCAACTCTGTGGGC |
| | | TGGGCCGTGATCACCGACGAGTACAAGGTGCCCAGCAAGAAATTCAAGGTGCTG |
| | | GGCAACACCGACCGGCACAGCATCAAGAAGAACCTGATCGGAGCCCTGCTGTTC |
| | | GACAGCGGCGAAACAGCCGAGGCCACCCGGCTGAAGAGAACCGCCAGAAGAAGA |
| | | TACACCAGACGGAAGAACCGGATCTGCTATCTGCAAGAGATCTTCAGCAACGAG |
| | | ATGGCCAAGGTGGACGACAGCTTCTTCCACAGACTGGAAGAGTCCTTCCTGGTG |
| | | GAAGAGGATAAGAAGCACGAGCGGCACCCCATCTTCGGCAACATCGTGGACGAG |
| | | GTGGCCTACCACGAGAAGTACCCCACCATCTACCACCTGAGAAAGAAACTGGTG |
| | | GACAGCACCGACAAGGCCGACCTGCGGCTGATCTATCTGGCCCTGGCCCACATG |
| | | ATCAAGTTCCGGGGCCACTTCCTGATCGAGGGCGACCTGAACCCCGACAACAGC |
| | | GACGTGGACAAGCTGTTCATCCAGCTGGTGCAGACCTACAACCAGCTGTTCGAG |
| | | GAAAACCCCATCAACGCCAGCGGCGTGGACGCCAAGGCCATCCTGTCTGCCAGA |
| | | CTGAGCAAGAGCAGACGGCTGGAAAATCTGATCGCCCAGCTGCCCGGCGAGAAG |
| | | AAGAATGGCCTGTTCGGCAACCTGATTGCCCTGAGCCTGGGCCTGACCCCCAAC |
| | | TTCAAGAGCAACTTCGACCTGGCCGAGGATGCCAAACTGCAGCTGAGCAAGGAC |
| | | ACCTACGACGACGACCTGGACAACCTGCTGGCCCAGATCGGCGACCAGTACGCC |
| | | GACCTGTTTCTGGCCGCCAAGAACCTGTCCGACGCCATCCTGCTGAGCGACATC |
| | | CTGAGAGTGAACACCGAGATCACCAAGGCCCCCCTGAGCGCCTCTATGATCAAG |
| | | AGATACGACGAGCACCACCAGGACCTGACCCTGCTGAAAGCTCTCGTGCGGCAG |
| | | CAGCTGCCTGAGAAGTACAAAGAGATTTTCTTCGACCAGAGCAAGAACGGCTAC |
| | | GCCGGCTACATTGACGGCGGAGCCAGCCAGGAAGAGTTCTACAAGTTCATCAAG |
| | | CCCATCCTGGAAAAGATGGACGGCACCGAGGAACTGCTCGTGAAGCTGAACAGA |
| | | GAGGACCTGCTGCGGAAGCAGCGGACCTTCGACAACGGCAGCATCCCCCACCAG |
| | | ATCCACCTGGGAGAGCTGCACGCCATTCTGCGGCGGCAGGAAGATTTTTACCCA |
| | | TTCCTGAAGGACAACCGGGAAAAGATCGAGAAGATCCTGACCTTCCGCATCCCC |
| | | TACTACGTGGGCCCTCTGGCCAGGGGAAACAGCAGATTCGCCTGGATGACCAGA |
| | | AAGAGCGAGGAAACCATCACCCCCTGGAACTTCGAGGAAGTGGTGGACAAGGGC |
| | | GCTTCCGCCCAGAGCTTCATCGAGCGGATGACCAACTTCGATAAGAACCTGCCC |
| | | AACGAGAAGGTGCTGCCCAAGCACAGCCTGCTGTACGAGTACTTCACCGTGTAT |
| | | AACGAGCTGACCAAAGTGAAATACGTGACCGAGGGAATGAGAAAGCCCGCCTTC |
| | | CTGAGCGGCGAGCAGAAAAAGGCCATCGTGGACCTGCTGTTCAAGACCAACCGG |
| | | AAAGTGACCGTGAAGCAGCTGAAAGAGGACTACTTCAAGAAAATCGAGTGCTTC |
| | | GACTCCGTGGAAATCTCCGGCGTGGAAGATCGGTTCAACGCCTCCCTGGGCACA |
| | | TACCACGATCTGCTGAAAATTATCAAGGACAAGGACTTCCTGGACAATGAGGAA |
| | | AACGAGGACATTCTGGAAGATATCGTGCTGACCCTGACACTGTTTGAGGACAGA |
| | | GAGATGATCGAGGAACGGCTGAAAACCTATGCCCACCTGTTCGACGACAAAGTG |
| | | ATGAAGCAGCTGAAGCGGCGGAGATACACCGGCTGGGGCAGGCTGAGCCGGAAG |
| | | CTGATCAACGGCATCCGGGACAAGCAGTCCGGCAAGACAATCCTGGATTTCCTG |
| | | AAGTCCGACGGCTTCGCCAACAGAAACTTCATGCAGCTGATCCACGACGACAGC |
| | | CTGACCTTTAAAGAGGACATCCAGAAAGCCCAGGTGTCCGGCCAGGGCGATAGC |
| | | CTGCACGAGCACATTGCCAATCTGGCCGGCAGCCCCGCCATTAAGAAGGGCATC |
| | | CTGCAGACAGTGAAGGTGGTGGACGAGCTCGTGAAAGTGATGGGCCGGCACAAG |
| | | CCCGAGAACATCGTGATCGAAATGGCCAGAGAGAACCAGACCACCCAGAAGGGA |
| | | CAGAAGAACAGCCGCGAGAGAATGAAGCGGATCGAAGAGGGCATCAAAGAGCTG |
| | | GGCAGCCAGATCCTGAAAGAACACCCCGTGGAAAACACCCAGCTGCAGAACGAG |
| | | AAGCTGTACCTGTACTACCTGCAGAATGGGCGGGATATGTACGTGGACCAGGAA |
| | | CTGGACATCAACCGGCTGTCCGACTACGATGTGGACGCCATCGTGCCTCAGAGC |
| | | TTTCTGAAGGACGACTCCATCGACAACAAGGTGCTGACCAGAAGCGACAAGAAC |
| | | CGGGGCAAGAGCGACAACGTGCCCTCCGAAGAGGTCGTGAAGAAGATGAAGAAC |
| | | TACTGGCGGCAGCTGCTGAACGCCAAGCTGATTACCCAGAGAAAGTTCGACAAT |
| | | CTGACCAAGGCCGAGAGAGGCGGCCTGAGCGAACTGGATAAGGCCGGCTTCATC |
| | | AAGAGACAGCTGGTGGAAACCCGGCAGATCACAAAGCACGTGGCACAGATCCTG |
| | | GACTCCCGGATGAACACTAAGTACGACGAGAATGACAAGCTGATCCGGGAAGTG |
| | | AAAGTGATCACCCTGAAGTCCAAGCTGGTGTCCGATTTCCGGAAGGATTTCCAG |
| | | TTTTACAAAGTGCGCGAGATCAACAACTACCACCACGCCCACGACGCCTACCTG |
| | | AACGCCGTCGTGGGAACCGCCCTGATCAAAAAGTACCCTAAGCTGGAAAGCGAG |
| | | TTCGTGTACGGCGACTACAAGGTGTACGACGTGCGGAAGATGATCGCCAAGAGC |
| | | GAGCAGGAAATCGGCAAGGCTACCGCCAAGTACTTCTTCTACAGCAACATCATG |
| | | AACTTTTTCAAGACCGAGATTACCCTGGCCAACGGCGAGATCCGGAAGCGGCCT |
| | | CTGATCGAGACAAACGGCGAAACCGGGGAGATCGTGTGGGATAAGGGCCGGGAT |
| | | TTTGCCACCGTGCGGAAAGTGCTGAGCATGCCCCAAGTGAATATCGTGAAAAAG |
| | | ACCGAGGTGCAGACAGGCGGCTTCAGCAAAGAGTCTATCCTGCCCAAGAGGAAC |
| | | AGCGATAAGCTGATCGCCAGAAAGAAGGACTGGGACCCTAAGAAGTACGGCGGC |
| | | TTCGACAGCCCCACCGTGGCCTATTCTGTGCTGGTGGTGGCCAAAGTGGAAAAG |
| | | GGCAAGTCCAAGAAACTGAAGAGTGTGAAAGAGCTGCTGGGGATCACCATCATG |
| | | GAAAGAAGCAGCTTCGAGAAGAATCCCATCGACTTTCTGGAAGCCAAGGGCTAC |
| | | AAAGAAGTGAAAAAGGACCTGATCATCAAGCTGCCTAAGTACTCCCTGTTCGAG |
| | | CTGGAAAACGGCCGGAAGAGAATGCTGGCCTCTGCCGGCGAACTGCAGAAGGGA |
| | | AACGAACTGGCCCTGCCCTCCAAATATGTGAACTTCCTGTACCTGGCCAGCCAC |
| | | TATGAGAAGCTGAAGGGCTCCCCCGAGGATAATGAGCAGAAACAGCTGTTTGTG |
| | | GAACAGCACAAGCACTACCTGGACGAGATCATCGAGCAGATCAGCGAGTTCTCC |
| | | AAGAGAGTGATCCTGGCCGACGCTAATCTGGACAAAGTGCTGTCCGCCTACAAC |
| | | AAGCACCGGGATAAGCCCATCAGAGAGCAGGCCGAGAATATCATCCACCTGTTT |
| | | ACCCTGACCAATCTGGGAGCCCCTGCCGCCTTCAAGTACTTTGACACCACCATC |
| | | GACCGGAAGAGGTACACCAGCACCAAAGAGGTGCTGGACGCCACCCTGATCCAC |
| | | CAGAGCATCACCGGCCTGTACGAGACACGGATCGACCTGTCTCAGCTGGGAGGC |

TABLE 18-continued

Sequence listing.

| SEQ | Description | Sequence |
|-----|-------------|----------|
| | | GACAGCCCCAAGAAGAAGAGAAAGGTGGGAGTCGACGGATCCAGCGGCTCCGAG<br>ACCCCAGGCACATCTGAGAGCGCCACCCCTGAGTCCACCGGTATGAACAATTCA<br>CAGGGGAGAGTGACATTCGAAGACGTGACCGTGAACTTCACCCAGGGGAGAATGG<br>CAGCGCTTGAACCCAGAACAAAGGAACCTCTATCGGGACGTGATGCTGGAAAAC<br>TACTCAAATTTGGTGAGCGTTGGGCAGGGTGAGACCACTAAGCCTGACGTGATC<br>CTGAGATTGGAACAGGGCAAGGAGCCTTGGCTCGAGGAAGAGGAAGTCCTGGGC<br>TCAGGGAGGGCCGAGAAAAACGGTGATATAGGAGGCCAGATATGGAAGCCTAAG<br>GACGTCAAGGAGAGCCTGAGCGCTCCCAAGAAGAAAAGGAAGGTCCCAAAGAAA<br>AAAAGAAAGGTGTGA |
| 1248 | CRISPR-Off<br>fusion protein (aa) | MPKKKRKVPKKKRKVYNHDQEFDPPKVYPPVPAEKRKPIRVLSLFDGIATGLLV<br>LKDLGIQVDRYIASEVCEDSITVGMVRHQGKIMYVGDVRSVTQKHIQEWGPFDL<br>VIGGSPCNDLSIVNPARKGLYEGTGRLFFEFYRLLHDARPKEGDDRPFFWLFEN<br>VVAMGVSDKRDISRFLESNPVMIDAKEVSAAHRARYFWGNLPGMNRPLASTVND<br>KLELQECLEHGRIAKFSKVRTITTRSNSIKQGKDQHFPVEMNEKEDILWCTEME<br>RVFGFPVHYTDVSNMSRLARQRLLGRSWSVPVIRHLFAPLKEYFACVSSGNSNA<br>NSRGPSFSSGLVPLSLRGSHMAAIPALDPEAEPSMDVILVGSSELSSSVSPGTG<br>RDLIAYEVKANQRNIEDICICCGSLQVHTQHPLFEGGICAPCKDKFLDALFLYD<br>DDGYQSYCSICCSGETLLICGNPDCTRCYCFECVDSLVGPGTSGKVHAMSNWVC<br>YLCLPSSRSGLLQRRRKWRSQLKAFYDRESENPLEMFETVPVWRRQPVRVLSLF<br>EDIKKELTSLGFLESGSDPGQLKHVVDVTDTVRKDVEEWGPFDLVYGATPPLGH<br>TCDRPPSWYLFQFHRLLQYARPKPGSPRPFFWMFVDNLVLNKEDLDVASRFLEM<br>EPVTIPDVHGGSLQNAVRVWSNIPAIRSRHWALVSEEELSLLAQNKQSSKLAAK<br>WPTKLVKNCFLPLREYFKYFSTELTSSLGGPSSGAPPPSGGSPAGSPTSTEEGT<br>SESATPESGPGTSTEPSEGSAPGSPAGSPTSTEEGTSTEPSEGSAPGTSTEPSE<br>LEDKKYSIGLAIGTNSVGWAVITDEYKVPSKKFKVLGNTDRHSIKKNLIGALLE<br>DSGETAEATRLKRTARRRYTRRKNRICYLQEIFSNEMAKVDDSFFHRLEESFLV<br>EEDKKHERHPIFGNIVDEVAYHEKYPTIYHLRKKLVDSTDKADLRLIYLALAHM<br>IKFRGHFLIEGDLNPDNSDVDKLFIQLVQTYNQLFEENPINASGVDAKAILSAR<br>LSKSRRLENLIAQLPGEKKNGLFGNLIALSLGLTPNFKSNEDLAEDAKLQLSKD<br>TYDDDLDNLLAQIGDQYADLFLAAKNLSDAILLSDILRVNTEITKAPLSASMIK<br>RYDEHHQDLTLLKALVRQQLPEKYKEIFFDQSKNGYAGYIDGGASQEEFYKFIK<br>PILEKMDGTEELLVKLNREDLLRKQRTFDNGSIPHQIHLGELHAILRRQEDFYP<br>FLKDNREKIEKILTFRIPYYVGPLARGNSRFAWMTRKSEETITPWNFEEVVDKG<br>ASAQSFIERMTNFDKNLPNEKVLPKHSLLYEYFTVYNELTKVKYVTEGMRKPAF<br>LSGEQKKAIVDLLFKTNRKVTVKQLKEDYFKKIECFDSVEISGVEDRENASLGT<br>YHDLLKIIKDKDFLDNEENEDILEDIVLTLTLFEDREMIEERLKTYAHLEDDKV<br>MKQLKRRRYTGWGRLSRKLINGIRDKQSGKTILDFLKSDGFANRNFMQLIHDDS<br>LTFKEDIQKAQVSGQGDSLHEHIANLAGSPAIKKGILQTVKVVDELVKVMGRHK<br>PENIVIEMARENQTTQKGQKNSRERMKRIEEGIKELGSQILKEHPVENTQLQNE<br>KLYLYYLQNGRDMYVDQELDINRLSDYDVDAIVPQSFLKDDSIDNKVLTRSDKN<br>RGKSDNVPSEEVVKKMKNYWRQLLNAKLITQRKFDNLTKAERGGLSELDKAGFI<br>KRQLVETRQITKHVAQILDSRMNTKYDENDKLIREVKVITLKSKLVSDERKDFQ<br>FYKVREINNYHHAHDAYLNAVVGTALIKKYPKLESEFVYGDYKVYDVRKMIAKS<br>EQEIGKATAKYFFYSNIMNFFKTEITLANGEIRKRPLIETNGETEIVWDKGRD<br>FATVRKVLSMPQVNIVKKTEVQTGGFSKESILPKRNSDKLIARKKDWDPKKYGG<br>FDSPTVAYSVLVAKVEKGKSKKLKSVKELLGITIMERSSFEKNPIDFLEAKGY<br>KEVKKDLIIKLPKYSLFELENGRKRMLASAGELQKGNELALPSKYVNFLYLASH<br>YEKLKGSPEDNEQKQLFVEQHKHYLDEIIEQISEFSKRVILADANLDKVLSAYN<br>KHRDKPIREQAENIIHLFTLTNLGAPAAFKYFDTTIDRKRYTSTKEVLDATLIH<br>QSITGLYETRIDLSQLGGDSPKKKRKVGVDGSSGSETPGTSESATPESTGMNNS<br>QGRVTFEDVTVNFTQGEWQRLNPEQRNLYRDVMLENYSNLVSVGQGETTKPDVI<br>LRLEQGKEPWLEEEEVLGSGRAEKNGDIGGQIWKPKDVKESLSAPKKKRKVPKK<br>KRKV |
| 1249 | gRNA #008 with<br>updated<br>modification<br>pattern<br>(m indicates a 2'-<br>OMe modified<br>nucleotide,<br>* indicates a<br>phosphorothioate<br>bond) | mA*mG*mG*rArGrUrUrCrCrGrCrArGrUrArUrGrGrArUrGrUrUrUrUr<br>ArGrArGmCmUmAmGmAmAmAmUmAmGmCrArArGrUrUrArArArArArUrArAr<br>GrGrCrUrArGrUrCrCrGrUrUrArUrCrAmCmCmUmUmGmAmAmAmAmAmGm<br>UmGrGmCmAmCmCmGmAmGmUmCmGmGmUmGmCmU*mU*mU*mU |
| 1250 | CRISPR-Off<br>variant 1 plasmid<br>sequence | AGGGGCGCTCGAGCAGGTTCAGAAGGAGATCAAAAACCCCCAAGGATCAAACAT<br>GAAGAGACCTGCTGCCACCAAGAAGGCCGGCCAGGCCAAGAAAAAGTACAATCA<br>CGATCAGGAGTTCGACCCCCCTAAGGTGTACCCACCAGTGCCTGCAGAGAAGAG<br>GAAGCCAATCCGGGTGCTGAGCCTGTTTGATGGCATCGCCACCGGCCTGCTGGT<br>GCTGAAGGATCTGGGCATCCAGGTGGACCGGTACATCGCCTCCGAGGTGTGCGA<br>GGATTCTATCACCGTGGGCATGGTGCGCCACCAGGGCAAGATCATGTATGTGGG<br>CGACGTGCGGTCCGTGACACAGAAGCACATCCAGGAGTGGGGCCCATTCGATCT<br>GGTGATCGGCGGCAGCCCCTGTAATGACCTGTCCATCGTGAACCCTGCAAGGAA<br>GGGACTGTACGAGGGAACCGGCCGGCTGTTCTTTGAGTTTTATAGACTGCTGCA<br>CGACGCCAGGCCTAAGGAGGGCGACGATAGACCATTCTTTTGGCTGTTCGAGAA |

TABLE 18-continued

Sequence listing.

| SEQ | Description | Sequence |
|-----|-------------|----------|
| | | TGTGGTGGCTATGGGCGTGAGCGATAAGAGGGACATCTCCAGGTTTCTGGAGTC |
| | | TAACCCCGTGATGATCGATGCAAAGGAGGTGTCCGCCGCACACAGAGCCAGGTA |
| | | TTTCTGGGGCAATCTGCCAGGAATGAACAGGCCACTGGCAAGCACCGTGAATGA |
| | | CAAGCTGGAGCTGCAGGAGTGCCTGGAGCACGGAAGGATCGCCAAGTTTTCCAA |
| | | GGTGCGCACAATCACCACACGGAGCAATTCCATCAAGCAGGGCAAGGATCAGCA |
| | | CTTCCCCGTGTTCATGAACGAGAAGGAGGACATCCTGTGGTGTACCGAGATGGA |
| | | GAGAGTGTTCGGCTTTCCAGTGCACTACACAGACGTGTCTAACATGAGCAGGCT |
| | | GGCAAGGCAGCGGCTGCTGGGCAGATCTTGGAGCGTGCCCGTGATCAGGCACCT |
| | | GTTCGCCCCTCTGAAGGAGTATTTTGCCTGCGTGAGCAGCGGCAACTCCAATGC |
| | | CAACAGCCGGGGCCCCTCTTTCAGCTCCGGATTGGTGCCTCTGAGCCTGAGGGG |
| | | CTCCCACAGTCCCCTTGAGATGTATAAAACTGTGCCTGTGTGGAAGAGAGAGCC |
| | | AGTGCGGGTGCTGTCCCTTTTTGGTGACATCAAGAAAGAGCTGACGACTTTGGG |
| | | CTTTCTGGAAAACGGCTCTGACCCGGGCCGACTGAAACATTTGGACGATGTCAC |
| | | CAATACGGTGAGGAGGGACGTGGAAGAATGGGGCCCGTTCGACCTCGTGTACGG |
| | | CTCCACGCCGCCCCTCGGCCACGCCTGTGACCATCCTCCCGGGTGGTACCTGTT |
| | | CCAGTTCCACCGTGTGCTTCAGTACGCGAGGCCCAGGCCGGGCAGCCCGCAGGC |
| | | CTTCTTCTGGATGTTTGTGGACAACCTGGTGCTGACCGAGGATGACCGGGCTGT |
| | | AGCCACTCGCTTCCTGGAGACTGACCCGGTGACCATCCAGGACGTCTGTGGCAG |
| | | AGCTGTCCGGAACGCCGTGCACGTGTGGAGCAACATCCCGGCCGTGAAAAGCAG |
| | | GCACTCGGCCCTGTTTTCCCAGGAGGAATCATTCCTGCGGGCTCAGGACAGGCA |
| | | GAGAGCAAAGCCCCCCGCCGGGGGCCAGCCAAGCTGGTGAAGAATTGTTTTCT |
| | | CCCCCTGAGAGAATATTTCAAGTATTTTTCAACAGAATTCACTTCCTCTTTGGG |
| | | AGGACCCTCCTCTGGCGCCCCACCACCTAGCGGCGGCTCCCCTGCCGGCTCTCC |
| | | AACCAGCACAGAGGAGGGCACCAGCGAGTCCGCCACACCAGAGTCTGGACCTGG |
| | | CACCAGCACAGAGCCATCCGAGGGCTCTGCCCCAGGCTCTCCTGCAGGCAGCCC |
| | | TACCTCCACCGAAGAGGGCACCAGCACAGAGCCTTCTGAGGGCAGCGCCCCAGG |
| | | CACCTCTACAGAGCCAAGCGAGCTCGAGGACAAGAAGTACAGCATCGGCCTGGC |
| | | CATCGGCACCAACTCTGTGGGCTGGGCCGTGATCACCGACGAGTACAAGGTGCC |
| | | CAGCAAGAAATTCAAGGTGCTGGGCAACACCGACCGGCACAGCATCAAGAAGAA |
| | | CCTGATCGGAGCCCTGCTGTTCGACAGCGGCGAAACAGCCGAGGCCACCCGGCT |
| | | GAAGAGAACCGCCAGAAGAAGATACACCAGACGGAAGAACCGGATCTGCTATCT |
| | | GCAAGAGATCTTCAGCAACGAGATGGCCAAGGTGGACGACAGCTTCTTCCACAG |
| | | ACTGGAAGAGTCCTTCCTGGTGGAAGAGGATAAGAAGCACGAGCGGCACCCCAT |
| | | CTTCGGCAACATCGTGGACGAGGTGGCCTACCACGAGAAGTACCCCACCATCTA |
| | | CCACCTGAGAAAGAAACTGGTGGACAGCACCGACAAGGCCGACCTGCGGCTGAT |
| | | CTATCTGGCCCTGGCCCACATGATCAAGTTCCGGGGCCACTTCCTGATCGAGGG |
| | | CGACCTGAACCCCGACAACAGCGACGTGGACAAGCTGTTCATCCAGCTGGTGCA |
| | | GACCTACAACCAGCTGTTCGAGGAAAACCCCATCAACGCCAGCGGCGTGGACGC |
| | | CAAGGCCATCCTGTCTGCCAGACTGAGCAAGAGCAGACGGCTGGAAAATCTGAT |
| | | CGCCCAGCTGCCCGGCGAGAAGAAGAATGGCCTGTTCGGCAACCTGATTGCCCT |
| | | GAGCCTGGGCCTGACCCCCAACTTCAAGAGCAACTTCGACCTGGCCGAGGATGC |
| | | CAAACTGCAGCTGAGCAAGGACACCTACGACGACGACCTGGACAACCTGCTGGC |
| | | CCAGATCGGCGACCAGTACGCCGACCTGTTTCTGGCCGCCAAGAACCTGTCCGA |
| | | CGCCATCCTGCTGAGCGACATCCTGAGAGTGAACACCGAGATCACCAAGGCCCC |
| | | CCTGAGCGCCTCTATGATCAAGAGATACGACGAGCACCACCAGGACCTGACCCT |
| | | GCTGAAAGCTCTCGTGCGGCAGCAGCTGCCTGAGAAGTACAAAGAGATTTTCTT |
| | | CGACCAGAGCAAGAACGGCTACGCCGGCTACATTGACGGCGGAGCCAGCCAGGA |
| | | AGAGTTCTACAAGTTCATCAAGCCCATCCTGGAAAAGATGGACGGCACCGAGGA |
| | | ACTGCTCGTGAAGCTGAACAGAGAGGACCTGCTGCGGAAGCAGCGGACCTTCGA |
| | | CAACGGCAGCATCCCCCACCAGATCCACCTGGGAGAGCTGCACGCCATTCTGCG |
| | | GCGGCAGGAAGATTTTTACCCATTCCTGAAGGACAACCGGGAAAAGATCGAGAA |
| | | GATCCTGACCTTCCGCATCCCCTACTACGTGGGCCCTCTGGCCAGGGGAAACAG |
| | | CAGATTCGCCTGGATGACCAGAAAGAGCGAGGAAACCATCACCCCCTGGAACTT |
| | | CGAGGAAGTGGTGGACAAGGGCGCTTCCGCCCAGAGCTTCATCGAGCGGATGAC |
| | | CAACTTCGATAAGAACCTGCCCAACGAGAAGGTGCTGCCCAAGCACAGCCTGCT |
| | | GTACGAGTACTTCACCGTGTATAACGAGCTGACCAAAGTGAAATACGTGACCGA |
| | | GGGAATGAGAAAGCCCGCCTTCCTGAGCGGCGAGCAGAAAAAGGCCATCGTGGA |
| | | CCTGCTGTTCAAGACCAACCGGAAAGTGACCGTGAAGCAGCTGAAAGAGGACTA |
| | | CTTCAAGAAAATCGAGTGCTTCGACTCCGTGGAAATCTCCGGCGTGGAAGATCG |
| | | GTTCAACGCCTCCCTGGGCACATACCACGATCTGCTGAAAATTATCAAGGACAA |
| | | GGACTTCCTGGACAATGAGGAAAACGAGGACATTCTGGAAGATATCGTGCTGAC |
| | | CCTGACACTGTTTGAGGACAGAGAGATGATCGAGGAACGGCTGAAAACCTATGC |
| | | CCACCTGTTCGACGACAAAGTGATGAAGCAGCTGAAGCGGCGGAGATACACCGG |
| | | CTGGGGCAGGCTGAGCCGGAAGCTGATCAACGGCATCCGGGACAAGCAGTCCGG |
| | | CAAGACAATCCTGGATTTCCTGAAGTCCGACGGCTTCGCCAACAGAAACTTCAT |
| | | GCAGCTGATCCACGACGACAGCCTGACCTTTAAAGAGGACATCCAGAAAGCCCA |
| | | GGTGTCCGGCCAGGGCGATAGCCTGCACGAGCACATTGCCAATCTGGCCGGCAG |
| | | CCCCGCCATTAAGAAGGGCATCCTGCAGACAGTGAAGGTGGTGGACGAGCTCGT |
| | | GAAAGTGATGGGCCGGCACAAGCCCGAGAACATCGTGATCGAAATGGCCAGAGA |
| | | GAACCAGACCACCCAGAAGGGACAGAAGAACAGCCGCGAGAGAATGAAGCGGAT |
| | | CGAAGAGGGCATCAAAGAGCTGGGCAGCCAGATCCTGAAAGAACACCCCGTGGA |
| | | AAACACCCAGCTGCAGAACGAGAAGCTGTACCTGTACTACCTGCAGAATGGGCG |
| | | GGATATGTACGTGGACCAGGAACTGGACATCAACCGGCTGTCCGACTACGATGT |
| | | GGACGCCATCGTGCCTCAGAGCTTTCTGAAGGACGACTCCATCGACAACAAGGT |
| | | GCTGACCAGAAGCGACAAGAACCGGGGCAAGAGCGACAACGTGCCCTCCGAAGA |
| | | GGTCGTGAAGAAGATGAAGAACTACTGGCGGCAGCTGCTGAACGCCAAGCTGAT |

TABLE 18-continued

| Sequence listing. | | |
| --- | --- | --- |
| SEQ | Description | Sequence |

TACCCAGAGAAAGTTCGACAATCTGACCAAGGCCGAGAGAGGCGGCCTGAGCGA
ACTGGATAAGGCCGGCTTCATCAAGAGACAGCTGGTGGAAACCCGGCAGATCAC
AAAGCACGTGGCACAGATCCTGGACTCCCGGATGAACACTAAGTACGACGAGAA
TGACAAGCTGATCCGGGAAGTGAAAGTGATCACCCTGAAGTCCAAGCTGGTGTC
CGATTTCCGGAAGGATTTCCAGTTTTACAAAGTGCGCGAGATCAACAACTACCA
CCACGCCCACGACGCCTACCTGAACGCCGTCGTGGGAACCGCCCTGATCAAAAA
GTACCCTAAGCTGGAAAGCGAGTTCGTGTACGGCGACTACAAGGTGTACGACGT
GCGGAAGATGATCGCCAAGAGCGAGCAGGAAATCGGCAAGGCTACCGCCAAGTA
CTTCTTCTACAGCAACATCATGAACTTTTTCAAGACCGAGATTACCCTGGCCAA
CGGCGAGATCCGGAAGCGGCCTCTGATCGAGACAAACGGCGAAACCGGGGAGAT
CGTGTGGGATAAGGGCCGGGATTTTGCCACCGTGCGGAAAGTGCTGAGCATGCC
CCAAGTGAATATCGTGAAAAAGACCGAGGTGCAGACAGGCGGCTTCAGCAAAGA
GTCTATCCTGCCCAAGAGGAACAGCGATAAGCTGATCGCCAGAAAGAAGGACTG
GGACCCTAAGAAGTACGGCGGCTTCGACAGCCCCACCGTGGCCTATTCTGTGCT
GGTGGTGGCCAAAGTGGAAAAGGGCAAGTCCAAGAAACTGAAGAGTGTGAAAGA
GCTGCTGGGGATCACCATCATGGAAAGAAGCAGCTTCGAGAAGAATCCCATCGA
CTTTCTGGAAGCCAAGGGCTACAAAGAAGTGAAAAAGGACCTGATCATCAAGCT
GCCTAAGTACTCCCTGTTCGAGCTGGAAAACGGCCGGAAGAGAATGCTGGCCTC
TGCCGGCGAACTGCAGAAGGGAAACGAACTGGCCCTGCCCTCCAAATATGTGAA
CTTCCTGTACCTGGCCAGCCACTATGAGAAGCTGAAGGGCTCCCCCGAGGATAA
TGAGCAGAAACAGCTGTTTGTGGAACAGCACAAGCACTACCTGGACGAGATCAT
CGAGCAGATCAGCGAGTTCTCCAAGAGAGTGATCCTGGCCGACGCTAATCTGGA
CAAAGTGCTGTCCGCCTACAACAAGCACCGGGATAAGCCCATCAGAGAGCAGGC
CGAGAATATCATCCACCTGTTTACCCTGACCAATCTGGGAGCCCCTGCCGCCTT
CAAGTACTTTGACACCACCATCGACCGGAAGAGGTACACCAGCACCAAAGAGGT
GCTGGACGCCACCCTGATCCACCAGAGCATCACCGGCCTGTACGAGACACGGAT
CGACCTGTCTCAGCTGGGAGGCGACAGCCCCAAGAAGAAGAGAAAGGTGGGAGT
CGACGGATCCAGCGGCTCCGAGACCCCAGGCACATCTGAGAGCGCCACCCCTGA
GTCCACCGGTATGAACAATTCACAGGGGAGAGTGACATTCGAAGACGTGACCGT
GAACTTCACCCAGGGAGAATGGCAGCGCTTGAACCCAGAACAAAGGAACCTCTA
TCGGGACGTGATGCTGGAAAACTACTCAAATTTGGTGAGCGTTGGGCAGGGTGA
GACCACTAAGCCTGACGTGATCCTGAGATTGGAACAGGGCAAGGAGCCTTGGCT
CGAGGAAGAGGAAGTCCTGGGCTCAGGGAGGGCCGAGAAAAACGGTGATATAGG
AGGCCAGATATGGAAGCCTAAGGACGTCAAGGAGAGCCTGAGCGCTAAACGTCC
GGCAGCAACCAAAAAAGCAGGTCAGGCCAAGAAAAAATGAGGATCCTGAGTCTA
GAAAAGATATATATAGGATTGAAGATCTCTCAGTTAAGTCTACAAAAAAAAAAA
AAAAAAAAAAAAAAAAAAAAAAAAAAAAAAAAAAAAAAAAAAAAAAAAAAAAAA
AAAAAAAAAAAAAAAAAAAAAAAAAAAAAAAAAAAAAAAAAAAAAAAAAAAAAA
AAGAAGAGCCTCCTGCAGGAAGCTTGGCGTAATCATGGTCATAGCTGTTTCCTG
TGTGAAATTGTTATCCGCTCACAATTCCACACAACATACGAGCCGGAAGCATAA
AGTGTAAAGCCTGGGGTGCCTAATGAGTGAGCTAACTCACATTAATTGCGTTGC
GCTCACTGCCCGCTTTCCAGTCGGGAAACCTGTCGTGCCAGCTGCATTAATGAA
TCGGCCAACGCGCGGGGAGAGGCGGTTTGCGTATTGGGCCGCTTCCTCGCTCAC
TGACTCGCTGCGCTCGGTCGTTCGGCTGCGGCGAGCGGTATCAGCTCACTCAAA
GGCGGTAATACGGTTATCCACAGAATCAGGGGATAACGCAGGAAAGAACATGTG
AGCAAAAGGCCAGCAAAAGGCCAGGAACCGTAAAAAGGCCGCGTTGCTGGCGTT
TTTCCATAGGCTCCGCCCCCCTGACGAGCATCACAAAAATCGACGCTCAAGTCA
GAGGTGGCGAAACCCGACAGGACTATAAAGATACCAGGCGTTTCCCCCTGGAAG
CTCCCTCGTGCGCTCTCCTGTTCCGACCCTGCCGCTTACCGGATACCTGTCCGC
CTTTCTCCCTTCGGGAAGCGTGGCGCTTTCTCATAGCTCACGCTGTAGGTATCT
CAGTTCGGTGTAGGTCGTTCGCTCCAAGCTGGGCTGTGTGCACGAACCCCCCGT
TCAGCCCGACCGCTGCGCCTTATCCGGTAACTATCGTCTTGAGTCCAACCCGGT
AAGACACGACTTATCGCCACTGGCAGCAGCCACTGGTAACAGGATTAGCAGAGC
GAGGTATGTAGGCGGTGCTACAGAGTTCTTGAAGTGGTGGCCTAACTACGGCTA
CACTAGAAGAACAGTATTTGGTATCTGCGCTCTGCTGAAGCCAGTTACCTTCGG
AAAAAGAGTTGGTAGCTCTTGATCCGGCAAACAAACCACCGCTGGTAGCGGTGG
TTTTTTTGTTTGCAAGCAGCAGATTACGCGCAGAAAAAAAGGATCTCAAGAAGA
TCCTTTGATCTTTTCTACGGGGTCTGACGCTCAGTGGAACGAAAACTCACGTTA
AGGGATTTTGGTCATGAGATTATCAAAAAGGATCTTCACCTAGATCCTTTTAAA
TTAAAAATGAAGTTTTAAATCAAGCCCAATCTGAATAATGTTACAACCAATTAA
CCAATTCTGATTAGAAAAACTCATCGAGCATCAAATGAAACTGCAATTTATTCA
TATCAGGATTATCAATACCATATTTTTGAAAAAGCCGTTTCTGTAATGAAGGAG
AAAACTCACCGAGGCAGTTCCATAGGATGGCAAGATCCTGGTATCGGTCTGCGA
TTCCGACTCGTCCAACATCAATACAACCTATTAATTTCCCCTCGTCAAAAATAA
GGTTATCAAGTGAGAAATCACCATGAGTGACGACTGAATCCGGTGAGAATGGCA
AAAGTTTATGCATTTCTTTCCAGACTTGTTCAACAGGCCAGCCATTACGCTCGT
CATCAAAATCACTCGCATCAACCAAACCGTTATTCATTCGTGATTGCGCCTGAG
CGAGACGAAATACGCGATCGCTGTTAAAAGGACAATTACAAACAGGAATCGAAT
GCAACCGGCGCAGGAACACTGCCAGCGCATCAACAATATTTTCACCTGAATCAG
GATATTCTTCTAATACCTGGAATGCTGTTTTTCCGGGGATCGCAGTGGTGAGTA
ACCATGCATCATCAGGAGTACGGATAAAATGCTTGATGGTCGGAAGAGGCATAA
ATTCCGTCAGCCAGTTTAGTCTGACCATCTCATCTGTAACATCATTGGCAACGC
TACCTTTGCCATGTTTCAGAAACAACTCTGGCGCATCGGGCTTCCCATACAAGC
GATAGATTGTCGCACCTGATTGCCCGACATTATCGCGAGCCCATTTATACCCAT
ATAAATCAGCATCCATGTTGGAATTTAATCGCGGCCTCGACGTTTCCCGTTGAA
TATGGCTCATAACACCCCTTGTATTACTGTTTATGTAAGCAGACAGTTTTATTG

TABLE 18-continued

Sequence listing.

| SEQ | Description | Sequence |
|-----|-------------|----------|
| | | TTCATGATGATATATTTTTATCTTGTGCAATGTAACATCAGAGATTTTGAGACA<br>CGGGCCAGAGCTGCATCGCGCGTTTCGGTGATGACGGTGAAAACCTCTGACACA<br>TGCAGCTCCCGGAGACGGTCACAGCTTGTCTGTAAGCGGATGCCGGGAGCAGAC<br>AAGCCCGTCAGGGCGCGTCAGCGGGTGTTGGCGGGTGTCGGGGCTGGCTTAACT<br>ATGCGGCATCAGAGCAGATTGTACTGAGAGTGCACCATATGCGGTGTGAAATAC<br>CGCACAGATGCGTAAGGAGAAAATACCGCATCAGGCGCCATTCGCCATTCAGGC<br>TGCGCAACTGTTGGGAAGGGCGATCGGTGCGGGCCTCTTCGCTATTACGCCAGC<br>TGGCGAAAGGGGGATGTGCTGCAAGGCGATTAAGTTGGGTAACGCCAGGGTTTT<br>CCCAGTCACGACGTTGTAAAACGACGGCCAGTGAATTGTAATACGACTCACTAT<br>A |
| 1251 | CRISPR-Off<br>variant 1<br>alternative plasmid<br>sequence | AGGGGCGCTCGAGCAGGTTCAGAAGGAGATCAAAAACCCCCAAGGATCAAACAT<br>GAAGAGACCTGCTGCCACCAAGAAGGCCGGCCAGGCCAAGAAAAAGTACAATCA<br>CGATCAGGAGTTCGACCCCCCTAAGGTGTACCCACCAGTGCCTGCAGAGAAGAG<br>GAAGCCAATCCGGGTGCTGAGCCTGTTTGATGGCATCGCCACCGGCCTGCTGGT<br>GCTGAAGGATCTGGGCATCCAGGTGGACCGGTACATCGCCTCCGAGGTGTGCGA<br>GGATTCTATCACCGTGGGCATGGTGCGCCACCAGGGCAAGATCATGTATGTGGG<br>CGACGTGCGGTCCGTGACACAGAAGCACATCCAGGAGTGGGGCCCATTCGATCT<br>GGTGATCGGCGGCAGCCCCTGTAATGACCTGTCCATCGTGAACCCTGCAAGGAA<br>GGGACTGTACGAGGGAACCGGCCGGCTGTTCTTTGAGTTTTATAGACTGCTGCA<br>CGACGCCAGGCCTAAGGAGGGCGACGATAGACCATTCTTTTGGCTGTTCGAGAA<br>TGTGGTGGCTATGGGCGTGAGCGATAAGAGGGACATCTCCAGGTTTCTGGAGTC<br>TAACCCCGTGATGATCGATGCAAAGGAGGTGTCCGCCGCACACAGAGCCAGGTA<br>TTTCTGGGGCAATCTGCCCAGGAATGAACAGGCCACTGGCAAGCACCGTGAATGA<br>CAAGCTGGAGCTGCAGGAGTGCCTGGAGCACGGAAGGATCGCCAAGTTTTCCAA<br>GGTGCGCACAATCACCACACGGAGCAATTCCATCAAGCAGGGCAAGGATCAGCA<br>CTTCCCCGTGTTCATGAACGAGAAGGAGGACATCCTGTGGTGTACCGAGATGGA<br>GAGAGTGTTCGGCTTTCCAGTGCACTACACAGACGTGTCTAACATGAGCAGGCT<br>GGCCAAGGCAGCGGCTGCTGGGCAGATCTTGGAGCGTGCCCGTGATCAGGCACCT<br>GTTCGCCCCTCTGAAGGAGTATTTTGCCTGCGTGAGCAGCGGCAACTCCAATGC<br>CAACAGCCGGGGCCCCTCTTTCAGCTCCGGATTGGTGCCTCTGAGCCTGAGGGG<br>CTCCCACAGTCCCCTTGAGATGTATAAAACTGTGCCTGTGTGGAAGAGAGAGCC<br>AGTGCGGGTGCTGTCCCTTTTTGGTGACATCAAGAAAGAGCTGACGACTTTGGG<br>CTTTCTGGAAAACGGCTCTGACCCGGGCCGACTGAAACATTTGGACGATGTCAC<br>CAATACGGTGAGGAGGGACGTGGAAGAATGGGGCCCGTTCGACCTCGTGTACGG<br>CTCCACGCCGCCCCTCGGCCACGCCTGTGACCATCCTCCCGGGTGGTACCTGTT<br>CCAGTTCCACCGTGTGCTTCAGTACGCGAGGCCCAGGCCGGGCAGCCCGCAGGC<br>CTTCTTCTGGATGTTTGTGGACAACCTGGTGCTGACCGAGGATGACCGGGCTGT<br>AGCCACTCGCTTCCTGGAGACTGACCCGGTGACCATCCAGGACGTCTGTGGCAG<br>AGCTGTCCGGAACGCCGTGCACGTGTGGAGCAACATCCCGGCCGTGAAAAGCAG<br>GCACTCGGCCCTGTTTTCCCAGGAGGAATCATTCCTGCGGGCTCAGGACAGGCA<br>GAGAGCAAAGCCCCCCGCCCGGGGGCCAGCCAAGCTGGTGAAGAATTGTTTTCT<br>CCCCCTGAGAGAATATTTCAAGTATTTTTCAACAGAATTCACTTCCTCTTTGGG<br>AGGACCCTCCTCTGGCGCCCCACCACCTAGCGGCGGCTCCCCTGCCGGCTCTCC<br>AACCAGCACAGAGGAGGGCACCAGCGAGTCCGCCACACCAGAGTCTGGACCTGG<br>CACCAGCACAGAGCCATCCGAGGGCTCTGCCCCAGGCTCTCCTGCAGGCAGCCC<br>TACCTCCACCGAAGAGGGCACCAGCACAGAGCCTTCTGAGGGCAGCGCCCCAGG<br>CACCTCTACAGAGCCAAGCGAGCTCGAGGACAAGAAGTACAGCATCGGCCTGGC<br>CATCGGCACCAACTCTGTGGGCTGGGCCGTGATCACCGACGAGTACAAGGTGCC<br>CAGCAAGAAATTCAAGGTGCTGGGCAACACCGACCGGCACAGCATCAAGAAGAA<br>CCTGATCGGAGCCCTGCTGTTCGACAGCGGCGAAACAGCCGAGGCCACCCGGCT<br>GAAGAGAACCGCCAGAAGAAGATACACCAGACGGAAGAACCGGATCTGCTATCT<br>GCAAGAGATCTTCAGCAACGAGATGGCCAAGGTGGACGACAGCTTCTTCCACAG<br>ACTGGAAGAGTCCTTCCTGGTGGAAGAGGATAAGAAGCACGAGCGGCACCCCAT<br>CTTCGGCAACATCGTGGACGAGGTGGCCTACCACGAGAAGTACCCCACCATCTA<br>CCACCTGAGAAAGAAACTGGTGGACAGCACCGACAAGGCCGACCTGCGGCTGAT<br>CTATCTGGCCCTGGCCCACATGATCAAGTTCCGGGGCCACTTCCTGATCGAGGG<br>CGACCTGAACCCCGACAACAGCGACGTGGACAAGCTGTTCATCCAGCTGGTGCA<br>GACCTACAACCAGCTGTTCGAGGAAAACCCCATCAACGCCAGCGGCGTGGACGC<br>CAAGGCCATCCTGTCTGCCAGACTGAGCAAGAGCAGACGGCTGGAAAATCTGAT<br>CGCCCAGCTGCCCGGCGAGAAGAAGAATGGCCTGTTCGGCAACCTGATTGCCCT<br>GAGCCTGGGCCTGACCCCCAACTTCAAGAGCAACTTCGACCTGGCCGAGGATGC<br>CAAACTGCAGCTGAGCAAGGACACCTACGACGACGACCTGGACAACCTGCTGGC<br>CCAGATCGGCGACCAGTACGCCGACCTGTTTCTGGCCGCCAAGAACCTGTCCGA<br>CGCCATCCTGCTGAGCGACATCCTGAGAGTGAACACCGAGATCACCAAGGCCCC<br>CCTGAGCGCCTCTATGATCAAGAGATACGACGAGCACCACCAGGACCTGACCCT<br>GCTGAAAGCTCTCGTGCGGCAGCAGCTGCCTGAGAAGTACAAAGAGATTTTCTT<br>CGACCAGAGCAAGAACGGCTACGCCGGCTACATTGACGGCGGAGCCAGCCAGGA<br>AGAGTTCTACAAGTTCATCAAGCCCATCCTGGAAAAGATGGACGGCACCGAGGA<br>ACTGCTCGTGAAGCTGAACAGAGAGGACCTGCTGCGGAAGCAGCGGACCTTCGA<br>CAACGGCAGCATCCCCCACCAGATCCACCTGGGAGAGCTGCACGCCATTCTGCG<br>GCGGCAGGAAGATTTTTACCCATTCCTGAAGGACAACCGGGAAAAGATCGAGAA<br>GATCCTGACCTTCCGCATCCCCTACTACGTGGGCCCTCTGGCCAGGGGAAACAG<br>CAGATTCGCCTGGATGACCAGAAAGAGCGAGGAAACCATCACCCCCTGGAACTT<br>CGAGGAAGTGGTGGACAAGGGCGCTTCCGCCCAGAGCTTCATCGAGCGGATGAC<br>CAACTTCGATAAGAACCTGCCCAACGAGAAGGTGCTGCCCAAGCACAGCCTGCT |

TABLE 18-continued

Sequence listing.

| SEQ | Description | Sequence |
|-----|-------------|----------|
|     |             | GTACGAGTACTTCACCGTGTATAACGAGCTGACCAAAGTGAAATACGTGACCGA |
|     |             | GGGAATGAGAAAGCCCGCCTTCCTGAGCGGCGAGCAGAAAAAGGCCATCGTGGA |
|     |             | CCTGCTGTTCAAGACCAACCGGAAAGTGACCGTGAAGCAGCTGAAAGAGGACTA |
|     |             | CTTCAAGAAAATCGAGTGCTTCGACTCCGTGGAAATCTCCGGCGTGGAAGATCG |
|     |             | GTTCAACGCCTCCCTGGGCACATACCACGATCTGCTGAAAATTATCAAGGACAA |
|     |             | GGACTTCCTGGACAATGAGGAAAACGAGGACATTCTGGAAGATATCGTGCTGAC |
|     |             | CCTGACACTGTTTGAGGACAGAGAGATGATCGAGGAACGGCTGAAAACCTATGC |
|     |             | CCACCTGTTCGACGACAAAGTGATGAAGCAGCTGAAGCGGCGGAGATACACCGG |
|     |             | CTGGGGCAGGCTGAGCCGGAAGCTGATCAACGGCATCCGGGACAAGCAGTCCGG |
|     |             | CAAGACAATCCTGGATTTCCTGAAGTCCGACGGCTTCGCCAACAGAAACTTCAT |
|     |             | GCAGCTGATCCACGACGACAGCCTGACCTTTAAAGAGGACATCCAGAAAGCCCA |
|     |             | GGTGTCCGGCCAGGGCGATAGCCTGCACGAGCACATTGCCAATCTGGCCGGCAG |
|     |             | CCCCGCCATTAAGAAGGGCATCCTGCAGACAGTGAAGGTGGTGGACGAGCTCGT |
|     |             | GAAAGTGATGGGCCGGCACAAGCCCGAGAACATCGTGATCGAAATGGCCAGAGA |
|     |             | GAACCAGACCACCCAGAAGGGACAGAAGAACAGCCGCGAGAGAATGAAGCGGAT |
|     |             | CGAAGAGGGCATCAAAGAGCTGGGCAGCCAGATCCTGAAAGAACACCCCGTGGA |
|     |             | AAACACCCAGCTGCAGAACGAGAAGCTGTACCTGTACTACCTGCAGAATGGGCG |
|     |             | GGATATGTACGTGGACCAGGAACTGGACATCAACCGGCTGTCCGACTACGATGT |
|     |             | GGACGCCATCGTGCCTCAGAGCTTTCTGAAGGACGACTCCATCGACAACAAGGT |
|     |             | GCTGACCAGAAGCGACAAGAACCGGGGCAAGAGCGACAACGTGCCCTCCGAAGA |
|     |             | GGTCGTGAAGAAGATGAAGAACTACTGGCGGCAGCTGCTGAACGCCAAGCTGAT |
|     |             | TACCCAGAGAAAGTTCGACAATCTGACCAAGGCCGAGAGAGGCGGCCTGAGCGA |
|     |             | ACTGGATAAGGCCGGCTTCATCAAGAGACAGCTGGTGGAAACCCGGCAGATCAC |
|     |             | AAAGCACGTGGCACAGATCCTGGACTCCCGGATGAACACTAAGTACGACGAGAA |
|     |             | TGACAAGCTGATCCGGGAAGTGAAAGTGATCACCCTGAAGTCCAAGCTGGTGTC |
|     |             | CGATTTCCGGAAGGATTTCCAGTTTTACAAAGTGCGCGAGATCAACAACTACCA |
|     |             | CCACGCCCACGACGCCTACCTGAACGCCGTCGTGGGAACCGCCCTGATCAAAAA |
|     |             | GTACCCTAAGCTGGAAAGCGAGTTCGTGTACGGCGACTACAAGGTGTACGACGT |
|     |             | GCGGAAGATGATCGCCAAGAGCGAGCAGGAAATCGGCAAGGCTACCGCCAAGTA |
|     |             | CTTCTTCTACAGCAACATCATGAACTTTTTCAAGACCGAGATTACCCTGGCCAA |
|     |             | CGGCGAGATCCGGAAGCGGCCTCTGATCGAGACAAACGGCGAAACCGGGGAGAT |
|     |             | CGTGTGGGATAAGGGCCGGGATTTTGCCACCGTGCGGAAAGTGCTGAGCATGCC |
|     |             | CCAAGTGAATATCGTGAAAAAGACCGAGGTGCAGACAGGCGGCTTCAGCAAAGA |
|     |             | GTCTATCCTGCCCAAGAGGAACAGCGATAAGCTGATCGCCAGAAAGAAGGACTG |
|     |             | GGACCCTAAGAAGTACGGCGGCTTCGACAGCCCCACCGTGGCCTATTCTGTGCT |
|     |             | GGTGGTGGCCAAAGTGGAAAAGGGCAAGTCCAAGAAACTGAAGAGTGTGAAAGA |
|     |             | GCTGCTGGGGATCACCATCATGGAAAGAAGCAGCTTCGAGAAGAATCCCATCGA |
|     |             | CTTTCTGGAAGCCAAGGGCTACAAAGAAGTGAAAAAGGACCTGATCATCAAGCT |
|     |             | GCCTAAGTACTCCCTGTTCGAGCTGGAAAACGGCCGGAAGAGAATGCTGGCCTC |
|     |             | TGCCGGCGAACTGCAGAAGGGAAACGAACTGGCCCTGCCCTCCAAATATGTGAA |
|     |             | CTTCCTGTACCTGGCCAGCCACTATGAGAAGCTGAAGGGCTCCCCCGAGGATAA |
|     |             | TGAGCAGAAACAGCTGTTTGTGGAACAGCACAAGCACTACCTGGACGAGATCAT |
|     |             | CGAGCAGATCAGCGAGTTCTCCAAGAGAGTGATCCTGGCCGACGCTAATCTGGA |
|     |             | CAAAGTGCTGTCCGCCTACAACAAGCACCGGGATAAGCCCATCAGAGAGCAGGC |
|     |             | CGAGAATATCATCCACCTGTTTACCCTGACCAATCTGGGAGCCCCTGCCGCCTT |
|     |             | CAAGTACTTTGACACCACCATCGACCGGAAGAGGTACACCAGCACCAAAGAGGT |
|     |             | GCTGGACGCCACCCTGATCCACCAGAGCATCACCGGCCTGTACGAGACACGGAT |
|     |             | CGACCTGTCTCAGCTGGGAGGCGACAGCCCCAAGAAGAAGAGAAAGGTGGGAGT |
|     |             | CGACGGATCCAGCGGCTCCGAGACCCCAGGCACATCTGAGAGCGCCACCCCTGA |
|     |             | GTCCACCGGTATGAACAATTCACAGGGGAGAGTGACATTCGAAGACGTGACCGT |
|     |             | GAACTTCACCCAGGGAGAATGGCAGCGCTTGAACCCAGAACAAAGGAACCTCTA |
|     |             | TCGGGACGTGATGCTGGAAAACTACTCAAATTTGGTGAGCGTTGGGCAGGGTGA |
|     |             | GACCACTAAGCCTGACGTGATCCTGAGATTGGAACAGGGCAAGGAGCCTTGGCT |
|     |             | CGAGGAAGAGGAAGTCCTGGGCTCAGGGAGGGCCGAGAAAAACGGTGATATAGG |
|     |             | AGGCCAGATATGGAAGCCTAAGGACGTCAAGGAGAGCCTGAGCGCTAAACGTCC |
|     |             | GGCAGCAACCAAAAAAGCAGGTCAGGCCAAGAAAAAATGAGGATCCTGAGTCTA |
|     |             | GAAAAGATATATATAGGATTGAAGATCTCTCAGTTAAGTCTACAAAAAAAAAAA |
|     |             | AAAAAAAAAAAAAAAAAAAAAAAAAAAAAAAAAAAAAAAAAAAAAAAAAAAAAA |
|     |             | AAAAAAAAAAAAAAAAAAAAAAAAAAAAAAAAAAAAAAAAAAAAAAAAAAAAAA |
|     |             | AAGAAGAGCGAATTCACTGGCCGTCGTTTTACAACGTCGTGACTGGGAAAACCC |
|     |             | TGGCGTTACCCAACTTAATCGCCTTGCAGCACATCCCCCTTTCGCCAGCTGGCG |
|     |             | TAATAGCGAAGAGGCCCGCACCGATCGCCCTTCCCAACAGTTGCGCAGCCTGAA |
|     |             | TGGCGAATGGCGCCTGATGCGGTATTTTCTCCTTACGCATCTGTGCGGTATTTC |
|     |             | ACACCGCATATGGTGCACTCTCAGTACAATCTGCTCTGATGCCGCATAGTTAAG |
|     |             | CCAGCCCCGACACCCGCCAACACCCGCTGACGCGCCCTGACGGGCTTGTCTGCT |
|     |             | CCCGGCATCCGCTTACAGACAAGCTGTGACCGTCTCCGGGAGCTGCATGTGTCA |
|     |             | GAGGTTTTCACCGTCATCACCGAAACGCGCGATGCAGCTCTGGCCCGTGTCTCA |
|     |             | AAATCTCTGATGTTACATTGCACAAGATAAAAATATATCATCATGAACAATAAA |
|     |             | ACTGTCTGCTTACATAAACAGTAATACAAGGGGTGTTATGAGCCATATTCAACG |
|     |             | GGAAACGTCGAGGCCGCGATTAAATTCCAACATGGATGCTGATTTATATGGGTA |
|     |             | TAAATGGGCTCGCGATAATGTCGGGCAATCAGGTGCGACAATCTATCGCTTGTA |
|     |             | TGGGAAGCCCGATGCGCCAGAGTTGTTTCTGAAACATGGCAAAGGTAGCGTTGC |
|     |             | CAATGATGTTACAGATGAGATGGTCAGACTAAACTGGCTGACGGAATTTATGCC |
|     |             | TCTTCCGACCATCAAGCATTTTATCCGTACTCCTGATGATGCATGGTTACTCAC |
|     |             | CACTGCGATCCCCGGAAAAACAGCATTCCAGGTATTAGAAGAATATCCTGATTC |
|     |             | AGGTGAAAATATTGTTGATGCGCTGGCAGTGTTCCTGCGCCGGTTGCATTCGAT |

TABLE 18-continued

Sequence listing.

| SEQ | Description | Sequence |
|-----|-------------|----------|
| | | TCCTGTTTGTAATTGTCCTTTTAACAGCGATCGCGTATTTCGTCTCGCTCAGGC |
| | | GCAATCACGAATGAATAACGGTTTGGTTGATGCGAGTGATTTTGATGACGAGCG |
| | | TAATGGCTGGCCTGTTGAACAAGTCTGGAAAGAAATGCATAAACTTTTGCCATT |
| | | CTCACCGGATTCAGTCGTCACTCATGGTGATTTCTCACTTGATAACCTTATTTT |
| | | TGACGAGGGGAAATTAATAGGTTGTATTGATGTTGGACGAGTCGGAATCGCAGA |
| | | CCGATACCAGGATCTTGCCATCCTATGGAACTGCCTCGGTGAGTTTTCTCCTTC |
| | | ATTACAGAAACGGCTTTTTCAAAAATATGGTATTGATAATCCTGATATGAATAA |
| | | ATTGCAGTTTCATTTGATGCTCGATGAGTTTTTCTAATCAGAATTGGTTAATTG |
| | | GTTGTAACATTATTCAGATTGGGCTTGATTTAAAACTTCATTTTTAATTTAAAA |
| | | GGATCTAGGTGAAGATCCTTTTTGATAATCTCATGACCAAAATCCCTTAACGTG |
| | | AGTTTTCGTTCCACTGAGCGTCAGACCCCGTAGAAAAGATCAAAGGATCTTCTT |
| | | GAGATCCTTTTTTTCTGCGCGTAATCTGCTGCTTGCAAACAAAAAAACCACCGC |
| | | TACCAGCGGTGGTTTGTTTGCCGGATCAAGAGCTACCAACTCTTTTTCCGAAGG |
| | | TAACTGGCTTCAGCAGAGCGCAGATACCAAATACTGTTCTTCTAGTGTAGCCGT |
| | | AGTTAGGCCACCACTTCAAGAACTCTGTAGCACCGCCTACATACCTCGCTCTGC |
| | | TAATCCTGTTACCAGTGGCTGCTGCCAGTGGCGATAAGTCGTGTCTTACCGGGT |
| | | TGGACTCAAGACGATAGTTACCGGATAAGGCGCAGCGGTCGGGCTGAACGGGGG |
| | | GTTCGTGCACACAGCCCAGCTTGGAGCGAACGACCTACACCGAACTGAGATACC |
| | | TACAGCGTGAGCTATGAGAAAGCGCCACGCTTCCCGAAGGGAGAAAGGCGGACA |
| | | GGTATCCGGTAAGCGGCAGGGTCGGAACAGGAGAGCGCACGAGGGAGCTTCCAG |
| | | GGGGAAACGCCTGGTATCTTTATAGTCCTGTCGGGTTTCGCCACCTCTGACTTG |
| | | AGCGTCGATTTTTGTGATGCTCGTCAGGGGGGCGGAGCCTATGGAAAAACGCCA |
| | | GCAACGCGGCCTTTTTACGGTTCCTGGCCTTTTGCTGGCCTTTTGCTCACATGT |
| | | TCTTTCCTGCGTTATCCCCTGATTCTGTGGATAACCGTATTACCGCCTTTGAGT |
| | | GAGCTGATACCGCTCGCCGCAGCCGAACGACCGAGCGCAGCGAGTCAGTGAGCG |
| | | AGGAAGCGGCCCAATACGCAAACCGCCTCTCCCCGCGCGTTGGCCGATTCATTA |
| | | ATGCAGCTGGCACGACAGGTTTCCCGACTGGAAAGCGGGCAGTGAGCGCAACGC |
| | | AATTAATGTGAGTTAGCTCACTCATTAGGCACCCCAGGCTTTACACTTTATGCT |
| | | TCCGGCTCGTATGTTGTGTGGAATTGTGAGCGGATAACAATTTCACACAGGAAA |
| | | CAGCTATGACCATGATTACGCCAAGCTTAATACGACTCACTATA |
| 1252 | CRISPR-Off variant 1 amino acid sequence | MKRPAATKKAGQAKKKYNHDQEFDPPKVYPPVPAEKRKPIRVLSLEDGIATGLL |
| | | VLKDLGIQVDRYIASEVCEDSITVGMVRHQGKIMYVGDVRSVTQKHIQEWGPFD |
| | | LVIGGSPCNDLSIVNPARKGLYEGTGRLFFEFYRLLHDARPKEGDDRPFFWLFE |
| | | NVVAMGVSDKRDISRFLESNPVMIDAKEVSAAHRARYFWGNLPGMNRPLASTVN |
| | | DKLELQECLEHGRIAKFSKVRTITTRSNSIKQGKDQHFPVEMNEKEDILWCTEM |
| | | ERVFGFPVHYTDVSNMSRLARQRLLGRSWSVPVIRHLFAPLKEYFACVSSGNSN |
| | | ANSRGPSFSSGLVPLSLRGSHSPLEMYKTVPVWKREPVRVLSLFGDIKKELTTL |
| | | GFLENGSDPGRLKHLDDVTNTVRRDVEEWGPFDLVYGSTPPLGHACDHPPGWYL |
| | | FQFHRVLQYARPRPGSPQAFFWMFVDNLVLTEDDRAVATRFLETDPVTIQDVCG |
| | | RAVRNAVHVWSNIPAVKSRHSALFSQEESFLRAQDRQRAKPPARGPAKLVKNCF |
| | | LPLREYFKYFSTEFTSSLGGPSSGAPPPSGGSPAGSPTSTEEGTSESATPESGP |
| | | GTSTEPSEGSAPGSPAGSPTSTEEGTSTEPSEGSAPGTSTEPSELEDKKYSIGL |
| | | AIGTNSVGWAVITDEYKVPSKKFKVLGNTDRHSIKKNLIGALLFDSGETAEATR |
| | | LKRTARRRYTRRKNRICYLQEIFSNEMAKVDDSFFHRLEESFLVEEDKKHERHP |
| | | IFGNIVDEVAYHEKYPTIYHLRKKLVDSTDKADLRLIYLALAHMIKERGHFLIE |
| | | GDLNPDNSDVDKLFIQLVQTYNQLFEENPINASGVDAKAILSARLSKSRRLENL |
| | | IAQLPGEKKNGLFGNLIALSLGLTPNFKSNFDLAEDAKLQLSKDTYDDDLDNLL |
| | | AQIGDQYADLFLAAKNLSDAILLSDILRVNTEITKAPLSASMIKRYDEHHQDLT |
| | | LLKALVRQQLPEKYKEIFFDQSKNGYAGYIDGGASQEEFYKFIKPILEKMDGTE |
| | | ELLVKLNREDLLRKQRTFDNGSIPHQIHLGELHAILRRQEDFYPFLKDNREKIE |
| | | KILTFRIPYYVGPLARGNSRFAWMTRKSEETITPWNFEEVVDKGASAQSFIERM |
| | | TNFDKNLPNEKVLPKHSLLYEYFTVYNELTKVKYVTEGMRKPAFLSGEQKKAIV |
| | | DLLFKTNRKVTVKQLKEDYFKKIECFDSVEISGVEDRFNASLGTYHDLLKIIKD |
| | | KDFLDNEENEDILEDIVLTLTLFEDREMIEERLKTYAHLEDDKVMKQLKRRRYT |
| | | GWGRLSRKLINGIRDKQSGKTILDFLKSDGFANRNFMQLIHDDSLTFKEDIQKA |
| | | QVSGQGDSLHEHIANLAGSPAIKKGILQTVKVVDELVKVMGRHKPENIVIEMAR |
| | | ENQTTQKGQKNSRERMKRIEEGIKELGSQILKEHPVENTQLQNEKLYLYYLQNG |
| | | RDMYVDQELDINRLSDYDVDAIVPQSFLKDDSIDNKVLTRSDKNRGKSDNVPSE |
| | | EVVKKMKNYWRQLLNAKLITQRKFDNLTKAERGGLSELDKAGFIKRQLVETRQI |
| | | TKHVAQILDSRMNTKYDENDKLIREVKVITLKSKLVSDFRKDFQFYKVREINNY |
| | | HHAHDAYLNAVVGTALIKKYPKLESEFVYGDYKVYDVRKMIAKSEQEIGKATAK |
| | | YFFYSNIMNFFKTEITLANGEIRKRPLIETNGETGEIVWDKGRDFATVRKVLSM |
| | | PQVNIVKKTEVQTGGFSKESILPKRNSDKLIARKKDWDPKKYGGFDSPTVAYSV |
| | | LVVAKVEKGKSKKLKSVKELLGITIMERSSFEKNPIDFLEAKGYKEVKKDLIIK |
| | | LPKYSLFELENGRKRMLASAGELQKGNELALPSKYVNFLYLASHYEKLKGSPED |
| | | NEQKQLFVEQHKHYLDEIIEQISEFSKRVILADANLDKVLSAYNKHRDKPIREQ |
| | | AENIIHLFTLTNLGAPAAFKYFDTTIDRKRYTSTKEVLDATLIHQSITGLYETR |
| | | IDLSQLGGDSPKKKRKVGVDGSSGSETPGTSESATPESTGMNNSQGRVTFEDVT |
| | | VNFTQGEWQRLNPEQRNLYRDVMLENYSNLVSVGQGETTKPDVILRLEQGKEPW |
| | | LEEEEVLGSGRAEKNGDIGGQIWKPKDVKESLSAKRPAATKKAGQAKKK |
| 1253 | CRISPR-Off variant 2 plasmid sequence | AGAAACTAGCGTAAATTCAAATATAGGTCAGGCTTCAACGTCAACAAATATGAT |
| | | GAAGAGACCTGCTGCCACCAAGAAGGCCGGCCAGGCCAAGAAAAAGTACAATCA |
| | | CGATCAGGAGTTCGACCCCCCTAAGGTGTACCCACCAGTGCCTGCAGAGAAGAG |
| | | GAAGCCAATCCGGGTGCTGAGCCTGTTTGATGGCATCGCCACCGGCCTGCTGGT |

TABLE 18-continued

| Sequence listing. | | |
|---|---|---|
| SEQ | Description | Sequence |
| | | GCTGAAGGATCTGGGCATCCAGGTGGACCGGTACATCGCCTCCGAGGTGTGCGA |
| | | GGATTCTATCACCGTGGGCATGGTGCGCCACCAGGGCAAGATCATGTATGTGGG |
| | | CGACGTGCGGTCCGTGACACAGAAGCACATCCAGGAGTGGGGCCCATTCGATCT |
| | | GGTGATCGGCGGCAGCCCCTGTAATGACCTGTCCATCGTGAACCCTGCAAGGAA |
| | | GGGACTGTACGAGGGAACCGGCCGGCTGTTCTTTGAGTTTTATAGACTGCTGCA |
| | | CGACGCCAGGCCTAAGGAGGGCGACGATAGACCATTCTTTTGGCTGTTCGAGAA |
| | | TGTGGTGGCTATGGGCGTGAGCGATAAGAGGGACATCTCCAGGTTTCTGGAGTC |
| | | TAACCCCGTGATGATCGATGCAAAGGAGGTGTCCGCCGCACACAGAGCCAGGTA |
| | | TTTCTGGGGCAATCTGCCAGGAATGAACAGGCCACTGGCAAGCACCGTGAATGA |
| | | CAAGCTGGAGCTGCAGGAGTGCCTGGAGCACGGAAGGATCGCCAAGTTTTCCAA |
| | | GGTGCGCACAATCACCACACGGAGCAATTCCATCAAGCAGGGCAAGGATCAGCA |
| | | CTTCCCCGTGTTCATGAACGAGAAGGAGGACATCCTGTGGTGTACCGAGATGGA |
| | | GAGAGTGTTCGGCTTTCCAGTGCACTACACAGACGTGTCTAACATGAGCAGGCT |
| | | GGCAAGGCAGCGGCTGCTGGGCAGATCTTGGAGCGTGCCCGTGATCAGGCACCT |
| | | GTTCGCCCCTCTGAAGGAGTATTTTGCCTGCGTGAGCAGCGGCAACTCCAATGC |
| | | CAACAGCCGGGGCCCCTCTTTCAGCTCCGGATTGGTGCCTCTGAGCCTGAGGGG |
| | | CTCCCACAGCCCTATGGAGATATACAAGACAGTGTCTGCATGGAAGAGACAGCC |
| | | AGTGAGGGTGCTGAGCCTTTTTGGGAATATTGATAAAGAACTAAAGAGTTTGGG |
| | | CTTTTTGGAAATCGGTTCTGATTCTGAGGGAGGAACACTGAAGTACGTGGAAGA |
| | | TGTCACGAATGTCGTGAGGAGAGACGTGGAGAAATGGGGCCCCTTTGACCTGGT |
| | | GTATGGCTCGACGAATCCCCTAGGCAACTCTTGTGACCGCTGTCCTGGCTGGTA |
| | | CATGTTCCAATTCCACCGGATCCTGCAGTATGCGCGGCCTCGCCAAGACAGTCA |
| | | GAAGCCCTTCTTCTGGATATTTATGGACAATCTGCTGCTGACTGAGGATGATCA |
| | | AGTGACAACTGTCCGCTTCCTTCAGACAGAGGCTGTGACCCTCCAGGATGTCCG |
| | | TGGCAGAGTCCTCCAGAATGCTGTGAGGGTATGGAGCAACATTCCAGGACTGAA |
| | | GAGTAAGCACTCAGTCCTGACGCCAAAGGAAGAACAGTCTCTGCAAGCCCAAGT |
| | | CAGAACCAGAAGCAAGCTGCCCACCCAGGTTAACCCCCTGGTGAAGACCTGCCT |
| | | TCTCCCCCTGAGAGAGTACTTCAAGTGTTTTTCTCAGAATTCACTTCCTCTTGG |
| | | AGGACCCTCCTCTGGCGCCCCACCACCTAGCGGCGGCTCCCCTGCCGGCTCTCC |
| | | AACCAGCACAGAGGAGGGCACCAGCGAGTCCGCCACACCAGAGTCTGGACCTGG |
| | | CACCAGCACAGAGCCATCCGAGGGCTCTGCCCCAGGCTCTCCTGCAGGCAGCCC |
| | | TACCTCCACCGAAGAGGGCACCAGCACAGAGCCTTCTGAGGGCAGCGCCCCAGG |
| | | CACCTCTACAGAGCCAAGCGAGCTCGAGGACAAGAAGTACAGCATCGGCCTGGC |
| | | CATCGGCACCAACTCTGTGGGCTGGGCCGTGATCACCGACGAGTACAAGGTGCC |
| | | CAGCAAGAAATTCAAGGTGCTGGGCAACACCGACCGGCACAGCATCAAGAAGAA |
| | | CCTGATCGGAGCCCTGCTGTTCGACAGCGGCGAAACAGCCGAGGCCACCCGGCT |
| | | GAAGAGAACCGCCAGAAGAAGATACACCAGACGGAAGAACCGGATCTGCTATCT |
| | | GCAAGAGATCTTCAGCAACGAGATGGCCAAGGTGGACGACAGCTTCTTCCACAG |
| | | ACTGGAAGAGTCCTTCCTGGTGGAAGAGGATAAGAAGCACGAGCGGCACCCCAT |
| | | CTTCGGCAACATCGTGGACGAGGTGGCCTACCACGAGAAGTACCCCACCATCTA |
| | | CCACCTGAGAAAGAAACTGGTGGACAGCACCGACAAGGCCGACCTGCGGCTGAT |
| | | CTATCTGGCCCTGGCCCACATGATCAAGTTCCGGGGCCACTTCCTGATCGAGGG |
| | | CGACCTGAACCCCGACAACAGCGACGTGGACAAGCTGTTCATCCAGCTGGTGCA |
| | | GACCTACAACCAGCTGTTCGAGGAAAACCCCATCAACGCCAGCGGCGTGGACGC |
| | | CAAGGCCATCCTGTCTGCCAGACTGAGCAAGAGCAGACGGCTGGAAAATCTGAT |
| | | CGCCCAGCTGCCCGGCGAGAAGAAGAATGGCCTGTTCGGCAACCTGATTGCCCT |
| | | GAGCCTGGGCCTGACCCCCAACTTCAAGAGCAACTTCGACCTGGCCGAGGATGC |
| | | CAAACTGCAGCTGAGCAAGGACACCTACGACGACGACCTGGACAACCTGCTGGC |
| | | CCAGATCGGCGACCAGTACGCCGACCTGTTTCTGGCCGCCAAGAACCTGTCCGA |
| | | CGCCATCCTGCTGAGCGACATCCTGAGAGTGAACACCGAGATCACCAAGGCCCC |
| | | CCTGAGCGCCTCTATGATCAAGAGATACGACGAGCACCACCAGGACCTGACCCT |
| | | GCTGAAAGCTCTCGTGCGGCAGCAGCTGCCTGAGAAGTACAAAGAGATTTTCTT |
| | | CGACCAGAGCAAGAACGGCTACGCCGGCTACATTGACGGCGGAGCCAGCCAGGA |
| | | AGAGTTCTACAAGTTCATCAAGCCCATCCTGGAAAAGATGGACGGCACCGAGGA |
| | | ACTGCTCGTGAAGCTGAACAGAGAGGACCTGCTGCGGAAGCAGCGGACCTTCGA |
| | | CAACGGCAGCATCCCCCACCAGATCCACCTGGGAGAGCTGCACGCCATTCTGCG |
| | | GCGGCAGGAAGATTTTTACCCATTCCTGAAGGACAACCGGGAAAAGATCGAGAA |
| | | GATCCTGACCTTCCGCATCCCCTACTACGTGGGCCCTCTGGCCAGGGGAAACAG |
| | | CAGATTCGCCTGGATGACCAGAAAGAGCGAGGAAACCATCACCCCCTGGAACTT |
| | | CGAGGAAGTGGTGGACAAGGGCGCTTCCGCCCAGAGCTTCATCGAGCGGATGAC |
| | | CAACTTCGATAAGAACCTGCCCAACGAGAAGGTGCTGCCCAAGCACAGCCTGCT |
| | | GTACGAGTACTTCACCGTGTATAACGAGCTGACCAAAGTGAAATACGTGACCGA |
| | | GGGAATGAGAAAGCCCGCCTTCCTGAGCGGCGAGCAGAAAAAGGCCATCGTGGA |
| | | CCTGCTGTTCAAGACCAACCGGAAAGTGACCGTGAAGCAGCTGAAAGAGGACTA |
| | | CTTCAAGAAAATCGAGTGCTTCGACTCCGTGGAAATCTCCGGCGTGGAAGATCG |
| | | GTTCAACGCCTCCCTGGGCACATACCACGATCTGCTGAAAATTATCAAGGACAA |
| | | GGACTTCCTGGACAATGAGGAAAACGAGGACATTCTGGAAGATATCGTGCTGAC |
| | | CCTGACACTGTTTGAGGACAGAGAGATGATCGAGGAACGGCTGAAAACCTATGC |
| | | CCACCTGTTCGACGACAAAGTGATGAAGCAGCTGAAGCGGCGGAGATACACCGG |
| | | CTGGGGCAGGCTGAGCCGGAAGCTGATCAACGGCATCCGGGACAAGCAGTCCGG |
| | | CAAGACAATCCTGGATTTCCTGAAGTCCGACGGCTTCGCCAACAGAAACTTCAT |
| | | GCAGCTGATCCACGACGACAGCCTGACCTTTAAAGAGGACATCCAGAAAGCCCA |
| | | GGTGTCCGGCCAGGGCGATAGCCTGCACGAGCACATTGCCAATCTGGCCGGCAG |
| | | CCCCGCCATTAAGAAGGGCATCCTGCAGACAGTGAAGGTGGTGGACGAGCTCGT |
| | | GAAAGTGATGGGCCGGCACAAGCCCGAGAACATCGTGATCGAAATGGCCAGAGA |
| | | GAACCAGACCACCCAGAAGGGACAGAAGAACAGCCGCGAGAGAATGAAGCGGAT |

TABLE 18-continued

Sequence listing.

| SEQ | Description | Sequence |
|-----|-------------|----------|
| | | CGAAGAGGGCATCAAAGAGCTGGGCAGCCAGATCCTGAAAGAACACCCCGTGGA |
| | | AAACACCCAGCTGCAGAACGAGAAGCTGTACCTGTACTACCTGCAGAATGGGCG |
| | | GGATATGTACGTGGACCAGGAACTGGACATCAACCGGCTGTCCGACTACGATGT |
| | | GGACGCCATCGTGCCTCAGAGCTTTCTGAAGGACGACTCCATCGACAACAAGGT |
| | | GCTGACCAGAAGCGACAAGAACCGGGGCAAGAGCGACAACGTGCCCTCCGAAGA |
| | | GGTCGTGAAGAAGATGAAGAACTACTGGCGGCAGCTGCTGAACGCCAAGCTGAT |
| | | TACCCAGAGAAAGTTCGACAATCTGACCAAGGCCGAGAGAGGCGGCCTGAGCGA |
| | | ACTGGATAAGGCCGGCTTCATCAAGAGACAGCTGGTGGAAACCCGGCAGATCAC |
| | | AAAGCACGTGGCACAGATCCTGGACTCCCGGATGAACACTAAGTACGACGAGAA |
| | | TGACAAGCTGATCCGGGAAGTGAAAGTGATCACCCTGAAGTCCAAGCTGGTGTC |
| | | CGATTTCCGGAAGGATTTCCAGTTTTACAAAGTGCGCGAGATCAACAACTACCA |
| | | CCACGCCCACGACGCCTACCTGAACGCCGTCGTGGGAACCGCCCTGATCAAAAA |
| | | GTACCCTAAGCTGGAAAGCGAGTTCGTGTACGGCGACTACAAGGTGTACGACGT |
| | | GCGGAAGATGATCGCCAAGAGCGAGCAGGAAATCGGCAAGGCTACCGCCAAGTA |
| | | CTTCTTCTACAGCAACATCATGAACTTTTTCAAGACCGAGATTACCCTGGCCAA |
| | | CGGCGAGATCCGGAAGCGGCCTCTGATCGAGACAAACGGCGAAACCGGGGAGAT |
| | | CGTGTGGGATAAGGGCCGGGATTTTGCCACCGTGCGGAAAGTGCTGAGCATGCC |
| | | CCAAGTGAATATCGTGAAAAAGACCGAGGTGCAGACAGGCGGCTTCAGCAAAGA |
| | | GTCTATCCTGCCCAAGAGGAACAGCGATAAGCTGATCGCCAGAAAGAAGGACTG |
| | | GGACCCTAAGAAGTACGGCGGCTTCGACAGCCCCACCGTGGCCTATTCTGTGCT |
| | | GGTGGTGGCCAAAGTGGAAAAGGGCAAGTCCAAGAAACTGAAGAGTGTGAAAGA |
| | | GCTGCTGGGGATCACCATCATGGAAAGAAGCAGCTTCGAGAAGAATCCCATCGA |
| | | CTTTCTGGAAGCCAAGGGCTACAAAGAAGTGAAAAAGGACCTGATCATCAAGCT |
| | | GCCTAAGTACTCCCTGTTCGAGCTGGAAAACGGCCGGAAGAGAATGCTGGCCTC |
| | | TGCCGGCGAACTGCAGAAGGGAAACGAACTGGCCCTGCCCTCCAAATATGTGAA |
| | | CTTCCTGTACCTGGCCAGCCACTATGAGAAGCTGAAGGGCTCCCCCGAGGATAA |
| | | TGAGCAGAAACAGCTGTTTGTGGAACAGCACAAGCACTACCTGGACGAGATCAT |
| | | CGAGCAGATCAGCGAGTTCTCCAAGAGAGTGATCCTGGCCGACGCTAATCTGGA |
| | | CAAAGTGCTGTCCGCCTACAACAAGCACCGGGATAAGCCCATCAGAGAGCAGGC |
| | | CGAGAATATCATCCACCTGTTTACCCTGACCAATCTGGGAGCCCCTGCCGCCTT |
| | | CAAGTACTTTGACACCACCATCGACCGGAAGAGGTACACCAGCACCAAAGAGGT |
| | | GCTGGACGCCACCCTGATCCACCAGAGCATCACCGGCCTGTACGAGACACGGAT |
| | | CGACCTGTCTCAGCTGGGGAGGCGACAGCCCCAAGAAGAAGAGAAAGGTGGGAGT |
| | | CGACGGATCCAGCGGCTCCGAGACCCCAGGCACATCTGAGAGCGCCACCCCTGA |
| | | GTCCACCGGTATGAACAATTCACAGGGGGAGAGTGACATTCGAAGACGTGACCGT |
| | | GAACTTCACCCAGGGAGAATGGCAGCGCTTGAACCCAGAACAAAGGAACCTCTA |
| | | TCGGGACGTGATGCTGGAAAACTACTCAAATTTGGTGAGCGTTGGGCAGGGTGA |
| | | GACCACTAAGCCTGACGTGATCCTGAGATTGGAACAGGGCAAGGAGCCTTGGCT |
| | | CGAGGAAGAGGAAGTCCTGGGCTCAGGGAGGGCCGAGAAAAACGGTGATATAGG |
| | | AGGCCAGATATGGAAGCCTAAGGACGTCAAGGAGAGCCTGAGCGCTGCTAAACG |
| | | TCCGGCAGCAACCAAAAAAGCAGGTCAGGCCAAGAAAAAATGAGGATCCTGAGT |
| | | CTAGAAAGAGCCTTCTGAGCCCAGCGACTTCTGAAGGGCCCCTTGCAAAGTAAT |
| | | AGGGCTTCTGCCTAAGCCTCTCCCTCCAGCCAATAGGCAGCTTTCTTAACTATC |
| | | CTAACAAGCCTTGGACCAAATGGAAATAAAGCTTTTTTGATGCAGTGTTAATTAA |
| | | AAAAAAAAAAAAAAAAAAAAAAAAAAAAAAAAAAAAAAAAAAAAAAAAAAAAAA |
| | | AAAAAAAAAAAAAAAAAAAAAAAAAAAAAAAAAAAAAAAAAAAAAAAAAAAAAA |
| | | AAAAAAAAAAGAAGAGCGAATTCACTGGCCGTCGTTTTACAACGTCGTGACTG |
| | | GGAAAACCCTGGCGTTACCCAACTTAATCGCCTTGCAGCACATCCCCCTTTCGC |
| | | CAGCTGGCGTAATAGCGAAGAGGCCCGCACCGATCGCCCTTCCCAACAGTTGCG |
| | | CAGCCTGAATGGCGAATGGCGCCTGATGCGGTATTTTCTCCTTACGCATCTGTG |
| | | CGGTATTTCACACCGCATATGGTGCACTCTCAGTACAATCTGCTCTGATGCCGC |
| | | ATAGTTAAGCCAGCCCCGACACCCGCCAACACCCGCTGACGCGCCCTGACGGGC |
| | | TTGTCTGCTCCCGGCATCCGCTTACAGACAAGCTGTGACCGTCTCCGGGAGCTG |
| | | CATGTGTCAGAGGTTTTCACCGTCATCACCGAAACGCGCGATGCAGCTCTGGCC |
| | | CGTGTCTCAAAATCTCTGATGTTACATTGCACAAGATAAAAATATATCATCATG |
| | | AACAATAAAACTGTCTGCTTACATAAACAGTAATACAAGGGGTGTTATGAGCCA |
| | | TATTCAACGGGAAACGTCGAGGCCGCGATTAAATTCCAACATGGATGCTGATTT |
| | | ATATGGGTATAAATGGGCTCGCGATAATGTCGGGCAATCAGGTGCGACAATCTA |
| | | TCGCTTGTATGGGAAGCCCGATGCGCCAGAGTTGTTTCTGAAACATGGCAAAGG |
| | | TAGCGTTGCCAATGATGTTACAGATGAGATGGTCAGACTAAACTGGCTGACGGA |
| | | ATTTATGCCTCTTCCGACCATCAAGCATTTTATCCGTACTCCTGATGATGCATG |
| | | GTTACTCACCACTGCGATCCCCGGAAAAACAGCATTCCAGGTATTAGAAGAATA |
| | | TCCTGATTCAGGTGAAAATATTGTTGATGCGCTGGCAGTGTTCCTGCGCCGGTT |
| | | GCATTCGATTCCTGTTTGTAATTGTCCTTTTAACAGCGATCGCGTATTTCGTCT |
| | | CGCTCAGGCGCAATCACGAATGAATAACGGTTTGGTTGATGCGAGTGATTTTGA |
| | | TGACGAGCGTAATGGCTGGCCTGTTGAACAAGTCTGGAAAGAAATGCATAAACT |
| | | TTTGCCATTCTCACCGGATTCAGTCGTCACTCATGGTGATTTCTCACTTGATAA |
| | | CCTTATTTTTGACGAGGGGAAATTAATAGGTTGTATTGATGTTGGACGAGTCGG |
| | | AATCGCAGACCGATACCAGGATCTTGCCATCCTATGGAACTGCCTCGGTGAGTT |
| | | TTCTCCTTCATTACAGAAACGGCTTTTTCAAAAATATGGTATTGATAATCCTGA |
| | | TATGAATAAATTGCAGTTTCATTTGATGCTCGATGAGTTTTTCTAATCAGAATT |
| | | GGTTAATTGGTTGTAACATTATTCAGATTGGGCTTGATTTAAAACTTCATTTTT |
| | | AATTTAAAAGGATCTAGGTGAAGATCCTTTTTGATAATCTCATGACCAAAATCC |
| | | CTTAACGTGAGTTTTCGTTCCACTGAGCGTCAGACCCCGTAGAAAAGATCAAAG |
| | | GATCTTCTTGAGATCCTTTTTTTTCTGCGCGTAATCTGCTGCTTGCAAACAAAAA |
| | | AACCACCGCTACCAGCGGTGGTTTGTTTGCCGGATCAAGAGCTACCAACTCTTT |

TABLE 18-continued

Sequence listing.

| SEQ | Description | Sequence |
|---|---|---|
| | | TTCCGAAGGTAACTGGCTTCAGCAGAGCGCAGATACCAAATACTGTTCTTCTAG<br>TGTAGCCGTAGTTAGGCCACCACTTCAAGAACTCTGTAGCACCGCCTACATACC<br>TCGCTCTGCTAATCCTGTTACCAGTGGCTGCTGCCAGTGGCGATAAGTCGTGTC<br>TTACCGGGTTGGACTCAAGACGATAGTTACCGGATAAGGCGCAGCGGTCGGGCT<br>GAACGGGGGGTTCGTGCACACAGCCCAGCTTGGAGCGAACGACCTACACCGAAC<br>TGAGATACCTACAGCGTGAGCTATGAGAAAGCGCCACGCTTCCCGAAGGGAGAA<br>AGGCGGACAGGTATCCGGTAAGCGGCAGGGTCGGAACAGGAGAGCGCACGAGGG<br>AGCTTCCAGGGGGAAACGCCTGGTATCTTTATAGTCCTGTCGGGTTTCGCCACC<br>TCTGACTTGAGCGTCGATTTTTGTGATGCTCGTCAGGGGGGCGGAGCCTATGGA<br>AAAACGCCAGCAACGCGGCCTTTTTACGGTTCCTGGCCTTTTGCTGGCCTTTTG<br>CTCACATGTTCTTTCCTGCGTTATCCCCTGATTCTGTGGATAACCGTATTACCG<br>CCTTTGAGTGAGCTGATACCGCTCGCCGCAGCCGAACGACCGAGCGCAGCGAGT<br>CAGTGAGCGAGGAAGCGGCCCAATACGCAAACCGCCTCTCCCCGCGCGTTGGCC<br>GATTCATTAATGCAGCTGGCACGACAGGTTTCCCGACTGGAAAGCGGGCAGTGA<br>GCGCAACGCAATTAATGTGAGTTAGCTCACTCATTAGGCACCCCAGGCTTTACA<br>CTTTATGCTTCCGGCTCGTATGTTGTGTGGAATTGTGAGCGGATAACAATTTCA<br>CACAGGAAACAGCTATGACCATGATTACGCCAAGCTTTAATACGACTCACTATA |
| 1254 | CRISPR-Off<br>variant 2 amino<br>acid sequence | MKRPAATKKAGQAKKKYNHDQEFDPPKVYPPVPAEKRKPIRVLSLEDGIATGLL<br>VLKDLGIQVDRYIASEVCEDSITVGMVRHQGKIMYVGDVRSVTQKHIQEWGPED<br>LVIGGSPCNDLSIVNPARKGLYEGTGRLFFEFYRLLHDARPKEGDDRPFFWLFE<br>NVVAMGVSDKRDISRFLESNPVMIDAKEVSAAHRARYFWGNLPGMNRPLASTVN<br>DKLELQECLEHGRIAKFSKVRTITTRSNSIKQGKDQHFPVFMNEKEDILWCTEM<br>ERVFGFPVHYTDVSNMSRLARQRLLGRSWSVPVIRHLFAPLKEYFACVSSGNSN<br>ANSRGPSFSSGLVPLSLRGSHSPMEIYKTVSAWKRQPVRVLSLFGNIDKELKSL<br>GFLEIGSDSEGGTLKYVEDVTNVVRRDVEKWGPFDLVYGSTNPLGNSCDRCPGW<br>YMFQFHRILQYARPRQDSQKPFFWIFMDNLLLTEDDQVTTVRFLQTEAVTLQDV<br>RGRVLQNAVRVWSNIPGLKSKHSVLTPKEEQSLQAQVRTRSKLPTQVNPLVKTC<br>LLPLREYFKCFSQNSLPLGGPSSGAPPPSGGSPAGSPTSTEEGTSESATPESGP<br>GTSTEPSEGSAPGSPAGSPTSTEEGTSTEPSEGSAPGTSTEPSELEDKKYSIGL<br>AIGTNSVGWAVITDEYKVPSKKFKVLGNTDRHSIKKNLIGALLEDSGETAEATR<br>LKRTARRRYTRRKNRICYLQEIFSNEMAKVDDSFFHRLEESFLVEEDKKHERHP<br>IFGNIVDEVAYHEKYPTIYHLRKKLVDSTDKADLRLIYLALAHMIKERGHFLIE<br>GDLNPDNSDVDKLFIQLVQTYNQLFEENPINASGVDAKAILSARLSKSRRLENL<br>IAQLPGEKKNGLFGNLIALSLGLTPNFKSNFDLAEDAKLQLSKDTYDDDLDNLL<br>AQIGDQYADLFLAAKNLSDAILLSDILRVNTEITKAPLSASMIKRYDEHHQDLT<br>LLKALVRQQLPEKYKEIFFDQSKNGYAGYIDGGASQEEFYKFIKPILEKMDGTE<br>ELLVKLNREDLLRKQRTFDNGSIPHQIHLGELHAILRRQEDFYPFLKDNREKIE<br>KILTFRIPYYVGPLARGNSRFAWMTRKSEETITPWNFEEVVDKGASAQSFIERM<br>TNFDKNLPNEKVLPKHSLLYEYFTVYNELTKVKYVTEGMRKPAFLSGEQKKAIV<br>DLLFKTNRKVTVKQLKEDYFKKIECFDSVEISGVEDRENASLGTYHDLLKIIKD<br>KDFLDNEENEDILEDIVLTLTLFEDREMIEERLKTYAHLEDDKVMKQLKRRRYT<br>GWGRLSRKLINGIRDKQSGKTILDFLKSDGFANRNFMQLIHDDSLTFKEDIQKA<br>QVSGQGDSLHEHIANLAGSPAIKKGILQTVKVVDELVKVMGRHKPENIVIEMAR<br>ENQTTQKGQKNSRERMKRIEEGIKELGSQILKEHPVENTQLQNEKLYLYYLQNG<br>RDMYVDQELDINRLSDYDVDAIVPQSFLKDDSIDNKVLTRSDKNRGKSDNVPSE<br>EVVKKMKNYWRQLLNAKLITQRKEDNLTKAERGGLSELDKAGFIKRQLVETRQI<br>TKHVAQILDSRMNTKYDENDKLIREVKVITLKSKLVSDFRKDFQFYKVREINNY<br>HHAHDAYLNAVVGTALIKKYPKLESEFVYGDYKVYDVRKMIAKSEQEIGKATAK<br>YFFYSNIMNFFKTEITLANGEIRKRPLIETNGETGEIVWDKGRDFATVRKVLSM<br>PQVNIVKKTEVQTGGFSKESILPKRNSDKLIARKKDWDPKKYGGFDSPTVAYSV<br>LVVAKVEKGKSKKLKSVKELLGITIMERSSFEKNPIDFLEAKGYKEVKKDLIIK<br>LPKYSLFELENGRKRMLASAGELQKGNELALPSKYVNFLYLASHYEKLKGSPED<br>NEQKQLFVEQHKHYLDEIIEQISEFSKRVILADANLDKVLSAYNKHRDKPIREQ<br>AENIIHLFTLTNLGAPAAFKYFDTTIDRKRYTSTKEVLDATLIHQSITGLYETR<br>IDLSQLGGDSPKKKRKVGVDGSSGSETPGTSESATPESTGMNNSQGRVTFEDVT<br>VNFTQGEWQRLNPEQRNLYRDVMLENYSNLVSVGQGETTKPDVILRLEQGKEPW<br>LEEEEVLGSGRAEKNGDIGGQIWKPKDVKESLSAAKRPAATKKAGQAKKK |
| 1255 | CRISPR-Off<br>variant 3 plasmid<br>sequence | AGAAACTAGCGTAAATTCAAATATAGGTCAGGCTTCAACGTCAACAAATATGAT<br>GAAGAGACCTGCTGCCACCAAGAAGGCCGGCCAGGCCAAGAAAAAGTACAATCA<br>CGATCAGGAGTTCGACCCCCCTAAGGTGTACCCACCAGTGCCTGCAGAGAAGAG<br>GAAGCCAATCCGGGTGCTGAGCCTGTTTGATGGCATCGCCACCGGCCTGCTGGT<br>GCTGAAGGATCTGGGCATCCAGGTGGACCGGTACATCGCCTCCGAGGTGTGCGA<br>GGATTCTATCACCGTGGGCATGGTGCGCCACCAGGGCAAGATCATGTATGTGGG<br>CGACGTGCGGTCCGTGACACAGAAGCACATCCAGGAGTGGGGCCCCATTCGATCT<br>GGTCGATCGGCGGCAGCCCCTGTAATGACCTGTCCATCGTGAACCCTGCAAGGAA<br>GGGACTGTACGAGGGAACCGGCCGGCTGTTCTTTGAGTTTTATAGACTGCTGCA<br>CGACGCCAGGCCTAAGGAGGGCGACGATAGACCATTCTTTTGGCTGTTCGAGAA<br>TGTGGTGGCTATGGGCGTGAGCGATAAGAGGGACATCTCCAGGTTTCTGGAGTC<br>TAACCCCGTGATGATCGATGCAAAGGAGGTGTCCGCCGCACACAGAGCCAGGTA<br>TTTCTGGGGCAATCTGCCCAGGAATGAACAGGCCACTGGCAAGCACCGTGAATGA<br>CAAGCTGGAGCTGCAGGAGTGCCTGGAGCACGGAAGGATCGCCAAGTTTTCCAA<br>GGTGCGCACAATCACCACACGGAGCAATTCCATCAAGCAGGGCAAGGATCAGCA<br>CTTCCCCGTGTTCATGAACGAGAAGGAGGACATCCTGTGGTGTACCGAGATGGA<br>GAGAGTGTTCGGCTTTCCAGTGCACTACACAGACGTGTCTAACATGAGCAGGCT |

TABLE 18-continued

Sequence listing.

| SEQ | Description | Sequence |
|-----|-------------|----------|
|  |  | GGCAAGGCAGCGGCTGCTGGGCAGATCTTGGAGCGTGCCCGTGATCAGGCACCT |
|  |  | GTTCGCCCCTCTGAAGGAGTATTTTGCCTGCGTGAGCAGCGGCAACTCCAATGC |
|  |  | CAACAGCCGGGGCCCCTCTTTCAGCTCCGGATTGGTGCCTCTGAGCCTGAGGGG |
|  |  | CTCCCACAGTCCCCTTGAGATGTATAAAACTGTGCCTGTGTGGAAGAGAGAGCC |
|  |  | AGTGCGGGTGCTGTCCCTTTTTGGTGACATCAAGAAAGAGCTGACGACTTTGGG |
|  |  | CTTTCTGGAAAACGGCTCTGACCCGGGCCGACTGAAACATTTGGACGATGTCAC |
|  |  | CAATACGGTGAGGAGGGACGTGGAAGAATGGGGCCCGTTCGACCTCGTGTACGG |
|  |  | CTCCACGCCGCCCCTCGGCCACGCCTGTGACCATCCTCCCGGGTGGTACCTGTT |
|  |  | CCAGTTCCACCGTGTGCTTCAGTACGCGAGGCCCAGGCCGGGCAGCCCGCAGGC |
|  |  | CTTCTTCTGGATGTTTGTGGACAACCTGGTGCTGACCGAGGATGACCGGGCTGT |
|  |  | AGCCACTCGCTTCCTGGAGACTGACCCGGTGACCATCCAGGACGTCTGTGGCAG |
|  |  | AGCTGTCCGGAACGCCGTGCACGTGTGGAGCAACATCCCGGCCGTGAAAAGCAG |
|  |  | GCACTCGGCCCTGTTTTCCCAGGAGGAATCATTCCTGCGGGCTCAGGACAGGCA |
|  |  | GAGAGCAAAGCCCCCCGCCCGGGGGCCAGCCAAGCTGGTGAAGAATTGTTTTCT |
|  |  | CCCCCTGAGAGAATATTTCAAGTATTTTTCAACAGAATTCACTTCCTCTTTGGG |
|  |  | AGGACCCTCCTCTGGCGCCCCACCACCTAGCGGCGGCTCCCCTGCCGGCTCTCC |
|  |  | AACCAGCACAGAGGAGGGCACCAGCGAGTCCGCCACACCAGAGTCTGGACCTGG |
|  |  | CACCAGCACAGAGCCATCCGAGGGCTCTGCCCCAGGCTCTCCTGCAGGCAGCCC |
|  |  | TACCTCCACCGAAGAGGGCACCAGCACAGAGCCTTCTGAGGGCAGCGCCCCAGG |
|  |  | CACCTCTACAGAGCCAAGCGAGCTCGAGGACAAGAAGTACAGCATCGGCCTGGC |
|  |  | CATCGGCACCAACTCTGTGGGCTGGGCCGTGATCACCGACGAGTACAAGGTGCC |
|  |  | CAGCAAGAAATTCAAGGTGCTGGGCAACACCGACCGGCACAGCATCAAGAAGAA |
|  |  | CCTGATCGGAGCCCTGCTGTTCGACAGCGGCGAAACAGCCGAGGCCACCCGGCT |
|  |  | GAAGAGAACCGCCAGAAGAAGATACACCAGACGGAAGAACCGGATCTGCTATCT |
|  |  | GCAAGAGATCTTCAGCAACGAGATGGCCAAGGTGGACGACAGCTTCTTCCACAG |
|  |  | ACTGGAAGAGTCCTTCCTGGTGGAAGAGGATAAGAAGCACGAGCGGCACCCCAT |
|  |  | CTTCGGCAACATCGTGGACGAGGTGGCCTACCACGAGAAGTACCCCACCATCTA |
|  |  | CCACCTGAGAAAGAAACTGGTGGACAGCACCGACAAGGCCGACCTGCGGCTGAT |
|  |  | CTATCTGGCCCTGGCCCACATGATCAAGTTCCGGGGCCACTTCCTGATCGAGGG |
|  |  | CGACCTGAACCCCGACAACAGCGACGTGGACAAGCTGTTCATCCAGCTGGTGCA |
|  |  | GACCTACAACCAGCTGTTCGAGGAAAACCCCATCAACGCCAGCGGCGTGGACGC |
|  |  | CAAGGCCATCCTGTCTGCCAGACTGAGCAAGAGCAGACGGCTGGAAAATCTGAT |
|  |  | CGCCCAGCTGCCCGGCGAGAAGAAGAATGGCCTGTTCGGCAACCTGATTGCCCT |
|  |  | GAGCCTGGGCCTGACCCCCAACTTCAAGAGCAACTTCGACCTGGCCGAGGATGC |
|  |  | CAAACTGCAGCTGAGCAAGGACACCTACGACGACGACCTGGACAACCTGCTGGC |
|  |  | CCAGATCGGCGACCAGTACGCCGACCTGTTTCTGGCCGCCAAGAACCTGTCCGA |
|  |  | CGCCATCCTGCTGAGCGACATCCTGAGAGTGAACACCGAGATCACCAAGGCCCC |
|  |  | CCTGAGCGCCTCTATGATCAAGAGATACGACGAGCACCACCAGGACCTGACCCT |
|  |  | GCTGAAAGCTCTCGTGCGGCAGCAGCTGCCTGAGAAGTACAAAGAGATTTTCTT |
|  |  | CGACCAGAGCAAGAACGGCTACGCCGGCTACATTGACGGCGGAGCCAGCCAGGA |
|  |  | AGAGTTCTACAAGTTCATCAAGCCCATCCTGGAAAAGATGGACGGCACCGAGGA |
|  |  | ACTGCTCGTGAAGCTGAACAGAGAGGACCTGCTGCGGAAGCAGCGGACCTTCGA |
|  |  | CAACGGCAGCATCCCCCACCAGATCCACCTGGGAGAGCTGCACGCCATTCTGCG |
|  |  | GCGGCAGGAAGATTTTTACCCATTCCTGAAGGACAACGGGAAAAGATCGAGAA |
|  |  | GATCCTGACCTTCCGCATCCCCTACTACGTGGGCCCTCTGGCCAGGGGAAACAG |
|  |  | CAGATTCGCCTGGATGACCAGAAAGAGCGAGGAAACCATCACCCCCTGGAACTT |
|  |  | CGAGGAAGTGGTGGACAAGGGCGCTTCCGCCCAGAGCTTCATCGAGCGGATGAC |
|  |  | CAACTTCGATAAGAACCTGCCCAACGAGAAGGTGCTGCCCAAGCACAGCCTGCT |
|  |  | GTACGAGTACTTCACCGTGTATAACGAGCTGACCAAAGTGAAATACGTGACCGA |
|  |  | GGGAATGAGAAAGCCCGCCTTCCTGAGCGGCGAGCAGAAAAAGGCCATCGTGGA |
|  |  | CCTGCTGTTCAAGACCAACCGGAAAGTGACCGTGAAGCAGCTGAAAGAGGACTA |
|  |  | CTTCAAGAAAATCGAGTGCTTCGACTCCGTGGAAATCTCCGGCGTGGAAGATCG |
|  |  | GTTCAACGCCTCCCTGGGCACATACCACGATCTGCTGAAAATTATCAAGGACAA |
|  |  | GGACTTCCTGGACAATGAGGAAAACGAGGACATTCTGGAAGATATCGTGCTGAC |
|  |  | CCTGACACTGTTTGAGGACAGAGAGATGATCGAGGAACGGCTGAAAACCTATGC |
|  |  | CCACCTGTTCGACGACAAAGTGATGAAGCAGCTGAAGCGGCGGAGATACACCGG |
|  |  | CTGGGGCAGGCTGAGCCGGAAGCTGATCAACGGCATCCGGGACAAGCAGTCCGG |
|  |  | CAAGACAATCCTGGATTTCCTGAAGTCCGACGGCTTCGCCAACAGAAACTTCAT |
|  |  | GCAGCTGATCCACGACGACAGCCTGACCTTTAAAGAGGACATCCAGAAAGCCCA |
|  |  | GGTGTCCGGCCAGGGCGATAGCCTGCACGAGCACATTGCCAATCTGGCCGGCAG |
|  |  | CCCCGCCATTAAGAAGGGCATCCTGCAGACAGTGAAGGTGGTGGACGAGCTCGT |
|  |  | GAAAGTGATGGGCCGGCACAAGCCCGAGAACATCGTGATCGAAATGGCCAGAGA |
|  |  | GAACCAGACCACCCAGAAGGGACAGAAGAACAGCCGCGAGAGAATGAAGCGGAT |
|  |  | CGAAGAGGGCATCAAAGAGCTGGGCAGCCAGATCCTGAAAGAACACCCCGTGGA |
|  |  | AAACACCCAGCTGCAGAACGAGAAGCTGTACCTGTACTACCTGCAGAATGGGCG |
|  |  | GGATATGTACGTGGACCAGGAACTGGACATCAACCGGCTGTCCGACTACGATGT |
|  |  | GGACGCCATCGTGCCTCAGAGCTTTCTGAAGGACGACTCCATCGACAACAAGGT |
|  |  | GCTGACCAGAAGCGACAAGAACCGGGGCAAGAGCGACAACGTGCCCTCCGAAGA |
|  |  | GGTCGTGAAGAAGATGAAGAACTACTGGCGGCAGCTGCTGAACGCCAAGCTGAT |
|  |  | TACCCAGAGAAAGTTCGACAATCTGACCAAGGCCGAGAGAGGCGGCCTGAGCGA |
|  |  | ACTGGATAAGGCCGGCTTCATCAAGAGACAGCTGGTGGAAACCCGGCAGATCAC |
|  |  | AAAGCACGTGGCACAGATCCTGGACTCCCGGATGAACACTAAGTACGACGAGAA |
|  |  | TGACAAGCTGATCCGGGAAGTGAAAGTGATCACCCTGAAGTCCAAGCTGGTGTC |
|  |  | CGATTTCCGGAAGGATTTCCAGTTTTACAAAGTGCGCGAGATCAACAACTACCA |
|  |  | CCACGCCCACGACGCCTACCTGAACGCCGTCGTGGGAACCGCCCTGATCAAAAA |
|  |  | GTACCCTAAGCTGGAAAGCGAGTTCGTGTACGGCGACTACAAGGTGTACGACGT |

TABLE 18-continued

Sequence listing.

| SEQ | Description | Sequence |
|-----|-------------|----------|

```
GCGGAAGATGATCGCCAAGAGCGAGCAGGAAATCGGCAAGGCTACCGCCAAGTA
CTTCTTCTACAGCAACATCATGAACTTTTTCAAGACCGAGATTACCCTGGCCAA
CGGCGAGATCCGGAAGCGGCCTCTGATCGAGACAAACGGCGAAACCGGGGAGAT
CGTGTGGGATAAGGGCCGGGATTTTGCCACCGTGCGGAAAGTGCTGAGCATGCC
CCAAGTGAATATCGTGAAAAAGACCGAGGTGCAGACAGGCGGCTTCAGCAAAGA
GTCTATCCTGCCCAAGAGGAACAGCGATAAGCTGATCGCCAGAAGAAGGACTG
GGACCCTAAGAAGTACGGCGGCTTCGACAGCCCCACCGTGGCCTATTCTGTGCT
GGTGGTGGCCAAAGTGGAAAAGGGCAAGTCCAAGAAACTGAAGAGTGTGAAAGA
GCTGCTGGGGATCACCATCATGGAAAGAAGCAGCTTCGAGAAGAATCCCATCGA
CTTTCTGGAAGCCAAGGGCTACAAAGAAGTGAAAAAGGACCTGATCATCAAGCT
GCCTAAGTACTCCCTGTTCGAGCTGGAAAACGGCCGGAAGAGAATGCTGGCCTC
TGCCGGCGAACTGCAGAAGGGAAACGAACTGGCCCTGCCCTCCAAATATGTGAA
CTTCCTGTACCTGGCCAGCCACTATGAGAAGCTGAAGGGCTCCCCCGAGGATAA
TGAGCAGAAACAGCTGTTTGTGGAACAGCACAAGCACTACCTGGACGAGATCAT
CGAGCAGATCAGCGAGTTCTCCAAGAGAGTGATCCTGGCCGACGCTAATCTGGA
CAAAGTGCTGTCCGCCTACAACAAGCACCGGGATAAGCCCATCAGAGAGCAGGC
CGAGAATATCATCCACCTGTTTACCCTGACCAATCTGGGAGCCCCTGCCGCCTT
CAAGTACTTTGACACCACCATCGACCGGAAGAGGTACACCAGCACCAAAGAGGT
GCTGGACGCCACCCTGATCCACCAGAGCATCACCGGCCTGTACGAGACACGGAT
CGACCTGTCTCAGCTGGGAGGCGACAGCCCCAAGAAGAAGAGAAAGGTGGGAGT
CGACGGATCCAGCGGCTCCGAGACCCCAGGCACATCTGAGAGCGCCACCCCTGA
GTCCACCGGTATGAACAATTCACAGGGGAGAGTGACATTCGAAGACGTGACCGT
GAACTTCACCCAGGGAGAATGGCAGCGCTTGAACCCAGAACAAAGGAACCTCTA
TCGGGACGTGATGCTGGAAAACTACTCAAATTTGGTGAGCGTTGGGCAGGGTGA
GACCACTAAGCCTGACGTGATCCTGAGATTGGAACAGGGCAAGGAGCCTTGGCT
CGAGGAAGAGGAAGTCCTGGGCTCAGGGAGGGCCGAGAAAAACGGTGATATAGG
AGGCCAGATATGGAAGCCTAAGGACGTCAAGGAGAGCCTGAGCGCTAAACGTCC
GGCAGCAACCAAAAAAGCAGGTCAGGCCAAGAAAAAATGAGGATCCTGAGTCTA
GAAAAGATATATATAGGATTGAAGATCTCTCAGTTAAGTCTACAAAAAAAAAAA
AAAAAAAAAAAAAAAAAAAAAAAAAAAAAAAAAAAAAAAAAAAAAAAAAAAAAA
AAAAAAAAAAAAAAAAAAAAAAAAAAAAAAAAAAAAAAAAAAAAAAAAAAAAAA
AAGAAGAGCGAATTCACTGGCCGTCGTTTTACAACGTCGTGACTGGGAAAACCC
TGGCGTTACCCAACTTAATCGCCTTGCAGCACATCCCCCTTTCGCCAGCTGGCG
TAATAGCGAAGAGGCCCGCACCGATCGCCCTTCCCAACAGTTGCGCAGCCTGAA
TGGCGAATGGCGCCTGATGCGGTATTTTCTCCTTACGCATCTGTGCGGTATTTC
ACACCGCATATGGTGCACTCTCAGTACAATCTGCTCTGATGCCGCATAGTTAAG
CCAGCCCCGACACCCGCCAACACCCGCTGACGCGCCCTGACGGGCTTGTCTGCT
CCCGGCATCCGCTTACAGACAAGCTGTGACCGTCTCCGGGAGCTGCATGTGTCA
GAGGTTTTCACCGTCATCACCGAAACGCGCGATGCAGCTCTGGCCCGTGTCTCA
AAATCTCTGATGTTACATTGCACAAGATAAAAATATATCATCATGAACAATAAA
ACTGTCTGCTTACATAAACAGTAATACAAGGGGTGTTATGAGCCATATTCAACG
GGAAACGTCGAGGCCGCGATTAAATTCCAACATGGATGCTGATTTATATGGGTA
TAAATGGGCTCGCGATAATGTCGGGCAATCAGGTGCGACAATCTATCGCTTGTA
TGGGAAGCCCGATGCGCCAGAGTTGTTTCTGAAACATGGCAAAGGTAGCGTTGC
CAATGATGTTACAGATGAGATGGTCAGACTAAACTGGCTGACGGAATTTATGCC
TCTTCCGACCATCAAGCATTTTATCCGTACTCCTGATGATGCATGGTTACTCAC
CACTGCGATCCCCGGAAAAACAGCATTCCAGGTATTAGAAGAATATCCTGATTC
AGGTGAAAATATTGTTGATGCGCTGGCAGTGTTCCTGCGCCGGTTGCATTCGAT
TCCTGTTTGTAATTGTCCTTTTAACAGCGATCGCGTATTTCGTCTCGCTCAGGC
GCAATCACGAATGAATAACGGTTTGGTTGATGCGAGTGATTTTGATGACGAGCG
TAATGGCTGGCCTGTTGAACAAGTCTGGAAAGAAATGCATAAACTTTTGCCATT
CTCACCGGATTCAGTCGTCACTCATGGTGATTTCTCACTTGATAACCTTATTTT
TGACGAGGGGAAATTAATAGGTTGTATTGATGTTGGACGAGTCGGAATCGCAGA
CCGATACCAGGATCTTGCCATCCTATGGAACTGCCTCGGTGAGTTTTCTCCTTC
ATTACAGAAACGGCTTTTTCAAAAATATGGTATTGATAATCCTGATATGAATAA
ATTGCAGTTTCATTTGATGCTCGATGAGTTTTTTCTAATCAGAATTGGTTAATTG
GTTGTAACATTATTCAGATTGGGCTTGATTTAAAACTTCATTTTTAATTTAAAA
GGATCTAGGTGAAGATCCTTTTTGATAATCTCATGACCAAAATCCCTTAACGTG
AGTTTTCGTTCCACTGAGCGTCAGACCCCGTAGAAAAGATCAAAGGATCTTCTT
GAGATCCTTTTTTTCTGCGCGTAATCTGCTGCTTGCAAACAAAAAAACCACCGC
TACCAGCGGTGGTTTGTTTGCCGGATCAAGAGCTACCAACTCTTTTTCCGAAGG
TAACTGGCTTCAGCAGAGCGCAGATACCAAATACTGTTCTTCTAGTGTAGCCGT
AGTTAGGCCACCACTTCAAGAACTCTGTAGCACCGCCTACATACCTCGCTCTGC
TAATCCTGTTACCAGTGGCTGCTGCCAGTGGCGATAAGTCGTGTCTTACCGGGT
TGGACTCAAGACGATAGTTACCGGATAAGGCGCAGCGGTCGGGCTGAACGGGGG
GTTCGTGCACACAGCCCAGCTTGGAGCGAACGACCTACACCGAACTGAGATACC
TACAGCGTGAGCTATGAGAAAGCGCCACGCTTCCCGAAGGGAGAAAGGCGGACA
GGTATCCGGTAAGCGGCAGGGTCGGAACAGGAGAGCGCACGAGGGAGCTTCCAG
GGGGAAACGCCTGGTATCTTTATAGTCCTGTCGGGTTTCGCCACCTCTGACTTG
AGCGTCGATTTTTGTGATGCTCGTCAGGGGGGCGGAGCCTATGGAAAAACGCCA
GCAACGCGGCCTTTTTACGGTTCCTGGCCTTTTGCTGGCCTTTTGCTCACATGT
TCTTTCCTGCGTTATCCCCTGATTCTGTGGATAACCGTATTACCGCCTTTGAGT
GAGCTGATACCGCTCGCCGCAGCCGAACGACCGAGCGCAGCGAGTCAGTGAGCG
```

TABLE 18-continued

Sequence listing.

| SEQ | Description | Sequence |
|---|---|---|
| | | AGGAAGCGGCCCAATACGCAAACCGCCTCTCCCCGCGCGTTGGCCGATTCATTA<br>ATGCAGCTGGCACGACAGGTTTCCCGACTGGAAAGCGGGCAGTGAGCGCAACGC<br>AATTAATGTGAGTTAGCTCACTCATTAGGCACCCCAGGCTTTACACTTTATGCT<br>TCCGGCTCGTATGTTGTGTGGAATTGTGAGCGGATAACAATTTCACACAGGAAA<br>CAGCTATGACCATGATTACGCCAAGCTTTAATACGACTCACTATA |
| 1256 | CRISPR-Off<br>variant 3 amino<br>acid sequence | MKRPAATKKAGQAKKKYNHDQEFDPPKVYPPVPAEKRKPIRVLSLEDGIATGLL<br>VLKDLGIQVDRYIASEVCEDSITVGMVRHQGKIMYVGDVRSVTQKHIQEWGPED<br>LVIGGSPCNDLSIVNPARKGLYEGTGRLFFEFYRLLHDARPKEGDDRPFFWLFE<br>NVVAMGVSDKRDISRFLESNPVMIDAKEVSAAHRARYFWGNLPGMNRPLASTVN<br>DKLELQECLEHGRIAKFSKVRTITTRSNSIKQGKDQHPFVFMNEKEDILWCTEM<br>ERVFGFPVHYTDVSNMSRLARQRLLGRSWSVPVIRHLFAPLKEYFACVSSGNSN<br>ANSRGPSFSSGLVPLSLRGSHSPLEMYKTVPVWKREPVRVLSLFGDIKKELTTL<br>GFLENGSDPGRLKHLDDVTNTVRRDVEEWGPFDLVYGSTPPLGHACDHPPGWYL<br>FQFHRVLQYARPRPGSPQAFFWMFVDNLVLTEDDRAVATRFLETDPVTIQDVCG<br>RAVRNAVHVWSNIPAVKSRHSALFSQEESFLRAQDRQRAKPPARGPAKLVKNCF<br>LPLREYFKYFSTEFTSSLGGPSSGAPPPSGGSPAGSPTSTEEGTSESATPESGP<br>GTSTEPSEGSAPGSPAGSPTSTEEGTSTEPSEGSAPGTSTEPSELEDKKYSIGL<br>AIGTNSVGWAVITDEYKVPSKKFKVLGNTDRHSIKKNLIGALLFDSGETAEATR<br>LKRTARRRYTRRKNRICYLQEIFSNEMAKVDDSFFHRLEESFLVEEDKKHERHP<br>IFGNIVDEVAYHEKYPTIYHLRKKLVDSTDKADLRLIYLALAHMIKERGHFLIE<br>GDLNPDNSDVDKLFIQLVQTYNQLFEENPINASGVDAKAILSARLSKSRRLENL<br>IAQLPGEKKNGLFGNLIALSLGLTPNFKSNFDLAEDAKLQLSKDTYDDDLDNLL<br>AQIGDQYADLFLAAKNLSDAILLSDILRVNTEITKAPLSASMIKRYDEHHQDLT<br>LLKALVRQQLPEKYKEIFFDQSKNGYAGYIDGGASQEEFYKFIKPILEKMDGTE<br>ELLVKLNREDLLRKQRTFDNGSIPHQIHLGELHAILRRQEDFYPFLKDNREKIE<br>KILTFRIPYYVGPLARGNSRFAWMTRKSEETITPWNFEEVVDKGASAQSFIERM<br>TNFDKNLPNEKVLPKHSLLYEYFTVYNELTKVKYVTEGMRKPAFLSGEQKKAIV<br>DLLFKTNRKVTVKQLKEDYFKKIECFDSVEISGVEDRENASLGTYHDLLKIIKD<br>KDFLDNEENEDILEDIVLTLTLFEDREMIEERLKTYAHLFDDKVMKQLKRRRYT<br>GWGRLSRKLINGIRDKQSGKTILDFLKSDGFANRNFMQLIHDDSLTFKEDIQKA<br>QVSGQGDSLHEHIANLAGSPAIKKGILQTVKVVDELVKVMGRHKPENIVIEMAR<br>ENQTTQKGQKNSRERMKRIEEGIKELGSQILKEHPVENTQLQNEKLYLYYLQNG<br>RDMYVDQELDINRLSDYDVDAIVPQSFLKDDSIDNKVLTRSDKNRGKSDNVPSE<br>EVVKKMKNYWRQLLNAKLITQRKFDNLTKAERGGLSELDKAGFIKRQLVETRQI<br>TKHVAQILDSRMNTKYDENDKLIREVKVITLKSKLVSDFRKDFQFYKVREINNY<br>HHAHDAYLNAVVGTALIKKYPKLESEFVYGDYKVYDVRKMIAKSEQEIGKATAK<br>YFFYSNIMNFFKTEITLANGEIRKRPLIETNGETGEIVWDKGRDFATVRKVLSM<br>PQVNIVKKTEVQTGGFSKESILPKRNSDKLIARKKDWDPKKYGGFDSPTVAYSV<br>LVVAKVEKGKSKKLKSVKELLGITIMERSSFEKNPIDFLEAKGYKEVKKDLIIK<br>LPKYSLFELENGRKRMLASAGELQKGNELALPSKYVNFLYLASHYEKLKGSPED<br>NEQKQLFVEQHKHYLDEIIEQISEFSKRVILADANLDKVLSAYNKHRDKPIREQ<br>AENIIHLFTLTNLGAPAAFKYFDTTIDRKRYTSTKEVLDATLIHQSITGLYETR<br>IDLSQLGGDSPKKKRKVGVDGSSGSETPGTSESATPESTGMNNSQGRVTFEDVT<br>VNFTQGEWQRLNPEQRNLYRDVMLENYSNLVSVGQGETTKPDVILRLEQGKEPW<br>LEEEEVLGSGRAEKNGDIGGQIWKPKDVKESLSAKRPAATKKAGQAKKK |

TABLE 19

Annotation of PLA003 amino acid sequence

| Name | Type | Minimum | Maximum | Length |
|---|---|---|---|---|
| SV40 NLS | CDS | 2 | 8 | 7 |
| SV40 NLS | CDS | 9 | 15 | 7 |
| DNMT3A | CDS | 17 | 317 | 301 |
| Linker | CDS | 318 | 344 | 27 |
| DNMT3L full-<br>length | CDS | 345 | 730 | 386 |
| XTEN80 | CDS | 731 | 810 | 80 |
| dCas9 | CDS | 811 | 2180 | 1370 |
| NLS | CDS | 2181 | 2187 | 7 |
| XTEN16 | CDS | 2188 | 2208 | 21 |
| ZIM3 | CDS | 2211 | 2310 | 100 |
| SV40 NLS | CDS | 2313 | 2319 | 7 |
| SV40 NLS | CDS | 2320 | 2326 | 7 |

TABLE 20

Annotation of PLA003 polynucleotide sequence

| Name | Type | Minimum | Maximum | Length |
|---|---|---|---|---|
| SV40 NLS | CDS | 4 | 24 | 21 |
| SV40 NLS | CDS | 25 | 45 | 21 |
| DNMT3A | CDS | 49 | 951 | 903 |
| Linker | CDS | 952 | 1032 | 81 |
| DNMT3L full-<br>length | CDS | 1033 | 2190 | 1158 |
| XTEN80 | CDS | 2191 | 2430 | 240 |
| dCas9 | CDS | 2431 | 6540 | 4110 |
| NLS | CDS | 6541 | 6561 | 21 |
| XTEN16 | CDS | 6562 | 6624 | 63 |
| ZIM3 | CDS | 6631 | 6930 | 300 |
| SV40 NLS | CDS | 6937 | 6957 | 21 |
| SV40 NLS | CDS | 6958 | 6978 | 21 |
| stop | terminator | 6979 | 6981 | 3 |

SEQUENCE LISTING

The patent contains a lengthy sequence listing. A copy of the sequence listing is available in electronic form from the USPTO web site (https://seqdata.uspto.gov/docdetail?docId=US12649003B2). An electronic copy of the sequence listing will also be available from the USPTO upon request and payment of the fee set forth in 37 CFR 1.19(b)(3).

The invention claimed is:

1. A method, comprising administering an epigenetic editing system to a subject, wherein the subject comprises detectable levels of HBV DNA, HBsAg, and/or HBeAg in plasma of the subject, wherein the epigenetic editing system comprises:
   a) a fusion protein comprising
      i) a dCas9 protein domain,
      ii) a DNMT3A domain, and
      iii) a human KRAB domain,
   or one or more nucleic acid molecules encoding the fusion protein, and
   b) a guide RNA (gRNA) consisting of
      i) a targeting domain, consisting of a targeting sequence that is 100% complementary to a target sequence, wherein the target sequence consists of the sequence of SEQ ID NO: 391, and
      ii) a Cas9 tracrRNA.

2. The method of claim 1, wherein the fusion protein further comprises a DNMT3L domain.

3. The method of claim 1, wherein the dCas9 protein domain is from *Streptococcus pyogenes* or *Staphylococcus aureus*.

4. The method of claim 3, wherein the dCas9 protein domain comprises a sequence selected from the group consisting of SEQ ID NOs: 12, 13, 27, 28 and 29.

5. The method of claim 3, wherein the dCas9 protein domain is from *Streptococcus pyogenes*.

6. The method of claim 4, wherein the dCas9 protein domain comprises the sequence of SEQ ID NO: 12.

7. The method of claim 1, wherein the DNMT3A domain comprises a sequence selected from the group consisting of SEQ ID NOs: 1028 and 1029.

8. The method of claim 1, wherein the DNMT3A domain comprises a sequence of SEQ ID NO: 1029.

9. The method of claim 1, wherein the human KRAB domain comprises a sequence selected from the group consisting of SEQ ID NOs: 495, 551, 536, 537, 707, and 717.

10. The method of claim 1, wherein the human KRAB domain is a ZIM3 KRAB domain.

11. The method of claim 10, wherein the ZIM3 KRAB domain comprises the sequence of SEQ ID NO: 495.

12. The method of claim 1, wherein the Cas9 tracrRNA sequence is the sequence of SEQ ID NO: 1087.

13. The method of claim 2, wherein the DNMT3L domain is a human DNMT3L domain.

14. The method of claim 2, wherein the DNMT3L domain comprises a sequence selected from the group consisting of SEQ ID NOs: 1032-1035.

15. The method of claim 14, wherein the DNMT3L domain comprises the sequence of SEQ ID NO: 1033.

16. The method of claim 1, wherein the dCas9 protein domain comprises a sequence of SEQ ID NO: 12, the DNMT3A domain comprises a sequence of SEQ ID NO: 1029, and the human KRAB domain comprises a sequence of SEQ ID NO: 495.

17. The method of claim 1, wherein the dCas9 protein domain comprises a sequence with at least 99% sequence identity to the sequence of SEQ ID NO: 12, the DNMT3A domain comprises a sequence with at least 99% sequence identity to the sequence of SEQ ID NO: 1029, and the human KRAB domain comprises a sequence with at least 99% sequence identity to the sequence of SEQ ID NO: 495.

18. A method, comprising administering an epigenetic editing system to a subject, wherein the subject comprises detectable levels of HBV DNA, HBsAg, and/or HBeAg in plasma of the subject, wherein the epigenetic editing system comprises:
   a) a fusion protein comprising
      i) a dCas9 protein domain,
      ii) a DNMT3A domain, and
      iii) a human KRAB domain, or one or more nucleic acid molecules encoding the fusion protein, and
   b) a guide RNA (gRNA) consisting of
      i) a targeting domain, consisting of a targeting sequence that is 100% complementary to a target sequence, wherein the target sequence consists of the sequence of SEQ ID NO: 391, and
      ii) a tracrRNA consisting of a sequence comprising the sequence of SEQ ID NO: 1089.

19. A method, comprising administering an epigenetic editing system to a subject, wherein the subject comprises detectable levels of HBV DNA, HBsAg, and/or HBeAg in plasma of the subject, wherein the epigenetic editing system comprises:
   a) a fusion protein comprising
      i) a dCas9 protein domain,
      ii) a DNMT3A domain, and
      iii) a human KRAB domain,
   or one or more nucleic acid molecules encoding the fusion protein, and
   b) a guide RNA (gRNA) consisting of
      i) a targeting domain, consisting of a targeting sequence that is 100% complementary to a target sequence, wherein the target sequence consists of the sequence of SEQ ID NO: 391, and
      ii) a tracrRNA consisting of a sequence comprising the sequence of SEQ ID NO: 1087.

* * * * *